(12) United States Patent
Augeri et al.

(10) Patent No.: US 6,720,338 B2
(45) Date of Patent: Apr. 13, 2004

(54) N-ACYLSULFONAMIDE APOPTOSIS PROMOTERS

(75) Inventors: David J. Augeri, Princeton, NJ (US); Steven A. Baumeister, South Milwaukee, WI (US); Milan Bruncko, Lake Bluff, IL (US); Daniel A. Dickman, Longmont, CO (US); Hong Ding, Gurnee, IL (US); Jurgen Dinges, Grayslake, IL (US); Stephen W. Fesik, Gurnee, IL (US); Philip J. Hajduk, Mundelein, IL (US); Aaron R. Kunzer, Vernon Hills, IL (US); William McClellan, Waukegan, IL (US); David G. Nettesheim, Lake Forest, IL (US); Thorsten Oost, Pleasant Prairie, WI (US); Andrew M. Petros, Mundelein, IL (US); Saul H. Rosenberg, Grayslake, IL (US); Wang Shen, San Mateo, CA (US); Sheela A. Thomas, Libertyville, IL (US); Xilu Wang, Skokie, IL (US); Michael D. Wendt, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/957,276

(22) Filed: Sep. 20, 2001

(65) Prior Publication Data

US 2002/0086887 A1 Jul. 4, 2002

Related U.S. Application Data

(60) Provisional application No. 60/233,866, filed on Sep. 20, 2000.

(51) Int. Cl.$^7$ ..................... A61K 31/445; C07D 211/32
(52) U.S. Cl. ....................................... 514/331; 546/234
(58) Field of Search ........................... 546/234; 514/331

(56) References Cited

FOREIGN PATENT DOCUMENTS

EP    0 837 056    4/1998
JP    60-152401    8/1985

OTHER PUBLICATIONS

CA 130:3787, Zhou et al. 1998.*
Pena, et al., *Bcl–X$_L$ and Bcl–2 Expression in Squamous Cell Carcinoma of the Head and Neck*, Cancer, 85: 164–170, 1999.

Sattler, et al., *Structure of Bcl–X$_L$ –Bak Peptide Complex: Recognition Between Regulators of Apoptosis*, Science, 275: 983–986, 1997.

Petros et al., "Solution structure of the antiapoptotic protein bcl–2," PNAS 98(6):3012–3017 (2001).

Dubina et al., "Arenesulphonyl benzamide chlorides. I. Synthesis and invetigation of hydrolysis and reaction with amines," Journal of Organic Chemistry of the USSR 2(10):1809–1812 (1966).

English et al., "Studies in chemotherapy. XIV. Antimalarials. The synthesis of substituted metanilamides and related compounds," Journal of the American Chemical Society, 68(6):1039–1049 (1946).

Habib et al., "Synthesis of some new N–aroylsulphonamides and sulphonate esters of xylene sulphonic acids of potential biological activity," Hungarian Journal of Industrial Chemistry 14(4):477–483 (1986).

Kremlev et al., "Investigation in the field of arensulphonamides. LXXXIX Aresulphonamidation of aromatic aldehydes and formamides," Journal of Organic Chemitry of the USSR 13(1):134–138 (1977).

Kremlev et al., Chemical Abstracts, vol. 77, No. 9, Aug. 28, 1972, abstract No. 61444j, "Arenesulphonylamides. LXII. Arenesulphonyl–p–halobenzamides," XP002200109.

Plotnikova et al., "Arenesulphonamides. LXXX. Aroylarenesulphonamides," vol. 82, No. 21, p. 579, May 26, 1975, abstract No. 139564y, XP002201725.

Srivastava et al., "Synthesis of diaryl sulphonates and N–acyl–aryl sulphonamides as potential fungicides," Agricultural and Biological Chemistry, 40(4):805–806 (1976).

* cited by examiner

Primary Examiner—Patricia L. Morris
(74) Attorney, Agent, or Firm—Gregory W. Steele; B. Gregory Donner

(57) ABSTRACT

N-Benzoyl arylsulfonamides having the formula:

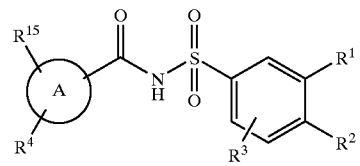

are BCL-X1 inhibitors and are useful for promoting apoptosis. Also disclosed are BCL-X1 inhibiting compositions and methods of promoting apoptosis in a mammal.

9 Claims, No Drawings

N-ACYLSULFONAMIDE APOPTOSIS PROMOTERS

CROSS REFERENCE TO RELATED APPLICATIONS

This application claims priority to U.S. Provisional Patent Application Ser. No. 60/233,866, filed Sep. 20, 2000, which is hereby incorporated by reference.

TECHNICAL FIELD

The present invention relates to substituted N-acylsulfonamides which are useful for promoting apoptosis, methods of making the compounds, compositions containing the compounds, and methods of treatment using the compounds.

BACKGROUND OF THE INVENTION

Apoptosis is a mode of cell death in which the cell commits suicide either to ensure proper development of the organism or to destroy cells that represent a threat to the organism's integrity. Morphologically, apoptosis is characterized by blebbing of the plasma membrane, shrinking of the cytoplasm and nucleus, and fragmenting into particles which are engulfed by phagocytic cells. Although apoptosis plays a critical role in normal development, its impairment is thought to be a significant factor in the etiology of such diseases as cancer, autoimmune disorders, inflammatory diseases, and viral infections. Conversely, increased apoptosis has been linked to AIDS and neurodegenerative diseases such as Parkinson's disease, stroke, and Alzheimer's disease.

BCL-X1 is a protein which, in healthy cells, is expressed in the outer membranes of the mitochondria, the endoplasmic reticulum, and the nuclear envelope. Its function is to bind to specific protein/protease complexes and prevent cell apoptosis. Upon internal damage to the cell the protein/protease complexes are released, and cause the process of apoptosis to begin. An over-expression of BCL-X1, often present in cancerous and other diseased cells, results in the blocking of apoptotic signals and allows the cells to proliferate (*Cancer* 1999, 85, 164–170; and references cited therein). It is believed that by blocking BCL-X1, apoptosis can be induced in diseased cells, and can provide an effective therapy for cancer and other diseases caused by the impairment of the apoptotic process. Based on these findings and the absence of BCL-X1 inhibitors from current cancer therapies, there is a continuing need for compounds which can trigger apoptosis through the inhibition of the BCL family of proteins.

SUMMARY OF THE INVENTION

In its principle embodiment the present invention provides a compound of formula (I):

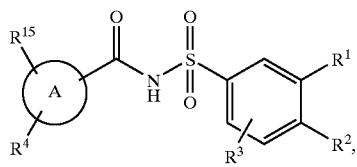

(I)

or a therapeutically acceptable salt thereof wherein

A is selected from the group consisting of phenyl and a five- or six-membered aromatic carbocyclic ring wherein from one to three carbon atoms are replaced by a heteroatom selected from the group consisting of nitrogen, oxygen, and sulfur, and wherein A is substituted through carbon atoms in the ring;

$R^1$ is selected from the group consisting of alkyl, haloalkyl, nitro, and —$NR^5R^6$;

$R^2$, and $R^3$ are independently selected from the group consisting of hydrogen, alkenyl, alkoxy, alkyl, alkylsulfanyl, alkynyl, aryl, arylalkoxy, aryloxy, aryloxyalkoxy, arylsulfanyl, arylsulfanylalkoxy, carbonyloxy, cycloalkylalkoxy, cycloalkyloxy, halo, haloalkoxy, haloalkyl, heterocycle, (heterocycle)oxy, hydroxy, nitro, and —$N^5R^6$, $R^4$ is selected from the group consisting of aryl, arylalkenyl, arylalkoxy, cycloalkenyl, cycloalkyl, halo, heterocycle, and (heterocycle)alkoxy;

$R^5$ and $R^6$ are independently selected from the group consisting of hydrogen, alkenyl, alkoxyalkyl, alkoxycarbonylalkyl, alkyl, alkylsulfanylalkyl, alkylsulfonylalkyl, aryl, arylalkyl, arylalkylsulfanylalkyl, aryloxyalkyl, arylsulfanylalkyl, arylsulfinylalkyl, arylsulfonylalkyl, carboxyalkyl, cycloalkenyl, cycloalkenylalkyl, cycloalkyl, (cycloalkyl)alkyl, cycloalkylcarbonyl, heterocycle, (heterocycle)alkyl, (heterocycle)sulfanylalkyl, hydroxyalkyl, a nitrogen protecting group, and —N=$CR^7R^8$; or $R^5$ and $R^6$, together with the nitrogen atom to which they are attached, form a ring selected from the group consisting of imidazolyl, morpholinyl, piperazinyl, piperidinyl, pyrrolidinyl, pyrrolyl, thiomorpholinyl, and thiomorpholinyl dioxide; and $R^7$ and $R^8$ are alkyl, or $R^7$ and $R^8$, together with the carbon atom to which they are attached, form an aryl group; and $R^{15}$ is selected from the group consisting of hydrogen, alkyl, and halo.

In another embodiment the present invention provides a compound of formula (I) wherein A is selected from the group consisting of phenyl, pyridinyl, and furyl; and $R^1$–$R^8$ and $R^{15}$ are as previously defined.

In another embodiment the present invention provides a compound of formula (I) wherein A is selected from the group consisting of phenyl, pyridinyl, and furyl; $R^3$ is selected from the group consisting of hydrogen, alkenyl, aryl, and heterocycle; and $R^1$, $R^2$, $R^{4-8}$, and $R^{15}$ are as previously defined.

In another embodiment the present invention provides a compound of formula (I) wherein A is selected from the group consisting of phenyl, pyridinyl, and furyl; $R^3$ is selected from the group consisting of hydrogen, alkenyl, aryl, and heterocycle; $R^2$ is selected from the group consisting of arylsulfanylalkoxy, cycloalkylalkoxy, and cycloalkyloxy; and $R^1$, $R^4$, and $R^{15}$ are as previously defined.

In another embodiment the present invention provides a compound of formula (I) wherein A is selected from the group consisting of phenyl, pyridinyl, and furyl; $R^3$ is selected from the group consisting of hydrogen, alkenyl, aryl, and heterocycle; $R^2$ is —$NR^5R^6$; and $R^1$, $R^4$, $R^7$, $R^8$, and $R^{15}$ are as previously defined.

In another embodiment the present invention provides a compound of formula (I) wherein A is selected from the group consisting of phenyl, pyridinyl, and furyl; $R^3$ is selected from the group consisting of hydrogen, alkenyl, aryl, and heterocycle; $R^2$ is —$NR^5R^6$; one of $R^5$ and $R^6$ is selected from the group consisting of alkyl, aryl, arylalkyl, arylalkylsulfanylalkyl, arylsulfinylalkyl, arylsulfonylalkyl, cycloalkylcarbonyl, heterocycle, (heterocycle)alkyl, heterocyclesulfanylalkyl, and —N=CR$^7$R$^8$; and the other is hydrogen; and R$^1$, R$^4$, R$^7$, R$^8$, and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is (cycloalkyl)alkyl and the other is arylsulfanylalkyl; and R$^1$, R$^4$, and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is cycloalkyl and the other is hydrogen; and R$^1$, R$^4$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is (cycloalkyl)alkyl and the other is hydrogen; and R$^1$, R$^4$, and R$^5$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; and R$^1$, R$^4$, and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylalkylsulfanyl and the other is hydrogen; R$^4$ is selected from the group consisting of arylalkenyl, arylalkoxy, cycloalkenyl, cycloalkyl, and (heterocycle)alkoxy; and R$^1$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; R$^4$ is aryl; and R$^1$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; R$^4$ is aryl wherein the aryl is unsubstituted or has one substituent; and R$^1$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; R$^4$ is aryl wherein the aryl has two substituents; and R$^1$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; R$^4$ is heterocycle; and R$^1$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; R$^4$ is heterocycle wherein the heterocycle is unsubstitued or has one substituent; and R$^1$ and R$^{15}$ are as previously defined.

In another embodiment the present invention provides a compound of formula (I) wherein A is selected from the group consisting of phenyl, pyridinyl, and furyl; R$^3$ is selected from the group consisting of hydrogen, alkenyl, aryl, and heterocycle; R$^2$ is —NR$^5$R$^6$; one of R$^5$ and R$^6$ is arylsulfanylalkyl and the other is hydrogen; R$^4$ is heterocycle wherein the heterocycle has two or three substituents; and R$^1$ and R$^{15}$ are as previously defined.

In another embodiment, the present invention provides a pharmaceutical composition comprising a compound of formula (I), or a therapeutically acceptable salt thereof, in combination with a therapeutically acceptable carrier.

In another embodiment, the present invention provides a method of promoting apoptosis in a mammal in recognized need thereof comprising administering to the mammal a therapeutically acceptable amount of a compound of formula (I) or a therapeutically acceptable salt thereof.

DETAILED DESCRIPTION OF THE INVENTION

Compounds of the present invention comprise substituted N-benzoyl arylsulfonamides which are useful for the treatment of apoptosis-mediated diseases.

As used in the present specification the following terms have the meanings indicated.

The term "alkanoyl," as used herein, represents an alkyl group attached to the parent molecular moiety through a carbonyl group. The alkanoyl groups of this invention can be optionally substituted with one or two groups independently selected from the group consisting of hydroxy and —NR$^5$R$^6$, wherein R$^5$ and R$^6$ are as previously defined.

The term "alkanoylalkyl," as used herein, represents an alkanoyl group attached to the parent molecular moiety through an alkyl group.

The term "alkenyl," as used herein, represents a straight or branched chain group of one to twelve carbon atoms derived from a straight or branched chain hydrocarbon containing at least one carbon-carbon double bond.

The term "alkoxy," as used herein, represents an alkyl group attached to the parent molecular moiety through an oxygen atom.

The term "alkoxyalkanoyl," as used herein, represents an alkoxy group attached to the parent molecular moiety through an alkanoyl group.

The term "alkoxyalkoxy," as used herein, represents an alkoxy group attached to the parent molecular moiety through another alkoxy group.

The term "alkoxyalkoxyalkyl," as used herein, represents an alkoxyalkoxy group attached to the parent molecular moiety through an alkyl group.

The term "alkoxyalkoxycarbonyl," as used herein, represents an alkoxyalkoxy group attached to the parent molecular moiety through a carbonyl group.

The term "alkoxyalkyl," as used herein, represents an alkoxy group attached to the parent molecular moiety through an alkyl group.

The term "alkoxycarbonyl," as used herein, represents an alkoxy group attached to the parent molecular moiety through a carbonyl group.

The term "alkoxycarbonylalkyl," as used herein, represents an alkoxycarbonyl group attached to the parent molecular moiety through an alkyl group.

The term "alkyl," as used herein, represents a group of one to twelve carbon atoms derived from a straight or branched chain saturated hydrocarbon.

The term "alkylamino," as used herein, represents —N($R^{14}$)$_2$, wherein $R^{14}$ is alkyl.

The term "alkylaminoalkyl," as used herein, represents an alkylamino group attached to the parent molecular moiety through an alkyl group.

The term "alkylaminocarbonyl," as used herein, represents an alkylamino group attached to the parent molecular moiety through a carbonyl group.

The term "alkylaminocarbonylalkyl," as used herein, represents an alkylaminocarbonyl group attached to the parent molecular moiety through an alkyl group.

The term "alkylidene," as used herein, represents an alkyl group attached to the parent molecular moiety through a carbon-carbon double bond.

The term "alkylsulfanyl," as used herein, represents an alkyl group attached to the parent molecular moiety through a sulfur atom.

The term "alkylsulfanylalkyl," as used herein, represents an alkylsulfanyl group attached to the parent molecular moiety through an alkyl group.

The term "alkylsulfonyl," as used herein, represents an alkyl group attached to the parent molecular moiety through a sulfonyl group.

The term "alkylsulfonylalkyl," as used herein, represents an alkylsulfonyl group attached to the parent molecular moiety through an alkyl group.

The term "alkynyl," as used herein, represents a straight or branched chain group of one to twelve carbon atoms containing at least one carbon-carbon triple bond.

The term "amino," as used herein, represents —NR$^9$R$^{10}$, wherein R$^9$ and R$^{10}$ are independently selected from the group consisting of hydrogen, alkanoyl, alkenyl, alkoxyalkyl, alkoxyalkoxyalkyl, alkoxycarbonyl, alkyl, alkylaminoalkyl, alkylaminocarbonylalkyl, aryl, arylalkyl, cycloalkyl, (cycloalkyl)alkyl, cycloalkylcarbonyl, haloalkanoyl, haloalkyl, (heterocycle)alkyl, heterocyclecarbonyl, hydroxyalkyl, a nitrogen protecting group, —C(NH)NH$_2$, and —C(O)NR$^5$R$^6$, wherein R$^5$ and R$^6$ are as previously defined; wherein the aryl; the aryl part of the arylalkyl; the cycloalkyl; the cycloalkyl part of the (cycloalkyl)alkyl and the cycloalkylcarbonyl; and the heterocycle part of the (heterocycle)alkyl and the heterocyclecarbonyl can be optionally substituted with one, two, three, four, or five substituents independently selected from the group consisting of alkanoyl, alkoxy, alkyl, cyano, halo, haloalkoxy, haloalkyl, hydroxy, and nitro.

The term "aminoalkanoyl," as used herein, represents an amino group attached to the parent molecular moiety through an alkanoyl group.

The term "aminoalkyl," as used herein, represents an amino group attached to the parent molecular moiety through an alkyl group.

The term "aminocarbonyl," as used herein, represents an amino group attached to the parent molecular moiety through a carbonyl group.

The term "aminocarbonylalkyl," as used herein, represents an aminocarbonyl group attached to the parent molecular moiety through an alkyl group.

The term "aminosulfonyl," as used herein, represents an amino group attached to the parent molecular moiety through a sulfonyl group.

The term "aryl," as used herein, represents a phenyl group or a bicyclic or tricyclic fused ring system wherein one or more of the fused rings is a phenyl group. Bicyclic fused ring systems are exemplified by a phenyl group fused to a cycloalkyl group as defined herein, a cycloalkenyl group as defined herein, or another phenyl group. Tricyclic fused ring systems are exemplified by a bicyclic fused ring system fused to a cycloalkyl group as defined herein, a cycloalkenyl group as defined herein, or another phenyl group. Representative examples of aryl include, but are not limited to, anthracenyl, azulenyl, fluorenyl, indanyl, indenyl, naphthyl, phenyl, and tetrahydronaphthyl. Aryl groups having an unsaturated or partially saturated ring fused to an aromatic ring can be attached through the saturated or the unsaturated part of the group. The aryl groups of this invention can be optionally substituted with one, two, three, four, or five substituents independently selected from the group consisting of alkanoyl, alkenyl, alkoxy, alkoxyalkanoyl, alkoxyalkyl, alkoxycarbonyl, alkoxycarbonylalkyl, alkyl, alkynyl, amino, aminoalkyl, aminocarbonyl, aminocarbonylalkyl, aminosulfonyl, aryl, aryloxy, arylsulfanyl, carbonyloxy, cyano, halo, haloalkoxy, haloalkyl, heterocycle, (heterocycle)alkyl, heterocyclecarbonylalkenyl, heterocyclecarbonylalkyl, hydroxy, hydroxyalkyl, nitro, oxo, and —C(NH)NH$_2$, wherein the aryl; the aryl part of the aryloxy and the arylsulfanyl; the heterocycle; and the heterocycle part of the (heterocycle)alkyl, the heterocyclecarbonylalkenyl, and the heterocyclecarbonylalkyl can be further optionally substituted with one, two, or three substituents independently selected from the group consisting of alkoxyalkanoyl, alkoxycarbonyl, alkyl, alkylsulfonyl, aminocarbonyl, aminosulfonyl, cyano, halo, haloalkoxy, haloalkyl, hydroxy, nitro, oxo, and —C(NH)NH$_2$. In addition, the heterocycle and the heterocycle part of the (heterocycle)alkyl, the heterocyclecarbonylalkenyl, and the heterocyclecarbonylalkyl can be further optionally substituted with an additional aryl group, wherein the aryl can be optionally substituted with one, two, or three substituents independently selected from the group consisting of alkoxy, alkyl, cyano, halo, hydroxy, and nitro.

The term "arylalkenyl," as used herein, represents an aryl group attached to the parent molecular moiety through an alkenyl group.

The term "arylalkoxy," as used herein, represents an aryl group attached to the parent molecular moiety through an alkoxy group.

The term "arylalkoxyalkanoyl," as used herein, represents an arylalkoxy group attached to the parent molecular moiety through an alkanoyl group.

The term "arylalkoxycarbonyl," as used herein, represents an arylalkoxy group attached to the parent molecular moiety through a carbonyl group.

The term "arylalkyl," as used herein, represents an alkyl group substituted with at least one aryl group. The alkyl part of the arylalkyl can be optionally substituted with one or two amino groups.

The term "arylalkylsulfanyl," as used herein, represents an arylalkyl group attached to the parent molecular moiety through a sulfur atom.

The term "arylalkylsulfanylalkyl," as used herein, represents an arylalkylsulfanyl group attached to the parent molecular moiety through an alkyl group.

The term "arylalkylsulfonyl," as used herein, represents an arylalkyl group attached to the parent molecular moiety through a sulfonyl group.

The term "arylcarbonyl," as used herein, represents an aryl group attached to the parent molecular moiety through a carbonyl group.

The term "aryloxy," as used herein, represents an aryl group attached to the parent molecular moiety through an oxygen atom.

The term "aryloxyalkoxy," as used herein, represents an aryloxy group attached to the parent molecular moiety through an alkoxy group.

The term "aryloxyalkyl," as used herein, represents an aryloxy group attached to the parent molecular moiety through an alkyl group.

The term "arylsulfanyl," as used herein, represents an aryl group attached to the parent molecular moiety through a sulfur atom.

The term "arylsulfanylalkoxy," as used herein, represents an arylsulfanyl group attached to the parent molecular moiety through an alkoxy group.

The term "arylsulfanylalkyl," as used herein, represents an arylsulfanyl group attached to the parent molecular moiety through an alkyl group. The alkyl part of the arylsulfanylalkyl can be optionally substituted with one or two substituents independently selected from the group consisting of alkoxy, alkoxycarbonyl, amino, aminocarbonyl, arylalkoxy, azido, carboxy, cycloalkyl, halo, heterocycle, (heterocycle)alkoxy, (heterocycle)carbonyl, and hydroxy.

The term "arylsulfinyl," as used herein, represents an aryl group attached to the parent molecular moiety through a sulfinyl group.

The term "arylsulfinylalkyl," as used herein, represents an arylsulfinyl group attached to the parent molecular moiety through an alkyl group. The alkyl part of the arylsulfinylalkyl can be optionally substituted with one or two amino groups.

The term "arylsulfonyl," as used herein, represents an aryl group attached to the parent molecular moiety through a sulfonyl group.

The term "arylsulfonylalkyl," as used herein, represents an arylsulfonyl group attached to the parent molecular moiety through an alkyl group. The alkyl part of the arylsulfonylalkyl can be optionally substituted with one or two amino groups.

The term "azido," as used herein, represents —$N_3$.

The term "carbonyl," as used herein, represents —C(O)—.

The term "carbonyloxy," as used herein, represents an alkanoyl group attached to the parent molecular moiety through an oxygen atom.

The term "carboxy," as used herein, represents —$CO_2H$.

The term "carboxyalkyl," as used herein, represents a carboxy group attached to the parent molecular moiety through an alkyl group.

The term "cyano," as used herein, represents —CN.

The term "cyanoalkyl," as used herein, represents a cyano group attached to the parent molecular moiety through an alkyl group.

The term "cycloalkenyl," as used herein, represents a non-aromatic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Examples of cycloalkenyl groups include cyclohexenyl, octahydronaphthalenyl, norbornylenyl, and the like. The cycloalkenyl groups of this invention can be optionally substituted with one, two, three, four, or five substituents independently selected from the group consisting of alkoxy, alkoxycarbonyl, alkyl, aminoalkyl, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy.

The term "cycloalkenylalkyl," as used herein, represents a cycloalkenyl group attached to the parent molecular moiety through an alkyl group.

The term "cycloalkyl," as used herein, represents a saturated ring system having three to twelve carbon atoms and one to three rings. Examples of cycloalkyl groups include cyclopropyl, cyclopentyl, bicyclo(3.1.1)heptyl, adamantyl, and the like. The cycloalkyl groups of this invention can be optionally substituted with one, two, three, four, or five substituents independently selected from the group consisting of alkoxy, alkoxycarbonyl, alkyl, aminoalkyl, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy.

The term "cycloalkylalkoxy," as used herein, represents a cycloalkyl group attached to the parent molecular moiety through an alkoxy group.

The term "(cycloalkyl)alkyl," as used herein, represents a cycloalkyl group attached to the parent molecular moiety through an alkyl group.

The term "cycloalkylcarbonyl," as used herein, represents a cycloalkyl group attached to the parent molecular moiety through a carbonyl group.

The term "cycloalkyloxy," as used herein, represents a cycloalkyl group attached to the parent molecular moiety through an oxygen atom.

The term "formyl," as used herein, represents —CHO.

The term "formylalkyl," as used herein, represents a formyl group attached to the parent molecular moiety through an alkyl group.

The term "halo," as used herein, represents F, Cl, Br, or I.

The term "haloalkanoyl," as used herein, represents a haloalkyl group attached to the parent molecular moiety through a carbonyl group.

The term "haloalkoxy," as used herein, represents a haloalkyl group attached to the parent molecular moiety through an oxygen atom.

The term "haloalkyl," as used herein, represents an alkyl group substituted by one, two, three, or four halogen atoms.

The term "heteroalkenylene," as used herein, represents a divalent group of three to eight atoms derived from a straight or branched chain containing at least one carbon-carbon double bond that contains one or two heteroatoms independently selected from the group consisting of nitrogen, oxygen, and sulfur, wherein the remaining atoms are carbon. The heteroalkenylene groups of the present invention can be attached to the parent molecular moiety through the carbon atoms or the heteroatoms in the chain.

The term "heteroalkylene," as used herein, represents a divalent group of two to eight atoms derived from a saturated straight or branched chain containing one or two heteroatoms independently selected from the group consisting of nitrogen, oxygen, and sulfur, wherein the remaining atoms are carbon. The heteroalkylene groups of the present invention can be attached to the parent molecular moiety through the carbon atoms or the heteroatoms in the chain.

The term "heterocycle," as used herein, represents a monocyclic, bicyclic, or tricyclic ring system wherein one or more rings is a four-, five-, six-, or seven-membered ring containing one, two, or three heteroatoms independently selected from the group consisting of nitrogen, oxygen, and sulfur. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 3- and 4-membered rings have no double bonds, the 5-membered ring has from 0–2 double bonds and the 6- and 7-membered rings have from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, a cycloalkenyl group, as defined herein, or another monocyclic heterocycle ring system. Representative examples of bicyclic ring system include but are not limited to, benzimidazole, benzothiazole, benzothiophene, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. Tricyclic rings systems are exemplified by any of the above bicyclic ring systems fused to an aryl group as defined herein, a cycloalkyl group as defined herein, a cycloalkenyl group as defined herein, or another monocyclic heterocycle ring system. Representative examples of tricyclic ring systems include, but are not limited to, acridine, carbazole, carboline, dibenzofuran, dibenzothiophene, naphthofuran, naphthothiophene, oxanthrene, phenazine, phenoxathiin, phenoxazine, phenothiazine, thianthrene, thioxanthene, xanthene, and the like. Heterocycle groups can be attached to the parent molecular moiety through a carbon atom or a nitrogen atom in the group.

The heterocycle groups of the present invention can be optionally substituted with one, two, three, four, or five substituents independently selected from the group consisting of alkanoyl, alkanoylalkyl, alkenyl, alkoxy, alkoxyalkoxycarbonyl, alkoxyalkyl, alkoxycarbonyl, alkoxycarbonylalkyl, alkyl, alkylsulfanylalkyl, alkynyl, amino, aminoalkanoyl, aminoalkyl, aminocarbonyl, aminocarbonylalkyl, aminosulfonyl, aryl, arylalkoxyalkanoyl, arylalkoxycarbonyl, arylalkyl, arylalkylsulfonyl, arylcarbonyl, aryloxy, arylsulfanyl, arylsulfanylalkyl, arylsulfonyl, carbonyloxy, carboxy, cyano, cyanoalkyl, cycloalkyl, (cycloalkyl)alkyl, cycloalkylcarbonyl, formyl, formylalkyl, halo, haloalkoxy, haloalkyl, heterocycle, (heterocycle)alkyl, (heterocycle)alkylidene, heterocyclecarbonyl, heterocyclecarbonylalkyl, hydroxy, hydroxyalkyl, nitro, oxo, spirocycle, spiroheterocycle, and —C(NH)NH$_2$; wherein the aryl; the aryl part of the arylalkylsulfonyl, the arylcarbonyl, the aryloxy, the arylalkoxyalkanoyl, the arylalkoxycarbonyl, the arylalkyl, the arylsulfanyl, the arylsulfanylalkyl, and the arylsulfonyl; the heterocycle; and the heterocycle part of the (heterocycle)alkyl, the (heterocycle)alkylidene, the heterocyclecarbonyl, and the heterocyclecarbonylalkyl can be further optionally substituted with one, two, three, four, or five substituents independently selected from the group consisting of alkanoyl, alkoxy, alkoxyalkoxycarbonyl, alkoxycarbonyl, alkyl, halo, haloalkoxy, haloalkyl, hydroxy, hydroxyalkyl, and nitro.

The term "(heterocycle)alkoxy," as used herein, represents a heterocycle group attached to the parent molecular moiety through an alkoxy group.

The term "(heterocycle)alkyl," as used herein, represents a heterocycle group attached to the parent molecular moiety through an alkyl group.

The term "(heterocycle)alkylidene," as used herein, represents a heterocycle group attached to the parent molecular moiety through an alkylidene group.

The term "heterocyclecarbonyl," as used herein, represents a heterocycle group attached to the parent molecular moiety through a carbonyl group.

The term "heterocyclecarbonylalkenyl," as used herein, represents a heterocyclecarbonyl group attached to the parent molecular moiety through an alkenyl group.

The term "heterocyclecarbonylalkyl," as used herein, represents a heterocyclecarbonyl group attached to the parent molecular moiety through an alkyl group.

The term "(heterocycle)oxy," as used herein, represents a heterocycle group attached to the parent molecular moiety through an oxygen atom.

The term "(heterocycle)sulfanyl," as used herein, represents a heterocycle group attached to the parent molecular moiety through a sulfur atom.

The term "(heterocycle)sulfanylalkyl," as used herein, represents a heterocyclesulfanyl group attached to the parent molecular moiety through an alkyl group.

The term "hydroxy," as used herein, represents —OH.

The term "hydroxyalkyl," as used herein, represents a hydroxy group attached to the parent molecular moiety through an alkyl group.

The term "nitro," as used herein, represents —NO$_2$.

The term "nitrogen protecting group," as used herein, represents groups intended to protect an amino group against undesirable reactions during synthetic procedures. Common N-protecting groups comprise acyl groups such as acetyl, benzoyl, 2-bromoacetyl, 4-bromobenzoyl, tert-butylacetyl, carboxaldehyde, 2-chloroacetyl, 4-chlorobenzoyl, a-chlorobutyryl, 4-nitrobenzoyl, o-nitrophenoxyacetyl, phthalyl, pivaloyl, propionyl, trichloroacetyl, and trifluoroacetyl; sulfonyl groups such as benzenesulfonyl, and p-toluenesulfonyl; carbamate forming groups such as benzyloxycarbonyl, benzyloxycarbonyl (Cbz), tert-butyloxycarbonyl (Boc), p-chlorobenzyloxycarbonyl, p-methoxybenzyloxycarbonyl, and the like.

The term "oxo," as used herein, represents (=O).

The term "spirocycle," as used herein, represents an alkyl diradical of two to eight atoms, each end of which is attached to the same carbon atom of the parent molecular moiety.

The term "spiroheterocycle," as used herein, represents a heteroalkylene diradical, each end of which is attached to the same carbon atom of the parent molecular moiety. Examples of spiroheterocycles include dioxolanyl, tetrahydrofuranyl, pyrrolidinyl, and the like.

The term "sulfinyl," as used herein, represents —S(O)—.

The term "sulfonyl," as used herein, represents —SO$_2$—.

The term "therapeutically acceptable salt," as use herein, represents those salts which are, within the scope of sound medical judgment, suitable for use in contact with the tissues of humans and lower animals without undue toxicity, irritation, allergic response and the like and are commensurate with a reasonable benefit/risk ratio. The salts can be prepared in situ during the final isolation and purification of the compounds of the present invention or separately by reacting a free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include calcium, lithium, magnesium, potassium, sodium, and the like, as well as non-toxic ammonium, quaternary ammonium, and amine cations, including, but not limited to, ammonium, dimethylamine, ethylamine, methylamine, tetraethylammonium, tetramethylammonium, triethylamine, trimethylamine, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the bility to induce apoptosis. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

According to methods of treatment, the compounds of the present invention can be useful for the prevention of metastases from the tumors described above either when used alone or in combination with radiotherapy and/or other chemotherapeutic treatments conventionally administered to patients for treating cancer. When using the compounds of the present invention for chemotherapy, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. For example, when used in the treatment of solid tumors, compounds of the present invention can be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PROMACE/MOPP (prednisone, methotrexate (w/leucovin rescue), doxorubicin, cyclophosphamide, taxol, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. For example, a tumor may be treated conventionally with surgery, radiation or chemotherapy and a compound of the present invention subsequently administered to extend the dormancy of micrometastases and to stabilize and inhibit the growth of any residual primary tumor.

The compounds of the present invention can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds of the present invention can be formulated with dispersing, wetting, or suspending agents. The injectable preparation can also be an injectable solution or suspension in a diluent or solvent. Among the acceptable diluents or solvents employed are water, saline, Ringer's solution, buffers, dilute acids or bases, dilute amino acid solutions, monoglycerides, diglycerides, fatty acids such as oleic acid, and fixed oils such as monoglycerides or diglycerides.

The chemotherapeutic effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents; and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds of the present invention with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of the present invention.

The total daily dose of the compounds of the present invention administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

Assays for the inhibition of BCL-X1 were performed in 96-well microtiter plates. Compounds of the present invention were diluted in DMSO to concentrations between 100 $\mu$M and 1 pM and introduced into each cell of the plate. A mixture totaling 125 $\mu$L per well of assay buffer (20 mM phosphate buffer (pH 7.4), 1 mM EDTA, 0.05% PEG-8000), 50 nM of BCL-X1 protein (prepared according to the procedure described in *Science* 1997, 275, 983–986), 5 nM fluorescein-labeled BAD peptide (purchased from Synpep, Calif.), and the DMSO solution of the compound of the present invention was shaken for 2 minutes and placed in a LJL Analyst (LJL Bio Systems, Calif.). A negative control (DMSO, 5 nM BAD peptide, assay buffer) and a positive control (DMSO, 5 nM BAD peptide, 50 nM BCL-X1, assay buffer) were used to determine the range of the assay. Polarization was measured at room temperature using a continuous Fluorescein lamp (excitation 485 mM, emission 530 mM). Percentage of inhibition was determined by (1-((mP value of well-negative control)/range))×100%. $IC_{50}$ values were calculated using Microsoft Excel. Compounds of the present invention have $IC_{50}$ values between 0.011 and 10 $\mu$M and are therefore useful for inhibiting BCL-X1 and treating apoptosis-mediated diseases. Preferred compounds of the present invention have $IC_{50}$ values between 0.011 and 0.5 $\mu$M, and most preferred compounds have IC50 values between 0.011 and 0.10 $\mu$M.

Assays for the inhibition of BCL-2 were performed in 96-well microtiter plates. Compounds of the instant invention were diluted in DMSO to concentrations between 100 $\mu$M and 1 pM and introduced into each well of the plate. A mixture totaling 125 $\mu$L per well of assay buffer (20 mM phosphate buffer (pH 7.4), 1 mM EDTA, 0.05% PF-68), 30 nM of BCL-2 protein (prepared according to the procedure described in *PNAS* 2001, 98, 3012–3017), 5 nM fluorescein-labeled BAX peptide (prepared in-house), and the DMSO solution of the compound of the instant invention was shaken for 2 minutes and placed in a LJL Analyst (LJL Bio Systems, Calif.). A negative control (DMSO, 5 nM BAX peptide, assay buffer) and a positive control (DMSO, 5 nM BAX peptide, 30 nM BCL-2, assay buffer) were used to determine the range of the assay. Polarization was measured at room temperature using a continuous Fluorescein lamp (excitation 485 mM, emission 530 mM). Percentage of inhibition was determined by (1-((mP value of well-negative control)/range))×100%. $IC_{50}$ values were calculated using Microsoft Excel. Compounds of the present invention have $IC_{50}$ values between 0.017 and 10 $\mu$M and are therefore useful for inhibiting BCL-2 and treating apoptosis-mediated diseases. Preferred compounds of the present invention have $IC_{50}$ values between 0.017 and 0.5 $\mu$M, and most preferred compounds have IC50 values between 0.017 and 0.20 $\mu$M.

Based upon the structural and functional similarity of the BCL antiapoptotic proteins, it is reasonable to expect that in addition to inducing apoptosis by the inhibition of BCL-X1 and BCL-2, the current invention may induce apoptosis through their action on other antiapoptotic proteins in the Bcl family of proteins, such as BCL-w, BCL-b, MCL-1 and/or A1/Bfl-1.

Synthetic Methods

Abbreviations which have been used in the descriptions of the scheme and the examples that follow are: OAc for acetate; CyMAP-1 for 2-dicyclohexylphosphino-2'-(N,N-dimethylamino)biphenyl; dba for dibenzylideneacetone; dppf for diphenylphosphinoferrocene; DMF for N,N-dimethylformamide; DME for 1,2-dimethoxyethane; THF for tetrahydrofuran; MTBE for methyl tert-butyl ether; NMP for N-methylpyrroldinone; TFP for tris-2-furylphosphine; EDCI for 1-ethyl-3-(3-(dimethylamino)propyl)-carbodiimide hydrochloride; DMAP for 4-dimethylaminopyridine; DCC for 1,3-dicyclohexylcarbodiimide; CDI for 1,1'-carbonyldiimidazole; DMSO for dimethylsulfoxide; TFA for trifluoroacetic acid; NaHMDS for sodium hexamethyldisilazide; LAH for lithium aluminum hydride; p-TsOH for p-toluenesulfonic acid; DIBAL-H for diisobutylaluminum hydride; Fmoc for 9-fluorenylmethyl carbamate; Asp (OtBu)—OH for aspartic acid (4-tert-butyl ester); Lys (BOC)—OH for $N_\epsilon$-tert-butyoxycarbonyl lysine; HOBT for 1-hydroxybenzotriazole; BOC for tert-butoxycarbonyl; DEAD for diethyl azodicarboxylate; TBAF for tetrabutylammonium fluoride; BINAP for 2,2'-bis(diphenylphosphino)-1,1'-binaphthyl; Boc-Ser-OMe for N-tert-butoxycarbonyl serine methyl ester; DMA for N,N-dimethylacetamide; and HMPA for hexamethylphosphoramide.

The compounds and processes of the present invention will be better understood in connection with the following synthetic schemes which illustrate the methods by which the compounds of the invention may be prepared. The groups $R^1$, $R^2$, $R^3$, and $R^4$ are as defined above unless otherwise noted below. It will be readily apparent to one of ordinary skill in the art that the compounds defined above can be synthesized by substitution of the appropriate reactants and agents in the syntheses shown below. It will also be apparent that protection and deprotection steps, as well as the order of the steps themselves, can be carried out in varying order to successfully complete the syntheses of compounds of the present invention.

This invention is intended to encompass compounds of formula (I) when prepared by synthetic processes or by metabolic processes. Preparation of the compounds of the invention by metabolic processes include those occurring in the human or animal body (in vivo) or processes occurring in vitro.

Scheme 1

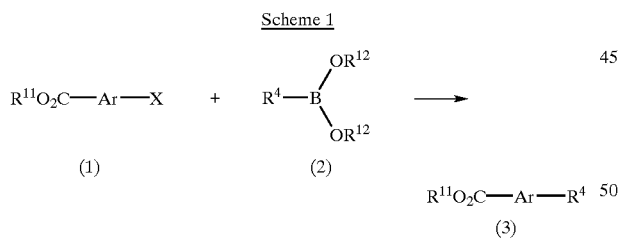

As shown in Scheme 1, compounds of formula (1) (Ar is aryl or heterocycle; X is halo; $R^{11}$ is alkyl) can be reacted with compounds of formula (2) ($R^4$ is an unsaturated group such as aryl or alkenyl; $R^{12}$ is hydrogen or alkyl) in the presence of catalytic palladium and base to provide compounds of formula (3). Examples of palladium catalysts include Pd(PPh$_3$)$_4$, Pd(OAc)$_2$/CyMAP-1, and Pd$_2$(dba)$_3$/AsPh$_3$, and Pd(dppf)Cl$_2$.CH$_2$Cl$_2$. Representative bases include Na$_2$CO$_3$, CsF, and Cs$_2$CO$_3$. Examples of solvents used in these reactions include toluene, dioxane, DMF, ethanol, DME, and mixtures thereof The reaction temperature is about 75° C. to about 120° C. and depends on the method chosen. Reaction times are typically about 1 to about 24 hours.

Compounds of formula (3) ($R^{11}$ is alkyl) can be hydrolyzed in the presence of aqueous base to form compounds of formula (3) ($R^{11}$ is hydrogen). Examples of bases include LiOH, NaOH, and KOH. Representative solvents include water, THF, dioxane, and mixtures thereof. The reaction temperature is about 25° C. to about 60° C. and depends on the method chosen. Reaction times are typically about 1 to about 18 hours.

Scheme 2

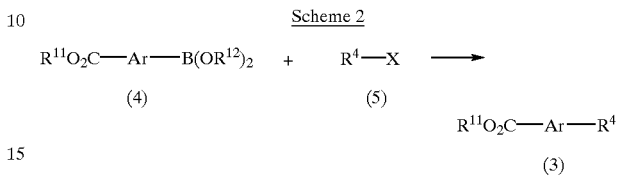

An alternative synthesis of compounds of formula (3) is shown in Scheme 2. Compounds of formula (4) (Ar is optionally substituted aryl or optionally substituted heterocycle; $R^{11}$ is hydrogen or alkyl; $R^{12}$ is hydrogen or alkyl) can be reacted with compounds of formula (5) ($R^4$ is previously defined; X is halo or triflate) using the conditions described in Scheme 1 to provide compounds of formula (3).

Scheme 3

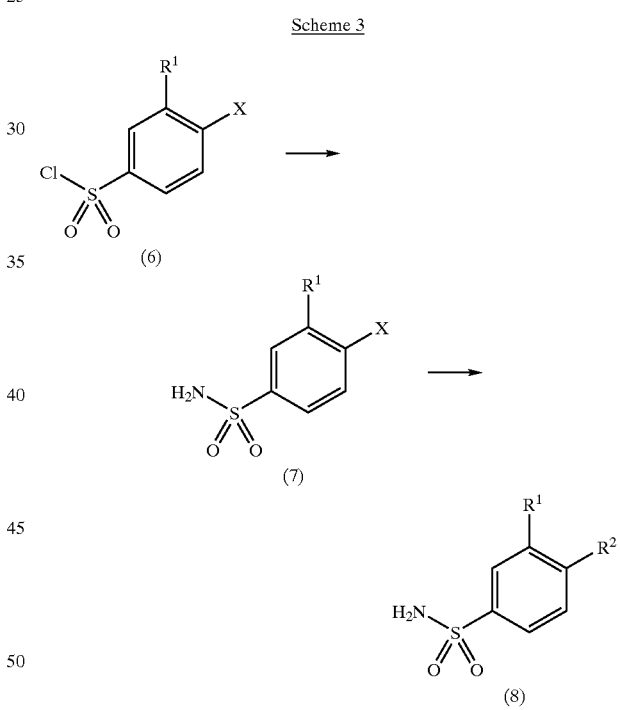

As shown in Scheme 3, compounds of formula (6) (X is F or Cl) can be converted to compounds of formula (7) by treatment with ammonium hydroxide. Examples of solvents used in this reaction include diethyl ether, THF, and MTBE. The reaction temperature is about −5° C. to about 25° C. and reaction times are typically about 15 minutes to about 1 hour. In a preferred embodiment, compounds of formula (6) in diethyl ether at 0° C. are treated with concentrated ammonium hydroxide and stirred for 30 minutes to provide compounds of formula (7).

The method chosen for the conversion of compounds of formula (7) to compounds of formula (8) is dependent on $R^2$. Compounds of formula (8) wherein $R^2$ is —NR$^5$R$^6$ can be formed by treating compounds of formula (7) with the appropriately substituted amine. Examples of solvents used in this reactions include DMF, dioxane, and NMP. Reaction temperatures are about 35° C. to about 130° C. and reaction times are typically about 8 to about 24 hours. Compounds of formula (8) wherein $R^2$ is alkoxy, alkylsulfanyl, aryloxy, arylsulfanyl, cycloalkylalkoxy, cycloalkyloxy, (heterocycle)oxy, or perfluoroalkoxy can be formed by treating compounds of formula (7) with the appropriately substituted alcohol in the presence of base. Representative bases include NaH/15-crown-5, and NaH, KH/18-crown-6. Examples of solvents used in this reaction include DMF, THF, NMP, and dioxane. The reaction temperature is about 20° C. to about 120° C. and the reaction times are typically about 30 minutes to about 24 hours.

Scheme 4

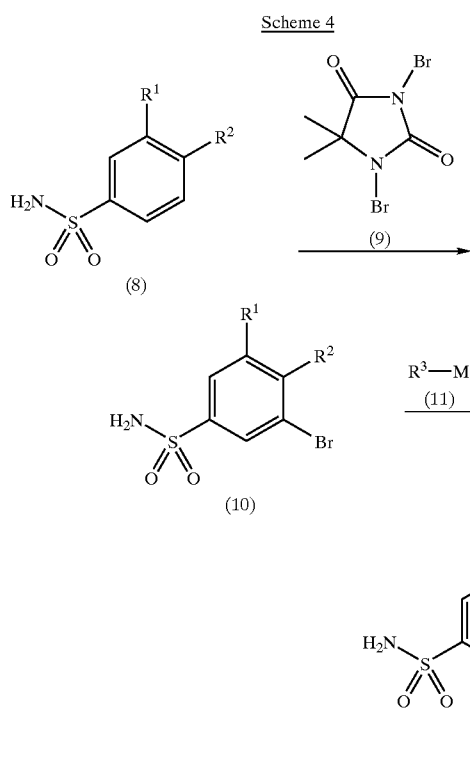

As shown in Scheme 4, compounds of formula (8) can be reacted with 1,3-dibromo-5,5-dimethylhydantoin (9) in the presence of trifluoracetic acid to provide compounds of formula (10). Examples of solvents used in this reaction include dichloromethane, 1,2-dichloroethane, and chloroform. The reaction temperature is about 20° C. to about 35° C., and the reaction time is typically about 6 to about 24 hours. In a preferred embodiment, compounds of formula (8) in dichloromethane at room temperature are treated with 1,3-dibromo-5,5-dimethylhydantoin (9) and stirred for 18 hours to provide compounds of formula (10).

Compounds of formula (10) can be converted to compounds of formula (12) by coupling with compounds of formula (11) (M is $SnBu_3$ or $B(OR^{13})_2$) in the presence of a palladium catalyst. Representative palladium catalysts include $Pd(PPh_3)_4$, $Pd(dppf)Cl_2 \cdot CH_2Cl_2$, and $Pd_2(dba)_3$/TFP. Examples of solvents include acetonitrile, dioxane, and DMF. The reaction temperature is about 35° C. to about 110° C. and depends on the method chosen. Reaction times are typically about 8 to about 48 hours.

Scheme 5

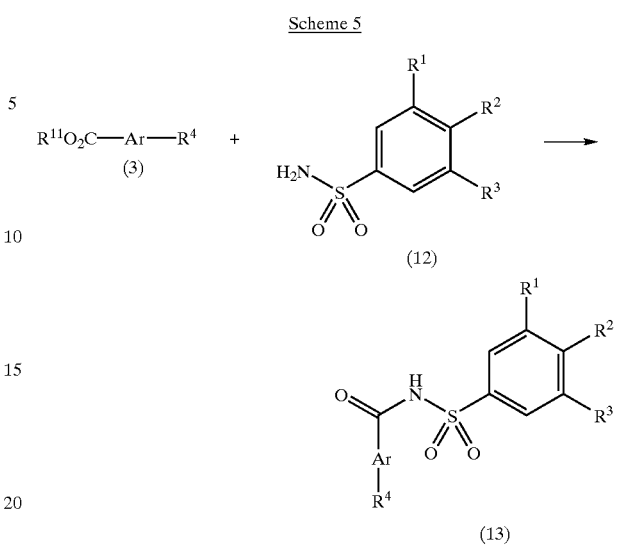

As shown in Scheme 5, compounds of formula (3) ($R^{11}$ is hydrogen) can be reacted with compounds of formula (13) in the presence of an activating agent to provide compounds of formula (14). Representative activating agents include EDCI/DMAP, DCC/DMAP, and CDI/DMAP. Examples of solvents used in these reactions include dichloromethane, chloroform, and DMF. The reaction temperature is about 20° C. to about 40° C. and depends on the method chosen. Reaction times are typically about 8 to about 24 hours.

Scheme 6

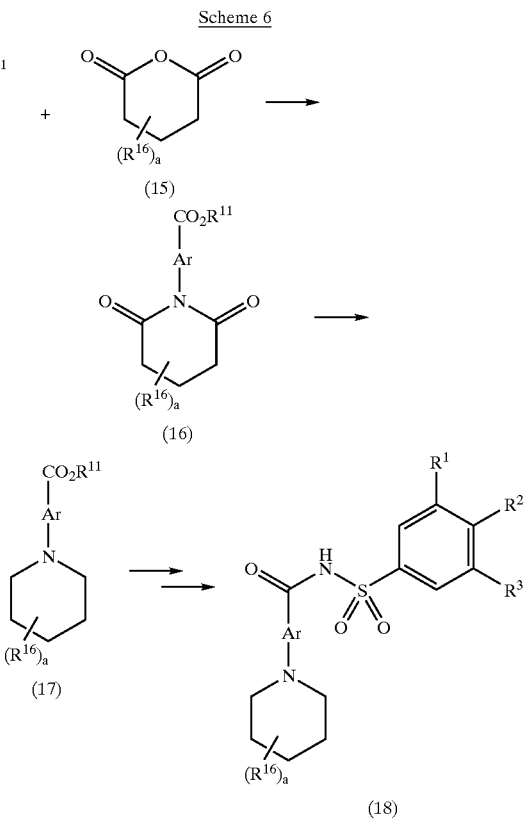

Scheme 6 shows the synthesis of compounds of formula (18) (a is 0–5 and each $R^{16}$ is a heterocycle substituent).

Compounds of formula (14) ($R^{11}$ is alkyl) can be reacted with compounds of formula (15) in the presence of acetyl chloride to provide compounds of formula (16). Examples of solvents used in these reactions include 1,2-dichloroethane, chloroform, and carbon tetrachloride. The reaction is conducted at about 80 to about 90° C. for about 1 to about 6 hours.

Conversion of compounds of formula (16) to compounds of formula (17) can be accomplished by treatment with a reducing agent. Representative reducing agents include $BF_3$—$Et_2O/NaBH_4$ and $B_2H_6$. Examples of solvents used in these reactions include diethyl ether, THF, toluene, and dichloromethane. The reaction is conducted at about 0° C. to about 100° C. and reaction times are typically about 1 to about 12 hours.

Compounds of formula (17) can be converted to compounds of formula (18) following the methods described in Scheme 5.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 4.5 (developed by Advanced Chemistry Development, Inc., Toronto, ON, Canada) or were given names which appeared to be consistent with ACD nomenclature.

EXAMPLE 1

4-((2,2-dimethylcyclopentyl)amino)-N-((4'-fluoro(1,1'-biphenyl)-4-yl)carbonyl)-3-nitrobenzenesulfonamide

EXAMPLE 1A methyl 4'-fluoro(1,1'-biphenyl)-4-carboxylate

A mixture of methyl 4-bromobenzoate (21.5 g, 100 mmol), 4-fluorophenylboronic acid (14.7 g, 105 mmol), $Pd(dppf)Cl_2 \cdot CH_2Cl_2$(1.48 g, 2.0 mmol), and 2M $Na_2CO_3$ (100 mL) in toluene (200 mL) and was heated to reflux, stirred for 10 hours, diluted with ethyl acetate (200 mL), washed with water (100 mL) and brine (50 mL), dried ($MgSO_4$), filtered, and concentrated. The concentrate was recrystallized from ethyl acetate/hexanes to provide the desired product. The mother liquor was concentrated and purified by flash column chromatography on silica gel with 10% ethyl acetate/hexanes to provide additional product. MS (DCI) m/e 231 $(M+H)^+$.

EXAMPLE 1B

4'-fluoro(1,1'-biphenyl)-4-carboxylic acid

A room temperature solution of Example 1A (10.0 g, 43.4 mmol) and saturated LiOH (50 mL) in THF (100 mL) was stirred for 16 hours, slowly adjusted to pH 2–4 with 6M HCl, diluted with ethyl acetate (200 mL), washed with water (100 mL) and brine (50 mL), dried ($MgSO_4$), filtered, and concentrated to provide the desired product of sufficient purity for subsequent use. MS (ESI(–)) m/e 215 $(M-H)^-$.

EXAMPLE 1C 4-chloro-3-nitrobenzenesulfonamide

A 0° C. solution of 4-chloro-3-nitrobenzenesulfonyl chloride (12.8 g, 50.0 mmol) in diethyl ether (1 L) was slowly treated with 0° C. concentrated $NH_4OH$ (50 mL) and stirred for 30 minutes. The organic layer was dried ($MgSO_4$), filtered, and concentrated to provide the desired product of sufficient purity for subsequent use.

EXAMPLE 1D 4-chloro-N-((4'-fluoro(1,1'-biphenyl)-4-yl)carbonyl)-3-nitrobenzenesulfonamide A room temperature solution of Example 1B (4.54 g, 21.0 mmol), Example 1C (4.74 g, 20.0 mmol), EDCI (4.80 g, 25.0 mmol), and DMAP (1.23 mg, 10.0 mmol) in dichloromethane (60 mL) was stirred for 16 hours, diluted with ethyl acetate (200 mL), washed sequentially with 1M HCl (50 mL), water (50 mL) and brine (20 mL), dried ($MgSO_4$), filtered, and concentrated. The concentrate was purified by flash column chromatography on silica gel with 50% ethyl acetate/hexanes to provide the desired product. MS (ESI(–)) m/e 433 $(M-H)^-$.

EXAMPLE 1E 4-((2,2-dimethylcyclopentyl)amino)-N-((4'-fluoro(1,1'-biphenyl)-4-yl)carbonyl)-3-nitrobenzenesulfonamide A solution of Example 1D (50 mg, 0.12 mmol) and 2,2-dimethylcyclopentylamine (65 mg, 0.58 mmol) in DMF (2.0 mL) was heated to 120° C. in a sealed vial with shaking for 16 hours. The mixture was concentrated, dissolved in 1:1/DMSO:methanol (1.0 mL) and purified by reverse phase preparative HPLC using 0.1% TFA in $H_2O/CH_3CN$ to provide the desired product. MS (APCI(+)) m/e 529 $(M+NH_4)^+$; $^1H$ NMR (500 MHz, DMSO-$d_6$) δ12.45 (br s, 1H), 8.69 (d, 1H), 8.49 (d, 1H), 7.99 (dd, 1H), 7.97 (d, 2H), 7.80 (2d, 4H), 7.39 (d, 1H), 7.33 (t, 2H), 3.88 (ddd, 1H), 2.28–2.25 (m, 1H), 1.75–1.55 (m, 5H), 1.07 (s, 3H), 1.02 (s, 3H).

EXAMPLE 2

4-(cyclohexylamino)-N-((4'-fluoro(1,1'-biphenyl)-4yl)-carbonyl)-3-nitrobenzenesulfonamide The desired product was prepared by substituting cyclohexylamine for 2,2-dimethylcyclopentylamine in Example 1E. MS (ESI(–)) m/e 496 $(M-H)^-$; $^1H$ NMR (300 MHz, $CDCl_3$) δ8.94 (d, 1H), 8.55 (m, 2H), 8.16 (dd, 1H), 7.83 (d, 2H), 7.62 (d, 2H), 7.55 (m, 5H), 7.16 (m, 2H), 6.98 (d, 1H), 3.60 (br s, 1H), 2.05 (m, 2H), 1.90–1.25 (m, 8H).

EXAMPLE 3

N-((4'-bromo(1,1'-biphenyl)-4-yl)carbonyl)-4-(cyclohexylamino)-3-nitrobenzenesulfonamide

EXAMPLE 3A 4-(cyclohexylamino)-3-nitrobenzenesulfonamide

A room temperature solution of Example 1C (2.36 g, 10.0 mmol) and cyclohexylamine (2.0 mL) in dioxane (5 mL)

EXAMPLE 3B 4-(4,4,5,5-tetramethyl-1,3,2-dioxaborolan-2-yl) benzoic acid

A solution of 4-(dihydroxyboryl)benzoic acid (1.66 g, 10 mmol) and pinacol (12 mmol) in toluene (70 mL) was refluxed in a Dean-Stark apparatus for 16 hours and concentrated. The concentrate was triturated with diethyl ether and filtered to provide the desired product of sufficient purity for subsequent use.

EXAMPLE 3C 4-(cyclohexylamino)-3-nitro-N-(4-(4,4,5,5-tetramethyl-1,3,2-dioxaborolan-2-yl) benzoyl) benzenesulfonamide A room temperature solution of Example 3A (1.24 g, 5.0 mmol), Example 3B (1.50 g, 5.0 mmol), EDCI (1.15 g, 6.0 mmol) and DMAP (124 mg) in dichloromethane (10 mL) was stirred for 16 hours, diluted with ethyl acetate (100 mL), washed sequentially with 1M HCl (20 mL), water (20 mL), and brine (10 mL), dried (MgSO$_4$), filtered, and concentrated. The concentrate was purified by flash column chromatography on silica gel with 50% ethyl acetate/hexanes to provide the desired product. MS (ESI(−)) m/e 528 (M−H)$^-$.

EXAMPLE 3D

N-((4'-bromo(1,1'-biphenyl)-4-yl)carbonyl)-4-(cyclohexylamino)-3-nitrobenzenesulfonamide A mixture of Example 3C (105 mg, 0.2 mmol), 4-bromo-1-iodobenzene (140 mg, 0.5 mmol), Pd$_2$(dba)$_3$ (18 mg, 0.04 mmol), triphenylarsine (36 mg, 0.12 mmol) and 1M Na$_2$CO$_3$ (0.5 mL) in dioxane (4 mL) was heated to 95° C. and stirred for 5 hours. The mixture was diluted with ethyl acetate (50 mL), washed sequentially with 1M HCl (5 mL), water (5 mL), and brine (5 mL), dried (MgSO$_4$), filtered, and concentrated. The concentrate was purified by flash column chromatography on silica gel with 50% ethyl acetate/hexanes to provide the desired product. MS (ESI(−)) m/e 556 (M−H)$^-$; $^1$H NMR (400 MHz, DMSO-d$_6$) δ8.53 (d, 1H), 8.16 (d, 1H), 7.95 (d, 2H), 7.91 (dd, 1H), 7.68–7.60 (m, 5H), 4.12 (d, 1H), 3.67 (m, 1H), 2.00–1.31 (m, 10H).

EXAMPLE 4

4-(cyclohexylamino)-N-(4-(1H-indol-6-yl)benzoyl)-3-nitrobenzenesulfonamide

EXAMPLE 4A 4-(1H-indol-6-yl)benzoic acid

A mixture of 6-bromoindole (480 mg, 2.45 mmol), 4-(dihydroxyboryl)benzoic acid (406 mg, 2.45 mmol), Pd(dppf)Cl$_2$.CH$_2$Cl$_2$ (10 mg, 0.01 mmol), and 2M Na$_2$CO$_3$ (5.6 mL, 11.2 mmol) in a mixture of ethanol (4 mL) and DMF (7 mL) was heated to 100° C., stirred for 16 hours, filtered, and concentrated. The concentrate was dissolved in ethyl acetate, washed sequentially with 1M H$_3$PO$_4$, water, and brine, dried (MgSO$_4$), filtered, and concentrated. The concentrate was purified by flash column chromatography on silica gel with 5% methanol/dichloromethane to provide the desired product. MS (ESI(−)) m/e 236 (M−H)$^-$.

EXAMPLE 4B 4-(cyclohexylamino)-N-(4-(1H-indol-6-yl)benzoyl)-3-nitrobenzenesulfonamide The desired product was prepared by substituting Example 4A and Example 3A for Example 1B and Example 1C, respectively, in Example 1D. MS (ESI(+)) m/e 519 (M+H)$^+$; $^1$H NMR (300 MHz, DMSO-d$_6$) δ8.67 (m, 1H), 7.96 (m, 3H), 7.82 (m, 2H), 7.68 (m, 2H), 7.48 (m, 3H), 6.47 (m, 1H), 1.96 (m, 2H), 1.71 (m, 2H), 1.43 (m, 7H).

EXAMPLE 5

N-(4-(4-tert-butylcyclohexyl)benzoyl)-4-(cyclohexylamino)-3-nitrobenzenesulfonamide

EXAMPLE 5A 4-tert-butyl-1-cyclohexen-1-yl trifluoromethanesulfonate

A −78° C. solution of 4-tert-butylcyclohexanone (1.54 g, 10 mmol) and N-phenyl(trifluoromethanesulfonamide) (3.75 g, 10.5 mmol) in THF (20 mmol) was treated with 1M NaHMDS in THF (11 mL), warmed to room temperature, filtered through a pad of silica gel (10 g) with diethyl ether (5 mL), and concentrated. The concentrate was purified by flash column chromatography on silica gel with 1% ethyl acetate/hexanes to provide the desired product.

EXAMPLE 5B methyl 4-(4-tert-butyl-1-cyclohexen-1-yl)benzoate

A mixture of Example 5A (286 mg, 1.0 mmol), (4-methoxycarbonylphenyl)-boronic acid (216 mg, 1.2 mmol), Pd(dppf)Cl$_2$.CH$_2$Cl$_2$ (37 mg, 0.05 mmol), and cesium fluoride (454 mg, 3.0 mmol) in dioxane (5 mL) was heated to 90° C., stirred for 16 hours, filtered through a pad of silica gel (10 g) with diethyl ether (5 mL) and concentrated. The concentrate was purified by flash column chromatography on silica gel with 5% ethyl acetate/hexanes to provide the desired product.

EXAMPLE 5C methyl 4-(4-tert-butylcyclohexyl)benzoate

A room temperature mixture of Example 5B (230 mg, 0.84 mmol) and 10% Pd/C (100 mg) in ethyl acetate (5 mL) was stirred under a hydrogen atmosphere for 3 hours, filtered through a pad of silica gel (10 g) with diethyl ether (10 mL), and concentrated to provide the desired product as a ~2:1 mixture of diastereomers. MS (DCI) m/e 275 (M+H)$^+$.

EXAMPLE 5D

N-(4-(4-tert-butylcyclohexyl)benzoyl)-4-(cyclohexylamino)-3-nitrobenzenesulfonamide A mixture of Example 5C (55 mg, 0.20 mmol) and 1M LiOH (0.3 mL) in THF (2 mL) was heated to 50° C., stirred for 3 hours, concentrated, dissolved in DMF (0.5 mL), and treated with a mixture of Example 3A (60 mg, 0.20 mmol), EDCI (96 mg, 0.50 mmol), and DMAP (10 mg) in dioxane (2.0 mL). The mixture was stirred for 16 hours, diluted with ethyl acetate (50 mL), washed sequentially with 1M HCl (5 mL), water (5 mL), and brine (5 mL), dried (MgSO$_4$), filtered, and concentrated. The concentrate was purified by flash column chromatography on silica gel, with 50% ethyl acetate/hexanes to provide a ~2:1 mixture of diastereomers. MS (ESI(-)) m/e 540 (M-H)$^-$; $^1$H NMR (400 MHz, DMSO-d$_6$) δ8.63 (2d, 1H total), 8.33 (2d, 1H total), 7.95 (m, 1H), 7.82 and 7.78 (2d, 2H total), 7.45 (m, 1H), 7.30 (m, 2H), 3.71 (m, 1H), 2.28–0.95 (m, 20H), 0.86 and 0.75 (2s, 9H total).

EXAMPLE 6

6-(cyclohexylamino)-N-((4'-fluoro(1,1'-biphenyl)-4-yl)carbonyl)-5-nitro(1,1'-biphenyl)-3-sulfonamide

EXAMPLE 6A 3-bromo-4-(cyclohexylamino)-5-nitrobenzenesulfonamide

A room temperature solution of Example 3A (1.81 g, 6.0 mmol) and 1,3-dibromo-5,5-dimethylhydantoin (950 mg, 3.3 mmol) in dichloromethane was treated with trifluoroacetic acid (796 uL, 9.0 mmol), stirred in darkness for 18 hours, treated with saturated NaHCO$_3$, and extracted with diethyl ether. The combined extracts were washed with brine, dried (Na$_2$SO$_4$), and concentrated. The concentrate was purified by flash column chromatography on silica gel with 15% ethyl acetate/hexanes to provide the desired product. MS (ESI(-)) m/e 376 (M-H)$^-$.

EXAMPLE 6B 6-(cyclohexylamino)-5-nitro(1,1'-biphenyl)-3-sulfonamide

The desired product was prepared by substituting Example 6A and phenylboronic acid for Example 5A and 4-(methoxycarbonylphenyl)boronic acid, respectively, in Example 5B. MS (ESI(-)) m/e 374 (M-H)$^-$.

EXAMPLE 6C 6-(cyclohexylamino)-N-((4'-fluoro(1,1'-biphenyl)-4-yl)carbonyl)-5-nitro(1,1'-biphenyl)-3-sulfonamide The desired product was prepared by substituting Example 6B for Example 1C in Example 1D. MS (ESI(-)) m/e 572 (M-H)$^-$; $^1$H NMR (300 MHz, DMSO-d$_6$) δ8.66 (d, 1H), 7.95 (m, 3H), 7.78 (m, 4H), 7.75 (d, 1H), 7.50 (m, 5H), 7.31 (m, 2H), 1.60–1.41 (m, 4H), 1.32 (m, 2H), 1.12–0.96 (m, 2H), 0.75–0.60 (m, 2H).

EXAMPLE 7

N-((4'-fluoro(1,1'-biphenyl)-4-yl)carbonyl)-3-nitro-4-((trans-2-(phenylsulfanyl)cyclohexyl)amino)benzenesulfonamide

EXAMPLE 7A trans-2-(phenylsulfanyl)cyclohexanol

A room temperature solution of cyclohexene oxide (9.81 g, 100 mmol) and N,N-diisopropylethylamine (2.60 g, 20.0 mmol) in 1,2-dichloroethane (200 mL) was treated with thiophenol (11 g, 100 mmol), stirred for 16 hours, and concentrated. The concentrate was purified by flash column chromatography on silica gel with 20% ethyl acetate/hexanes to provide the desired product.

EXAMPLE 7B ((trans-2-azidocyclohexyl)sulfanyl)benzene

A 0° C. solution of Example 7A (1.04 g, 5.0 mmol), and N,N-diisopropylethylamine (1.1 mL, 6.5 mmol) in dichloromethane (20 mL) was treated with methanesulfonyl chloride (0.46 mL, 6.0 mmol), warmed to room temperature, stirred for 16 hours, diluted with hexanes (20 mL), filtered through a pad of silica gel (15 g) with 10% diethyl ether in hexanes, and concentrated. The concentrate was dissolved in DMF (10 mL), treated with tetrabutylammonium iodide (400 mg, 1.1 mmol), 15-crown-5 (100 mg, 0.40 mmol), and sodium azide (1.0 g, 15.4 mmol), heated to 100° C., and stirred for 16 hours. The mixture was diluted with ethyl acetate (100 mL), washed with water (15 mL) and brine (15 mL), dried (MgSO$_4$), filtered, and concentrated. The concentrate was purified by flash column chromatography on silica gel with 5% ethyl acetate/hexanes to provide the desired product. MS (DCI) m/e 234 (M+H)$^+$.

EXAMPLE 7C trans-2-(phenylsulfanyl)cyclohexanamine

A room temperature solution of Example 7B (777 mg, 3.3 mmol), triphenylphosphine (2.62 g, 10.0 mmol), and water (180 mg, 10 mmol) in THF (5 mL) was stirred for 16 hours and concentrated. The concentrate was purified by flash column chromatography on silica gel with 50% ethyl acetate/hexanes followed by 10% methanol/dichloromethane to provide the desired product. MS (DCI) m/e 208 (M+H)$^+$.

EXAMPLE 7D

N-((4'-fluoro(1,1'-biphenyl)-4-yl)carbonyl)-3-nitro-4-((trans-2-(phenylsulfanyl)cyclohexyl)amino)benzenesulfonamide A solution of Example 7C (50 mg, 0.24 mmol), Example 1D (50 mg, 0.11 mmol) and 2,6-lutidine (50 mg, 0.47 mmol) in dioxane (5 mL) was heated to reflux, stirred for 16 hours, cooled to room temperature, filtered through a pad of silica gel (5 g) with 5% methanol/ethyl acetate, and concentrated. The concentrate was purified by flash column chromatography on silica gel with 30–100% ethyl acetate/hexanes to provide the desired product. MS (ESI(-)) m/e 604 (M-H)$^-$; $^1$H NMR (400 MHz, DMSO-d$_6$) δ8.54 (d, 1H), 8.45 (d, 1H), 7.97 (d, 2H), 7.93 (m, 1H), 7.78 (m, 3H), 7.44–7.10 (m, 9H), 3.85 (m, 1H), 3.61 (m, 1H), 2.15–1.30 (m, 8H).

EXAMPLE 8

N-((4'-fluoro(1,1'-biphenyl)-4-yl)carbonyl)-3-nitro-4-(((1S,2R)-2-(phenylsulfanyl)cyclohexyl)amino)benzenesulfonamide

EXAMPLE 8A (2RS)-2-(phenylsulfanyl)cyclohexanone

A -40° C. solution of 2M oxalyl chloride in dichloromethane (10 mL) in dichloromethane (20 mL) was slowly treated with DMSO (3.12 g, 40 mmol), stirred for 30 minutes, treated with Example 7A (1.80 g, 8.6 mmol), stirred for 1 hour, and treated with triethylamine (10.1 g, 100 mmol). The mixture was warmed to room temperature, stirred for 16 hours, diluted with diethyl ether (100 mL), washed with water (15 mL) and brine (5 mL), dried (MgSO$_4$), filtered, and concentrated. The concentrate was purified by flash column chromatography on silica gel with 10–25% ethyl acetate/hexanes to provide the desired product. MS (DCI/NH$_3$) m/e 224 (M+NH$_4$)$^+$.

EXAMPLE 8B cis-2-(phenylsulfanyl)cyclohexanamine

A room temperature solution of Example 8A (847 mg, 4.1 mmol) and hydroxylamine hydrochloride (1.0 g, 14.4 mmol) in methanol (5 mL) was stirred for 3 hours, diluted with ethyl acetate (50 mL), washed with water (5 mL) and brine (5 mL), dried (MgSO$_4$), filtered, and concentrated. The concentrate was treated with 1M LAH in THF (5 mL, 5.0 mmol), stirred for 16 hours, carefully added to ice cold saturated NaH$_2$PO$_4$ (10 mL), and extracted with ethyl acetate. The combined extracts were washed with brine (20 mL), dried (MgSO$_4$), filtered, and concentrated. The concentrate was purified by flash column chromatography on silica gel with 2–5% methanol/dichloromethane to provide the desired product as a 3.3:1 mixture of cis- and trans-isomers. MS (DCI) m/e 208 (M+H)$^+$.

EXAMPLE 8C

N-((4'-fluoro(1,1'-biphenyl)-4-yl)carbonyl)-3-nitro-4-((cis-2-(phenylsulfanyl)cyclohexyl)amino)benzenesulfonamide Example 8B was processed according to the procedure described in Example 7D to provide a 2:1 mixture of the desired product and Example 7D. MS (ESI(−) m/e 604 (M−H)$^-$; $^1$H NMR (400 MHz, DMSO-d$_6$) δ8.67 (2d, 1H total), 8.56 and 8.49 (2d, 1H total), 7.97 (dt, 1H), 7.91 (dt, 1H), 7.78 (m, 3H), 7.38–7.05 (m, 9H), 4.15 (m, 1H), 3.90 (m, 1H), 2.00–1.20 (m, 8H).

EXAMPLE 9

N-(4-(1-cyclohexen-1-yl)benzoyl)-3-nitro-4-(((1R,2R)-2-(phenylsulfanyl)cyclohexyl)amino)benzenesulfonamide

EXAMPLE 9A methyl 4-(1-cyclohexen-1-yl)benzoate

The desired product was prepared by substituting cyclohexanone for tert-butylcyclohexanone in Examples 5A and 5B. MS (DCI) m/e 217 (M+H$^+$).

EXAMPLE 9B 4-chloro-N-(4-(1-cyclohexen-1-yl)benzoyl)-3-nitrobenzenesulfonamide The desired product was prepared by substituting Example 9A and Example 1C for Example 5C and Example 3A, respectively, in Example 5D. MS (ESI(−)) m/e 419 (M−H)$^-$.

EXAMPLE 9C

N-(4-(1-cyclohexen-1-yl)benzoyl)-3-nitro-4-(((1R,2R)-2-(phenylsulfanyl)cyclohexyl)amino)benzenesulfonamide The desired product was prepared by substituting Example 9B for Example 1D in Example 7D. MS (ESI(−)) m/e 590 (M−H)$^-$; $^1$H NMR (400 MHz, DMSO-d$_6$) δ8.51 (d, 1H), 8.42 (d, 1H), 7.90 (dd, 1H), 7.53 (d, 2H), 7.50 (m, 2H), 7.40 (m, 1H), 7.20–7.09 (m, 5H), 6.32 (m, 1H), 3.85 (m, 1H), 3.61 (m, 1H), 2.40–1.20 (m, 16H).

EXAMPLE 10

N-(4-(1-cyclohexen-1-yl)benzoyl)-3-nitro-4-((cis-2-(phenylsulfanyl)cyclohexyl)amino)benzenesulfonamide The desired product was prepared by substituting Example 9B and Example 8B for Example 1D and Example 7C, respectively, in Example 7D. MS (ESI(−)) m/e 590 (M−H)$^-$; $^1$H NMR (400 MHz, DMSO-d$_6$) δ8.69 (d, 1H), 8.54 (d, 1H), 7.90 (dd, 1H), 7.84 (d, 2H), 7.51 (d, 2H), 7.27 (m, 3H), 7.13–7.00 (m, 3H), 6.33 (m, 1H), 4.15 (m, 1H), 3.90 (m, 1H), 2.39 (m, 2H), 2.20 (m, 2H), 1.95 (m, 2H), 1.90–1.20 (m, 10H).

EXAMPLE 11

4-(((1S,2S)-2-(benzyloxy)cyclohexyl)amino)-N-(4-(1-cyclohexen-1-yl)benzoyl)-3-nitrobenzenesulfonamide The desired product was prepared by substituting Example 9B and (1S,2S)-2-benzyloxycyclohexylamine for Example 1D and Example 7C, respectively, in Example 7D. MS (ESI(−)) m/e 588 (M−H)$^-$; $^1$H NMR (400 MHz, DMSO-d$_6$) δ8.90 (d, 1H), 8.55 (d, 1H), 8.51 (s, 1H), 8.06 (dd, 1H), 7.68 (d, 2H), 7.44 (d, 2H), 7.21 (m, 2H), 7.12 (m, 3H), 6.28 (m, 1H), 4.61 (d, 1H), 4.39 (d, 1H), 3.60 (m, 1H), 3.35 (m, 1H), 2.40 (m, 2H), 2.23 (m, 2H), 1.90–0.80 (m, 12H).

EXAMPLE 12

4-(cycloheptylamino)-N-((4'-fluoro(1,1'-biphenyl)-4-yl)carbonyl)-3-nitrobenzenesulfonamide The desired product was prepared by substituting cycloheptylamine for 2,2-dimethylcyclopentylamine in Example 1E. MS (APCI(+)) m/e 512 (M+H)$^+$; $^1$H NMR (500 MHz, DMSO-d$_6$) δ12.45 (br s, 1H), 8.67 (d, 1H), 8.39 (d, 1H), 7.99 (dd, 1H), 7.95 (d, 2H), 7.78 (2d, 4H), 7.32 (t, 2H), 7.23 (d, 1H), 3.89 (ddddd, 1H), 1.98–1.92 (m, 2H), 1.71–1.52 (m, 10H).

EXAMPLE 13

4-((2RS)-bicyclo(2.2.1)hept-2-ylamino)-N-((4'-fluoro(1,1'-biphenyl)-4-yl)carbonyl)-3-nitrobenzenesulfonamide A solution of Example 1D (50 mg, 0.12 mmol), 2-aminonorbornane hydrochloride (106 mg, 0.58 mmol), and triethylamine (0.08 ml, 0.58 mmol) in DMF (2 mL) were heated to 120° C. in a sealed vial with shaking for 16 hours, then concentrated. The concentrate was dissolved in 1:1/DMSO:methanol (1.0 ml) and purified by reverse phase preparative HPLC with 0.1% TFA in H$_2$O/CH$_3$CN to provide the desired product. MS (APCI(+)) m/e 510 (M+H)$^+$; $^1$H NMR (500 MHz, DMSO-d$_6$) δ12.45 (br s, 1H), 8.67 (d, 1H), 8.48 (d, 1H), 7.99 (dd, 1H), 7.95 (d, 2H), 7.78 (2d, 4H), 7.32 (t, 2H), 7.24 (d, 1H), 4.04 (m, 1H), 2.58 (m, 1H), 2.27 (m, 1H), 2.24–2.21 (m, 1H), 1.59–1.29 (m, 6H), 0.97 (dt, 1H).

EXAMPLE 14

N-((4'-fluoro(1,1'-biphenyl)-4-yl)carbonyl)-3-nitro-4-(((1R,2R,3R,5S)-2,6,6-trimethylbicyclo(3.1.1)hept-3-yl)amino)benzenesulfonamide The desired product was prepared by substituting (1R,2R,3R,5S)-(−)-isopinocampheylamine for 2,2- dimethylcyclpentylamine in Example 1E. MS (APCI(+)) m/e 552 (M+H)+; $^1$H NMR (500 MHz, DMSO-d$_6$) δ12.45 (br s, 1H), 8.68 (d, 1H), 8.38 (d, 1H), 7.98 (dd, 1H), 7.96 (d, 2H), 7.79 (2d, 4H), 7.37 (d, 1H), 7.32 (t, 2H), 4.07–4.01 (m, 1H), 2.76–2.71 (m, 1H), 2.42–2.37 (m, 1H), 2.11–2.08 (m, 1H), 1.98–1.96 (m, 1H), 1.95–1.86 (m, 1H), 1.67–1.63 (m, 1H), 1.24 (s, 3H), 1.13 (d, 3H), 1.08 (s, 3H), 1.07 (s, 1H).

EXAMPLE 15

N-((4'-fluoro(1,1'-biphenyl)-4-yl)carbonyl)-3-nitro-4-(((1R,2R,4R)-1,7,7-trimethylbicyclo(2.2.1)hept-2-yl)amino)benzenesulfonamide The desired product was prepared by substituting (R)-(+)-bornylamine for 2,2-dimethylcyclopentylamine in Example 1E. MS (APCI(+)) m/e 569 (M+NH$_4$)+; $^1$H NMR (500 MHz, DMSO-d$_6$) δ12.55 (br s, 1H), 8.73 (d, 1H), 8.70 (d, 1H), 7.98 (dd, 1H), 7.97 (d, 2H), 7.80 (2d, 4H), 7.34 (t, 2H), 7.31 (d, 1H), 3.98–3.95 (m, 1H), 2.58–2.54 (m, 1H), 1.82–1.68 (m, 3H), 1.58–1.51 (m, 1H), 1.29–1.25 (m, 1H), 1.02 (s, 3H), 0.98 (dd, 1H), 0.94 (s, 3H), 0.90 (s, 3H).

EXAMPLE 16

N-((4'-fluoro(1,1'-biphenyl)-4-yl)carbonyl)-3-nitro-4-(((1S,2S,4S)-1,7,7-trimethylbicyclo(2.2.1)hept-2-yl)amino)benzenesulfonamide (S)-(−)-Bornylamine was processed according to the procedure described in Example 1E to provide the desired product. MS (DCI/NH$_3$) m/e 569 (M+NH$_4$)+; $^1$H NMR (500 MHz, DMSO-d$_6$) δ12.45 (br s, 1H), 8.71 (d, 1H), 8.67 (t, 1H), 7.98 (dd, 1H), 7.95 (d, 2H), 7.78 (2d, 4H total), 7.32 (t, 2H), 7.28 (2d, 1H total), 3.97–3.91 and 3.70–3.66 (2m, 1H total), 2.56–2.50 (m, 1H), 2.06–0.95 (m, 6H), 1.01 and 1.00 (2s, 3H total), 0.95 and 0.91 (2s, 3H total), 0.88 and 0.87 (2s, 3H total).

EXAMPLE 17

N-(4-(2-methyl-1,3-benzothiazol-5-yl)benzoyl)-3-nitro-4-(((1S,2S,4S)-1,7,7-trimethylbicyclo(2.2.1)hept-2-yl)amino)benzenesulfonamide

EXAMPLE 17A 4-(2-methyl-1,3-benzothiazol-5-yl)benzoic acid

The desired product was prepared by substituting 5-bromo-2-methyl-1,3-benzothiazole for 6-bromoindole in Example 4A. MS (DCI) m/e 270 (M+H)+.

EXAMPLE 17B 3-nitro-4-(((1S,2S,4S)-1,7,7-trimethylbicyclo(2.2.1)hept-2-yl)amino)benzenesulfonamide The desired product was prepared by substituting (S)-(−)-bornylamine for cyclohexylamine in Example 3A. MS (ESI(−)) m/e 352 (M−H)−;

EXAMPLE 17C

N-(4-(2-methyl-1,3-benzothiazol-5-yl)benzoyl)-3-nitro-4-(((1S,2S,4S)-1,7,7-trimethylbicyclo(2.2.1)hept-2-yl)amino)benzenesulfonamide The desired product was prepared by substituting Example 17A and Example 17B for Example 1B and Example 1C, respectively, in Example 1D. MS (ESI(−)) m/e 603 (M−H)−; $^1$H NMR (300 MHz, DMSO-d$_6$) δ8.72 (d, 1H), 8.68 (d, 1H), 8.26 (d, 1H), 8.14 (d, 1H), 7.98 (m, 3H), 7.89 (d, 2H), 7.77 (dd, 1H), 7.30 (d, 1H), 3.94 (m, 1H), 2.82 (s, 3H), 1.82–1.64 (m, 3H), 1.54 (m, 1H), 1.25 (m, 2H), 1.00 (s, 3H), 0.92 (m, 1H), 0.91 (s, 3H), 0.89 (s, 3H).

EXAMPLE 18

4-(1-adamantylamino)-N-((4'-fluoro(1,1'-biphenyl)-4-yl)carbonyl)-3-nitrobenzenesulfonamide The desired product was prepared by substituting 1-adamantanamine for 2,2-dimethylcyclopentylamine in Example 1E. MS (APCI(+)) m/e 550 (M+H)+; $^1$H NMR (500 MHz, DMSO-d$_6$) δ12.45 (br s, 1H), 8.68 (d, 1H), 8.48 (s, 1H), 7.96 (d, 2H), 7.95 (dd, 1H), 7.78 (2d, 4H), 7.58 (d, 1H), 7.32 (t, 2H), 2.13–2.08 (m, 9H), 1.76–1.60 (m, 6H).

EXAMPLE 19

N-((4'-fluoro(1,1'-biphenyl)-4-yl)carbonyl)-3-nitro-4-(2-phenoxyanilino)benzenesulfonamide

EXAMPLE 19A 3-nitro-4-(2-phenoxyanilino)benzenesulfonamide

A −78° C. solution of Example 1C (236 mg, 1.0 mmol) and 2-phenoxyaniline (370 mg, 2.0 mmol) in THF (10 mL) was treated with 1M lithium hexamethyldisilazide in THF (4 mL, 4.0 mmol), warmed to room temperature over 4 hour, diluted with ethyl acetate (50 mL), washed sequentially with 1M HCl (5 mL), water (5 mL), and brine (5 mL), dried (MgSO$_4$), filtered, and concentrated. The concentrate was purified by flash column chromatography on silica gel with 10–30% ethyl acetate/hexanes to provide the desired product. MS (ESI(−)) m/e 384 (M−H)−.

EXAMPLE 19B

N-((4'-fluoro(1,1'-biphenyl)-4-yl)carbonyl)-3-nitro-4-(2-phenoxyanilino)benzenesulfonamide The desired product was prepared by substituting Example 19A for Example 1C in Example 1D. MS (ESI(−)) m/e 582 (M−H)−; $^1$H NMR (400 MHz, DMSO-d$_6$) δ9.74 (s, 1H), 8.63 (d, 1H), 7.97 (m, 3H), 7.79 (m, 4H), 7.52 (dd 1H), 7.40–7.20 (m, 6H), 7.14–7.00 (m, 3H), 6.83 (m, 2H).

EXAMPLE 20

N-((4'-fluoro(1,1'-biphenyl)-4-yl)carbonyl)-3-nitro-4-(2-(phenylsulfanyl)anilino)benzenesulfonamide

EXAMPLE 20A 2-(phenylsulfanyl)aniline

A room temperature solution of 2-fluoronitrobenzene (1.41 g, 10.0 mmol), thiophenol (1.21 g, 11.0 mmol), and triethylamine (2 mL) in THF (20 mL) was stirred for 16 hours, treated with 3M HCl (10 mL) and tin(II) chloride dihydrate (11.4 g, 50 mmol), stirred for 4 hour, and extracted with ethyl acetate (50 mL). The combined extracts were dried (MgSO$_4$), filtered, and concentrated. The concentrate was purified by flash column chromatography on silica gel with 50% hexanes/dichloromethane to provide the desired product. MS (DCI) m/e 202 (M+H)+.

EXAMPLE 20B 3-nitro-4-(2-(phenylsulfanyl)anilino)benzenesulfonamide

The desired product was prepared by substituting Example 20A for 2-phenyoxyaniline in Example 19A. MS (ESI(−)) m/e 400 (M−H)−.

EXAMPLE 20C

N-((4'-fluoro(1,1'-biphenyl)-4-yl)carbonyl)-3-nitro-4-(2-(phenylsulfanyl)anilino)benzenesulfonamide The desired product was prepared by substituting Example 20B for Example 1C in Example 1D. MS (ESI(−)) m/e 598 (M−H)−; $^1$H NMR (400 MHz, DMSO-d$_6$) δ 9.91 (s, 1H), 8.68 (d, 1H), 7.97 (d, 2H), 7.93 (dd, 1H), 7.81 (m, 4H), 7.49 (m, 2H), 7.41–7.23 (m, 8H), 7.17 (m, 1H), 6.97 (d, 1H).

EXAMPLE 21

4-((cyclohexylmethyl)amino)-N-((2'-methoxy(1,1'-biphenyl)-4-carbonyl)-3-nitrobenzenesulfonamide

EXAMPLE 21A

2'-methoxy(1,1'-biphenyl)-4-carboxylic acid

The desired product was prepared by substituting 2-methoxyphenylboronic acid for 4-methoxyphenylboronic acid in Example 31A. MS (APCI(+)) m/e 246 (M+NH$_4$)+; $^1$H NMR (500 MHz, DMSO-$_6$) δ 12.89 (br s, 1H), 7.96 (d, 2H), 7.60 (d, 2H), 7.39 (ddd, 1H), 7.33 (dd, 1H), 7.14 (dd, 1H), 7.05 (dt, 1H), 3.78 (s, 3H).

EXAMPLE 21B 4-((cyclohexylmethyl)amino)-3-nitrobenzenesulfonamide

The desired product was prepared by substituting cyclohexylmethylamine for cyclohexylamine in Example 3A. MS (DCI) m/e 314 (M+H)+.

EXAMPLE 21C 4-((cyclohexylmethyl)amino)-N-((2'-methoxy(1,1'-biphenyl)-4-yl)carbonyl)-3-nitrobenzenesulfonamide The desired product was prepared by substituting Example 21A and Example 21B for Example 1B and Example 1C, respectively, in Example 1D. MS (APCI(+)) m/e 524 (M+H)+; $^1$H NMR (500 MHz, DMSO-d$_6$) δ 12.45 (br s, 1H), 8.66 (d, 1H), 8.63 (t, 1H), 7.96 (dd, 1H), 7.90 (d, 2H), 7.57 (d, 2H), 7.38 (dt, 1H), 7.31 (dd, 1H), 7.26 (d, 1H), 7.13 (d, 1H), 7.04 (t, 1H), 3.76 (s, 3H), 3.36–3.26 (m, 2H), 1.76–1.61 (m, 6H), 1.23–1.12 (m, 3H), 1.04–0.96 (m, 2H).

EXAMPLE 22

4-((cyclohexylmethyl)amino)-N-((4'-fluoro(1,1'-biphenyl)-4-yl)carbonyl)-3-nitrobenzenesulfonamide The desired product was prepared by substituting Example 21B for Example 1C in Example 1D. MS (ESI(−)) m/e 510 (M−H)−; $^1$H NMR (300 MHz, DMSO-d$_6$) δ 8.68 (d, 1H); 7.94 (m, 3H), 7.82–7.74 (m, 4H), 7.36–7.26 (m, 3H), 3.16 (t, 1H), 1.80–1.50 (m, 6H), 1.30–0.90 (m, 6H).

EXAMPLE 23

N-((4'-chloro-3'-(trifluoromethoxy)(1,1'-biphenyl)-4-yl)carbonyl)-4-((cyclohexylmethyl)amino)-3-nitrobenzenesulfonamide

EXAMPLE 23A 4-bromo-1-chloro-2-(trifluoromethoxy)benzene

A mixture of tert-butyl nitrite (1.78 mL, 15.0 mmol), copper (II) chloride (1.61 g, 12.0 mmol) and 4-bromo-2-(trifluoromethoxy)aniline (2.56 g, 10.0 mmol) in acetonitrile (40 mL) was heated to 70° C., stirred for 3 hours, cooled to room temperature, poured into 0.5M HCl, and extracted with diethyl ether. The combined extracts were washed with water and brine, dried (MgSO$_4$), filtered, and concentrated to provide the desired product. MS (ESI(+)) m/e 275 (M+H)+.

EXAMPLE 23B

4'-chloro-3'-(trifluoromethoxy)(1,1'-biphenyl)-4-carboxylic acid

The desired product was prepared by substituting Example 23A for 6-bromoindole in Example 4A. MS (ESI(−)) m/e 315 (M−H)−.

EXAMPLE 23C

N-((4'-chloro-3'-(trifluoromethoxy)(1,1'-biphenyl)-4-yl)carbonyl)-4-((cyclohexylmethyl)amino)-3-nitrobenzenesulfonamide The desired product was prepared by substituting Example 23B and Example 21B for Example 1B and Example 1C, respectively, in Example 1D. MS (ESI(−)) m/e 610 (M−H)−; $^1$H NMR (300 MHz, DMSO-d$_6$) δ 8.66 (m, 2H), 7.92 (m, 7H), 7.27 (m, 1H), 3.32 (m, 2H), 1.70 (m, 6H), 1.19 (m, 3H), 1.02 (m, 2H).

EXAMPLE 24

4-((cyclohexylmethyl)amino)-N-(4-(1H-indol-6-yl)benzoyl)-3-nitrobenzenesulfonamide The desired product was prepared by substituting Example 4A and Example 21B for Example 1B and Example 1C in Example 1D. MS (ESI(−)) m/e 531 (M−H)−; $^1$H NMR (300 MHz, DMSO-d$_6$) δ 8.64 (m, 1H), 7.95 (m, 3H), 7.78 (m, 2H), 7.70 (m, 1H), 7.63 (m, 1H) 7.42 (m, 1H), 7.38 (m, 1H), 7.24 (m, 1H), 6.48 (m, 1H), 3.23 (m, 2H), 1.70 (m, 8H), 1.21 (m, 1H), 1.01 (m, 2H).

EXAMPLE 25

4-((cyclohexylmethyl)amino)-N-(4-(2-methyl-1,3-benzothiazol-5-yl)benzoyl)-3-nitrobenzenesulfonamide The desired product was prepared by substituting Example 17A and Example 21B for Example 1B and Example 1C, respectively, in Example 1D. MS (ESI(−)) m/e 563 (M−H)−; $^1$H NMR (400 MHz, DMSO-d$_6$) δ 8.69 (d, 1H), 8.65 (t, 1H), 8.26 (s, 1H), 8.14 (d, 1H), 7.98 (m, 3H), 7.90 (d, 2H), 7.77 (dd, 1H), 7.28 (d, 1H), 3.30 (t, 2H), 2.82 (s, 3H), 1.80–1.60 (m, 6H), 1.40–0.95 (m, 5H).

EXAMPLE 26

4-((cyclohexylmethyl)amino)-N-((4'-fluoro(1,1'-biphenyl)-4-yl)carbonyl)-3-nitro-5-(2-pyrimidinyl)benzenesulfonamide

EXAMPLE 26A 3-bromo-4-((cyclohexylmethyl)amino)-5-nitrobenzenesulfonamide

The desired product was prepared by substituting Example 21B for Example 3A in Example 6A. MS (ESI(+)) m/e 392 (M+H)+.

EXAMPLE 26B 4-((cyclohexylmethyl)amino)-3-nitro-5-(2-pirimidinyl)benzenesulfonamide A solution of Example 26A (270 mg, 0.69 mmol), 2-(tributylstannyl)pyrimidine (305 uL, 0.83 mmol), Pd$_2$ (dba)$_3$ (32 mg, 0.034 mmol), and tris-(2-furyl)phosphine (32 mg, 0.10 mmol) in acetonitrile (2 mL) was heated to reflux for 48 hours and concentrated. The concentrate was purified by flash column chromatography on silica gel with 50% ethyl acetate/hexanes to provide the desired product. MS (ESI(+)) m/e 392 (M+H)$^+$.

EXAMPLE 26C 4-((cyclohexylmethyl)amino)-N-((4'-fluoro(1,1'-biphenyl)-4-yl)carbonyl)-3-nitro-5-(2-pyrimidinyl)benzenesulfonamide The desired product was prepared by substituting Example 26B for Example 1C in Example 1D. MS (ESI(+)) m/e 590 (M+H)$^+$; $^1$H NMR (300 MHz, DMSO-d$_6$) δ8.04–7.90 (m, 4H); 7.82–7.70 (m, 6H), 7.31 (m, 2H), 7.05 (dd, 1H), 2.73 (t, 2H), 1.70–1.53 (m, 6H), 1.52 (m, 1H), 1.16–1.07 (m, 2H), 0.92–0.79 (m, 2H).

EXAMPLE 27

N-((4'-fluoro(1,1'-biphenyl)-4-yl)carbonyl)-3-nitro-4-(((cis-2-(phenylsulfanyl)cyclohexyl)methyl)amino)benzenesulfonamide

EXAMPLE 27A

N-((4'-fluoro(1,1'-biphenyl)-4-yl)carbonyl)-4-(((trans-2-hydroxycyclohexyl)methyl)amino)-3-nitrobenzenesulfonamide The desired product was prepared by substituting Example 1D and trans-2-methyl-aminocyclohexanol for Example 1C and cyclohexylamine, respectively, in Example 3A. MS (ESI(+)) m/e 528 (M+H)$^+$.

EXAMPLE 27B

N-((4'-fluoro(1,1'-biphenyl)-4-yl)carbonyl)-3-nitro-4-(((cis-2-(phenylsulfanyl)cyclohexyl)methyl)amino)benzenesulfonamide A room temperature solution of tri-n-butylphosphine (90 μL, 0.36 mmol) and 1,1'-(azodicarbonyl)dipiperidine (91 mg, 0.36 mmol) in THF (4 mL) was treated with Example 27A (90 mg, 0.17 mmol) and thiophenol (21 mg, 0.19 mmol), stirred for 18 hours, and concentrated. The concentrate was purified by flash column chromatography on silica gel with 50% ethyl acetate/hexanes to provide the desired product. MS (ESI(–)) m/e 618 (M–H)$^-$; $^1$H NMR (300 MHz, DMSO-d$_6$) δ8.61 (d, 1H), 7.94 (m, 2H), 7.90 (d, 1H), 7.73 (m, 2H), 7.68–7.55 (m, 7H), 7.29 (d, 2H), 6.87 (d, 1H), 3.44 (m, 2H), 1.59 (m, 4H), 1.37 (m, 4H), 0.89 (m, 2H).

EXAMPLE 28

4-((1-adamantylmethyl)amino)-N-(4-iodobenzoyl)-3-nitrobenzenesulfonamide

EXAMPLE 28A 4-((1-adamantylmethyl)amino)-N-(4-iodobenzoyl)-3-nitrobenzenesulfonamide The desired product was prepared by substituting 1-adamantylmethylamine for cyclohexylamine in Example 3A. MS (DCI) m/e 366 (M+H)$^+$.

EXAMPLE 28B 4-((1-adamantylmethyl)amino)-N-(4-iodobenzoyl)-3-nitrobenzenesulfonamide The desired product was prepared by substituting 4-iodobenzoic acid and Example 28A for Example 1B and Example 1C, respectively, in Example 1D. MS (ESI(–)) m/e 594 (M–H)$^-$; $^1$H NMR (300 MHz, DMSO-d$_6$) δ8.51 (d, 1H), 8.40 (t, 1H), 7.87 (dd, 1H), 7.72–7.62 (q, 4H), 7.16 (d, 1H), 3.12 (d, 2H), 1.97 (m, 2H), 1.72–1.54 (m, 13H).

EXAMPLE 29

4-((1-adamantylmethyl)amino)-N-(4-(2-chloro-3-thienyl)benzoyl)-3-nitrobenzenesulfonamide

EXAMPLE 29A 4-(2-chloro-3-thienyl)-benzoic acid

Solid Pd(PPh$_3$)$_4$ (11.0 mg, 0.01 mmol) was treated with a room temperature solution of 2-bromo-5-chlorothiophene (143 mg, 0.72 mmol) in DME (4 mL), stirred for 5 minutes, treated with a solution of 4-(dihydroxyboryl)benzoic acid (100 mg, 0.60 mmol) in DME (2 mL), and stirred for 5 minutes. The mixture was treated with 2M Na$_2$CO$_3$ (1.5 mL, 3.0 mmol), heated to 75° C., stirred for 18 hours, cooled to room temperature, filtered, triturated with water (3 mL), and concentrated. The concentrate was treated with boiling water (4 mL), filtered through celite, cooled to room temperature, adjusted to pH<7 with HCl, and filtered to provide the desired product. MS (APCI(+)) m/e 239 (M+H)$^+$.

EXAMPLE 29B 4-((1-adamantylmethyl)amino)-N-(4-(2-chloro-3-thienyl)benzoyl)-3-nitrobenzenesulfonamide A room temperature mixture of Example 29A (39.4 mg, 0.17 mmol), resin-bound dicyclohexylcarbodiimide (225.0 mg, 1.83 mmol/g), and dimethylaminopyridine (60.0 mg, 4.95 mmol) was treated with a solution of Example 28A (40 mg, 0.11 mmol) in a 1:1 mixture of 1,2-dichloroethane and 2-methyl-2-propanol (3 mL), and agitated overnight on an Argonaut Technologies Quest 210. The mixture was treated with resin bound p-TsOH (990 mg, 1.44 mmol/g), agitated for 1 hour, decanted, and washed with dichloromethane. The combined extracts were concentrated and purified by HPLC using 0.1% TFA in H$_2$O/CH$_3$CN to provide the desired product. MS (APCI(+)) m/e 586 (M+H)$^+$; $^1$H NMR (500 MHz, DMSO-d$_6$) δ12.50 (s, 1H), 8.66 (d, 1H), 8.57 (t, 1H), 7.96 (d, 2H), 7.95 (dd, 1H), 7.71 (d, 2H), 7.59 (d, 1H), 7.36 (d, 1H), 7.29 (d, 1H), 7.29 (d, 1H), 3.17 (d, 2H), 1.97 (s, 3H), 1.58 (m, 12H).

EXAMPLE 30

4-((1-adamantylmethyl)amino)-N-((1,1'-biphenyl)-4-ylcarbonyl)-3-nitrobenzenesulfonamide The desired product was prepared by substituting (1,1'-biphenyl)carboxylic acid for Example 29A in Example 29B. MS (APCI(+)) m/e 546 (M+H)$^+$; $^1$H NMR (500 MHz, DMSO-d$_6$) δ12.46 (s, 1H), 8.68 (d, 1H), 8.58 (t, 1H), 7.96 (d, 2H), 7.95 (dd, 1H), 7.80 (d, 2H), 7.73 (d, 2H), 7.50 (t, 2H), 7.42 (t, 1H), 7.37 (d, 1H), 3.17 (m, 2H), 1.97 (s, 3H), 1.58 (m, 12H).

EXAMPLE 31

4-((1-adamantylmethyl)amino)-N-((4'-methyl(1,1'-biphenyl)-4-yl)carbonyl)-3-nitrobenzenesulfonamide

EXAMPLE 31A

4'-methyl(1,1'-biphenyl)-4-carboxylic acid

A room temperature solution of ethyl 4-bromobenzoate (0.70 mL, 4.3 mmol) in DME (20 mL) was treated with Pd(PPh$_3$)$_4$ (246 mg, 0.2 mmol), stirred for 5 minutes, treated with a solution of 4-methylphenylboronic acid (870 mg, 6.4 mmol) in ethanol (10 mL), stirred for 5 minutes, treated with 2M Na$_2$CO$_3$ (18.0 mL, 36.0 mmol), heated to reflux, stirred for 16 hours, and concentrated. The concentrate was dissolved in water (75 mL) and diethyl ether (50 mL), filtered through celite, and extracted with diethyl ether. The combined extracts were washed with brine, dried (MgSO$_4$), filtered, and concentrated. The concentrate was purified by flash column chromatography on silica gel with 33% acetone/hexanes. The resulting product was dissolved in methanol (10 mL) and THF (5 mL), treated with 1M NaOH (4.3 mL, 4.3 mmol), stirred for 48 hours, concentrated, dissolved in water (10 mL), adjusted to pH 1 with 12M HCl, and filtered. Recrystallization from ethyl acetate provided the desired product. MS (APCI(+)) m/e 213 (M+H)$^+$.

EXAMPLE 31B 4-((1-adamantylmethyl)amino)-N-((4'-methyl(1,1'-biphenyl)-4-yl)carbonyl)-3-nitrobenzenesulfonamide The desired product was prepared by substituting Example 31A for Example 29A in Example 29B. MS (APCI(+)) m/e 560 (M+H)$^+$; $^1$H NMR (500 MHz, DMSO-d$_6$) δ12.44 (s, 1H), 8.67 (d, 1H), 8.57 (t, 1H), 7.95 (dd, 1H), 7.94 (d, 2H), 7.77 (d, 2H), 7.63 (d, 2H), 7.36 (d, 1H), 7.30 (d, 2H), 3.17 (d, 2H), 2.35 (s, 3H), 1.97 (s, 3H), 1.58 (m, 12H).

EXAMPLE 32

4-((1-adamantylmethyl)amino)-N-((4'-ethyl(1,1'-biphenyl)-4-yl)carbonyl)-3-nitrobenzenesulfonamide

EXAMPLE 32A

4'-ethyl(1,1'-biphenyl)-4-carboxylic acid

The desired product was prepared by substituting 1-bromo-4-ethylbenzene for 2-bromo-5-chlorothiophene in Example 29A. MS (APCI(−)) m/e 225 (M−H)$^-$.

EXAMPLE 32B 4-((1-adamantylmethyl)amino)-N-((4'-ethyl(1,1'-biphenyl)-4-yl)carbonyl)-3-nitrobenzenesulfonamide The desired product was prepared by substituting Example 32A for Example 29A in Example 29B. MS (APCI(+)) m/e 574 (M+H)$^+$; $^1$H NMR (500 MHz, DMSO-d$_6$) δ12.45 (s, 1H), 8.67 (d, 1H), 8.57 (t, 1H), 7.95 (dd, 1H), 7.94 (d, 2H), 7.77 (d, 2H), 7.65 (d, 2H), 7.36 (d, 1H), 7.32 (d, 2H), 3.17 (d, 2H), 2.65 (q, 2H), 1.97 (s, 3H), 1.58 (m, 12H), 1.20 (t, 3H).

EXAMPLE 33

4-((1-adamantylmethyl)amino)-3-nitro-N-((4'-propyl(1,1'-biphenyl)-4-yl)carbonyl)benzenesulfonamide

EXAMPLE 33A

4'-propyl(1,1'-biphenyl)-4-carboxylic acid

The desired product was prepared by substituting 1-bromo-4-propylbenzene for 2-bromo-5-chlorothiophene in Example 29A. MS (APCI(−)) m/e 239 (M−H)$^-$.

EXAMPLE 33B 4-((1-adamantylmethyl)amino)-3-nitro-N-((4'-propyl(1,1'-biphenyl)-4-yl)carbonyl)benzenesulfonamide The desired product was prepared by substituting Example 33A for Example 29A in Example 29B. MS (APCI(+)) m/e 588 (M+H)$^+$; $^1$H NMR (500 MHz, DMSO-d$_6$) δ12.43 (s, 1H), 8.67 (d, 1H), 8.57 (t, 1H), 7.95 (dd, 1H), 7.94 (d, 2H), 7.77 (d, 2H), 7.64 (d, 2H), 7.36 (d, 1H), 7.30 (d, 2H), 3.18 (d, 2H), 2.60 (t, 2H), 1.97 (s, 3H), 1.58 (m, 14H), 0.90 (t, 3H).

EXAMPLE 34

4-((1-adamantylmethyl)amino)-N-((3'-chloro(1,1'-biphenyl)-4-yl)carbonyl)-3-nitrobenzenesulfonamide

EXAMPLE 34A

3'-chloro-1,1'-biphenyl-4-carboxylic acid

The desired product was prepared by substituting 3-chlorophenylboronic acid for 4-methylphenylboronic acid in Example 31A.

EXAMPLE 34B 4-((1-adamantylmethyl)amino)-N-((3'-chloro(1,1'-biphenyl)-4-yl)carbonyl)-3-nitrobenzenesulfonamide The desired product was prepared by substituting Example 34A for Example 29A in Example 29B. MS (APCI(+)) m/e 580 (M+H)$^+$; $^1$H NMR (500 MHz, DMSO-d$_6$) δ8.67 (d, 1H), 8.57 (t, 1H), 8.57 (t, 1H), 7.96 (d, 2H), 7.95 (d, 1H), 7.83 (d, 2H), 7.80 (t, 1H), 7.70 (dt, 1H), 7.50 (m, 2H), 7.36 (d, 1H), 3.18 (m, 2H), 1.97 (s, 3H), 1.58 (m, 12H).

EXAMPLE 35

N-((3'-acetyl(1,1'-biphenyl)-4-yl)carbonyl)-4-((1-adamantylmethyl)amino)-3-nitrobenzenesulfonamide

EXAMPLE 35A

3'-acetyl(1,1'-biphenyl)-4-carboxylic acid

The desired product was prepared by substituting 1-(3-bromophenyl)ethanone for 2-bromo-5-chlorothiophene in Example 29A. MS (APCI(−)) m/e 239 (M−H)$^-$.

EXAMPLE 35B

N-((3'-acetyl(1,1'-biphenyl)-4-yl)carbonyl)-4-((1-adamantylmethyl)amino)-3-nitrobenzenesulfonamide The desired product was prepared by substituting Example 35A for Example 29A in Example 29B. MS (APCI(+)) m/e 588 (M+H)$^+$; $^1$H NMR (500 MHz, DMSO-d$_6$) δ8.68 (d, 1H), 8.57 (t, 1H), 8.24 (t, 1H), 7.99 (d, 4H), 7.95 (dd, 1H), 7.88 (d, 2H), 7.64 (t, 1H), 7.36 (d, 1H),), 3.17 (m, 2H), 2.66 (s, 3H), 1.97 (s, 3H), 1.58 (m, 12H).

EXAMPLE 36

4-((1-adamantylmethyl)amino)-N-((4'-chloro(1,1'-biphenyl)-4-yl)carbonyl)-3-nitrobenzenesulfonamide

EXAMPLE 36A

4'-chloro(1,1'-biphenyl)-4-carboxylic acid

The desired product was prepared by substituting 4-chlorophenylboronic acid for 4-methylphenylboronic acid in Example 31A. MS (APCI(−)) m/e 231 (M−H)$^-$.

EXAMPLE 36B 4-((1-adamantylmethyl)amino)-N-((4'-chloro(1,1'-biphenyl)-4-yl)carbonyl)-3-nitrobenzenesulfonamide The desired product was prepared by substituting Example 36A for Example 29A in Example 29B. MS (APCI(+)) m/e 580 (M+H)$^+$; $^1$H NMR (500 MHz, DMSO-d$_6$) δ8.67 (d, 1H), 8.57 (t, 1H), 7.95 (m, 3H), 7.80 (d, 2H), 7.77 (d, 2H), 7.54 (d, 2H), 7.36 (d, 1H), 3.17 (d, 2H), 2.66 (s, 3H), 1.97 (s, 3H), 1.58 (m, 12H).

EXAMPLE 37

4-((1-adamantylmethy)amino)-N-((3',4'-dichloro(1,1'-biphenyl)-4-yl)carbonyl)-3-nitrobenzenesulfonamide

EXAMPLE 37A

3',4'-dichloro(1,1'-biphenyl)-4-carboxylic acid

The desired product was prepared by substituting 4-bromo-1,2-dichlorobenzene for 2-bromo-5-chlorothiophene in Example 29A. MS (APCI(−)) m/e 265 (M−H)$^+$.

EXAMPLE 37B 4-((1-adamantylmethyl)amino)-N-((3',4'-dichloro(1,1'-biphenyl)-4-yl)carbonyl)-3-nitrobenzenesulfonamide The desired product was prepared by substituting Example 37A for Example 29A in Example 29B. MS (APCI(+)) m/e 614 (M+H)$^+$; $^1$H NMR (500 MHz, DMSO-d$_6$) δ8.67 (d, 1H), 8.57 (t, 1H), 7.94 (m, 3H), 7.85 (d, 2H), 7.74 (m, 2H), 7.36 (d, 1H), 3.17 (d, 2H), 1.97 (s, 3H), 1.58 (m, 12H).

EXAMPLE 38

4-((1-adamantylmethyl)amino)-N-((4'-methoxy(1,1'-biphenyl)-4-yl)carbonyl)-3-nitrobenzenesulfonamide

EXAMPLE 38A

4'-methoxy(1,1'-biphenyl)-4-carboxylic acid

The desired product was prepared by substituting 1-bromo-4-methoxybenzene for 2-bromo-5-chlorothiophene in Example 29A. MS (APCI(−)) m/e 227 (M−H)$^-$.

EXAMPLE 38B 4-((1-adamantylmethyl)amino)-N-((4'-methoxy(1,1'-biphenyl)-4-yl)carbonyl)-3-nitrobenzenesulfonamide The desired product was prepared by substituting Example 38A for Example 29A in Example 29B. MS (APCI(+)) m/e 576 (M+H)$^+$; $^1$H NMR (500 MHz, DMSO-d$_6$) δ8.67 (d, 1H), 8.57 (t, 1H), 7.94 (dd, 1H), 7.92 (d, 2H), 7.74 (d, 2H), 7.69 (d, 2H), 7.36 (d, 1H), 7.00 (d, 2H), 3.80 (s, 3H), 3.18 (d, 2H), 1.97 (s, 3H), 1.58 (m, 12H).

EXAMPLE 39

4-((1-adamantylmethyl)amino)-N-((4'-fluoro(1,1'-biphenyl)-4-yl)carbonyl)-3-nitrobenzenesulfonamide The desired product was prepared by substituting 1-adamantanemethylamine for 2,2-dimethylcyclopentylamine in Example 1E. MS (APCI(+)) m/e 581 (M+NH$_4$)$^+$; $^1$H NMR (500 MHz, DMSO-d$_6$) δ12.45 (br s, 1H), 8.67 (d, 1H), 8.57 (t, 1H), 7.95 (m, 3H), 7.78 (2d, 4H), 7.36 (d, 1H), 7.32 (t, 2H), 3.18 (d, 2H), 1.97 (s, 3H), 1.70–1.60 (m, 12H).

EXAMPLE 40

N-((4'-acetyl(1,1'-biphenyl)-4-yl)carbonyl)-4-((1-adamantylmethyl)amino)-3-nitrobenzenesulfonamide

EXAMPLE 40A

4'-acetyl(1,1'-biphenyl)-4-carboxylic acid

The desired product was prepared by substituting 1-(4-bromophenyl)ethanone for 2-bromo-5-chlorothiophene in Example 29A. MS (APCI(−)) m/e 239 (M−H)$^-$.

EXAMPLE 40B

N-((4'-acetyl(1,1'-biphenyl)-4-yl)carbonyl)-4-((1-adamantylmethyl)amino)-3-nitrobenzenesulfonamide The desired product was prepared by substituting Example 40A for Example 29A in Example 29B. MS (APCI(+)) m/e 588 (M+H)$^+$; $^1$H NMR (500 MHz, DMSO-d$_6$) δ8.67 (d, 1H), 8.57 (t, 1H), 8.05 (d, 2H), 7.99 (d, 2H), 7.95 (dd, 1H), 7.88 (t, 4H), 7.36 (d, 1H), 3.18 (m, 2H), 2.60 (s, 3H), 1.97 (s, 3H), 1.58 (m, 12H).

EXAMPLE 41

4-((1-adamantylmethyl)amino)-N-((2',3'-dimethyl(1,1'-biphenyl)-4-yl)carbonyl)-3-nitrobenzenesulfonamide

EXAMPLE 41A

2',3'-dimethyl(1,1'-biphenyl)-4-carboxylic acid

The desired product was prepared by substituting 1-bromo-2,3-dimethylbenzene for 2-bromo-5-chlorothiophene in Example 29A. MS (APCI(−)) m/e 225 (M−H)$^-$.

EXAMPLE 41B 4-((1-adamantylmethyl)amino)-N-((2',3'-dimethyl(1,1'-biphenyl)-4-yl)carbonyl)-3-nitrobenzenesulfonamide The desired product was prepared by substituting Example 41A for Example 29A in Example 29B. MS (APCI(+)) m/e 574 (M+H)$^+$; $^1$H NMR (300 MHz, DMSO-d$_6$) δ8.62 (d, 1H), 8.56 (m, 1H), 7.89 (m, 3H), 7.36 (m, 3H), 7.15 (m, 2H), 6.96 (d, 1H), 3.14 (d, 2H), 2.25 (s, 3H), 2.03 (s, 3H), 1.92 (s, 3H), 1.58 (m, 12H).

EXAMPLE 42

4-((1-adamantylmethyl)amino)-N-((4'-fluoro-2'-nitro(1,1'-biphenyl)-4-yl)carbonyl)-3-nitrobenzenesulfonamide

EXAMPLE 42A methyl 4'-fluoro-2'-nitro(1,1'-biphenyl)-4-carboxylate

The desired product was prepared by substituting 1-bromo-4-fluoro-2-nitrobenzene for Example 5A in Example 5B. MS (DCI) m/e 276 (M+H)$^+$.

EXAMPLE 42B 4-((1-adamantylmethyl)amino)-N-((4'-fluoro-2'-nitro (1,1'-biphenyl)-4-yl)carbonyl)-3-nitrobenzenesulfonamide The procedure used in Example 5 was used here to convert the products from Examples 42A and 28A to the title compound. MS (ESI(−)) m/e 607 (M−H)$^-$; $^1$H NMR (400 MHz, DMSO-d$_6$) δ8.67 (d, 1H), 8.58 (t, 1H), 8.07 (dd, 1H), 7.94 (m, 3H), 7.71 (dt, 1H), 7.63 (d, 1H), 7.46 (d, 2H), 7.36 (d, 1H), 3.18 (d, 2H), 1.99 (m, 3H), 1.75–1.50 (m, 12H).

EXAMPLE 43

4-((1-adamantylmethyl)amino)-N-((2'-amino-4'-fluoro(1,1'-biphenyl)-4-yl)carbonyl)-3-nitrobenzenesulfonamide

EXAMPLE 43A methyl 2'-amino-4'-fluoro(1,1'-biphenyl)-4-carboxylate

The desired product was prepared by substituting Example 42A for Example 5B in Example 5C. MS (DCI) m/e 246 (M+H)$^+$.

EXAMPLE 43B 4-((1-adamantylmethyl)amino)-N-((2'-amino-4'-fluoro(1,1'-biphenyl)-4-yl)carbonyl)-3-nitrobenzenesulfonamide The desired product was prepared by substituting Example 43A and Example 28A for Example 5C and Example 3A, respectively, in Example 5D. MS (ESI(−)) m/e 577 (M−H)$^-$; $^1$H NMR (400 MHz, DMSO-d$_6$) δ8.60 (t, 1H), 7.94 (m, 3H), 7.50 (d, 2H), 7.38 (d, 1H), 7.00 (dd, 1H), 6.55 (dd, 1H), 6.42 (dt, 1H), 5.22 (br s, 2H), 3.17 (d, 2H), 1.98 (m, 3H), 1.72–1.55 (m, 12H).

EXAMPLE 44

4-((1-adamantylmethyl)amino)-N-((4'-fluoro-2'-(methylamino)(1,1'-biphenyl)-4-yl)carbonyl)-3-nitrobenzenesulfonamide

EXAMPLES 44A and 44B methyl 4'-fluoro-2'-(methylamino)(1,1'-biphenyl)-4-carboxylate and methyl 2'-(dimethylamino)-4'-fluoro(1,1'-biphenyl)-4-carboxylate A room temperature suspension of sodium hydride (31 mg, 1.3 mmol) in THF (2 mL) was treated sequentially with a solution of Example 44A (123 mg, 0.50 mmol) in THF (2 mL) and methyl iodide (144 mg, 1.0 mmol), stirred for 1 hour, diluted with ethyl acetate (50 mL). washed sequentially with 1M HCl (5 mL), water (5 mL), and brine (5 mL), dried (MgSO$_4$), filtered, and concentrated. The concentrate was purified by flash column chromatography on silica gel with 70:25:51/hexanes:dichloromethane:ethyl acetate to provide the desired products.

EXAMPLE 44C 4-((1-adamantylmethyl)amino)-N-((4'-fluoro-2'-(methylamino)(1,1'-biphenyl)-4-yl)carbonyl)-3-nitrobenzenesulfonamide The desired product was prepared by substituting Example 44A and Example 28A for Example 5C and Example 3A, respectively, in Example 5D. MS (ESI(−)) m/e 591 (M−H)$^-$; $^1$H NMR (400 MHz, DMSO-d$_6$) δ8.67 (d, 1H), 8.57 (t, 1H), 7.94 (m, 3H), 7.45 (d, 2H), 7.36 (d, 1H), 6.97 (dd, 1H), 6.40 (m, 2H), 5.19 (br s, 1H), 3.18 (d, 2H), 2.63 (d, 3H), 1.98 (m, 3H), 1.72–1.55 (m, 12H).

EXAMPLE 45

4-((1-adamantylmethyl)amino)-N-((2'-(dimethylamino)-4'-fluoro(1,1'-biphenyl)-4-yl)carbonyl)-3-nitrobenzenesulfonamide The desired product was prepared by substituting Example 44B and Example 28A for Example 5C and Example 3A, respectively, in Example 5D. MS (ESI(−)) m/e 605 (M−H)$^-$; $^1$H NMR (400 MHz, DMSO-d$_6$) δ8.60 (d, 1H), 8.50 (t, 1H), 7.92 (m, 3H), 7.52 (m, 2H), 7.28 (m, 1H), 7.18 (dd, 1H), 6.81 (m, 2H), 3.17 (d, 2H), 2.46 (s, 6H), 1.98 (m, 3H), 1.72–1.55 (m, 12H).

EXAMPLE 46

4-((((4-((1-adamantylmethyl)amino)-3-nitrophenyl)sulfonyl)amino)carbonyl)-4'-fluoro-2'-((methoxycarbonyl)amino)-1,1'-biphenyl A room temperature solution of Example 43B (30 mg, 0.051 mmol), methyl chloroformate (0.05 mL, 0.65 mmol), N,N-diisopropylethylamine (0.1 mL, 0.57 mmol) and DMAP (3 mg, 0.02 mmol) in dichloromethane (1 mL) was stirred for 16 hours, treated with 4M HCl (0.3 mL), and concentrated. The concentrate was purified by flash column chromatography on silica gel with 50–100% ethyl acetate/hexanes to provide the desired product. MS (ESI(−)) m/e 635 (M−H)$^-$; $^1$H NMR (400 MHz, DMSO-d$_6$) δ8.89 (br s, 1H), 8.65 (d, 1H), 8.56 (t, 1H), 7.92 (m, 3H), 7.43 (d, 2H), 7.35 (m, 3H), 7.12 (dt, 1H), 3.50 (s, 3H), 3.18 (d, 2H), 1.98 (m, 3H), 1.72–1.55 (m, 12H).

EXAMPLE 47

4-((1-adamantylmethyl)amino)-N-((2'-(((dimethylamino)carbonyl)amino)-4'-fluoro(1,1'-biphenyl)-4-yl)carbonyl)-3-nitrobenzenesulfonamide

EXAMPLE 47A methyl 2'-(((dimethylamino)carbonyl)amino)-4'-fluoro(1,1'-biphenyl)-4-carboxylate A room temperature solution of Example 43A (100 mg, 0.41 mmol) in dichloromethane (2 mL) was treated with 1.9M phosgene in toluene (0.26 mL) and N,N-diisopropylethylamine (0.2 mL, 1.2 mmol), stirred for 16 hours, treated with 2M dimethylamine in THF (0.5 mL), stirred for 1 hour, and concentrated. The concentrate was purified by flash column chromatography on silica gel with 50% ethyl acetate/hexanes to provide the desired product.

EXAMPLE 47B 4-((1-adamantylmethyl)amino)-N-((2'-(((dimethylamino)carbonyl)amino)-4'-fluoro(1,1'-biphenyl)-4-yl)carbonyl)-3-nitrobenzenesulfonamide The desired product was prepared by substituting Example 47A and Example 28A for Example 5C and Example 3A, respectively, in Example 5D. MS (ESI(+)) m/e 650 (M+H)$^+$; $^1$H NMR (400 MHz, DMSO-d$_6$) δ8.67 (d, 1H), 8.59 (t, 1H), 7.95 (dd, 1H), 7.91 (d, 2H), 7.78 (s, 1H), 7.50

(d, 2H) 7.42 (dd, 1H), 7.37 (d, 1H), 7.31 (dd, 1H), 7.05 (dt, 1H), 3.18 (d, 2H), 2.75 (s, 6H), 1.98 (m, 3H), 1.72–1.55 (m, 12H).

EXAMPLE 48

N-(4'-((((4-((1-adamantylmethyl)amino)-3-nitrophenyl)sulfonyl)amino)carbonyl)-4-fluoro(1,1'-biphenyl)-2-yl)-4-morpholinecarboxamide The desired product was prepared by substituting morpholine for dimethylamine in Example 47. MS (ESI(−)) m/e 690 (M−H)−; 1H NMR (400 MHz, DMSO-d6) δ8.66 (d, 1H), 8.57 (t, 1H), 8.20 (br s, 1H), 7.92 (m, 3H), 7.46 (d, 2H), 7.47–7.24 (m, 4H), 7.08 (dt, 1H), 3.47 (m, 4H), 3.24 (m, 4H), 3.18 (d, 2H), 1.98 (m, 3H), 1.72–1.55 (m, 12H).

EXAMPLE 49

N-(4'-((((4-((1-adamantylmethyl)amino)-3-nitrophenyl)sulfonyl)amino)carbonyl)-4-fluoro(1,1'-biphenyl)-2-yl)-3-aminopropanamide

EXAMPLE 49A 4-((((4-((1-adamantylmethyl)amino)-3-nitrophenyl)sulfonyl)amino)carbonyl)-2'-((3-((tert-butoxycarbonyl)amino)propanoyl)amino)-4'-fluoro-1,1'-biphenyl A room temperature solution of Example 43 (25 mg, 0.04 mmol), N-(tert-butoxycarbonyl)-β-alanine (25 mg, 0.13 mmol), EDCI (38 mg, 0.20 mmol), and DMAP (2 mg, 0.02 mmol) in dichloromethane (2 mL) was stirred for 16 hours, diluted with ethyl acetate (50 mL), washed sequentially with 1M HCl (5 mL), water (5 mL), and brine (5 mL), dried (MgSO4), filtered, and concentrated. The concentrate was purified by flash column chromatography on silica gel with 2–8% methanol/dichloromethane to provide the desired product. MS (ESI(−)) m/e 748 (M−H)−.

EXAMPLE 49B

N-(4'-((((4-((1-adamantylmethyl)amino)-3-nitrophenyl)sulfonyl)amino)carbonyl)-4-fluoro(1,1'-biphenyl)-2-yl)-3-aminopropanamide A room temperature solution of Example 49A (19 mg, 0.03 mmol) in dichloromethane (1 mL) was treated with 4M HCl in dioxane, stirred for 4 hours, and concentrated to provide the desired product. MS (ESI(+)) m/e 650 (M+H)+; 1H NMR (400 MHz, DMSO-d6) δ9.12 (br s, 1H), 8.65 (d, 1H), 8.56 (t, 1H), 7.95 (dd, 1H), 7.94 (m, 3H), 7.65 (br s, 3H), 7.50–7.35 (m, 4H), 7.15 (dt, 1H), 3.18 (d, 2H), 2.75 (s, 6H), 1.98 (m, 3H), 1.72–1.55 (m, 12H).

EXAMPLE 50

4-((1-adamantylmethyl)amino)-3-nitro-N-((2',4',5'-trimethyl(1,1'-biphenyl)-4-yl)carbonyl)benzenesulfonamide

EXAMPLE 50A

2',4',5'-trimethyl(1,1'-biphenyl)-4-carboxylic acid

The desired product was prepared by substituting 1-bromo-2,4,5-trimethylbenzene for 2-bromo-5-chlorothiophene in Example 29A. MS (APCI(−)) m/e 239 (M−H)−.

EXAMPLE 50B 4-((1-adamantylmethyl)amino)-3-nitro-N-((2',4',5'-trimethyl(1,1'-biphenyl)-4-yl)carbonyl)benzenesulfonamide The desired product was prepared by substituting Example 50A for Example 29A in Example 29B. MS (APCI(+) m/e 588 (M+H)+; 1H NMR (500 MHz, DMSO-d6) δ8.67 (d, 1H), 8.57 (t, 1H), 7.95 (dd, 1H), 7.91 (d, 2H), 7.41 (d, 2H), 7.36 (d, 1H), 7.06 (s, 1H), 6.97 (s, 1H), 3.18 (d, 2H), 2.21 (s, 3H), 2.20 (s, 3H), 2.13 (s, 3H), 1.97 (s, 3H), 1.58 (m, 12H).

EXAMPLE 51

4-((1-adamantylmethyl)amino)-N-(4-mesitylbenzoyl)-3-nitrobenzenesulfonamide

EXAMPLE 51A

2',4',6'-trimethyl(1,1'-biphenyl)-4-carboxylic acid

The desired product was prepared by substituting 2-bromo-1,3,5-trimethylbenzene for 2-bromo-5-chlorothiophene in Example 29A. MS (APCI(−)) m/e 239 (M−H)−.

EXAMPLE 51B 4-((1-adamantylmethyl)amino)-N-(4-mesitylbenzoyl)-3-nitrobenzenesulfonamide The desired product was prepared by substituting Example 51A for Example 29A in Example 29B. MS (APCI(+)) m/e 588 (M+H)+; 1H NMR (500 MHz, DMSO-d6) δ8.67 (d, 1H), 8.57 (t, 1H), 7.95 (m, 3H), 7.36 (d, 1H), 7.23 (d, 2H), 6.93 (s, 2H), 3.18 (d, 2H), 2.26 (s, 3H), 1.97 (s, 3H), 1.89 (s, 6H), 1.58 (m, 12H).

EXAMPLE 52

4-((1-adamantylmethyl)amino)-N-(4-(1,3-benzodioxol-5-yl)benzoyl)-3-nitrobenzenesulfonamide

EXAMPLE 52A 4-(1,3-benzodioxol-5-yl)benzoic acid

The desired product was prepared by substituting 5-bromo-1,3-benzodioxole for 2-bromo-5-chlorothiophene in Example 29A.

EXAMPLE 52B 4-((1-adamantylmethyl)amino)-N-(4-(1,3-benzodioxol-5-yl)benzoyl)-3-nitrobenzenesulfonamide The desired product was prepared by substituting Example 52A for Example 29A in Example 29B. MS (APCI(+)) m/e 590 (M+H)+; 1H NMR (500 MHz, DMSO-d6) δ8.66 (d, 1H), 8.57 (t, 1H), 7.95 (dd, 1H), 7.91 (d, 2H), 7.73 (d, 2H), 7.36 (d, 1H), 7.33 (d, 1H), 7.24 (dd, 1H), 7.01 (d, 1H), 6.08 (s, 2H), 3.18 (d, 2H), 1.97 (s, 3H), 1.58 (m, 12H).

EXAMPLE 53

4-((1-adamantylmethyl)amino)-N-(4-(1H-indol-6-yl)benzoyl)-3-nitrobenzenesulfonamide The desired product was prepared by substituting Example 4A and Example 28A for Example 1B and Example 1C, respectively, in Example 1D. MS (ESI(−)) m/e 583 (M−H)⁻; ¹H NMR (300 MHz, DMSO-d₆) δ8.65 (m, 1H), 8.55 (m, 1H), 7.97 (m, 2H), 7.77 (m, 2H), 7.67 (m, 2H), 7.38 (m, 3H), 6.48 (m, 1H), 3.18 (m, 2H), 1.98 (m, 3H), 1.62 (m, 12H).

EXAMPLE 54

4-((1-adamantylmethyl)amino)-N-(4-(2-methyl-1,3-benzoxazol-5-yl)benzoyl)-3-nitrobenzenesulfonamide

EXAMPLE 54A methyl 4-(2-methyl-1,3-benzoxazol-5-yl)benzoate

A room temperature solution of 5-chloro-2-methyl-1,3-benzoxazole (110 mg, 0.71 mmol), CsF (325 mg, 2.14 mmol), Pd(OAc)₂ (6.0 mg, 0.028 mmol), 2-dicyclohexylphosphino-2'-(N,N-dimethylamino)biphenyl (14 mg, 0.036 mmol) and 4-(methoxycarbonyl)phenylboronic acid (180 mg, 1.0 mmol) in dioxane (4 mL) was stirred for 18 hours and concentrated. The concentrate was purified by flash column chromatography on silica gel with 15% ethyl acetate/hexanes to provide the desired product. ¹H NMR (300 MHz, DMSO-d₆) δ8.06 (d, 2H), 8.03 (d, 1H), 7.90 (d, 2H), 7.78 (d, 2H), 7.71 (dd, 1H), 7.29 (d, 2H), 3.90 (s, 3H), 2.65 (s, 3H).

EXAMPLE 54B 4-(2-methyl-1,3-benzoxazol-5-yl)benzoic acid

A room temperature solution of Example 54A (80 mg, 3.0 mmol) and LiOH (630 mg, 15.0 mmol) in a mixture of THF (15 mL), water (4 mL), and methanol (4 mL) was stirred for 1 hour, poured into 1M HCl, and extracted with ethyl acetate. The combined extracts were washed with brine, dried (Na₂SO₄), filtered, and concentrated to provide the desired product of sufficient purity for subsequent use.

EXAMPLE 54C 4-((1-adamantylmethyl)amino)-N-(4-(2-methyl-1,3-benzoxazol-5-yl)benzoyl)-3-nitrobenzenesulfonamide The desired product was prepared by substituting Example 54B and Example 28A for Example 1B and Example 1C, respectively, in Example 1D. MS (ESI(−)) m/e 599 (M−H)⁻; ¹H NMR (300 MHz, DMSO-d₆) δ8.52 (d, 1H), 7.99–7.92 (m, 3H), 7.90 (dd, 1H), 7.64–7.52 (m, 4H), 7.17 (d, 1H), 3.12 (d, 2H), 2.63 (s, 3H), 1.97 (m, 2H), 1.71–1.54 (m, 13H).

EXAMPLE 55

4-((1-adamantylmethyl)amino)-N-(4-(2-methyl-1,3-benzothiazol-5-yl)benzoyl)-3-nitrobenzenesulfonamide The desired product was prepared by substituting Example 17A and Example 28A for Example 1B and Example 1C, respectively, in Example 1D. MS (ESI(−)) m/e 615 (M−H)⁻; ¹H NMR (300 MHz, DMSO-d₆) δ8.68 (d, 1H), 8.59 (t, 1H), 8.26 (s, 1H), 8.14 (d, 1H), 7.98 (d, 2H), 7.95 (dd, 1H), 7.90 (d, 2H), 7.77 (dd, 1H), 7.37 (d, 1H), 3.19 (d, 2H), 2.82 (s, 3H), 1.98 (br s, 3H), 1.73–1.55 (m, 12H).

EXAMPLE 56

4-((1-adamantylmethyl)amino)-N-(4-(2-ethyl-1,3-benzothiazol-5-yl)benzoyl)-3-nitrobenzenesulfonamide

EXAMPLE 56A 5-bromo-2-ethyl-1,3-benzothiazole

A 0° C. solution of diisopropylamine (340 μL, 2.41 mmol) in THF (3 mL) was treated with 2.5M n-butyllithium in hexanes (0.88 mL), stirred for 20 minutes, added to a −78° C. solution of 5-bromo-2-methyl-1,3-benzothiazole (250 mg, 1.10 mmol) in THF (3 mL), stirred for 30 minutes, treated with iodomethane (340 μL, 5.50 mmol), and stirred for 1 hour. The mixture was diluted with ethyl acetate (50 mL), washed sequentially with 1M HCl (5 mL), water (5 mL), and brine (5 mL), dried (MgSO₄), filtered, and concentrated. The concentrate was purified by flash column chromatography on silica gel with 30% hexanes/dichloromethane to provide the desired product. MS (DCI) m/e 242 (M+H)⁺.

EXAMPLE 56B 4-(2-ethyl-1,3-benzothiazol-5-yl)benzoic acid

The desired product was prepared by substituting Example 56A for 6-bromoindole in Example 4A. MS (ESI(+)) m/e 284 (M+H)⁺.

EXAMPLE 56C 4-((1-adamantylmethyl)amino)-N-(4-(2-ethyl-1,3-benzothiazol-5-yl)benzoyl)-3-nitrobenzenesulfonamide The desired product was prepared by substituting Example 56 B and Example 28A for Example 1B and Example 1C, respectively, in Example 1D. MS (ESI(−)) m/e 629(M−H)⁻; ¹H NMR (300 MHz, DMSO-d₆) δ8.68 (d, 1H), 8.57 (t, 1H), 8.28 (s, 1H), 8.16 (d, 1H), 7.98 (d, 2H), 7.95 (dd, 1H), 7.90 (d, 2H), 7.77 (dd, 1H), 7.36 (d, 1H), 3.19 (d, 2H), 3.15 (q, 2H), 1.98 (br s, 3H), 1.73–1.55 (m, 12H), 1.40 (t, 3H).

EXAMPLE 57

N-(4-(3,4,4a,5,6,7,8,8a-octahydro-1-naphthalenyl)benzoyl)-4-((1-adamantylmethyl)amino)-3-nitrobenzenesulfonamide and 4-((1-adamantylmethyl)amino)-N-(4-(2,3,4,4a,5,6,7,8-octahydro-1-naphthalenyl)benzoyl)-3-nitrobenzenesulfonamide

EXAMPLE 57A methyl 4-(3,4,4a,5,6,7,8,8a-octahydro-1-naphthalenyl)benzoate and methyl 4-(2,3,4,4a,5,6,7,8-octahydro-1-naphthalenyl)benzoate The desired product was prepared by substituting 1-decalone for 4-tert-butylcyclohexanone in Examples 5A and 5B. MS (DCI) m/e 271 (M+H)⁺.

EXAMPLE 57B

N-(4-(3,4,4a,5,6,7,8,8a-octahydro-1-naphthalenyl)benzoyl)-4-((1-adamantylmethyl)amino)-3-nitrobenzenesulfonamide and 4-((1-adamantylmethyl)amino)-N-(4-(2,3,4,4a,5,6,7,8-octahydro-1-naphthalenyl)benzoyl)-3-nitrobenzenesulfonamide The desired product was prepared by substituting Example 57A and Example 28A for Example 5C and Example 3A, respectively, in Example 5D. MS (ESI(+)) m/e 604 (M+H)⁺; ¹H NMR (400 MHz, DMSO-d₆) δ8.64 (d, 1H), 8.59 (t, 1H), 7.92 (dd, 1H), 7.80 (d, 2H), 7.36 (d, 1H), 7.28 (d, 2H), 5.80 (m, 1H), 3.18 (d, 2H), 2.30–2.20 (m, 3H), 1.96 (m, 3H), 1.70–1.55 (m, 17H), 1.40–1.20 (m, 6H).

EXAMPLE 58

N-(4-(1,4,4a,5,6,7,8,8a-octahydro-2-naphthalenyl) benzoyl)-4-((1-adamantylmethyl)amino)-3-nitrobenzenesulfonamide and N-(4-(3,4,4a,5,6,7,8,8a-octahydro-2-naphthalenyl)benzoyl)-4-((1-adamantylmethyl)amino)-3-nitrobenzenesulfonamide

EXAMPLE 58A methyl 4-(1,4,4a,5,6,7,8,8a-octahydro-2-naphthalenyl)benzoate and methyl 4-(3,4,4a,5,6,7,8,8a-octahydro-2-naphthalenyl)benzoate The desired product was prepared by substituting 2-decalone for 4-tert-butylcyclohexanone in Examples 5A and 5B. MS (DCI) m/e 271 (M+H)$^+$.

EXAMPLE 58B

N-(4-(1,4,4a,5,6,7,8,8a-octahydro-2-naphthalenyl) benzoyl)-4-((1-adamantylmethyl)amino)-3-nitrobenzenesulfonamide and N-(4-(3,4,4a5,6,7,8,8a-octahydro-2-naphthalenyl)benzoyl)-4-((1-adamantylmethyl)amino)-3-nitrobenzenesulfonamide The desired product was prepared by substituting Example 58A and Example 28A for Example 5C and Example 3A, respectively, in Example 5D. MS (ESI(+)) m/e 604 (M+H)$^+$; $^1$H NMR (400 MHz, DMSO-d$_6$) δ8.52 (d, 1H), 8.40 (t, 1H), 7.88 (dd, 1H), 7.80 (d, 2H), 7.36 (d, 2H), 7.28 (d, 2H), 6.13 and 6.07 (m, 1H total), 3.12 (d, 2H), 2.38 (m, 3H), 1.96 (m, 3H), 1.70–1.40 (m, 23H).

EXAMPLE 59

4-((1-adamantylmethyl)amino)-N-(4-decahydro-1-naphthalenylbenzoyl)-3-nitrobenzenesulfonamide

EXAMPLE 59A methyl 4-decahydro-1-naphthalenylbenzoate

The desired product was prepared by substituting Example 57A for Example 5B in Example 5C. MS (DCI) m/e 273 (M+H)$^+$.

EXAMPLE 59B 4-((1-adamantylmethyl)amino)-N-(4-decahydro-1-naphthalenylbenzoyl)-3-nitrobenzenesulfonamide The desired product was prepared by substituting Example 59A and Example 28A for Example 5C and Example 3A, respectively, in Example 5D. MS (ESI(+)) m/e 606 (M+H)$^+$; $^1$H NMR (400 MHz, DMSO-d$_6$) δ8.64 (d, 1H), 8.59 (t, 1H), 7.92 (dd, 1H), 7.78 (d, 2H), 7.36 (d, 1H), 7.28 (d, 2H), 3.18 (d, 2H), 2.30 (m, 1H), 1.96 (m, 3H), 1.75–1.10 (m, 28H).

EXAMPLE 60

4-((1-adamantylmethyl)amino)-N-(4-decahydro-2-naphthalenylbenzoyl)-3-nitrobenzenesulfonamide

EXAMPLE 60A methyl 4-decahydro-2-naphthalenylbenzoate

The desired product was prepared by substituting Example 58A for Example 5B in Example 5C. MS (DCI) m/e 273 (M+H)$^+$.

EXAMPLE 60B 4-((1-adamantylmethyl)amino)-N-(4-decahydro-2-naphthalenylbenzoyl)-3-nitrobenzenesulfonamide The desired product was prepared by substituting Example 60A and Example 28A for Example 5C and Example 3A, respectively, in Example 5D. MS (ESI) m/e 606 (M+H)$^+$; $^1$H NMR (400 MHz, DMSO-d$_6$) δ8.62 (d, 1H), 8.55 (t, 1H), 7.92 (dd, 1H), 7.78 (d, 2H), 7.36 (m, 4H), 3.18 (d, 2H), 2.55 (m, 1H), 1.96 (m, 3H), 1.75–1.20 (m, 28H).

EXAMPLE 61

4-((1-adamantylmethyl)amino)-3-nitro-N-(4-(3,5,5,8,8-pentamethyldecahydro-2-naphthalenyl)benzoyl) benzenesulfonamide

EXAMPLE 61A methyl 4-(3,5,5,8,8-pentamethyldecahydro-2-naphthalenyl)benzoate The desired product was prepared by substituting 3,5,5,8,8-pentamethyloctahydro-2(1H)-naphthalenone for 4-tert-butylcyclohexanone in Examples 5A–5C. MS (DCI) m/e 343 (M+H)$^+$.

EXAMPLE 61B 4-((1-adamantylmethyl)amino)-3-nitro-N-(4-(3,5,5,8,8-pentamethyldecahydro-2-naphthalenyl)benzoyl) benzenesulfonamide The desired product was prepared by substituting Example 61A and Example 28A for Example 5C and Example 3A, respectively, in Example 5D. MS (ESI(+)) m/e 676 (M+H)$^+$; $^1$H NMR (400 MHz, DMSO-d$_6$) δ8.62 (d, 1H), 8.55 (t, 1H), 7.92 (dd, 1H), 7.78 (d, 2H), 7.36 (m, 4H), 3.18 (d, 2H), 2.49 (m, 1H), 1.96 (m, 3H), 1.80–1.20 (m, 22H), 0.90 (m, 6H), 0.87 (s, 3H), 0.78 (s, 3H), 0.71 (s, 3H).

EXAMPLE 62

4-((1-adamantylmethyl)amino)-N-(4-(1-cyclohexen-1-yl)benzoyl)-3-nitrobenzenesulfonamide The desired product was prepared by substituting Example 9A and Example 28A for Example 5C and Example 3A, respectively, in Example 5D. MS (ESI(−)) m/e 548 (M−H)$^−$; $^1$H NMR (400 MHz, CD$_3$OD) δ8.86 (d, 1H), 8.03 (dd, 1H), 7.76 (dt, 2H), 7.47 (dt, 2H), 7.21 (d, 1H), 6.27 (m, 1H), 3.14 (t, 2H), 2.42 (m, 2H), 2.24 (m, 2H), 2.01 (m, 3H), 1.85–1.65 (m, 16H).

EXAMPLE 63

4-((1-adamantylmethyl)amino)-N-(4-(1-cyclohepten-1-yl)benzoyl)-3-nitrobenzenesulfonamide

EXAMPLE 63A methyl 4-(1-cyclohepten-1-yl)benzoate

The desired product was prepared by substituting cycloheptanone for 4-tert-butylcyclohexanone in Examples 5A and 5B. MS (DCI) m/e 231 (M+H)$^+$.

EXAMPLE 63B 4-((1-adamantylmethyl)amino)-N-(4-(1-cyclohepten-1-yl)benzoyl)-3-nitrobenzenesulfonamide The desired product was prepared by substituting Example 63A and Example 28A for Example 5C and Example 3A, respectively, in Example 5D. MS (ESI(+)) m/e 564 (M+H)+; $^1$H NMR (400 MHz, DMSO-d$_6$) δ8.63 (d, 1H), 8.45(t, 1H), 7.92 (dd, 1H), 7.80 (d, 2H), 7.40 (d, 2H), 7.35 (d, 1H), 6.21 (t, 1H), 3.18 (d, 2H), 2.55 (m, 2H), 2.29 (m, 2H), 1.98 (m, 3H), 1.80–1.20 (m, 18H).

EXAMPLE 64

4-((1-adamantylmethyl)amino)-N-(4-cycloheptylbenzoyl)-3-nitrobenzenesulfonamide

EXAMPLE 64A methyl 4-cycloheptylbenzoate

The desired product was prepared by substituting Example 63A for Example 5B in Example 5C. MS (DCI) m/e 233 (M+H)+.

EXAMPLE 64B 4-((1-adamantylmethyl)amino)-N-(4-cycloheptylbenzoyl)-3-nitrobenzenesulfonamide The desired product was prepared by substituting Example 64A and Example 28A for Example 5C and Example 3A, respectively, in Example 5D. MS (ESI(+)) m/e 566 (M+H)+; $^1$H NMR (400 MHz, DMSO-d$_6$) δ8.63 (d, 1H), 8.55 (t, 1H), 7.92 (dd, 1H), 7.79 (d, 2H), 7.35 (d, 1H), 7.30 (d, 2H), 3.18 (d, 2H), 2.73 (m, 1H), 1.98 (m, 3H), 1.80–1.50 (m, 24H).

EXAMPLE 65

4-((1-adamantylmethyl)amino)-N-(4-(1-cycloocten-1-yl)benzoyl)-3-nitrobenzenesulfonamide

EXAMPLE 65A methyl 4-(1-cycloocten-1-yl)benzoate

The desired product was prepared by substituting cyclooctanone for 4-tert-butylcyclohexanone in Examples 5A and 5B. MS (DCI) m/e 245 (M+H)+.

EXAMPLE 65B 4-((1-adamantylmethyl)amino)-N-(4-(1-cycloocten-1-yl)benzoyl)-3-nitrobenzenesulfonamide The desired product was prepared by substituting Example 65A and Example 28A for Example 5C and Example 3A, respectively, in Example 5D. MS (ESI(+)) m/e 578 (M+H)+; $^1$H NMR (400 MHz, DMSO-d$_6$) δ8.63 (d, 1H), 8.55(t, 1H), 7.92 (dd, 1H), 7.80 (d, 2H), 7.50 (d, 2H), 7.35 (d, 1H), 6.21 (t, 1H), 3.18 (d, 2H), 2.60 (m, 2H), 2.29 (m, 2H), 1.98 (m, 3H), 1.80–1.20 (m, 20H).

EXAMPLE 66

4-((1-adamantylmethyl)amino)-N-(4-cyclooctylbenzoyl)-3-nitrobenzenesulfonamide

EXAMPLE 66A methyl 4-cyclooctylbenzoate

The desired product was prepared by substituting Example 65A for Example 5B in Example 5C. MS (DCI) m/e 247 (M+H)+.

EXAMPLE 66B 4-((1-adamantylmethyl)amino)-N-(4-cyclooctylbenzoyl)-3-nitrobenzenesulfonamide The desired product was prepared by substituting Example 66A and Example28A for Example 5C and Example 3A, respectively, in Example 5D. MS (ESI(+)) m/e 580 (M+H)+; $^1$H NMR (400 MHz, DMSO-d$_6$) δ8.63 (d, 1H), 8.57 (t, 1H), 7.92 (dd, 1H), 7.78 (d, 2H), 7.35 (d, 1H), 7.31 (d, 2H), 3.18 (d, 2H), 2.71 (m, 1H), 1.98 (m, 3H), 1.80–1.50 (m, 26H).

EXAMPLE 67

4-((1-adamantylmethyl)amino)-3-nitro-N-(4-(5-nitro-2-pyridinyl)benzoyl)benzenesulfonamide

EXAMPLE 67A 4-(5-nitro-2-pyridinyl)benzoic acid

The desired product was prepared by substituting 2-bromo-5-nitropyridine for 2-bromo-5-chlorothiophene in Example 29A. MS (APCI(–)) m/e 243 (M–H)−.

EXAMPLE 67B 4-((1-adamantylmethyl)amino)-3-nitro-N-(4-(5-nitro-2-pyridinyl)benzoyl)benzenesulfonamide The desired product was prepared by substituting Example 67A for Example 29A in Example 29B. MS (APCI(+)) m/e 592 (M+H)+; $^1$H NMR (500 MHz, DMSO-d$_6$) δ8.68 (m, 2H), 8.57 (t, 1H), 8.35 (d, 1H), 8.30 (d, 2H), 8.04 (d, 2H), 7.96 (m, 1H), 7.36 (m, 2H), 3.18 (d, 2H), 1.97 (s, 3H), 1.58 (m, 12H).

EXAMPLE 68

4-((1-adamantylmethy)(2-(phenylsulfanyl)ethyl)amino)-N-(4-(1-cyclohexen-1-yl)benzoyl)-3-nitrobenzenesulfonamide

EXAMPLE 68A

N-(1-adamantylmethyl)-2-(phenylsulfanyl)acetamide

A room temperature solution of (phenylsulfanyl)acetic acid (1.68 g, 10.0 mmol) in dichloromethane (10 mL) was treated with 2M oxalyl chloride in dichloromethane (8 mL, 16.0 mmol) and DMF (1 drop), stirred for 2 hours, concentrated, dissolved in dichloromethane (10 mL), treated with 1-adamantylmethylamine (1.65 g, 10.0 mmol) and N,N-diisopropylethylamine (2.1 mL, 12.0 mmol), and stirred for 1 hour. The mixture was filtered through a pad of silica gel (20 g) and concentrated to provide the desired product of sufficient purity for subsequent use.

EXAMPLE 68B

N-(1-adamantylmethyl)-2-(phenylsulfanyl)ethanamine

A solution of Example 68A in THF (5 mL)was treated with 1M LAH in THF (20 mL, 20.0 mmol), heated to reflux, stirred for 24 hours, cooled to room temperature, treated sequentially with water (0.8 mL), 15% NaOH (0.8 mL), and water (2.4 mL), stirred for 30 minutes, filtered through diatomaceous earth (Celite®), and concentrated. The concentrate was purified by flash column chromatography on silica gel with 20–100% ethyl acetate/hexanes to provide the desired product.

EXAMPLE 68C 4-((1-adamantylmethyl)(2-(phenylsulfanyl)ethyl)amino)-N-(4-(1-cyclohexen-1-yl)benzoyl)-3-nitrobenzenesulfonamide The desired product was prepared by substituting Example 9B and Example 68B for Example 7C and Example 1D, respectively, in Example 7D. MS (ESI(–)) m/e 684 (M–H)⁻; $^1$H NMR (400 MHz, DMSO-d$_6$) δ8.69 and 8.60 (2br s, 1H total), 8.92 and 8.38 (2d, 1H), 8.16 and 8.06 (2dd, 1H), 7.60 (t, 2H), 7.46 (dd, 2H), 7.40 (d, 1H), 7.35–7.10 (m, 5H), 6.28 (m, 1H), 3.40–2.90 (m, 6H), 2.40 (m, 2H), 2.23 (m, 2H), 2.05–1.20 (m, 19H).

EXAMPLE 69

4-(benzhydrylamino)-N-((4'-fluoro(1,1'-biphenyl)-4-yl)carbonyl)-3-nitrobenzenesulfonamide The desired product was prepared by substituting benzhydrylamine for 2,2-dimethylcyclopentylamine in Example 1E. MS (APCI(+)) m/e 582 (M+H)⁺; $^1$H NMR (500 MHz, DMSO-d$_6$) δ12.55 (br s, 1H), 8.88 (d, 1H), 8.71 (d, 1H), 7.96 (dd, 1H), 7.94 (d, 2H), 7.80–7.76 (m, 4H), 7.48–7.46 (m, 4H), 7.41–7.37 (m, 4H), 7.34–7.29 (m, 4H), 7.05 (d, 1H), 6.19 (d, 1H).

EXAMPLE 70

4-((1,2-diphenylethyl)amino)-N-((4'-fluoro(1,1'-biphenyl)-4-yl)carbonyl)-3-nitrobenzenesulfonamide The desired product was prepared by substituting 1,2-diphenylethanamine for 2,2-dimethylcyclopentylamine in Example 1E. MS (APCI(+)) m/e 613 (M+NH$_4$)⁺; $^1$H NMR (500 MHz, DMSO-d$_6$) δ12.45 (br s, 1H), 8.81 (d, 1H), 8.63 (d, 1H), 7.93 (d, 2H), 7.86 (dd, 1H), 7.81–7.76 (m, 4H), 7.48 (d, 2H), 7.37–7.26 (m, 9H), 7.22–7.18 (m, 1H), 7.03 (d, 1H), 5.19 (ddd, 1H), 3.30 (dd, 1H), 1.61 (dd, 1H).

EXAMPLE 71

4-((1-cyclohexyl-2-(phenylsulfanyl)ethyl)amino)-N-((4'-fluoro(1,1'-biphenyl)-4-yl)carbonyl)-3-nitrobenzenesulfonamide

EXAMPLE 71A 1-cyclohexyl-2-(phenylsulfanyl)ethanol

A room temperature solution of vinylcyclohexane (1.71 g, 15.5 mmol) in dichloromethane (20 mL) was treated with 70% mCPBA (4.90 g, 19.9 mmol), stirred for 3 hours, diluted with diethyl ether (100 mL), washed with saturated NaHCO$_3$ and brine, dried (MgSO$_4$), filtered, and concentrated. The concentrate was dissolved in 1,2-dichloroethane (20 mL), treated with thiophenol (1.8 g, 16.3 mmol), heated to 80° C., stirred for 5 hours, and concentrated. The concentrate was purified by flash column chromatography on silica gel with 20% ethyl acetate/hexanes to provide the desired product. MS (DCI/NH$_3$) m/e 254 (M+NH$_4$).

EXAMPLE 71B 1-cyclohexyl-2-(phenylsulfanyl)ethanamine

The desired product was prepared by substituting Example 71A for Example 7A in Examples 7B and 7C.

EXAMPLE 71C 4-((1-cyclohexyl-2-(phenylsulfanyl)ethyl)amino)-N-((4'-fluoro(1,1'-biphenyl)-4-yl)carbonyl)-3-nitrobenzenesulfonamide The desired product was prepared by substituting Example 71B for Example 7C in Example 7D. MS (ESI(–)) m/e 632 (M–H)⁻; $^1$H NMR (400 MHz, DMSO-d$_6$) δ8.55 (d, 1H), 8.20 (t, 1H), 8.02–7.72 (m, 4H), 7.43–7.10 (m, 11H), 3.20–3.15 (m, 3H), 1.60–1.00 (m, 11H).

EXAMPLE 72

N-(4-(1-cyclohexen-1-yl)benzoyl)-4-((1-cyclohexyl-2-(phenylsulfanyl)ethyl)amino)-3-nitrobenzenesulfonamide The desired product was prepared by substituting Example 71B and Example 9B for Example 7C and Example 1D in Example 7. MS (ESI(–)) m/e 618 (M–H)⁻; $^1$H NMR (400 MHz, DMSO-d$_6$) δ8.70 (m, 1H), 8.53 (d, 1H), 7.73 (m, 3H), 7.49 (m, 2H), 7.28 (m, 2H), 7.20–7.06 (m, 4H), 6.32 (m, 1H), 4.05–3.48 (m, 3H), 2.37 (m, 2H), 2.19 (m, 2H), 2.00–1.10 (m, 15H).

EXAMPLE 73

4-((2E)-2-(3,4-dihydro-1(2H)-naphthalenylidene)hydrazino)-N-((4'-fluoro(1,1'-biphenyl)-4-yl)carbonyl)-3-nitrobenzenesulfonamide

EXAMPLE 73A tert-butyl 2-(4-(aminosulfonyl)-2-nitrophenyl)hydrazinecarboxylate A solution of Example 1D (212 mg, 0.49 mmol) and tert-butylcarbazate (976 mg, 2.3 mmol) in ethanol (5 mL) was heated to reflux, stirred for 16 hours, diluted with ethyl acetate (50 mL), washed with water and brine, dried (MgSO$_4$), filtered, and concentrated. The concentrate was purified by flash column chromatography on silica gel with 1:0.5:98.5/methanol:acetic acid:dichloromethane, then 2:0.5:97.5/methanol:acetic acid:dichloromethane to provide the desired product. MS (ESI(–)) m/e 331 (M–H)⁻.

EXAMPLE 73B 4-((2E)-2-(3,4-dihydro-1(2H)-naphthalenylidene)hydrazino)-3-nitrobenzenesulfonamide A room temperature solution of Example 73A (145 mg, 0.44 mmol) in 1:1 TFA/dichloromethane (10 mL) was stirred for 4 hours and concentrated. The concentrate was dissolved in ethanol (2 mL), treated with 3,4-dihydro-1(2H)-naphthalenone (8.2 mg, 0.06 mmol) and pyridinium p-toluenesulfonate (2 mg, 0.008 mmol), heated to reflux, stirred for 2 hours, cooled to room temperature, and concentrated. The concentrate was purified by flash column chromatography on silica gel with 4% methanol/dichloromethane to provide the desired product. MS (ESI(–)) m/e 359 (M–H)⁻.

EXAMPLE 73C 4-((2E)-2-(3,4-dihydro-1(2H)-naphthalenylidene)hydrazino)-N-((4'-fluoro(1,1'-biphenyl)-4-yl)carbonyl)-3-nitrobenzenesulfonamide The desired product was prepared by substituting Example 73B for Example 1C in Example 1D. MS (ESI(–)) m/e 557 (M–H)⁻; $^1$H NMR (300 MHz, DMSO-d$_6$) δ11.10 (s, 1H), 8.70 (t, 1H), 8.19 (dd, 1H), 8.14 (s, 2H), 7.96 (dt, 2H), 7.80–7.70 (m, 4H), 7.36–7.23 (m, 5H), 2.80 (m, 4H), 1.95 (m, 2H).

EXAMPLE 74

4-((3-cyclohexylpropyl)amino)-N-((4'-fluoro(1,1'-biphenyl)-4-yl)carbonyl)-3-nitrobenzenesulfonamide The desired product was prepared by substituting 3-cyclohexyl-1-propanamine and Example 1D for cyclohexylamine and Example 1C, respectively, in Example 3A. MS (ESI(+)) m/e 540 (M+H)+; $^1$H NMR (300 MHz, DMSO-d$_6$) δ8.59 (d, 1H), 8.47 (t, 1H), 7.95 (m, 3H), 7.75 (dd, 2H), 7.68 (d, 2H), 7.30 (dd, 2H), 7.13 (d, 1H), 3.39 (m, 2H), 1.71–1.55 (m, 6H), 1.29–1.12 (m, 7H), 0.93–0.79 (m, 2H).

EXAMPLE 75

N-((4'-fluoro(1,1'-biphenyl)-4-yl)carbonyl)-3-nitro-4-(2-(phenylsulfanyl)ethoxy)benzenesulfonamide

EXAMPLE 75A

N-((4'-fluoro(1,1'-biphenyl)-4-yl)carbonyl)-4-(2-hydroxyethoxy)-3-nitrobenzenesulfonamide A room temperature solution of NaH (1.52 g, 38.0 mmol) in DMF (100 mL) was treated with ethylene glycol (4.23 mL, 76.0 mmol) over 10 minutes, then treated sequentially with 15-crown-5 (7.54 mL, 38.0 mmol) and Example 1D (3.30 g, 7.6 mmol), and stirred for 30 minutes, quenched with 1M HCl, and extracted with ethyl acetate. The combined extracts were washed with water and brine, dried (Na$_2$SO$_4$), filtered, and concentrated. The concentrate was purified by flash column chromatography on silica gel with ethyl acetate to provide the desired product. MS (ESI(+)) m/e 461 (M+H)+.

EXAMPLE 75B

N-((4'-fluoro(1,1'-biphenyl)-4-yl)carbonyl)-3-nitro-4-(2-(phenylsulfanyl)ethoxy)benzenesulfonamide The desired product was prepared by substituting Example 75A for Example 27A in Example 27B. MS (ESI(−)) m/e 551 (M−H)−; $^1$H NMR (300 MHz, DMSO-d$_6$) δ8.29 (d, 1H), 8.04 (dd, 1H), 7.96 (d, 2H), 7.73 (dd, 2H), 7.61 (d, 2H), 7.40 (d, 2H), 7.39 (s, 1H), 7.32 (d, 2H), 7.28 (d, 2H), 7.21 (dd, 1H), 4.39 (t, 2H), 3.40 (t, 2H).

EXAMPLE 76

N-(4-(1-cyclohexen-1-yl)benzoyl)-3-nitro-4-((2-(phenylsulfonyl)ethyl)amino)benzenesulfonamide

EXAMPLE 76A 2-(phenylsulfonyl)ethanamine

A mixture of ((2-chloroethyl)sulfonyl)benzene (1.02 g, 5.0 mmol), potassium phthalimide (1.02 g, 5.5 mmol), 18-crown-6 (50 mg), and tetrabutylammonium iodide (50 mg) in dioxane was heated to reflux, stirred for 24 hours, cooled to room temperature, diluted with ethyl acetate (100 mL), washed with water and brine, dried (MgSO$_4$), filtered, and concentrated. The concentrate was dissolved in ethanol (10 mL), treated with hydrazine hydrate (1 mL), heated to reflux, stirred for 2 hours, cooled to room temperature, filtered through diatomaceous earth (Celite®), and rinsed with ethyl acetate. The filtrate was treated with ethyl acetate, washed with water and brine, dried (MgSO$_4$), filtered, and concentrated. The concentrate was dissolved in diethyl ether (5 mL), treated with 1M HCl in diethyl ether (10 mL), and filtered. The solid was washed with diethyl ether, suspended in ethyl acetate (80 mL), washed with 2M Na$_2$CO$_3$ and brine, dried (MgSO$_4$), filtered, and concentrated to provide the desired product.

EXAMPLE 76B

N-(4-(1-cyclohexen-1-yl)benzoyl)-3-nitro-4-((2-(phenylsulfonyl)ethyl)amino)benzenesulfonamide The desired product was prepared by substituting Example 76A and Example 9B for Example 7C and Example 1D, respectively, in Example 7D. MS (ESI(−)) m/e 568 (M−H)−; $^1$H NMR (400 MHz, DMSO-d$_6$) δ8.59 (d, 1H), 8.57 (t, 1H), 7.93 (dd, 1H), 7.84 (m, 4H), 7.67 (m, 1H), 7.56 (d, 2H), 7.51 (d, 2H), 7.14 (d, 1H), 6.33 (m, 1H), 3.79 (s, 2H), 2.38 (m, 2H), 2.19 (m, 2H), 1.72 (m, 2H), 1.59 (m, 2H).

EXAMPLE 77

N-(4-(4,4-dimethylcyclohexyl)benzoyl)-3-nitro-4-((2-(phenylsulfanyl)ethyl)amino)benzenesulfonamide

EXAMPLE 77A methyl 4-(4,4-dimethylcyclohexyl)benzoate

The desired product was prepared by substituting 4,4-dimethylcyclohexanone for 4-tert-butylcyclohexanone in Examples 5A–5C. MS (DCI) m/e 247 (M+H)+.

EXAMPLE 77B 3-nitro-4-((2-(phenylsulfanyl)ethyl)amino)benzenesulfonamide

A solution Example 1C (2.36 g, 10.0 mmol), 2-(phenylsulfanyl)ethanamine (1.68 g, 11.0 mmol), and triethylamine in dioxane (5 mL) was heated to 80° C., stirred for 16 hours, diluted with ethyl acetate (100 mL), washed sequentially with 3M HCl, water, and brine, dried (MgSO$_4$), filtered, and concentrated to provide the desired product. MS (DCI) m/e 354 (M+H)+.

EXAMPLE 77C

N-(4-(4,4-dimethylcyclohexyl)benzoyl)-3-nitro-4-((2-(phenylsulfanyl)ethyl)amino)benzenesulfonamide The procedure used in Example 5 was used here to convert the products from Examples 78A and 78B to the title compound. MS (ESI(−)) m/e 566 (M−H)−; $^1$H NMR (400 MHz, DMSO-d$_6$) δ8.80 (t, 1H), 8.61 (d, 1H), 7.91 (dd, 1H), 7.79 (d, 2H), 7.48 (m, 4H), 7.40–7.15 (m, 4H), 3.66 (q, 2H), 3.29 (t, 2H), 2.49 (m, 1H) 1.65–1.20 (m, 8H), 0.96 (s, 3H), 0.93 (s, 3H).

EXAMPLE 78

N-((4'-fluoro(1,1'-biphenyl)-4-yl)carbonyl)-4-((2-((2-methylphenyl)sulfanyl)ethyl)amino)-3-nitrobenzenesulfonamide

EXAMPLE 78A

N-((4'-fluoro(1,1'-biphenyl)-4-yl)carbonyl)-4-((2-hydroxyethyl)amino)-3-nitrobenzenesulfonamide The desired product was prepared by substituting 2-aminoethanol and Example 1D for cyclohexylamine and Example 1C, respectively, in Example 3A. MS (ESI(−)) m/e 458 (M−H)−.

EXAMPLE 78B

N-((4'-fluoro(1,1'-biphenyl)-4-yl)carbonyl)-4-((2-((2-methylphenyl)sulfanyl)ethyl)amino)-3-nitrobenzenesulfonamide The desired product was prepared by substituting 2-methylbenzenethiol and Example 78A for Example 27A and thiophenol, respectively, in Example 27B. MS (ESI(−)) m/e 564 (M−H)⁻; ¹H NMR (300 MHz, DMSO-$d_6$) δ8.54 (t, 1H), 8.52 (d, 1H), 7.95 (d, 2H), 7.87 (dd, 1H), 7.74 (dd, 2H), 7.59 (d, 2H), 7.45–7.37 (m, 1H), 7.28 (t, 2H), 7.23–7.08 (m, 3H), 6.98 (d, 1H), 3.59 (dt, 2H), 3.25 (t, 2H), 2.28 (s, 3H).

EXAMPLE 79

4-((2-((2-chlorophenyl)sulfanyl)ethyl)amino)-N-((4'-fluoro(1,1'-biphenyl)-4-yl)carbonyl)-3-nitrobenzenesulfonamide The desired product was prepared by substituting 2-chlorobenzenethiol and Example 78A for thiophenol and Example 27A, respectively, in Example 27B. MS (ESI(−)) m/e 584 (M−H)⁻; ¹H NMR (300 MHz, DMSO-$d_6$) δ8.60 (t, 1H), 8.55 (d, 1H), 7.98–7.88 (m, 3H), 7.75 (dd, 2H), 7.63 (d, 2H), 7.54 (dd, 1H), 7.45 (dd, 1H), 7.34–7.25 (m, 3H), 7.19 (td, 1H), 7.12 (d, 1H), 3.67 (dt, 2H), 3.28 (t, 2H).

EXAMPLE 80

N-((4'-fluoro(1,1'-biphenyl)-4-yl)carbonyl-3-nitro-4-((2-((2-(trifluoromethyl)phenyl)sulfanyl)ethyl)amino)benzenesulfonamide The desired product was prepared by substituting 2-(trifluoromethyl)benzenethiol and Example 78A for thiophenol and Example 27A, respectively, in Example 27B. MS (ESI(−)) m/e 618 (M−H)⁻; ¹H NMR (300 MHz, DMSO-$d_6$) δ8.52 (d, 1H), 8.50 (t, 1H), 7.95 (d, 2H), 7.90 (dd, 1H), 7.78–7.67 (m, 4H), 7.61 (d, 3H), 7.38 (t, 1H), 7.28 (t, 2H), 7.05 (d, 1H), 3.64 (dt, 2H), 3.38 (t, 2H).

EXAMPLE 81

N-((4'-fluoro(1,1'-biphenyl)-4-yl)carbonyl)-4-((2-((3-methylphenyl)sulfanyl)ethyl)amino)-3-nitrobenzenesulfonamide The desired product was prepared by substituting 3-methylbenzenethiol and Example 78A for thiophenol and Example 27A, respectively, in Example 27B. MS (ESI(−)) m/e 564 (M−H)⁻; ¹H NMR (300 MHz, DMSO-$d_6$) δ8.56 (t, 1H), 8.54 (d, 1H), 7.95 (d, 2H), 7.89 (dd, 1H), 7.75 (dd, 2H), 7.64 (d, 2H), 7.28 (t, 2H), 7.22–7.15 (m, 3H), 7.06–6.96 (m, 2H), 3.62 (dt, 2H), 3.25 (t, 2H), 2.25 (s, 3H).

EXAMPLE 82

N-((4'-fluoro(1,1'-biphenyl)-4-yl)carbonyl)-4-((2-((4-methylphenyl)sulfanyl)ethyl)amino)-3-nitrobenzenesulfonamide The desired product was prepared by substituting 4-methylbenzenethiol and Example 78A for thiophenol and Example 27A in Example 27B. MS (ESI(−)) m/e 564 (M−H)⁻; ¹H NMR (300 MHz, DMSO-$d_6$) δ8.78 (t, 1H), 8.61 (d, 1H), 7.96 (d, 2H), 7.92 (dd, 1H), 7.80 (m, 4H), 7.37–7.24 (m, 4H), 7.20 (d, 1H), 7.07 (d, 2H), 3.64 (dt, 2H), 3.23 (t, 2H), 2.24 (s, 3H).

EXAMPLE 83

N-((4'-fluoro(1,1'-biphenyl)-4-yl)carbonyl)-3-nitro-4-((2-((4-nitrophenyl)sulfanyl)ethyl)amino)benzenesulfonamide The desired product was prepared by substituting 4-nitrobenzenethiol and Example 78A for thiophenol and Example 27A, respectively, in Example 27B. MS (ESI(−)) m/e 595 (M−H)⁻; ¹H NMR (300 MHz, DMSO-$d_6$) δ8.56 (t, 1H), 8.51 (d, 1H), 8.11 (d, 2H), 7.97–7.89 (m, 3H), 7.74 (dd, 2H), 7.64–7.56 (m, 4H), 7.28 (t, 2H), 7.14 (d, 1H), 3.72 (dt, 2H), 3.45 (t, 2H).

EXAMPLE 84

4-((2-((2,4-difluorophenyl)sulfanyl)ethyl)amino)-N-((4'-fluoro(1,1'-biphenyl)-4-yl)carbonyl)-3-nitrobenzenesulfonamide The desired product was prepared by substituting 2,4-difluorobenzenethiol and Example 78A for thiophenol and Example 27A, respectively, in Example 27B. MS (ESI(−)) m/e 586 (M−H)⁻; ¹H NMR (300 MHz, DMSO-$d_6$) δ8.51 (d, 1H), 8.47 (t, 1H), 7.95 (d, 2H), 7.89 (dd, 1H), 7.74 (dd, 2H), 7.62–7.53 (m, 3H), 7.34–7.23 (m, 3H), 7.11–7.03 (m, 1H), 7.00 (d, 1H), 3.57 (dt, 2H), 3.21 (t, 2H).

EXAMPLE 85

4-((2-((2,4-dimethylphenyl)sulfanyl)ethyl)amino)-N-((4'-fluoro(1,1'-biphenyl)-4-yl)carbonyl)-3-nitrobenzenesulfonamide The desired product was prepared by substituting 2,4-dimethylbenzenethiol and Example 78A for thiophenol and Example 27A, respectively, in Example 27B. MS (ESI(−)) m/e 578 (M−H)⁻; ¹H NMR (300 MHz, DMSO-$d_6$) δ8.52 (t, 1H), 8.50 (d, 1H), 7.95 (d, 2H), 7.87 (dd, 1H), 7.73 (dd, 2H), 7.60 (d, 2H), 7.34–7.24 (m, 3H), 7.03–6.92 (m, 3H), 3.54 (dt, 2H), 3.18 (t, 2H), 2.27 (s, 3H), 2.22 (s, 3H).

EXAMPLE 86

N-(4-(2-methyl-1,3-benzoxazol-5-yl)benzoyl)-3-nitro-4-((2-(phenylsulfanyl)ethyl)amino)benzenesulfonamide The desired product was prepared by substituting Example 54B and Example 77B for Example 1B and Example 1C, respectively, in Example 1D. MS (ESI(−)) m/e 587 (M−H)⁻; ¹H NMR (300 MHz, DMSO-$d_6$) δ8.53 (t, 1H), 8.52 (d, 1H), 7.99–7.86 (m, 4H), 7.69 (dd, 2H), 7.65 (d, 2H), 7.40 (d, 2), 7.31 (t, 2H), 7.20 (t, 1H), 7.00 (d, 1H), 3.51 (dt, 2H), 3.28 (t, 2H), 2.63 (s, 3H).

EXAMPLE 87

4-((3,3-diphenylpropyl)amino)-N-((4'-fluoro(1,1'-biphenyl)-4-yl)carbonyl)-3-nitrobenzenesulfonamide The desired product was prepared by substituting 3,3-diphenyl-1-propanamine for 2,2-dimethylcyclopentylamine in Example 1E. MS (APCI(+)) m/e 627 (M+NH$_4$)⁺; ¹H NMR (500 MHz, DMSO-$d_6$) δ12.45 (br s, 1H), 8.65 (d, 1H), 8.61 (t, 1H), 7.97 (d, 2H), 7.93 (dd, 1H), 7.82–7.78 (m, 4H), 7.36–7.33 (m, 6H), 7.30–7.27 (m, 4H), 7.19–7.16 (m, 2H), 7.08 (d, 1H), 4.12 (t, 1H), 3.40 (d, 1H), 3.37 (d, 1H), 2.45 (d, 1H), 2.42 (d, 1H).

EXAMPLE 88

4-((2-(benzylsulfanyl)ethyl)amino)-N-((4'-fluoro(1,1'-biphenyl)-4-yl)carbonyl)-3-nitrobenzenesulfonamide The desired product was prepared by substituting 2-(benzylsulfanyl)ethanamine and Example 1D for cyclohexylamine and Example 1C, respectively, in Example 3A. MS (ESI(−)) m/e 564 (M−H)⁻; ¹H NMR (300 MHz, DMSO-d₆) δ8.54 (d, 1H), 8.52 (t, 1H), 7.96 (d, 2H), 7.90 (dd, 1H), 7.73 (m, 2H), 7.62 (t, 2H), 7.37–7.20 (m, 7H), 7.00 (d, 1H), 3.81 (s, 2H), 3.56 (dt, 2H), 2.70 (t, 2H).

EXAMPLE 89

N-((4'-fluoro(1,1'-biphenyl)-4-yl)carbonyl)-3-nitro-4-(3-(phenylsulfanyl)propoxy)benzenesulfonamide

EXAMPLE 89A

N-((4'-fluoro(1,1'-biphenyl)-4-yl)carbonyl)-4-(3-hydroxypropoxy)-3-nitrobenzenesulfonamide The desired product was prepared by substituting 1,3-propanediol for ethylene glycol in Example 75A. MS (ESI (−)) m/e 473 (M−H)⁻.

EXAMPLE 89B

N-((4'-fluoro(1,1'-biphenyl)-4-yl)carbonyl)-3-nitro-4-(3-(phenylsulfanyl)propoxy)benzenesulfonamide The desired product was prepared by substituting Example 89A for Example 27A in Example 27B. MS (ESI(−)) m/e 565 (M−H)⁻; ¹H NMR (300 MHz, DMSO-d₆) δ8.29 (d, 1H), 8.06 (dd, 1H), 7.96 (d, 2H), 7.74 (dd, 2H), 7.62 (d, 2H), 7.39–7.24 (m, 7H), 7.14 (tt, 1H), 4.29 (t, 2H), 3.13 (t, 2H), 2.02 (m, 2H).

EXAMPLE 90

N-((4'-fluoro(1,1'-biphenyl)-4-yl)carbonyl)-4-(3-((2-methylphenyl)sulfanyl)propoxy)-3-nitrobenzenesulfonamide The desired product was prepared by substituting 2-methylbenzenethiol and Example 89A for thiophenol and Example 27A, respectively, in Example 27B. MS (ESI(−)) m/e 579 (M−H)⁻; ¹H NMR (300 MHz, DMSO-d₆) δ8.31 (d, 1H), 8.06 (dd, 1H), 7.96 (d, 2H), 7.74 (dd, 2H), 7.63 (d, 2H), 7.38 (d, 1H), 7.28 (t, 3H), 7.16 (dd, 2H), 7.05 (td, 1H), 4.31 (t, 2H), 3.10 (t, 2H), 2.26 (s, 3H), 2.04 (m, 2H).

EXAMPLE 91

N-((4'-fluoro(1,1'-biphenyl)-4-yl)carbonyl)-3-nitro-4-(3-((2-(trifluoromethyl)phenyl)sulfanyl)propoxy)benzenesulfonamide The desired product was prepared by substituting 2-trifluoromethylbenzenethiol and Example 89A for thiophenol and Example 27A, respectively, in Example 27B. MS (ESI(−)) m/e 633 (M−H)⁻; ¹H NMR (300 MHz, DMSO-d₆) δ8.31 (d, 1H), 8.06 (dd, 1H), 7.96 (d, 2H), 7.77–7.70 (m, 3H), 7.69–7.54 (m, 4H), 7.38 (m, 2H), 7.28 (t, 2H), 4.30 (t, 2H), 3.24 (t, 2H), 2.05 (m, 2H).

EXAMPLE 92

4-(3-((2,4-difluorophenyl)sulfanyl)propoxy)-N-((4'-fluoro(1,1'-biphenyl)-4-yl)carbonyl)-3-nitrobenzenesulfonamide The desired product was prepared by substituting 2,4-difluorobenzenethiol and Example 89A for thiophenol and Example 27A, respectively, in Example 27B. MS (ESI(−)) m/e 601 (M−H)⁻; ¹H NMR (300 MHz, DMSO-d₆) δ8.28 (d, 1H), 8.07 (dd, 1H), 7.96 (d, 2H), 7.74 (dd, 2H), 7.62 (d, 2H), 7.59–7.48 (m, 1H), 7.38 (d, 1H), 7.35–7.25 (m, 3H), 7.12–7.04 (m, 1H), 4.29 (t, 2H), 3.08 (t, 2H), 1.97 (m, 2H).

EXAMPLE 93

N-((4'-fluoro(1,1'-biphenyl)-4-yl)carbonyl)-4-(neopentylamino)-3-nitrobenzenesulfonamide The desired product was prepared by substituting 2,2-dimethyl-1-propanamine for 2,2-dimethylcyclopentylamine in Example 1E. MS (APCI(+)) m/e 486 (M+H)⁺; ¹H NMR (500 MHz, DMSO-d₆) δ12.45 (br s, 1H), 8.70 (d, 1H), 8.58 (t, 1H), 7.99 (dd, 1H), 7.97 (d, 2H), 7.81 (2d, 4H), 7.38 (d, 1H), 7.34 (t, 2H), 3.30 (d, 2H), 1.02 (s, 9H).

EXAMPLE 94

4-(2-adamantylamino)-N-((4'-fluoro(1,1'-biphenyl)-4-yl)carbonyl)-3-nitrobenzenesulfonamide The desired product was prepared by substituting 2-adamantanamine hydrochloride for 2-aminoborane hydrochloride in Example 13. MS (APCI(+)) m/e 550 (M+H)⁺; ¹H NMR (500 MHz, DMSO-d₆) δ12.45 (br s, 1H), 8.83 (d, 1H), 8.70 (d, 1H), 7.98 (dd, 1H), 7.95 (d, 2H), 7.78 (2d, 4H), 7.32 (t, 2H), 7.30 (d, 1H), 4.01 (m, 1H), 2.04–1.65 (m, 14H).

EXAMPLE 95

4-((1-adamantylmethyl)amino)-N-(4-(1-isopropyl-2-methyl-1H-benzimidazol-5-yl)benzoyl)-3-nitrobenzenesulfonamide

EXAMPLE 95A methyl 4'-fluoro-3'-nitro(1,1'-biphenyl)-4-carboxylate

The desired product was prepared by substituting 4-bromo-1-fluoro-2-nitrobenzene for Example 5A in Example 5B.

EXAMPLE 95B methyl 4-(1-ethyl-2-methyl-1H-benzimidazol-5-yl)benzoate

A room temperature solution of Example 95A (275 mg, 1.0 mmol) in isopropylamine (2 mL) was stirred for 16 hours and concentrated. The concentrate was suspended in dichloromethane (5 mL) and filtered through a pad of silica gel (5 g) with 1:1 dichloromethane/diethyl ether, and concentrated.

The concentrate was dissolved in ethyl acetate (5 mL), treated with 10% Pd/C (100 mg), then stirred under a hydrogen atmosphere for 3 hours. The mixture was filtered through a pad of silica gel (10 g) with ethyl acetate and concentrated.

The concentrate was dissolved in acetic acid (5 mL), treated with acetic anhydride (0.5 mL), heated to reflux, stirred for 16 hours, and concentrated. The concentrate was dissolved in ethyl acetate (50 mL), washed sequentially with saturated NaHCO₃, water, and brine, dried (MgSO₄), filtered, and concentrated. The concentrate was purified by flash column chromatography on silica gel with 2–8% methanol/dichloromethane to provide the desired product. MS (DCI) m/e 309 (M+H)⁺.

EXAMPLE 95C 4-((1-adamantylmethyl)amino)-N-(4-(1-isopropyl-2-methyl-1H-benzimidazol-5-yl)benzoyl)-3-nitrobenzenesulfonamide The desired product was prepared by substituting Example 95B and Example 28A for Example 5C and Example 3A, respectively, in Example 5D. MS (ESI(−)) m/e 640 (M−H)⁻; ¹H NMR (400 MHz, DMSO-d₆) δ 8.52 (d, 1H), 8.39 (t, 1H), 7.95 (d, 2H), 7.89 (dd, 1H), 7.78 (s, 1H), 7.70 (d, 1H), 7.62 (d, 2H), 7.48 (d, 1H), 7.16 (d, 1H), 4.75 (m, 1H), 3.12 (d, 2H), 2.57 (s, 3H), 1.97 (m, 3H), 1.73–1.50 (m, 18H).

EXAMPLE 96

N-((4'-fluoro(1,1'-biphenyl)-4-yl)carbonyl)-3-nitro-4-((2-(phenylsulfanyl)ethyl)amino)benzenesulfonamide The desired product was prepared by substituting 2-(phenylsulfanyl)ethanamine for 2,2-dimethylcyclopentylamine in Example 1E. MS (APCI(+)) m/e 569 (M+NH₄)⁺, ¹H NMR (500 MHz, DMSO-d₆) δ 12.40 (br s, 1H), 8.68 (t, 1H), 8.53 (d, 1H), 7.86 (d, 2H), 7.84 (dd, 1H), 7.69 (2d, 4H), 7.27 (dd, 2H), 7.22 (t, 2H), 7.17 (t, 2H), 7.12 (d, 1H), 7.08 (t, 1H), 3.60–3.56 (m, 2H), 3.21–3.18 (m, 2H).

EXAMPLE 97

N-(4-(1-cyclohexen-1-yl)benzoyl)-3-nitro-4-((2-(phenylsulfanyl)ethyl)amino)benzenesulfonamide The desired product was prepared by substituting Example 9A and Example 77B for Example 5C and Example 3A, respectively, in Example 5D. MS (ESI(−)) m/e 536 (M−H)⁻; ¹H NMR (400 MHz, CD₃OD) δ 8.77 (d, 1H), 7.99 (dd, 1H), 7.77 (d, 2H), 7.47 (d, 2H), 7.38 (m, 2H), 7.20 (m, 2H), 7.14 (m, 1H), 7.02 (d, 1H), 6.27 (m, 1H), 3.67 (t, 2H), 3.27 (t, 2H), 2.41 (m, 2H), 2.22 (m, 2H), 1.79 (m, 2H), 1.67 (m, 2H).

EXAMPLE 98

4-(cyclohexyloxy)-N-((4'-fluoro(1,1'-biphenyl)-4-yl)carbonyl)-3-(trifluoromethyl)benzenesulfonamide

EXAMPLE 98A 4-chloro-3-(trifluoromethyl)benzenesulfonamide

A −10° C. solution of 4-chloro-3-(trifluoromethyl)aniline (5.37 g, 27.5 mmol) in acetic acid (25 mL) and concentrated HCl (30 mL) was treated with a solution of NaNO₂ (2.09 g, 30.3 mmol) in water (10 mL), stirred for 20 minutes, and poured into a saturated solution of SO₂ and CuCl₂.2H₂O (1.70 g, 10 mmol) in acetic acid (80 mL) and water (10 mL). The reaction was stirred for 1 hour, poured into ice, and extracted with dichloromethane. The combined extracts were washed with brine and concentrated. The concentrate was dissolved in saturated NH₄OH (150 mL) and THF (150 mL), stirred for 30 minutes, and extracted with ethyl acetate. The combined extracts were washed with brine, dried (Na₂SO₄), filtered, and concentrated. The concentrate was purified by flash column chromatography on silica gel with 10% ethyl acetate/hexanes to provide the desired product. MS (DCI) m/e 277 (M+NH₄)⁺.

EXAMPLE 98B 4-(cyclohexyloxy)-3-(trifluoromethyl)benzenesulfonamide

A 0° C. solution of KH (8.7 g, 76.0 mmol) in DMF (100 mL) was treated with cyclohexanol (8.02 mL, 76.0 mmol) over 10 minutes, then treated with 18-crown-6 (7.9 g, 30.0 mmol) and Example 98A (3.95 g, 15.2 mmol), heated to 100° C., and stirred for 30 minutes. The reaction was cooled to room temperature, quenched with 1M HCl, and extracted with ethyl acetate. The combined extracts were washed with water and brine, dried (Na₂SO₄), filtered, and concentrated. The concentrate was purified by flash column chromatography on silica gel with 50% ethyl acetate/hexanes to provide the desired product. MS (ESI) m/e 322 (M−H)⁻.

EXAMPLE 98C 4-(cyclohexyloxy)-N-((4'-fluoro(1,1'-biphenyl)-4-yl)carbonyl)-3-(trifluoromethyl)benzenesulfonamide The desired product was prepared by substituting Example 98B for Example 1C in Example 1D. MS (ESI(−)) m/e 520 (M−H)⁻; ¹H NMR (300 MHz, DMSO-d₆) δ 8.28 (d, 1H), 8.20 (dd, 1H), 8.15 (d, 2H), 7.99 (d, 2H), 7.90 (d, 2H), 7.78 (dd, 1H), 7.56 (d, 1H), 4.79 (m, 1H), 2.82 (s, 3H), 1.88 (m, 2H), 1.65 (m, 4H), 1.43 (m, 4H).

EXAMPLE 99

4-(cyclohexyloxy)-N-(4-(2-methyl-1,3-benzothiazol-5-yl)benzoyl)-3-(trifluoromethyl)benzenesulfonamide The desired product was prepared by substituting Example 98B and Example 17A for Example 1C and Example 1B, respectively, in Example 1D. MS (ESI) m/e 573 (M−H)⁻; ¹H NMR (300 MHz, DMSO-d₆) δ 8.19 (d, 1H), 8.08 (m, 2H), 7.99 (d, 2H), 7.73 (m, 4H), 7.31 (d, 1H), 4.65 (m, 1H), 2.82 (s, 3H), 1.87 (m, 2H), 1.75–1.35 (m, 8H).

EXAMPLE 100

4-((cyclohexylmethyl)amino)-N-((4'-fluoro(1,1'-biphenyl)-4-yl)carbonyl)-3-nitro-5-vinylbenzenesulfonamide

EXAMPLE 100A 4-((cyclohexylmethyl)amino)-3-nitro-5-vinylbenzenesulfonamide

The desired product was prepared by substituting tributyl(vinyl)stannane for 2-(tributylstannyl)pyrimidine in Example 26B. MS (ESI) m/e 338 (M−H)⁻.

EXAMPLE 100B 4-((cyclohexylmethyl)amino)-N-((4'-fluoro(1,1'-biphenyl)-4-yl)carbonyl)-3-nitro-5-vinylbenzenesulfonamide The desired product was prepared by substituting Example 100A for Example 1C in Example 1D. MS (ESI) m/e 536 (M−H)⁻; ¹H NMR (300 MHz, DMSO-d₆) δ 8.39 (d, 1H), 7.98–7.93 (m, 3H), 7.74 (dd, 2H), 7.61 (d, 2H), 7.47 (t, 1H), 7.28 (t, 2H), 6.92 (dd, 1H), 5.65 (d, 1H), 5.40 (d, 1H), 3.18 (t, 2H), 1.70–1.53 (m, 5H), 1.25–1.04 (m, 3H), 0.94–0.80 (m, 3H).

EXAMPLE 101

4-((2-((2,6-dimethylphenyl)sulfanyl)ethyl)amino)-N-((4'-fluoro(1,1'-biphenyl)-4-yl)carbonyl)-3-nitrobenzenesulfonamide The desired product was prepared by substituting 2,6-dimethylbenzenethiol and Example 78A for thiophenol and Example 27A, respectively, in Example 27B. MS (ESI) m/e 578 (M–H)⁻; ¹H NMR (300 MHz, DMSO-d₆) δ8.53 (d, 1H), 8.48 (t, 1H), 7.95 (d, 2H), 7.85 (dd, 1H), 7.73 (dd, 2H), 7.62 (d, 2H), 7.28 (t, 2H), 7.19–7.09 (m, 3H), 6.83 (d, 1H), 3.45 (dt, 2H), 2.97 (t, 2H), 2.46 (s, 6H).

EXAMPLE 102

4-((2-((2-bromophenyl)sulfanyl)ethyl)amino)-N-((4'-fluoro(1,1'-biphenyl)-4-yl)carbonyl)-3-nitrobenzenesulfonamide The desired product was prepared by substituting 2-bromobenzenethiol and Example 78A for thiophenol and Example 27A, respectively, in Example 27B. MS (ESI(–)) m/e 628 (M–H)⁻; ¹H NMR (300 MHz, DMSO-d₆) δ8.61 (t, 1H), 8.56 (d, 1H), 7.98–7.89 (m, 3H), 7.75 (dd, 2H), 7.64 (d, 2H), 7.59 (dd, 1H), 7.52 (dd, 1H), 7.36 (td, 1H), 7.28 (t, 2H), 7.15–7.06 (m, 2H), 3.68 (dt, 2H), 3.27 (t, 2H).

EXAMPLE 103

N-((4'-fluoro(1,1'-biphenyl)-4-yl)carbonyl)-4-((2-methyl-2-(phenylsulfanyl)propyl)amino)-3-nitrobenzenesulfonamide

EXAMPLE 103A methyl (phenylsulfanyl)acetate

A room temperature solution of (phenylsulfanyl)acetic acid (8.4 g, 50.0 mmol) in methanol (100 mL) was treated with chlorotrimethylsilane (13 mL, 100.0 mmol), stirred for 16 hours, and concentrated. The concentrate was dissolved in 5:1/hexanes:diethyl ether, filtered through a pad of silica gel (80 g), rinsed with 5:1/hexanes:diethyl ether, and concentrated to provide the desired product.

EXAMPLE 103B methyl 2-methyl-2-(phenylsulfanyl)propanoate

A –78° C. solution of Example 103A (911 mg, 5.0 mmol) and iodomethane (2.2 g, 15.0 mmol) in THF (20 mL) was treated with 1.0M sodium hexamethyldisilazide in THF (11 mL, 11.0 mmol), warmed to room temperature over 16 hours, diluted with hexanes (50 mL), filtered through a pad of silica gel, and concentrated. The concentrate was purified by flash column chromatography on silica gel with 5% ethyl acetate/hexanes to provide the desired product. MS (DCI) m/e 211 (M+H)⁺.

EXAMPLE 103C 2-methyl-2-(phenylsulfanyl)-1-propanol

A –78° C. solution of Example 103B (860 mg, 4.1 mmol) in dichloromethane (10 mL) was treated with 1.0M DIBAL-H in toluene (11 mL), warmed to room temperature over 4 hours, poured into a mixture of 3M HCl (15 mL) and ice (~10 g), and extracted with ethyl acetate (100 mL). The combined extracts were washed with 1M HCl (10 mL) and brine (10 mL), dried (MgSO₄), filtered, and concentrated. The concentrate was purified by flash column chromatography on silica gel with 10–30% ethyl acetate/hexanes to provide the desired product. MS (DCI) m/e 183 (M+H)⁺.

EXAMPLE 103D 2-methyl-2-(phenylsulfanyl)propylamine

The desired product was prepared by substituting Example 103C for Example 7A in Examples 7B and 7C.

EXAMPLE 103E

N-((4'-fluoro(1,1'-biphenyl)-4-yl)carbonyl)-4-((2-methyl-2-(pheylsulfanyl)propyl)amino)-3-nitrobenzenesulfonamide The desired product was prepared by substituting Example 103D for Example 7C in Example 7D. MS (ESI (–)) m/e 578 (M–H)⁻; ¹H NMR (400 MHz, DMSO-d₆) δ8.55 (m, 2H), 8.00 (d, 2H), 7.91 (d, 1H), 7.86 (dd, 1H), 7.78 (m, 4H), 7.51–7.25 (m, 6H), 7.00 (m, 2H), 3.55 (s, 2H), 1.57 (s, 6H).

EXAMPLE 104

N-((4'-fluoro(1,1'-biphenyl)-4-yl)carbonyl)-3-nitro-4-((1-(phenylsulfanyl)cycloheptyl)methoxy)benzenesulfonamide

EXAMPLE 104A methyl 1-(phenylsulfanyl)cycloheptanecarboxylate

A –78° C. solution of Example 104A (911 mg, 5.0 mmol) and 1,6-diiodohexane (845 mg, 2.5 mmol) in THF (70 mL) was treated with 1.0M sodium hexamethyldisilazide in THF (15 mL), warmed to room temperature over 16 hours, diluted with hexanes (50 mL), filtered through a pad of silica gel, and concentrated. The concentrate was purified by flash column chromatography on silica gel with 2–5% ethyl acetate/hexanes to provide the desired product. MS (DCI) m/e 265 (M+H)⁺.

EXAMPLE 104B (1-(phenylsulfanyl)cycloheptyl)methanol

The desired product was prepared by substituting Example 104A for Example 103B in Example 103C. MS (DCI) m/e 237 (M+H)⁺.

EXAMPLE 104C

N-((4'-fluoro(1,1'-biphenyl)-4-yl)carbonyl)-3-nitro-4-((1-(phenylsulfanyl)cycloheptyl)methoxy)benzenesulfonamide A room temperature solution of Example 104B (117 mg 0.50 mmol) and Example 1D (100 mg, 0.23 mmol) in THF (3 mL) was treated with 60% sodium hydride dispersion in oil (80 mg, 2.0 mmol), stirred for 16 hours, diluted with ethyl acetate (50 mL), washed sequentially with 1M HCl (5 mL), water (5 mL), and brine (5 mL), dried (MgSO₄), filtered, and concentrated. The concentrate was purified by flash column chromatography on silica gel with 50% ethyl acetate/hexanes to provide the desired product. MS (ESI(–)) m/e 633 (M–H)⁻; ¹H NMR (400 MHz, DMSO-d₆) δ8.46 (d, 1H), 8.20 (dd, 1H), 8.00 (d, 2H), 7.97 (d, 2H), 7.79 (m, 4H), 7.58 (d, 1H), 7.45 (m, 2H), 7.40–7.28 (m, 5H), 4.06 (s, 2H), 1.90–1.50 (m, 12H).

EXAMPLE 105

4-((1-adamantylmethyl)amino)-N-((2'-methoxy(1,1'-biphenyl)-4-yl)carbonyl)-3-nitrobenzenesulfonamide The desired product was prepared by substituting Example 21A and Example 28A for Example 1B and Example 1C, respectively, in Example 1D. MS (ESI(–)) m/e 574 (M–H)⁻; ¹H NMR (400 MHz, DMSO-d₆) δ8.67 (d, 1H), 8.59 (t, 1H), 7.94 (dd, 1H), 7.89 (dt, 2H), 7.58 (dt, 2H), 7.39

(m, 2H), 7.31 (dd, 1H), 7.24 (dd, 1H), 7.05 (dt, 1H), 3.76 (s, 3H), 3.19 (d, 2H), 2.00–1.55 (m, 15H).

EXAMPLE 106

N-((2'-methoxy(1,1'-biphenyl)-4-yl)carbonyl)-3-nitro-4-((2-(phenylsulfanyl)ethyl)amino)benzenesulfonamide The desired product was prepared by substituting Example 21A and Example 77B for Example 1B and Example 1C, respectively, in Example 1D. MS (ESI(−)) m/e 562 (M−H)$^-$; $^1$H NMR (400 MHz, DMSO-d$_6$) δ8.79 (t, 1H), 8.52 (d, 1H), 7.93 (dd, 1H), 7.89 (d, 2H), 7.58 (d, 2H), 7.40–7.00 (m, 10H), 3.76 (s, 3H), 3.67 (q, 2H), 3.28 (t, 2H).

EXAMPLE 107

N-((4'-fluoro(1,1'-biphenyl)-4-yl)carbonyl)-3-nitro-4-((2-(2-pyridinylsulfanyl)ethyl)amino)benzenesulfonamide The desired product was prepared by substituting 2-pyridinethiol and Example 78A for thiophenol and Example 27A in Example 27B. MS (ESI(−)) m/e 551 (M−H)$^-$; $^1$H NMR (300 MHz, DMSO-d$_6$) δ8.72 (t, 1H), 8.58 (d, 1H), 8.51–8.47 (m, 1H), 8.01 (dd, 1H), 7.96 (d, 2H), 7.76 (dd, 2H), 7.69 (d, 2H), 7.64 (td, 1H), 7.44 (d, 1H), 7.35–7.25 (m, 3H), 7.16–7.09 (m, 1H), 3.72 (dt, 2H), 3.42 (t, 2H).

EXAMPLE 108

3-nitro-N-(4-(1-oxo-2,3-dihydro-1H-inden-5-yl)benzoyl)-4-((2-(phenylsulfanyl)ethyl)amino)benzenesulfonamide

EXAMPLE 108A 3-nitro-4-((2-(phenylsulfanyl)ethyl)amino)-N-(4-(4,4,5,5-tetramethyl-1,3,2-dioxaborolan-2-yl)benzoyl)benzenesulfonamide The desired product was prepared by substituting Example 77B for Example 3A in Example 3C. MS (ESI(−)) m/e 582 (M−H)$^-$.

EXAMPLE 108B 3-nitro-N-(4-(1-oxo-2,3-dihydro-1H-inden-5-yl)benzoyl)-4-((2-(phenylsulfanyl)ethyl)amino)benzenesulfonamide The desired product was prepared by substituting 5-bromo-1-indanone and Example 108A for 4-bromo-1-iodobenzene and Example 3C, respectively, in Example 3D. MS (ESI(−)) m/e 586 (M−H)$^-$; $^1$H NMR (300 MHz, DMSO-d$_6$) δ8.51 (d, 1H), 8.50 (t, 1H), 7.98 (m, 2H), 7.89 (m, 2H), 7.71 (m, 4H), 7.40 (d, 2H), 7.31 (t, 2H), 7.20 (t, 2H), 6.98 (d, 1H), 3.60 (t, 2H), 3.27 (t, 2H), 3.15 (t, 2H), 2.67 (t, 8H).

EXAMPLES 109-1 and 109-2

N-(4-(3,4,4a,5,6,7,8,8a-octahydro-1-naphthalenyl)benzoyl)-3-nitro-4-((2-(phenylsulfanyl)ethyl)amino)benzenesulfonamide and N-(4-(2,3,4,4a,5,6,7,8-octahydro-1-naphthalenyl)benzoyl)-3-nitro-4-((2-(phenylsulfanyl)ethyl)amino)benzenesulfonamide The desired product was prepared by substituting Example and Example 77B for Example 1B and Example 1C, respectively, in Example 1D. MS (ESI(−)) m/e 590 (M−H)$^-$; $^1$H NMR (400 MHz, DMSO-d$_6$) δ8.77 (t, 1H), 8.60 (d, 1H), 7.92 (dd, 1H), 7.80 (d, 2H), 7.36 (d, 2H), 7.40–7.15 (m, 6H), 5.80 (m, 1H), 3.67 (q, 2H), 3.30 (t, 2H), 2.30–2.20 (m, 3H), 1.80–1.60 (m, 5H), 1.40–1.20 (m, 6H).

EXAMPLE 110

N-(4-(1,4,4a,5,6,7,8,8a-octahydro-2-naphthalenyl)benzoyl)-3-nitro-4-((2-(phenylsulfanyl)ethyl)amino)benzenesulfonamide and N-(4-(3,4,4a,5,6,7,8,8a-octahydro-2-naphthalenyl)benzoyl)-3-nitro-4-((2-(phenylsulfanyl)ethyl)amino)benzenesulfonamide The desired product was prepared by substituting Example 57A and Example 78B for Example 5C and Example 3A, respectively, in Example 5D. MS (ESI(−)) m/e 590 (M−H)$^-$; $^1$H NMR (400 MHz, DMSO-d$_6$) δ8.77 (t, 1H), 8.60 (d, 1H), 7.92 (dd, 1H), 7.82 (d, 2H), 7.50 (d, 2H), 7.40–7.15 (m, 6H), 6.25 (m, 1H), 6.18 (m, 1H), 3.67 (q, 2H), 3.30 (t, 2H), 2.40 (m, 3H), 1.70–1.20 (m, 12H).

EXAMPLE 111

N-(4-decahydro-1-naphthalenylbenzoyl)-3-nitro-4-((2-(phenylsulfanyl)ethyl)amino)benzenesulfonamide The desired product was prepared by substituting Example 59A and Example 77B for Example 5C and Example 3A, respectively, in Example 5D. MS (ESI(−)) m/e 592 (M−H)$^-$; $^1$H NMR (400 MHz, DMSO-d$_6$) δ8.77 (t, 1H), 8.60 (d, 1H), 7.92 (dd, 1H), 7.78 (d, 2H), 7.45 (d, 1H), 7.37 (d, 2H), 7.30–7.15 (m, 5H), 3.67 (q, 2H), 3.30 (t, 2H), 2.35 (m, 1H), 1.70–1.20 (m, 16H).

EXAMPLE 112

The desired product was prepared by substituting Example 60A and Example 77B for Example 5C and Example 3A, respectively, in Example 5D. MS (ESI(−)) m/e 592 (M−H)$^-$; $^1$H NMR (400 MHz, DMSO-d$_6$) δ8.77 (t, 1H), 8.60 (d, 1H), 7.92 (dd, 1H), 7.80 (d, 2H), 7.45 (d, 1H), 7.37 (d, 2H), 7.30–7.15 (m, 5H), 3.67 (q, 2H), 3.30 (t, 2H), 2.55 (m, 1H), 1.70–1.20 (m, 16H).

EXAMPLE 113

3-nitro-4-((2-(phenylsulfanyl)ethyl)amino)-N-(4-(5,6,7,8-tetrahydro-1-naphthalenyl)benzoyl)benzenesulfonamide

EXAMPLE 113A methyl 4-(5,6,7,8-tetrahydro-1-naphthalenyl)benzoate

The desired product was prepared by substituting 5,6,7,8-tetrahydro-1-naphthalenol for 4-tert-butylcyclohexanone in Examples 5A and 5B. MS (DCI) m/e 267 (M+H)$^+$.

EXAMPLE 113B 3-nitro-4-((2-(phenylsulfanyl)ethyl)amino)-N-(4-(5,6,7,8-tetrahydro-1-naphthalenyl)benzoyl)benzenesulfonamide The desired product was prepared by substituting Example 113A and Example 77A for Example 5C and Example 3A, respectively, in Example 5D. MS (ESI(−)) m/e 586 (M−H)$^-$; $^1$H NMR (400 MHz, DMSO-d$_6$) δ8.77 (t, 1H), 8.62 (d, 1H), 7.92 (dd, 1H), 7.90 (d, 2H), 7.40–7.18 (m, 10H), 6.95 (dd, 1H), 3.67 (q, 2H), 3.30 (t, 2H), 2.80 (t, 2H), 2.49 (t, 2H), 1.75–1.60 (m, 4H).

EXAMPLE 114A 1-bromo-4-fluoro-2-methoxybenzene

A mixture of 2-bromo-5-fluorophenol (2 mL, 17.8 mmol)), sodium hydride (0.5 g, 20.8 mmol) and iodomethane (5 mL, 82 mmol) in DMF (20 mL) was heated to 60° C., stirred for 16 hours, diluted with ethyl acetate (100 mL), washed sequentially with 1M HCl, water, and brine, dried (MgSO$_4$), filtered, and concentrated to provide the desired product.

EXAMPLE 114B methyl 4'-fluoro-2'-methoxy(1,1'-biphenyl)-4-carboxylate

The desired product was prepared by substituting Example 114A for Example 5A in Example 5B. MS (DCI) m/e 262 (M+H)$^+$.

EXAMPLE 114C 4-((1-adamantyl)methylamino)-4'-fluoro(1,1'-biphenyl)-4-yl)carbonyl)-2'-methoxy-3-nitrobenzenesulfonamide The desired product was prepared by substituting Example 114B and Example 28A for Example 5C and Example 3A, respectively, in Example 5D. MS (ESI(–)) m/e 592 (M–H)$^-$; $^1$H NMR (400 MHz, DMSO-d$_6$) δ8.67 (d, 1H), 8.56 (t, 1H), 7.92 (m, 3H), 7.52 (m, 2H), 7.33 (m, 2H), 7.05 (dd, 1H), 6.86 (m, 1H), 3.59 (s, 3H), 3.18 (d, 2H), 2.46 (s, 6H), 1.98 (m, 3H), 1.72–1.55 (m, 12H).

EXAMPLE 115

4-((2-(phenylsulfanyl)ethyl)amino)-4'-fluoro(1,1'-biphenyl)-4-yl)carbonyl)-2'-methoxy-3-nitrobenzenesulfonamide The desired product was prepared by substituting Example 114B and Example 77B for Example 5C and Example 3A, respectively, in Example 5D. MS (ESI(–)) m/e 580 (M–H)$^-$; $^1$H NMR (400 MHz, DMSO-d$_6$) δ8.79 (t, 1H), 8.52 (d, 1H), 7.93 (dd, 1H), 7.89 (d, 2H), 7.58 (d, 2H), 7.40–7.19 (m, 7H), 7.05 (dd, 1H), 6.86 (m, 1H), 3.78 (s, 3H), 3.67 (q, 2H), 3.28 (t, 2H).

EXAMPLE 116

4-((2-(phenylsulfanyl)ethyl)amino)-4'-fluoro(1,1'-biphenyl)-4-yl)carbonyl)-2'-hydroxy-3-nitrobenzenesulfonamide A –78° C. solution of Example 115 (20 mg, 5.0 mmol) in dichloromethane (1 mL) was treated with 1.0M boron tribromide in dichloromethane (0.2 mL, 0.2 mmol), warmed to room temperature over 16 hours, diluted with methanol (5 mL), and concentrated. The concentrate was purified by flash column chromatography on silica gel with 50–100% ethyl acetate/hexanes to provide the desired product. MS (ESI(–)) m/e 566 (M–H)$^-$; $^1$H NMR (400 MHz, DMSO-d$_6$) δ10.25 (s, 1H) 8.79 (t, 1H), 8.52 (d, 1H), 7.93 (dd, 1H), 7.89 (d, 2H), 7.61 (d, 2H), 7.40–7.19 (m, 6H), 6.73 (m, 2H), 3.67 (q, 2H), 3.28 (t, 2H).

EXAMPLE 117

4-((2-(phenylsulfanyl)ethyl)amino)-(1,8'-quinoline)-4-yl)carbonyl)-2'-hydroxy-3-nitrobenzenesulfonamide The desired product was prepared by substituting 8-bromoquinoline and Example 108A for 4-bromo-1-iodobenzene and Example 3C, respectively, in Example 3D. MS (ESI(–)) m/e 583 (M–H)$^-$; $^1$H NMR (400 MHz, DMSO-d$_6$) δ8.89 (dd, 1H), 8.79 (t, 1H), 8.65 (d, 1H), 8.45 (dd, 1H), 8.05 (dd, 1H), 7.99 (d, 2H), 7.83–7.70 (m, 4H), 7.59 (dd, 1H), 7.38 (d, 2H), 7.30–7.19 (m, 4H), 3.69 (q, 2H), 3.28 (t, 2H).

EXAMPLE 118

4-(((1R)-5-(dimethylamino)-1-((phenylthio)methyl)pentyl)amino)-N-((2'-methoxy-4'-(3-morpholin-4-ylpropyl)-1,1'-biphenyl-4-yl)carbonyl)-3-nitrobenzenesulfonamide A solution of Example 194 (128 mg, 0.153 mmol) and 37% aqueous formaldehyde (0.15 mL) in 1:1 methanol/dichloromethane (4 mL) at room temperature was treated with MP-sodium cyanoborohydride (0.32 g, 0.767 mmol (2.42 mmol/g) and stirred for 6 hours at room temperature. The resin was filtered and washed with dichloromethane and the resulting solution was concentrated. The concentrate was purified by reverse phase preparative HPLC (using a C-18 column and a solvent system increasing in gradient from 10% to 100% acetonitrile/water containing 0.1% TFA) to provide the desired product. MS (ESI(–)) m/e 788 (M–H)$^-$; $^1$H NMR (500 MHz, DMSO-d$_6$) δ10.4 (br s, 1H), 9.5 (br s, 1H), 8.56 (d, 1H), 8.32 (d, 1H), 7.92 (d, 2H), 7.90 (dd, 1H), 7.59 (d, 2H), 7.28–7.23 (m, 4H), 7.17–7.09 (m, 3H), 7.01 (d, 1H), 6.93 (dd, 1H), 4.16–4.10 (m, 1H), 3.97 (br s, 2H), 3.78 (s, 3H), 3.46 (br s, 2H), 3.41–3.33 (m, 2H), 3.16–3.12 (m, 2H), 3.08 (br s, 2H), 2.99 (br s, 2H), 2.73 (s, 3H), 2.72 (s, 3H), 2.69 (t, 2H), 2.06–2.01 (m, 2H), 1.82–1.76 (m, 2H), 1.60 (quint, 2H), 1.39–1.32 (m, 2H).

EXAMPLE 119

N-(4-(4,4-dimethylpiperidin-1-yl)benzoyl)-4-(((1R)-3-morpholin-4-yl-1-((phenylthio)methyl)propyl)amino)-3-nitrobenzenesulfonamide

EXAMPLE 119A ethyl 4-(4,4-dimethyl-2,6-dioxopiperidin-1-yl)benzoate

A solution of ethyl 4-aminobenzoate (1.0 g, 6.1 mmol) and 3,3-dimethylglutaric anhydride (0.95 g, 6.7 mmol) in 1,2-dichloroethane (15 mL) was heated to reflux for 1 hour, cooled to room temperature, and treated dropwise with acetyl chloride (0.88 mL, 12.5 mmol). The mixture was heated to reflux for 1 hour, cooled to room temperature, diluted with dichloromethane, washed sequentially with water, saturated NaHCO$_3$, and brine, dried (MgSO$_4$), filtered, and concentrated to provide the desired product. MS(DCI(+)) m/e 290 (M+H)$^+$.

EXAMPLE 119B ethyl 4-(4,4-dimethylpiperidin-1-yl)benzoate

Example 119A was processed according to the procedure described in *Liebigs Ann. Chem.* 1979, p. 461 to provide the desired product. MS(DCI(+)) m/e 262 (M+H)$^+$.

EXAMPLE 119C 4-(4,4-dimethylpiperidin-1-yl)benzoic acid

A solution of Example 119B (260 mg, 1.0 mmol) and LiOH.H$_2$O (158 mg, 4.0 mmol) in THF (19 mL), water (5 mL), and methanol (5 mL) was heated to 75° C. for 18 hours, cooled to room temperature, concentrated, and adjusted to pH 3–4 with 1N HCl. The precipitate was collected by filtration, washed with water, and dried under vacuum to provide the desired product. MS(DCI(+)) m/e 234 (M+H)$^+$.

EXAMPLE 119D

N-(4-(4,4-dimethylpiperidin-1-yl)benzoyl)-4-(((1R)-3-morpholin-4-yl-1-((phenylthio)methyl)propyl)amino)-3-nitrobenzenesulfonamide The desired product was prepared by substituting Examples 119C and 463A for Examples 1B and 1C, respectively, in Example 1D. MS(ESI(+)) m/e 682 (M+H)$^+$; $^1$H NMR (300 MHz, DMSO-d$_6$) δ8.52 (d, 1H), 8.40 (d, 1H), 7.82 (dd, 1H), 7.72 (d, 2H), 7.28 (dd, 2H), 7.27–7.07 (m, 4H), 6.89 (d, 2H), 4.15 (s, 1H), 3.54 (s, 4H), 3.30–3.25 (m, 6H), 2.50–2.32 (m, 6H), 1.95–1.82 (m, 1H), 2.08–1.98 (m, 1H), 1.38 (t, 4H), 0.94 (s, 6H).

EXAMPLE 120

4-(((1R)-5-amino-1-((phenylthio)methyl)pentyl)amino)-N-(4-(2-azaspiro(4.4)non-2-yl)benzoyl)-3-nitrobenzenesulfonamide

EXAMPLE 120A methyl 4-(1,3-dioxo-2-azaspiro(4.4)non-2-yl)benzoate

The desired product was prepared by substituting methyl 4-aminobenzoate and 2-oxapiro(4.4)nonane-1,3-dione for ethyl-4-aminobenzoate and 3,3-dimethylglutaric anhydride, respectively, in Example 119A. MS(DCI(+)) m/e 288 (M+H)$^+$.

EXAMPLE 120B methyl 4-(2-azaspiro(4.4)non-2-yl)benzoate

The desired product was prepared by substituting Example 120A for Example 119A in Example 119B. MS(DCI(+)) m/e 260 (M+H)$^+$.

EXAMPLE 120C 4-(2-azaspiro(4.4)non-2-yl)benzoic acid

The desired product was prepared by substituting Example 120B for Example 119B in Example 119C. MS(DCI(+)) m/e 246 (M+H)$^+$.

EXAMPLE 120D tert-butyl(5R)-5-((4-(((4-(2-azaspiro(4.4)non-2-yl)benzoyl)amino)sulfonyl)-2-nitrophenyl)amino)-6-(phenylthio)hexylcarbamate The desired product was prepared by substituting Examples 120C and 124C for Examples 1B and 1C, respectively, in Example 1D. MS(ESI(−)) m/e 750 (M−H)$^−$.

EXAMPLE 120E 4-(((1R)-5-amino-1-((phenylthio)methyl)pentyl)amino)-N-(4-(2-azaspiro(4.4)non-2-yl)benzoyl)-3-nitrobenzenesulfonamide A solution of Example 120D (24 mg, 0.03 mmol) and 4N HCl (0.5 mL) in dioxane at room temperature was stirred for 4 hours, partially concentrated, and treated with diethyl ether. The precipitate was filtered, washed with diethyl ether, and was dried under vacuum to provide the desired product. MS(ESI(+)) m/e 652 (M+H)$^+$; $^1$H NMR (300 MHz, DMSO-d$_6$) δ11.89 (s, 1H), 8.52 (d, 1H), 8.31 (d, 1H), 7.86 (dd, 1H), 7.74 (d, 2H), 7.70 (s, 2H), 7.24–7.07 (m, 6H), 6.51 (d, 2H), 4.10 (m, 1H), 3.57 (s, 4H), 3.35 (m, 4H), 3.18 (s, 2H), 2.74 (m, 2H), 1.86 (t, 2H), 1.76 (m, 2H), 1.65 (m, 4H), 1.55 (t, 4H).

EXAMPLE 121

4-(((1R)-3-(dimethylamino-1-((phenylthio)methyl)propyl)amino)-N-(4-(4,4-dimethylpiperidin-1-yl)benzoyl)-3-nitrobenzenesulfonamide The desired product was prepared by substituting Examples 119C and 122G for Examples 1B and 1C, respectively, in Example 1D. MS(ESI(+)) m/e 640 (M+H)$^+$; $^1$H NMR (300 MHz, DMSO-d$_6$) δ8.46 (d, 1H), 8.23 (d, 1H), 7.81 (dd, 1H), 7.72 (d, 2H), 7.82–7.15 (m, 5H), 6.91 (d, 2H), 6.82 (d, 2H), 4.08 (m, 1H), 3.35 (m, 2H), 3.21 (t, 4H), 2.9 (m, 2H), 2.56 (s, 6H), 2.04 (m, 2H), 1.39 (t, 4H), 0.94 (s, 6H).

EXAMPLE 122

4-(((1R)-3-(dimethylamino)-1-((phenylthio)methyl)propyl)amino)-N-((2'-methoxy-4'-(3-morpholin-4-ylpropyl)-1,1'-biphenyl-4-yl)carbonyl)-3-nitrobenzenesulfonamide

EXAMPLE 122A tert-butyl(3R)-3-(((9H-fluoren-9-ylmethoxy)carbonyl)amino)-4-hydroxybutanoate A solution of Fmoc-D-Asp(OtBu)-OH (9.0 g, 21.8 mmol) and N,N-diisopropylethylamine (4.6 mL) in THF (100 mL) at −40° C. was treated with isobutyl chloroformate (3.1 mL, 24.1 mmol), warmed to 0° C. over 30 minutes, cooled to −20° C., and treated slowly with sodium borohydride (1.64 g, 43.6 mmol) and methanol (10 mL). The reaction was gradually warmed to room temperature over 2 hours, diluted with ethyl acetate (200 mL), washed with water (100 mL) and brine (50 mL), dried (MgSO$_4$), filtered, and concentrated to provide the desired product. MS (ESI(+)) m/e 398 (M+H)$^+$.

EXAMPLE 122B tert-butyl(3R)-3-(((9H-fluoren-9-ylmethoxy)carbonyl)amino)-4-(phenylthio)butanoate The desired product was prepared by substituting Example 122A for Example 27A in Example 27B. MS (ESI(+)) m/e 490 (M+H)$^+$.

EXAMPLE 122C 4-fluoro-3-nitrobenzenesulfonamide

A mixture of 2-fluoronitrobenzene (141 g, 1.0 mol) and chlorosulfonic acid (300 mL) was heated to 60° C. for 10 hours, cooled to room temperature, and slowly poured over ice (about 1 kg). The mixture was extracted with ether (4 L) and the combined extracts were concentrated to a final volume of approximately 2 L. The solution was cooled to −40° C. and treated with concentrated ammonium hydroxide (300 mL) at such a rate as to maintain an internal temperature of <10° C. The mixture was separated and the aqueous phase was extracted with ethyl acetate (2 L). The combined organic phase and extracts were washed with 4M HCl (300 mL) and brine (100 mL), dried (MgSO$_4$), filtered, and concentrated. The concentrate was crystallized from ethyl acetate/hexane to provide the desired product. Concentration of the mother liquor and crystallization of the concentrate provided additional product. MS (ESI(−)) m/e 219 (M−H)$^-$.

EXAMPLE 122D tert-butyl (3R)-3-((4-(aminosulfonyl)-2-nitrophenyl) amino)-4-(phenylthio)butanoate A mixture of Example 122B (600 mg, 1.23 mmol), Example 122C (298 mg, 1.34 mmol), and N,N-diisopropylethylamine (3 mL) in DMF (3 mL) at 60° C. was stirred for 12 hours, diluted with ethyl acetate (100 mL), washed with water (45 mL) and brine (10 mL), dried (MgSO$_4$), filtered, and concentrated. The concentrate was purified by flash column chromatography on silica gel with 30% ethyl acetate/dichloromethane to provide the desired product. MS (ESI(+)) m/e 468 (M+H)$^+$.

EXAMPLE 122E (3R)-3-((4-(aminosulfonyl)-2-nitrophenyl)amino)-4-(phenylthio)butanoic acid A mixture of Example 122D and 4M HCl in 1,4-dioxane (10 mL) was stirred at 50° C. for 5 hours and concentrated to provide the desired product. MS (ESI(+)) m/e 412 (M+H)$^+$.

EXAMPLE 122F (3R)-3-((4-(aminosulfonyl)-2-nitrophenyl)amino)-N,N-dimethyl-4-(phenylthio)butanamide A solution of Example 122E (411 mg, 1 mmol), 2M dimethylamine in THF (1 mL), EDCI (296 mg, 1.5 mmol), and DMAP (10 mg) in DMF (10 mL) at room temperature was stirred for 16 hours, diluted with ethyl acetate (200 mL), washed sequentially with 1N HCl (50 mL), water (50 mL), and brine (20 mL), dried (MgSO$_4$), filtered, and concentrated. The concentrate was purified by flash column chromatography on silica gel with 100% ethyl acetate to provide the desired product. MS (ESI(+)) m/e 439 (M+H)$^+$.

EXAMPLE 122G 4-(((1R)-3-(dimethylamino)-1-((phenylthio)methyl) propyl)amino)-3-nitrobenzenesulfonamide A mixture of Example 122F (4.06 g, 9.25 mmol) and 1M borane in THF (20 mL) at room temperature was stirred for 16 hours, treated with methanol (5.0 mL) and concentrated HCl (2 mL), stirred at 80° C. for 3 hours, cooled to room temperature, adjusted to pH>7 with 4M sodium carbonate, diluted with ethyl acetate (150 mL), washed with water (50 mL) and brine (10 mL), dried (MgSO$_4$), filtered, and concentrated. The concentrate was purified by flash column chromatography on silica gel with 20% methanol/dichloromethane to provide the desired product. MS (ESI (+)) m/e 425 (M+H)$^+$.

EXAMPLE 122H 4-formyl-2-methoxyphenyl trifluoroacetate

A solution of vanillin (5.0 g, 32.9 mmol), N,N-phenyl (trifluoromethanesulfonimide (36 mmol), and triethylamine (36 mmol) in dichloromethane (100 mL) was stirred at room temperature overnight. The reaction mixture was diluted with ether (100 mL), filtered through silica gel (100 g), rinsed with a mixed solvent of ether/dichloromethane and concentrated. The concentrate was purified by flash column chromatography on silica gel with 10% ethyl acetate/ hexanes to provide the desired product. MS (DCI) m/e 285 (M+H)$^+$.

EXAMPLE 122I methyl 4'-formyl-2'-methoxy-1,1'-biphenyl-4-carboxylate

The desired product was prepared by substituting Example 122H for Example 5A in Example 5B. MS (DCI (+)) m/e 288 (M+H)$^+$.

EXAMPLE 122J methyl 4'-((1E)-3-tert-butoxy-3-oxoprop-1-enyl)-2'-methoxy-1,1'-biphenyl-4-carboxylate A mixture of (tert-butoxycarbonylmethylene) triphenylphospharane (2.25 g, 5.5 mmol) and Example 122I (1.35 g, 5.0 mmol) in THF (20 mL) at room temperature was stirred for 3 hours, diluted with hexanes (30 mL), and filtered through silica gel (50 g). The silica gel was rinsed with 50% dichloromethane/ether and the combined solutions were concentrated to provide the desired product. MS (ESI(−)) m/e 367 (M−H)$^-$.

EXAMPLE 122K methyl 4'-(3-tert-butoxy-3-oxopropyl)-2'-methoxy-1, 1'-biphenyl-4-carboxylate The desired product was prepared by substituting Example 122J for Example 5B in Example 5C. MS (ESI(−)) m/e 369 (M−H)$^-$.

EXAMPLE 122L 3-(2-methoxy-4'-(methoxycarbonyl)-1,1'-biphenyl-4-yl)propanoic acid The desired product was prepared by substituting Example 122K for Example 122D in Example 122E.

EXAMPLE 122M methyl 2'-methoxy-4'-(3-morpholin-4-yl-3-oxopropyl)-1,1'-biphenyl-4-carboxylate A solution of Example 122L (500 mg, 1.59 mmol) in dichloromethane (5 mL) was treated with 2M oxalyl chloride in dichloromethane (1 mL) and a drop of DMF, stirred for 1 hour, concentrated under vacuum, and dissolved in dichloromethane (5 mL). The mixture was treated with morpholine (0.5 mL) and the resulted slurry was filtered through silica gel (10 g). The silica gel was rinsed with ethyl acetate and concentrated. The concentrate was purified by flash column chromatography on silica gel with 30% ethyl acetate/hexanes to provide the desired product. MS (ESI(+)) m/e 384 (M+H)$^+$.

EXAMPLE 122N methyl 2'-methoxy-4'-(3-morpholin-4-ylpropyl)-1,1'-biphenyl-4-carboxylate The desired product was prepared by substituting Example 122M for Example 122F in Example 122G. MS (ESI(+)) m/e 369 (M+H)$^+$.

EXAMPLE 122O

2'-methoxy-4'-(3-morpholin-4-ylpropyl)-1,1'-biphenyl-4-carboxylic acid

The desired product was prepared by substituting Example 122N for Example 1A in Example 1B.

EXAMPLE 122P 4-(((1R)-3-(dimethylamino)-1-((phenylthio)methyl)propyl)amino)-N-((2'-methoxy-4'-(3-morpholin-4-ylpropyl)-1,1'-biphenyl-4-yl)carbonyl)-3-nitrobenzenesulfonamide The desired product was prepared by substituting Examples 122O and 122G for Example 1B and 1C, respectively, in Example 1D. MS (ESI(−)) m/e 760 (M−H)−; $^1$H NMR (500 MHz, CD$_3$OD) δ8.73 (d, 1H), 8.31 (d, 1H), 7.99 (dd, 1H), 7.86 (d, 2H), 7.60 (d, 2H), 7.28–7.25 (m, 3H), 7.09 (m, 4H), 7.00 (s, 1H), 6.94 (d, 1H), 4.22 (m, 1H), 4.03 (m, 2H), 3.81 (s, 3H), 3.74 (t, 1H), 3.58 (t, 1H), 3.49 (m, 2H), 3.42 (dd, 1H), 3.25 (m, 3H), 3.18 (m, 3H), 3.14 (m, 1H), 2.88 (s, 6H), 2.78 (t, 2H), 2.30 (m, 1H), 2.22 (m, 1H), 2.14 (m, 2H).

EXAMPLE 123

4-(((1R)-5-amino-1-((phenylthio)methyl)pentyl)amino)-N-(4-(4-ethyl-4-methylpiperidin-1-yl)benzoyl)-3-nitrobenzenesulfonamide

EXAMPLE 123A methyl 4-(4-ethyl-4-methyl-2,6-dioxopiperidin-1-yl)benzoate

The desired product was prepared by substituting 3-ethyl-3-methylglutaric anhydride and methyl 4-aminobenzoate for 3,3-dimethylglutaric anhydride and ethyl 4-aminobenzoate, respectively, in Example 119A. MS(DCI(+)) m/e 290 (M+H)+.

EXAMPLE 123B methyl 4-(4-ethyl-4-methylpiperidin-1-yl)benzoate

The desired product was prepared by substituting Example 123A for Example 119A in Example 119B. MS(DCI(+)) m/e 262 (M+H)+.

EXAMPLE 123C 4-(4-ethyl-4-methylpiperidin-1-yl)benzoic acid

The desired product was prepared by substituting Example 123B for Example 119B in Example 119C. MS(DCI(+)) m/e 248 (M+H)+.

EXAMPLE 123D tert-butyl (5R)-5-((4-(((4-(4-ethyl-4-methylpiperidin-1-yl)benzoyl)amino)sulfonyl)-2-nitrophenyl)amino)-6-(phenylthio)hexylcarbamate The desired product was prepared by substituting Examples 123C and 124C for Examples 1B and 1C, respectively, in Example 1D. MS (ESI(−)) m/e 752 (M−H)−.

EXAMPLE 123E 4-(((1R)-5-amino-1-((phenylthio)methyl)pentyl)amino)-N-(4-(4-ethyl-4-methylpiperidin-1-yl)benzoyl)-3-nitrobenzenesulfonamide The desired product was prepared by substituting Example 123D for Example 120D in Example 120E. MS (ESI(−)) m/e 652 (M−H)−; $^1$H NMR (300 MHz, DMSO-d$_6$) δ12.0 (s, 1H), 8.54 (d, 1H), 8.31 (d, 1H), 7.86 (dd, 1H), 7.75 (d, 2H), 7.10–7.25 (m, 6H), 6.94 (d, 2H), 6.82 (d, 2H), 4.10 (m, 1H), 3.50 (m, 4H), 3.37 (m, 2H), 3.21 (m, 2H), 2.72 (m, 2H), 1.75 (m, 2H), 1.52 (m, 2H), 1.38 (m, 4H), 1.29 (m, 2H), 0.90 (s, 3H), 0.80 (t, 3H).

EXAMPLE 124

N-(4-(8-azaspiro(4.5)dec-8-yl)benzoyl)-4-(((1R)-5-(dimethylamino)-1-((phenylthio)methyl)pentyl)amino)-3-nitrobenzenesulfonamide

EXAMPLE 124A tert-butyl N-((5R)-5-(((9H-fluoren-9-ylmethoxy)carbonyl)amino)-6-hydroxyhexyl)carbamate A solution of Fmoc-D-Lys(BOC)—OH (2.102 g, 4.5 mmol) in DME (5 mL) at −15° C. was treated successively with N-methylmorpholine (0.56 mL, 5.0 mmol) and isobutyl chloroformate (0.7 mL, 5 mmol), stirred for 2 minutes, and filtered. The filter cake was washed with DME (3×5 mL) and the combined filtrate and washings were cooled to −5° C. and treated with NaBH$_4$ (0.3 g, 7.5 mmol) in water (5 mL) and additional water(250 mL) immediately afterwards. The mixture was stirred for 15 minutes and filtered. The filter cake was washed with water and dried to provide the desired product. MS (APCI) m/e 455 (M+H)+.

EXAMPLE 124B tert-butyl N-((5R)-5-(((9H-fluoren-9-ylmethoxy)carbonyl)amino)-6-(phenylthio)hexyl)carbamate A mixture of Example 124A (2.0 g, 4.4 mmol), PhSSPh (1.44 g, 6.6 mmol), and n-Bu$_3$P (1.65 mL, 6.6 mmol) in toluene (50 mL) at 80° C. was stirred for 18 hours and concentrated. The concentrate was purified by flash column chromatography on silica gel with 25% ethyl acetate/hexanes. MS (APCI) m/e 547 (M+H)+.

EXAMPLE 124C tert-butyl (5R)-5-((4-(aminosulfonyl)-2-nitrophenyl)amino)-6-(phenylthio)hexylcarbamate A solution of Example 124B (0.65 g, 1.2 mmol), Example 122C (0.262 g, 1.2 mmol), and diisopropylethylamine (0.5 mL) in DMSO (5 mL) at 50° C. was stirred for 18 hours, diluted with ethyl acetate (100 mL), washed with water and brine, dried (Na$_2$SO$_4$), filtered, and concentrated. The concentrate was purified by flash column chromatography on silica gel with 50% ethyl acetate/hexanes to provide the desired product. MS (ESI) m/e 523 (M−H)−.

EXAMPLE 124D 9H-fluoren-9-ylmethyl (1R)-5-(dimethylamino)-1-((phenylthio)methyl)pentylcarbamate A solution of Example 124B (1.36 g, 2.4 mmol) in dichloromethane (5 mL) and TFA (5 mL) was stirred at room temperature for 30 minutes, and concentrated. The concentrate was dissolved in acetic acid (1 mL) and 37% aqueous formaldehyde (5 mL), treated with 1M NaCNBH$_3$ in THF (10 mL), stirred for 30 minutes, adjusted to pH 7 with aqueous NaHCO$_3$, and extracted with ethyl acetate(3×100 mL). The combined extracts were washed with water and brine, dried (Na$_2$SO$_4$), filtered, and concentrated. The concentrate was purified by flash column chromatography on silica gel with 48:48:4 ethyl acetate/dichloromethane/methanol to provide the desired product. MS (ESI) m/e 475 (M+H)$^+$.

EXAMPLE 124E 4-(((1R)-5-(dimethylamino)-1-((phenylthio)methyl) pentyl)amino)-3-nitrobenzenesulfonamide A solution of Example 124D (1.2 g, 2.5 mmol), Example 122C (0.66 g, 3.0 mmol), and diisopropylethylamine (1.0 mL) in DMSO (10 mL) was heated to 50° C., stirred for 18 hours, diluted with ethyl acetate (100 mL), washed with water and brine, dried (Na$_2$SO$_4$), filtered, and concentrated. The concentrate was purified by flash column chromatography on silica gel with 50% ethyl acetate/dichloromethane to provide the desired product. MS (ESI) m/e 453, 451 (M+H)$^+$, (M−H)$^-$.

EXAMPLE 124F

N-(4-(8-azaspiro(4.5)dec-8-yl)benzoyl)-4-(((1R)-5-(dimethylamino)-1-((phenylthio)methyl)pentyl) amino)-3-nitrobenzenesulfonamide A mixture of Example 124E (35 mg, 0.07 mmol), Example 257C (35 mg, 0.135 mmol), EDCI (50 mg, 0.28 mmol), and DMAP (50 mg, 0.35 mmol) in t-butanol (0.5 mL) and 1,2-dichloroethane (0.5 mL) at room temperature was stirred for 18 hours and concentrated. The concentrate was dissolved in 1:1 DMSO/methanol (1 mL) and purified by preparative HPLC (using a C-18 column and a solvent system increasing in gradient from 10–95% acetontrile/water containing 0.1% TFA). The purified product was dissolved in 1:1 dichloromethane/methanol, treated with 2M HCl in diethyl ether (1 mL), and concentrated to provide the hydrochloride salt. MS (ESI) m/e 694 (M+H)$^+$, m/e 692 (M−H)$^-$. $^1$H NMR (500 MHz, DMSO-d$_6$) δ10.01 (m, 1H), 8.54 (d, 1H), 8.30 (d, 1H), 7.87 (dd, 1H), 7.75 (d, 2H), 7.27–7.09 (m, 6H), 6.94 (d, 2H), 4.12 (m, 1H), 3.34 (m, 4H), 3.20 (d, 2H), 2.95 (m, 2H), 2.69 (s, 3H), 2.68 (s, 3H), 1.78 (m, 2H), 1.60 (m, 4H), 1.52–1.34 (m, 12H).

EXAMPLE 125

4-((4-amino-1-((phenylthio)methyl)butyl)amino)-N-((4'-fluoro-1,1'-biphenyl-4-yl)carbonyl)-3-nitrobenzenesulfonamide A mixture of Example 384E (53 mg), triphenylphosphine (131 mg), and water (50 mg) in THF (3 mL) was heated to 60° C. for 24 hours, cooled to room temperature, treated with 1M lithium hydroxide (2 mL), and stirred for 48 hours. The mixture was treated with 4M HCl (1 mL) and silica gel (2.0 g) and concentrated. The concentrate was purified by flash column chromatography on silica gel with 10–30% methanol/dichloromethane to provide the desired product. MS (ESI(−)) m/e 607 (M−H)$^-$; $^1$H NMR (300 MHz, DMSO-d$_6$) δ8.57 (d, 1H), 8.31 (d, 1H), 7.98 (d, 2H), 7.91 (dd, 1H), 7.70 (m, 4H), 7.57 (m, 3H), 7.32 (m, 2H), 7.23 (dd, 2H), 7.13 (m, 4H), 4.20 (m, 1H), 3.37 (m, 2H), 2.78 (m, 2H), 1.81 (m, 2H), 1.60 (m, 2H).

EXAMPLE 126

(3R)-3-((4-((((2'-methoxy-4'-(3-(neopentylamino)-3-oxopropyl)-1,1'-biphenyl-4-yl)carbonyl)amino) sulfonyl)-2-nitrophenyl)amino)-N,N-dimethyl-4-(phenylthio)butanamide

EXAMPLE 126A

4'-(3-tert-butoxy-3-oxopropyl)-2'-methoxy-1,1'-biphenyl-4-carboxylic acid

A mixture of Example 122K (3.5 g), and potassium trimethylsilanolate (1.70 g) in THF (250 mL) at room temperature was stirred for 18 hours, diluted with ethyl acetate (400 mL) and water (50 mL), and adjusted to pH 3 with 2N HCl. The organic phase was washed with water (150 mL) and brine (100 mL), dried (MgSO$_4$), filtered, and concentrated to provide the desired product. MS (DCI (+)) m/e 357 (M+H)$^+$.

EXAMPLE 126B tert-butyl 3-(4'-((((4-(((1R)-3-(dimethylamino)-3-oxo-1-((phenylthio)methyl)propyl)amino)-3-nitrophenyl)sulfonyl)amino)carbonyl)-2-methoxy-1,1'-biphenyl-4-yl)propanoate A solution of Example 122F (2.7 g, 6.15 mmol), Example 126A (3.2 g, 9.2 mmol), EDCI (2.349 g, 12.3 mmol), and DMAP (3.752 g, 30.75 mmol) in DMF (30 mL) and dichloroethane (30 mL) at room temperature was stirred for 16 hours, diluted with ethyl acetate, washed with water and brine, dried (MgSO$_4$), filtered, and concentrated. The concentrate was purified by flash column chromatography on silica gel with 50% ethyl acetate/hexanes to provide the desired product. MS (ESI (−)) m/e 775 (M−H)$^-$.

EXAMPLE 126C 3-(4'-((((4-(((1R)-3-(dimethylamino)-3-oxo-1-((phenylthio)methyl)propyl)amino)-3-nitrophenyl) sulfonyl)amino)carbonyl)-2-methoxy-1,1'-biphenyl-4-yl)propanoic acid A mixture of Example 126B in TFA (20 mL) and dichloromethane (20 mL) at room temperature was stirred for 1 hour and concentrated to provide the desired product. MS (ESI (+)) m/e 721 (M+H)$^+$.

EXAMPLE 126D (3R)-3-((4-((((2'-methoxy-4'-(3-(neopentylamino)-3-oxopropyl)-1,1'-biphenyl-4-yl)carbonyl)amino) sulfonyl)-2-nitrophenyl)amino)-N,N-dimethyl-4-(phenylthio)butanamide A solution of Example 126C (50 mg, 0.069 mmol), neopentylamine (21 mg, 0.20 mmol), EDCI (20 mg, 0.104 mmol), and HOBT (15 mg, 0.104 mmol) in N,N-dimethylacetamide (1 mL) and dichloroethane (0.5 mL) at room temperature was stirred for 16 hours. The mixture was concentrated, dissolved in 1:1 DMSO/methanol (1.0 mL) and purified by reverse phase preparative HPLC (using a C-18 column and a solvent system increasing in gradient from 20 to 95% acetonitrile/water containing 0.1% TFA) to provide the desired product. MS (ESI(−)) m/e 788 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.70(br t, 1H), 7.58 (d, 2H), 7.30–7.12 (m, 7H), 7.00 (d, 1H), 6.90 (dd, 1H), 4.45 (m, 1H), 3.75 (s, 3H), 3.42 (t, 2H), 2.90 (s, 3H), 2.79 (s, 3H), 3.00–2.70 (m, 8H), 0.80 (s, 9H).

EXAMPLE 127

(3R)-3-((4-((((4'-(3-hydroxypropyl)-2'-methoxy-1,1'-biphenyl-4-yl)carbonyl)amino)sulfonyl)-2-nitrophenyl)amino)-N,N-dimethyl-4-(phenylthio) butanamide

EXAMPLE 127A (3R)-3-((4-((((4'-(3-((tert-butyl)dimethyl)silyl)oxy) propyl)-2'-methoxy-1,1'-biphenyl-4-yl)carbonyl) amino)sulfonyl)-2-nitrophenyl)amino)-N,N-dimethyl-4-(phenylthio)butanamide The desired product was prepared by substituting Example 451B for Example 126A in Example 126B. MS (ESI(−)) m/e 803 (M−H)$^-$.

EXAMPLE 127B (3R)-3-((4-((((4'-(3-hydroxypropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting Example 127A for Example 126B in Example 126C. The mixture was concentrated, dissolved in 1:1 DMSO/methanol (1 mL) and purified by reverse phase preparative HPLC (using a C-18 column and a solvent system increasing in gradient from 20–95% acetonitrile/water containing 0.1% TFA). MS (ESI(−)) m/e 691 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (m, 4H), 2.90 (s, 3H), 2.79 (s, 3H), 3.10–2.70 (m, 2H), 2.65 (t, 2H), 1.75 (m, 2H).

EXAMPLE 128

(3R)-3-((4-((((2'-methoxy-4'-(3-oxo-3-pyrrolidin-1-ylpropyl)-1,1'-biphenyl-4-yl)carbonyl)amino) sulfonyl)-2-nitrophenyl)amino)-N,N-dimethyl-4-(phenylthio)butanamide The desired product was prepared by substituting pyrrolidine for neopentylamine in Example 126. MS (ESI(−)) m/e 772 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.58 (d, 2H), 7.30–7.12 (m, 7H), 7.02 (d, 1H), 6.92 (dd, 1H), 4.45 (m, 1H), 3.75 (s, 3H), 3.42 (t, 2H), 3.28 (t, 2H), 2.90 (s, 3H), 2.79 (s, 3H), 3.00–2.70 (m, 6H), 2.60 (t, 2H), 1.80 (m, 4H).

EXAMPLE 129

(3R)-3-((4-((((2'-methoxy-4'-(3-oxo-3-(propylamino)propyl)-1,1'-biphenyl-4-yl)carbonyl)amino) sulfonyl)-2-nitrophenyl)amino)-N,N-dimethyl-4-(phenylthio)butanamide The desired product was prepared by substituting propylamine hydrochloride for neopentylamine in Example 126 and adding N,N-diisopropylethylamine (0.1 mL) to the reaction mixture of Example 126D. MS (ESI(−)) m/e 760 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.81 (br t, 1H) 7.58 (d, 2H), 7.30–7.12 (m, 7H), 7.00 (d, 1H), 6.90 (dd, 1H), 4.45 (m, 1H), 3.75 (s, 3H), 3.42 (t, 2H), 2.90 (s, 3H), 2.79 (s, 3H), 3.00–2.70 (m, 6H), 2.40 (t, 2H), 1.48 (m, 2H), 0.80 (t, 3H).

EXAMPLE 130

(3R)-3-((4-((((2'-methoxy-4'-(3-oxo-3-piperidin-1-ylpropyl)-1,1'-biphenyl-4-yl)carbonyl)amino) sulfonyl)-2-nitrophenyl)amino)-N,N-dimethyl-4-(phenylthio)butanamide The desired product was prepared by substituting piperidine for neopentylamine in Example 126. MS (ESI(−)) m/e 786 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.58 (d, 2H), 7.30–7.12 (m, 7H), 7.02 (d, 1H), 6.92 (dd, 1H), 4.45 (m, 1H), 3.75 (s, 3H), 3.42 (t, 2H), 2.90 (s, 3H), 2.79 (s, 3H), 3.00–2.70 (m, 6H), 2.60 (t, 2H), 2.50 (t, 2H), 1.60 (m, 2H), 1.48 (m, 4H).

EXAMPLE 131 isobutyl 4-(4-((((4-(((1R)-3-(dimethylamino)-1-((phenylthio)methyl)propyl)amino)-3-nitrophenyl) sulfonyl)amino)carbonyl)phenyl)piperazine-1-carboxylate

EXAMPLE 131A isobutyl piperazine-1-carboxylate

A solution of piperazine (8.61 g, 0.1 mmol) in 1M HCl (200 mL) at room temperature was treated with isobutyl chloroformate (13.66 g, 13 mL, 0.1 mol), adjusted to pH 3 with 1M NaOH over 1 to 2 hours, stirred for 18 hours, quenched with 4M KOH, and extracted with dichloromethane (2×100 mL). The combined extracts were dried (MgSO$_4$), filtered, and concentrated to provide 10.9 g (59%) the desired product. MS (ESI(+)) m/e 187 (M+H)$^+$.

EXAMPLE 131B isobutyl 4-(4-(ethoxycarbonyl)phenyl)piperazine-1-carboxylate

The mixture of ethyl 4-fluorobenzoate (4.88 g, 29 mmol, 4.3 mL), Example 131A (5.4 g, 29 mmol), and potassium carbonate (4.007 g, 29 mmol) in NMP (10 mL) was heated to 140° C. for 18 hours, poured into water, and filtered. The filter cake was washed with water and hexanes and dried under vacuum at 50° C. to provide 2.8 g (29%) of the desired product. MS (ESI(+)) m/e 335 (M+H)$^+$.

EXAMPLE 131C 4-(4-(isobutoxycarbonyl)piperazin-1-yl)benzoic acid

A solution of Example 131B (2.8 g, 8.37 mmol) and 4M aqueous NaOH (10 mL) in 1:1 THF/methanol (40 mL) was heated to reflux for 18 hours, and concentrated. The concentrate was diluted with water and adjusted to pH 1 with concentrated HCl, treated with isobutyl chloroformate (3 mL), slowly adjusted to pH 12 with NaOH, and adjusted to pH 2 with HCl. The mixture was filtered and the filter cake was dried under vacuum to provide the desired product. MS (ESI(−)) m/e 305 (M−H)$^-$.

EXAMPLE 131D isobutyl 4-(4-((((4-(((1R)-3-(dimethylamino)-1-((phenylthio)methyl)propylamino)-3-nitrophenyl) sulfonyl)amino)carbonyl)phenyl)piperazine-1-carboxylate The desired product was prepared by substituting Example 131C and Example 122G for Example 1B and Example 1C, respectively, in Example 1D. MS (ESI(−)) m/e 711 (M−H)$^-$; $^1$H NMR (300 MHz, DMSO-d$_6$) δ8.46 (d, 1H), 8.23 (d, 1H), 7.81 (dd, 1H), 7.75 (d, 2H), 7.34–7.30 (m, 2H), 7.28–7.21 (m, 2H), 7.19–7.12 (m, 1H), 6.89 (d, 1H), 6.84 (d, 2H), 4.11–4.01 (m, 1H), 3.81 (d, 2H), 3.54–3.46 (m, 4H), 3.33 (d, 2H), 3.21–3.17 (m, 4H), 2.85–2.75 (m, 2H), 2.52 (s, 6H), 2.09–1.96 (m, 2H), 1.88 (hept, 1H), 0.90 (d, 6H).

EXAMPLE 132

(3R)-3-((4-((((2'-methoxy-4'-(3-oxo-3-((2,2,2-trifluoroethyl)amino)propyl)-1,1'-biphenyl-4-yl) carbonyl)amino)sulfonyl)-2-nitrophenyl)amino)-N,N-dimethyl-4-(phenylthio)butanamide The desired product was prepared by substituting trifluoroethylamine hydrochloride for neopentylamine in Example 126 and also adding N,N-diisopropylethylamine (0.1 mL) to the reaction mixture in Example 126D. MS (ESI(−)) m/e 800 (M−H)$^-$; $^1$H NMR (300 MHz, DMSO-d$_6$) δ8.89 (br d, 1H), 8.57 (d, 1H), 8.52 (br t, 1H), 7.90 (d, 2H), 7.85 (dd, 1H), 7.58 (d, 2H), 7.30–7.12 (m, 7H), 7.00 (d, 1H), 6.90 (dd, 1H), 4.45 (m, 1H), 3.90 (m, 2H), 3.75 (s, 3H), 3.42 (t, 2H), 2.90 (s, 3H), 2.79 (s, 3H), 3.00–2.70 (m, 4H), 2.60 (t, 2H).

EXAMPLE 133 methyl N-(4-((((4'-(3-hydroxypropyl)-2'-methoxy-1,1'-biphenyl-4-yl)carbonyl)amino)sulfonyl)-2-nitrophenyl)-S-phenyl-L-cysteinate

EXAMPLE 133A methyl N-(tert-butoxycarbonyl)-S-phenyl-L-cysteinate

A 0° C. solution of N-(tert-butoxycarbonyl)-L-serine methyl ester (30 g, 137 mmol) and diisopropylamine (58 mL, 330 mmol) in dichloromethane (250 mL) was treated with methanesulfonyl chloride (11.65 mL, 151 mmol), stirred for 20 minutes, treated with thiophenol (15.5 mL, 151 mmol), warmed to room temperature, stirred for 30 minutes, and concentrated. The concentrate was purified by flash column chromatography on silica gel with 10% ethyl acetate/hexanes to provide the desired product. MS (ESI(−)) m/e 310 (M−H)⁻.

EXAMPLE 133B methyl S-phenyl-L-cysteinate

A mixture of Example 133A in 1:1 dioxane/4M HCl at room temperature was stirred for 3 hours, poured into saturated $Na_2CO_3$ (400 mL), and extracted with ethyl acetate (3×300 mL). The combined extracts were dried ($Na_2SO_4$), filtered, and concentrated to provide the desired product.

EXAMPLE 133C methyl N-(4-(aminosulfonyl)-2-nitrophenyl)-S-phenyl-L-cysteinate The desired product was prepared by substituting Example 133B and Example 122C for 2,2-dimethylcyclopentylamine and Example 1D, respectively, in Example 1E. MS (ESI(−)) m/e 410 (M−H)⁻.

EXAMPLE 133D methyl N-(4-((((4'-(3-hydroxypropyl)-2'-methoxy-1,1'-biphenyl-4-yl)carbonyl)amino)sulfonyl)-2-nitrophenyl)-S-phenyl-L-cysteinate The desired product was prepared by substituting Example 133C and Example 451B for Example 1C and Example 1B, respectively, in Example 1D. The crude product was dissolved in TFA (5 mL), heated to 50° C. for 2 hours, and concentrated. The concentrate was purified by flash column chromatography on silica gel with ethyl acetate to provide the desired product. $^1$H NMR (300 MHz, DMSO-$d_6$) δ1.76 (tt, 2H), 2.65 (t, 2H), 3.43 (t, 2H), 3.62 (s, 3H), 3.62 (m, 1H), 3.72 (m, 1H), 3.76 (s, 3H), 5.14 (m, 1H), 6.88 (d, 1H), 6.96 (s, 1H), 7.10 (dd, 2H), 7.22 (d, 1H), 7.26 (dd, 2H), 7.58 (dd, 2H), 7.88 (dd, 2H), 7.93 (dd, 1H), 8.58 (d, 1H), 8.88 (d, 1H). MS (ESI(−)) m/e 678 (M−H)⁻.

EXAMPLE 134

N-(4-(8-azaspiro(4.5)dec-8-yl)benzoyl)-4-(((1R)-2-(dimethylamino)-1-((phenylthio)methyl)ethyl)amino)-3-nitrobenzenesulfonamide

EXAMPLE 134A tert-butyl (1R)-1-formyl-2-(phenylthio)ethylcarbamate

A solution of Example 133A (8.1 g, 26.0 mmol) in dichloromethane at −78° C. was treated with 1M DIBAL-H in dichloromethane (52 mL, 52 mmol), stirred for 3 hours, quenched with methanol (20 mL), and poured into saturated $NaH_2PO_4$. The mixture was extracted with ethyl acetate (3×300 mL), and the combined extracts were dried ($Na_2SO_4$), filtered, concentrated, and purified by flash column chromatography on silica gel with 30% ethyl acetate/hexanes to provide the desired product. MS (ESI(−)) m/e 280 (M−H)⁻.

EXAMPLE 134B tert-butyl (1R)-2-(dimethylamino)-1-((phenylthio)methyl)ethylcarbamate A solution of Example 134A (1.25 g, 4.44 mmol), 2M dimethylamine in THF (2.7 mL, 5.4 mmol), and NaBH(OAc)₃ (1.32 g, 6.22 mmol) in dichloromethane at room temperature was stirred for 18 hours, and concentrated. The concentrate was purified by flash column chromatography on silica gel with 10% ethyl acetate/hexanes to provide the desired product. MS (ESI(+)) m/e 311 (M+H)⁺.

EXAMPLE 134C (2R)-$N^1$,$N^1$-dimethyl-3-(phenylthio)propane-1,2-diamine

The desired product was prepared by substituting Example 134B for Example 133A in Example 133B.

EXAMPLE 134D 4-(((1R)-2-(dimethylamino)-1-((phenylthio)methyl)ethyl)amino)-3-nitrobenzenesulfonamide The desired product was prepared by substituting Example 134C and Example 122C for 2,2-dimethylcyclopentylamine and Example 1D, respectively, in Example 1E. MS (ESI(−)) m/e 409 (M−H)⁻.

EXAMPLE 134E

N-(4-(8-azaspiro(4.5)dec-8-yl)benzoyl)-4-(((1R)-2-(dimethylamino)-1-((phenylthio)methyl)ethyl)amino)-3-nitrobenzenesulfonamide The desired product was prepared by substituting Example 134D and Example 257C for Example 1C and Example 1B, respectively, in Example 1D. MS (ESI(−)) m/e 650 (M−H)⁻; $^1$H NMR (300 MHz, DMSO-$d_6$) δ1.41 (m, 4H), 1.48 (m, 4H), 1.59(m, 4H), 2.31 (s, 6H), 2.63 (br s, 2H), 3.20 (m, 4H), 3.28 (dd, 1H), 3.35 (dd, 1H), 4.13 (m, 1H), 6.81 (d, 2H), 6.95 (d, 1H), 7.13 (dd, 1H), 7.21 (dd, 2H), 7.31 (d, 2H), 7.72 (d, 2H), 7.82 (dd, 1H), 8.35 (d, 1H), 8.43 (s, 1H).

EXAMPLE 135

(3R)-3-((4-((((2'-methoxy-4'-(3-oxo-3-((tetrahydrofuran-3-ylmethyl)amino)propyl)-1,1'-biphenyl-4-yl)carbonyl)amino)sulfonyl)-2-nitrophenyl)amino)-N,N-dimethyl-4-(phenylthio)butanamide The desired product was prepared by substituting 1-tetrahydrofuran-3-ylmethanamine for neopentylamine in Example 126. MS (ESI(−)) m/e 802 (M−H)⁻; $^1$H NMR (300 MHz, DMSO-$d_6$) δ12.5 (br s, 1H), 8.89 (br d, 1H), 8.57 (d, 1H), 7.92 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.70–3.60(m, 4H), 3.42 (t, 2H), 2.90 (s, 3H), 2.79 (s, 3H), 3.10–2.70 (m, 4H), 2.40 (t, 2H), 2.35(m, 1H), 1.85 (m, 1H), 1.5 (m, 1H).

EXAMPLE 136

(3R)-3-((4-((((2'-methoxy-4'-(3-oxo-3-(pentylamino)propyl)-1,1'-biphenyl-4-yl)carbonyl)amino)sulfonyl)-2-nitrophenyl)amino)-N,N-dimethyl-4-(phenylthio)butanamide The desired product was prepared by substituting pentylamine for neopentylamine in Example 126. MS (ESI(−)) m/e 788 (M−H)⁻; $^1$H NMR (300 MHz, DMSO-$d_6$) δ12.5 (br s, 1H), 8.89 (br d, 1H), 8.57 (d, 1H), 7.90 (d, 2H), 7.85 (dd, 1H), 7.80(br t, 1H), 7.58 (d, 2H), 7.30–7.12 (m, 7H), 7.00 (d, 1H), 6.89 (dd, 1H), 4.45 (m, 1H), 3.75 (s, 3H), 3.42 (t, 2H), 2.90 (s, 3H), 2.79 (s, 3H), 3.10–2.70 (m, 6H), 2.40 (t, 2H), 1.35(m, 2H), 1.25 (m, 4H), 0.85 (t, 3H).

EXAMPLE 137

(3R)-3-((4-((((4'-(2-(dimethylamino)-2-oxoethyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting Example 441A and Example 122F for Example 5C and Example 3A, respectively, in Example 5D. The mixture was concentrated, dissolved in 1:1 DMSO/methanol (1.0 mL) and purified by reverse phase preparative HPLC with 20–95% acetonitrile/water containing 0.1% TFA to provide the desired product. MS (ESI(−)) m/e 732 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (m, 5H), 3.45 (t, 2H), 3.05 (s, 3H), 2.90 (s, 3H), 2.85 (s, 3H), 2.79 (s, 3H), 3.10 (m, 2H).

EXAMPLE 138

(3R)-3-((4-((((4'-(3-(4-acetylpiperazin-1-yl)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting 1-acetylpiperazine for neopentylamine in Example 126. MS (ESI(−)) m/e 829 (M−H)$^-$. $^1$H NMR (300 MHz, DMSO-d$_6$) δ12.5 (br s, 1H), 8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.70–3.40 (m, 10H), 2.90 (s, 3H), 2.79 (s, 3H), 3.10–2.70 (m, 6H), 2.00 (s, 3H).

EXAMPLE 139

N-((5R)-5-((4-(((4-(8-azaspiro(4.5)dec-8-yl)benzoyl)amino)sulfonyl)-2-nitrophenyl)amino)-6-(phenylthio)hexyl)-1H-imidazole-1-carboxamide A solution of Example 287 (200 mg, 0.3 mmol) and 1,1'-carbonyldiimidazole (60 mg, 0.33 mmol) in THF(10 mL) was heated to reflux for 5 hours. The mixture was concentrated and the concentrate was purified by flash column chromatography on silica gel with 1:1 dichloromethane/ethyl acetate to provide the desired product. MS (ESI) m/e 760 (M+H)$^+$; $^1$H NMR (300 MHz, DMSO-d$_6$) δ9.46 (m, 1H), 8.48 (d, 1H), 8.20 (m, 1H), 7.87 (dd, 1H), 7.73 (d, 2H), 7.62 (s, 1H), 7.28–6.98 (m, 7H), 6.94 (d, 2H), 4.12 (m, 1H), 3.30–3.10 (m, 7H), 1.75 (m, 2H), 1.60 (m, 4H), 1.52–1.34 (m, 12H).

EXAMPLE 140

(3R)-3-((4-((((2'-methoxy-4'-(3-oxo-3-(tetrahydrofuran-2-ylmethyl)amino)propyl)-1,1'-biphenyl-4-yl)carbonyl)amino)sulfonyl)-2-nitrophenyl)amino)-N,N-dimethyl-4-(phenylthio)butanamide The desired product was prepared by substituting 1-tetrahydrofuran-2-ylmethanamine for neopentylamine in Example 126. MS (ESI(−)) m/e 802 (M−H)$^-$; $^1$H NMR (300 MHz, DMSO-d$_6$) δ12.3 (br s, 1H), 8.89 (br d, 1H), 8.57 (d, 1H), 7,92 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.70–3.40 (m, 3H), 3.45 (t, 2H), 3.10 (t, 2H), 2.90 (s, 3H), 2.79 (s, 3H), 3.10–2.70 (m, 4H), 2.48 (t, 2H), 1.75 (m, 3H), 1.45 (m, 1H).

EXAMPLE 141

(3R)-3-((4-((((4'-(3-amino-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting ammonium chloride for neopentylamine in Example 126 and adding N,N-diisopropylethylamine (0.1 mL) to the reaction mixture in Example 126D. MS (ESI(−)) m/e 718 (M−H)$^-$; $^1$H NMR (300 MHz, DMSO-d$_6$) δ12.4 (br s, 1H), 8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 6.80 (br s, 2H), 4.45 (m, 1H), 3.75 (s, 3H), 3.40 (t, 2H), 2.90 (s, 3H), 2.79 (s, 3H), 3.10–2.70 (m, 4H), 2.42 (t, H).

EXAMPLE 142

(3R)-3-((4-((((4'-(3-(cyclobutylamino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting cyclobutylamine for neopentylamine in Example 126. MS (ESI(−)) m/e 772 (M−H)$^-$; $^1$H NMR (300 MHz, DMSO-d$_6$) δ12.4 (br s, 1H), 8.89 (br d, 1H), 8.57 (d, 1H), 8.05 (br d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 4.20 (m, 1H), 3.75 (s, 3H), 3.45 (t, 2H), 2.90 (s, 3H), 2.79 (s, 3H), 3.10–2.70 (m, 4H), 2.45 (t, 2H), 2.12 (m, 2H), 1.82 (m, 2H), 1.62 (m, 2H).

EXAMPLE 143

(3R)-3-((4-((((4'-(3-(tert-butylamino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting tert-butylamine for neopentylamine in Example 126. MS (ESI(−)) m/e 774 (M−H)$^-$; $^1$H NMR (300 MHz, DMSO-d$_6$) δ12.4 (br s, 1H), 8.89 (br d, 1H), 8.57 (d, 1H), 7.90 (d, 2H), 7.85 (dd, 1H), 7.58 (d, 2H), 7.42 (br s, 1H), 7.30–7.12 (m, 7H), 7.00 (d, 1H), 6.89 (dd, 1H), 4.45 (m, 1H), 3.75 (s, 3H), 3.45 (t, 2H), 2.90 (s, 3H), 2.79 (s, 3H), 3.10–2.70 (m, 4H), 2.45 (t, 2H), 1.25 (s, 9H).

EXAMPLE 144

(3R)-3-((4-((((2'-methoxy-4'-(3-(methylamino)-3-oxopropyl)-1,1'-biphenyl-4-yl)carbonyl)amino)sulfonyl)-2-nitrophenyl)amino)-N,N-dimethyl-4-(phenylthio)butanamide The desired product was prepared by substituting methylamine hydrochloride for neopentylamine in Example 126 and adding N,N-diisopropylethylamine (0.1 mL) to the reaction mixture in Example 126D. MS (ESI(−)) m/e 732 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.78 (br q, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 2.90 (s, 3H), 2.79 (s, 3H), 3.10–2.70 (m, 4H), 2.52 (d, 3H), 2.45 (t, 2H).

EXAMPLE 145

(3R)-3-((4-((((2'-methoxy-4'-(3-((2-(2-methoxyethoxy)ethyl)amino)-3-oxopropyl)-1,1'-biphenyl-4-yl)carbonyl)amino)sulfonyl)-2-nitrophenyl)amino)-N,N-dimethyl-4-(phenylthio)butanamide The desired product was prepared by substituting 2-(2-methoxyethoxy)ethylamine hydrochloride for neopentylamine in Example 126 and adding N,N-diisopropylethylamine (0.1 mL) to the reaction mixture in Example 126D. MS (ESI(−)) m/e 820 (M−H)$^-$; $^1$H NMR (300 MHz, DMSO-d$_6$) δ8.89 (br d, 1H), 8.57 (d, 1H), 7.92 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.50–3.45 (m, 8H), 3.26 (s, 3H), 3.20 (t, 2H), 2.90 (s, 3H), 2.79 (s, 3H), 3.10–2.70 (m, 4H), 2.45 (t, 2H).

EXAMPLE 146

N-(4-(8-azaspiro(4.5)dec-8-yl)benzoyl)-4-(((1R)-2-morpholin-4-yl-1-((phenylthio)methyl)ethyl)amino)-3-nitrobenzenesulfonamide

EXAMPLE 146A tert-butyl(1R)-2-morpholin-4-yl-1-((phenylthio)methyl)ethylcarbamate The desired product was prepared by substituting morpholine for dimethylamine in Example 134B. MS (ESI(−)) m/e 351 (M−H)$^-$.

EXAMPLE 146B (2R)-1-morpholin-4-yl-3-(phenylthio)propan-2-amine

The desired product was prepared by substituting Example 146A for Example 133A in Example 133B.

EXAMPLE 146C 4-(((1R)-2-morpholin-4-yl-1-((phenylthio)methyl)ethyl)amino)-3-nitrobenzenesulfonamide The desired product was prepared by substituting Example 146B and Example 122C for 2,2-dimethylcyclopentylamine and Example 1D, respectively, in Example 1E. MS (ESI(−)) m/e 451 (M−H)$^-$.

EXAMPLE 146D

N-(4-(8-azaspiro(4.5)dec-8-yl)benzoyl)-4-(((1R)-2-morpholin-4-yl-1-((phenylthio)methyl)ethyl)amino)-3-nitrobenzenesulfonamide The desired product was prepared by substituting Example 146C and Example 257C for Example 1C and Example 1B, respectively, in Example 1D. MS (ESI(−)) m/e 692 (M−H)$^-$; $^1$H NMR (300 MHz, DMSO-d$_6$) δ1.41 (m, 4H), 1.48 (m, 4H), 1.59(m, 4H), 2.38 (m, 2H), 2.42 (m, 2H), 2.61 (d, 2H), 3.25 (m, 4H), 3.28 (dd, 1H), 3.42 (dd, 1H), 3.51 (m, 4H), 4.18 (m, 1H), 6.85 (d, 2H), 7.05 (d, 1H), 7.11 (dd, 1H), 7.19 (dd, 2H), 7.31 (d, 2H), 7.71 (d, 2H), 7.83 (dd, 1H), 8.40 (d, 1H), 8.48 (s, 1H).

EXAMPLE 147 methyl N-(4-((((4'-(3-(dimethylamino)-3-oxopropyl)-2'-methoxy-1,1'-biphenyl-4-yl)carbonyl)amino)sulfonyl)-2-nitrophenyl)-S-phenyl-L-cysteinate

EXAMPLE 147A

4'-(3-(dimethylamino)-3-oxopropyl)-2'-methoxy-1,1'-biphenyl-4-carboxylic acid

The desired product was prepared by substituting Example 427A for Example 1A in Example 1B.

EXAMPLE 147B methyl N-(4-((((4'-(3-(dimethylamino)-3-oxopropyl)-2'-methoxy-1,1'-biphenyl-4-yl)carbonyl)amino)sulfonyl)-2-nitrophenyl)-S-phenyl-L-cysteinate The desired product was prepared by substituting Example 147A and Example 133C for Example 1B and Example 1C, respectively, in Example 1D. MS (ESI(−)) m/e 719 (M−H)$^-$; $^1$H NMR (300 MHz, DMSO-d$_6$) δ2.64 (t, 2H), 2.82 (t, 2H), 2.82 (s, 3H), 2.95 (s, 3H), 3.61 (s, 3H), 3.72 (m, 1H), 3.75 (m, 1H), 3.76 (s, 3H), 5.11 (m, 1H), 6.90 (d, 1H), 7.01 (s, 1H), 7.11 (m, 2H), 7.21 (d, 1H), 7.26 (dd, 2H), 7.53 (dd, 2H), 7.89 (dd, 2H), 7.93 (dd, 1H), 8.55 (d, 1H), 8.81 (d, 1H).

EXAMPLE 148

N-(4-(8-azaspiro(4.5)dec-8-yl)benzoyl)-4-(((1R)-2-(4-methylpiperazin-1-yl)-1-((phenylthio)methyl)ethyl)amino)-3-nitrobenzenesulfonamide

EXAMPLE 148A tert-butyl (1R)-2-(4-methylpiperazin-1-yl)-1-((phenylthio)methyl)ethylcarbamate The desired product was prepared by substituting N-methylpiperazine for dimethylamine in Example 134B. MS (ESI(+)) m/e 366 (M+H)$^+$.

EXAMPLE 148B (2R)-1-(4-methylpiperazin-1-yl)-3-(phenylthio)propan-2-amine

The desired product was prepared by substituting Example 148A for Example 133A in Example 133B.

EXAMPLE 148C 4-(((1R)-2-(4-methylpiperazin-1-yl)-1-((phenylthio)methyl)ethyl)amino)-3-nitrobenzenesulfonamide The desired product was prepared by substituting Example 148B and Example 122C for 2,2-dimethylcyclopentylamine and Example 1D, respectively, in Example 1E. MS (ESI(−)) m/e 464 (M−H)$^-$.

EXAMPLE 148D

N-(4-(8-azaspiro(4.5)dec-8-yl)benzoyl)-4-(((1R)-2-(4-methylpiperazin-1-yl)-1-((phenylthio)methyl)ethyl)amino)-3-nitrobenzenesulfonamide The desired product was prepared by substituting Example 148C and Example 257C for Example 1C and Example 1B, respectively, in Example 1D. MS (ESI(−)) m/e 705 (M−H)⁻; ¹H NMR (300 MHz, DMSO-d₆) δ1.42 (m, 4H), 1.49 (m, 4H), 1.59 (m, 4H), 2.42 (s, 3H), 3.20(m, 4H), 3.22–3.40 (m, 12H), 4.12 (m, 1H), 6.80 (d, 2H), 6.95 (d, 1H), 7.16 (dd, 1H), 7.23 (dd, 2H), 7.31 (d, 2H), 7.71 (d, 2H), 7.81 (dd, 1H), 8.30 (d, 1H), 8.44 (s, 1H).

EXAMPLE 149

4-(((1R)-3-(dimethylamino)-1-((phenylthio)methyl)propyl)amino)-N-((2'-methoxy-4'-(3-(4-methylpiperazin-1-yl)-3-oxopropyl)-1,1'-biphenyl-4-yl)carbonyl)-3-nitrobenzenesulfonamide

EXAMPLE 149A

2'-methoxy-4'-(3-(4-methylpiperazin-1-yl)-3-oxopropyl)-1,1'-biphenyl-4-carboxylic acid The desired product was prepared by substituting Example 362A for Example 1A in Example 1B.

EXAMPLE 149B 4-(((1R)-3-(dimethylamino)-1-((phenylthio)methyl)propyl)amino)-N-((2'-methoxy-4'-(3-(4-methylpiperazin-1-yl)-3-oxopropyl)-1,1'-biphenyl-4-yl)carbonyl)-3-nitrobenzenesulfonamide The desired product was prepared by substituting Example 149A and Example 122G for Example 1B and Example 1C, respectively, in Example 1D. MS (ESI) m/e 787, 789 (M−H)⁻, (M+H)⁺; ¹H NMR (300 MHz, DMSO-d₆) δ2.05 (m, 2H), 2.20 (s, 3H), 2.28 (t, 4H), 2.56 (s, 6H), 2.66 (t, 2H), 2.84 (t, 2H), 3.28 (d, 2H), 3.41 (m, 2H), 3.46 (t, 4H), 3.74 (s, 3H), 4.08 (m, 1H), 6.89 (t, 2H), 6.98 (s, 1H), 7.16 (d, 1H), 7.18 (d, 1H), 7.25 (t, 2H), 7.32 (d, 2H), 7.38 (d, 2H), 7.82 (dd, 1H), 7.88 (d, 2H), 8.21 (d, 1H), 8.48 (d, 1H).

EXAMPLE 150

(3R)-3-((4-((((4'-(3-azetidin-1-yl-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting azetidine hydrochloride for neopentylamine in Example 126 and adding N,N-diisopropylethylamine (0.1 mL) to the reaction mixture in Example 126D. MS (ESI(−)) m/e 758 (M−H)⁻; ¹H NMR (300 MHz, DMSO-d₆) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 4.05 (t, 2H), 3.82 (t, 2H), 3.75 (s, 3H), 3.45 (t, 2H), 2.90 (s, 3H), 2.79 (s, 3H), 3.10–2.70 (m, 4H), 2.35 (t, 2H).

EXAMPLE 151

(3R)-3-((4-((((4'-(3-(isopropylamino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting isopropylamine for neopentylamine in Example 126. MS (ESI(−)) m/e 760 (M−H)⁻; ¹H N (300 MHz, DMSO-d₆) δ8.89 (br d, 1H), 8.57 (d, 1H), 7.90 (d, 2H), 7.85 (dd, 1H), 7.60 (br d, 1H), 7.58 (d, 2H), 7.30–7.12 (m, 7H), 7.00 (d, 1H), 6.89 (dd, 1H), 4.45 (m, 1H), 3.85 (m, 1H), 3.75 (s, 3H), 3.45 (t, 2H), 2.90 (s, 3H), 2.79 (s, 3H), 3.10–2.70 (m, 4H), 2.45 (t, 2H), 1.02 (d, 6H).

EXAMPLE 152

(3R)-3-((4-((((2'-methoxy-4'-(3-(methyl(propyl)amino)-3-oxopropyl)-1,1'-biphenyl-4-yl)carbonyl)amino)sulfonyl)-2-nitrophenyl)amino)-N,N-dimethyl-4-(phepylthio)butanamide The desired product was prepared by substituting N-methyl-N-propylamine for neopentylamine in Example 126. MS (ESI(−)) m/e 774 (M−H)⁺; ¹H NMR (300 MHz, DMSO-d₆) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 3.25 (t, 2H), 2.95 (s, 3H), 2.90 (s, 3H), 2.79 (s, 3H), 3.10–2.70 (m, 4H), 2.65 (t, 2H), 1.50 (m, 9H), 0.85 (t, 3H).

EXAMPLE 153

(3R)-3-((4-((((4'-(3-((2-(dimethylamino)ethyl)amino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting N,N-dimethylethylenediamine for neopentylamine in Example 126. MS (ESI(−)) m/e 789 (M−H)⁻; ¹H NMR (300 MHz, DMSO-d₆) δ9.25 (br s, 1H), 8.89 (br d, 1H), 8.57 (d, 1H), 8.12 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (m, 6H), 3.15 (t, 2H), 2.95 (s, 3H), 2.80 (s, 3H), 2.79 (s, 6H), 3.10–2.70 (m, 4H).

EXAMPLE 154

(3R)-3-((4-((((4'-(3-((2-(dimethylamino)ethyl)(methyl)amino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting N,N,N'-trimethylethylenediamine for neopentylamine in Example 126. MS (ESI(−)) m/e 803 (M−H)⁻; ¹H NMR (300 MHz, DMSO-d₆) δ9.25 (br s, 1H), 8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.65 (m, 4H), 3.45 (t, 2H), 3.15 (t, 2H), 2.95 (s, 3H), 2.90 (s, 3H), 2.82 (s, 6H), 2.79 (s, 3H), 3.10–2.70 (m, 4H).

EXAMPLE 155

(3R)-3-((4-((((4'-(3-(tert-butyl(methyl)amino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting N-methyl-tert-butylamine for neopentylamine in Example 126. MS (ESI(−)) m/e 788 (M−H)⁻; ¹H NMR (300 MHz, DMSO-d₆) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 2.95 (s, 3H), 2.85 (s, 3H), 2.79 (s, 3H), 3.10–2.70 (m, 4H), 2.60 (t, 2H), 1.35 (s, 9H).

EXAMPLE 156 isobutyl 4-(4-((((4-(((1R)-5-amino-1-((phenylthio)methyl)penthyl)amino)-3-nitrophenyl)sulfonyl)amino)carbonyl)phenyl)piperazine-1-carboxylate

EXAMPLE 156A isobutyl 4-(4-((((4-(((1R)-5-((tert-butoxycarbonyl)amino)-1-((phenylthio)methyl)pentyl)amino)-3-nitrophenyl)sulfonyl)amino)carbonyl)phenyl)piperazine-1-carboxylate The desired product was prepared by substituting Example 131C and Example 124C for Example 1B and Example 1C, respectively, in Example 1D.

EXAMPLE 156B isobutyl 4-(4-((((4-(((1R)-5-amino-1-((phenylthio)
methyl)pentyl)amino)-3-nitrophenyl)sulfonyl)amino)
carbonyl)phenyl)piperazine-1-carboxylate The desired product was prepared by substituting Example 156A for Example 120D in Example 120E. MS (ESI(−)) m/e 711 (M−H)⁻; $^1$H NMR (300 MHz, DMSO-d$_6$) δ12.07 (br S, 1H), 8.54 (d, 1H), 8.32 (d, 1H), 7.86 (dd, 1H), 7.78 (d, 2H), 7.76 (br s, 1H), 7.26–7.08 (m, 6H), 6.96 (d, 1H), 4.12–4.01 (m, 1H), 3.81 (d, 2H), 3.74–3.65 (m, 2H), 3.54–3.46 (m, 4H), 3.38–3.34 (m, 4H), 2.78–2.70 (m, 2H), 1.88 (hept, 1H), 1.8–1.72 (m, 2H), 1.56–1.47 (m, 2H), 1.45–1.35 (m, 2H), 0.90 (d, 6H).

EXAMPLE 157

(3R)-3-((4-((((4'-(3-(diethylamino)-3-oxopropyl)-2'-
methoxy-1,1'-biphenyl-4-yl)carbonyl)amino)
sulfonyl)-2-nitrophenyl)amino)-N,N-dimethyl-4-
(phenylthio)butanamide The desired product was prepared by substituting diethylamine hydrochloride for neopentylamine in Example 126 and adding N,N-diisopropylethylamine (0.1 mL) to the reaction mixture in Example 126D. MS (ESI(−)) m/e 774 (M−H)⁻; $^1$H NMR (300 MHz, DMSO-d$_6$) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 3.30 (m, 4H), 2.90 (s, 3H), 2.79 (s, 3H), 3.10–2.70 (m, 4H), 2.60 (t, 2H), 1.05 (2t, 6H).

EXAMPLE 158

4-(((1R)-5-amino-1-((phenylthio)methyl)pentyl)
amino)-N-(4-(6-azaspiro(2.5)oct-6-yl)benzoyl)-3-
nitrobenzenesulfonamide

EXAMPLE 158A ethyl 4-(1,4-dioxa-8-azaspiro(4.5)dec-8-yl)benzoate

A mixture of ethyl 4-fluorobenzoate (6.0 mL, 41 mmol), 1,4-dioxa-8-azaspiro(4,5)decane (13.5 mL, 102 mmol), and K$_2$CO$_3$ (5.7 g, 41 mmol) in NMP (35 mL) was stirred at 150° C. for 4 hours, cooled to room temperature, treated with water (0.5 L) and filtered. The filter cake was washed with water and dried briefly. The crude product was triturated with hexane, filtered, and dried under vacuum to provide the desired product. MS (DCI) m/e 292 (M+H)⁺.

EXAMPLE 158B ethyl 4-(4-oxopiperidin-1-yl)benzoate

A solution of Example 158A (6.31 g, 21.7 mmol) and 30% aqueous acetic acid (100 mL) in THF (50 mL) was stirred at 95° C. for 6 hours, cooled to room temperature, concentrated, treated with water, and extracted with dichloromethane. The combined extracts were washed with water and brine, dried (MgSO$_4$), filtered, and concentrated to provide the desired product. MS (DCI) m/e 248 (M+H)⁺.

EXAMPLE 158C ethyl 4-(4-methylenepiperidin-1-yl)benzoate

A 0° C. solution of methyltriphenylphosphonium bromide (500 mg, 1.4 mmol) in THF (1.5 mL) was treated dropwise with 1M sodium hexamethyldisilazide in THF (1.4 mL), stirred for 15 minutes, and added dropwise to a 0° C. solution of Example 158B (0.25 g, 1.0 mmol) in THF (2.1 mL). After stirring for 15 minutes, the reaction was quenched with water and was extracted with ethyl acetate. The combined extracts were washed with brine, dried (MgSO$_4$), filtered, and concentrated. The concentrate was purified by flash column chromatography on silica gel with 9:1 hexanes/ethyl acetate to provide the desired product. MS (DCI) m/e 246 (M+H)⁺.

EXAMPLE 158D ethyl 4-(6-azaspiro(2.5)oct-6-yl)benzoate

A mixture of methyl-3-nitro-1-nitrosoguanidine (1.18 g, 8.1 mmol), 40% KOH (3.4 mL), and diethyl ether (12 mL) at 0° C. was stirred for 10 minutes. The organic phase was added slowly to a −25° C. solution of Example 158C and Pd(OAc)$_2$ (18 Mg, 0.11 mmol) in THF (8.8 mL). The mixture was stirred for 1 hour at −20° C. and concentrated. The concentrate was purified by flash column chromatography on silica gel with 9:1 hexanes/ethyl acetate to provide the desired product. MS (DCI) m/e 260 (M+H)⁺.

EXAMPLE 158E 4-(6-azaspiro(2.5)oct-6-yl)benzoic acid

The desired product was prepared by substituting Example 158D for Example 119B in Example 119C. MS (DCI) m/e 232 (M+H)⁺.

EXAMPLE 158F tert-butyl(5R)-5-((4-(((4-(6-azaspiro(2.5)oct-6-yl)
benzoyl)amino)sulfonyl)-2-nitrophenyl)amino)-6-
(phenylthio)hexylcarbamate The desired product was prepared by substituting Example 158E and Example 124C for Example 1B and Example 1C, respectively, in Example 1D. MS (ESI(−)) m/e 736 (M−H)⁻.

EXAMPLE 158G 4-(((1R)-5-amino-1-((phenylthio)methyl)pentyl)
amino)-N-(4-(6-azaspiro(2.5)oct-6-yl)benzoyl)-3-
nitrobenzenesulfonamide The desired product was prepared by substituting Example 158F for Example 120D in Example 120E. MS (ESI(+)) m/e 654 (M+H)⁺; $^1$H NMR (300 MHz, DMSO-d$_6$) δ12.0 (s, 1H), 8.54 (d, 1H), 8.32 (d, 1H), 7.86 (dd, 1H), 7.75 (d, 2H), 7.25–7.05 (m, 6H), 6.96 (d, 2H), 6.82 (d, 2H), 4.10 (m, 1H), 3.50 (m, 4H), 3.90 (m, 6H), 3.43 (m, 4H), 3.36 (m, 2H), 2.72 (m, 2H), 1.78 (m, 2H), 1.52 (m, 2H), 1.39 (m, 4H).

EXAMPLE 159

4-(((1R)-5-(dimethylamino)-1-((phenylthio)methyl)
pentyl)amino)-N-(4-(4,4-dimethylpiperidin-1-yl)
benzoyl)-3-nitrobenzenesulfonamide The desired product was prepared by substituting Example 124E and Example 119C for Example 1C and Example 1B, respectively, in Example 1D. MS(ESI(+)) m/e 694 (M+H)⁺, $^1$H NMR (500 MHz, DMSO-d$_6$) δ12.06 (s, 1H), 10.57 (s, 1H), 8.55 (d, 1H), 8.31 (d, 1H), 7.88 (dd, 1H), 7.78 (d, 2H), 7.24 (m, 3H), 7.30 (m, 2H), 7.15 (t, 2H), 7.10 (d, 1H), 7.05 (m, 2H), 4.13 (m, 1H), 3.35 (d, 6H), 2.94 (m, 2H), 2.67 (d, 6H), 1.77 (m, 2H), 1.65 (m, 2H), 1.59 (m, 4H), 1.51 (m, 4H), 1.43 (m, 4H), 1.38 (m, 2H).

EXAMPLE 160

(3R)-3-((4-((((2'-methoxy-4'-(3-((2-methoxyethyl)
(methyl)amino)-3-oxopropyl)-1,1'-biphenyl-4-yl)
carbonyl)amino)sulfonyl)-2-nitrophenyl)amino)-N,
N-dimethyl-4-(phenylthio)butanamide The desired product was prepared by substituting N-(2-methoxyethyl)methylamine for neopentylamine in Example 126. MS (ESI(−)) m/e 790 (M−H)$^-$; $^1$H NMR (300 MHz, DMSO-d$_6$) δ12.45 (br s, 1H), 8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 4H), 3.25 (s, 3H), 2.90 (s, 3H), 2.85 (s, 3H), 2.79 (s, 3H), 3.10–2.70 (m, 6H), 2.60 (t, 2H).

EXAMPLE 161

(3R)-3-((4-(((4'-(3-((3-(dimethylamino)propyl)
amino)-3-oxopropyl)-2'-methoxy-1,1'-biphenyl-4-yl)
carbonyl)amino)sulfonyl)-2-nitrophenyl)amino)-N,
N-dimethyl-4-(phenylthio)butanamide The desired product was prepared by substituting N,N-dimethylpropanediamine for neopentylamine in Example 126. MS (ESI(−)) m/e 803 (M−H)$^-$; $^1$H NMR (300 MHz, DMSO-d$_6$) δ9.25 (br s, 1H), 8.89 (br d, 1H), 8.57 (d, 1H), 8.05 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (m 4H), 3.15 (t, 2H), 2.90 (s, 3H), 2.80 (s, 3H), 2.75 (2s, 6H), 3.10–2.70 (m, 4H), 2.45 (m, 2H), 1.75 (m, 2H).

EXAMPLE 162

4-(((4-(aminomethyl)bicyclo(2.2.2)oct-1-yl)methyl)
amino)-N-(4-(8-azaspiro(4.5)dec-8-yl)benzoyl)-3-
nitrobenzenesulfonamide

EXAMPLE 162A tert-butyl(4-(((4-(aminosulfonyl)-2-nitrophenyl)
amino)methyl)bicyclo(2.2.2)oct-1-yl)
methylcarbamate A suspension of 1,4-diaminomethyl(2,2,2)bicyclooctane (1.04 g, 6.2 mmol), diisopropylethylamine (2 mL) and Example 122C (1.36 g, 6.2 mmol) in 1,2-dichloroethane (20 mL) was stirred for 3 days at 75° C. and concentrated. The concentrate was redissolved in methanol (30 mL), treated with diisopropylethylamine (2 mL) and BOC$_2$O (1.636 g), heated to 50° C., filtered, and concentrated. The concentrate was purified by flash column chromatography on silica gel with 0–3% methanol/dichloromethane to provide the desired product. MS (ESI(−)) m/e 467 (M−H)$^-$.

EXAMPLE 162B tert-butyl (4-(((4-(((4-(8-azaspiro(4.5)dec-8-yl)
benzoyl)amino)sulfonyl)-2-nitrophenyl)amino)
methyl)bicyclo(2.2.2)oct-1-yl)methylcarbamate The desired product was prepared by substituting Example 162A and Example 257C for Example 1C and Example 1B, respectively, in Example 1D.

EXAMPLE 162C 4-(((4-(aminomethyl)bicyclo(2.2.2)oct-1-yl)methyl)
amino)-N-(4-(8-azaspiro(4.5)dec-8-yl)benzoyl)-3-
nitrobenzenesulfonamide The desired product was prepared by substituting Example 162B for Example 120D in Example 120E. MS (ESI(−)) m/e 608 (M−H)$^-$; $^1$H NMR (300 MHz, DMSO-d$_6$) δ11.97 (br s, 1H), 8.63 (d, 1H), 8.48 (t, 1H), 7.93 (dd, 1H), 7.71 (d, 2H), 7.70 (br s, 3H), 7.31 (d, 1H), 6.92 (d, 2H), 3.74–3.64 (m, 2H), 3.36–3.31 (m, 4H), 3.23 (d, 2H), 2.56 (q, 2H), 1.62–1.57 (m, 4H), 1.52–1.40 (m, 16H).

EXAMPLE 163

(3R)-3-((4-((((4'-(3-(bis(2-methoxyethyl)amino)-3-
oxopropyl)-2'-methoxy-1,1'-biphenyl-4-yl)carbonyl)
amino)sulfonyl)-2-nitrophenyl)amino)-N,N-
dimethyl-4-(phenylthio)butanamide The desired product was prepared by substituting bis(2-methoxyethyl)amine for neopentylamine in Example 126. MS (ESI(−)) m/e 834 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (m, 10H), 3.25 (s, 6H), 2.90 (s, 3H), 2.79 (s, 3H), 3.10–2.70 (m, 6H).

EXAMPLE 164

(3R)-3-((4-((((4'-(3-((3-(dimethylamino)propyl)
(methyl)amino)-3-oxopropyl)-2'-methoxy-1,1'-
biphenyl-4-yl)carbonyl)amino)sulfonyl)-2-
nitrophenyl)amino)-N,N-dimethyl-4-(phenylthio)
butanamide The desired product was prepared by substituting N,N,N'-trimethylpropylenediamine for neopentylamine in Example 126. MS (ESI(−)) m/e 817 (M−H)$^-$; $^1$H NMR (300 MHz, DMSO-d$_6$) δ9.25 (br s, 1H), 8.89 (br d, 1H), 8.57 (d, 1H), 7.90 (d, 2H), 7.85 (dd, 1H), 7.58 (d, 2), 7.30–7.12 (m, 7H), 7.00 (d, 1H), 6.89 (dd, 1H), 4.45 (m, 1H), 3.75 (s, 3H), 3.45 (m 4H), 3.15 (t, 2H), 2.98 (s, 3H), 2.90 (s, 3H), 2.80 (s, 3H), 2.75 (2s, 6H), 3.10–2.70 (m, 4H), 2.45 (m, 2H), 1.75 (m, 2H).

EXAMPLE 165

4-(3-(2-methoxy-4'-(((((3-nitro-4-((2-(phenylthio)
ethyl)amino)phenyl)sulfonyl)amino)carbonyl)-1,1'-
biphenyl-4-yl)propyl)piperazine-1-carboximidamide A solution Example 183D (200 mg, 0.29 mmol), 1H-pyrazole-1-carboxamidine hydrochloride (42 mg, 0.29 mmol), and diisoopropylethylamine (0.101 mL, 0.58 mmol) in DMF was stirred at 45° C. for 24 hours. The mixture was purified by reverse-phase HPLC using 50% CH$_3$CN/water to provide the desired product. MS (ESI(−)) m/e 730 (M−H)$^-$; $^1$H NMR (300 MHz, DMSO-d$_6$) δ2.12 (m, 2H), 2.70 (m, 2H), 3.10 (m, 2H), 3.30 (dd, 2H), 3.25–3.55 (m, 6H), 3.68 (m, 4H), 3.79 (s, 3H), 6.92 (d, 1H), 7.04 (s, 1H), 7.15 (s, 2H), 7.19 (dd, 1H), 7.25 (d, 2H), 7.32 (m, 2H), 7.49 (s, 1H), 7.58 (d, 1H), 7.92 (dd, 1H), 8.62 (d, 1H), 8.80 (dd, 1H).

EXAMPLE 166

N-(4-(1-butyl-2-oxo-2,3-dihydro-1H-benzimidazol-
5-yl)benzoyl)-4-(((1R)-3-(dimethylamino)-1-
((phenylthio)methyl)propyl)amino)-3-
nitrobenzenesulfonamide

EXAMPLE 166A 4-bromo-N-butyl-2-nitroaniline

A solution of butylamine (1.25 g, 17.1 mmol) in DMSO (14 mL) was treated with 4-bromo-1-fluoro-2-nitrobenzene (1.50 g, 6.82 mmol), heated to 70° C. for 1 hour, added to 1M HCl (60 mL), and extracted with diethyl ether (3×75 mL). The combined extracts were washed with brine (20 mL), dried (Na$_2$SO$_4$), filtered, and concentrated to provide the desired product.

EXAMPLE 166B 4-bromo-N$^1$-butylbenzene-1,2-diamine

A mixture of Example 166A (1.82 g, 6.66 mmol) and tin(II) chloride dihydrate (3.76 g, 16.6 mmol), and concentrated HCl (22 mL) in isopropanol (30 mL) at room temperature was stirred for 90 minutes, adjusted to pH 6.5–7.5 using NaHCO$_3$ and 6M NaOH, and filtered. The filter cake was washed with water and ethyl acetate, and the filtrate was separated. The aqueous phase was extracted with ethyl acetate (3×50 mL) and the combined organic phases were washed with brine (20 mL), dried (Na$_2$SO$_4$), filtered, and concentrated. The concentrate was purified by flash column chromatography on silica gel with 20–50% ethyl acetate/hexanes to provide the desired product.

EXAMPLE 166C 5-bromo-1-butyl-1,3-dihydro-2H-benzimidazol-2-one

A mixture of Example 166B (1.36 g, 5.59 mmol) and triphosgene (582 mg, 1.96 mmol) in dioxane was heated to reflux for 16 hours and concentrated. The concentrate was purified by flash column chromatography on silica gel with 30% ethyl acetate/hexanes to provide the desired product.

EXAMPLE 166D 4-(1-butyl-2-oxo-2,3-dihydro-1H-benzimidazol-5-yl)benzoic acid

The desired product was prepared by substituting Example 166C for 6-bromoindole in Example 4A.

EXAMPLE 166E

N-(4-(1-butyl-2-oxo-2,3-dihydro-1H-benzimidazol-5-yl)benzoyl)-4-(((1R)-3-(dimethylamino)-1-((phenylthio)methyl)propyl)amino)-3-nitrobenzenesulfonamide The desired product was prepared by substituting Example 166D and Example 122G for Example 1B and Example 1C, respectively, in Example 1D. MS (ESI) m/e 715, 717 (M–H)$^-$, (M+H)$^+$; $^1$H NMR (300 MHz, DMSO-d$_6$) δ0.91 (t, 3H), 1.30 (q, 2H), 1.63 (tt, 2H), 2.15 (m, 2H), 2.70 (s, 6H), 3.10 (m, 2H), 3.30 (d, 2H), 3.80 (t, 2H), 4.10 (m, 1H), 6.89 (t, 2H), 6.95 (s, 1H), 6.98 (d, 1H), 7.15–7.25 (m, 3H), 7.26–7.36 (m, 3H), 7.56 (d, 2H), 7.85 (dd, 1H), 7.94 (d, 2H), 8.13 (d, 1H), 8.20 (d, 1H), 8.48 (d, 1H), 10.91 (s, 1H).

EXAMPLE 167 isobutyl 4-(4-(((((4-(((1R)-3-morpholin-4-yl-1-((phenylthio)methyl)propyl)amino)-3-nitrophenyl)sulfonyl)amino)carbonyl)phenyl)piperazine-1-carboxylate The desired product was prepared by substituting Example 131C and Example 463A for Example 1B and Example 1C, respectively, in Example 1D. MS (ESI)(–)) m/e 753. (M–H)$^-$; $^1$H NMR (300 MHz, DMSO-d$_6$) δ8.51 (d, 1H), 8.37 (d, 1H), 7.81 (dd, 1H), 7.76 (d, 2H), 7.32–7.11 (m, 5H), 7.06 (d, 1H), 6.91 (d, 2H), 4.20–4.08 (m, 1H), 3.81 (d, 2H), 3.56–3.46 (m, 8H), 3.36 (d, 4H), 3.35–3.26 (m, 4H), 2.57–2.45 (m, 2H), 2.09–1.97 (m, 2H), 1.88 (heptet, 1H), 0.90 (d, 6H).

EXAMPLE 168

4-(3-(2-methoxy-4'-((((3-nitro-4-((2-(phenylthio)ethyl)amino)phenyl)sulfonyl)amino)carbonyl)-1,1'-biphenyl-4-yl)propyl)piperazine-1-carboxamide A solution of Example 183D and trimethylsilyl isocyanate in THF at room temperature was stirred for 24 hours and concentrated. The concentrate was purified by flash column chromatography on silica gel with 10/10/80 methanol/acetonitrile/ethyl acetate to provide the desired product. MS (ESI(–)) m/e 731 (M–H)$^-$; $^1$H NMR (300 MHz, DMSO-d$_6$) δ1.79 (m, 2H), 2.31 (br s, 6H), 2.51 (dd, 2H), 3.28 (m, 4H), 3.32 (s, 3H), 3.60 (m, 2H), 3.73 (s, 3H), 5.91 (s, 2H), 6.85 (d, 1H), 6.92 (s, 1H), 6.97 (d, 1H), 7.18 (d, 1H), 7.20 (d, 1H), 7.31 (dd, 2H), 7.39 (m, 3H), 7.88 (d, 2H), 8.50 (s, 1H).

EXAMPLE 169

N-(4-(2-azaspiro(4.4)non-2-yl)benzoyl)-3-nitro-4-((2-(phenylthio)ethyl)amino)benzenesulfonamide The desired product was prepared by substituting Example 120C and Example 77B for Example 1B and Example 1C, respectively, in Example 1D. MS (ESI(–)) m/e 579 (M–H)$^-$; $^1$H NMR (300 MHz, DMSO-d$_6$) δ11.87 (s, 1H), 8.76 (t, 1H), 8.60 (d, 1H), 8.32 (d, 1H), 7.91 (dd, 1H), 7.72 (d, 2H), 7.37 (dd, 2H), 7.26 (t, 2H), 7.17 (m, 2H), 6.50 (d, 2H), 3.65 (m, 2H), 3.25–3.38 (m, 4H), 3.17 (s, 2H), 1.85 (t, 2H), 1.65 (m, 4H), 1.55 (m, 4H).

EXAMPLE 170

3-nitro-N-(4-(1-(3-phenylpropyl)-1H-benzimidazol-5-yl)benzoyl)-4-((2-(phenylthio)ethyl)amino)benzenesulfonamide

EXAMPLE 170A 4-bromo-N$^1$-(3-phenylpropyl)benzene-1,2-diamine

The desired product was prepared by substituting 3-phenylpropylamine for butylamine in Examples 166A and 166B.

EXAMPLE 170B 5-bromo-1-(3-phenylpropyl)-1H-benzimidazole

A solution of Example 170A (560 mg, 1.83 mmol) in trimethyl orthoformate (10 mL) at 95° C. was stirred for 16 hours and concentrated. The concentrate was purified by flash column chromatography on silica gel with 50–100% ethyl acetate/hexanes to provide the desired product.

EXAMPLE 170C 4-(1-(3-phenylpropyl)-1H-benzimidazol-5-yl)benzoic acid

The desired product was prepared by substituting Example 170B for 6-bromoindole in Example 4A.

EXAMPLE 170D 3-nitro-N-(4-(1-(3-phenylpropyl)-1H-benzimidazol-5-yl)benzoyl)-4-((2-(phenylthio)ethyl)amino)benzenesulfonamide The desired product was prepared by substituting Example 170C and Example 77B for Example 1B and Example 1C, respectively, in Example 1D. $^1$H NMR (300 MHz, DMSO-d$_6$) δ2.51 (tt, 2H), 2.61 (tt, 2H), 3.28 (t, 2H), 3.61 (dt, 2H), 4.30 (t, 2H), 7.00 (d, 1H), 7.15–7.35 (m, 9H), 7.40 (dt, 2H), 7.59 (dd, 1H), 7.69 (dd, 2H), 7.89 (dd, 1H), 7.97 (m, 3H), 8.28 (s, 1H), 8.52 (d, 1H), 8.52 (t, 1H).

EXAMPLE 171 tert-butyl(5R)-5-((4-(((4-(4-ethyl-4-methylpiperidin-1-yl)benzoyl)amino)sulfonyl)-2-nitrophenyl)amino)-6-(phenylthio)hexylcarbamate The desired product was prepared by substituting Example 123C and Example 124C for Example 1B and Example 1C, respectively, in Example 1D. MS (ESI(–)) m/e 752 (M–H)$^-$; $^1$H NMR (300 MHz, DMSO-d$_6$) δ11.95 (s, 1H), 8.54 (d, 1H), 8.31 (d, 1H), 7.84 (dd, 1H), 7.74 (d, 2H), 7.25–7.08 (m, 6H), 6.92 (d, 2H), 6.72 (t, 1H), 4.08 (s, 1H, 3.46 (t, 1H), 3.44 (t, 1H), 3.24–3.14 (m, 2H), 2.87 (m, 2H), 1.73 (m, 2H), 1.31 (s, 9H), 1.40–1.22 (m, 10H), 0.90 (s, 3H), 0.80 (t, 3H).

EXAMPLE 172

(3R)-3-((4-((((2'-methoxy-4'-(3-((3-methoxypropyl)amino)-3-oxopropyl)-1,1'-biphenyl-4-yl)carbonyl)amino)sulfonyl)-2-nitrophenyl)amino)-N,N-dimethyl-4-(phenylthio)butanamide The desired product was prepared by substituting 3-methoxypropylamine for neopentylamine in Example 126. MS (ESI(–)) m/e 790 (M–H)$^-$; $^1$H NMR (300 MHz, DMSO-d$_6$) δ12.45 (br s, 1H), 8.89 (br d, 1H), 8.57 (d, 1H), 7.90 (d, 2H), 7.85 (dd, 1H), 7.82 (br t, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 3.25 (t, 2H), 3.18 (s, 3H), 2.90 (s, 3H), 2.79 (s, 3H), 3.10–2.70 (m, 6H), 2.45 (t, 2H), 1.60 (m, 2H).

EXAMPLE 173 tert-butyl 1-benzyl-2-(4-(4-((((3-nitro-4-((2-(phenylthio)ethyl)amino)phenyl)sulfonyl)amino)carbonyl)phenyl)piperazin-1-yl)ethylcarbamate

EXAMPLE 173A 3-nitro-4-((2-(phenylthio)ethyl)amino)-N-(4-piperazin-1-ylbenzoyl)benzenesulfonamide The desired product was prepared by substituting Example 405 for Example 120D in Example 120E. MS (ESI(–)) m/e 540 (M–H)$^-$.

EXAMPLE 173B tert-butyl 1-benzyl-2-(4-(4-((((3-nitro-4-((2-phenylthio)ethyl)amino)phenyl)sulfonyl)amino)carbonyl)phenyl)piperazin-1-yl)ethylcarbamate A solution of Example 173A (108 mg, 0.2 mmol) and (1-benzyl-2-oxo-ethyl)-carbamic acid tert-butyl ester (50 mg, 0.2 mmol) in 1:1 methanol/THF (8 mL) at room temperature was treated with 1M sodium cyanoborohydride in THF (0.4 mL, 0.4 mmol), stirred for 18 hours, and concentrated. The concentrate was partitioned between ethyl acetate and saturated sodium bicarbonate, and the organic phase was dried (MgSO$_4$), filtered, and concentrated. The concentrate was purified by flash column chromatography on silica gel with 0–10% methanol/dichloromethane to provide the desired product. MS (ESI(–)) m/e 773 (M–H)$^-$; $^1$H NMR (300 MHz, DMSO-d$_6$) δ8.67 (t, 1H), 8.55 (d, 1H), 7.88 (dd, 1H), 7.74 (d, 2H), 7.37 (d, 2H), 7.30–7.08 (m, 9H), 6.90 (d, 2H), 6.67 (br d, 1H), 3.88–3.80 (m, 1H), 3.64 (q, 2H), 3.31–3.20 (m, 10H), 2.81 (dd, 1H), 2.62–2.50 (m, 3H), 1.30 (s, 9H).

EXAMPLE 174

(3R)-3-((4-((((4'-(3-(isobutylamino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting isobutylamine for neopentylamine in Example 126. MS (ESI(–)) m/e 774 (M–H)$^-$; $^1$H NMR (300 MHz, DMSO-d$_6$) δ12.45 (br s, 1H), 8.89 (br d, 1H), 8.57 (d, 1H), 7.90 (d, 2H), 7.85 (dd, 1H), 7.80 (br t, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 2.90 (s, 3H), 2.79 (s, 3H), 3.10–2.70 (m, 6H), 2.45 (t, 2H), 1.65 (m, 1H), 0.80(d, 6H).

EXAMPLE 175

N-((4'-fluoro-1,1'-biphenyl-4-yl)carbonyl)-4-((2-hydroxy-1-((phenylthio)methyl)ethyl)amino)-3-nitrobenzenesulfonamide

EXAMPLE 175A methyl N-(tert-butoxycarbonyl)-S-phenylcysteinate

The desired product was prepared by substituting DL-BOC-serine methyl ester for Example 27A in Example 27B.

EXAMPLE 175B tert-butyl 2-hydroxy-1-((phenylthio)methyl)ethylcarbamate

A solution of Example 175A (1.22 g, 3.91 mmol) in toluene (10 mL) at –78° C. was treated with 1M DIBAL-H in toluene (8.6 mL), warmed to room temperature over 4 hours, diluted with ethyl acetate (100 mL), washed sequentially with 0.1N HCl (30 mL), water (15 mL), and brine (50 mL), dried (MgSO$_4$), filtered, and concentrated. The concentrate was purified by flash column chromatography on silica gel with 30% ethyl acetate/hexanes to provide the desired product. MS (DCI) m/e 284 (M+H)$^+$.

EXAMPLE 175C 4-fluoro-N-((4'-fluoro-1,1'-biphenyl-4-yl)carbonyl)-3-nitrobenzenesulfonamide The desired product was prepared by substituting Example 122C for Example 1C in Example 1D. MS (ESI(–)) m/e 417 (M–H)$^-$.

EXAMPLE 175D

N-((4'-fluoro-1,1'-biphenyl-4yl)-carbonyl)-4-((2-hydroxy-1-((phenylthio)methyl)ethyl)amino)-3-nitrobenzenesulfonamide A mixture of Example 175B (100 mg, 0.35 mmol)) and 4M HCl in 1,4-dioxane (10 mL) was stirred at room temperature for 3 hours and concentrated. A mixture of the concentrate and Example 175C (160 mg, 0.38 mmol) was treated with DMF (2 mL) and N,N-diisopropylethylamine (0.5 mL), stirred for 18 hours, diluted with ethyl acetate (60 mL), washed with 1N HCl (20 mL) and brine (10 mL), dried (MgSO$_4$), filtered, and concentrated. The concentrate was purified by flash column chromatography on silica gel with 30–100% ethyl acetate/dichloromethane to provide the desired product. MS (ESI(-)) m/e 580 (M-H)$^-$; $^1$H NMR (400 MHz, DMSO-d$_6$) δ8.50 (d, 1H), 8.42 (d, 1H), 7.95 (d, 2H), 7.70 (dd, 1H), 7.73 (m, 2H), 7.60 (d, 2H), 7.40–7.19 (m, 8H), 3.95 (m, 1H), 3.71 (m, 1H), 3.62 (m, 1H), 3.29 (m, 2H).

EXAMPLE 176 tert-butyl(5R)-5-((4-(((4-(6-azaspiro(2.5)oct-6-yl) benzoyl)amino)sulfonyl)-2-nitrophenyl)amino)-6-(phenylthio)hexylcarbamate The desired product was prepared by substituting Example 158E and Example 124C for Example 1B and Example 1C, respectively, in Example 1D. MS (ESI(-)) m/e 736; $^1$H NMR (300 MHz, DMSO-d$_6$) δ11.96 (s, 1H), 8.54 (d, 1H), 8.31 (d, 1H), 7.84 (dd, 1H), 7.74 (d, 2H), 7.08–7.25 (m, 6H), 6.95 (d, 2H), 6.72 (t, 1H), 4.08 (s, 1H), 3.43 (m, 4H), 3.30 (m, 4H), 2.87 (m, 2H), 1.37 (m, 4H), 1.31 (s, 9H), 1.25 (m, 2H), 0.33 (s, 4H).

EXAMPLE 177

N-(4-(1-butyl-2-oxo-2,3-dihydro-1H-benzimidazol-5-yl)benzoyl)-4-(((1R)-2-hydroxy-1-((phenylthio) methyl)ethyl)amino)-3-nitrobenzenesulfonamide

EXAMPLE 177A

N-((4-(((1R)-2-((tert-butyl(dimethyl)silyl)oxy)-1-((phenylsulfanyl)methyl)ethyl)amino)-3-nitrophenyl) sulfonyl)-4-(1-butyl-2-oxo-2,3-dihydro-1H-benzimidazol-5-yl)benzamide The desired product was prepared by substituting Example 166D and Example 278A for Example 1B and Example 1C, respectively, in Example 1D.

EXAMPLE 177B

N-(4-(1-butyl-2-oxo-2,3-dihydro-1H-benzimidazol-5-yl)benzoyl)-4-(((1R)-2-hydroxy-1-((phenylthio) methyl)ethyl)amino)-3-nitrobenzenesulfonamide A mixture of Example 177A (40 mg, 0.05 mmol) and 1M tetrabutylammonium fluoride in THF (130 uL, 0.13 mmol) in THF (3 mL) at room temperature was stirred for 3 hours, treated with 1M HCl (10 mL), and extracted with 5% methanol in ethyl acetate (3×20 mL). The combined extracts were washed with brine (5 mL), dried (Na$_2$SO$_4$), filtered, and concentrated. The concentrate was purified by flash column chromatography on silica gel with 20% methanol/ ethyl acetate to provide the desired product. MS (ESI) m/e 674, 676 (M-H)$^-$, (M+H)$^+$; $^1$H NMR (300 MHz, DMSO-d$_6$) δ0.91 (t, 3H), 1.30 (q, 2H), 1.59 (tt, 2H), 3.28 (t, 2H), 3.67 (m, 1H), 3.80 (t, 2H), 3.92 (m, 2H), 5.21 (t, 1H), 6.83 (d, 1H), 7.21 (m, 3H), 7.29 (td, 2H), 7.38 (dd, 2H), 7.55 (d, 2H), 7.80 (dd, 1H), 7.94 (d, 2H), 7.95 (d, 1H), 8.41 (d, 1H), 8.49 (d, 1H), 10.90 (s, 1H).

EXAMPLE 178

N-(2-(dimethylamino)ethyl)-3-(4'-((((4-(((1R)-3-(dimethylamino)-1-((phenylthio)methyl)propyl) amino)-3-nitrophenyl)sulfonyl)amino)carbonyl)-2-methoxy-1,1'-biphenyl-4-yl)-N-methylpropanamide

EXAMPLE 178A methyl 4'-(3-((2-(dimethylamino)ethyl)(methyl) amino)-3-oxopropyl)-2'-methoxy-1,1'-biphenyl-4-carboxylate The desired product was prepared by substituting N,N,N'-trimethylethylenediamine and Example 122L for Example 1C and Example 1B, respectively, in Example 1D. MS (ESI(+)) m/e 399 (M+H)$^+$.

EXAMPLE 178B

4'-(3-((2-(dimethylamino)ethyl)(methyl)amino)-3-oxopropyl)-2'-methoxy-1,1'-biphenyl-4-carboxylic acid The desired product was prepared by substituting Example 178A for Example 1A in Example 1B. MS (ESI(-)) m/e 383 (M-H)$^-$.

EXAMPLE 178C

N-(2-(dimethylamino)ethyl)-3-(4'-((((4-(((1R)-3-(dimethylamino)-1-((phenylthio)methyl)propyl) amino)-3-nitrophenyl)sulfonyl)amino)carbonyl)-2-methoxy-1,1'-biphenyl-4-yl)-N-methylpropanamide The desired product was prepared by substituting Example 122G and Example 178B for Example 1C and Example 1B, respectively, in Example 1D. MS (ESI(-)) m/e 789 (M-H)$^-$; $^1$H NMR (300 MHz, DMSO-d$_6$) δ2.32 (s, 2H), 2.50 (s, 12H), 2.62–2.89 (m, 10H), 2.96 (s, 3H), 3.05 (m, 1H), 3.18 (d, 1H), 3.51 (dd, 1H), 3.73 (s, 3H), 4.08 (m, 1H), 6.89 (m, 2H), 6.98 (d, 1H), 7.18 (d, 2H), 7.26 (dd, 2H), 7.31 (dd, 2H), 7.38 (d, 2H), 7.81 (dd, 1H), 7.89 (d, 2H), 8.26 (d, 1H), 8.48 (d, 1H).

EXAMPLE 179

N-(2-(dimethylamino)ethyl)-3-(4'-((((4-(((1R)-5-(dimethylamino)-1-((phenylthio)methyl)pentyl) amino)-3-nitrophenyl)sulfonyl)amino)carbonyl)-2-methoxy-1,1'-biphenyl-4-yl)-N-methylpropanamide The desired product was prepared by substituting Example 124E and Example 178B for Example 1C and Example 1B, respectively, in Example 1D. MS (ESI(-)) m/e 817 (M-H)$^-$; $^1$H NMR (300 MHz, DMSO-d$_6$) δ0.99 (t, 2H), 1.18 (t, 2H), 1.55 (m, 2H), 1.78 (s, 3H), 1.90 (s, 3H), 2.22 (s, 1H), 2.40 (s, 3H), 2.59 (s, 3H), 2.65 (m, 2H), 2.82 (s, 3H), 2.83 (m, 1H), 2.96 (s, 1H), 3.03 (m, 4H), 3.27 (m, 1H), 3.33 (m, 1H), 3.49 (dd, 1H), 3.73 (s, 3H), 4.04 (m, 1H), 6.89 (m, 2H), 6.98 (d, 1H), 7.18 (d, 2H), 7.24 (dd, 2H), 7.31 (dd, 2H), 7.38 (d, 2H), 7.82 (dd, 1H), 7.89 (d, 2H), 8.15 (d, 1H), 8.48 (d, 1H).

EXAMPLE 180

N~2~-(4-(((4-(4,4-dimethylcyclohexyl)benzoyl) amino)sulfonyl)-2-nitrophenyl)-N~1~,N~1~-bis(4-(N-(4-(((4-(4,4-dimethylcyclohexyl)benzoyl)amino) sulfonyl)-2-nitrophenyl)-S-phenylcysteinyl) morpholin-3-yl)-S-phenylcysteinamide

EXAMPLE 180A

N-tert-butoxycarbonyl-1-morpholin-4-yl-1-oxo-3-(phenylthio)propan-2-amine

A solution of Example 175A (600 mg, 1.92 mmol) and 2M aqueous lithium hydroxide (4 mL) in methanol (10 mL) at room temperature was stirred for 5 hours and concentrated. The concentrate was treated with morpholine (263 mg, 3 mmol), EDCI (555 mg, 2.88 mmol), DMAP (20 mg) and DMF (20 mL), stirred for 16 hours, diluted with ethyl acetate (100 mL), washed sequentially with water (50 mL), and brine (20 mL), dried (MgSO$_4$), filtered, and concentrated. The concentrate was purified by flash column chromatography on silica gel with 50% ethyl acetate/hexanes to provide the desired product. MS (ESI(+)) m/e 367 (M+H)⁺.

EXAMPLE 180B

N²-(4-(aminosulfonyl)-2-nitrophenyl)-N¹,N¹-bis(4-(N-(4-(aminosulfonyl)-2-nitrophenyl)-S-phenylcysteinyl)morpholin-3-yl)-S-phenylcysteinamide The desired product was prepared by substituting Example 180A and Example 122C for Example 175B and Example 175C, respectively, in Example 175D. MS (ESI (+)) m/e 467 (M+H)⁺.

EXAMPLE 180C

N~2~-(4-(((4-(4,4-dimethylcyclohexyl)benzoyl) amino)sulfonyl)-2-nitrophenyl)-N~1~,N~1~-bis(4-(N-(4-(((4-(4,4-dimethylcyclohexyl)benzoyl)amino) sulfonyl)-2-nitrophenyl)-S-phenylcysteinyl) morpholin-3-yl)-S-phenylcysteinamide The desired product was prepared by substituting Example 77A and Example 180B for Example 5C and Example 3A, respectively, in Example 5D. MS (ESI(−)) m/e 679 (M−H)⁻; ¹H NMR (400 MHz, methanol-d₄) δ8.98 (d, 1H), 8.63 (d, 1H), 7.92 (m, 3H), 7.27 (m, 2H), 7.20 (d, 2H), 7.09 (m, 3H), 6.92 (d, 1H), 5.06 (m, 1H), 3.67–3.50 (m, 4H), 3.42 (t, 2H), 2.43 (m, 1H), 2.36 (t, 2H), 2.02 (m, 2H), 1.62 (m, 4H), 1.49 (m, 2H), 1.35 (m, 2H), 0.98 (s, 3H), 0.94 (s, 3H).

EXAMPLE 181

N-(4-(3-(cyclohexylmethyl)-2-oxo-2,3-dihydro-1,3-benzoxazol-6-yl)benzoyl)-3-nitro-4-((2-(phenylthio) ethyl)amino)benzenesulfonamide A mixture of Example 251D (80 mg, 0.14 mmol), 60% NaH in mineral oil (12 mg, 0.29 mmol), 15-crown-5 (64 mg, 0.29 mmol), and bromomethylcyclohexane (27 mg, 0.15 mmol) in DMF (5 mL) was heated to 95° C. and stirred for 16 hours, treated with 1M HCl (20 mL), and extracted with 5% methanol in ethyl acetate (3×20 mL). The combined extracts were washed with brine (5 mL), dried (Na₂SO₄), filtered, and concentrated. The concentrate was purified by flash column chromatography on silica gel with ethyl acetate to provide the desired product. MS (ESI(−)) m/e 685 (M−H)⁻; ¹H NMR (300 MHz, DMSO-d₆) δ0.98–1.26 (m, 5H), 1.57–1.74 (m, 5H), 1.84 (m, 1H), 3.28 (t, 2H), 3.62 (dt, 2H), 3.68 (d, 2H), 7.05 (d, 1H), 7.19 (tt, 1H), 7.29 (t, 2H), 7.39 (d, 3H), 7.58 (dd, 1H), 7.68 (d, 2H), 7.72 (d, 1H), 7.90 (dd, 1H), 7.95 (d, 2H), 8.54 (d, 1H), 8.59 (t, 1H).

EXAMPLE 182

N-(4-(1-benzyl-1H-benzimidazol-5-yl)benzoyl)-3-nitro-4-((2-(phenylthio)ethyl)amino) benzenesulfonamide

EXAMPLE 182A

N¹-benzyl-4-bromobenzene-1,2-diamine

The desired product was prepared by substituting benzylamine for 3-phenylpropylamine in Examples 166A and 166B.

EXAMPLE 182B

N-(4-(1-benzyl-1H-benzimidazol-5-yl)benzoyl)-3-nitro-4-((2-(phenylthio)ethyl)amino) benzenesulfonamide The desired product was prepared by substituting Example 182A for Example 170A in Examples 170B–170D.

MS (ESI) m/e 662, 664 (M−H)⁻, (M+H)⁺; ¹H NMR (300 MHz, DMSO-d₆) δ3.27 (t, 2H), 3.61 (dt, 2H), 5.52 (s, 2H), 6.99 (d, 1H), 7.20 (tt, 1H), 7.28–7.36 (m, 7H), 7.40 (dd, 2H), 7.52–7.67 (m, 5H), 7.88 (dd, 1H), 7.95 (d, 2H), 8.45 (s, 1H), 8.52 (d, 1H), 8.52 (t, 1H).

EXAMPLE 183

N-((2'-methoxy-4'-(3-piperazin-1-ylpropyl)-1,1'-biphenyl-4-yl)carbonyl)-3-nitro-4-((2-(phenylthio) ethyl)amino)benzenesulfonamide

EXAMPLE 183A tert-butyl 4-(3-(2-methoxy-4'-(methoxycarbonyl)-1, 1'-biphenyl-4-yl)propanoyl)piperazine-1-carboxylate The desired product was prepared by substituting N-tert-butoxycarbonylpiperazine and Example 122L for Example 1C and Example 1B, respectively, in Example 1D. MS (ESI(+)) m/e 483 (M+H)⁺.

EXAMPLE 183B tert-butyl 4-(3-(2-methoxy-4'-(methoxycarbonyl)-1, 1'-biphenyl-4-yl)propyl)piperazine-1-carboxylate The desired product was prepared by substituting Example 183A for Example 122F in Example 122G.

EXAMPLE 183C

4'-(3-(4-(tert-butoxycarbonyl)piperazin-1-yl)propyl)-2'-methoxy-1,1'-biphenyl-4-carboxylic acid The desired product was prepared by substituting Example 183B for Example 1A in Example 1B. MS (ESI(−)) m/e 453 (M−H)⁻.

EXAMPLE 183D

N-((2'-methoxy-4'-(3-piperazin-1-ylpropyl)-1,1'-biphenyl-4-yl)carbonyl)-3-nitro-4-((2-(phenylthio) ethyl)amino)benzenesulfonamide The desired product was prepared by substituting Example 77B and Example 183C for Example 1B and Example 1C, respectively, in Example 1D. The product was dissolved in TFA (5 mL) and stirred at room temperature for 90 minutes, concentrated, dissolved in toluene, and concentrated again to provide the desired product. MS (ESI(+)) m/e 690 (M+H)⁺; ¹H NMR (300 MHz, DMSO-d₆) δ1.99 (m, 2H), 2.69 (t, 2H), 3.10 (m, 2H), 3.30 (t, 4H), 3.49 (m, 6H), 3.68 (m, 2H), 3.77 (s, 3H), 6.91 (d, 1H), 7.01 (s, 1H), 7.20 (m, 2H), 7.25 (m, 3H), 7.39 (d, 2H), 7.58 (d, 2H), 7.90 (d, 1H), 7.93 (dd, 1H), 8.62 (d, 1H), 8.81 (t, 1H).

EXAMPLE 184

4-(((1R)-2-hydroxy-1-((phenylthio)methyl)ethyl) amino)-N-((4'-(3-hydroxypropyl)-2'-methoxy-1,1'-biphenyl-4-yl)carbonyl)-3-nitrobenzenesulfonamide A solution of Example 133D (300 mg, 0.38 mmol) in THF (4 mL) at room temperature was treated with 2M LiBH₄ in THF (470 μL, 2.5 eq), stirred for 2 hours, quenched with a drop of water, and concentrated. The concentrate was purified by flash column chromatography on silica gel with 100% ethyl acetate to provide the desired product. MS (ESI(−)) m/e 650 (M−H)⁻; ¹H NMR (300 MHz, DMSO-d₆) δ1.75 (m, 2H), 2.65 (t, 2H), 3.32 (m, 4H), 3.43 (t, 2H), 3.61

(dd, 1H), 3.72 (dd, 1H), 3.77 (s, 3H), 4.06 (m, 1H), 6.68 (d, 1H), 6.96 (s, 1H), 7.11 (m, 2H), 7.22 (m, 2H), 7.31 (m, 2H), 7.59 (m, 2H), 7.88 (m, 3H), 8.10 (d, 1H), 8.12 (d, 1H).

EXAMPLE 185 tert-butyl (5R)-5-((4-(((4-(2-azaspiro(4.4)non-2-yl)benzoyl)amino)sulfonyl)-2-nitrophenyl)amino)-6-(phenylthio)hexylcarbamate The desired product was prepared by substituting Example 120C and Example 124C for Example 1B and Example 1C, respectively, in Example 1D. MS(ESI(−)) m/e 750 (M−H)$^-$; $^1$H NMR (300 MHz, DMSO-d$_6$) δ11.87 (s, 1H), 8.53 (d, 1H), 8.30 (d, 1H), 7.84 (dd, 1H), 7.74 (d, 2H), 7.25–7.08 (m, 6H), 6.72 (t, 1H), 6.51 (d, 2H), 4.08 (s, 1H), 3.17 (s, 2H), 2.87 (m, 2H), 1.85 (t, 2H), 1.73 (m, 2H), 1.63 (m, 4H), 1.55 (m, 4H), 1.32 (s, 9H), 1.35–1.22 (m, 8H).

EXAMPLE 186

N-((4'-(4-(4-methylphenyl)-1,3-oxazol-2-yl)-1,1'-biphenyl-4-yl)carbonyl)-3-nitro-4-((2-(phenylthio)ethyl)amino)benzenesulfonamide

EXAMPLE 186A 4-(ethoxycarbonyl)phenylboronic acid

A suspension of 4-(dihydroxyboryl)benzoic acid (5.0 g, 30.13 mmol) in ethanol (16.0 mL) was treated with 4N HCl in dioxane (34.0 mL), heated to reflux, stirred for 1.5 hours, and concentrated. The concentrate was partitioned between water (150.0 mL) and diethyl ether (100.0 mL) and the aqueous layer was extracted with diethyl ether (2×100 mL). The combined organic extracts were dried (MgSO$_4$), filtered, and concentrated to provide the desired product. MS (APCI) m/e 194 (M+H)$^+$; $^1$H NMR (300 MHz, DMSO-d$_6$) δ8.07 (m, 2H), 7.81 (m, 2H), 4.41 (q, 2H), 1.41 (t, 3H).

EXAMPLE 186B 2-(4-bromophenyl)-4-(4-methylphenyl)-1,3-oxazole

A mixture of 2-bromo-4'-methylacetophenone (152 mg, 0.7 mmol) and 4-bromobenzamide (200 mg, 1.0 mmol) was heated to 160° C. for 3 hours, cooled to room temperature, dissolved in ethyl acetate (20 mL), and treated with 5% sodium bicarbonate (20 mL). The layers were separated and the aqueous layer was extracted with ethyl acetate (2×10 mL). The combined extracts were dried (MgSO$_4$), filtered, and concentrated. The concentrate was purified by flash column chromatography on silica gel with 50% ethyl acetate/hexanes to provide the desired product. MS (DCI) m/e 314, 316 (M−H)$^-$, (M+H)$^+$; $^1$H NMR (300 MHz, DMSO-d$_6$) δ8.70 (s, 1H), 8.00–7.97 (m, 2H), 7.79–7.76 (m, 2H), 7.77–7.74 (m, 2H), 7.29–7.27 (m, 2H), 2.34 (s, 3H).

EXAMPLE 186C ethyl 4'-(4-(4-methylphenyl)-1,3-oxazol-2-yl)-1,1'-biphenyl-4-carboxylate A solution of Example 186B (140 mg, 0.45 mmol) in ethylene glycol dimethyl ether (7.0 mL) at room temperature was treated with tetrakis(triphenylphosphine)palladium (26 mg, 0.02 mmol), stirred for 5 minutes, treated with a solution of Example 186A (104 mg, 0.54 mmol) in ethanol (1.5 mL), stirred for 5 minutes, treated with 2M sodium carbonate (1.1 mL, 2.23 mmol), heated to reflux, and stirred for 4 hours. The reaction mixture was cooled to room temperature and concentrated. The concentrate was dissolved in water (20 mL) and extracted with diethyl ether (4×20 mL). The combined extracts were dried (MgSO$_4$), filtered, and concentrated. The concentrate was purified by flash column chromatography on silica gel with 50% ethyl acetate/hexanes to provide the desired product. MS (DCI) m/e 384 (M+H)$^+$; $^1$H NMR (300 MHz, DMSO-d$_6$) δ8.71 (s, 1H), 8.18–8.16 (m, 2H), 8.09–8.06 (m, 4H), 7.97–7.89 (m, 4H), 7.30–7.28 (m, 2H), 4.35 (q, 2H), 2.34 (s, 3H), 1.35 (t, 3H).

EXAMPLE 186D

4'-(4-(4-methylphenyl)-1,3-oxazol-2-yl)-1,1'-biphenyl-4-carboxylic acid

A solution of Example 186C (130 mg, 0.34 mmol) in THF (15.0 mL) and methanol (5.0 mL) at room temperature was treated with 2N sodium hydroxide (3.0 mL), stirred for 18 hours, concentrated, treated with water (2.0 mL), and adjusted to pH<7 with 2N HCl. The precipitate was filtered and dried under vacuum to provide the desired product. MS (DCI) m/e 356 (M+H)$^+$; $^1$H NMR (300 MHz, DMSO-d$_6$) δ8.72 (s, 1H), 8.18–8.15 (m, 2H), 8.08–8.04 (m, 4H), 7.97–7.86 (m, 4H), 7.31–7.28 (m, 2H), 2.35 (s, 3H).

EXAMPLE 186E

N-((4'-(4-(4-methylphenyl)-1,3-oxazol-2-yl)-1,1'-biphenyl-4-yl)carbonyl)-3-nitro-4-((2-(phenylthio)ethyl)amino)benzenesulfonamide The desired product was prepared by substituting Example 186D and Example 77B for Example 1B and Example 1C, respectively, in Example 1D. MS (DCI) m/e 691 (M+H)$^+$; $^1$H NMR (300 MHz, DMSO-d$_6$) δ12.51 (br s, 1H), 8.79 (t, 1H), 8.69 (s, 1H), 8.65 (d, 1H), 8.16–8.15 (m, 2H), 8.02–8.00 (m, 2H), 7.96–7.94 (m, 2H), 7.91–7.89 (m, 2H), 7.79–7.77 (m, 2H), 7.38–7.37 (m, 2H), 7.29–7.16 (m, 6H), 3.68 (q, 2H), 3.31 (q, 2H), 2.35 (s, 3H).

EXAMPLE 187

4-(((1R)-2-(dimethylamino)-1-((phenylthio)methyl)ethyl)amino)-N-((2'-methoxy-4'-(3-morpholin-4-ylpropyl)-1,1'-biphenyl-4-yl)carbonyl)-3-nitrobenzenesulfonamide The desired product was prepared by substituting Example 134D and Example 122O for Example 1C and Example 1B, respectively, in Example 1D. MS (ESI(−)) m/e 746 (M−H)$^-$; $^1$H NMR (300 MHz, DMSO-d$_6$) δ1.78 (m, 1H), 2.31 (dd, 1H), 2.35 (m, 2H), 2.58 (d, 1H), 2.62 (dd, 1H), 3.00 (s, 6H), 3.48 (m, 1H), 3.58 (m, 4H), 3.74 (s, 3H), 4.11 (m, 1H), 6.84 (d, 1H), 6.92 (d, 1H), 6.95 (s, 1H), 7.18 (dd, 1H), 7.20 (dd, 2H), 7.30(s, 1H), 7.33 (d, 1H), 7.39 (d, 2H), 7.82 (dd, 1H), 7.90 (d, 2H), 8.26 (d, 1H), 8.48 (d, 1H).

EXAMPLE 188

(3R)-3-((4-((((4'-(3-(cyclopentylamino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting cyclobutylamine for neopentylamine in Example 126. MS (ESI(−)) m/e 786 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.78 (br d, 1H), 7.58 (d, 2H), 7.30–7.12 (m, 7H), 7.00 (d, 1H), 6.89 (dd, 1H), 4.45 (m, 1H), 4.00 (m, 1H), 3.75 (s, 3H), 3.45 (t, 2H), 2.90 (s, 3H), 2.79 (s, 3H), 3.10–2.70 (m, 4H), 2.45 (t, 2H), 1.78 (m, 2H), 1.60 (m, 2H), 1.50 (m, 2H), 1.35 (m, 2H).

EXAMPLE 189 methyl N-(4-((((2'-methoxy-4'-(3-morpholin-4-yl-3-oxopropyl)-1,1'-biphenyl-4-yl)carbonyl)amino)sulfonyl)-2-nitrophenyl)-S-phenyl-L-cysteinate

EXAMPLE 189A

2'-methoxy-4'-(3-morpholin-4-yl-3-oxopropyl)-1,1'-biphenyl-4-carboxylic acid

The desired product was prepared by substituting Example 122M for Example 1A in Example 1B.

EXAMPLE 189B methyl N-(4-((((2'-methoxy-4'-(3-morpholin-4-yl-3-oxopropyl)-1,1'-biphenyl-4-yl)carbonyl)amino)sulfonyl)-2-nitrophenyl)-S-phenyl-L-cysteinate The desired product was prepared by substituting Example 189A and Example 133C for Example 1B and Example 1C, respectively, in Example 1D. MS (ESI(−)) m/e 761 (M−H)$^-$; $^1$H NMR (300 MHz, DMSO-d$_6$) δ2.68 (t, 2H), 2.85 (t, 2H), 3.43 (m, 4H), 3.51 (m, 4H), 3.61 (s, 3H), 3.62 (dd, 1H), 3.72 (dd, 1H), 3.75 (s, 1H), 3.78 (dd, 1H), 6.91 (d, 1H), 7.02 (s, 1H), 7.11 (m, 2H), 7.21 (dd, 2H), 7.32 (m, 2H), 7.52 (d, 2H), 7.89 (d, 2H), 7.93 (dd, 1H), 8.54 (d, 1H), 8.82 (d, 1H).

EXAMPLE 190

(3R)-3-((4-((((2'-methoxy-4'-(3-((2-methoxyethyl)amino)-3-oxopropyl)-1,1'-biphenyl-4-yl)carbonyl)amino)sulfonyl)-2-nitrophenyl)amino)-N,N-dimethyl-4-(phenylthio)butanamide The desired product was prepared by substituting 2-methoxyethylamine for neopentylamine in Example 126. MS (ESI(−)) m/e 776 (M−H)$^-$; $^1$H NMR (300 MHz, DMSO-d$_6$) δ12.45 (br s, 1H), 8.89 (br d, 1H), 8.57 (d, 1H), 7.95 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.75 (s, 3H), 3.45 (t, 2H), 3.35 (t, 2H), 3.25 (s, 3H), 3.25 (t, 2H), 2.90 (s, 3H), 2.79 (s, 3H), 3.10–2.70 (m, 6H), 2.45 (t, 2H).

EXAMPLE 191

N-((4'-(2-((2-(dimethylamino)ethyl)(methyl)amino)ethyl)-2'-methoxy-1,1'-biphenyl-4-yl)carbonyl)-4-(((1R)-2-(4-methylpiperazin-1-yl)-1-((phenylthio)methyl)ethyl)amino)-3-nitrobenzenesulfonamide

EXAMPLE 191A methyl 2'-methoxy-4'-(2-oxoethyl)-1,1'-biphenyl-4-carboxylate

A solution of methoxymethyltriphenylphosphonium chloride (5.8 g, 16.9 mmol) in THF (80 mL) at room temperature was treated with 1M LiHMDS in THF (16.9 mL, 16.9 mmol), stirred for 10 minutes, treated with Example 122I, (4.14 g, 15.3 mmol), stirred for 30 minutes, poured into brine, and extracted with ether three times. The combined extracts were washed with brine, dried (Na$_2$SO$_4$), filtered, and concentrated. The concentrate was purified by flash column chromatography on silica gel with 15% ethyl acetate/hexanes to provide the desired product. MS (ESI(−)) m/e 283 (M−H)$^-$.

EXAMPLE 191B methyl 4'-(2-((2-(dimethylamino)ethyl)(methyl)amino)ethyl)-2'-methoxy-1,1'-biphenyl-4-carboxylate The desired product was prepared by substituting N,N,N'-trimethylethylenediamine and Example 191A for dimethylamine and Example 134A, respectively, in Example 134B. MS (ESI(+)) m/e 371 (M+H)$^+$.

EXAMPLE 191C

4'-(2-((2-(dimethylamino)ethyl)(methyl)amino)ethyl)-2'-methoxy-1,1'-biphenyl-4-carboxylic acid The desired product was prepared by substituting Example 191B for Example 1A in Example 1B. MS (ESI(+)) m/e 357 (M+H)$^+$.

EXAMPLE 191D

N-((4'-(2-((2-(dimethylamino)ethyl)(methyl)amino)ethyl)-2'-methoxy-1,1'-biphenyl-4-yl)carbonyl)-4-(((1R)-2-(4-methylpiperazin-1-yl)-1-((phenylthio)methyl)ethyl)amino)-3-nitrobenzenesulfonamide The desired product was prepared by substituting Example 148C and Example 191C for Example 1C and Example 1B, respectively, in Example 1D. MS (ESI(−)) m/e 788 (M−H)$^-$; $^1$H NMR (300 MHz, DMSO-d$_6$) δ2.21 (s, 3H), 2.38 (s, 3H), 2.44 (s, 3H), 2.57 (s, 3H), 2.62 (m, 4H), 2.79 (m, 2H), 3.00 (m, 2H), 3.23 (t, 2H), 3.44 (m, 10H), 3.59 (dd, 1H), 3.75 (s, 3H), 3.77 (dd, 1H), 4.11 (m, 1H), 6.92 (d, 1H), 6.96 (d, 1H), 7.05 (s, 1H), 7.15 (dd, 1H), 7.24 (dd, 2H), 7.34 (m, 2H), 7.40 (d, 2H), 7.82 (dd, 1H), 7.90 (dd, 2H), 8.31 (d, 1H), 8.48 (d, 1H).

EXAMPLE 192

(3R)-3-((4-((((4'-(3-((cyclopropylmethyl)amino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting aminomethylcyclopropane for neopentylamine in Example 126. MS (ESI(−)) m/e 758 (M−H)$^-$; $^1$H NMR (300 MHz, DMSO-d$_6$) δ8.89 (br d, 1H), 8.57 (d, 1H), 7.99 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 3.45 (t, 2H), 2.90 (s, 3H), 2.79 (s, 3H), 3.10–2.70 (m, 6H), 2.45 (t, 2H), 0.90 (m, 1H), 0.38 (m, 2H), 0.20 (m, 2H).

EXAMPLE 193

(3R)-3-((4-((((4'-(3-(cyclopropylamino)-3-oxopropyl)-2'-methoxy-1,1'-biphenyl-4-yl)carbonyl)amino)sulfonyl)-2-nitrophenyl)amino)-N,N-dimethyl-4-(phenylthio)butanamide The desired product was prepared by substituting cyclopropylamine for neopentylamine in Example 126. MS (ESI(−)) m/e 758 (M−H)$^-$; $^1$H NMR (300 MHz, DMSO-d$_6$) δ12.45 (br s, 1H), 8.89 (br d, 1H), 8.57 (d, 1H), 7.90 (br t, 1H), 7.90 (d, 2H), 7.85 (dd, 1H), 7.58 (d, 2H), 7.30–7.12 (m, 7H), 7.00 (d, 1H), 6.89 (dd, 1H), 4.45 (m, 1H), 2.90 (s, 3H), 2.79 (s, 3H), 3.10–2.70 (m, 6H), 2.60 (M, 1h), 2.45 (t, 2H), 0.60 (m, 2H), 0.38 (m 2H).

EXAMPLE 194

4-(((1R)-5-amino-1-((phenylthio)methyl)pentyl)amino)-N-((2'-methoxy-4'-(3-morpholin-4-ylpropyl)-1,1'-biphenyl-4-yl)carbonyl)-3-nitrobenzenesulfonamide A mixture of Example 122N (150 mg, 0.39 mmol ) and LiOH (25 mg, 0.58 mmol) in THF (3 mL), methanol (1 mL), and water (0.5 mL) was heated to 50° C. for 3 hours and concentrated. The concentrate was treated with a mixture of Example 124C (205 mg, 0.39 mmol), EDCI (150 mg, 0.78 mmol), and DMAP (240 mg, 1.96 mmol) in DMF (1.5 mL) and 1,2-dichloroethane (1.5 mL), stirred at room temperature for 16 hours, diluted with ethyl acetate, washed with water and brine, dried (MgSO$_4$), filtered, and concentrated. The concentrate was purified by flash column chromatography on silica gel with 5% methanol/dichloromethane. The product was treated with 1:1 TFA:dichloromethane (2 mL), stirred for 30 minutes, and concentrated to provide the desired product. MS (ESI(–)) m/e 760 (M–H)$^-$; $^1$H NMR (300 MHz, DMSO-d$_6$) δ10.05 (br s, 1H), 8.55 (d, 1H), 8.35 (br d, 1H), 7.90 (d, 2H), 7.85 (dd, 1H), 7.70 (br s, 2H), 7.58 (d, 2H), 7.30–7.12 (m, 7H), 7.00 (d, 1H), 6.89 (dd, 1H), 4.10 (m, 1H), 3.75 (s, 3H), 3.45–3.35 (m, 8H), 3.15 (m, 4H), 2.75 (m, 2H), 2.70 (t, 2H), 2.00 (m, 2H), 1.75 (m, 2H), 1.50 (m, 2H), 1.40 (m, 2H).

EXAMPLE 195

4-((2,2-difluoro-2-(phenylthio)ethyl)amino)-N-((4'-fluoro-1,1'-biphenyl-4-yl)carbonyl)-3-nitrobenzenesulfonamide

EXAMPLE 195A 2,2-difluoro-2-(phenylthio)ethanamine

A mixture of 2,2-difluoro-2-phenylsulfanylacetamide (1 g, 4.92 mmol) in THF at room temperature was treated with BH$_3$.THF (1M, 25 mL), stirred for 18 hours, quenched with methanol (5 mL), and concentrated. The concentrate was treated with 2M HCl and heated to 80° C. for 30 minutes and concentrated. The concentrate was partitioned between dichloromethane and saturated sodium bicarbonate, and the organic phase was dried (MgSO$_4$), filtered, and concentrated to provide the desired product. MS (ESI(+)) m/e 190 (M+H)$^+$.

EXAMPLE 195B 4-((2,2-difluoro-2-(phenylthio)ethyl)amino)-3-nitrobenzenesulfonamide A suspension of Example 195A (0.26 g, 1.37 mmol), diisopropylethylamine (0.5 mL), and Example 122C (0.3 g, 1.37 mmol) in 1,2-dichloroethane (10 mL) at room temperature was stirred for 16 hours at 75° C., diluted with dichloromethane, washed with water, dried (MgSO$_4$), filtered, and concentrated. The concentrate was purified by flash column chromatography on silica gel with 0–5% methanol/dichloromethane to provide the desired product. MS (ESI(–)) m/e 388 (M–H)$^-$.

EXAMPLE 195C 4-((2,2-difluoro-2-(phenylthio)ethyl)amino)-N-((4'-fluoro-1,1'-biphenyl-4-yl)carbonyl)-3-nitrobenzenesulfonamide The desired product was prepared by substituting Example 195B for Example 1C in Example 1D. MS (ESI(–)) m/e 586 (M–H)$^-$; $^1$H NMR (300 MHz, DMSO-d$_6$) δ8.73 (t, 1H), 8.64 (d, 1H), 7.99 (dd, 1H), 7.95 (d, 2H), 7.71–7.80 (m, 4H), 7.59–7.64 (m, 2H), 7.54–7.43 (m, 3H), 7.36–7.27 (m, 3H), 4.37–4.24 (m, 2H).

EXAMPLE 196

N-(4-(1-butyl-2-oxo-2,3-dihydro-1H-benzimidazol-5-yl)benzoyl)-3-nitro-4-((2-(phenylthio)ethyl)amino)benzenesulfonamide The desired product was prepared by substituting Example 166D and Example 77B for Example 1B and Example 1C, respectively, in Example 1D. MS (ESI(–)) m/e 644 (M–H)$^-$; $^1$H NMR (300 MHz, DMSO-d$_6$) δ0.90 (t, 3H), 1.30 (qt, 2H), 1.65 (tt, 2H), 3.28 (t, 2H), 3.61 (dt, 2H), 3.82 (t, 2H), 7.02 (d, 1H), 7.16–7.25 (m, 3H), 7.31 (d, 2H), 7.35 (dd, 1H), 7.40 (d, 2H), 7.58 (d, 2H), 7.90 (dd, 1H), 7.95 (d, 2H), 8.50 (t, 1H), 8.52 (d, 1H), 10.90 (s, 1H).

EXAMPLE 197

N-(4-(8-azaspiro(4.5)dec-8-yl)benzoyl)-4-((2,2-difluoro-2-(phenylthio)ethyl)amino)-3-nitrobenzenesulfonamide The desired product was prepared by substituting Example 257C and Example 195B for Example 1B and Example 1C, respectively, in Example 1D. MS (ESI(–)) m/e 629 (M–H)$^-$; $^1$H NMR (300 MHz, DMSO-d$_6$) δ8.77 (t, 1H), 8.64 (d, 1H), 7.99 (dd, 1H), 7.71 (d, 2H), 7.61 (d, 2H), 7.42–7.52 (m, 3H), 7.36 (d, 1H), 6.91 (d, 2H), 4.27–4.37 (m, 2H), 1.56–1.63 (m, 4H), 1.38–1.48 (m, 6H).

EXAMPLE 198

3-nitro-N-(4-(1-octyl-1H-pyrazol-4-yl)benzoyl)-4-((2-(phenylthio)ethyl)amino)benzenesulfonamide

EXAMPLE 198A 4-iodo-1-octyl-1H-pyrazole

A solution of 4-iodopyrazole (11.25 g, 6.44 mmol) in DMF (20 mL) at room temperature was treated with 60% NaH (271 mg, 6.77 mmol), stirred for 10 minutes, treated with 1-bromooctane (1.22 mL, 7.08 mmol), stirred for 30 minutes, poured into water, and extracted three times with ether/hexanes. The combined extracts were washed with water and brine, dried (MgSO$_4$), filtered, and concentrated to provide the desired product. MS (ESI(+)) m/e 307 (M+H)$^+$.

EXAMPLE 198B 4-(1-octyl-1H-pyrazol-4-yl)benzoic acid

The desired product was prepared by substituting Example 198A for 6-bromoindole in Example 4A. MS (ESI(–)) m/e 299 (M–H)$^-$.

EXAMPLE 198C 3-nitro-N-(4-(1-octyl-1H-pyrazol-4-yl)benzoyl)-4-((2-(phenylthio)ethyl)amino)benzenesulfonamide The desired product was prepared by substituting Example 77B and Example 198B for Example 1C and Example 1B, respectively, in Example 1D. MS (ESI(–)) m/e 634 (M–H)$^-$; $^1$H NMR (300 MHz, DMSO-d$_6$) δ0.83 (t, 3H), 1.23 (m, 10H), 1.79 (tt, 2H), 3.37 (t, 2H), 3.61 (q, 2H), 4.09 (t, 2H), 7.00 (d, 1H), 7.20 (d, 1H), 7.30 (t, 2H), 7.40 (d, 2H), 7.51 (d, 2H), 7.87 (t, 2H), 7.89 (dd, 1H), 8.21 (s, 1H), 8.51 (d, 1H), 8.55 (t, 1H).

EXAMPLE 199

N-(4-(4-(2-(1,3-dioxan-2-yl)ethylidene)piperidin-1-yl)benzoyl)-3-nitro-4-((2-(phenylthio)ethyl)amino) benzenesulfonamide

EXAMPLE 199A ethyl 4-(4-(2-(1,3-dioxan-2-yl)ethylidene)piperidin-1-yl)benzoate The desired product was prepared by substituting (2-(1,3-dioxan-2-yl)ethyl)triphenylphosphonium bromide for methyltriphenylphosphonium bromide in Example 158C. MS (DCI) m/e 346 $(M+H)^+$.

EXAMPLE 199B 4-(4-(2-(1,3-dioxan-2-yl)ethylidene)piperidin-1-yl) benzoic acid The desired product was prepared by substituting Example 199A for Example 119B in Example 119C. MS(DCI) m/e 318 $(M+H)^+$.

EXAMPLE 199C

N-(4-(4-(2-(1,3-dioxan-2-yl)ethylidene)piperidin-1-yl)benzoyl)-3-nitro-4-((2-(phenylthio)ethyl)amino) benzenesulfonamide The desired product was prepared by substituting Example 199B and Example 77B for Example 1B and Example 1C, respectively, in Example 1D. MS (ESI(−)) m/e 651; $^1$H NMR (300 MHz, DMSO-$d_6$) δ11.97 (s, 1H), 8.77 (t, 1H), 8.60 (d, 1H), 7.91 (dd, 1H), 7.74 (d, 2H), 7.37 (dd, 2H), 7.31–7.14 (m, 4H), 6.93 (d, 2H), 5.23 (t, 1H,), 4.48 (t, 1H), 3.97 (dd, 2H), 3.72–3.61 (m, 4H), 3.39 (t, 4H), 3.31 (m, 2H), 2.23 (m, 6H), 1.91–1.78 (m, 1H), 1.32 (m, 1H).

EXAMPLE 200

4-(3-(2-methoxy-4'-((((3-nitro-4-((2-(phenylthio) ethyl)amino)phenyl)sulfonyl)amino)carbonyl)-1,1'-biphenyl-4-yl)propyl)-N,N-dimethylpiperazine-1-carboxamide A solution of Example 183D (108 mg, 0.157 mmol) and triethylamine (45 µL, 0.32 mmol) in THF (2 mL) at room temperature was treated with dimethylcarbamic chloride (14 uL, 0.157 mmol), and stirred for 30 minutes. The mixture was purified by flash column chromatography on silica gel with 10:10:80 methanol/acetonitrile/ethyl acetate to provide the desired product. MS (ESI(−)) m/e 759 $(M-H)^-$; $^1$H NMR (300 MHz, DMSO-$d_6$) δ1.93 (m, 2H), 2.65 (t, 2H), 2.74 (s, 6H), 2.89 (m, 2H), 3.08 (m, 4H), 3.34 (m, 6H), 3.61 (m, 2H), 3.75 (s, 3H), 6.88 (d, 1H), 6.96 (s, 1H), 7.01 (d, 1H), 7.21 (m, 2H), 7.30 (t, 2H), 7.41 (m, 3H), 7.88 (d, 1H), 7.89 (d, 2H), 8.51 (d, 1H), 8.54 (t, 1H).

EXAMPLE 201

N-(4-(5-(3-(4-methylpiperazin-1-yl)-3-oxopropyl) quinolin-8-yl)benzoyl)-3-nitro-4-((2-(phenylthio) ethyl)amino)benzenesulfonamide

EXAMPLE 201A 5-iodoquinolin-8-ol

A solution of 8-hydroxyquinoline (25.00 g, 172 mmol), sodium iodide (27.10 g, 181 mmol), and 6M NaOH (30.14 mL, 181 mmol) in methanol at 0° C. was treated with 5.25% aqueous NaOCl (13.46 g, 181 mmol) dropwise over 4 hours, stirred for 16 hours, adjusted to pH 7 with 6M HCl and pH 7 buffer, and extracted with 5% methanol in ethyl acetate (3×200 mL). The combined extracts were washed with brine (100 mL), dried ($Na_2SO_4$), filtered, and concentrated. The concentrate was dissolved in 10% methanol/ethyl acetate and filtered. The filtrate was dried ($Na_2SO_4$), filtered, and concentrated to provide the desired product.

EXAMPLE 201B 8-((tert-butyl(dimethyl)silyl)oxy)-5-iodoquinoline

A mixture of Example 201A (10.40 g, 38.4 mmol), tert-butyldimethylsilyl chloride (6.07 g, 40.3 mmol), and imidazole (5.49 g, 80.6 mmol) in DMF (75 mL) at room temperature was stirred for 16 hours, treated with water (300 mL), and extracted with diethyl ether (3×400 mL). The combined extracts were washed with brine (100 mL), dried ($Na_2SO_4$), filtered, and concentrated. The concentrate was purified by flash column chromatography on silica gel with 10% ethyl acetate/hexanes to provide the desired product.

EXAMPLE 201C tert-butyl (2E)-3-(8-((tert-butyl(dimethyl)silyl)oxy) quinolin-5-yl)prop-2-enoate A mixture of Example 201B (5.00 g, 13.0 mmol), tert-butylacrylate (2.00 g, 15.6 mmol), palladium(II) acetate (175 mg, 0.78 mmol), and tri-o-tolylphosphine (951 mg, 3.12 mmol) in a sealed tube with triethylamine (8 mL) and acetonitrile (38 mL) was heated to 120° C. for 16 hours and then concentrated. The concentrate was purified by flash column chromatography on silica gel with 10–100% ethyl acetate/hexanes to provide the desired product.

EXAMPLE 201D tert-butyl 3-(8-((tert-butyl(dimethyl)silyl)oxy) quinolin-5-yl)propanoate A mixture of Example 201C (4.03 g, 10.5 mmol) and $Rh(PPh_3)_3Cl$ (972 mg, 1.05 mmol) in toluene (40 mL) was degassed and flushed with hydrogen three times. The solution was heated to 60° C. under a hydrogen atmosphere for 16 hours and concentrated. The concentrate was purified by flash column chromatography on silica gel with 5–10% ethyl acetate/hexanes to provide the desired product.

EXAMPLE 201E tert-butyl 3-(8-hydroxyquinolin-5-yl)propanoate

The desired product was prepared by substituting Example 201D for Example 177A in Example 177B.

EXAMPLE 201F tert-butyl 3-(8-(((trifluoromethyl)sulfonyl)oxy) quinolin-5-yl)propanoate A mixture of Example 201E (1.57 g, 5.74 mmol), N-(2-pyridyl)triflimide (2.16 g, 6.03 mmol), and N,N-diisopropylethylamine (816 mg, 6.31 mmol) in dichloromethane (25 mL) was heated to reflux for 16 hours and then concentrated. The concentrate was purified by flash column chromatography on silica gel with 30% ethyl acetate/hexanes to provide the desired product.

EXAMPLE 201G methyl 4-(5-(3-tert-butoxy-3-oxopropyl)quinolin-8-yl)benzoate

The desired product was prepared by substituting Example 201F for Example 5A in Example 5B.

EXAMPLE 201H 3-(8-(4-(methoxycarbonyl)phenyl)quinolin-5-yl)propanoic acid

A mixture of Example 201G (1.26 g, 3.22 mmol) and triethylsilane (1.12 g, 9.66 mmol) in TFA (10 mL) was heated to 50° C. for 16 hours and concentrated. The concentrate was purified by flash column chromatography on silica gel with 5% methanol/ethyl acetate to provide the desired product.

EXAMPLE 201I methyl 4-(5-(3-chloro-3-oxopropyl)quinolin-8-yl)benzoate

A solution of Example 201H (1.65 g, 4.92 mmol) in dichloromethane (15 mL) at room temperature was treated oxalyl chloride (344 mg, 2.71 mmol), stirred for 20 minutes, treated with toluene (25 mL), and concentrated to provide the desired product.

EXAMPLE 201J methyl 4-(5-(3-(4-methylpiperazin-1-yl)-3-oxopropyl)quinolin-8-yl)benzoate A mixture of Example 201I (300 mg, 0.85 mmol), 1-methylpiperazine (111 mg, 1.11 mmol), and pyridine (74 mg, 0.94 mmol) in dioxane (4 mL) at room temperature was stirred for 75 minutes and purified by flash column chromatography on silica gel with 90:10:0.5 dichloromethane/methanol/concentrated ammonium hydroxide to provide the desired product.

EXAMPLE 201K 4-(5-(3-(4-methylpiperazin-1-yl)-3-oxopropyl)quinolin-8-yl)benzoic acid The desired product was prepared by substituting Example 201J for Example 1A in Example 1B.

EXAMPLE 201L

N-(4-(5-(3-(4-methylpiperazin-1-yl)-3-oxopropyl)quinolin-8-yl)benzoyl)-3-nitro-4-((2-(phenylthio)ethyl)amino)benzenesulfonamide The desired product was prepared by substituting Example 201K and Example 77B for Example 1B and Example 1C, respectively, in Example 1D. MS (ESI) m/e 737, 739 (M−H)⁻, (M+H)⁺; $^1$H NMR (300 MHz, DMSO-d$_6$) δ2.37 (s, 3H), 2.53 (m, 4H), 2.78 (t, 2H), 3.17 (t, 2H), 3.27 (t, 2H), 3.40–3.57 (m, 4H), 3.61 (dt, 2H), 7.01 (d, 1H), 7.20 (tt, 1H), 7.31 (t, 2H), 7.40 (d, 2H), 7.54–7.62 (m, 4H), 7.68 (d, 1H), 7.90 (dd, 1H), 7.96 (d, 2H), 8.52 (d, 1H), 8.54 (t, 1H), 8.57 (d, 1H), 8.89 (dd, 1H).

EXAMPLE 202 tert-butyl 4-(3-(2-methoxy-4'-((((3-nitro-4-((2-(phenylthio)ethyl)amino)phenyl)sulfonyl)amino)carbonyl)-1,1'-biphenyl-4-yl)propyl)piperazine-1-carboxylate The desired product was prepared by substituting (BOC)$_2$O for dimethylcarbamic chloride in Example 200. MS (ESI(−)) m/e 788 (M−H)⁻; $^1$H NMR (300 MHz, DMSO-d$_6$) δ1.93 (m, 2H), 2.65 (t, 2H), 2.74 (s, 6H), 2.89 (m, 2H), 3.08 (m, 4H), 3.34 (m, 6H), 3.61 (m, 2H), 3.75 (s, 3H), 6.86 (d, 1H), 6.96 (s, 1H), 7.01 (d, 1H), 7.21 (m, 2H), 7.31 (t, 2H), 7.40 (m, 4H), 7.89 (d, 2H), 8.51 (d, 1H), 8.54 (t, 1H).

EXAMPLE 203

N-(4-(4-(2-(1,3-dioxan-2-yl)ethyl)piperidin-1-yl)benzoyl)-3-nitro-4-((2-(phenylthio)ethyl)amino)benzenesulfonamide

EXAMPLE 203A ethyl 4-(4-(2-(1,3-dioxan-2-yl)ethyl)piperidin-1-yl)benzoate

A mixture of Example 199A (1.2 g, 3.6 mmol), Pd/C (0.42 g), and ethyl acetate (25 mL) was hydrogenated at 4 atmospheres in a Parr shaker at room temperature for 3 days. The catalyst was removed by filtration, solvent was evaporated, and the crude product was purified by flash column chromatography on silica gel with 30% ethyl acetate/hexanes to provide the desired product. MS(DCI) m/e 348 (M+H)⁺.

EXAMPLE 203B 4-(4-(2-(1,3-dioxan-2-yl)ethyl)piperidin-1-yl)benzoic acid

The desired product was prepared by substituting Example 203A for Example 119B in Example 119C. MS(DCI) m/e 320 (M+H)⁺.

EXAMPLE 203C

N-(4-(4-(2-(1,3-dioxan-2-yl)ethyl)piperidin-1-yl)benzoyl)-3-nitro-4-((2-(phenylthio)ethyl)amino)benzenesulfonamide The desired product was prepared by substituting Example 203B and Example 77B for Example 1B and Example 1C, respectivley, in Example 1D to obtain the desired product. MS (ESI(−)) m/e 653; $^1$H NMR (300 MHz, DMSO-d$_6$) δ11.96 (s, 1H), 8.77 (t, 1H), 8.60 (d, 1H), 7.91 (dd, 1H), 7.72 (d, 2H), 7.37 (m, 2H), 7.14–7.31 (m, 4H), 6.91 (d, 2H), 4.47 (t, 1H), 3.87–3.99 (m, 4H), 3.62–3.70 (m, 4H), 3.30 (m, 4H), 2.78 (m, 2H), 1.75–1.90 (m, 1H), 1.70 (m, 2H), 1.48 (m, 2H), 1.22–1.32 (m, 3H) 1.05–1.13 (m, 1H).

EXAMPLE 204

N-(2-(dimethylamino)ethyl)-3-(2-methoxy-4'-((((4-(((1R)-2-(4-methylpiperazin-1-yl)-1-((phenylthio)methyl)ethyl)amino)-3-nitrophenyl)sulfonyl)amino)carbonyl)-1,1'-biphenyl-4-yl)-N-methylpropanamide The desired product was prepared by substituting Example 148C and Example 178B for Example 1C and Example 1B, respectively, in Example 1D. MS (ESI(−)) m/e 830 (M−H)⁻; $^1$H NMR (300 MHz, DMSO-d$_6$) δ2.42–2.59 (m, 2H), 2.68 (s, 6H), 2.71 (s, 3H), 2.89 (m, 2H), 3.02 (m, 2H), 3.14 (s, 3H), 3.29 (m, 12H), 3.62 (m, 2H), 3.75 (s, 3H), 4.04 (m, 1H), 6.89 (d, 1H), 6.94 (s, 1H), 6.98 (d, 1H), 7.18 (m, 2H), 7.26 (t, 2H), 7.37 (m, 3H), 7.84 (d, 1H), 7.89 (d, 2H), 8.46 (d, 1H), 8.54 (t, 1H).

EXAMPLE 205 methyl 4-(3-(2-methoxy-4'-((((3-nitro-4-((2-(phenylthio)ethyl)amino)phenyl)sulfonyl)amino)carbonyl)-1,1'-biphenyl-4-yl)propyl)piperazine-1-carboxylate The desired product was prepared by substituting methyl chloroformate for dimethylcarbamic chloride in Example 200. MS (ESI(−)) m/e 746 (M−H)⁻; $^1$H NMR (300 MHz, DMSO-d$_6$) δ1.79 (m, 2H), 2.35 (m, 4H), 2.61 (t, 2H), 3.28 (t, 2H), 3.35 (m, 6H), 3.59 (s, 3H), 3.61 (m, 2H), 3.74 (s, 3H), 6.85 (d, 1H), 6.94 (s, 1H), 6.98 (d, 1H), 7.20 (m, 2H), 7.31 (t, 2H), 7.40 (m, 3H), 7.88 (d, 1H), 7.89 (d, 2H), 8.51 (d, 1H), 8.52 (t, 1H).

EXAMPLE 206

N-(4-(8-azaspiro(4.5)dec-8-yl)benzoyl)-4-(((1R)-2-((2-(dimethylamino)ethyl)(methyl)amino)-1-((phenylthio)methyl)ethyl)amino)-3-nitrobenzenesulfonamide

EXAMPLE 206A tert-butyl (1R)-2-((2-(dimethylamino)ethyl)(methyl)amino)-1-((phenylthio)methyl)ethylcarbamate The desired product was prepared by substituting N,N,N'-trimethylethylenediamine for dimethylamine in Example 134B. MS (ESI(−)) m/e 366 (M−H)⁻.

EXAMPLE 206B (2R)-N$^1$-(2-(dimethylamino)ethyl)-N$^1$-methyl-3-(phenylthio)propane-1,2-diamine The desired product was prepared by substituting Example 206A for Example 133A in Example 133B.

EXAMPLE 206C 4-(((1R)-2-((2-(dimethylamino)ethyl)(methyl)amino)-1-((phenylthio)methyl)ethyl)amino)-3-nitrobenzenesulfonamide The desired product was prepared by substituting Example 122C and Example 206B for Example 1D and 2,2-dimethylcyclopentylamine, respectively, in Example 1E. MS (ESI(−)) m/e 466 (M−H)⁻.

EXAMPLE 206D

N-(4-(8-azaspiro(4.5)dec-8-yl)benzoyl)-4-(((1R)-2-((2-(dimethylamino)ethyl)(methyl)amino)-1-((phenylthio)methyl)ethyl)amino)-3-nitrobenzenesulfonamide The desired product was prepared by substituting Example 257C and Example 206C for Example 1B and Example 1C, respectively, in Example 1D. MS (ESI(−)) m/e 707 (M−H)⁻; $^1$H NMR (300 MHz, DMSO-d$_6$) δ1.41 (m, 4H), 1.48 (m, 4H), 1.59 (m, 4H), 2.23 (m, 2H), 2.64 (s, 6H), 2.67 (s, 3H), 2.72 (m, 2H), 3.20 (m, 4H), 3.26–3.42 (m, 5H), 6.81 (d, 2H), 6.97 (d, 1H), 7.18 (dd, 1H), 7.21 (dd, 2H), 7.31 (d, 2H), 7.72 (d, 2H), 7.82 (dd, 1H), 8.20 (d, 1H), 8.43 (s, 1H).

EXAMPLE 207

N-(4-(4-(2-amino-3-phenylpropyl)piperazin-1-yl)benzoyl)-3-nitro-4-((2-(phenylthio)ethyl)amino)benzenesulfonamide The desired product was prepared by substituting Example 173B for Example 120D in Example 120E. MS (ESI(−)) m/e 673 (M−H)⁻; $^1$H NMR (300 MHz, DMSO-d$_6$) δ8.78 (t, 1H), 8.60 (d, 1H), 7.91 (dd, 1H), 7.77 (d, 2H), 7.12–7.40 (m, 9H), 6.90–7.04 (m, 2H), 3.60–3.72 (m, 4H), 3.26–3.40 (m, 6H), 2.98–3.08 (m, 2H), 2.70–2.84 (m, 4H)

EXAMPLE 208

4-(((4-(aminomethyl)bicyclo(2.2.2)oct-1-yl)methyl)amino)-N-((2'-methoxy-4'-(3-morpholin-4-ylpropyl)-1,1'-biphenyl-4-yl)carbonyl)-3-nitrobenzenesulfonamide

EXAMPLE 208A tert-butyl (4-(((4-((((2'-methoxy-4'-(3-morpholin-4-ylpropyl)-1,1'-biphenyl-4-yl)carbonyl)amino)sulfonyl)-2-nitrophenyl)amino)methyl)bicyclo(2.2.2)oct-1-yl)methylcarbamate The desired product was prepared by substituting Example 122O and Example 162A for Example 1B and Example 1C, respectively, in Example 1D. MS (ESI(−)) m/e 804 (M−H)⁻

EXAMPLE 208B 4-(((4-(aminomethyl)bicyclo(2.2.2)oct-1-yl)methyl)amino)-N-((2'-methoxy-4'-(3-morpholin-4-ylpropyl)-1,1'-biphenyl-4-yl)carbonyl)-3-nitrobenzenesulfonamide The desired product was prepared by substituting Example 208A for Example 120D in Example 120E. MS (ESI(−)) m/e 704 (M−H)⁻; $^1$H NMR (300 MHz, DMSO-d$_6$) δ0.3 (br s, 1H), 8.65 (d, 1H), 8.48 (d, 1H), 7.95 (dd, 1H), 7.92 (d, 2H), 7.66 (br s, 2H), 7.56 (d 2H), 7.32 (d, 1H), 7.26 (d, 1H), 7.02 (d, 1H), 6.93 (dd, 1H), 3.92–4.02 (m, 2H), 3.78 (s, 3H), 3.38–3.47 (m, 2H), 3.26–3.37 (m, 4H), 3.10 (br s, 2H), 2.63–2.76 (m, 4H), 2.52–2.60 (m, 2H), 2.01–2.08 (m, 2H), 1.42–1.55 (m, 12H).

EXAMPLE 209

N-(4-((4-butylbenzyl)oxy)benzoyl)-3-nitro-4-((2-(phenylthio)ethyl)amino)benzenesulfonamide

EXAMPLE 209A methyl 4-((4-butylbenzyl)oxy)benzoate

A solution of triphenylphosphine (656 mg, 2.50 mmol) in THF (12 mL) at 0° C. was treated with diethyl azodicarboxylate (442 mg, 2.54 mmol), stirred for 20 minutes, treated with ethyl 4-hydroxybenzoate (350 mg, 2.30 mmol) and 4-butylbenzyl alcohol (414 mg, 2.52 mmol), warmed to room temperature, stirred for 16 hours, and concentrated. The concentrate was purified by flash column chromatography on silica gel with 30% ethyl acetate/hexanes to provide the desired product.

EXAMPLE 209B 4-((4-butylbenzyl)oxy)benzoic acid

The desired product was prepared by substituting Example 209A for Example 1A in Example 1B.

EXAMPLE 209C

N-(4-((4-butylbenzyl)oxy)benzoyl)-3-nitro-4-((2-(phenylthio)ethyl)amino)benzenesulfonamide The desired product was prepared by substituting Example 209B and Example 77B for Example 1B and Example 1C, respectively, in Example 1D. MS (ESI(−)) m/e 618 (M−H)⁻; $^1$H NMR (300 MHz, DMSO-d$_6$) δ0.88 (t, 3H), 1.29 (tq, 2H), 1.54 (tt, 2H), 2.57 (t, 2H), 3.28 (t, 2H), 3.63 (dt, 2H), 5.08 (s, 2H), 6.96 (d, 2H), 7.06 (d, 1H), 7.19 (d, 2H), 7.21 (s, 1H), 7.34 (m, 6H), 7.83 (d, 2H), 7.88 (dd, 1H), 8.54 (d, 1H), 8.61 (t, 1H).

EXAMPLE 210

4-(3-(2-methoxy-4'-((((3-nitro-4-((2-(phenylthio)ethyl)amino)phenyl)sulfonyl)amino)carbonyl)-1,1'-biphenyl-4-yl)propyl)-N,N-dimethylpiperazine-1-sulfonamide The desired product was prepared by substituting dimethylsulfamoyl chloride for dimethylcarbamic chloride in Example 200. MS (ESI(−)) m/e 795 (M−H)$^-$; $^1$H NMR (300 MHz, DMSO-d$_6$) δ1.89 (m, 2H), 2.65 (m, 2H), 2.77 (s, 6H), 2.84 (m, 2H), 3.10 (m, 8H), 3.28 (m, 2H), 3.63 (dd, 2H), 3.76 (s, 3H), 6.89 (d, 1H), 6.97 (s, 1H), 7.09 (d, 1H), 7.21 (m, 2H), 7.29 (t, 2H), 7.39 (m, 2H), 7.47 (d, 2H), 7.88 (d, 1H), 7.90 (dd, 1H), 8.55 (d, 1H), 8.64 (t, 1H).

EXAMPLE 211

4-(((1R)-2-(2,5-dioxopyrrolidin-1-yl)-1-((phenylthio)methyl)ethyl)amino)-N-((2'-methoxy-4'-(3-morpholin-4-yl-3-oxopropyl)-1,1'-biphenyl-4-yl)carbonyl)-3-nitrobenzenesulfonamide A solution of succinimide (24 mg, 0.245 mmol), triphenylphosphine (71 mg, 0.27 mmol), and DEAD (43 uL, 0.27 mmol) in THF (3 mL) at room temperature was treated with Example 281B (90 mg, 0.122 mmol), stirred for 30 minutes, and purified by flash column chromatography on silica gel with 5% methanol/ethyl acetate to provide the desired product. MS (ESI(−)) m/e 814 (M−H)$^-$; $^1$H NMR (300 MHz, DMSO-d$_6$) δ1.79 (m, 2H), 2.35 (m, 4H), 2.61 (t, 2H), 3.28 (t, 2H), 3.35 (m, 6H), 3.59 (s, 3H), 3.61 (m, 2H), 3.74 (s, 3H), 6.91 (d, 1H), 7.01 (s, 1H), 7.03 (d, 1H), 7.16 (m, 1H), 7.21 (t, 2H), 7.31 (m, 2H), 7.56 (d, 2H), 7.89 (d, 3H), 8.37 (d, 1H), 8.54 (t, 1H).

EXAMPLE 212

N-(4-(8-azaspiro(4.5)dec-8-yl)benzoyl)-4-((3-(dimethylamino)-2-(phenylthio)propyl)amino)-3-nitrobenzenesulfonamide

EXAMPLE 212A 2-cyano-N,N-dimethyl-2-(phenylthio)acetamide

A suspension of 2-bromo-2-cyano-N,N-dimethylacetamide (3.80 g, 20 mmol), potassium carbonate (2.902 g, 21 mmol) and thiophenol (2.314 g, 21 mmol, 2.16 mL) in acetonitrile (20 mL) was heated to 50° C. for 3 days. The mixture was diluted with water (100 mL) and extracted with ethyl acetate (2×50 mL). The combined extracts were combined and concentrated. The concentrate was purified by column chromatography on silica gel with 0–50% ethyl acetate/hexanes to provide the desired product. MS (ESI(+)) m/e 221 (M+H)$^+$.

EXAMPLE 212B

N,N-dimethyl-2-(phenylthio)propane-1,3-diamine

Example 212A (0.76 g, 3.45 mmol) was treated with 1M BH$_3$.THF (15 mL), stirred at room temperature for 18 hours, quenched with methanol (5 mL), and concentrated. The concentrate was heated with 2M HCl (50 mL) concentrated, treated with 40% KOH (1–2 mL) and extracted with dichloromethane (25 mL×2). The combined extracts were dried (MgSO$_4$), filtered, and concentrated to provide the desired product. MS (ESI(+)) m/e 211 (M+H)$^+$.

EXAMPLE 212C 4-((3-(dimethylamino)-2-(phenylthio)propyl)amino)-3-nitrobenzenesulfonamide The desired product was prepared by substituting Example 212B for Example 195A in Example 195B. MS (ESI(−)) m/e 409 (M−H)$^-$.

EXAMPLE 212D

N-(4-(8-azaspiro(4.5)dec-8-yl)benzoyl)-4-((3-(dimethylamino)-2-(phenylthio)propyl)amino)-3-nitrobenzenesulfonamide The desired product was prepared by substituting Example 257C and Example 212C for Example 1B and Example 1C, respectively, in Example 1D. MS (ESI(−)) m/e 650 (M−H)$^-$; $^1$H NMR (300 MHz, DMSO-d$_6$) δ8.98 (t, 1H), 8.56 (d, 1H), 7.88 (dd, 1H), 7.71 (d, 2H), 7.48–7.44 (m, 2H), 7.35–7.26 (m, 3H), 7.02 (d, 1H), 6.87 (d, 2H), 3.82–3.79 (m, 1H), 3.67–3.59 (m, 2H), 3.32–3.24 (m, 4H), 2.86–2.67 (m, 2H), 2.39 (br s, 6H), 1.61–1.56 (m, 4), 1.51–1.40 (m, 8H).

EXAMPLE 213

N-(4-(2-but-3-enyl-1,3-benzothiazol-5-yl)benzoyl)-3-nitro-4-((2-(phenylthio)ethyl)amino)benzenesulfonamide

EXAMPLE 213A 5-bromo-2-but-3-enyl-1,3-benzothiazole

A solution of 5-bromo-2-methylbenzothioazole (1.00 g, 4.38 mmol) in THF (25 mL) at −78° C. was treated with 1.5M LDA in cyclohexane (4.40 mL, 6.60 mmol), stirred for 45 minutes, treated with allyl bromide (1.33 g, 10.99 mmol), stirred for 1 hour, quenched with 1M HCl, warmed to room temperature, added to water (50 mL), and extracted with ethyl acetate (3×200 mL). The combined extracts were washed with brine (25 mL), dried (Na$_2$SO$_4$), filtered, and concentrated. The concentrate was purified by flash column chromatography on silica gel with 8% ethyl acetate/hexanes to provide the desired product.

EXAMPLE 213B 4-(2-but-3-enyl-1,3-benzothiazol-5-yl)benzoic acid

The desired product was prepared by substituting Example 213A for 6-bromoindole in Example 4A.

EXAMPLE 213C

N-(4-(2-but-3-enyl-1,3-benzothiazol-5-yl)benzoyl)-3-nitro-4-((2-(phenylthio)ethyl)amino)benzenesulfonamide The desired product was prepared by substituting Example 213B and Example 77B for Example 1B and Example 1C, respectively, in Example 1D. MS (ESI) m/e 643, 645 (M−H)$^-$, (M+H)$^+$; $^1$H NMR (300 MHz, DMSO-d$_6$) δ2.59 (dt, 2H), 3.24 (t, 2H), 3.26 (t, 2H), 3.61 (dt, 2H), 5.02 (dq, 1H), 5.14 (dq, 1H), 5.92 (m, 1H), 7.02 (d, 1H), 7.19 (tt, 1H), 7.30 (t, 2H), 7.39 (d, 2H), 7.74 (d, 3H), 7.89 (dd, 1H), 7.97 (d, 2H), 8.10 (d, 1H), 8.22 (d, 1H), 8.54 (d, 1H), 8.56 (t, 1H).

EXAMPLE 214

N-(4-(1-((1-hydroxycyclohexyl)methyl)-1H-benzimidazol-5-yl)benzoyl)-3-nitro-4-((2-(phenylthio)ethyl)amino)benzenesulfonamide

EXAMPLE 214A 1-(((2-amino-4-bromophenyl)amino)methyl)cyclohexanol

The desired product was prepared by substituting 1-aminomethyl-1-cyclohexanol hydrochloride for butylamine in Examples 166A, adding 2M NaOH (2.5 mL) to the reaction, and then substituting the resulting product for Example 166A in Example 166B.

EXAMPLE 214B 1-((5-bromo-1H-benzimidazol-1-yl)methyl)cyclohexanol

The desired product was prepared by substituting Example 214A for Example 170A in Example 170B.

EXAMPLE 214C 4-(1,3,2-dioxaborinan-2-yl)benzoic acid

A mixture of 4-(dihydroxyboryl)benzoic acid (30.00 g, 181 mmol) and 1,3-propanediol (15.20 g, 200 mmol) in toluene (750 mL) at 140° C. was stirred for 6 hours while collecting the water removed by azeotrope formation. The mixture was concentrated to provide the desired product.

EXAMPLE 214D

N-(4-(1,3,2-dioxaborinan-2-yl)benzoyl)-3-nitro-4-((2-(phenylthio)ethyl)amino)benzenesulfonamide The desired product was prepared by substituting Example 214C and Example 77B for Example 1B and Example 1C, respectively, in Example 1D.

EXAMPLE 214E

N-(4-borylbenzoyl)-3-nitro-4-((2-(phenylthio)ethyl)amino)benzenesulfonamide

A solution of Example 214D (26.26 g, 48.5 mmol) in THF (250 mL) at room temperature was treated with 2M KOH (225 mL), stirred for 16 hours, and concentrated. The concentrate was purified by flash column chromatography on silica gel with 70–100% ethyl acetate/hexanes to provide the desired product.

EXAMPLE 214F

N-(4-(1-((1-hydroxycyclohexyl)methyl)-1H-benzimidazol-5-yl)benzoyl)-3-nitro-4-((2-(phenylthio)ethyl)amino)benzenesulfonamide The desired product was prepared by substituting Example 214B and Example 214E for 6-bromoindole and 4-(dihydroxyboryl)benzoic acid in Example 4A. MS (ESI) m/e 684, 686 (M–H)$^-$, (M+H)$^+$; $^1$H NMR (300 MHz, DMSO-d$_6$) δ1.17–1.58 (m, 10H), 3.27 (t, 2H), 3.61 (dt, 2H), 4.15 (s, 2H), 4.58 (s, 1H), 7.00 (d, 1H), 7.20 (tt, 1H), 7.31 (td, 2H), 7.40 (d, 2H), 7.49–7.58 (m, 2H), 7.65 (d, 2H), 7.73 (d, 1H), 7.89 (dd, 1H), 7.96 (d, 2H), 8.14 (s, 1H), 8.52 (d, 1H), 8.53 (t, 1H).

EXAMPLE 215 tert-butyl 2-((4-(4-((((3-nitro-4-((2-(phenylthio)ethyl)amino)phenyl)sulfonyl)amino)carbonyl)phenyl)piperazin-1-yl)methyl)pyrrolidine-1-carboxylate The desired product was prepared by substituting 2-formylpyrrolidine-1-carboxylic acid tert-butyl ester for (1-benzyl-2-oxo-ethyl)-carbamic acid tert-butyl ester in Example 173B. MS (ESI(–)) m/e 723 (M–H)$^-$; $^1$H NMR (300 MHz, DMSO-d$_6$) δ8.61 (t, 1H), 8.53 (d, 1H), 7.88 (dd, 1H), 7.73 (d, 2H), 7.38 (d, 2H), 7.30–7.25 (m, 2H), 7.21–7.15 (m, 1H), 7.07 (d, 1H), 6.87 (d, 2H), 3.88–3.78 (m, 1H), 3.62 (q, 2H), 3.18–3.30 (m, 10H), 2.72–2.60 (m, 2H), 2.38–2.26 (m, 2H), 1.90–1.76 (m, 4H), 1.40 (s, 9H).

EXAMPLE 216

N,N-dimethyl-3-(8-(4-((((3-nitro-4-((2-(phenylthio)ethyl)amino)phenyl)sulfonyl)amino)carbonyl)phenyl)quinolin-5-yl)propanamide The desired product was prepared by substituting dimethylamine for 1-methylpiperazine in Example 201. MS (ESI(–)) m/e 682 (M–H)$^-$; $^1$H NMR (300 MHz, DMSO-d$_6$) δ2.73 (t, 2H), 2.83 (s, 3H), 2.92 (s, 3H), 3.26 (t, 2H), 3.28 (t, 2H), 3.65 (dt, 2H), 7.15 (d, 1H), 7.19 (tt, 1H), 7.29 (td, 2H), 7.38 (d, 2H), 7.55–7.62 (m, 2H), 7.66 (d, 2H), 7.69 (d, 1H), 7.90–7.98 (m, 3H), 8.57 (d, 1H), 8.60 (t, 1H), 8.70 (m, 1H), 8.88 (dd, 1H).

EXAMPLE 217

N-((2'-methoxy-4'-((1E)-3-morpholin-4-yl-3-oxoprop-1-enyl)-1,1'-biphenyl-4-yl)carbonyl)-3-nitro-4-((2-(phenylthio)ethyl)amino)benzenesulfonamide

EXAMPLE 217A ethyl 2'-methoxy-4'-((1E)-3-morpholin-4-yl-3-oxoprop-1-enyl)-1,1'-biphenyl-4-carboxylate The desired product was prepared by substituting Example 122L and morpholine for Example 1B and Example 1C, respectively, in Example 1D.

EXAMPLE 217B

2'-methoxy-4'-((1E)-3-morpholin-4-yl-3-oxoprop-1-enyl)-1,1'-biphenyl-4-carboxylic acid The desired product was prepared by substituting Example 217A for Example 1A in Example 1B. MS (ESI(–)) m/e 366 (M–H)$^-$.

EXAMPLE 217C

N-((2'-methoxy-4'-((1E)-3-morpholin-4-yl-3-oxoprop-1-enyl)-1,1'-biphenyl-4-yl)carbonyl)-3-nitro-4-((2-(phenylthio)ethyl)amino)benzenesulfonamide The desired product was prepared by substituting Example 217B and Example 77B for Example 1B and Example 1C, respectively, in Example 1D. MS (ESI(–)) m/e 701 (M–H)$^-$; $^1$H NMR (300 MHz, DMSO-d$_6$) δ3.25 (m, 4H), 3.47 (m, 2H), 3.61 (m, 4H), 3.68 (s, 3H), 3.72 (dd, 2H), 4.58 (d, 1H), 6.92 (m, 3H), 7.20 (t, 1H), 7.31 (m, 3H), 7.40 (m, 4H), 7.58 (dd, 1H), 7.90 (m, 3H), 8.48 (m, 2H).

EXAMPLE 218 isobutyl 4-(3-(2-methoxy-4'-((((3-nitro-4-((2-(phenylthio)ethyl)amino)phenyl)sulfonyl)amino)carbonyl)-1,1'-biphenyl-4-yl)propyl)piperazine-1-carboxylate The desired product was prepared by substituting isobutyl chloroformate for dimethylcarbamic chloride in Example 200. MS (ESI(−)) m/e 788 (M−H)⁻; $^1$H NMR (300 MHz, DMSO-d$_6$) δ0.89 (d, 6H), 1.80 (m, 2H), 1.85 (m, 1H), 2.39 (m, 4H), 2.62 (t, 2H), 3.28 (t, 2H), 3.40 (m, 4H), 3.59 (m, 3H), 3.73 (s, 3H), 3.79 (dd, 1H), 4.02 (m, 1H), 6.86 (d, 1H), 6.94 (s, 1H), 6.98 (d, 1H), 7.20 (m, 2H), 7.31 (t, 2H), 7.40 (m, 3H), 7.88 (d, 1H), 7.89 (d, 2H), 8.50 (d, 1H), 8.52 (t, 1H).

EXAMPLE 219

3-nitro-4-((2-(phenylthio)ethyl)amino)-N-(4-(1,8,8-trimethyl-3-azabicyclo(3.2.1)oct-3-yl)benzoyl)benzenesulfonamide

EXAMPLE 219A methyl 4-(1,8,8-trimethyl-2,4-dioxo-3-azabicyclo(3.2.1)oct-3-yl)benzoate The desired product was prepared by substituting methyl 4-aminobenzoate and (+/−)-camphoric anhydride for ethyl 4-aminobenzoate and 3,3-dimethylglutaric anhydride, respectively, in Example 119A. MS (DCI) m/e 333 (M+NH$_4$)⁺.

EXAMPLE 219B methyl 4-(1,8,8-trimethyl-3-azabicyclo(3.2.1)oct-3-yl)benzoate

The desired product was prepared by substituting Example 219A for Example 119A in Example 119B. MS (DCI) m/e 288 (M+H)⁺.

EXAMPLE 219C 4-(1,8,8-trimethyl-3-azabicyclo(3.2.1)oct-3-yl)benzoic acid

The desired product was prepared by substituting Example 219B for Example 119B in Example 119C. MS (DCI) m/e 274 (M+H)⁺.

EXAMPLE 219D 3-nitro-4-((2-(phenylthio)ethyl)amino)-N-(4-(1,8,8-trimethyl-3-azabicyclo(3.2.1)oct-3-yl)benzoyl)benzenesulfonamide The desired product was prepared by substituting Example 219C and Example 77B for Example 1B and Example 1C, respectively, in Example 1D. MS (ESI(−)) m/e 607 (M−H)⁻; $^1$H NMR (300 MHz, DMSO-d$_6$) δ11.96 (s, 1H), 8.76 (t, 1H), 8.60 (d, 1H), 7.91 (dd, 1H), 7.74 (d, 2H), 7.37 (d, 2H), 7.15–7.29 (m, 4H), 6.80 (d, 2H), 3.67 (m, 2H), 3.43 (d, 1H), 3.29 (m, 2H), 3.15 (m, 2H), 2.85 (d, 1H, J=11.5), 1.90 (m, 2H), 1.60 (m, 2H), 1.40 (m, 1H), 0.91 (m, 9H).

EXAMPLE 220

3-nitro-4-((2-(phenylthio)ethyl)amino)-N-(4-pyrrolidin-1-ylbenzoyl)benzenesulfonamide

EXAMPLE 220A methyl 4-(2,5-dioxopyrrolidin-1-yl)benzoate

The desired product was prepared by substituting methyl 4-aminobenzoate and succinic anhydride for ethyl 4-aminobenzoate and 3,3-dimethylglutaric anhydride, respectively, in Example 119A. MS (DCI) m/e 251 (M+NH$_4$)⁺.

EXAMPLE 220B methyl 4-pyrrolidin-1-ylbenzoate

The desired product was prepared by substituting Example 220A for Example 119A in Example 119B MS (DCI) m/e 206 (M+H)⁺.

EXAMPLE 220C 4-pyrrolidin-1-ylbenzoic acid

The desired product was prepared by substituting Example 220B for Example 119B in Example 119C. MS (DCI) m/e 192 (M+H)⁺.

EXAMPLE 220D 3-nitro-4-((2-(phenylthio)ethyl)amino)-N-(4-pyrrolidin-1-ylbenzoyl)benzenesulfonamide The desired product was prepared by substituting Example 220C and Example 77B for Example 1B and Example 1C, respectively, in Example 1D. MS (ESI(−)) m/e 527 (M−H)⁻; $^1$H NMR (300 MHz, DMSO-d$_6$) δ11.87 (s, 1H), 8.77 (t, 1H), 8.60 (d, 1H), 7.91 (dd, 1H), 7.73 (d, 2H), 7.37 (d, 2H), 7.15–7.28 (m, 4H), 6.53 (d, 2H), 3.67 (m, 2H), 3.30 (m, 6H), 1.95 (m, 4H).

EXAMPLE 221

N-(4-(5-(3-morpholin-4-yl-3-oxopropyl)quinolin-8-yl)benzoyl)-3-nitro-4-((2-(phenylthio)ethyl)amino)benzenesulfonamide The desired product was prepared by substituting morpholine for 1-methylpiperazine in Example 201. MS (ESI) m/e 724, 726 (M−H)⁻, (M+H)⁺; $^1$H NMR (300 MHz, DMSO-d$_6$) δ2.76 (t, 2H), 3.27 (t, 2H), 3.29 (t, 2H), 3.34–3.53 (m, 8H), 3.60 (dt, 2H), 6.99 (d, 1H), 7.20 (t, 1H), 7.31 (t, 2H), 7.40 (d, 2H), 7.50–7.61 (m, 4H), 7.67 (d, 1H), 7.89 (d, 1H), 7.95 (d, 2H), 8.50 (t, 1H), 8.51 (d, 1H), 8.56 (d, 1H), 8.89 (d, 1H).

EXAMPLE 222

N-((4'-(3-(4-acetylpiperazin-1-yl)propyl)-2'-methoxy-1,1'-biphenyl-4-yl)carbonyl)-3-nitro-4-((2-(phenylthio)ethyl)amino)benzenesulfonamide The desired product was prepared from acetyl chloride for dimethylcarbamic chloride in Example 200. MS (ESI(−)) m/e 703 (M−H)⁻; $^1$H NMR (300 MHz, DMSO-d$_6$) δ1.91 (m, 2H), 2.01 (s, 3H), 2.67 (m, 4H), 2.72 (m, 2H), 3.28 (m, 4H), 3.59 (m, 6H), 3.75 (s, 3H), 4.05 (dd, 1H), 6.88 (d, 1H), 6.95 (s, 1H), 7.01 (d, 1H), 7.20 (m, 2H), 7.31 (t, 2H), 7.40 (m, 3H), 7.70 (d, 1H), 7.89 (d, 2H), 8.51 (d, 1H), 8.54 (t, 1H).

EXAMPLE 223

N-(4-(1-(cyclohexylmethyl)-2-oxo-2,3-dihydro-1H-benzimidazol-5-yl)benzoyl)-3-nitro-4-((2-(phenylthio)ethyl)amino)benzenesulfonamide

EXAMPLE 223A 4-(1-(cyclohexylmethyl)-2-oxo-2,3-dihydro-1H-benzimidazol-5-yl)benzoic acid The desired product was prepared by substituting cyclohexylmethylamine for n-butylamine in Examples 166A, 166B, 166C, and 166D.

EXAMPLE 223B

N-(4-(1-(cyclohexylmethyl)-2-oxo-2,3-dihydro-1H-benzimidazol-5-yl)benzoyl)-3-nitro-4-((2-(phenylthio)ethyl)amino)benzenesulfonamide The desired product was prepared by substituting Example 223A and Example 77B for Example 1B and Example 1C, respectively, in Example 1D. MS (ESI) m/e 684, 686 (M−H)⁻; (M+H)⁺; ¹H NMR (300 MHz, DMSO-$d_6$) δ0.96–1.26 (m, 5H), 1.55–1.72 (m, 5H), 1.80 (m, 1H), 3.27 (t, 2H), 3.63 (m, 4H), 6.98 (d, 1H), 7.15–7.25 (m, 3H), 7.30 (t, 3H), 7.40 (d, 2H), 7.55 (d, 2H), 7.88 (dd, 1H), 7.93 (d, 2H), 8.51 (d, 1H), 8.51 (t, 1H), 10.89 (s, 1H).

EXAMPLE 224 tert-butyl (5R)-5-((4-((((4'-(2-((2-(dimethylamino)ethyl)(methyl)amino)ethyl)-2'-methoxy-1,1'-biphenyl-4-yl)carbonyl)amino)sulfonyl)-2-nitrophenyl)amino)-6-(phenylthio)hexylcarbamate The desired product was prepared by substituting Example 124C and Example 191C for Example 1C and Example 1B, respectively, in Example 1D. MS (ESI(−)) m/e 861 (M−H)⁻; ¹H NMR (300 MHz, DMSO-$d_6$) δ1.32 (s, 9H), 2.37 (s, 3H), 2.52 (s, 6H), 2.54 (m, 6H), 2.72 (t, 2H), 2.80 (d, 2H), 2.88 (d, 2H), 3.02 (m, 2H), 3.27 (m, 4H), 3.77 (s, 3H), 3.98 (m, 1H), 6.70 (m, 1H), 6.89 (d, 1H), 6.90 (s, 1H), 6.99 (d, 1H), 7.18 (m, 1H), 7.22 (m, 2H), 7.30 (d, 2H), 7.39 (t, 2H), 7.81 (d, 1H), 7.89 (d, 2H), 8.14 (d, 1H), 8.47 (d, 1H)

EXAMPLE 225

N-(4-(1-cyclopentyl-2-oxo-2,3-dihydro-1H-benzimidazol-5-yl)benzoyl)-3-nitro-4-((2-(phenylthio)ethyl)amino)benzenesulfonamide

EXAMPLE 225A 4-(1-cyclopentyl-2-oxo-2,3-dihydro-1H-benzimidazol-5-yl)benzoic acid The desired product was prepared by substituting cyclopentylamine for butylamine in Examples 166A, 166B, 166C, and 166D.

EXAMPLE 225B

N-(4-(1-cyclopentyl-2-oxo-2,3-dihydro-1H-benzimidazol-5-yl)benzoyl)-3-nitro-4-((2-(phenylthio)ethyl)amino)benzenesulfonamide The desired product was prepared by substituting Example 225A and Example 77B for Example 1B and Example 1C, respectively, in Example 1D. MS (ESI(−)) m/e 656 (M−H)⁻; ¹H NMR (300 MHz, DMSO-$d_6$) δ1.68 (m, 2H), 1.91 (m, 4H), 2.05 (m, 2H), 3.28 (t, 2H), 3.62 (dt, 2H), 4.74 (m, 1H), 7.03 (d, 1H), 7.15–7.25 (m, 3H), 7.27–7.35 (m, 3H), 7.39 (d, 2H), 7.57 (d, 2H), 7.89 (dd, 1H), 7.94 (d, 2H), 8.52 (d, 1H), 8.56 (t, 1H), 10.95 (s, 1H),

EXAMPLE 226

3-nitro-N-(4-(4-(3-oxopropyl)piperidin-1-yl)benzoyl)-4-((2-(phenylthio)ethyl)amino)benzenesulfonamide A solution of Example 203C (250 mg, 0.4 mmol), in dichloromethane (5 mL), TFA (1.5 mL), and 1 drop water was stirred at room temperature for 48 hours. The reaction mixture was diluted with dichloromethane, washed sequentially with water, saturated NaHCO₃, and brine, dried (MgSO₄), filtered, and concentrated. The concentrate was purified by flash column chromatography on silica gel with dichloromethane 0.5–1.0% methanol to provide the desired product. MS (APCI) m/e 597 (M+H)⁺; ¹H NMR (300 MHz, CDCl₃) δ9.80 (s, 1H), 8.87 (d, 1H), 8.67 (t, 1H), 8.47 (s, 1H), 8.15 (dd, 1H), 7.63 (d, 2H), 7.40 (m, 2H), 7.24–7.34 (m, 4H), 6.87 (d, 2H), 6.82 (m, 2H), 3.87 (d, 2H), 3.58 (m, 4H), 3.21 (t, 2H), 2.86 (m, 2H), 2.50 (m, 2H), 1.80 (m, 2H), 1.62 (m, 2H), 1.55 (s, 4H) 1.31 (m, 2H).

EXAMPLE 227

N-(4-(3-butyl-2-oxo-2,3-dihydro-1,3-benzoxazol-6-yl)benzoyl)-3-nitro-4-((2-(phenylthio)ethyl)amino)benzenesulfonamide The desired product was prepared by substituting 1-bromobutane for bromomethylcyclohexane in Example 181. MS (ESI) m/e 645, 647 (M−H)⁻, (M+H)⁺; ¹H NMR (300 MHz, DMSO-$d_6$) δ0.92 (t, 3H), 1.33 (qt, 2H), 1.69 (tt, 2H), 3.26 (t, 2H), 3.62 (dt, 2H), 3.85 (t, 2H), 7.05 (d, 1H), 7.19 (tt, 1H), 7.29 (t, 2H), 7.39 (d, 3H), 7.58 (dd, 1H), 7.68 (d, 2H), 7.73 (d, 1H), 7.89 (dd, 1H), 7.94 (d, 2H), 8.54 (d, 1H), 8.59 (t, 1H).

EXAMPLE 228

3-nitro-N-(4-(2-nonyl-1,3-benzothiazol-5-yl)benzoyl)-4-((2-(phenylthio)ethyl)amino)benzenesulfonamide The desired product was prepared by substituting 1-bromooctane for allyl bromide in Example 213. MS (ESI) m/e 715, 717 (M−H)⁻, (M+H)⁺; ¹H NMR (300 MHz, DMSO-$d_6$) δ0.85 (t, 3H), 1.12–1.43 (m, 12H), 1.82 (tt, 2H), 3.12 (t, 2H), 3.28 (t, 2H) 3.61 (dt, 2H), 7.02 (d, 1H), 7.19 (t, 1H), 7.30 (t, 2H), 7.39 (d, 2H), 7.73 (d, 2H), 7.88 (d, 1H), 7.98 (d, 2H), 8.11 (d, 1H), 8.21 (s, 1H), 8.53 (d, 1H), 8.55 (t, 1H).

EXAMPLE 229

N-((4'-(3-(4-(2,2-dimethylpropanoyl)piperazin-1-yl)propyl)-2'-methoxy-1,1'-biphenyl-4-yl)carbonyl)-3-nitro-4-((2-(phenylthio)ethyl)amino)benzenesulfonamide The desired product was prepared by substituting pivaloyl chloride for dimethylcarbamic chloride in Example 200. MS (ESI(−)) m/e 772 (M−H)⁻; ¹H NMR (300 MHz, DMSO-$d_6$) δ1.18 (s, 9H), 1.79 (m, 2H), 2.35 (m, 6H), 2.62 (t, 2H), 3.28 (t, 2H), 3.54 (m, 4H), 3.60 (dd, 2H), 3.75 (s, 3H), 6.86 (d, 1H), 6.94 (s, 1H), 6.98 (d, 1H), 7.18 (d, 1H), 7.20 (m, 1H), 7.31 (t, 2H), 7.40 (t, 4H), 7.88 (d, 1H), 7.89 (d, 2H), 8.49 (d, 1H), 8.51 (t, 1H).

EXAMPLE 230

N-(4-(3-methoxycyclohept-1-en-1-yl)benzoyl)-3-nitro-4-((2-(phenylthio)ethyl)amino)benzenesulfonamide and N-(4-(6-methoxycyclohept-1-en-1-yl)benzoyl-3-nitro-4-((2-(phenylthio)ethyl)amino)benzenesulfonamide

EXAMPLE 230A 3-methoxycyclohet-1-en-1-yl trifluoroacetate and 6-methoxycyclohept-1-en-1-yl trifluoroacetate The desired product was prepared by substituting 3-methoxycycloheptanone for 4-tert-butylcyclohexanone in Example 5A.

EXAMPLE 230B methyl 4-(3-methoxycyclohept-1-en-1-yl)benzoate and methyl 4-(6-methoxycyclohept-1-en-1-yl)benzoate The desired product was prepared by substituting Example 230A for Example 5A in Example 5B. MS (DCI (+)) m/e 261 (M+H)$^+$.

EXAMPLE 230C

N-(4-(3-methoxycyclohept-1-en-1-yl)benzoyl)-3-nitro-4-((2-(phenylthio)ethyl)amino)benzenesulfonamide and N-(4-(6-methoxycyclohept-1-en-1-yl)benzoyl)-3-nitro-4-((2-(phenylthio)ethyl)amino)benzenesulfonamide A mixture of Example 230B (70 mg, 0.27 mmol) and LiOH (14 mg, 0.32 mmol) in THF (3 mL), methanol (1.5 mL), and water (0.5 mL) was heated to 50° C. for 3 hour and concentrated. The concentrate was dissolved in DMF (0.5 mL) and treated with a mixture of Example 77B (38 mg, 0.104 mmol), EDCI (50 mg, 0.26 mmol), and DMAP (79 mg, 0.65 mmol) in dichloroethane (0.5 mL). The mixture was stirred for 16 hours, diluted with ethyl acetate (50 mL), washed sequentially with 1N HCl (5 mL), water (30 mL) and brine (30 mL), dried (MgSO$_4$), filtered, and concentrated. The concentrate was purified by flash column chromatography on silica gel with 5% methanol/dichloromethane to provide the desired product. MS (ESI (−)) m/e 580 (M−H)$^−$; $^1$H NMR (300 MHz, DMSO-d$_6$) δ8.78 (br t, 1H), 8.60 (d, 1H), 7.92 (dd, 1H), 7.85 (d, 2H), 7.40–7.15 (m, 8H), 6.30 and 6.10 (t, 1H), 4.00 and 3.70 (m, 2H), 2.90 and 2.75 (s, 3H), 2.30–1.55 (m, 11H).

EXAMPLE 231 tert-butyl (5R)-5-((4-(((4-(1-benzyl-2-oxo-2,3-dihydro-1H-benzimidazol-5-yl)benzoyl)amino)sulfonyl-2-nitrophenyl)amino)-6-(phenylthio)hexylcarbamate

EXAMPLE 231A 4-(1-benzyl-2-oxo-2,3-dihydro-1H-benzimidazol-5-yl)benzoic acid The desired product was prepared by substituting benzylamine for n-butylamine in Examples 166A, 166B, 166C, and 166D.

EXAMPLE 231B tert-butyl (5R)-5-((4-(((4-(1-benzyl-2-oxo-2,3-dihydro-1H-benzimidazol-5-yl)benzoyl)amino)sulfonyl)-2-nitrophenyl)amino)-6-(phenylthio)hexylcarbamate The desired product was prepared by substituting Example 231A and Example 124C for Example 1B and Example 1C, respectively, in Example 1D. MS (ESI(−)) m/e 849 (M−H)$^−$; $^1$H NMR (300 MHz, DMSO-d$_6$) δ1.32 (m, 11H), 1.54 (m, 2H), 1.72 (m, 2H), 2.87 (m, 2.87H), 3.98 (t, 2H), 4.12 (m, 1H), 5.02 (d, 2H), 6.72 (t, 2H), 7.01 (d, 1H), 7.07–7.23 (m, 4H), 7.26–7.38 (m, 8H), 7.60 (d, 2H), 7.84 (dd, 1H), 7.94 (d, 2H), 8.20 (m, 2H), 8.49 (d, 1H), 11.08 (s, 1H).

EXAMPLE 232

N-(4-(4-(3-hydroxypropyl)piperidin-1yl)benzoyl)-3-nitro-4-((2-(phenylthio)ethyl)amino)benzenesulfonamide A solution of Example 226 (15 mg, 0.025 mmol) in methanol (0.5 mL) and dichloromethane (2 drops) at 0° C. was treated with NaBH$_4$ (24 mg, 0.6 mmol), stirred for 1 hour, warmed to room temperature, and stirred for 90 minutes. The mixture was treated with water and filtered. The filter cake was treated with dichloromethane (5 mL) and methanol (1 drop), stirred for 2 hours, and filtered. The filter cake was washed with diethyl ether, and dried under vacuum to provide the desired product. MS(ESI(−)) m/e 597 (M−H)$^−$; $^1$H NMR (300 MHz, DMSO-d$_6$) δ8.49 (d, 1H), 8.45 (d, 1H), 7.85 (dd, 1H), 7.71 (d, 2H), 7.40 (m, 2H), 7.30 (m, 2H), 7.20 (m, 2H), 6.95 (d, 1H), 6.90 (d, 2H), 4.34 (t, 1H), 3.75 (m, 2H), 3.60 (m, 2H), 3.39 (m, 2H), 3.25 (m, 2H), 2.65 (m, 2H), 1.71 (m, 2H), 1.45 (m, 2H), 1.25–1.11 (m, 4H).

EXAMPLE 233

N-(2-(dimethylamino)ethyl)-3-(2-methoxy-4'-((((4-(((1R)-2-morpholin-4-yl-1-((phenylthio)methyl)ethyl)amino)-3-nitrophenyl)sulfonyl)amino)carbonyl)-1,1'-biphenyl-4-yl)-N-methylpropanamide The desired product was prepared by substituting Example 146C and Example 178B for Example 1C and Example 1B, respectively, in Example 1D. MS (ESI(−)) m/e 817 (M−H)$^−$; $^1$H NMR (300 MHz, DMSO-d$_6$) δ2.18 (dd, 2H), 2.21 (s, 6H), 2.32 (dd, 2H), 2.50 (dd, 2H), 2.62 (m, 2H), 2.82 (dd, 2H), 2.94 (s, 3H), 2.98 (m, 4H), 3.34 (m, 4H), 3.52 (dd, 2H), 3.74 (s, 3H), 4.14 (m, 1H), 0.88 (d, 1H), 6.94 (s, 1H), 6.98 (d, 1H), 7.18 (d, 1H), 7.24 (m, 1H), 7.34 (t, 2H), 7.39 (t, 2H), 7.82 (d, 1H), 7.89 (d, 2H), 8.32 (d, 1H), 8.46 (d, 1H).

EXAMPLE 234

N,N-bis(2-methoxyethyl)-3-(8-(4-((((3-nitro-4-((2-(phenylthio)ethyl)amino)phenyl)sulfonyl)amino)carbonyl)phenyl)quinolin-5-yl)propanamide The desired product was prepared by substituting bis(2-methoxyethyl)amine for 1-methylpiperazine in Example 201. MS (ESI) m/e 770, 772 (M−H)$^−$, (M+H)$^+$; $^1$H NMR (300 MHz, DMSO-d$_6$) δ2.79 (t, 2H), 3.16 (s, 3H), 3.22 (s, 3H), 3.28 (t, 2H), 3.32 (t, 2H), 3.38 (m, 4H), 3.45 (m, 4H), 3.62 (dt, 2H), 7.02 (d, 1H), 7.20 (t, 1H), 7.30 (t, 2H), 7.40 (d, 2H), 7.52–7.61 (m, 4H), 7.67 (d, 1H), 7.89 (dd, 1H), 7.95 (d, 2H), 8.52–8.58 (m, 3H), 8.88 (dd, 1H).

EXAMPLE 235 tert-butyl 2-(4-(4-((((3-nitro-4-((2-(phenylthio)ethyl)amino)phenyl)sulfonyl)amino)carbonyl)phenyl)piperazin-1-yl)ethylcarbamate The desired product was prepared by substituting (2-oxoethyl)-carbamic acid tert-butyl ester for (1-benzyl-2-oxoethyl)-carbamic acid tert-butyl ester in Example 173B. MS (ESI(−)) m/e 683 (M−H)$^−$; $^1$H NMR (300 MHz, DMSO-d$_6$) δ8.63 (t, 1H), 8.53 (d, 1H), 7.88 (dd, 1H), 7.74 (d, 2H), 7.38 (d, 2H), 7.25–7.31 (m, 2H), 7.15–7.21 (m, 1H), 7.08 (d, 1H), 6.89 (d, 2H), 6.74 (br s, 1H), 3.63 (q, 2H), 3.22–3.31 (m, 10H), 3.08–3.17 (m, 2H), 2.60–2.74 (m, 2H), 1.38 (s, 9H).

EXAMPLE 236

3-(4'-(((((4-(((1R)-2-((2-(dimethylamino)ethyl)(methyl)amino)-1-((phenylthio)methyl)ethyl)amino)-3-nitrophenyl)sulfonyl)amino)carbonyl)-2-methoxy-1,1'-biphenyl-4-yl)-N,N-dimethylpropanamide

EXAMPLE 236A

4'-(3-(dimethylamino)-3-oxopropyl)-2'-methoxy-1,1'-biphenyl-4-carboxylic acid

The desired product was prepared by substituting Example 427A for Example 1A in Example 1B.

EXAMPLE 236B 3-(4'-((((4-(((1R)-2-((2-(dimethylamino)ethyl)
(methyl)amino)-1-((phenylthio)methyl)ethyl)amino)-
3-nitrophenyl)sulfonyl)amino)carbonyl)-2-methoxy-
1,1'-biphenyl-4-yl)-N,N-dimethylpropanamide The desired product was prepared by substituting Example 236A and Example 206C for Example 1B and Example 1C, respectively, in Example 1D. MS (ESI(−)) m/e 775 (M−H)−; $^1$H NMR (300 MHz, DMSO-d$_6$) δ1.18 (s, 9H), 1.79 (m, 2H), 2.35 (m, 6H), 2.62 (t, 2H), 3.28 (t, 2H), 3.54 (m, 4H), 3.60 (dd, 2H), 3.75 (s, 3H), 6.88 (d, 1H), 6.94 (s, 1H), 6.98 (d, 1H), 7.18 (d, 1H), 7.23 (m, 1H), 7.32 (t, 2H), 7.39 (d, 2H), 7.82 (d, 1H), 7.89 (d, 2H), 8.20 (d, 2H), 8.48 (d, 1H).

EXAMPLE 237

N-((2'-methoxy-4'-(3-(4-(methoxyacetyl)piperazin-
1-yl)propyl-1,1'-biphenyl-4-yl)carbonyl)-3-nitro-4-
((2-(phenylthio)ethyl)amino)benzenesulfonamide The desired product was prepared by substituting methoxyacetyl chloride for dimethylcarbamic chloride in Example 200. MS (ESI(−)) m/e 760 (M−H)−; $^1$H NMR (300 MHz, DMSO-d$_6$) δ1.80 (m, 2H), 2.42 (m, 4H), 2.62 (t, 2H), 3.26 (m, 4H), 3.28 (s, 3H), 3.40 (m, 4H), 3.48 (m, 2H), 3.60 (dd, 2H), 3.75 (s, 3H), 4.08 (s, 2H), 6.86 (d, 1H), 6.95 (s, 1H), 6.99 (d, 1H), 7.18 (d, 1H), 7.20 (dd, 1H), 7.31 (t, 2H), 7.40 (t, 4H), 7.88 (d, 1H), 7.89 (d, 2H), 8.49 (d, 1H), 8.51 (t, 1H).

EXAMPLE 238

N-((2'-methoxy-4'-(3-(4-(methylsulfonyl)piperazin-
1-yl)propyl)-1,1'-biphenyl-4-yl)carbonyl)-3-nitro-4-
((2-(phenylthio)ethyl)amino)benzenesulfonamide The desired product was prepared by substituting methanesulfonyl chloride for dimethylcarbamic chloride in Example 200. MS (ESI(−)) m/e 766 (M−H)−; $^1$H NMR (300 MHz, DMSO-d$_6$) δ1.99 (m, 2H), 2.68 (m, 4H), 2.86 (s, 3H), 2.96 (m, 4H), 3.08 (m, 4H), 3.30 (m, 4H), 3.77 (s, 3H), 4.08 (m, 1H), 6.91 (d, 1H), 6.99 (s, 1H), 7.18 (m, 1H), 7.22 (dd, 1H), 7.28 (m, 3H), 7.38 (d, 2H), 7.52 (d, 2H), 7.89 (d, 2H), 8.58 (d, 1H), 8.62 (t, 1H).

EXAMPLE 239

N-(4-(3,3-dimethylpiperidin-1-yl)benzoyl)-3-nitro-4-
((2-(phenylthio)ethyl)amino)benzenesulfonamide

EXAMPLE 239A ethyl 4-(3,3-dimethyl-2,6-dioxopiperidin-1-yl)
benzoate

The desired product was prepared by substituting 2,2-dimethylglutaric anhydride for 3,3-dimethylglutaric anhydride in Example 119A. MS (DCI) m/e 307 (M+NH$_4$)+.

EXAMPLE 239B ethyl 4-(3,3-dimethylpiperidin-1-yl)benzoate

The desired product was prepared by substituting Example 239A for Example 119A in Example 119B. MS (DCI) m/e 262 (M+H)+.

EXAMPLE 239C 4-(3,3-dimethylpiperidin-1-yl)benzoic acid

The desired product was prepared by substituting Example 239B for Example 119B in Example 119C. MS (DCI) m/e 234 (M+H)+.

EXAMPLE 239D

N-(4-(3,3-dimethylpiperidin-1-yl)benzoyl)-3-nitro-4-
((2-(phenylthio)ethyl)amino)benzenesulfonamide The desired product was prepared by substituting Example 239C and Example 77B for Example 1B and Example 1C, respectively, in Example 1D. MS (ESI(−)) m/e 567 (M−M)−; $^1$H NMR (300 MHz, DMSO-d$_6$) δ11.92 (s, 1H), 8.77 (t, 1H), 8.60 (d, 1H), 7.90 (dd, 1H), 7.70 (d, 2H), 7.37 (d, 2H), 7.26 (t, 2H), 7.18 (m, 2H), 6.89 (d, 2H), 3.67 (m, 2H), 3.30 (m, 4H), 3.09 (s, 2H), 1.59 (m, 2H), 1.38 (t, 2H), 0.89 (s, 6H).

EXAMPLE 240

4-(((1R)-2-(dimethylamino)-1-((phenylthio)methyl)
ethyl)amino)-N-((2'-methoxy-4'-(3-morpholin-4-yl-
3-oxopropyl)-1,1'-biphenyl-4-yl)carbonyl)-3-
nitrobenzenesulfonamide

EXAMPLE 240A

2'-methoxy-4'-(3-morpholin-4-yl-3-oxopropyl)-1,1'-
biphenyl-4-carboxylic acid

The desired product was prepared by substituting Example 122M for Example 1A in Example 1B.

EXAMPLE 240B 4-(((1R)-2-(dimethylamino)-1-((phenylthio)methyl)
ethyl)amino)-N-((2'-methoxy-4'-(3-morpholin-4-yl-
3-oxopropyl)-1,1'-biphenyl-4-yl)carbonyl)-3-
nitrobenzenesulfonamide The desired product was prepared by substituting Example 240A and Example 134D for Example 1B and Example 1C, respectively, in Example 1D. MS (ESI(−)) m/e 760 (M−H)−; $^1$H NMR (300 MHz, DMSO-d$_6$) δ2.61 (m, 2H), 2.66 (t, 2H), 2.84 (t, 2H), 3.31 (dd, 1H), 3.32 (s, 6H), 3.37 (dd, 1H), 3.44 (m, 4H), 3.52 (m, 4H), 3.74 (s, 3H), 4.12 (m, 1H), 6.89 (d, 1H), 6.94 (d, 1H), 6.99 (s, 1H), 7.16 (d, 1H), 7.20 (dd, 1H), 7.22 (dd, 2H), 7.31 (d, 2H), 7.38 (d, 2H), 7.81 (d, 1H), 7.89 (d, 2H), 8.24 (d, 1H), 8.44 (d, 1H).

EXAMPLE 241

4-((3-(dimethylamino)-2-(phenylthio)propyl)amino)-
N-((4'-fluoro-1,1'-biphenyl-4-yl)carbonyl)-3-
nitrobenzenesulfonamide The desired product was prepared by substituting Example 212C for Example 1C in Example 1D. MS (ESI(−)) m/e 607 (M−H)−; $^1$H NMR (300 MHz, DMSO-d$_6$) δ8.80 (t, 1H), 8.52 (d, 1H), 7.93 (d, 2H), 7.87 (dd, 1H), 7.76–7.70 (m, 2H), 7.60 (d, 2H), 7.51–7.47 (m, 2H), 7.35–7.25 (m, 5H), 6.95 (d, 1H), 3.82–3.75 (m, 1H), 3.62–3.50 (m, 2H), 2.86–2.62 (m, 2H), 2.41 (br s, 6H).

EXAMPLE 242

N-((2'-methoxy-4'-(2-(4-methylpiperazin-1-yl)
ethyl)-1,1'-biphenyl-4-yl)carbonyl)-3-nitro-4-((2-
(phenylthio)ethyl)amino)benzenesulfonamide

EXAMPLE 242A methyl 2'-methoxy-4'-(2-(4-methylpiperazin-1-yl)
ethyl)-1,1'-biphenyl-4-carboxylate The desired product was prepared by substituting N-methylpiperidine and Example 191A for dimethylamine and Example 134A, respectively, in Example 134B. MS (ESI(+)) m/e 369 (M+H)⁺.

EXAMPLE 242B

2'-methoxy-4'-(2-(4-methylpiperazin-1-yl)ethyl)-1,1'-biphenyl-4-carbolic acid

The desired product was prepared by substituting Example 242A for Example 1A in Example 1B. MS (ESI(−)) m/e 353 (M−H)⁻.

EXAMPLE 242C

N-((2'-methoxy-4'-(2-(4-methylpiperazin-1-yl)ethyl)-1,1'-biphenyl-4-yl)carbonyl)-3-nitro-4-((2-(phenylthio)ethyl)amino)benzenesulfonamide The desired product was prepared by substituting Example 242B and Example 77B for Example 1B and Example 1C, respectively, in Example 1D. MS (ESI(−)) m/e 688 (M−H)⁻; ¹H NMR (300 MHz, DMSO-d₆) δ2.58 (s, 3H), 2.82 (m, 2H), 3.40 (m, 4H), 2.98 (m, 6H), 3.15 (d, 2H), 3.28 (dd, 2H), 3.76 (s, 3H), 4.05 (dd, 1H), 6.91 (d, 1H), 6.99 (d, 1H), 7.00 (s, 1H), 7.18 (d, 1H), 7.20 (dd, 1H), 7.32 (t, 2H), 7.40 (t, 4H), 7.90 (m, 2H), 8.49 (t, 1H), 8.51 (d, 1H).

EXAMPLE 243

3-nitro-N-(4-(5-(3-oxo-3-piperidin-1-ylpropyl)quinolin-8-yl)benzoyl)-4-((2-(phenylthio)ethyl)amino)benzenesulfonamide The desired product was prepared by substituting piperidine for 1-methylpiperazine in Example 201. MS (ESI) m/e 722, 724 (M−H)⁻, (M+H)⁺; ¹H NMR (300 MHz, DMSO-d₆) δ1.35 (m, 4H), 1.52 (m, 2H), 2.74 (t, 2H), 3.27 (t, 2H), 3.29 (t, 2H), 3.35 (t, 2H), 3.43 (t, 2H) 3.61 (dt, 2H), 6.99 (d, 1H), 7.20 (tt, 1H), 7.31 (td, 2H), 7.40 (dd, 2H), 7.52–7.60 (m, 4H), 7.67 (d, 1H), 7.89 (dd, 1H), 7.95 (d, 2H), 8.51 (t, 1H), 8.52 (d, 1H), 8.56 (dd, 1H), 8.88 (dd, 1H).

EXAMPLE 244

N-(2-(dimethylamino)ethyl)-3-(8-(4-((((3-nitro-4-((2-(phenylthio)ethyl)amino)phenyl)sulfonyl)amino)carbonyl)phenyl)quinolin-5-yl)propanamide The desired product was prepared by substituting N,N-dimethylethylenediamine for 1-methylpiperazine in Example 201. MS (ESI) m/e 725, 727 (M−H)⁻, (M+H)⁺; ¹H NMR (300 MHz, DMSO-d₆) δ2.56 (t, 2H), 2.68 (s, 6H), 2.97 (t, 2H), 3.08 (q, 2H), 3.08 (q, 2H), 3.27 (t, 2H), 3.36 (t, 2H), 3.61 (dt, 2H), 7.00 (d, 1H), 7.20 (tt, 1H), 7.31 (t, 2H), 7.40 (d, 2H), 7.51 (d, 1H), 7.57 (d, 2H), 7.60 (dd, 1H), 7.68 (d, 1H), 7.89 (dd, 1H), 7.96 (d, 2H), 8.11 (t, 1H), 8.52 (t, 1H), 8.53 (d, 1H), 8.58 (dd, 1H), 8.90 (dd, 1H).

EXAMPLE 245

N-((4'-fluoro-1,1'-biphenyl-4-yl)carbonyl)-4-((2-morpholin-4-yl-1-((phenylthio)methyl)ethyl)amino)-3-nitrobenzenesulfonamide

EXAMPLE 245A 4-((2-morpholin-4-yl-1-((phenylthio)methyl)ethyl)amino)-3-nitrobenzenesulfonamide The desired product was prepared by substituting Example 180B for Example 122F in Example 122G. MS (ESI(+)) m/e 453 (M+H)⁺.

EXAMPLE 245B

N-((4'-fluoro-1,1'-biphenyl-4-yl)carbonyl)-4-((2-morpholin-4-yl-1-((phenylthio)methyl)ethyl)amino)-3-nitrobenzenesulfonamide The desired product was prepared by substituting Example 245A for Example 1C in Example 1D. MS (ESI(−)) m/e 649 (M−H)⁻; ¹H NMR (400 MHz, DMSO-d₆) δ8.55 (d, 1H), 8.45 (d, 1H), 7.97 (d, 2H), 7.88 (dd, 1H), 7.75 (m, 5H), 7.30 (m, 4H), 7.15 (m, 3H), 4.30 (m, 1H), 3.55 (t, 4H), 3.42 (dd, 1H), 3.31 (dd, 1H), another 4 protons were buried under solvent peaks.

EXAMPLE 246

3-(2-methoxy-4'-((((4-(((1R)-2-morpholin-4-yl-1-((phenylthio)methyl)ethyl)amino)-3-nitrophenyl)sulfonyl)amino)carbonyl)-1,1'-biphenyl-4-yl)-N,N-dimethylpropanamide The desired product was prepared by substituting Example 236A and Example 146C for Example 1B and Example 1C, respectively, in Example 1D. MS (ESI(−)) m/e 760 (M−H)⁻; ¹H NMR (300 MHz, DMSO-d₆) δ2.36 (t, 2H), 2.44 (t, 2H), 2.62 (dd, 4H), 2.81 (dd, 2H), 2.82 (s, 3H), 2.96 (s, 3H), 3.31 (m, 1H), 3.41 (dd, 1H), 3.52 (dd, 4H), 3.74 (s, 3H), 4.15 (m, 1H), 6.89 (d, 1H), 6.94 (d, 1H), 6.99 (s, 1H), 7.18 (d, 1H), 7.20 (dd, 1H), 7.32 (t, 2H), 7.45 (m, 4H), 7.81 (dd, 1H), 7.89 (d, 2H), 8.32 (d, 1H), 8.48 (d, 1H).

EXAMPLE 247

N-(4-(3,3-dimethylpyrrolidin-1-yl)benzoyl)-3-nitro-4-((2-(phenylthio)ethyl)amino)benzenesulfonamide

EXAMPLE 247A methyl 4-(3,3-dimethyl-2,5-dioxopyrrolidin-1-yl)benzoate

The desired product was prepared by substituting methyl 4-aminobenzoate and 2,2-dimethylsuccinic anhydride for ethyl 4-aminobenzoate and 3,3-dimethylglutaric anhydride, respectively, in Example 119A. MS (DCI) m/e 262 (M+H)⁺.

EXAMPLE 247B methyl 4-(3,3-dimethylpyrrolidin-1-yl)benzoate

The desired product was prepared by substituting Example 247A for Example 119A in Example 119B. MS (DCI) m/e 234 (M+H)⁺.

EXAMPLE 247C 4-(3,3-dimethylpyrrolidin-1-yl)benzoic acid

The desired product was prepared by substituting Example 247B for Example 119B in Example 119C. MS (DCI) m/e 220 (M+H)⁺.

EXAMPLE 247D

N-(4-(3,3-dimethylpyrrolidin-1-yl)benzoyl)-3-nitro-4-((2-(phenylthio)ethyl)amino)benzenesulfonamide The desired product was prepared by substituting Example 247C and Example 77B for Example 1B and Example 1C, respectively, in Example 1D. MS (ESI(−)) m/e 553 (M−H)⁻; ¹H NMR (300 MHz, DMSO-d₆) δ11.87 (s, 1H), 8.76 (t, 1H), 8.60 (d, 1H), 7.91 (dd, 1H), 7.72 (d, 2H), 7.37 (d, 2H), 7.26 (t, 2H), 7.18 (m, 2H), 6.50 (d, 2H), 3.67 (m, 2H), 3.38 (t, 2H), 3.30 (m, 2H), 3.07 (s, 2H), 1.77 (t, 2H), 1.09 (s, 6H).

EXAMPLE 248

N-((2'-methoxy-4'-(3-(4-methylpiperazin-1-yl) propyl)-1,1'-biphenyl-4-yl)carbonyl)-3-nitro-4-((2-(phenylthio)ethyl)amino)benzenesulfonamide

EXAMPLE 248A methyl 2'-methoxy-4'-(3-(4-methylpiperazin-1-yl) propyl)-1,1'-biphenyl-4-carboxylate A solution of Example 362A (1.00 g, 2.52 mmol) in THF (5 mL) at room temperature was slowly treated with 1M $BH_3$ in THF (7.57 mL, 7.57 mmol), stirred for 16 hours, quenched with methanol (30 mL) and water (5 mL), treated with concentrated HCl (1 mL), heated to 60° C., and stirred for 2 hours. The mixture was treated with 1M NaOH (50 mL) and extracted with 80:20:0.5 dichloromethane/ methanol/concentrated ammonium hydroxide (3×250 mL). The combined extracts were washed with brine (50 mL), and concentrated. The concentrate was purified by flash column chromatography on silica gel with 80:20:0.5 dichloromethane/methanol/concentrated ammonium hydroxide to provide the desired product.

EXAMPLE 248B

2'-methoxy-4'-(3-(4-methylpiperazin-1-yl)propyl)-1, 1'-biphenyl-4-carboxylic acid The desired product was prepared by substituting Example 248A for Example 1A in Example 1B.

EXAMPLE 248C

N-((2'-methoxy-4'-(3-(4-methylpiperazin-1-yl) propyl)-1,1'-biphenyl-4-yl)carbonyl)-3-nitro-4-((2-(phenylthio)ethyl)amino)benzenesulfonamide The desired product was prepared by substituting Example 248B and Example 77B for Example 1B and Example 1C, respectively, in Example 1D. MS (ESI) m/e 702, 704 (M−H)⁻, (M+H)⁺; $^1$H NMR (300 MHz, DMSO-d$_6$) δ1.87 (m, 2H), 2.23 (s, 3H), 2.57 (m, 8H), 2.63 (t, 2H), 3.06 (q, 2H), 3.26 (t, 2H), 3.60 (dt, 2H), 3.75 (s, 3H), 6.87 (d, 1H), 6.95 (s, 1H), 7.00 (d, 1H), 7.19 (tt, 1H), 7.21 (d, 2H), 7.30 (td, 2H), 7.47–7.53 (m, 3H), 7.88 (d, 3H), 8.50 (d, 1H), 8.53 (d, 1H).

EXAMPLE 249

3-nitro-4-((2-(phenylthio)ethyl)amino)-N-(4-(thien-3-ylmethoxy)benzoyl)benzenesulfonamide The desired product was prepared by substituting 3-thiophenemethanol for 4-butylbenzyl alcohol in Example 209. MS (ESI) m/e 568, 570 (M−H)⁻, (M+H)⁺; $^1$H NMR (300 MHz, DMSO-d$_6$) δ3.27 (t, 2H), 3.62 (dt, 2H), 5.12 (s, 2H), 6.97 (d, 2H), 7,06 (d, 1H), 7.18 (t, 2), 7.28 (t, 2H), 7.38 (d, 2H), 7.54 (dd, 1H), 7.58 (s, 1H), 7.83 (d, 2H), 7.87 (dd, 1H), 8.54 (d, 1H), 8.62 (t, 1H).

EXAMPLE 250

N-(4-(4-(3-(4-methylpiperidin-1-yl)propyl)piperidin-1-yl)benzoyl)-3-nitro-4-((2-(phenylthio)ethyl)amino) benzenesulfonamide A solution Example 226 (20 mg, 0.03 mmol) and 4-methylpiperidine (0.02 mL, 0.17 mmol), and methanol (0.4 mL) at room temperature was treated with NaCNBH$_3$ (5.5 mg, 0.08 mmol) and acetic acid (1 drop), stirred for 18 hours, diluted with dichloromethane, washed with saturated NaHCO$_3$ and brine, dried (MgSO$_4$), filtered, and concentrated. The concentrate was purified by reverse phase chromatography, eluting with 0–100% CH$_3$CN/water containing 0.1% TFA to provide the desired product. MS (ESI) m/e 678 (M−H)⁻; $^1$H NMR (300 MHz, DMSO-d$_6$) δ11.87 (s, 1H), 8.79 (t, 1H), 8.60 (d, 1H), 7.91 (dd, 1H), 7.72 (d, 2H), 7.35 (d, 2H), 7.28–7.15 (m, 4H), 6.93 (d, 2H), 3.67 (m, 2H), 3.38 (t, 2H), 3.29 (m, 2H), 2.28 (m, 1H), 1.85–1.60 (m, 8H), 1.36–1.00 (m, 6H), 0.92 (d, 3H).

EXAMPLE 251

3-nitro-N-(4-(2-oxo-2,3-dihydro-1,3-benzoxazol-6-yl)benzoyl)-4-((2-(phenylthio)ethyl)amino) benzenesulfonamide

EXAMPLE 251A 6-bromo-1,3-benzoxazol-2(3H)-one

A mixture of 2-benzoxazolinone (3.00 g, 22.2 mmol), 1,3-dibromo-5,5-dimethylhydantoin (3.49 g, 12.2 mmol), and trifluoromethanesulfonic acid (5.00 g, 33.3 mmol) in dichloromethane (100 mL) at room temperature was protected from light, stirred for 1 hour, and concentrated. The concentrate was purified by flash column chromatography on silica gel with 50% ethyl acetate/hexanes to provide the desired product.

EXAMPLE 251B methyl 4-(2-oxo-2,3-dihydro-1,3-benzoxazol-6-yl) benzoate

The desired product was prepared by substituting Example 251A for Example 5A in Example 5B.

EXAMPLE 251C 4-(2-oxo-2,3-dihydro-1,3-benzoxazol-6-yl)benzoic acid

The desired product was prepared by substituting Example 251B for Example 1A in Example 1B.

EXAMPLE 251D 3-nitro-N-(4-(2-oxo-2,3-dihydro-1,3-benzoxazol-6-yl)benzoyl)-4-((2-(phenylthio)ethyl)amino) benzenesulfonamide The desired product was prepared by substituting Example 251C and Example 77B for Example 1B and Example 1C, respectively, in Example 1D. MS (ESI) m/e 589 (M−H)⁻; $^1$H NMR (300 MHz, DMSO-d$_6$) δ3.27 (t, 2H), 3.61 (dt, 2H), 7.01 (d, 1H), 7.15 (d, 1H), 7.18 (tt, 1H), 7.29 (td, 2H), 7.39 (d, 2H), 7.48 (dd, 1H), 7.62 (d, 2H), 7.65 (d, 1H), 7.89 (dd, 1H), 7.94 (d, 2H), 8.52 (d, 1H), 8.53 (t, 1H), 11.70 (s, 1H).

EXAMPLE 252

N-(4-(6-chloropyridin-3-yl)benzoyl)-3-nitro-4-(((4-(phenylthio)piperidin-4-yl)methyl)amino) benzenesulfonamide

EXAMPLE 252A tert-butyl 4-cyano-4-(phenylthio)piperidine-1-carboxylate

A solution of diisopropylamine (3.36 mL, 24 mmol) in THF (20 mL) at −78° C. was slowly treated with 2.5M n-butyllithium (7.2 mL, 18 mmol) in hexanes, warmed to 0° C. for 15 minutes, cooled to −78° C., treated slowly with a solution of N-BOC-4-cyanopiperidine (2.5 g, 12 mmol) in THF (10 mL), stirred for 30 minutes, and treated with a solution of PhSSPh (5.24 g, 24 mmol) in THF (20 mL). The mixture was stirred for 2 hours, warmed to room temperature, and quenched with saturated $NH_4Cl$ (50 mL). The mixture was extracted with ethyl acetate (3×50 mL) and the combined extracts were washed with water and brine, dried ($Na_2SO_4$), filtered, and concentrated. The concentrate was purified by flash column chromatography on silica gel with 3:1 hexanes/ethyl acetate to provide the desired product. MS (ESI) m/e 319 $(M+H)^+$.

EXAMPLE 252B tert-butyl 4-(aminomethyl)-4-(phenylthio)piperidine-1-carboxylate A solution of Example 252A (1.0 g, 3.1 mmol) in THF (5 mL) at 0° C. was treated dropwise with 1M $LiAlH_4$ in THF (3 mL), warmed to room temperature, stirred for 2 hours, quenched with methanol (1 mL), treated with 1N NaOH (50 mL), and extracted with ethyl acetate (3×100 mL). The combined extracts were washed with water and brine, dried ($Na_2SO_4$), filtered, and concentrated to provide the desired product. MS (APCI) m/e 323$(M+H)^+$.

EXAMPLE 252C tert-butyl 4-(((4-(aminosulfonyl)-2-nitrophenyl) amino)methyl)-4-(phenylthio)piperidine-1-carboxylate A mixture of Example 252B (1.0 g, 3.1 mmol), Example 122C (0.683 g, 3.1 mmol), and diisopropylethylamine (2 mL) in DMSO (10 mL) was heated to 50° C. for 18 hours, diluted with ethyl acetate (100 mL), washed with water and brine, dried ($Na_2SO_4$), filtered, and concentrated. The concentrate was purified by flash column chromatography on silica gel with 1:1 hexanes/ethyl acetate to provide the desired product. MS (ESI(−)) m/e 521 $(M−H)^−$.

EXAMPLE 252D methyl 4-(6-methoxypyridin-3-yl)benzoate

A mixture of 5-bromo-2-methoxypyridine (2.93 g, 10 mmol), 4-methylcarboxybenzeneboronic acid (1.80 g, 10 mmol), $Pd(Ph_3P)_4$ (0.346 g, 0.3 mmol) and CsF (1.52 g, 10 mmol) in DME (60 mL) and methanol (30 mL) was heated to reflux for 18 hours and concentrated. The concentrate was dissolved in water (50 mL) and ethyl acetate (300 mL) and the organic phase was washed with water (2×50 mL) and brine (50 mL), dried ($Na_2SO_4$), filtered, and concentrated. The concentrate was purified by flash column chromatography on silica gel with 3:1 hexanes/ethyl acetate to provide the desired product. MS (APCI) m/e 278, 280 $(M−H)^−$, $(M+H)^+$.

EXAMPLE 252E methyl 4-(6-hydroxypyridin-3-yl)benzoate

A solution of Example 252D (0.5 g, 2.2 mmol) in dichloromethane at −78° C. was treated with 1M $BBr_3$ in dichloromethane (15 mL), warm to room temperature, and stirred for 18 hours. The reaction was quenched with methanol (5 mL), diluted with dichloromethane (100 mL), washed with water (30 mL), brine (30 mL), dried ($Na_2SO_4$), filtered, and concentrated. The concentrate was purified by flash column chromatography on silica gel with 2:1 hexanes/ethyl acetate to provide the desired product. MS (ESI) m/e 228, 230 $(M−H)^−$, $(M+H)^+$.

EXAMPLE 252F methyl 4-(6-chloropyridin-3-yl)benzoate

A solution of Example 252E (1.2 g, 5 mmol) in $POCl_3$ (30 mL) was heated to reflux for 30 minutes. The excess $POCl_3$ was removed under vacuum and the remaining product was purified by flash column chromatography on silica gel with 4:1 ethyl acetate/hexanes to provide the desired product. MS (ESI) m/e 248 $(M+H)^+$.

EXAMPLE 252G 4-(6-chloropyridin-3-yl)benzoic acid

A solution of Example 252F (1.56 g, 6.4 mmol) in THF (30 mL) at room temperature treated with a solution of $LiOH.H_2O$ (0.537 g, 12.8 mmol) in water (5 mL), heated to reflux for 4 hours, cooled to room temperature and concentrated. The mixture was neutralized with 1N HCl and extracted ethyl acetate (3×50 mL). The combined extracts were washed with brine, dried ($Na_2SO_4$), filtered, and concentrated to provide the desired product. MS (APCI) m/e 234 $(M+H)^+$.

EXAMPLE 252H

N-(4-(6-chloropyridin-3-yl)benzoyl)-3-nitro-4-(((4-(phenylthio)piperidin-4-yl)methyl)amino) benzenesulfonamide The desired product was prepared by substituting Example 252C and Example 252G for Example 124E and Example 257C, respectively, in Example 124F. MS (ESI(−)) m/e 636 $(M−H)^−$; $^1H$ NMR (500 MHz, DMSO-$d_6$) δ9.10 (m, 1H), 8.98 (t, 1H), 8.93 (m, 1H), 8.81 (dd, 1H), 8.74 (d, 1H), 8.24 (dd, 1H), 8.01 (d, 2H), 7.90 (d, 2H), 7.64 (d, 1H), 7.54 (dt, 2H), 7.48 (tt, 1H), 7.41 (td, 2H), 7.33 (d, 1H), 3.40 (d, 2H), 3.23 (m, 4H), 1.97–1.82 (m, 4H).

EXAMPLE 253

3-nitro-4-(((4-(phenylthio)piperidin-4-yl)methyl) amino)-N-(4-(5-(trifluoromethyl)pyridin-2-yl) benzoyl)benzenesulfonamide

EXAMPLE 253A methyl 4-(5-(trifluoromethyl)pyridin-2-yl)benzoate

The desired product was prepared by substituting 2-chloro-5-trifluoromethylpyridine for 5-bromo-2-methoxypyridine in Example 252D. MS (ESI(+)) m/e 282 $(M+H)^+$.

EXAMPLE 253B 4-(5-(trifluoromethyl)pyridin-2-yl)benzoic acid

The desired product was prepared by substituing Example 253A for Example 252F in Example 252G. MS (ESI(+)) m/e 268 $(M+H)^+$.

EXAMPLE 253C 3-nitro-4-(((4-(phenylthio)piperidin-4-yl)methyl) amino)-N-(4-(5-(trifluoromethyl)pyridin-2-yl) benzoyl)benzenesulfonamide The desired product was prepared by substituting Example 252C and Example 253B for Example 124E and Example 257C, respectively, in Example 124F. MS (ESI(−)) m/e 636 (M−H)⁻; ¹H NMR (500 MHz, DMSO-d₆) δ9.09 (d, 1H), 9.08 (m, 1H), 8.98 (t, 1H), 8.89 (m, 1H), 8.74 (d, 1H), 8.34 (dd, 1H), 8.30 (d, 1H), 8.29 (d, 2H), 8.04 (d, 2H), 8.01 (dd, 1H), 7.54 (dt, 2H), 7.48 (tt, 1H), 7.41 (td, 2H), 7.33 (d, 1H), 3.40 (d, 2H), 3.23 (m, 4H), 1.97–1.82 (m, 4H).

EXAMPLE 254

N-(4-(5-chloropyridin-2-yl)benzoyl)-3-nitro-4-(((4-(phenylthio)piperidin-4-yl)methyl)amino)benzenesulfonamide

EXAMPLE 254A methyl 4-(5-chloropyridin-2-yl)benzoate

The desired product was prepared by substituting 2,5-dichloropyridine for 5-bromo-2-methoxypyridine in Example 252D. MS (ESI(+)) m/e 248 (M+H)⁺.

EXAMPLE 254B 4-(5-chloropyridin-2-yl)benzoic acid

The desired product was prepared by substituting Example 254A for Example 252F in Example 252G. MS (ESI(+)) m/e 234 (M+H)⁺.

EXAMPLE 254C

N-(4-(5-chloropyridin-2-yl)benzoyl)-3-nitro-4-(((4-(phenylthio)piperidin-4-yl)methyl)amino)benzenesulfonamide The desired product was prepared by substituting Example 252C and Example 254B for 124E and 257C, respectively, in Example 124F. MS (ESI(−)) m/e 636 (M−H)⁻; ¹H NMR (500 MHz, DMSO-d₆) δ9.05 (m, 1H), 8.98 (t, 1H), 8.85 (m, 1H), 8.74 (m, 2H), 8.21 (d, 2H), 8.11 (d, 1H), 8.06 (dd, 1H), 8.00 (d, 2H), 7.54 (dt, 2H), 7.48 (tt, 1H), 7.41 (td, 2H), 7.32 (d, 1H), 3.40 (d, 2H), 3.23 (m, 4H), 1.97–1.82 (m, 4H).

EXAMPLE 255

4-((2-adamantylmethyl)amino)-3-nitro-N-(4-quinolin-8-ylbenzoyl)benzenesulfonamide

EXAMPLE 255A 4-((1-adamantylmethyl)amino)-3-nitro-N-(4-(4,4,5,5-tetramethyl-1,3,2-dioxaborolan-2-yl)benzoyl)benzenesulfonamide The desired product was prepared by substituting Example 28A for Example 3A in Example 3C.

EXAMPLE 255B 4-((2-adamantylmethyl)amino)-3-nitro-N-(4-quinolin-8-ylbenzoyl)benzenesulfonamide The desired product was prepared by substituting Example 255A and 8-bromoquinoline for Example 108A and Example 389A, respectively, in Example 389B. MS (ESI(−)) m/e 595 (M−H)⁻; ¹H NMR (300 MHz, methanol-d₄) δ8.81 (m, 2H), 8.52 (7, 1H), 8.39 (dd, 1H), 8.16 (d, 2H), 8.03 (d, 1H), 7.95 (d, 1H), 7.74 (d, 1H), 7.68 (d, 1H), 7.63 (d, 2H), 7.52 (dd, 2H), 7.13 (d, 1H), 3.12 (d, 2H), 1.98 (m, 3H), 1.72–1.55 (m, 12H).

EXAMPLE 256

N-(4-(2-methylquinolin-8-yl)benzoyl)-3-nitro-4-((2-(phenylthio)ethyl)amino)benzenesulfonamide

EXAMPLE 256A 2-methylquinolin-8-yl trifluoroacetate

The desired product was prepared by substituting 8-hydroxy-2-methylquinoline for vanillin in Example 122H.

EXAMPLE 256B

N-(4-(2-methylquinolin-8-yl)benzoyl)-3-nitro-4-((2-(phenylthio)ethyl)amino)benzenesulfonamide The desired product was prepared by substituting Example 256A for Example 389A in Example 389B. MS (ESI(−)) m/e 597 (M−H)⁻; ¹H NMR (400 MHz, DMSO-d₆) δ8.57 (m, 2H), 8.29 (d, 1H), 7.94 (m, 4H), 7.72 (m, 1H), 7.65 (d, 2H), 7.59 (t, 1H), 7.44 (d, 1H), 7.40 (m, 2H), 7.30 (t, 2H), 7.20 (tt, 1H), 7.06 (d, 1H), 3.63 (q, 2H), 3.26 (t, 2H), 2.59 (s, 3H).

EXAMPLE 257 tert-butyl (5R)-5-((4-(((4-(8-azaspiro(4.5)dec-8-yl)benzoyl)amino)sulfonyl)-2-nitrophenyl)amino)-6-(phenylthio)hexylcarbamate

EXAMPLE 257A methyl 4-(7,9-dioxo-8-azaspiro(4.5)dec-8-yl)benzoate

The desired product was prepared by substituting methyl 4-aminobenzoate and 3,3-tetramethyleneglutaric anhydride for ethyl 4-aminobenzoate and 3,3-dimethylglutaric anhydride, respectively, in Example 119A. MS (DCI) m/e 302 (M+H)⁺.

EXAMPLE 257B methyl 4-(8-azaspiro(4.5)dec-8-yl)benzoate

The desired product was prepared by substituting Example 257A for Example 119A in Example 119B. MS (DCI) m/e 274 (M+H)⁺.

EXAMPLE 257C 4-(8-azaspiro(4.5)dec-8-yl)benzoic acid

The desired product was prepared by substituting Example 257B for Example 119B in Example 119C. MS (DCI) m/e 260 (M+H)⁺.

EXAMPLE 257D tert-butyl (5R)-5-((4-(((4-(8-azaspiro(4.5)dec-8-yl)benzoyl)amino)sulfonyl)-2-nitrophenyl)amino)-6-(phenylthio)hexylcarbamate The desired product was prepared by substituting Example 257C and Example 124C for Example 1B and Example 1C, respectively, in Example 1D. MS (ESI(+)) m/e 766; ¹H NMR (300 MHz, DMSO-d₆) δ11.96 (s, 1H), 8.52 (d, 1H), 8.29 (d, 1H), 7.83 (dd, 1H), 7.74 (d, 2H), 7.24 (d, 2H), 7.18–7.08 (m, 4H), 6.91 (d, 2H), 6.72 (t, 1H), 4.04 (s, 1H), 3.98 (t, 1H), 2.86 (m, 2H), 1.72 (m, 2H), 1.59 (m, 4H), 1.45 (m, 8H), 1.31 (s, 9H).

EXAMPLE 258

N-(4-(3-azabicyclo(3.1.0)hex-3-yl)benzoyl)-3-nitro-4-((2-(phenylthio)ethyl)amino)benzenesulfonamide

EXAMPLE 258A methyl 4-(2,4-dioxo-3-azabicyclo(3.1.0)hex-3-yl)benzoate

The desired product was prepared by substituting methyl 4-aminobenzoate and 3-oxabicyclo(3.1.0)hexane-2,4-dione for ethyl 4-aminobenzoate and 3,3-dimethylglutaric anhydride, respectively, in Example 119A. MS (DCI) m/e 263 $(M+NH_4)^+$.

EXAMPLE 258B methyl 4-(3-azabicyclo(3.1.0)hex-3-yl)benzoate

The desired product was prepared by substituting Example 258A for Example 119A in Example 119B. MS (DCI) m/e 218 $(M+H)^+$.

EXAMPLE 258C 4-(3-azabicyclo(3.1.0)hex-3-yl)benzoic acid

The desired product was prepared by substituting Example 258B for Example 119B in Example 119C. MS (DCI) m/e 204 $(M+H)^+$.

EXAMPLE 258D

N-(4-(3-azabicyclo(3.1.0)hex-3-yl)benzoyl)-3-nitro-4-((2-(phenylthio)ethyl)amino)benzenesulfonamide The desired product was prepared by substituting Example 258C and Example 77B for Example 1B and Example 1C, respectively, in Example 1D. MS (ESI(+)) m/e 561 $(M+H)^+$; $^1$H NMR (300 MHz, DMSO-$d_6$) δ11.91 (s, 1H), 8.74 (t, 1H), 8.58 (d, 1H), 7.90 (dd, 1H), 7.71 (d, 2H), 7.37 (d, 2H), 7.27 (t, 2H), 7.18 (m, 2H), 6.52 (d, 2H), 3.36 (m, 2H), 3.51 (d, 2H), 3.25 (m, 4H), 1.71 (m, 2H), 0.75 (m, 1H), 0.18 (m, 1H).

EXAMPLE 259

N-(4-(4-ethyl-4-methylpiperidin-1-yl)benzoyl-3-nitro-4-((2-(phenylthio)ethyl)amino)benzenesulfonamide The desired product was prepared by substituting Example 123C and Example 77B for Example 1B and Example 1C, respectively, in Example 1D. MS (ESI(−)) m/e 581 $(M-H)^-$; $^1$H NMR (300 MHz, DMSO-$d_6$) δ11.96 (s, 1H), 8.77 (t, 1H), 8.60 (d, 1H), 7.91 (dd, 1H), 7.73 (d, 2H), 7.37 (d, 2H), 7.26 (t, 2H), 7.18 (m, 2H), 6.91 (d, 2H), 3.67 (m, 2H), 3.45 (m, 2H), 3.30 (m, 2H), 3.20 (m, 2H), 1.36 (m, 3H), 1.29 (m, 3H), 0.90 (s, 3H), 0.80 (t, 3H).

EXAMPLE 260

3-nitro-N-(4-(2-(2-phenylethyl)-1,3-benzothiazol-5-yl)benzoyl)-4-((2-(phenylthio)ethyl)amino)benzenesulfonamide The desired product was prepared by substituting benzyl bromide for allyl bromide in Example 213. MS (ESI) m/e 693, 695 $(M-H)^-$, $(M+H)^+$; $^1$H NMR (300 MHz, DMSO-$d_6$) δ3.18 (t, 2H), 3.29 (t, 2H), 3.47 (t, 2H), 3.64 (dt, 2H), 7.11 (d, 1H), 7.19 (dt, 2H), 7.25–7.34 (m, 6H), 7.39 (dd, 2H), 7.75 (dd, 1H), 7.81 (d, 2H), 7.92 (dd, 1H), 7.98 (d, 2H), 8.12 (d, 1H), 8.26 (d, 1H), 8.57 (d, 1H), 8.65 (t, 1H).

EXAMPLE 261 tert-butyl (5R)-5-((4-(((4-(4,4-dimethylpiperidin-1-yl)benzoyl)amino)sulfonyl)-2-nitrophenyl)amino)-6-(phenylthio)hexylcarbamate The desired product was prepared by substituting Example 119C and Example 124C, for Example 1B and Example 1C, respectively, in Example 1D. MS(ESI(+)) m/e 740 $(M+H)^+$; $^1$H NMR (300 MHz, DMSO-$d_6$) δ11.96 (s, 1H), 8.49 (d, 1H), 8.23 (d, 1H), 7.81 (dd, 1H), 7.73 (d, 2H), 7.26 (d, 2H), 7.21–7.11 (m, 3H), 7.04 (d, 1H), 6.87 (d, 2H), 6.72 (t, 1H), 4.00 (m, 2H), 3.28 (m, 6H), 1.71 (m, 2H), 1.35 (m, 8H), 1.32 (s, 9H), 0.94 (s, 6H).

EXAMPLE 262

4-(((1R)-5-amino-1-((phenylthio)methyl)pentyl)amino)-N-((2'-methoxy-4'-(3-morpholin-4-yl-3-oxopropyl)-1,1'-biphenyl-4-yl)carbonyl)-3-nitrobenzenesulfonamide The desired product was prepared by substituting Example 122M for Example 122N in Example 194. MS (ESI(−)) m/e 774 $(M-H)^-$; $^1$H NMR(300MHz, DMSO-$d_6$), δ12.50 (br s, 1H), 8.55 (d, 1H), 8.35 (br d, 1H), 7.90 (d, 2H), 7.85 (dd, 1H), 7.70 (br s, 2H), 7.58 (d, 2H), 7.30–7.12 (m, 7H), 7.00 (d, 1H), 6.89 (dd, 1H), 4.10 (m, 1H), 3.75 (s, 3H), 3.50(m, 4H), 3.45 (m, 4H), 3.35 (m, 2H), 2.85 (t, 2H), 2.75 (m, 2H), 2.70 (t, 2H), 1.75 (m, 2H), 1.50 (m, 2H), 1.40 (m, 2H).

EXAMPLE 263

2-(4'-((((4-(((1R)-5-amino-1-((phenylthio)methyl)pentyl)amino)-3-nitrophenyl)sulfonyl)amino)carbonyl)-2-methoxy-1,1'-biphenyl-4-yl)-N,N-dimethylacetamide The desired product was prepared by substituting Example 441A for Example 122N in Example 194. MS (ESI(−)) m/e M−H)$^-$; $^1$H NMR (300 MHz, DMSO-$d_6$) δ12.5 (br s, 1H), 8.55 (d, 1H), 8.35 (br d, 1H), 7.90 (d, 2H), 7.85 (dd, 1H), 7.70 (br s, 2H), 7.58 (d, 2H), 7.25 (dd, 1H), 7.20 (d, 1H), 7.0–7.12 (m, 5H), 7.00 (d, 1H), 6.89 (dd, 1H), 4.10 (m, 1H), 3.75 (s, 3H), 3.72 (s, 2H), 3.35 (m, 2H), 3.04 (s, 3H), 2.85 (s, 3H), 2.75 (m, 2H), 1.75 (m, 2H), 1.50 (m, 2H), 1.40 (m, 2H).

EXAMPLE 264

4-((cyclohexylmethyl)amino)-3-nitro-N-(4-quinolin-8-ylbenzoyl)benzenesulfonamide

EXAMPLE 264A methyl 4-quinolin-8-ylbenzoate

The desired product was prepared by substituting 8-bromoquinoline for Example 5A in Example 5B.

EXAMPLE 264B 4-quinolin-8-ylbenzoic acid

The desired product was prepared by substituting Example 264A for Example 1A in Example 1B.

EXAMPLE 264C 4-((cyclohexylmethyl)amino)-3-nitro-N-(4-quinolin-8-ylbenzoyl)benzenesulfonamide The desired product was prepared by substituting Example 264B and Example 21B for Example 1B and Example 1C, respectively, in Example 1D. MS (ESI(−)) m/e 543 (M−H)−; $^1$H NMR (500 MHz, DMSO-d$_6$) δ8.91 (dd, 1H), 8.53 (d, 1H), 8.43 (dd, 1H), 8.40 (t, 1H), 8.00 (d, 1H), 7.97 (d, 2H), 7.92 (dd, 1H), 7.77 9dd, 1H), 7.68 (t, 1H), 7.60 9d, 2H), 7.56 (dd, 1H), 7.08 (d, 1H), 3.25 (t, 2H), 1.80–1.60 (m, 6H), 1.25–1.12 (m, 3H), 1.00 (m, 2H).

EXAMPLE 265

N-(4-(4-(4-fluorophenyl)piperazin-1-yl)benzoyl)-3-nitro-4-((2-(phenylthio)ethyl)amino)benzenesulfonamide

EXAMPLE 265A ethyl 4-(4-(4-fluorophenyl)piperazin-1-yl)benzoate

The desired product was prepared by substituting 4-fluorophenyl-1-piperazine for Example 131A in Example 131B. MS (ESI(+)) m/e 329 (M+H)+.

EXAMPLE 265B 4-(4-(4-fluorophenyl)piperazin-1-yl)benzoic acid

The desired product was prepared by substituting Example 265A for Example 131B in Example 131C. MS (ESI(−)) m/e 299 (M−H)−.

EXAMPLE 265C

N-(4-(4-(4-fluorophenyl)piperazin-1-yl)benzoyl)-3-nitro-4-((2-(phenylthio)ethyl)amino)benzenesulfonamide The desired product was prepared by substituting Example 265B and Example 77B for Example 1B and Example 1C, respectively, in Example 1D. MS (ESI(−)) m/e 634 (M−H)−; $^1$H NMR (300 MHz, DMSO-d$_6$) δ12.05 (br s, 1H), 8.78 (t, 1H), 8.60 (d, 1H), 7.91 (dd, 1H), 7.77 (d, 2H), 7.35–7.39 (m, 2H), 6.97–7.29 (m, 10H), 3.67(q, 2H), 3.41–3.52 (m, 4H), 3.25–3.31 (m, 2H), 3.17–3.23 (m, 4H).

EXAMPLE 266

N-(4-(8-azaspiro(4.5)dec-8-yl)benzoyl)-4-((2-methyl-2-(phenylthio)propyl)amino)-3-nitrobenzenesulfonamide

EXAMPLE 266A 2-methyl-2-(phenylthio)propanenitrile

A solution of isobutyronitrile (1.382 g, 1.82 mL, 20 mmol) in THF (12 mL) at −78° C. was treated dropwise with 1.5M LDA.THF in cyclohexane (14 mL, 21 mmol), stirred for 30 minutes, treated with PhSSPh (4.36 g, 20 mmol), stirred for 30 minutes, warmed to room temperature, quenched with NaHCO$_3$, and extracted with diethyl ether. The combined extracts were dried (MgSO$_4$), filtered, and concentrated. The concentrate was purified by flash column chromatography on silica gel with 0–10% ethyl acetate/pentane to provide the desired product. MS (DCI(+)) m/e 195 (M+18)+.

EXAMPLE 266B 2-methyl-2-(phenylthio)propan-1-amine

A solution of Example 266A (0.5 g, 2.82 mmol) in THF at room temperature was treated with 1M BH$_3$.THF (15 mL), stirred for 18 hours, quenched with methanol (5 mL), and concentrated. The concentrate was treated with 2M HCl (50 mL) and concentrated. The concentrate was partitioned between dichloromethane and saturated sodium bicarbonate, and the organic phase was dried (MgSO$_4$), filtered, and concentrated to provide the desired product. MS (DCI(+)) m/e 182 (M+H)+.

EXAMPLE 266C 4-((2-methyl-2-(phenylthio)propyl)amino)-3-nitrobenzenesulfonamide The desired product was prepared by substituting Example 266B for Example 195A in Example 195B. MS (ESI(−)) m/e 380 (M−H)−.

EXAMPLE 266D

N-(4-(8-azaspiro(4.5)dec-8-yl)benzoyl)-4-((2-methyl-2-(phenylthio)propyl)amino)-3-nitrobenzenesulfonamide The desired product was prepared by substituting Example 257C and Example 266C for Example 1B and Example 1C, respectively, in Example 1D. MS (ESI(−)) m/e 621 (M−H)−; $^1$H NMR (300 MHz, DMSO-d$_6$) δ8.84 (t, 1H), 8.63 (d, 1H), 7.92 (dd, 1H), 7.72 (d, 2H), 7.51–7.35 (m, 5H), 7.16 (d, 1H), 6.87 (d, 2H), 3.32–3.24 (m, 6H), 1.62–1.57 (m, 4), 1.51–1.40 (m, 8H), 1.31 (s, 6H).

EXAMPLE 267

N-(4-(8-azaspiro(4.5)dec-8-yl)benzoyl)-4-((1,1-dimethyl-2-(phenylthio)ethyl)amino)-3-nitrobenzenesulfonamide

EXAMPLE 267A 2-methyl-1-(phenylthio)propan-2-amine

A mixture of anhydrous CeCl$_3$ (7.64 g, 31 mmol) in THF (40 ML) at room temperature was stirred for 2 hours, cooled to −78° C., treated dropwise with 1.4M methyllithium in diethyl ether (21.4 mL, 30 mmol), stirred for 1 hour, treated with PhSCH$_2$CN (1.492 g, 10 mmol, 1.3 mL), stirred for 2 hours, warmed to −35° C. over 1 hour, quenched with NH$_4$OH, warmed to room temperature, and filtered through diatomaceous earth (Celite®). The pad was washed with dichloromethane and the organic phase was dried over (MgSO$_4$), filtered, and concentrated. The concentrate was dissolved in 2M HCl, washed with dichloromethane (2×), and the aqueous phase was concentrated. The concentrate was treated with dichloromethane and neutralized with saturated sodium bicarbonate. The organic phase was dried (MgSO$_4$), filtered, and concentrated to provide the desired product. MS (DCI(+)) m/e 182 (M+H)+.

EXAMPLE 267B 4-((1,1-dimethyl-2-(phenylthio)ethyl)amino)-3-nitrobenzenesulfonamide The desired product was prepared by substituting Example 267A for Example 195A in Example 195B. MS (ESI(−)) m/e 380 (M−H)−.

EXAMPLE 267C

N-(4-(8-azaspiro(4.5)dec-8-yl)benzoyl)-4-((1,1-dimethyl-2-(phenylthio)ethyl)amino)-3-nitrobenzenesulfonamide The desired product was prepared by substituting Example 257C and Example 267B for Example 1B and Example 1C, respectively, in Example 1D. MS (ESI(−)) m/e 621 (M−H)−; $^1$H NMR (300 MHz, DMSO-d$_6$) δ11.98 (br s, 1H), 8.50–8.48 (m, 2H), 7.84 (dd, 1H), 7.75 (d, 2H), 7.34 (d, 1H), 7.29–7.24 (m, 2H), 7.08–6.98 (m, 2H), 6.98 (d, 1H), 6.89 (d, 2H), 3.54 (s, 2H), 3.32–3.24 (m, 4H), 1.62–1.56 (m, 4H), 1.56 (s, 6H), 1.51–1.40 (m, 8H).

EXAMPLE 268

4-(((1R)-5-amino-1-((phenylthio)methyl)pentyl)amino)-N-(4-(4,4-dimethylpiperidin-1-yl)benzoyl)-3-nitrobenzenesulfonamide The desired product was prepared by substituting Example 261 for Example 120D in Example 120E. MS (ESI(+)) m/e 640 (M+H)+; $^1$H NMR (300 MHz, DMSO-d$_6$) δ11.96 (s, 1H), 8.55 (d, 1H), 8.31 (d, 1H), 7.85 (dd, 1H), 7.73 (d, 2H), 7.26 (d, 2H), 7.21–7.11 (m, 3H), 7.04 (d, 1H), 6.92 (d, 2H), 4.09 (m, 2H), 3.37 (m, 4H), 2.72 (t, 4H), 1.76 (m, 2H), 1.52 (m, 2H), 1.35 (m, 8H), 1.48 (m, 6H), 0.95 (s, 6H).

EXAMPLE 269

4-(((4-(aminomethyl)bicyclo(2.2.2)oct-1-yl)methyl)amino)-N-((4'-fluoro-1,1'-biphenyl-4-yl)carbonyl-3-nitrobenzenesulfonamide

EXAMPLE 269A tert-butyl (4-(((4-((((4'-fluoro-1,1'-biphenyl-4-yl)carbonyl)amino)sulfonyl)-2-nitrophenyl)amino)methyl)bicyclo(2.2.2)oct-1-yl)methylcarbamate The desired product was prepared by substituting Example 162A for Example 1C in Example 1D. MS (ESI (−)) m/e 665 (M−H)−.

EXAMPLE 269B 4-(((4-(aminomethyl)bicyclo(2.2.2)oct-1-yl)methyl)amino)-N-((4'-fluoro-1,1'-biphenyl-4-yl)carbonyl)-3-nitrobenzenesulfonamide The desired product was prepared by substituting Example 269A for Example 120D in Example 120E. MS (ESI(−)) m/e 565 (M−H)−; $^1$H NMR (300 MHz, DMSO-d$_6$) δ8.67 (d, 1H), 8.50 (t, 1H), 7.99–7.93(m, 3H), 7.82–7.77 (mn, 3H), 7.71 (br s, 2H), 7.36–7.27 (m, 3H), 3.26–3.17 (d, 2H), 2.55 (q, 2H), 2.52–2.41 (m, 12H).

EXAMPLE 270

4-((1,1-dimethyl-2-(phenylthio)ethyl)amino)-N-((4'-fluoro-1,1'-biphenyl-4-yl)carbonyl)-3-nitrobenzenesulfonamide The desired product was prepared by substituting Example 267B for Example 1C in Example 1D. MS (ESI (−)) m/e 578 (M−H)−; $^1$H NMR (300 MHz, DMSO-d6) δ8.47–8.51 (m, 2H), 7.98 (d, 2H), 7.86 (dd, 1H), 7.72–7.78 (m, 2H), 7.69 (d, 2H), 7.25–7.35 (m, 5H), 7.06–7.12 (m, 2H), 6.97–7.02 (m, 1H), 3.54 (s, 2H), 1.56 (s, 6H).

EXAMPLE 271

4-((1,1-dimethyl-2-(phenylthio)ethyl)amino)-N-(4-(4,4-dimethylpiperidin-1-yl)benzoyl)-3-nitrobenzenesulfonamide The desired product was prepared by substituting Example 267B and Example 119C for Example 1C and Example 1B, respectively, in Example 1D. MS (ESI(−)) m/e 595 (M−H)−; $^1$H NMR (300 MHz, DMSO-d$_6$) δ11.97 (br s, 1H), 8.50–8.47 (m, 2H), 7.85 (dd, 1H), 7.75 (d, 2H), 7.34 (d, 1H), 7.26 (d, 2H), 7.08–7.00 (m, 2H), 6.98 (d, 1H), 6.90 (d, 2H), 3.54 (s, 2H), 3.36–3.25 (m, 4H), 1.56 (s, 6H), 1.40–1.36 (m, 4H), 0.95 (s, 6H).

EXAMPLE 272 tert-butyl 4-(4-((((4-((1,1-dimethyl-2-(phenylthio)ethyl)amino)-3-nitrophenyl)sulfonyl)amino)carbonyl)phenyl)piperazine-1-carboxylate The desired product was prepared by substituting 4-(4-((neopentyloxy)carbonyl)piperazin-1-yl)benzoic acid and Example 267B for Example 1B and Example 1C, respectively, in Example 1D. MS (ESI(−)) m/e 668 (M−H)−; $^1$H NMR (300 MHz, DMSO-d$_6$) δ8.49 (t, 1H), 7.84 (dd, 1H), 7.79 (d, 2H), 7.33 (d, 1H), 7.26 (d, 2H), 7.08–7.02 (m, 2H), 6.98 (d, 1H), 6.92 (d, 2H), 3.45 (s, 2H), 3.45–3.38 (m, 4H), 3.31–3.26 (m, 4H), 1.56 (s, 6H), 1.41 (s, 9H).

EXAMPLE 273

N-((4'-fluoro-2-methyl-1,1'-biphenyl-4-yl)carbonyl)-3-nitro-4-((2-(phenylthio)ethyl)amino)benzenesulfonamide

EXAMPLE 273A ethyl 4'-fluoro-2-methyl-1,1'-biphenyl-4-carboxylate

The desired product was prepared by substituting 4-bromo-3-methylbenzoic acid ethyl ester and 4-fluorophenylboronic acid for Example 186B and Example 186A, respectively, in Example 186C.

EXAMPLE 273B

4'-fluoro-2-methyl-1,1'-biphenyl-4-carboxylic acid

The desired product was prepared by substituting Example 273A for Example 186C in Example 186D. MS (DCI) m/e 231 (M+H)+.

EXAMPLE 273C

N-((4'-fluoro-2-methyl-1,1'-biphenyl-4-yl)carbonyl)-3-nitro-4-((2-(phenylthio)ethyl)amino)benzenesulfonamide The desired product was prepared by substituting Example 273B and Example 77B for Example 1B and Example 1C, respectively, in Example 1D. MS (DCI) m/e 566 (M+H)+; $^1$H NMR (300 MHz, DMSO-d$_6$) δ12.43 (br s, 1H), 8.78 (t, 1H), 8.64 (d, 1H), 7.94 (dd, 1H), 7.83 (d, 1H), 7.75 (dd, 1H), 7.41–7.37 (m, 4H), 7.32–7.27 (m, 5H), 7.22 (d, 1H), 7.18 (m, 1H), 3.68 (q, 2H), 3.29 (q, 2H), 2.25 (s, 3H).

EXAMPLE 274 tert-butyl 5-(4-((((3-nitro-4-((2-(phenylthio)ethyl)amino)phenyl)sulfonyl)amino)carbonyl)phenyl)-1-benzothiophene-2-carboxylate

EXAMPLE 274A methyl 5-bromo-1-benzothiophene-2-carboxylate

A solution of 5-bromo-2-fluorobenzaldehyde (6 g, 29.6 mmol), methyl thioglycolate (2.64 mL, 29.6 mmol), and Na$_2$CO$_3$ (3.14 g, 29.6 mmol) in methanol was heated to reflux for 1 hour, poured into brine, and extracted with ethyl acetate (3×). The combined extracts were washed with brine and filtered through silica gel to provide the desired product. MS (ESI(−)) m/e 270 (M−H)$^−$.

EXAMPLE 274B 5-bromo-1-benzothiophene-2-carboxylic acid

The desired product was prepared by substituting Example 274A for Example 1A in Example 1B. MS (ESI(−)) m/e 254 (M−H)$^−$.

EXAMPLE 274C tert-butyl 5-bromo-1-benzothiophene-2-carboxylate

A mixture of Example 274B and concentrated H$_2$SO$_4$ (0.5 mL) in dichloromethane (100 mL) saturated with isobutylene at room temperature was stirred for 4 hours and concentrated. The concentrate was purified by flash column chromatography on silica gel with 2% ethyl acetate/hexanes to provide the desired product.

EXAMPLE 274D tert-butyl 5-(4-(methoxycarbonyl)phenyl)-1-benzothiophene-2-carboxylate The desired product was prepared by substituting Example 274C and 4-(methoxycarbonyl)phenylboronic acid for methyl 4-bromobenzoate and 4-fluorophenylboronic acid, respectively, in Example 1A.

EXAMPLE 274E 4-(2-(tert-butoxycarbonyl)-1-benzothien-5-yl)benzoic acid

The desired product was prepared by substituting Example 274D for Example 1A in Example 1B. MS (ESI (−)) m/e 353 (M−H)$^−$.

EXAMPLE 274F tert-butyl 5-(4-((((3-nitro-4-((2-(phenylthio)ethyl)amino)phenyl)sulfonyl)amino)carbonyl)phenyl)-1-benzothiophene-2-carboxylate The desired product was prepared by substituting Example 274E and Example 77B for Example 1B and Example 1C, respectively, in Example 1D. MS (ESI(−)) m/e 688 (M−H)$^−$; $^1$H NMR (300 MHz, DMSO-d$_6$) δ1.58 (s, 9H), 3.29 (t, 2H), 3.65 (dt, 2H), 7.16 (m, 3H), 7.28 (t, 2H), 7.38 (m, 3H), 7.41 (m, 1H), 7.81 (d, 1H), 7.88 (d, 2H), 7.92 (dd, 1H), 8.01 (d, 1H), 8.14 (d, 1H), 8.61 (dd, 1H), 8.71 (t, 1H).

EXAMPLE 275

(3R)-3-((4-((((4'-fluoro-1,1'-biphenyl-4-yl)carbonyl)amino)sulfonyl)-2-nitrophenyl)amino)-4-(phenylthio)butanoic acid The desired product was prepared by substituting Example 435 for Example 122D in Example 122E. MS (ESI(−)) m/e 608 (M−H)$^−$; $^1$H NMR (300 MHz, methanol-d$_4$) δ8.71 (d, 1H), 7.99 (d, 2H), 7.92 (dd, 1H), 7.68 (m, 4H), 7.26 (m, 2H), 7.21–7.12 (m, 5H), 6.98 (d, 1H), 4.40 (m, 1H), 3.37 (dd, 1H), 3.30 (dd, 1H), 2.83 (m, 2H).

EXAMPLE 276

(3R)-3-((4-((((2'-methoxy-4'-(3-morpholin-4-ylpropyl)-1,1'-biphenyl-4-yl)carbonyl)amino)sulfonyl)-2-nitrophenyl)amino)-N,N-dimethyl-4-(phenylthio)butanamide The desired product was prepared by substituting Example 122F and Example 122O for Example 1C and Example 1B, respectively, in Example 1D. MS (ESI(−)) m/e 774 (M−H)$^−$; $^1$H NMR (500 MHz, methanol-d$_4$) δ8.72 (d, 1H), 8.70 (d, 1H), 7.94 (d, 2H), 7.91 (dd, 1H), 7.45 (d, 2H), 7.35 (d, 1H), 7.18 (m, 4H), 6.92 (s, 1H), 6.87 (d, 2H), 3.77 (s, 3H), 3.75 (m, 4H), 3.35 (m, 2H), 2.95 (m, 2H), 2.84 (m, 2H), 2.80 (m, 4H), 2.70 (t, 2H), 1.94 (m, 2H).

EXAMPLE 277 methyl N-(4-((((4'-fluoro-1,1'-biphenyl-4-yl)carbonyl)amino)sulfonyl)-2-nitrophenyl)-S-phenyl-L-cysteinate The desired product was prepared by substituting Example 133C for Example 1C in Example 1D. MS (ESI (−)) m/e 608 (M−H)$^−$; $^1$H NMR (300 MHz, DMSO-d$_6$) δ3.61 (dd, 1H), 3.62 (s, 3H), 3.70 (dd, 1H), 5.10 (m, 1H), 7.11 (m, 3H), 7.19 (d, 1H), 7.27 (d, 2H), 7.31 (dd, 2H), 7.75 (m, 4H), 7.92 (dd, 1H), 7.97 (d, 2H), 8.55 (d, 1H), 8.80 (d, 1H).

EXAMPLE 278

N-(4-(1-(cyclohexylmethyl)-1H-benzimidazol-5-yl)benzoyl)-4-(((1R)-2-hydroxy-1-((phenylthio)methyl)ethyl)amino)-3-nitrobenzenesulfonamide

EXAMPLE 278A 4-(((1R)-2-((tert-butyl(dimethyl)silyl)oxy)-1-((phenylthio)methyl)ethyl)amino)-3-nitrobenzenesulfonamide A solution of Example 133B (3 g, 9.63 mmol) in 1:1 dioxane/4M HCl (400 mL) was stirred for 90 minutes, poured into saturated Na$_2$CO$_3$, and extracted with ethyl acetate (3×). The combined extracts were washed with brine and concentrated.

The concentrate was purified by flash column chromatography on silica gel with ethyl acetate. A solution of the purified product (1.7 g, 8.04 mmol) in THF (100 mL) was treated with 1M LAH in THF (16.1 mL), stirred for 30 minutes, treated sequentially with water (4 mL), 1M NaOH (4 mL), and water (4 mL), diluted with THF, filtered through a pad of silica gel, and concentrated.

A solution of the concentrate (1.35 g, 7.37 mmol), tert-butyldimethylsilyl triflate (1.86 mL, 8.10 mmol), and 2,6-lutidine (0.943 mL, 8.10 mmol) in dichloromethane (50 mL) at 0° C. was stirred for 30 minutes, added to a solution of Example 122C (1.76 g, 8 mmol) in DMF (50 mL) and diisopropylethylamine (15 mL), heated to 50° C., stirred for 18 hours, poured into water, and extracted with ethyl acetate (333 ). The combined extracts were washed with water and brine, dried (Na$_2$SO$_4$), filtered, and concentrated. The concentrate was purified by flash column chromatography on silica gel with 50% ethyl acetate/hexanes to provide the desired product. MS (ESI(−)) m/e 496 (M−H)$^−$.

EXAMPLE 278B

N-(4-(1-(cyclohexylmethyl)-1H-benzimidazol-5-yl)benzoyl)-4-(((1R)-2-hydroxy-1-((phenylthio)methyl)ethyl)amino)-3-nitrobenzenesulfonamide The desired product was prepared by substituting Example 286A and Example 278B for Example 1B and Example 1C, respectively, in Example 1D. The product was dissolved in TFA (5 mL), stirred for 2 hours, concentrated, dissolved in toluene, and concentrated again to provide the desired product. MS (ESI(–)) m/e 698 (M–H)⁻; ¹H NMR (300 MHz, DMSO-d$_6$) δ0.90–1.35 (m, 6H), 1.58 (m, 5H), 3.02 (m, 3H), 3.18 (m, 2H), 3.54 (dd, 1H), 3.68 (dd, 1H), 4.19 (m, 1H), 7.16 (m, 2H), 7.21 (d, 2H), 7.30 (d, 2H), 7.62 (m, 1H), 7.73 (m, 2H), 7.87 (m, 4H), 7.98 (d, 1H), 8.04 (s, 1H), 8.59 (d, 1H), 8.61 (d, 1H).

EXAMPLE 279

(3R)-3-((4-((((4'-fluoro-1,1'-biphenyl-4-yl)carbonyl) amino)sulfonyl)-2-nitrophenyl)amino)-N-(3-morpholin-4-ylpropyl)-4-(phenylthio)butanamide The desired product was prepared by substituting Example 275 and 4-(3-aminopropyl)morpholine for Example 1B and Example 1C, respectively, in Example 1D. MS (ESI(–)) m/e 734 (M–H)⁻; ¹H NMR (500 MHz, methanol-d$_4$) δ8.65 (d, 1H), 8.50 (d, 1H), 8.13 (d, 2H), 7.89 (dd, 1H), 7.64 (m, 2H), 7.58 (d, 2H), 7.29 (d, 2H), 7.14 (m, 5H), 6.89 (d, 1H), 4.40 (m, 1H), 3.62 (t, 4H), 3.32 (dd, 1H), 3.21 (m, 2H), 3.09 (m, 1H), 2.68 (m, 2H), 2.37 (m, 4H), 2.29 (t, 2H), 1.58 (m, 2H).

EXAMPLE 280

N-((4'-fluoro-1,1'-biphenyl-4-yl)carbonyl)-4-(((1R)-3-hydroxy-1-((phenylthio)methyl)propyl)amino)-3-nitrobenzenesulfonamide

EXAMPLE 280A 4-(((1R)-3-hydroxy-1-((phenylthio)methyl)propyl) amino)-3-nitrobenzenesulfonamide A mixture of Example 122E (206 mg, 0.50 mmol) and 1M borane in THF (20 mL) was stirred for 16 hours, treated sequentially with methanol (5.0 mL) and 1N HCl (2.0 mL), diluted with ethyl acetate (50 mL), washed with water (2 mL) and brine (10 mL), dried (MgSO$_4$), filtered, and concentrated The concentrate was purified by flash column chromatography on silica gel with 20–50% ethyl acetate/dichloromethane to provide the desired product. MS (ESI (+)) m/e 398 (M+H)⁺.

EXAMPLE 280B

N-((4'-fluoro-1,1'-biphenyl-4-yl)carbonyl)-4-(((1R)-3-hydroxy-1-((phenylthio)methyl)propyl)amino)-3-nitrobenzenesulfonamide A room temperature solution of Example 280A (150 mg, 0.38 mmol), Example 1B (180 mg, 0.83 mmol), EDCI (193 mg, 1.0 mmol), and DMAP (25 mg, 0.20 mmol) in dichloromethane (10 mL) was stirred for 16 hours, diluted with ethyl acetate (100 mL), washed sequentially with 1M HCl (20 mL), water (30 mL) and brine (20 mL), dried (MgSO$_4$), filtered, and concentrated.

The concentrate was dissolved in THF (5 mL), treated with 1M LiOH (1.0 mL), stirred for 3 hours, diluted with ethyl acetate (60 mL), washed sequentially with 1M HCl (10 mL), water (20 mL), and brine (10 mL), dried (MgSO$_4$), filtered, and concentrated. The concentrate was purified by flash column chromatography on silica gel with 30–100% ethyl acetate/dichloromethane to provide the desired product. MS (ESI(–)) m/e 594 (M–H)⁻; ¹H NMR (500 MHz, methanol-d$_4$) δ8.72 (d, 1H), 7.92 (m, 3H), 7.70 (m, 4H), 7.26 (m, 2H), 7.18 (tt, 2H), 7.11 (m, 3H), 7.00 (d, 1H), 4.25 (m, 1H), 3.68 (m, 2H), 3.39 (d, 2H), 3.21 (m, 3H), 2.08 (m, 1H), 1,97 (m, 1H).

EXAMPLE 281

4-(((1R)-2-hydroxy-1-((phenylthio)methyl)ethyl) amino)-N-((2'-methoxy-4'-(3-morpholin-4-yl-3-oxopropyl)-1,1'-biphenyl-4-yl)carbonyl)-3-nitrobenzenesulfonamide

EXAMPLE 281A

2'-methoxy-4'-(3-morpholin-4-yl-3-oxopropyl)-1,1'-biphenyl-4-carboxylic acid

The desired product was prepared by substituting Example 122M for Example 1A in Example 1B.

EXAMPLE 281B 4-(((1R)-2-hydroxy-1-((phenylthio)methyl)ethyl) amino)-N-((2'-methoxy-4'-(3-morpholin-4-yl-3-oxopropyl)-1,1'-biphenyl-4-yl)carbonyl)-3-nitrobenzenesulfonamide The desired product was prepared by substituting Example 281A and Example 278A for Example 1B and Example 1C, respectively, in Example 1D. The product was dissoved in TFA (5 mL), stirred for 2 hours, concentrated, dissolved in toluene, and concentrated again to provide the desired product. MS (ESI(–)) m/e 733 (M–H)⁻; ¹H NMR (300 MHz, DMSO-d$_6$) δ2.66 (t, 2H), 2.85 (t, 2H), 3.28 (m, 2H), 3.43 (m, 4H), 3.52 (m, 4H), 3.62 (m, 1H), 3.71 (m, 1H), 3.76 (s, 3H), 3.96 (m, 1H), 5.41(dd, 1H), 6.90 (d, 2H), 6.99 (s, 1H), 7.20 (dd, 2H), 7.28 (dd, 2H), 7.35 (d, 2H), 7.43 (d, 2H), 7.81 (dd, 1H), 7.89 (d, 2H), 8.47 (d, 1), 8.51 (t, 1H).

EXAMPLE 282

N-(4-(8-azaspiro(4.5)dec-8-yl)benzoyl)-4-(((1R)-2-hydroxy-1-((phenylthio)methyl)ethyl)amino)-3-nitrobenzenesulfonamide The desired product was prepared by substituting Example 257C and Example 278A for Example 1B and Example 1C, respectively, in Example 1D. The product was dissoved in TFA (5 mL), stirred for 2 hours, concentrated, dissolved in toluene, and concentrated again to provide the desired product. MS (ESI(–)) m/e 623 (M–H)⁻; ¹H NMR (300 MHz, DMSO-d$_6$) δ1.45 (m, 8H), 1.59 (m, 4H), 3.27 (m, 4H), 3.62 (dd, 1H), 3.69 (dd, 1H), 4.04 (m, 1H), 5.21 (t, 1H), 6.84 (d, 1H), 6.92 (d, 2H), 7.08 (d, 1H), 7.18 (d, 1H), 7.21 (m, 2H), 7.31 (d, 2H), 7.71 (d, 1H), 7.82 (dd, 1H), 8.56 (d, 1H), 8.57 (t, 1H).

EXAMPLE 283

4-(((1R)-5-amino-1-((phenylthio)methyl)pentyl) amino)-N-((4'-(3-hydroxypropyl)-2'-methoxy-1,1'-biphenyl-4-yl)carbonyl)-3-nitrobenzenesulfonamide The desired product was prepared by substituting Example 451B for Example 122N in Example 194. MS (ESI(–)) m/e 691 (M–H)⁻; ¹H NMR (300 MHz, DMSO-d$_6$) δ8.55 (d, 1H), 8.35 (br d, 1H), 7.90 (d, 2H), 7.85 (dd, 1H), 7.58 (d, 2H), 7.25–7.12 (m, 7H), 7.00 (d, 1H), 6.89 (dd, 1H), 4.10 (m, 1H), 3.75 (s, 3H), 3.72 (s, 2H), 3.35 (m, 2H), 2.70–2.605 (m, 6H), 1.75 (m, 4H), 1.50 (m, 2H), 1.40 (m, 2H).

EXAMPLE 284

4-(((1R)-5-amino-1-((phenylthio)methyl)pentyl) amino)-N-(4-(5-fluoroquinolin-8-yl)benzoyl)-3-nitrobenzenesulfonamide

EXAMPLE 284A methyl 4-(5-fluoroquinolin-8-yl)benzoate

The desired product was prepared by substituting Example 389A for Example 5A in Example 5B.

EXAMPLE 284B

4-(5-fluoroquinolin-8-yl)benzoic acid

The desired product was prepared by substituting Example 284A for Example 1A in Example 1B.

EXAMPLE 284C

4-(((1R)-5-amino-1-((phenylthio)methyl)pentyl) amino)-N-(4-(5-fluoroquinolin-8-yl)benzoyl)-3-nitrobenzenesulfonamide The desired product was prepared by substituting Example 284B for Example 122N in Example 194. MS (ESI(−)) m/e 674 (M−H)$^-$; $^1$H NMR (300 MHz, DMSO-d$_6$) δ9.00 (dd, 1H), 8.90 (br d, 1H), 8.60 (d, 1H), 8.58 (dd, 1H), 7.90 (d, 2H), 7.85 (m, 2H), 7.75 (d, 2H), 7.70 (m, 1H), 7.55 (m, 1H), 7.25–7.12 (m, 6H), 4.15 (m, 1H), 3.45 (m, 2H), 2.75 (m, 2H), 2.80 (s, 3H), 1.80 (m, 2H), 1.55 (m, 2H), 1.40 (m, 2H).

EXAMPLE 285

N-(4-(6-methoxy-3,4-dihydroisoquinolin-2(1H)-yl) benzoyl)-3-nitro-4-((2-(phenylthio)ethyl)amino) benzenesulfonamide

EXAMPLE 285A ethyl 4-(6-methoxy-3,4-dihydroisoquinolin-2(1H)-yl)benzoate

The desired product was prepared by subtituting 6-methoxy-1,2,3,4-tetrahydroisoquinoline (prepared according to the procedure described in U.S. Pat. No. 1,845,403) for 1,4-dioxa-8-azasprio(4,5)decane in Example 158A. MS (DCI) m/e 312 (M+H)$^+$.

EXAMPLE 285B

4-(6-methoxy-3,4-dihydroisoquinolin-2(1H)-yl) benzoic acid

The desired product was prepared by subtituting Example 285A for Example 119B in Example 119C. MS (DCI) m/e 283 (M+H)$^+$.

EXAMPLE 285C

N-(4-(6-methoxy-3,4-dihydroisoquinolin-2(1H)-yl) benzoyl)-3-nitro-4-((2-(phenylthio)ethyl)amino) benzenesulfonamide The desired product was prepared by substituting Example 285B and Example 77B for Example 1B and Example 1C, respectively, in Example 1D. MS (ESI(−)) m/e 617 (M−H)$^-$; $^1$H NMR (300 MHz, DMSO-d$_6$) δ11.98 (s, 1H), 8.71 (t, 1H), 8.56 (d, 1H), 7.90 (dd, 1H), 7.77 (d, 2H), 7.37 (d, 2H), 7.27 (t, 2H), 7.16 (m, 3H) 6.93 (d, 2H), 6.78 (m, 2H), 4.43 (s, 2H), 3.72 (s, 3H), 3.65 (m, 2H), 3.58 (t, 2H), 3.28 (m, 2H), 2.88 (t, 2H).

EXAMPLE 286 tert-butyl (5R)-5-((4-(((4-(1-(cyclohexylmethyl)-1H-benzimidazol-5-yl)benzoyl)amino)sulfonyl)-2-nitrophenol)amino)-6-(phenylthio)hexylcarbamate

EXAMPLE 286A

4-bromo-N$^1$-(cyclohexylmethyl)benzene-1,2-diamine

The desired product was prepared by substituting cyclohexylmethylamine for butylamine in Examples 166A and 166B.

EXAMPLE 286B

4-(1-(cyclohexylmethyl)-1H-benzimidazol-5-yl) benzoic acid

The desired product was prepared by substituting Example 286A for Example 170A in Examples 170B and 170C.

EXAMPLE 286C tert-butyl(5R)-5-((4-(((4-(1-(cyclohexylmethyl)-1H-benzimidazol-5-yl)benzoyl)amino)sulfonyl)-2-nitrophenyl)amino)-6-(phenylthio)hexylcarbamate The desired product was prepared by substituting Example 286B and Example 124C for Example 1B and Example 1C, respectively, in Example 1D. MS (ESI) m/e 839, 841 (M−H)$^-$, (M+H)$^+$; $^1$H NMR (300 MHz, DMSO-d$_6$) δ0.95–1.20 (m, 7H), 1.32 (m, 11H), 1.48–1.76 (m, 7H), 1.85 (m, 1H), 2.86 (m, 2H), 3.98 (t, 2H), 4.02 (m, 1H), 4.12 (d, 2H), 6.72 (t, 1H), 6.98 (d, 1H), 7.14 (tt, 1H), 7.21 (t, 2H), 7.29 (dd, 2H), 7.59 (dd, 1H), 7.68 (d, 3H), 7.84 (dd, 1H), 7.95 (d, 1H), 7.97 (d, 2H), 8.19 (d, 1H), 8.23 (t, 1H), 8.49 (d, 1H).

EXAMPLE 287

4-(((1R)-5-amino-1-((phenylthio)methyl)pentyl) amino)-N-(4-(8-azaspiro(4.5)dec-8-yl)benzoyl)-3-nitrobenzenesulfonamide The desired product was prepared by substituting Example 257D for Example 120D in Example 120E. MS (ESI(+)) m/e 766 (M+H)$^+$; $^1$H NMR (300 MHz, DMSO-d$_6$) δ8.52 (d, 1H), 8.31 (d, 1H), 8.85 (dd, 1H), 7.72 (d, 2H), 7.68 (s, 2H), 7.24 (t, 2H), 7.12 (m, 2H), 6.91 (d, 2H), 4.10 (m, 1H), 3.42 (m, 4H), 3.31 (m, 6H), 2.71 (mn, 2H), 1.77 (m, 2H), 1.59 (m, 4H), 1.52 (m, 2H), 1.45 (m, 6H).

EXAMPLE 288

(3R)-3-((4-(((4-(5-fluoroquinolin-8-yl)benzoyl) amino)sulfonyl)-2-nitrophenyl)amino)-N,N-dimethyl-4-(phenylthio)butanamide The desired product was prepared by substituting Example 284B for Example 126A in Example 126B. MS (ESI(−)) m/e 686 (M−H)$^-$; $^1$H NMR (300 MHz, DMSO-d$_6$) δ9.00 (dd, 1H), 8.90 (br d, 1H), 8.60 (d, 1H), 8.58 (dd, 1H), 7.90 (d, 2H), 7.85 (m, 2H), 7.75 (d, 2H), 7.70 (m, 1H), 7.55 (m, 1H), 7.25–7.12 (m, 6H), 4.45 (m, 1H), 3.45 (m, 2H), 2.90 (s, 3H), 2.80 (s, 3H), 3.00–2.80 (m, 2H).

EXAMPLE 289

(3R)-3-((4-((((2'-methoxy-4'-(3-morpholin-4-yl-3-oxopropyl)-1,1'-biphenyl-4-yl)carbonyl)amino) sulfonyl)-2-nitrophenyl)amino)-N,N-dimethyl-4-(phenylthio)butanamide The desired product was prepared by substituting Example 122M for Example 126A in Example 126B. MS (ESI(−)) m/e 788 (M−H)$^-$; $^1$H NMR (300 MHz, DMSO-d$_6$) δ8.89 (br d, 1H), 8.57 (d, 1H), 7.90 (d, 2H), 7.85 (dd, 1H), 7.78 (br d, 1H), 7.58 (d, 2H), 7.30–7.12 (m, 7H), 7.00 (d, 1H), 6.89 (dd, 1H), 4.45 (m, 1H), 3.75 (s, 3H), 3.55 (m, 4H), 3.45 (m, 6H), 2.90 (s, 3H), 2.79 (s, 3H), 3.10–2.70 (m, 4H), 2.65 (t, 2H).

EXAMPLE 290

4-(((1R)-3-hydroxy-1-((phenylthio)methyl)propyl) amino)-N-((2'-methoxy-4'-(3-morpholin-4-ylpropyl)-1,1'-biphenyl-4-yl)carbonyl)-3-nitrobenzenesulfonamide The desired product was prepared by substituting Example 122O for Example 1B in Example 280B. MS (ESI(−)) m/e 774 (M−H)⁻; $^1$H NMR (500 MHz, methanol-d$_4$) δ8.72 (d, 1H), 8.69 (d, 1H), 7.95 (d, 2H), 7.90 (dd, 1H), 7.45 (d, 2H), 7.34 (d, 2H), 7.22–7.10 (m, 5H), 6.92 (s, 1H), 6.85 (d, 1H), 4.40 (m, 1H), 3.77 (s, 3H), 3.80–3.72 (m, 4H), 3.36 (m, 3H), 2.95 (m, 2H), 2.85 (m, 2H), 2.79 (m, 3H), 2.70 (m, 4H), 1.95 (m, 3H).

EXAMPLE 291

4-((2-((4-chlorophenyl)thio)ethyl)amino)-N-((4'-fluoro-1'-biphenyl-4-yl)carbonyl)-3-nitrobenzenesulfonamide

EXAMPLE 291A 2-((4-chlorophenyl)thio)ethanamine

A solution of sodium metal (22.5 mg, 0.98 mmol) in ethanol (2.0 mL) was treated with 2-bromoethylamine hydrobromide (100.0 mg, 0.49 mmol) and 4-chlorobenzenethiol (71.0 mg, 0.49 mmol), heated to 75° C. for 18 hours, and concentrated. The concentrate was partitioned between water (2.0 mL) and diethyl ether (5.0 mL) and the organic phase was dried (MgSO$_4$), filtered, and concentrated to provide the desired product. MS (DCI) m/e 188 (M+H)⁺.

EXAMPLE 291B 4-((2-((4-chlorophenyl)thio)ethyl)amino)-N-((4'-fluoro-1,1'-biphenyl-4-yl)carbonyl)-3-nitrobenzenesulfonamide The desired product was prepared by substituting Example 291A for 2,2-dimethylcyclopentylamine in Example 1E. MS (DCI) m/e 603 (M+NH$_4$)⁺; $^1$H NMR (300 MHz, DMSO-d$_6$) δ12.49 (br s, 1H), 8.76 (t, 1H), 8.64 (d, 1H), 7.97–7.95 (m, 3H), 7.80–7.77 (m, 4H), 7.39–7.38 (m, 2H), 7.34–7.30 (m, 4H), 7.24 (d, 1H), 3.68 (q, 2H), 3.30 (q, 2H).

EXAMPLE 292

4-(((1R)-5-amino-1-((phenylthio)methyl)pentyl)amino)-3-nitro-N-(4-(5-(trifluoromethyl)pyridin-2-yl)benzoyl)benzenesulfonamide The desired product was prepared by substituting Example 124C and Example 253B for Example 124E and Example 257C, respectively, in Example 124F. MS (ESI) m/e 674, 672 (M+H)⁺, (M−H)⁻; $^1$H NMR (500 MHz, DMSO-d$_6$) δ9.09 (dd, 1H), 8.59 (d, 1H), 8.35–8.29 (m, 5H), 8.06 (d, 2H), 7.90 (dd, 1H), 7.25 (dt, 2H), 7.15 (td, 2H), 7.10 (tt, 1H), 4.12 (m, 1H), 3.37 (t, 2H), 2.73 (m, 2H), 1.77 (q, 2H), 1.54 (m, 2H), 1.39 (m, 2H).

EXAMPLE 293

N-(4-(5-chloropyridin-2-yl)benzoyl)-4-(((1R)-5-(dimethylamino)-1-((phenylthio)methyl)pentyl)amino)-3-nitrobenzenesulfonamide The desired product was prepared by substituting Example 254B for Example 257C in Example 124F. MS (ESI) m/e 668, 666 (M+H)⁺, (M−H)⁻; $^1$H NMR (500 MHz, DMSO-d$_6$) δ10.02 (s, 1H), 8.75 (dd, 1H), 8.58 (d, 1H), 8.33 (d, 1H), 8.21 (d, 2H), 8.12 (dd, 1H), 8.06 (dd, 1H), 8.01 (d, 2H), 7.90 (dd, 1H), 7.25 (dt, 2H), 7.15 (td, 2H), 7.10 (tt, 1H), 4.12 (m, 1H), 3.36 (d, 2H), 2.95 (m, 2H), 2.69 (s, 3H), 2.69 (s, 3H), 1.78 (q, 2H), 1.63 (m, 2H), 1.36 (m, 2H).

EXAMPLE 294

4-(((1R)-5-(dimethylamino)-1-((phenylthio)methyl)pentyl)amino)-3-nitro-N-(4-quinolin-8-ylbenzoyl)benzenesulfonamide

EXAMPLE 294A methyl 4-quinolin-8-ylbenzoate

The desired product was prepared by substituting 8-bromoquinoline for 5-bromo-2-methoxypyridine in Example 252D. MS (ESI) m/e 250, 248 (M+H)⁺, (M−H)⁻.

EXAMPLE 294B 4-quinolin-8-ylbenzoic acid

The desired product was prepared by substituting Example 294A for Example 252F in Example 252G.

EXAMPLE 294C 4-((((1R)-5-(dimethylamino)-1-((phenylthio)methyl)pentyl)amino)-3-nitro-N-(4-quinolin-8-ylbenzoyl)benzenesulfonamide The desired product was prepared by substituting Example 294B for Example 257C in Example 124F. MS (ESI) m/e 684, 682 (M+H)⁺, (M−H)⁻; $^1$H NMR (500 MHz, DMSO-d$_6$) δ10.34 (s, 1H), 8.94 (dd, 1H), 8.59 (d, 1H), 8.55 (dd, 1H), 8.33 (d, 1H), 8.19 (dd, 1H), 8.07 (d, 2H), 8.00 (d, 1H), 7.92 (dd, 1H), 7.86 (dd, 1H), 7.82 (d, 2H), 7.80–7.72 (m, 2H), 7.65 (m, 1H), 7.31–7.10 (m, 5H), 4.16 (m, 1H), 3.37 (m, 2H), 2.95 (m, 2H), 2.69 (s, 3H), 1.78 (m, 2H), 1.64 (m, 2H), 1.38 (m, 2H).

EXAMPLE 295

4-(((1R)-5-(dimethylamino)-1-((phenylthio)methyl)pentyl)amino)-N-((4'-(3-hydroxypropyl)-2'-methoxy-1,1'-biphenyl-4-yl)carbonyl)-3-nitrobenzenesulfonamide The desired product was prepared by substituting Example 451B for Example 257C in Example 124F. The crude product was dissolved in THF, treated with TBAF (50 mg), stirred for 3 hours, and concentrated. The concentrate was purified by HPLC (using a C-18 column and a solvent system increasing in gradient from 10–95% acetonitrile/water containing 0.1% TFA) to provide the desired product which was converted to the hydrochloride salt by dissolving the product in methanol and 2M HCl in diethyl ether then concentrating. MS (ESI) m/e 721, 719 (M+H)⁺, (M−H)⁻; $^1$H NMR (500 MHz, DMSO-d$_6$) δ8.57 (d, 1H), 8.32 (d, 1H), 7.89 (d, 2H), 7.59 (d, 2H), 7.27–7.10 (m, 8H), 6.97 (d, 1H), 6.87 (d, H), 4.12 (m, 1H), 3.76 (s, 3H), 3.44 (t, 2H), 3.36 (m, 2H), 2.95 (m 2H), 2.69 (s, 3H), 2.67 (s, 3H), 2.65 (m, 2H), 1.77 (m, 2H), 1.64 (m, 2H), 1.36 (m, 2H).

EXAMPLE 296

4-(((1R)-5-(dimethylamino)-1-((phenylthio)methyl)pentyl)amino)-N-(4-(4-methoxy-2-oxopyridin-1(2H)-yl)benzoyl)-3-nitrobenzenesulfonamide

EXAMPLE 296A methyl 4-(4-hydroxy-2-oxopyridin-1(2H)-yl)benzoate

A mixture of methyl 4-iodobenzoate (0.421 g, 1.6 mmol), 2,4-dihydroxypyridine (0.174 g, 1.34 mmol), CuI (25 mg, 0.134 mmol) and K$_2$CO$_3$ (200 mg) in DMF (2 mL) was heated to 150° C. in a sealed vial for 4 hours, diluted with ethyl acetate (100 mL), washed with water (30 mL) and brine (30 mL), dried (Na$_2$SO$_4$), filtered, and concentrated. The concentrate was purified by flash column chromatography on silica gel with 2:1 hexanes/ethyl acetate to provide the desired product. MS (APCI) m/e 246 (M+H)$^+$.

EXAMPLE 296B methyl 4-(4-methoxy-2-oxopyridin-1(2H)-yl)benzoate

A solution of Example 296A (2.3 g, 10 mmol) in acetone (300 mL) was treated with iodomethane (5 mL) and K$_2$CO$_3$ (15 g), heated to reflux for 18 hours, and filtered. The filtrate was concentrated and he concentrate purified by flash column chromatography on silical gel with 4:1 hexanes/ethyl acetate to provide the desired product. MS (ESI) m/e 260 (M+H)$^+$.

EXAMPLE 296C 4-(4-methoxy-2-oxopyridin-1(2H)-yl)benzoic acid

The desired product was prepared by substituting Example 296B for Example 252F in Example 252G. MS (ESI) m/e 246, 244 (M+H)$^+$, (M−H)$^−$.

EXAMPLE 296D 4-(((1R)-5-(dimethylamino)-1-((phenylthio)methyl)pentyl)amino)-N-(4-(4-methoxy-2-oxopyridin-1(2H)-yl)benzoyl)-3-nitrobenzenesulfonamide The desired product was prepared by substituting Example 296C for Example 257C in Example 124F. MS (ESI) m/e 680, 678 (M+H)$^+$, (M−H)$^−$; $^1$H NMR (500 MHz, DMSO-d$_6$) δ8.57 (d, 1H), 8.33 (d, 1H), 8.05 (d, 1H), 7.99 (d, 2H), 7.89 (dd, 1H), 7.57 (d, 1H), 7.52 (d, 2H), 7.10–7.33 (m, 5H), 6.07 (dd, 1H), 5.88 (d, 1H), 4.12 (m, 1H), 3.89 (s, 3H), 3.36 (m, 2H), 2.95 (m, 2H), 2.69 (s, 3H), 2.67 (s, 3H), 1.77 (m, 2H), 1.64 (m, 2H), 1.34 (m, 2H).

EXAMPLE 297

4-(((1R)-5-amino-1-((phenylthio)methyl)pentyl)amino)-N-(4-(4-methoxy-2-oxopyridin-1(2H)-yl)benzoyl)-3-nitrobenzenesulfonamide The desired product was prepared by substituting Example 124C and Example 296C for Example 124E and Example 257C, respectively, in Example 124F. MS (ESI) m/e 652, 650 (M+H)$^+$, (M−H)$^−$; $^1$H NMR (500 MHz, DMSO-d$_6$) δ8.57 (d, 1H), 8.33 (d, 1H), 8.05 (d, 1H), 7.99 (d, 2H), 7.89 (dd, 1H), 7.57 (d, 1H), 7.52 (d, 2H), 7.25 (dt, 2H), 7.15 (td, 2H), 7.10 (tt, 1H), 6.08 (dd, 1H), 5.88 (d, 1H), 4.12 (m, 1H), 3.89 (s, 3H), 3.36 (t, 2H), 2.73 (m, 2H), 1.76 (q, 2H), 1.56 (m, 2H), 1.39 (m, 2H).

EXAMPLE 298

4-(((1R)-5-amino-1-((phenylthio)methyl)pentyl)amino)-N-((6-(4-fluorophenyl)pyridin-3-yl)carbonyl)-3-nitrobenzenesulfonamide

EXAMPLE 298A methyl 6-(4-fluorophenyl)nicotinate

The desired product was prepared by substituting methyl 6-chloronicotinate and 4-fluorobenzeneboronic acid for 5-bromo-2-methoxypyridine and 4-methylcarboxybenzeneboronic acid, respectively, in Example 252D. MS (APCI) m/e 232 (M+H)$^+$.

EXAMPLE 298B 6-(4-fluorophenyl)nicotinic acid

The desired product was prepared by substituting Example 298A for Example 252F in Example 252G. MS (ESI) m/e 218, 216 (M+H)$^+$, 216(M−H)$^−$.

EXAMPLE 298C 4-(((1R)-5-amino-1-((phenylthio)methyl)pentyl)amino)-N-((6-(4-fluorophenyl)pyridin-3-yl)carbonyl)-3-nitrobenzenesulfonamide The desired product was prepared by substituting Example 124C and Example 298B for Example 124E and Example 257C, respectively, in Example 124F. MS (ESI) m/e 624, 622, (M+H)$^+$, (M−H)$^−$; $^1$H NMR(500 MHz, DMSO-d$_6$) δ9.10(d, 1H), 8.59 (d, 1H), 8.36–8.33 (m, 2H), 8.24–8.21 (m, 2H), 8.16–8.12 (m, 1H), 7.91 (dd, 1H), 7.39–7.31 (m, 2H), 7.25 (dt, 2H), 7.15 (td, 2H), 7.10 (tt, 1H), 6.94 (d, 1H), 4.12 (m, 1H), 3.37 (t, 2H), 3.37 (t, 2H), 2.73 (m, 2H), 1.76 (q, 2H), 1.56 (m, 2H), 1.39 (m, 2H).

EXAMPLE 299

4-(((1R)-5-amino-1-((phenylthio)methyl)pentyl)amino)-N-(4-(6-methoxypyridin-3-yl)benzoyl)-3-nitrobenzenesulfonamide

EXAMPLE 299A 4-(6-methoxypyridin-3-yl)benzoic acid

The desired product was prepared by substituting Example 252D for Example 252F in Example 252G. MS (ESI) m/e 230(M+H)$^+$, m/e 228 (M−H)$^−$.

EXAMPLE 299B 4-(((1R)-5-amino-1-((phenylthio)methyl)pentyl)amino)-N-(4-(6-methoxypyridin-3-yl)benzoyl)-3-nitrobenzenesulfonamide The desired product was prepared by substituting Example 124C and Example 299A for Example 124E and Example 257C, respectively, in Example 124F. MS (ESI) m/e 636, 634 (M+H)$^+$, (M−H)$^−$; $^1$H NMR (500 MHz, DMSO-d$_6$) δ8.58 (d, 1H), 8.33 (d, 1H), 8.06 (dd, 1H), 8.09 (dd, 1H), 8.02 (d, 2H), 7.98 (d, 1H), 7.91 (dd, 1H), 7.83 (d, 2H), 7.81 (s, 1H), 7.25 (dt, 2H), 7.15 (td, 2H), 7.10 (tt, 1H), 6.94 (d, 1H), 4.12 (m, 1H), 3.91 (s, 3H), 3.36 (t, 2H), 2.73 (m, 2H), 1.76 (q, 2H), 1.56 (m, 2H), 1.39 (m, 2H).

EXAMPLE 300

2-(4'-((((4-(((1R)-5-(dimethylamino)-1-((phenylthio)methyl)pentyl)amino)-3-nitrophenyl)sulfonyl)amino)carbonyl)-2-methoxy-1,1'-biphenyl-4-yl)-N,N-dimethylacetamide The desired product was prepared by substituting Example 441A and Example 122F for Example 5C and Example 3A, respectively, in Example 5D. MS (ESI) m/e 748, 746 (M+H)$^+$, (M−H)$^−$; $^1$H NMR (500 MHz, DMSO-d$_6$) δ9.95 (s, 1H), 8.57 (d, 1H), 8.34 (d, 1H), 7.98 (d, 2H), 7.90 (d, 1H), 7.62 (d, 2H), 7.60 (d, 1H), 7.28–7.24 (m, 3H), 7.18–7.08 (m, 3H), 7.01 (dd, 1H), 6.90 (dd, 2H), 4.12 (m, 1H), 3.87 (s, 3H), 3.76 (s, 3H), 3.73 (t, 2H), 3.36 (m, 2H), 3.03 (s, 3H), 2.85 (s, 3H), 2.68 (d, 2H), 1.77 (q, 2H), 1.64 (m, 2H), 1.36 (m, 2H).

EXAMPLE 301

4-(((1R)-5-(dimethylamino)-1-((phenylthio)methyl) pentyl)amino)-N-((2'-methoxy-4'-(3-morpholin-4-yl-3-oxopropyl)-1,1'-biphenyl-4-yl)carbonyl)-3-nitrobenzenesulfonamide The desired product was prepared by substituting Example 122O for Example 257C in Example 124F. MS (ESI) m/e 804, 802 (M+H)$^+$, (M–H)$^-$; $^1$H NMR (500 MHz, DMSO-d$^6$) δ10.02 (s, 1H), 8.57 (d, 1H), 8.34 (d, 1H), 7.97 (d, 1H), 7.90 (d, 2H), 7.60 (d, 1H), 7.58 (d, 2H), 7.27–7.10 (m, 6H), 7.03 (dd, 1H), 6.94 (dd, 1H), 4.12 (m, 1H), 3.75 (s, 3H), 3.51 (m, 4H), 3.44 (m, 4H), 3.36 (m, 2H), 2.95 (m, 2H), 2.86 (m, 2H), 2.69 (s, 3H), 2.67 (s, 3H), 1.77 (q, 2H), 1.64 (m, 2H), 1.36 (m, 2H).

EXAMPLE 302

4-(((1R)-5-amino-1-((phenylthio)methyl)pentyl) amino)-N-(4-(6-chloropyridin-3-yl)benzoyl)-3-nitrobenzenesulfonamide The desired was prepared by substituting Example 124C and Example 252G for Example 124E and Example 257C, respectively, in Example 124F. MS (ESI) m/e 638 (M–H)$^-$; $^1$H NMR (500 MHz, DMSO-d$_6$) δ8.81 (dd, 1H), 8.58 (d, 1H), 8.34 (d, 1H), 8.23 (dd, 1H), 8.02 (d, 2H), 7.90 (d, 2H), 7.89 (dd, 1H), 7.64 (d, 1H), 7.25 (dt, 2H), 7.15 (td, 2H), 7.10 (tt, 1H), 4.12 (m, 1H), 3.36 (t, 2H), 2.73 (m, 2H), 1.76 (q, 2H), 1.56 (m, 2H), 1.39 (m, 2H).

EXAMPLE 303

4-(((1R)-5-amino-1-((phenylthio)methyl)pentyl) amino)-N-(4-(5-chloropyridin-2-yl)benzoyl)-3-nitrobenzenesulfonamide The desired product was prepared by substituting Example 124C and Example 254B for Example 124E and Example 257C, respectively, in Example 124F. MS (ESI) m/e 640, 638 (M+H)$^+$, (M–H)$^-$; $^1$H NMR (500 MHz, DMSO-d$_6$) δ8.74 (dd, 1H), 8.58 (d, 1H), 8.34 (d, 1H), 8.20 (d, 2H), 8.12 (d, 1H), 8.06 (dd, 1H), 8.01 (d, 2H), 7.90 (dd, 1H), 7.25 (dt, 2H), 7.15 (td, 2H), 7.10 (tt, 1H), 4.12 (m, 1H), 3.36 (t, 2H), 2.73 (m, 2H), 1.76 (q, 2H), 1.56 (m, 2H), 1.39 (m, 2H).

EXAMPLE 304

4-(((1R)-5-(dimethylamino)-1-((phenylthio)methyl) pentyl)amino)-N-(4-(5-fluoroquinolin-8-yl)benzoyl)-3-nitrobenzenesulfonamide The desired product was prepared by substituting Example 284B for Example 257C in Example 124F. MS (ESI) m/e 702, 700 (M+H)$^+$, (M–H)$^-$; $^1$H NMR (500 MHz, DMSO-d$_6$) δ8.98 (dd, 1H), 8.59 (d, 1H), 8.87 (d, 1H), 8.06 (d, 1H), 7.99 (d, 2H), 7.92 (dd, 1H), 7.84 (d, 1H), 7.80 (d, 1H), 7.77 (d, 2H), 7.70 (q, 1H), 7.67 (t, 1H), 7.29–7.10 (m, 5H), 4.12 (m, 1H), 3.36 (m, 2H), 2.95 (m, 2H), 2.69 (s, 3H), 2.67 (s, 3H), 1.77 (q, 2H), 1.64 (m, 2H), 1.36 (m, 2H).

EXAMPLE 305

4-(((1R)-5-(dimethylamino)-1-((phenylthio)methyl) pentyl)amino)-3-nitro-N-(4-(5-(trifluoromethyl) pyridin-2-yl)benzoyl)benzenesulfonamide The desired product was prepared by substituting Example 253B for Example 257C in Example 124F. MS (ESI) m/e 702, 700 (M+H)$^+$, (M–H)$^-$; $^1$H NMR (500 MHz, DMSO-d$_6$) δ9.08 (d, 1H), 8.58 (d, 1H), 8.34–8.30 (m, 2H), 8.30 (d, 2H), 8.10 (d, 1H), 8.06 (d, 2H), 7.92 (dd, 1H), 7.27–7.10 (m, 5H), 4.12 (m, 1H), 3.36 (m, 2H), 2.95 (m, 2H), 2.69 (s, 3H), 2.67 (s, 3H), 1.77 (q, 2H), 1.64 (m, 2H), 1.36 (m, 2H).

EXAMPLE 306

4-(((1R)-5-amino-1-((phenylthio)methyl)pentyl) amino)-N-(4-(5-chloro-2-oxopyridin-1(2H)-yl) benzoyl)-3-nitrobenzenesulfonamide

EXAMPLE 306A methyl 4-(5-chloro-2-oxopyridin-1(2H)-yl)benzoate

The desired product was prepared by substituting 5-chloro-2-hydroxypyridine for 2,4-dihydroxypyridine in Example 296A. MS (ESI) m/e 264 (M+H)$^+$.

EXAMPLE 306B 4-(5-chloro-2-oxopyridin-1(2H)-yl) benzoic acid

The desired product was prepared by substituting Example 306A for Example 252F in Example 252G. MS (ESI) m/e 250, 248 (M+H)$^+$, (M–H)$^-$.

EXAMPLE 306C 4-(((1R)-5-amino-1-((phenylthio)methylpentyl) amino)-N-(4-(5-chloro-2-oxopyridin-1(2H)-yl) benzoyl)-3-nitrobenzenesulfonamide The desired product was prepared by substituting Example 124C and Example 306B for Example 124E and Example 257C, respectively, in Example 124F. MS (ESI) m/e 656, 654 (M+H)$^+$, (M–H)$^-$; $^1$H NMR (500 MHz, DMSO-d$_6$) δ8.58 (d, 1H), 8.34 (d, 1H), 8.01 (d, 2H), 7.95 (d, 1H), 7.89 (dd, 1H), 7.60 (d, 2H), 7.58 (dd, 1H), 7.26 (dt, 2H), 7.14 (td, 2H), 7.10 (tt, 1H), 6.54 (d, 1H), 4.12 (m, 1H), 3.36 (t, 2H), 3.73 (m, 2H), 1.76 (q, 2H), 1.56 (m, 2H), 1.39 (m, 2H).

EXAMPLE 307

4-(((1R)-5-(dimethylamino)-1-((phenylthio)methyl) pentyl)amino)-N-(4-(1-methyl-6-oxo-1,6-dihydropyridin-3-yl)benzoyl)-3-nitrobenzenesulfonamide

EXAMPLE 307A methyl 4-(1-methyl-6-oxo-1,6-dihydropyridin-3-yl) benzoate

The desired product was prepared by substituting Example 252E for Example 296A in Example 296B. MS (APCI) m/e 244 (M+H)$^+$.

EXAMPLE 307B 4-(1-methyl-6-oxo-1,6-dihydropyridin-3-yl)benzoic acid

The desired product was prepared by substituting Example 307A for Example 252F in Example 252G. MS (APCI) m/e 230 (M+H)$^+$.

EXAMPLE 307C 4-(((1R)-5-(dimethylamino)-1-((phenylthio)methyl) pentyl)amino)-N-(4-(1-methyl-6-oxo-1,6-dihydropyridin-3-yl)benzoyl)-3-nitrobenzenesulfonamide The desired product was prepared by substituting Example 307B for Example 257C in Example 124E. MS (ESI) m/e 664(M+H)$^+$, m/e 662 (M–H)$^-$; $^1$H NMR (500 MHz, DMSO-d$_6$) δ8.57 (d, 1H), 8.33 (d, 1H), 8.31 (d, 1H), 7.95 (d, 2H), 7.92–7.88 (m, 2H), 7.81 (m, 3H), 7.73 (d, 2H), 7.24 (dt, 2H), 7.22 (d, 1H), 7.14 (td, 1H), 7.10 (tt, 1H), 6.49 (d, 1H), 4.12 (m, 1H), 3.52 (s, 3H), 3.36 (m, 2H), 2.95 (m, 2H), 2.69 (s, 3H), 2.67 (s, 3H), 1.77 (q, 2H), 1.64 (m, 2H), 1.36 (m, 2H).

EXAMPLE 308

4-(((1R)-5-amino-1-((phenylthio)methyl)pentyl)amino)-N-(4-(1-methyl-6-oxo-1,6-dihydropyridin-3-yl)benzoyl)-3-nitrobenzenesulfonamide The desired product was prepared by substituting Example 124C and Example 307B for Example 124E and Example 257C, respectively, in Example 124F. MS (ESI) m/e 634 (M–H)$^-$; $^1$H NMR (500 MHz, DMSO-d$_6$) δ8.57 (d, 1H), 8.33 (d, 1H), 8.31 (d, 1H), 7.95 (d, 2H), 7.92–7.88 (m, 2H), 7.81 (m, 3H), 7.73 (d, 2H), 7.24 (dt, 2H), 7.22 (d, 1H), 7.14 (td, 1H), 7.10 (tt, 1H), 6.49 (d, 1H), 4.12 (m, 1H), 3.52 (s, 3H), 3.36 (t, 2H), 3.73 (m, 2H), 1.76 (q, 2H), 1.54 (m, 2H), 1.39 (m, 2H).

EXAMPLE 309

3-nitro-N-(4-(3-phenylpyrrolidin-1-yl)benzoyl)-4-((2-(phenylthio)ethyl)amino)benzenesulfonamide

EXAMPLE 309A ethyl 4-(2,5-dioxo-3-phenylpyrrolidin-1-yl)benzoate

The desired product was prepared by substituting 3-phenyldihydrofuran-2,5-dione for 3,3-dimethylglutaric anhydride in Example 119A. MS (DCI) m/e 324 (M+H)$^+$.

EXAMPLE 309B ethyl 4-(3-phenylpyrrolidin-1-yl)benzoate

The desired product was prepared by substituting Example 309A for Example 119A in Example 199B. MS(DCI) m/e 296 (M+H)$^+$.

EXAMPLE 309C 4-(3-phenylpyrrolidin-1-yl)benzoic acid

The desired product was prepared by substituting Example 309B for Example 119B in Example 119C. MS (DCI) m/e 268 (M+H)$^+$.

EXAMPLE 309D 3-nitro-N-(4-(3-phenylpyrrolidin-1-yl)benzoyl)-4-((2-(phenylthio)ethyl)amino)benzenesulfonamide The desired product was prepared by substituting Example 309C and Example 77B for Example 1B and Example 1C, respectively, in Example 1D. MS (ESI(+)) m/e 603 (M+H)$^+$; $^1$H NMR (300 MHz, DMSO-d$_6$) δ11.90 (s, 1H), 8.75 (t, 1H), 8.59 (d, 1H), 7.91 (dd, 1H), 7.74 (d, 2H), 7.35 (m, 5H), 7.27 (t, 2H), 7.14–7.30 (m, 5H) 6.58 (d, 2H), 3.78 (dd, 1H), 3.66 (m, 2H), 3.53 (t, 2H), 3.42 (m, 1H), 3.30 (m, 3H), 2.40 (m, 1H), 2.10 (m, 1H).

EXAMPLE 310

N-(2-((4-(((((4'-fluoro-1,1'-biphenyl-4-yl)carbonyl)amino)sulfonyl)-2-nitrophenyl)amino)-3-(phenylthio)propyl)acetamide A solution of Example 408 (16 mg, 0.026 mmol) in THF (1 mL) and dichloromethane (0.5 mL) at room temperature was treated with saturated sodium bicarbonate (0.2 mL) and acetyl chloride (0.1 mL), stirred for 18 hours, and concentrated. The concentrate was purified by flash column chromatography on silica gel with 30–100% ethyl acetate/dichloromethane to provide the desired product. MS (ESI (–)) m/e 621 (M–H)$^-$; $^1$H NMR (300 MHz, DMSO-d$_6$) δ8.54 (d, 1H), 8.35 (d, 1H), 8.23 (t, 1H), 7.96 (d, 2H), 7.84 (dd, 1H), 7.75 (m, 5H), 7.35–7.10 (m, 7H), 4.05 (m, 1H), 1.74 (t, 3H), and remaining protons (4) are buried under solvent peaks.

EXAMPLE 311

N-((2,4'-difluoro-1,1'-biphenyl-4-yl)carbonyl)-3-nitro-4-((2-(phenylthio)ethyl)amino)benzenesulfonamide

EXAMPLE 311A methyl 4-bromo-3-fluorobenzoate

A solution of 4-bromo-3-fluorobenzoic acid (117 mg, 0.50 mmol) in methanol (1 mL) and dichloromethane (2 mL) at room temperature was slowly treated with 2M trimethylsilyldiazomethane in hexanes until the solution became light yellow. The mixture was concentrated to provide the desired product.

EXAMPLE 311B methyl 2,4'-difluoro-1,1'-biphenyl-4-carboxylate

The desired product was prepared by substituting Example 311A and 4-fluorophenylboronic acid for Example 5A and (4-methoxycarbonylphenyl)boronic acid, respectively, in Example 5B.

EXAMPLE 311C

N-((2,4'-difluoro-1,1'-biphenyl-4-yl)carbonyl)-3-nitro-4-((2-(phenylthio)ethyl)amino)benzenesulfonamide The desired product was prepared by substituting Example 311B and Example 77B for Example 5C and Example 3A, respectively, in Example 5D. MS (ESI(–)) m/e 568 (M–H)$^-$; $^1$H NMR (300 MHz, DMSO-d$_6$) δ8.76 (t, 1H), 8.61 (d, 1H), 7.94 (dd, 1H), 7.82 (m, 1H), 7.79 (s, 1H), 7.65 (m, 3H), 7.40–7.15 (m, 8H), 3.66 (q, 2H), 3.20 (t, 2H).

EXAMPLE 312

4-((2-(((ethylamino)carbonyl)amino)-1-((phenylthio)methyl)ethyl)amino)-N-((4'-fluoro-1,1'-biphenyl-4-yl)carbonyl)-3-nitrobenzenesulfonamide The desired product was prepared by substituting ethyl isocyanate for acetyl chloride in Example 310. MS (ESI(–)) m/e 650 (M–H)$^-$; $^1$H NMR (400 MHz, methanol-d$_4$) δ8.74 (d, 1H), 7.93 (m, 3H), 7.68 (m, 4H), 7.31 (m, 2H), 7.15 (m, 5H), 7.03 (d, 1H), 4.16 (m, 1H), 3.45 (m, 2H), 3.35 (dd, 1H), 3.17 (dd, 1H), 3.05 (q, 2H), 1.01 (7, 3H), and remaining proton is buried under solvent peaks.

EXAMPLE 313

N-(4-(4-benzylpiperazin-1-yl)benzoyl)-3-nitro-4-((2-(phenylthio)ethyl)amino)benzenesulfonamide The desired product was prepared by substituting benzaldehyde for (1-benzyl-2-oxo-ethyl)-carbamic acid tert-butyl ester in Example 173. MS (ESI(–)) m/e 630 (M–H)⁻; $^1$H NMR (300 MHz, DMSO-d$_6$) δ8.56 (t, 1H), 8.51 (d, 1H), 7.87 (dd, 1H), 7.73 (d, 2H), 7.41–7.26 (m, 8H), 7.21 (d, 2H), 7.02 (d, 1H), 6.84 (d, 2H), 3.63 (q, 2H), 3.55 (s, 2H), 3.31–3.20 (m, 10H), 2.81 (dd, 1H).

EXAMPLE 314

N-(4-(2-(4,4-dimethyl-3-oxopentyl)-1,3-benzothiazol-5-yl)benzoyl)-3-nitro-4-((2-(phenylthio)ethyl)amino)benzenesulfonamide The desired product was prepared by substituting 1-bromopinacolone for allyl bromide in Example 213. MS (ESI) m/e 701, 703 (M–H)⁻, (M+H)⁺; $^1$H NMR (300 MHz, DMSO-d$_6$) δ0.95 (s, 3H), 2.52 (t, 2H), 2.73 (s, 3H), 2.89 (s, 3H), 3.27 (t, 2H), 3.29 (t,2H), 3.61 (dt, 2H), 7.02 (d, 1H), 7.19 (t, 1H), 7.31 (t, 1H), 7.39 (d, 2H), 7.70–7.77 (m, 3H), 7.89 (dd, 1H), 7.93–8.02 (m, 3H), 8.12 (d, 1H), 8.24 (s, 1H), 8.53 (d, 1H), 8.55 (t, 1H).

EXAMPLE 315

N-((4'-fluoro-1,1'-biphenyl-4-yl)carbonyl)-4-(((1S)-3-morpholin-4-yl-3-oxo-1-((phenylthio)methyl)propyl)amino)-3-nitrobenzenesulfonamide

EXAMPLE 315A (3S)-3-((4-(aminosulfonyl)-2-nitrophenyl)amino)-4-(phenylthio)butanoic acid The desired product was prepared by substituting Fmoc-L-Asp(OtBu)-OH for Fmoc-D-Asp(OtBu)-OH in Examples 122A–122E.

EXAMPLE 315B 4-(((1S)-3-morpholin-4-yl-3-oxo-1-((phenylthio)methyl)propyl)amino)-3-nitrobenzenesulfonamide The desired product was prepared by substituting Example 315A and morpholine for Example 122E and dimethylamine in Example 122F.

EXAMPLE 315C

N-((4'-fluoro-1,1'-biphenyl-4-yl) carbonyl)-4-(((1S)-3-morpholin-4-yl-3-oxo-1-((phenylthio)methyl)propyl)amino)-3-nitrobenzenesulfonamide The desired product was prepared by substituting Example 315B for Example 1C in Example 1D. MS (ESI (–)) m/e 677 (M–H)⁻; $^1$H NMR (300 MHz, methanol-d$_4$) δ8.79 (d, 1H), 8.75 (d, 1H), 7.94 (m, 3H), 7.70 (m, 4H), 7.30 (m, 2H), 7.24–7.13 (m, 5H), 7.01 (d, 1H), 4.50 (m, 1H), 3.62–3.52 (m, 4H), 3.52–3.46 (m, 4H), 3.37 (m, 2H), 3.00 (dd(1H), 2.85 (dd, 1H).

EXAMPLE 316

N-(4-(2-(hydroxymethyl)-3-methyl-1-benzothien-5-yl)benzoyl)-3-nitro-4-((2-(phenylthio)ethyl)amino)benzenesulfonamide A mixture of Example 351E (40 mg, 0.063 mmol) and NaBH$_4$ (20 mg) in methanol at room temperature was stirred for 10 minutes and concentrated. The concentrate was purified by flash column chromatography on silica gel with ethyl acetate to provide the desired product. MS (ESI(–)) m/e 632 (M–H)⁻; $^1$H NMR (300 MHz, DMSO-d$_6$) δ2.38 (s, 3H), 3.19 (t, 2H), 3.60 (m, 1H), 4.05 (m, 1H), 4.76 (d, 2H), 5.08 (m, 1H), 6.99 (d, 1H), 7.16 (m, 1H), 7.21 (dd, 1H), 7.31 (dd, 2H), 7.39 (dd, 2H), 7.66 (m, 1H), 7.71 (d, 1H), 7.87 (d, 2H), 7.97 (dd, 3H), 8.51 (dd, 1H), 8.52 (d, 1H).

EXAMPLE 317

N-(4-(1-(morpholin-4-ylcarbonyl)-1,2,3,6-tetrahydropyridin-4-yl)benzoyl)-3-nitro-4-((2-(phenylthio)ethyl)amino)benzenesulfonamide A mixture of Example 340A (50 mg, 0.08 mmol), 4-morpholinecarbonyl chloride (15 mg, 0.012 mmol), and N,N-diisopropylethylamine (0.07 mL, 0.4 mmol) in dichloromethane (0.5 mL) at room temperature was stirred for 16 hours and concentrated. The concentrate was dissolved in 1:1 DMSO/methanol (1.0 mL) and purified by reverse phase preparative HPLC using 20–95% acetonitrile/0.1% TFA to provide the desired product. MS (ESI(–)) m/e 650 (M–H)⁻; $^1$H NMR (300 MHz, DMSO-d$_6$) δ8.78 (br t, 1H), 8.60 (d, 1H), 7.92 (dd, 1H), 7.85 (d, 2H), 7.55 (d, 2H), 7.40–7.15 (m, 6H), 6.35 (m, 1H), 3.92 (d, 2H), 3.70 (m, 2H), 3.60 (t, 4H), 3.40–3.25 (m, 6H), 3.15 (t, 4H), 2.79 (s, 3H), 3.10–2.70 (m, 4H), 2.65 (t, 2H).

EXAMPLE 318

N-(4-(1,4-dioxa-8-azaspiro(4.5)dec-8-yl)benzoyl)-3-nitro-4-((2-(phenylthio)ethyl)amino)benzenesulfonamide

EXAMPLE 318A 4-(1,4-dioxa-8-azaspiro(4.5)dec-8-yl)benzoic acid

The desired product was prepared by substituting Example 158A for Example 119B in Example 119C. MS (DCI) m/e 264 (M+H)⁺.

EXAMPLE 318B

N-(4-(1,4-dioxa-8-azaspiro(4.5)dec-8-yl)benzoyl)-3-nitro-4-((2-(phenylthio)ethyl)amino)benzenesulfonamide The desired product was prepared by substituting Example 318A and Example 77B for Example 1B and Example 1C, respectively, in Example 1D. MS (ESI(+)) m/e 599 (M+H)⁺; $^1$H NMR (300 MHz, CDCl$_3$) δ8.88 (d, 1H), 8.67 (t, 1H), 8.55 (s, 1H), 8.15 (dd, 1H), 7.64 (d, 2H), 7.41 (dd, 2H), 7.30 (m, 2H), 6.86 (d, 2H), 6.82 (d, 2H), 3.99 (s, 4H), 3.57 (m, 2H), 3.50 (t, 4H), 3.21 (t, 2H), 1.78 (t, 4H).

EXAMPLE 319

N-(4-(2,8-bis(trifluoromethyl)quinolin-4-yl)benzoyl)-3-nitro-4-((2-(phenylthio)ethylamino)benzenesulfonamide A solution of Example 214D (100 mg, 0.15 mmol) and 2,8-bistrifluoromethyl-3-chloroquinoline (100 mg, 0.343 mmol) in dioxane (2 mL) was treated with Pd$_2$(dba)$_3$ (10 mg, 0.011 mmol), P(t-Bu)$_3$ (20 mg, 0.1 mmol) and Cs$_2$CO$_3$ (150 mg, 0.50 mmol), purged with argon, sealed, and heated to 85° C. for 18 hours. The mixture was concentrated and the concentrate was dissolved in 1:1 DMSO/methanol (1 mL) and filtered. The filtrate was purified by preparative HPLC (using a Nova-Pak HR C-18 column and a solvent system varying in gradient from 10–95% acetonitrile/water containing 0.1% TFA) to provide the desired product. MS (ESI(+))

m/e 721 (M+H)+, m/e 719 (M−H)−; 1H NMR (500 MHz, DMSO-d6) δ8.80 (t, 1H), 8.67 (d, 1H), 8.41 (d, 1H), 8.14 (d, 1H), 8.12 (d, 2H), 8.08 (s, 1H), 7.97 (dd, 1H), 7.91 (t, 1H), 7.77 (d, 2H), 7.38 (dt, 2H), 7.28 (td, 2H), 7.24 (d, 1H), 7.17 (tt, 1H), 3.69 (q, 2H), 3.31 (t, 2H).

EXAMPLE 320

3-nitro-N-(4-(2-(3-oxo-3-piperidin-1-ylpropyl)-1,3-benzothiazol-5-yl)benzoyl)-4-((2-(phenylthio)ethylamino)benzenesulfonamide

EXAMPLE 320A tert-butyl 3-(5-bromo-1,3-benzothiazol-2-yl)propanoate

The desired product was prepared by substituting tert-butyl bromoacetate for allyl bromide in Example 213A.

EXAMPLE 320B 3-(5-bromo-1,3-benzothiazol-2-yl)propanoic acid

The desired product was prepared by substituting Example 320A for Example 201G in Example 201H.

EXAMPLE 320C 5-bromo-2-(3-oxo-3-piperidin-1-ylpropyl)-1,3-benzothiazole

The desired product was prepared by substituting Example 320B and piperidine for Example 1B and Example 1C, respectively, in Example 1D.

EXAMPLE 320D 4-(2-(3-oxo-3-piperidin-1-ylpropyl)-1,3-benzothiazol-5-yl)benzoic acid The desired product was prepared by substituting Example 320C for 6-bromoindole in Example 4A.

EXAMPLE 320E 3-nitro-N-(4-(2-(3-oxo-3-piperidin-1-ylpropyl)-1,3-benzothiazol-5-yl)benzoyl)-4-((2-(phenylthio)ethyl)amino)benzenesulfonamide The desired product was prepared by substituting Example 320D and Example 77B for Example 1B and Example 1C, respectively, in Example 1D. MS (ESI) m/e 728, 730 (M−H)−(M+H)+; 1H NMR (300 MHz, DMSO-d6) δ1.42 (t, 2H), 1.55 (tt, 4H), 2.93 (t, 2H), 3.28 (t, 2H), 3.36 (t, 2H), 3.44 (t, 4H), 3.61 (dt, 2H), 7.01 (d, 1H), 7.19 (t, 1H), 7.31 (t, 2H), 7.39 (d, 2H), 7.73 (d, 3H), 7.89 (dd, 1H), 7.98 (d, 2H), 8.10 (d, 1H), 8.19 (s, 1H), 8.52 (d, 1H), 8.54 (t, 1H).

EXAMPLE 321

N-(4-(3-(cyanomethyl)-1-benzothien-5-yl)benzoyl)-3-nitro-4-((2-(phenylthio)ethyl)amino)benzenesulfonamide

EXAMPLE 321A methyl 4-(3-(cyanomethyl)-1-benzothien-5-yl)benzoate

The desired product was prepared by substituting 3-cyanomethyl-5-chlorobenzthiophene for 5-chloro-2-methyl-1,3-benzoxazole in Example 54A. MS (ESI(+)) m/e 308 (M+H)+.

EXAMPLE 321B 4-(3-(cyanomethyl)-1-benzothien-5-yl)benzoic acid

The desired product was prepared by substituting Example 321A for Example 1A in Example 1B. MS (ESI(−)) m/e 292 (M−H)−.

EXAMPLE 321C

N-(4-(3-(cyanomethyl)-1-benzothien-5-yl)-benzoyl)-3-nitro-4-((2-(phenylthio)ethyl)amino)benzenesulfonamide The desired product was prepared by substituting Example 321B and Example 77B for Example 1B and Example 1C, respectively, in Example 1D. MS (ESI(−)) m/e 627 (M−H)−; 1H NMR (300 MHz, DMSO-d6) δ3.29 (m, 2H), 3.61 (m, 2H), 4.04 (m, 1H), 4.40 (s, 2H), 6.99 (d, 1H), 7.21 (dd, 1H), 7.31 (dd, 2H), 7.40 (d, 2H), 7.54 (dd, 2H), 7.56 (d, 1H), 7.91 (d, 1H), 8.02 (d, 2H), 8.10 (d, 1H), 8.19 (s, 1H), 8.52 (m, 2H).

EXAMPLE 322

N~2~-(2-nitro-4-(((4-(1-pentyl-1H-pyrazol-4-yl)benzoyl)amino)sulfonyl)phenyl)-N~1~,N~1~-bis(4-(N-(2-nitro-4-(((4-(1-pentyl-1H-pyrazol-4-yl)benzoyl)amino)sulfonyl)phenyl)-S-phenylcysteinyl)morpholin-3-yl)-S-phenylcysteinamide

EXAMPLE 322A 4-iodo-1-pentyl-1H-pyrazole

The desired product was prepared by substituting 1-iodopentane for 1-bromooctane in Example 198A. MS (ESI(+)) m/e 265 (M+H)+.

EXAMPLE 322B 4-(1-pentyl-1H-pyrazol-4-yl)benzoic acid

The desired product was prepared by substituting Example 322A for 6-bromoindole in Example 4A. MS (ESI(−)) m/e 257 (M−H)−.

EXAMPLE 322C

N~2~-(2-nitro-4-(((4-(1-pentyl-1H-pyrazol-4-yl)benzoyl)amino)sulfonyl)phenyl)-N~1~,N~1~-bis(4-(N-(2-nitro-4-(((4-(1-pentyl-1H-pyrazol-4-yl)benzoyl)amino)sulfonyl)phenyl)-S-phenylcysteinyl)morpholin-3-yl)-S-phenylcysteinamide The desired product was prepared by substituting Example 322B and Example 180B for Example 1B and Example 1C, respectively, in Example 1D. MS (ESI(−)) m/e 705 (M−H)−; 1H NMR (300 MHz, DMSO-d6) δ0.88 (t, 3H), 1.28 (m, 4H), 1.80 (m, 2H), 3.19 (dd, 1H), 3.51 (m, 4H), 3.59 (m, 4H), 3.69 (dd, 1H), 4.10 (t, 2H), 5.30 (m, 1H), 7.18 (m, 4H), 7.27 (d, 2H), 7.51 (m, 2H), 7.89 (m, 4H), 8.20 (dd, 1H), 8.49 (dd, 1H), 8.95 (d, 1H).

EXAMPLE 323

N-(4-(2-(4-acetylpiperazin-1-yl)quinolin-8-yl)benzoyl)-3-nitro-4-((2-(phenylthio)ethyl)amino)benzenesulfonamide A solution of 1-acetylpiperazine (100 mg, 0.80 mmol), Example 336E (30 mg, 0.08 mmol), and triethyl amine (100

μL) in DMSO (0.5 mL) was heated to 120° C. for 18 hours, diluted with methanol (0.5 mL), and purified by preparative HPLC (using a Nova-Pak HR C-18 column and a solvent system increasing in gradient from 10–95% acetonitrile/water containing 0.1%) to provide the desired product. MS (ESI) m/e 711, 709 (M+H)$^+$, (M−H)$^-$; $^1$H NMR (500 MHz, DMSO-d$_6$) δ8.78 (t, 1H), 8.65 (d, 1H), 8.14 (d, 1H), 7.97 (d, 2H), 7.95 (d, 1H), 7.86 (d, 2H), 7.77 (dd, 1H), 7.64 (dd, 1H), 7.38 (dt, 2H), 7.33 (td, 1H), 7.29 (d, 1H), 7.28 (td, 2H), 7.23 (d, 1H), 7.17 (tt, 1H), 3.69 (q, 2H), 3.67–3.50 (m, 8H), 3.31 (t, 2H), 2.02 (s, 3H).

EXAMPLE 324

N-(4-(1H-indol-4-yl)benzoyl)-3-nitro-4-((2-(phenylthio)ethyl)amino)benzenesulfonamide

EXAMPLE 324A methyl 4-(1H-indol-4-yl)benzoate

The desired product was prepared by substituting 4-bromoindole for Example 5A in Example 5B.

EXAMPLE 324B 4-(1H-indol-4-yl)benzoic acid

The desired product was prepared by substituting Example 324A for Example 1A in Example 1B.

EXAMPLE 324C

N-(4-(1H-indol-4-yl)benzoyl)-3-nitro-4-((2-(phenylthio)ethyl)amino)benzenesulfonamide The desired product was prepared by substituting Example 324B and Example 77B for Example 1B and Example 1C, respectively, in Example 1D. MS (ESI(−)) m/e 571 (M−H)$^-$; $^1$H NMR (400 MHz, methanol-d$_4$) δ8.81 (d, 1H), 8.02 (dd, 1H), 7.96 (d, 2H), 7.78 (d, 2H), 7.40 (m, 2H), 7.31 (d, 1H), 7.25–7.10 (m, 4H), 7.06 (d, 1H), 6.59 (d, 1H), 3.68 (q, 2H), 3.27 (t, 2H).

EXAMPLE 325

2-methoxyethyl 4-(4-((((3-nitro-4-((2-(phenylthio)ethyl)amino)phenyl)sulfonyl)amino)carbonyl)phenyl)piperazine-1-carboxylate A solution of Example 173A (54.1 mg, 0.1 mmol) in pyridine (2 mL) and triethylamine (1 mL) at room temperature was treated with 2-methoxyethyl chloroformate (0.2 mmol), stirred for 18 hours, and concentrated. The concentrate was purified by flash column chromatography on silica gel with 0–5% methanol/dichloromethane) to provide the desired product. MS (ESI(−)) m/e 642 (M−H)$^-$; $^1$H NMR (300 MHz, DMSO-d$_6$) δ8.66 (t, 1H), 8.55 (d, 1H), 7.89 (dd, 1H), 7.75 (d, 2H), 7.30–7.40 (m, 2H), 7.31–7.25 (m, 2H), 7.21–7.07 (m, 2H), 6.90 (d, 2H), 4.16–4.12 (m, 2H), 3.63 (q, 2H), 3.54–3.43 (m, 4H), 3.31–3.20 (m, 8H), 3.23 (s, 3H).

EXAMPLE 326

N-(4-(3-formyl-1-benzothien-5-yl)benzoyl)-3-nitro-4-((2-(phenylthio)ethyl)amino)benzenesulfonamide

EXAMPLE 326A (5-chloro-1-benzothien-3-yl)methanol

A solution of 3-bromomethyl-5-chlorobenzothiophene (2.5 g, 9.56 mmol) and potassium acetate (1.96 g, 20 mmol) in 1M NaOH (40 mL) and dioxane (40 mL) was heated to reflux for 24 hours, adjusted to pH<7 with 1M HCl, and extracted with ethyl acetate (3×). The combined extracts were washed with brine, concentrated, and purified by flash column chromatography on silica gel with 50% ethyl acetate/hexanes to provide the desired product.

EXAMPLE 326B methyl 4-(3-(hydroxymethyl)-1-benzothien-5-yl)benzoate

The desired product was prepared by substituting Example 326A for 5-chloro-2-methyl-1,3-benzoxazole in Example 54A. MS (ESI(+)) m/e 299 (M+H)$^+$.

EXAMPLE 326C methyl 4-(3-formyl-1-benzothien-5-yl)benzoate

A solution of Example 326B (298 mg, 1 mmol) and Dess-Martin periodinane (466 mg, 1.1 mmol) in dichloromethane at room temperature was stirred for 90 minutes and purified by flash chromatography on silica gel with 20% ethyl acetate/hexanes to provide the desired product. MS (ESI(+)) m/e 297 (M+H)$^+$.

EXAMPLE 326D 4-(3-formyl-1-benzothien-5-yl)benzoic acid

The desired product was prepared by substituting Example 326C for Example 1A in Example 1B. MS (ESI(−)) m/e 281 (M−H)$^-$.

EXAMPLE 326E

N-(4-(3-formyl-1-benzothien-5-yl)benzoyl)-3-nitro-4-((2-(phenylthio)ethyl)amino)benzenesulfonamide The desired product was prepared by substituting Example 326D and Example 77B for Example 1B and Example 1C, respectively, in Example 1D. MS (ESI(−)) m/e 616 (M−H)$^-$; $^1$H NMR (300 MHz, DMSO-d$_6$) δ3.29 (m, 2H), 3.69 (m, 2H), 4.00 (m, 1H), 7.19 (dd, 2H), 7.21 (dd, 1H), 7.30 (dd, 2H), 7.38 (d, 2H), 7.85 (m, 3H), 7.95 (dd, 1H), 8.01 (d, 2H), 8.24 (d, 1H), 8.51 (d, 1H), 8.79 (dd, 1H), 8.82 (d, 1H), 9.02 (s, 1H).

EXAMPLE 327

N-(5-(4-chlorophenyl)-2-furoyl)-3-nitro-4-((2-(phenylthio)ethyl)amino)benzenesulfonamide The desired product was prepared by substituting 5-(4-chlorophenyl)-2-furoic acid and Example 77B for Example 1B and Example 1C, respectively, in Example 1D. MS (ESI(−)) m/e 556 (M−H)$^-$; $^1$H NMR (300 MHz, DMSO-d$_6$) δ8.52 (t, 1H), 7.88 (dd, 1H), 7.75 (d, 2H), 7.49 (d, 2H), 7.41–7.39 (m, 2H), 7.33–7.29 (m, 2H), 7.22–7.18 (m, 1H), 7.01–6.98 (m, 3H), 6.89 (d, 1H), 3.63–3.59 (m, 2H), 3.31–3.20 (m, 2H).

EXAMPLE 328

N-((2'-methoxy-4'-(2-(4-methylpiperazin-1-yl)-2-oxoethyl)-1,1'-biphenyl-4-yl)-carbonyl)-3-nitro-4-((2-(phenylthio)ethyl)amino)benzenesulfonamide

EXAMPLE 328A methyl 4'-(2,2-dibromovinyl)-2'-methoxy-1,1'-biphenyl-4-carboxylate A solution of Example 122I (1.35 g, 5.0 mmol) in dichloromethane (30 mL) at room temperature was treated with carbon tetrabromide (1.82 g, 5.5 mmol) and triphenylphosphine (2.88 g, 11 mmol), stirred for 1 hour, treated with hexanes (50 mL), and filtered through silica gel (50 g). The solution was rinsed with 1:1 water/dichloromethane, separated, and the organic phase was concentrated. The concentrate was purified by flash column chromatography on silica gel with 2–10% ethyl acetate/hexanes to provide the desired product.

EXAMPLE 328B methyl 2'-methoxy-4'-(2-(4-methylpiperazin-1-yl)-2-oxoethyl)-1,1'-biphenyl-4-carboxylate A mixture of Example 328A (213 mg, 0.5 mmol), 1-methylpiperazine (2.5 mmol), and bis(tricyclohexylphosphine)palladium chloride (0.0025 mmol) in DMF (1.5 mL) and water (0.25 mL) was heated to 80° C. for 8 hours, diluted with ethyl acetate (100 mL), washed with water (45 mL) and brine (10 mL), dried (MgSO$_4$), filtered, and concentrated. The concentrate was purified by flash column chromatography on silica gel with 2–10% methanol/dichloromethane to provide the desired product.

EXAMPLE 328C

N-((2'-methoxy-4'-(2-(4-methylpiperazin-1-yl)-2-oxoethyl)-1,1'-biphenyl-4-yl)carbonyl)-3-nitro-4-((2-(phenylthio)ethyl)amino)benzenesulfonamide The desired product was prepared by substituting Example 328B and Example 77B for Example 5C and Example 3A, respectively, in Example 5D. MS (ESI(−)) m/e 702 (M−H)$^-$; $^1$H NMR (500 MHz, DMSO-d$_6$) δ8.78 (t, 1H), 8.63 (d, 1H), 7.93 (dd, 1H), 7.90 (d, 2H), 7.59 (d, 2H), 7.36 (m, 2H), 7.27 (m, 3H), 7.22 (d, 1H), 7.19 (tt, 1H), 6.99 (d, 1H), 6.90 (dd, 1H), 3.82 (s, 2H), 3.75 (s, 3H), 3.68 (q, 2H), 3.29 (t, 4H), 2.82 (s, 3H), remaining 6 protons are buried under very broad water peak (3.60–3.30 ppm).

EXAMPLE 329

4-((2-morpholin-4-yl-1-((phenylthio)methyl)ethyl)amino)-3-nitro-N-(4-(1-pentyl-1H-pyrazol-4-yl)benzoyl)benzenesulfonamide The desired product was prepared by substituting Example 322B and racemic Example 146C for Example 1B and Example 1C, respectively, in Example 1D. MS (ESI(−)) m/e 691 (M−H)$^-$; $^1$H NMR (300 MHz, DMSO-d$_6$) δ0.86 (t, 3H), 1.28 (m, 4H), 1.79 (m, 2H), 2.38 (m, 2H), 2.44 (m, 2H), 2.62 (d, 2H), 3.40 (dd, 1H), 3.52 (m, 4H), 3.59 (m, 4H), 3.69 (dd, 1H), 4.02 (m, 1H), 4.09 (t, 2H), 4.16 (m, 1H), 5.30 (m, 1H), 6.98 (d, 1H), 7.12 (dd, 1H), 7.21 (dd, 2H), 7.32 (d, 2H), 7.52 (m, 2H), 7.86 (m, 4H), 8.21 (s, 1H), 8.36 (d, 1H), 8.48 (s, 1H).

EXAMPLE 330

3-(5-(4-((((4-((1-adamantylmethyl)amino)-3-nitrophenyl)sulfonyl)amino)carbonyl)phenyl)-1,3-benzothiazol-2-yl)-N-butylpropanamide

EXAMPLE 330A 3-(5-bromo-1,3-benzothiazol-2-yl)-N-butylpropanamide

The desired product was prepared by substituting Example 320B and butylamine for Example 1B and Example 1C, respectively, in Example 1D.

EXAMPLE 330B 4-(2-(3-(butylamino)-3-oxopropyl)-1,3-benzothiazol-5-yl)benzoic acid The desired product was prepared by substituting Example 330A for 6-bromoindole in Example 4A.

EXAMPLE 330C 3-(5-(4-((((4-((1-adamantylmethyl)amino)-3-nitrophenyl)sulfonyl)amino)carbonyl)phenyl)-1,3-benzothiazol-2-yl)-N-butylpropanamide The desired product was prepared by substituting Example 330B and Example 28A for Example 1B and Example 1C, respectively, in Example 1D. MS (ESI) m/e 728, 730 (M−H)$^-$, (M+H)$^+$; $^1$H NMR (300 MHz, DMSO-d$_6$) δ0.82 (t, 3H), 1.25 (m, 2H), 1.35 (tt, 2H), 1.55–1.73 (m, 11H), 1.97 (m, 2H), 2.65 (t, 2H), 3.04 (dt, 2H), 3.12 (d, 2H), 3.33 (t, 2H), 7.16 (d, 1H), 7.71 (d, 2H), 7.73 (d, 1H), 7.90 (dd, 1H), 7.93 (t, 1H), 7.98 (d, 2H), 8.10 (d, 1H), 8.18 (s, 1H), 8.38 (t, 1H), 8.54 (d, 1H).

EXAMPLE 331

N-(4-(2-(hydroxymethyl)quinolin-8-yl)benzoyl)-3-nitro-4-((2-(phenylthio)ethyl)amino)benzenesulfonamide A mixture of Example 339B (10 mg) and sodium borohydride (4 mg) in methanol (1 mL) was stirred at room temperature for 4 hours, diluted with ethyl acetate (30 mL), washed with water (5 mL) and brine (5 mL), dried (MgSO$_4$), filtered, and concentrated. The concentrate was purified by flash column chromatography on silica gel with ethyl acetate to provide the desired product. MS (ESI(−)) m/e 613 (M−H)$^-$; $^1$H NMR (400 MHz, DMSO-d$_6$) δ8.77 (d, 2H), 8.33 (d, 1H), 8.09 (d, 2H), 8.00 (dd, 1H), 7.91 (dd, 1H), 7.75 (dd, 1H), 7.69 (d,H), 7.51 (m, 2H), 7.39 (m, 2H), 7.23 (t, 2H), 7.18 (ttt, 1H), 6.94 (d, 1H), 4.75 (s, 2H), 3.62 (m, 2H), 3.24 (t, 2H).

EXAMPLE 332

N-((6-(4-fluorophenyl)pyridin-3-yl)carbonyl)-3-nitro-4-((2-(phenylthio)ethyl)amino)benzenesulfonamide The desired product was prepared by substituting Example 77B and Example 298B for Example 124E and Example 257C, respectively, in Example 124F. MS (ESI) m/e 553, 551 (M+H)$^+$, (M−H)$^-$; $^1$H NMR (500 MHz, DMSO-d$_6$) δ9.07 (d, 1H), 8.78 (t, 1H), 8.64 (d, 1H), 8.30 (dd, 1H), 8.22 (q, 2H), 8.10 (d, 1H), 7.95 (dd, 1H), 7.38–7.16 (m, 8H), 3.67 (q, 2H), 3.29 (t, 2H).

EXAMPLE 333

N-(4-(3,5-dimethyl-1-pentyl-1H-pyrazol-4-yl)benzoyl)-3-nitro-4-((2-(phenylthio)ethyl)amino)benzenesulfonamide

EXAMPLE 333A 4-bromo-3,5-dimethyl-1-pentyl-1H-pyrazole

The desired product was prepared by substituting 5-iodopentane and 4-bromo-3,5-dimethylpyrazole for 1-bromooctane and 4-iodopyrazole, respectively, in Example 198A. MS (ESI(+)) m/e 245, 247 (M+H)$^+$.

EXAMPLE 333B 4-(3,5-dimethyl-1-pentyl-1H-pyrazol-4-yl)benzoic acid

The desired product was prepared by substituting Example 333A for 6-bromoindole in Example 4A. MS (ESI(−)) m/e 285 (M−H)⁻.

EXAMPLE 333C

N-(4-(3,5-dimethyl-1-pentyl-1H-pyrazol-4-yl)benzoyl)-3-nitro-4-((2-(phenylthio)ethyl)amino)benzenesulfonamide The desired product was prepared by substituting Example 333B and Example 77B for Example 1B and Example 1C, respectively, in Example 1D. MS (ESI(−)) m/e 620 (M−H)⁻; $^1$H NMR (300 MHz, DMSO-$d_6$) δ 0.89 (t, 3H), 1.30 (m, 4H), 1.71 (tt, 2H), 2.11 (s, 3H), 2.21 (s, 3H), 3.27 (t, 2H), 3.61 (q, 2H), 3.96 (t, 2H), 4.39 (m, 1H), 6.99 (d, 1H), 7.19 (d, 1H), 7.20 (dd, 2H), 7.31 (dd, 2H), 7.40 (d, 2H), 7.89 (dd, 1H), 7.90 (d, 2H), 8.51 (d, 1H), 8.52 (t, 1H).

EXAMPLE 334

3-nitro-4-((2-(phenylthio)ethyl)amino)-N-(4-quinolin-2-ylbenzoyl)benzenesulfonamide The desired product was prepared by substituting 2-chloroquinoline and Example 108A for 4-bromo-1-iodobenzene and Example 3C, respectively, in Example 3D. MS (ESI(−)) m/e 583 (M−H)⁻; $^1$H NMR (400 MHz, DMSO-$d_6$) δ 8.55 (d, 1H), 8.52 (t, 1H), 8.44 (d, 1H), 8.23 (d, 2H), 8.17 (d, 1H), 8.08 (d, 1H), 8.05 (d, 2H), 8.00 (d, 1H), 7.90 (t, 1H), 7.78 (dt, 1H), 7.60 (m, 2H), 7.40 (dd, 1H), 7.30 (t, 2H), 7.20 (tt, 1H), 7.00 (d, 1H), 3.63 (q, 2H), 3.26 (t, 2H).

EXAMPLE 335

N-(4-(2-methyl-1,3-benzothiazol-5-yl)benzoyl)-4-((2-morpholin-4-yl-1-((phenylthio)methyl)ethyl)amino)-3-nitrobenzenesulfonamide The desired product was prepared by substituting Example 17A and Example 245A for Example 1B and Example 1C, respectively, in Example 1D. MS (ESI(+)) m/e 704 (M+H)⁺; $^1$H NMR (400 MHz, methanol-$d_4$) δ 8.68 (d, 1H), 8.10 (m, 3H), 7.96 (d, 1H), 7.91 (dd, 1H), 7.68 (m, 3H), 7.32 (m, 2H), 7.13 (m, 3H), 6.93 (d, 1H), 4.11 (m, 1H), 3.63 (t, 4H), 3.39 (dd, 1H), 3.21 (dd, 1H), 2.84 (s, 3H), 2.49 (m, 4H).

EXAMPLE 336

N-(4-(2-chloroquinolin-8-yl)benzoyl)-3-nitro-4-((2-(phenylthio)ethyl)amino)benzenesulfonamide

EXAMPLE 336A 2-hydroxyquinolin-8-yl trifluoromethanesulfonate

A mixture of 2,8-quinolinediol (4.23 g, 26.3 mmol), 2-(N,N-bis(trifluoromethylsulfonyl)amino)pyridine (9.4 g, 26.3 mmol) and diisopropylethylamine (14 mL, 80.5 mmol) in dichloromethane (50 mL) at room temperature was stirred for 18 hours, diluted with ethyl acetate (200 mL), washed with water (2×50 mL) and brine (50 mL), dried (Na$_2$SO$_4$), filtered, and concentrated. The concentrate was purified by flash column chromatography on silica gel with 1:4 ethyl acetate/hexanes to provide the desired product. MS (APCI) m/e 292 (M−H)⁻.

EXAMPLE 336B methyl 4-(2-hydroxyquinolin-8-yl)benzoate

A mixture of Example 336A (2.93 g, 10 mmol), 4-(methoxycarbonyl)phenylboronic acid (1.80 g, 10 mmol), Pd(Ph$_3$P)$_4$ (0.346 g, 0.3 mmol), and CsF(1.52 g, 10 mmol) in DME (60 mL) and methanol (30 mL) was heated to reflux for 18 hours and concentrated. The concentrate was dissolved in water (50 mL) and ethyl acetate (300 mL) and the organic phase was washed with water (2×50 mL) and brine (50 mL), dried (Na$_2$SO$_4$), filtered, and concentrated. The concentrate was purified by flash column chromatography on silica gel with 4:1 hexanes/ethyl acetate to provide the desired product. MS (APCI) m/e 280, 278 (M+H)⁺, (M−H)⁻.

EXAMPLE 336C methyl 4-(2-chloroquinolin-8-yl)benzoate

A mixture of Example 336B (1.76 g, 6.3 mmol) in POCl$_3$(50 mL) was heated to reflux for 30 minutes and concentrated. The concentrate was purified through a silica gel pad with 4:1 hexanes/ethyl acetate to provide the desired product. MS (ESI) m/e 298(M+H)⁺.

EXAMPLE 336D 4-(2-chloroquinolin-8-yl)benzoic acid

The desired product was prepared by substituting Example 336C for Example 1A in Example 1B. MS (ESI) m/e 284 (M+H)⁺.

EXAMPLE 336E

N-(4-(2-chloroquinolin-8-yl)benzoyl)-3-nitro-4-((2-(phenylthio)ethyl)amino)benzenesulfonamide The desired product was prepared by substituting Example 336C and Example 77B for Example 1B and Example 1C, respectively, in Example 1D. MS (ESI(−)) m/e 617 (M−H)⁻; $^1$H NMR (400 MHz, DMSO-$d_6$) δ 8.77 (t, 1H), 8.54 (d,2H), 8.52 (d, 1H), 8.11 (dd, 1H), 7.97 (d, 2H), 7.90 (dd, 1H), 7.87 (dd, 1H), 7.75 (m, 3H), 7.63 (d, 1H), 7.37 (m, 1H), 7.27 (tt, 2H), 7.21 (d, 1H), 7.19 (t, 1H), 3.67 (q, 2H), 3.28 (t, 2H).

EXAMPLE 337

3-nitro-N-(4-((E)-2-phenylethenyl)benzoyl)-4-((2-(phenylthio)ethyl)amino)benzenesulfonamide

EXAMPLE 337A methyl 4-((E)-2-phenylethenyl)benzoate

The desired product was prepared by substituting beta-styryl boronic acid for 4-fluorophenylboronic acid in Example 1A. MS (ESI(−)) m/e 237 (M−H)⁻.

EXAMPLE 337B 4-((E)-2-phenylethenyl)benzoic acid

The desired product was prepared by substituting Example 337A for Example 1A in Example 1B. MS (ESI(−)) m/e 223 (M−H)⁻.

EXAMPLE 337C 3-nitro-N-(4-((E)-2-phenylethenyl)benzoyl)-4-((2-(phenylthio)ethyl)amino)benzenesulfonamide The desired product was prepared by substituting Example 337B and Example 77B for Example 1B and Example 1C, respectively, in Example 1D. MS (ESI(−)) m/e 558 (M−H)⁻; ¹H NMR (300 MHz, DMSO-d₆) δ3.27 (t, 2H), 3.61 (t, 2H), 4.01 (m, 1H), 6.99 (d, 1H), 7.20 (d, 1H), 7.27 (d, 2H), 7.29 (d, 2H), 7.34 (d, 1H), 7.39 (s, 1H), 7.40 (d, 2H), 7.54 (d, 2H), 7.61 (d, 2H), 7.88 (d, 2H), 7.89 (d, 2H), 8.51 (d, 1H), 8.52 (t, 1H).

EXAMPLE 338 tert-butyl 3-((4-((((4'-fluoro-1,1'-biphenyl-4-yl) carbonyl)amino)sulfonyl)-2-nitrophenyl)amino)-4-(phenylthio)butanoate

EXAMPLE 338A tert-butyl 3-((4-(aminosulfonyl)-2-nitrophenyl) amino)-4-(phenylthio)butanoate The desired product was prepared by substituting Fmoc-DL-Asp(OtBu)-OH for Fmoc-D-Asp(OtBu)-OH in Examples 122A–122D.

EXAMPLE 338B tert-butyl 3-((4-((((4'-fluoro-1,1'-biphenyl-4-yl) carbonyl)amino)sulfonyl)-2-nitrophenyl)amino)-4-(phenylthio)butanoate The desired product was prepared by substituting Example 338A for Example 1C in Example 1D. MS (ESI (−)) m/e 664 (M−H)⁻; ¹H NMR (300 MHz, methanol-d₄) δ8.73 (d, 1H), 8.58 (d, 1H), 7.95 (dd, 1H), 7.93 (d, 2H), 7.70 (m, 4H), 7.28 (m, 2H), 7.23–7.12 (m, 5H), 6.98 (d, 1H), 4.40 (m, 1H), 2.78 (m, 2H), 1.36 (s, 9H), and remaining two protons are buried under solvent peaks (3.35–3.28 ppm).

EXAMPLE 339

N-(4-(2-formylquinolin-8-yl)benzoyl)-3-nitro-4-((2-(phenylthio)ethyl)amino)benzenesulfonamide

EXAMPLE 339A 2-formylquinolin-8-yl trifluoroacetate

The desired product was prepared by substituting 8-hydroxyquinoline-2-carboxaldehyde for vanillin in Example 122H.

EXAMPLE 339B

N-(4-(2-formylquinolin-8-yl)benzoyl)-3-nitro-4-((2-(phenylthio)ethyl)amino)benzenesulfonamide The desired product was prepared by substituting Example 339A for Example 389A in Example 389B. MS (ESI(−)) m/e 611 (M−H)⁻; ¹H NMR (500 MHz, DMSO-d₆) δ9.97 (s, 1H), 8.66 (d, 1H), 8.54 (d, 1H), 8.52 (t, 1H), 8.12 (dd, 1H), 8.02 (d, 2H), 7.95 (s, 1H), 7.93 (dt, 1H), 7.87 (dd, 1H), 7.72 (d, 2H), 7.41 (td, 2H), 7.32 (t, 2H), 7.21 (tt, 1H), 7.01 (d, 1H), 3.62 (q, 2H), 3.28 (t, 2H).

EXAMPLE 340

3-nitro-4-((2-(phenylthio)ethyl)amino)-N-(4-(1-(pyridin-3-ylmethyl)-1,2,3,6-tetrahydropyridin-4-yl) benzoyl)benzenesulfonamide

EXAMPLE 340A

N-((3-nitro-4-((2-(phenylsulfanyl)ethyl)amino) phenyl)sulfonyl)-4-(1,2,3,6-tetrahydropyridin-4-yl) benzamide A room temperature mixture of Example 455C in TFA (10 mL) and dichloromethane (10 mL) was stirred for 30 minutes and concentrated to provide the desired product. MS (ESI(+)) m/e 539 (M+H)⁺.

EXAMPLE 340B 3-nitro-4-((2-(phenylthio)ethyl)amino)-N-(4-(1-(pyridin-3-ylmethyl)-1,2,3,6-tetrahydropyridin-4-yl) benzoyl)benzenesulfonamide A mixture of Example 340A (65 mg, 0.1 mmol), NaBH₃CN (48 mg, 0.75 mmol), 2N NaOH (0.15 mL), and 3-pyridinecarboxaldehyde (214 mg, 2 mmol) in acetic acid (0.5 mL) and methanol (1 mL) was stirred for 16 hours. The reaction mixture was concentrated, dissolved in 1:1 DMSO/methanol (1.0 mL) and purified by reverse phase preparative HPLC using 20–90% acetonitrile/water containing 0.1% TFA to provide the desired product. MS (ESI(−)) m/e 628 (M−H)⁻; ¹H NMR (300 MHz, DMSO-d₆) δ8.78 (br t, 1H), 8.70 (d, 1H), 8.70 (dd, 1H), 8.60 (d, 1H), 8.05 (m, 1H), 7.95 (d, 2H), 7.62 (d, 2H), 7.60 (dd, 1H), 7.40–7.15 (m, 6H), 6.35 (m, 1H), 4.52 (d, 2H), 3.92 (m, 4H), 3.45 (t, 4H), 2.82 (m, 2H).

EXAMPLE 341

3-(5-(4-((((3-nitro-4-((2-(phenylthio)ethyl)amino) phenyl)sulfonyl)amino)carbonyl)phenyl)-1,3-benzothiazol-2-yl)-N-(thien-2-ylmethyl) propanamide The desired product was prepared by substituting thiophene-2-methylamine for piperidine in Example 320. MS (ESI) m/e 756, 758 (M−H)⁻, (M+H)⁺; ¹H NMR (300 MHz, DMSO-d₆) δ2.18 (t, 2H), 2.74 (t, 2H), 3.28 (t, 2H), 3.63 (dt, 2H), 4.44 (d, 2H), 6.88–6.95 (m, 2H), 7.08 (d, 1H), 7.19 (t, 2H), 7.29 (t, 2H), 7.35 (dd, 1H), 7.39 (d, 2H), 7.75 (dd, 1H), 7.78 (d, 2H), 7.92 (dd, 1H), 7.99 (d, 2H), 8.12 (d, 1H), 8.21 (s, 1H), 8.56 (d, 1H), 8.58–8.65 (m, 2H).

EXAMPLE 342

N-(4-(4-methylpyridin-2-yl)benzoyl)-3-nitro-4-((2-(phenylthio)ethyl)amino)benzenesulfonamide The desired product was prepared by substituting 2-chloro-4-methylpyridine for 2,8-bistrifluoromethyl-3-chloroquinoline in Example 319. MS (ESI) m/e 549, 547 (M+H)⁺, (M−H)⁻; ¹H NMR(500 MHz, DMSO-d₆) δ8.78 (t, 1H), 8.64 (d, 1H), 8.54 (d, 1H), 8.19 (d, 2H), 7.98 (d, 2H), 7.94 (dd, 1H), 7.92 (d, 1H), 7.37 (dt, 2H), 7.27 (td, 2H), 7.25 (dd, 1H), 7.22 (d, 1H), 7.17 (tt, 1H), 3.67 (q, 2H), 3.29 (t, 2H), 2.40 (s, 3H).

EXAMPLE 343

N-(4-(2-butyl-1-cyclopentyl-1H-benzimidazol-5-yl) benzoyl)-3-nitro-4-((2-(phenylthio)ethyl)amino) benzenesulfonamide

EXAMPLE 343A 4-bromo-N¹-cyclopentylbenzene-1,2-diamine

The desired product was prepared by substituting cyclopentylamine for butylamine in Examples 166A and 166B.

EXAMPLE 343B 5-bromo-2-butyl-1-cyclopentyl-1H-benzimidazole

Valeric acid (8 mL) and Example 343A (250 mg, 0.98 mmol) was heated to 160° C. for 18 hours, treated with 1M NaOH (10 mL), extracted with ethyl acetate (3×50 mL), washed with brine (10 mL), dried (Na$_2$SO$_4$), filtered, and concentrated to provide the desired product.

EXAMPLE 343C

N-(4-(2-butyl-1-cyclopentyl-1H-benzimidazol-5-yl)benzoyl)-3-nitro-4-((2-(phenylthio)ethyl)amino)benzenesulfonamide The desired product was prepared by substituting Example 343B and Example 214E for 6-bromoindole and 4-(dihydroxyboryl)benzoic acid, respectively, in Example 4A. MS (ESI(+)) m/e 698 (M+H)$^+$; $^1$H NMR (300 MHz, DMSO-d$_6$) δ0.95 (t, 3H), 1.43 (dt, 2H), 1.76 (m, 4H), 2.00 (m, 2H), 2.11 (m, 4H), 2.94 (t, 2H), 3.27 (t, 2H), 3.62 (dt, 2H), 4.93 (tt, 1H), 7.04 (d, 1H), 7.19 (t, 1H), 7.30 (t, 2H), 7.39 (d, 1H), 7.45–7.64 (m, 4H), 7.69 (d, 2H), 7.90 (dd, 1H), 7.95 (d, 2H), 8.54 (d, 1H), 8.58 (t, 1H).

EXAMPLE 344

N-(4-(6-chloropyrazin-2-yl)benzoyl)-3-nitro-4-((2-(phenylthio)ethyl)amino)benzenesulfonamide The desired product was prepared by substituting 2,6-dichloropyrazine for 2,8-bistrifluoromethyl-3-chloroquinoline in Example 319. MS (ESI(+)) m/e 570, 568 (M+H)$^+$, (M−H)$^−$; $^1$H NMR (500 MHz, DMSO-d$_6$) δ9.35 (s, 1H), 8.81 (s, 1H), 8.78 (t, 1H), 8.64 (d, 1H), 8.24 (d, 2H), 8.04 (d, 2H), 7.94 (dd, 1H), 7.37 (dt, 2H), 7.27 (td, 2H), 7.22 (d, 1H), 7.17 (tt, 1H), 3.68 (q, 2H), 3.29 (t, 2H).

EXAMPLE 345 tert-butyl 5-((4-((((4'-fluoro-1,1'-biphenyl-4-yl)carbonyl)amino)sulfonyl)-2-nitrophenyl)amino)-6-(phenylthio)hexylcarbamate

EXAMPLE 345A 9H-fluoren-9-ylmethyl 1-(hydroxymethyl)-5-(tert-butoxycarbonylamino)pentylcarbamate The desired product was prepared by substituting Fmoc-DL-Lys(BOC)-OH for Fmoc-D-Asp(OtBu)-OH in Example 122A.

EXAMPLE 345B 9H-fluoren-9-ylmethyl1-(phenylthiomethyl)-5-(tert-butoxycarbonylamino)pentylcarbamate The desired product was prepared by substituting Example 345A for Example 122A in Example 122B.

EXAMPLE 345C tert-butyl 5-((4-(aminosulfonyl-2-nitrophenyl)amino)-6-(phenylthio)hexylcarbamate The desired product was prepared by substituting Example 345B for Example 122B in Example 122D.

EXAMPLE 345D tert-butyl 5-((4-((((4'-fluoro-1,1'-biphenyl-4-yl)carbonyl)amino)sulfonyl)-2-nitrophenyl)amino)-6-(phenylthio)hexylcarbamate The desired product was prepared by substituting Example 345C for Example 1C in Example 1D. MS (ESI(−)) m/e 721 (M−H)$^−$; $^1$H NMR (300 MHz, DMSO-d$_6$) δ8.48 (d, 1H), 8.17 (d, 1H), 7.97 (d, 2H), 7.82 (dd, 1H), 7.73 (m, 2H), 7.61 (d, 2H), 7.32–7.10 (m, 8H), 4.12 (m, 1H), 3.67 (m, 2H), 2.74 (m, 2H), 1.75 (m, 2H), 1.53 (m, 2H), 1.40 (m, 2H) 1.32 (s, 9H).

EXAMPLE 346 ethyl N-(((2-((4-((((4'-fluoro-1,1'-biphenyl-4-yl)carbonyl)amino)sulfonyl)-2-nitrophenyl)amino)-3-(phenylthio)propyl)amino)carbonyl)glycinate The desired product was prepared by substituting ethyl isocyanatoacetate for acetyl chloride in Example 310. MS (ESI(−)) m/e 708 (M−H)$^−$; $^1$H NMR (300 MHz, DMSO-d$_6$) δ8.59 (d, 1H), 8.42 (d, 1H), 7.97 (d, 2H), 7.87 (dd, 1H), 7.78 (m, 4H), 7.35–7.10 (m, 7H), 6.55 (t, 1H), 6.29 (t, 1H), 4.34 (m, 1H), 4.02 (q, 2H), 3.72 (d, 2H), 3.37 (m, 2H, 1.17 (t, 3H), and remaining protons (4) are buried under solvent peaks.

EXAMPLE 347 methyl 5-ethyl-2-(4-((((3-nitro-4-((2-(phenylthio)ethyl)amino)phenyl)sulfonyl)amino)carbonyl)phenyl)-1,3-thiazole-4-carboxylate

EXAMPLE 347A 4-(5-ethyl-4-(methoxycarbonyl)-1,3-thiazol-2-yl)benzoic acid

The desired product was prepared by substituting methyl 2-bromo-5-ethylthiazole-4-carboxylate (prepared according to the procedure described in *J. Chem. Soc. Perkin I* 1982, 159–164) for 6-bromoindole in Example 4A.

EXAMPLE 347B methyl 5-ethyl-2-(4-((((3-nitro-4-((2-(phenylthio)ethyl)amino)phenyl)sulfonyl)amino)carbonyl)phenyl)-1,3-thiazole-4-carboxylate The desired product was prepared by substituting Example 347A and Example 77B for Example 1B and Example 1C, respectively, in Example 1D. MS (ESI) m/e 625, 627 (M−H)$^−$, (M+H)$^+$; $^1$H NMR (300 MHz, DMSO-d$_6$) δ1.31 (t, 3H), 3.25 (t, 2H), 3.28 (q, 2H), 3.62 (dt, 2H), 3.86 (s, 3H), 7.03 (d, 1H), 7.19 (t, 1H), 7.30 (t, 2H), 7.39 (d, 2H), 7.88 (d, 2H), 7.99 (d, 2H), 8.54 (d, 1H), 8.56 (t, 1H).

EXAMPLE 348

N,N-dimethyl-4-(4-((((3-nitro-4-((2-(phenylthio)ethyl)amino)phenyl)sulfonyl)amino)carbonyl)phenyl)-1H-pyrazole-1-sulfonamide

EXAMPLE 348A 4-iodo-N,N-dimethyl-1H-pyrazole-1-sulfonamide

The desired product was prepared by substituting dimethylaminosulfonyl chloride for 1-bromooctane in Example 198A. MS (ESI(−)) m/e 300 (M−H)$^−$.

EXAMPLE 348B 4-(1-((dimethylamino)sulfonyl)-1H-pyrazol-4-yl)benzoic acid

The desired product was prepared by substituting Example 348A for 6-bromoindole in Example 4A. MS (ESI(−)) m/e 294 (M−H)$^−$.

EXAMPLE 348C

N,N-dimethyl-4-(4-((((3-nitro-4-((2-(phenylthio)
ethyl)amino)phenyl)sulfonyl)amino)carbonyl)
phenyl)-1H-pyrazole-1-sulfonamide The desired product was prepared by substituting Example 348B and Example 77B for Example 1B and Example 1C, respectively, in Example 1D. MS (ESI(−)) m/e 629 (M−H)⁻; ¹H NMR (300 MHz, DMSO-d₆) δ2.89 (s, 6H), 3.28 (t, 2H), 3.61 (dt, 2H), 3.64 (dt, 2H), 7.01 (d, 1H), 7.20 (t, 1H), 7.30 (t, 2H), 7.40 (d, 2H), 7.72 (d, 2H), 7.89 (d, 1H), 7.90 (d, 2H), 8.41 (s, 1H), 8.51 (d, 1H), 8.54 (t, 1H), 8.78 (s, 1H).

EXAMPLE 349

N-(4-(1-cyclopentyl-1H-benzimidazol-5-yl)
benzoyl)-3-nitro-4-((2-(phenylthio)ethyl)amino)
benzenesulfonamide

EXAMPLE 349A 4-bromo-N¹-cyclopentylbenzene-1,2-diamine

The desired product was prepared by substituting cyclopentylamine for butylamine in Examples 166A and 166B.

EXAMPLE 349B 5-bromo-1-cyclopentyl-1H-benzimidazole

The desired product was prepared by substituting Example 349A for Example 170A in Example 170B.

EXAMPLE 349C

N-(4-(1-cyclopentyl-1H-benzimidazol-5-yl)
benzoyl)-3-nitro-4-((2-(phenylthio)ethyl)amino)
benzenesulfonamide The desired product was prepared by substituting Example 349B and Example 214E for 6-bromoindole and 4-(dihydroxyboryl)benzoic acid, respectively, in Example 4A. MS (ESI) m/e 640, 642 (M−H)⁻, (M+H)⁺; ¹H NMR (300 MHz, DMSO-d₆) δ1.75 (m, 2H), 1.85–2.06 (m, 4H), 2.23 (m, 2H), 3.28 (t, 2H), 3.61 (dt, 2H), 4.89 (tt, 1H), 6.99 (d, 1H), 7.19 (t, 1H), 7.31 (t, 2H), 7.38 (d, 2H), 7.53 (dd, 1H), 7.56–7.72 (m, 4H), 7.88 (dd, 1H), 7.95 (t, 2H), 8.35 (s, 1H), 8.53 (t, 1H), 8.54 (d, 1H).

EXAMPLE 350

3-(5-(4-((((4-((1-adamantylmethyl)amino)-3-
nitrophenyl)sulfonyl)amino)carbonyl)phenyl)-1,3-
benzothiazol-2-yl)-N-(thien-2-ylmethyl)
propanamide

EXAMPLE 350A 3-(5-bromo-1,3-benzothiazol-2-yl)-N-(thien-2-
ylmethyl)propanamide The desired product was prepared by substituting Example 320B and thiophene-2-methylamine for Example 1B and Example 1C, respectively, in Example 1D.

EXAMPLE 350B 4-(2-(3-oxo-3-((thien-2-ylmethyl)amino)propyl)-1,3-
benzothiazol-5-yl)benzoic acid The desired product was prepared by substituting Example 350A for 6-bromoindole in Example 4A.

EXAMPLE 350C 3-(5-(4-((((4-((1-adamantylmethyl)amino)-3-
nitrophenyl)sulfonyl)amino)carbonyl)phenyl)-1,3-
benzothiazol-2-yl)-N-(thien-2-ylmethyl)
propanamide The desired product was prepared by substituting Example 350B and Example 28A for Example 1B and Example 1C, respectively, in Example 1D. MS (ESI) m/e 768, 770 (M−H)⁻, (M+H)⁺; ¹H NMR (300 MHz, DMSO-d₆) δ1.54–1.75 (m, 13H), 1.94–2.02 (m, 2H), 3.14 (d, 2H), 3.75 (t, 2H), 4.44 (d, 2H), 6.88–6.96 (m, 2H), 7.16 (d, 1H), 7.35 (dd, 1H), 7.68–7.76 (m, 3H), 7.89 (dd, 1H), 7.98 (d, 2H), 8.11 (d, 1H), 8.18 (s, 1H), 8.39 (t, 1H), 853 (d, 1H), 8.63 (t, 1H).

EXAMPLE 351

N-(4-(2-formyl-3-methyl-1-benzothien-5-yl)
benzoyl)-3-nitro-4-((2-(phenylthio)ethyl)amino)
benzenesulfonamide

EXAMPLE 351A 5-chloro-3-methyl-2-vinyl-1-benzothiophene

A solution of 2-bromo-5-chloro-3-methylbenzthiophene (5 g, 19.1 mmol), vinyltributylstannane (5.59 mL, 19.1 mmol), Pd₂dba₃ (525 mg, 0.57 mmol), and tri(2-furyl)phosphine (532 mg, 2.29 mmol) in NMP (70 mL) at 90° C. was stirred for 18 hours and concentrated. The concentrate was purified by flash column chromatography on silica gel with hexanes to provide the desired product. MS (ESI(−)) m/e 207 (M−H)⁻.

EXAMPLE 351B methyl 4-(3-methyl-2-vinyl-1-benzothien-5-yl)
benzoate

The desired product was prepared by substituting Example 351A for 5-chloro-2-methyl-1,3-benzoxazole in Example 54A. MS (ESI(+)) m/e 310 (M+H)⁺.

EXAMPLE 351C methyl 4-(2-formyl-3-methyl-1-benzothien-5-yl)
benzoate

A mixture of Example 351B (900 mg, 3 mmol), 0.08M OsO₄ in tert-butanol (4 mL) and N-morpholine-N-oxide (352 mg, 3 mmol) in THF (25 mL) and water (10 mL) at room temperature was stirred for 18 hours and partitioned between water and ethyl acetate. The organic phase was concentrated and the concentrate was purified by flash column chromatography on silica gel with 50% ethyl acetate/hexanes.

A mixture of the purified product (500 mg, 1.5 mmol) and NaIO₄ (500 mg, 2.3 mmol) in 1:1 THF/water (40 mL) at room temperature was stirred for 3 hours, poured into 1M HCl, and extracted with ethyl acetate (3×). The combined extracts were washed with brine and concentrated.

EXAMPLE 351D 4-(2-formyl-3-methyl-1-benzothien-5-yl)benzoic
acid

The desired product was prepared by substituting Example 351C for Example 1A in Example 1B. MS (ESI(−)) m/e 295 (M−H)⁻.

EXAMPLE 351E

N-(4-(2-formyl-3-methyl-1-benzothien-5-yl)benzoyl)-3-nitro-4-((2-(phenylthio)ethyl)amino)benzenesulfonamide The desired product was prepared by substituting Example 351D and Example 77B for Example 1B and Example 1C, respectively, in Example 1D. MS (ESI(−)) m/e 630 (M−H)⁻; $^1$H NMR (300 MHz, DMSO-d$_6$) δ2.89 (d, 3H), 3.29 (t, 2H), 3.69 (dt, 2H), 7.19 (m, 2H), 7.26 (dd, 2H), 7.38 (d, 2H), 7.95 (m, 4H), 8.00 (dd, 2H), 8.16 (d, 1H), 8.39 (d, 1H), 8.63 (d, 1H), 8.79 (dd, 1H), 10.38 (s, 1H).

EXAMPLE 352

N-(4-(4-(cyclohexylcarbonyl)piperazin-1-yl)benzoyl)-3-nitro-4-((2-(phenylthio)ethyl)amino)benzenesulfonamide The desired product was prepared by substituting cyclohexanoyl chloride for 2-methoxyethyl chloroformate in Example 325. MS (ESI(−))m/e 650 (M−H)⁻; $^1$H NMR (300 MHz, DMSO-d$_6$) δ8.76 (t, 1H), 8.59 (d, 1H), 7.91 (dd, 1H), 7.76 (d, 2H), 7.39–7.34 (m, 2H), 7.29–7.24 (m, 2H), 7.21–7.14 (m, 2H), 6.94 (d, 2H), 3.70–3.56 (m, 4H), 3.32–3.23 (m, 8H), 2.60–2.56 (m, 1H), 1.72–1.63 (m, 4H), 1.36–1.17 (m, 6H).

EXAMPLE 353 dimethyl 1-(2-((4-(((((4'-fluoro-1,1'-biphenyl-4-yl)carbonyl)amino)sulfonyl)-2-nitrophenyl)amino)-3-(phenylthio)propyl)-1H-1,2,3-triazole-4,5-dicarboxylate A solution of Example 434D (40 mg) and dimethyl acetylenedicarboxylate (100 mg) in toluene (2 mL) was heated to 90° C. for 16 hours and purified by flash column chromatography on silica gel with 30–100% ethyl acetate/hexanes to provide the desired product. MS (ESI(−)) m/e 747 (M−H)⁻; $^1$H NMR (300 MHz, DMSO-d$_6$) δ8.45 (d, 1H), 8.17 (d, 1H), 7.94 (d, 2H), 7.73 (m, 3H), 7.59 (d, 2H), 7.32–7.15 (m, 8H), 5.00 (m, 2H), 4.51 (m, 1H), 3.80 (s, 3H), 3.75 (s, 3H), 3.45 (m, 2H).

EXAMPLE 354

N-(4-(2-(3-(4-methylpiperazin-1-yl)-3-oxopropyl)-1,3-benzothiazol-5-yl)benzoyl)-3-nitro-4-((2-(phenylthio)ethyl)amino)benzenesulfonamide The desired product was prepared by substituting 1-methylpiperazine for piperidine in Example 320. MS (ESI) m/e 743, 745 (M−H)⁻, (M+H)⁺; $^1$H NMR (300 MHz, DMSO-d$_6$) δ2.43 (s, 3H), 2.68 (m, 4H), 2.97 (t, 2H), 3.17 (d, 2H), 3.27 (t, 2H), 3.38)t, 2H), 3.61 (m, 4H), 4.44 (d, 2H), 6.99 (d, 1H), 7.21 (tt, 2H), 7.32 (t, 2H), 7.40 (dd, 2H), 7.71 (d, 1H), 7.74 (dd, 1H), 7.88 (dd, 1H), 7.98 (d, 2H), 8.10 (d, 1H), 8.18 (d, 1H), 8.62 (t, 1H), 8.63 (d, 1H).

EXAMPLE 355

4-((2-adamantylmethyl)amino)-N-(4-(2-aminoquinolin-8-yl)benzoyl)-3-nitrobenzenesulfonamide

EXAMPLE 355A 2-aminoquinolin-8-yl trifluoroacetate

The desired product was prepared by substituting 2-amino-8-hydroxyquinoline for vanillin in Example 122H.

EXAMPLE 355B 4-((2-adamantylmethyl)amino)-N-(4-(2-aminoquinolin-8-yl)benzoyl)-3-nitrobenzenesulfonamide The desired product was prepared by substituting Example 255A and Example 355A for Example 108A and Example 389A, respectively, in Example 389B. MS (ESI (−)) m/e 610 (M−H)⁻; $^1$H NMR (400 MHz, DMSO-d$_6$) δ8.73 (d, 1H), 8.50 (t, 1H), 8.12 (br s, 1H), 7.97 (d, 2H), 7.93 (dd, 1H), 7.77 (br s, 1H), 7.62 (d, 2H), 7.53 (d, 1H), 7.32 (br s, 1H), 7.30 (d, 1H), 6.90 (br s, 1H), 3.17 (d, 2H), 1.98 (m, 3H), 1.72–1.55 (m, 12H).

EXAMPLE 356

N-((4'-fluoro-1,1'-biphenyl-4-yl)carbonyl)-4-((3-hydroxy-1-((phenylthio)methyl)propyl)amino)-3-nitrobenzenesulfonamide

EXAMPLE 356A 3-((4-(aminosulfonyl)-2-nitrophenyl)amino)-4-(phenylthio)butanoic acid The desired product was prepared by substituting Fmoc-DL-Asp(OtBu)-OH for Fmoc-D-Asp(OtBu)-OH in Examples 122A–122E.

EXAMPLE 356B

N-((4'-fluoro-1,1'-biphenyl-4-yl)carbonyl)-4-((3-hydroxy-1-((phenylthio)methyl)propyl)amino)-3-nitrobenzenesulfonamide The desired product was prepared by substituting Example 356A for Example 122E in Example 280. MS (ESI(−)) m/e 594 (M−H)⁻; $^1$H NMR (500 MHz, methanol-d$_4$) δ8.72 (d, 1H), 7.92 (m, 3H), 7.70 (m, 4H), 7.26 (m, 2H), 7.18 (tt, 2H), 7.11 (m, 3H), 7.00 (d, 1H), 4.25 (m, 1H), 3.68 (m, 2H), 3.39 (d, 1H), 3.21 (m, 3H), 2.08 (m, 1H), 1,97 (m, 1H).

EXAMPLE 357 methyl 4-(4-(((((3-nitro-4-((2-(phenylthio)ethyl)amino)phenyl)sulfonyl)amino)carbonyl)phenyl)-3,6-dihydropiridine-1(2H)-carboxylate The desired product was prepared by substituting methyl chloroformate for 4-morpholinecarbonyl chloride in Example 317. MS (ESI(−)) m/e 595 (M−H)⁻; $^1$H NMR (300 MHz, DMSO-d$_6$) δ8.78 (br t, 1H), 8.60 (d, 1H), 7.92 (dd, 1H), 7.85 (d, 2H), 7.55 (d, 2H), 7.40–7.15 (m, 6H), 6.35 (m, 1H), 4.08 (d, 2H), 3.70 (m, 2H), 3.62 (s, 3H), 3.60 (t, 2H), 3.40–3.25 (m, 4H).

EXAMPLE 358

N-(4-(4-((benzyloxy)acetyl)piperazin-1-yl)benzoyl)-3-nitro-4-((2-(phenylthio)ethyl)amino)benzenesulfonamide The desired product was prepared by substituting benzyloxyacetyl chloride for 2-methoxyethyl chloroformate in Example 325. MS (ESI(−)) m/e 688 (M−H)⁻; $^1$H NMR (300 MHz, DMSO-d$_6$) δ8.74 (t, 1H), 8.59 (d, 1H), 7.90 (dd, 1H), 7.76 (d, 2H), 7.39–7.14 (m, 11H), 6.94 (d, 2H), 4.52 (s, 2H), 4.24 (s, 2H), 3.66 (q, 2H), 3.70–3.56 (m, 4H), 3.32–3.23 (m, 6H).

EXAMPLE 359

N-(4-(1-(2,2-dimethylpropanoyl)-1,2,3,6-tetrahydropyridin-4-yl)benzoyl)-3-nitro-4-((2-(phenylthio)ethyl)amino)benzenesulfonamide The desired product was prepared by substituting trimethylacetyl chloroformate for 4-morpholinecarbonyl chloride in Example 317. MS (ESI(−)) m/e 621 (M−H)$^-$; $^1$H NMR (300 MHz, DMSO-d$_6$) δ8.78 (br t, 1H), 8.60 (d, 1H), 7.92 (dd, 1H), 7.85 (d, 2H), 7.55 (d, 2H), 7.40–7.15 (m, 6H), 6.35 (m, 1H), 4.18 (d, 2H), 3.75 (t, 2H), 3.70 (m, 2H), 3.40–3.25 (m, 4H), 1.25 (s, 9H).

EXAMPLE 360

N-(4-(2-((ethylthio)methyl)-1,3-benzothiazol-5-yl)benzoyl)-3-nitro-4-((2-(phenylthio)ethyl)amino)benzenesulfonamide The desired product was prepared by substituting diethyl disulfide for allyl bromide in Example 213. MS (ESI) m/e 663, 665 (M−H)$^-$, (M+H)$^+$; $^1$H NMR (300 MHz, DMSO-d$_6$) δ1.22 (t, 3H), 2.61 (q, 2H), 3.27 (t, 2H), 3.62 (dt, 2H), 4.25 (s, 2H), 7.03 (d, 1H), 7.19 (tt, 1H), 7.30 (td, 2H), 7.40 (dd, 1H), 7.75 (d, 2H), 7.76 (dd, 1H), 7.90 (dd, 1H), 7.98 (d, 2H), 8.14 (d, 1H), 8.23 (d, 1H), 8.54 (d, 1H), 8.56 (t, 1H).

EXAMPLE 361

N-(4-(1-cyclopentyl-2-(2-methoxyethyl)-1H-benzimidazol-5-yl)benzoyl)-3-nitro-4-((2-(phenylthio)ethyl)amino)benzenesulfonamide The desired product was prepared by substituting 3-methoxypropionic acid for valeric acid in Example 343. MS (ESI) m/e 698, 700 (M−H)$^-$, (M+H)$^+$; $^1$H NMR (300 MHz, DMSO-d$_6$) δ1.76 (m, 2H), 1.99 (m, 2H), 2.12 (m, 4H), 3.19 (t, 2H), 3.26 (t, 2H), 3.28 (s, 3H), 3.62 (dt, 2H), 3.38 (t, 2H), 4.96 (tt, 1H), 7.02 (d, 1H), 7.20 (tt, 1H), 7.31 (td, 2H), 7.40 (dd, 2H), 7.48 (dd, 1H), 7.57 (d, 1H), 7.65 (d, 2H), 7.85 (d, 2H), 7.89 (dd, 1H), 7.96 (d, 2H), 8.53 (d, 1H), 8.55 (t, 1H).

EXAMPLE 362

N-((2'-methoxy-4'-(3-(4-methylpiperazin-1-yl)-3-oxopropyl)-1,1'-biphenyl-4-yl)carbonyl)-3-nitro-4-((2-(phenylthio)ethyl)amino)benzenesulfonamide

EXAMPLE 362A methyl 2'-methoxy-4'-(3-(4-methylpiperazin-1-yl)-3-oxopropyl)-1,1'-biphenyl-4-carboxylate The desired product was prepared by substituting 1-methylpiperazine for morpholine in Example 122M. MS (ESI(−)) m/e 716 (M−H)$^-$; $^1$H NMR (300 MHz, DMSO-d$_6$) δ8.79 (t, 1H), 8.63 (d, 1H), 7.94 (dd, 1H), 7.88 (d, 2H), 7.57 (d, 2H), 7.37 (m, 2H), 7.30–7.14 (m, 5H), 7.02 (d, 1H), 6.92 (dd, 1H), 3.76 (s, 3H), 3.67 (q, 2H), 3.44 (m, 4H), 3.28 (t, 2H), 2.85 (t, 2H), 2.80 (s, 3H), 2.72 (t, 2H), and the 8 remaining protons are buried under a very broad water peak (3.75–3.40 ppm).

EXAMPLE 362B

N-((2'-methoxy-4'-(3-(4-methylpiperazin-1-yl)-3-oxopropyl)-1,1'-biphenyl-4-yl)carbonyl)-3-nitro-4-((2-(phenylthio)ethyl)amino)benzenesulfonamide The desired product was prepared by substituting Example 362A and Example 77B for Example 5C and Example 3A, respectively, in Example 5D.

EXAMPLE 363

N-(4-(1-methyl-1H-benzimidazol-5-yl)benzoyl)-3-nitro-4-((2-(phenylthio)ethyl)amino)benzenesulfonamide The desired product was prepared by substituting methylamine for cyclopentylamine in Example 349. MS (ESI) m/e 586, 588 (M−H)$^-$, (M+H)$^+$; $^1$H NMR (300 MHz, DMSO-d$_6$) δ3.28 (t, 2H), 3.60 (dt, 2H), 3.87 (s, 3H), 6.98 (d, 1H), 7.19 (tt, 1H), 7.32 (t, 2H), 7.40 (d, 2H), 7.47–7.68 (m, 5H), 7.88 (dd, 1H), 7.95 (t, 2H), 8.21 (s, 1H), 8.51 (t, 1H), 8.52 (d, 1H),

EXAMPLE 364 ethyl 4-(4-((((3-nitro-4-((2-(phenylthio)ethyl)amino)phenyl)sulfonyl)amino)carbonyl)phenyl)piperazine-1-carboxylate The desired product was prepared by substituting benzyloxyacetyl chloride for 2-methoxyethyl chloroformate in Example 325. MS (ESI(−)) m/e 612 (M−H)$^-$; $^1$H NMR (300 MHz, DMSO-d$_6$) δ8.71 (t, 1H), 8.57 (d, 1H), 7.88 (dd, 1H), 7.76 (d, 2H), 7.39–7.35 (m, 2H), 7.23–7.29 (m, 2H), 7.20–7.14 (m, 2H), 6.92 (d, 2H), 4.06 (q, 2H), 3.65 (q, 2H), 3.50–3.46 (m, 4H), 3.32–3.23 (m, 6H), 1.20 (t, 3H).

EXAMPLE 365

N-(4-(3-methyl-2-vinyl-1-benzothien-5-yl)benzoyl)-3-nitro-4-((2-(phenylthio)ethyl)amino)benzenesulfonamide

EXAMPLE 365A 4-(3-methyl-2-vinyl-1-benzothien-5-yl)benzoic acid

The desired product was prepared by substituting Example 351B for Example 1A in Example 1B. MS (ESI(−)) m/e 293 (M−H)$^-$.

EXAMPLE 365B

N-(4-(3-methyl-2-vinyl-1-benzothien-5-yl)benzoyl)-3-nitro-4-((2-(phenylthio)ethyl)amino)benzenesulfonamide The desired product was prepared by substituting Example 365A and Example 77B for Example 1B and Example 1C, respectively, in Example 1D. MS (ESI(−)) m/e 628 (M−H)$^-$; $^1$H NMR (300 MHz, DMSO-d$_6$) δ2.49 (s, 3H), 3.29 (t, 2H), 3.69 (dt, 2H), 5.39 (d, 1H), 5.61 (d, 1H), 7.19 (m, 2H), 7.28 (dd, 2H), 7.38 (d, 2H), 7.74(dd, 1H), 7.90–8.08 (m, 8H), 8.53 (d, 1H), 8.80 (dd, 1H).

EXAMPLE 366

4-(4-((((3-nitro-4-((2-(phenylthio)ethyl)amino)phenyl)sulfonyl)amino)carbonyl)phenyl)-N-(2-phenylethyl)piperazine-1-carboxamide A solution of Example 173A (54.1 mg, 0.1 mmol) in NMP (2 mL) at room temperature was treated with phenethylisocyanate (0.2 mmol), stirred for 18 hours, diluted with water, and centrifuged. The solid was purified by flash column chromatography on silica gel with 0–5% methanol/dichloromethane to provide the desired product. MS (ESI(−)) m/e 687 (M−H)$^-$; $^1$H NMR (300 MHz, DMSO-d$_6$) δ8.75 (t, 1H), 8.58 (d, 1H), 7.90 (dd, 1H), 7.75 (d, 2H), 7.39–7.34 (m, 2H), 7.31–7.14 (m, 9H), 6.94 (d, 2H), 6.71 (t, 1H), 3.66 (q, 2H), 3.42–3.39 (m, 4H), 3.30–3.21 (m, 8H), 2.72 (dd, 2H).

EXAMPLE 367

N-(4-(2-(3-morpholin-4-yl-3-oxopropyl)-1,3-benzothiazol-5-yl)benzoyl)-3-nitro-4-((2(phenylthio)ethyl)amino)benzenesulfonamide The desired product was prepared by substituting morpholine for piperidine in Example 320. MS (ESI) m/e 730, 732 (M−H)⁻, (M+H)⁺; ¹H NMR (300 MHz, DMSO-d₆) δ2.95 (t, 3H), 3.27 (t, 2H), 3.36 (t, 2H), 3.42–3.65 (m, 10H), 6.99 (d, 1H), 7.22 (tt, 1H), 7.32 (td, 2H), 7.40 (dd, 2H), 7.72 (d, 2H), 7.74 (dd, 1H), 7.88 (dd, 1H), 7.98 (d, 2H), 8.10 (d, 1H), 8.18 (d, 1H), 8.52 (d, 1H), 8.52 (t, 1H).

EXAMPLE 368

3-nitro-N-(4-(1-pentyl-1H-pyrazol-4-yl)benzoyl)-4-((2-(phenylthio)ethyl)amino)benzenesulfonamide The desired product was prepared by substituting Example 322B and Example 77B for Example 1B and Example 1C, respectively, in Example 1D. MS (ESI(−)) m/e 592 (M−H)⁻; ¹H NMR (300 MHz, DMSO-d₆) δ0.85 (t, 3H), 1.25 (m, 4H), 1.80 (tt, 2H), 3.27 (t, 2H), 3.61 (dt, 2H), 4.09 (t, 2H), 7.00 (d, 1H), 7.20 (t, 1H), 7.30 (t, 2H), 7.40 (d, 2H), 7.51 (d, 2H), 7.87 (m, 4H), 8.21 (s, 1H), 8.51 (d, 1H), 8.54 (t, 1H).

EXAMPLE 369

N-(4-(1-benzyl-1H-pyrrol-3-yl)benzoyl)-3-nitro-4-((2-(phenylthio)ethyl)amino)benzenesulfonamide

EXAMPLE 369A 1-benzyl-2,5-dihydro-1H-pyrrol-3-yl trifluoroacetate

The desired product was prepared by substituting 1-benzyl-3-pyrrolidinone for 4-tert-butylcyclohexanone in Example 5A.

EXAMPLE 369B methyl 4-(1-benzyl-1H-pyrrol-3-yl)benzoate

The desired product was prepared by substituting Example 369A for Example 5A in Example 5B. MS (DCI (+)) m/e 292 (M+H)⁺.

EXAMPLE 369C

N-(4-(1-benzyl-1H-pyrrol-3-yl)benzoyl)-3-nitro-4-((2-(phenylthio)ethyl)amino)benzenesulfonamide The desired product was prepared by substituting Example 369B for Example 230B in Example 230C. MS (ESI(−)) m/e 611 (M−H)⁻; ¹H NMR (300 MHz, DMSO-d₆) δ8.78 (br t, 1H), 8.62 (d, 1H), 7.92 (dd, 1H), 7.80 (d, 2H), 7.60 (d, 2H), 7.50 (t, 1H), 7.40–7.15 (m, 11H), 6.92 (t, 1H), 6.55 (t, 1H), 5.10 (s, 2H), 3.65 (m, 2H), 3.35 (m, 2H).

EXAMPLE 370

(3R)-N-(tert-butyl)-3-((4-(((((4'-fluoro-1,1'-biphenyl-4-yl)carbonyl)amino)sulfonyl)-2-nitrophenyl)amino)-4-(phenylthio)butanamide

EXAMPLE 370A (3R)-3-((4-(aminosulfonyl)-2-nitrophenyl)amino)-N-(tert-butyl)-4-(phenylthio)butanamide The desired product was prepared by substituting tert-butylamine for dimethylamine in Example 122F.

EXAMPLE 370B (3R)-N-(tert-butyl)-3-((4-(((((4'-fluoro-1,1'-biphenyl-4-yl)carbonyl)amino)sulfonyl)-2-nitrophenyl)amino)-4-(phenylthio)butanamide The desired product was prepared by substituting Example 370A for Example 1C in Example 1D. MS (ESI (−)) m/e 663 (M−H)⁻; ¹H NMR (500 MHz, methanol-d₄) δ8.73 (d, 1H), 8.09 (d, 1H), 7.93 (dd, 1H), 7.67 (m, 4H), 7.32 (m, 2H), 7.20–7.10 (m, 4H), 6.97 (d, 1H), 4.40 (m, 1H), 3.36 (dd, 1H), 3.22 (dd, 1H), 2.62 (m, 2H), 1.22 (s, 9H).

EXAMPLE 371

4-((2-(((tert-butylamino)carbonyl)amino)-1-((phenylthio)methyl)ethyl)amino)-N-((4'-fluoro-1,1'-biphenyl-4-yl)carbonyl)-3-nitrobenzenesulfonamide The desired product was prepared by substituting tert-butyl isocyanate for acetyl chloride in Example 310. MS (ESI(−)) m/e 678 (M−H)⁻; ¹H NMR (400 MHz, methanol-d₄) δ8.76 (d, 1H), 7.93 (m, 3H), 7.72 (d, 1H), 7.69 (m, 2H), 7.31 (m, 2H), 7.22–7.10 (m, 5H), 7.04 (d, 1H), 4.16 (m, 1H), 3.38 (m, 2H), 3.17 (dd, 1H), 1.21 (s, 9H), and the remaining proton is buried under solvent peaks.

EXAMPLE 372

3-nitro-4-((2-(phenylthio)ethyl)amino)-N-(4-((1S,4R)-1,7,7-trimethylbicyclo(2.2.1)hept-2-yl)benzoyl)benzenesulfonamide

EXAMPLE 372A (1R,4R)-1,7,7-trimethylbicyclo(2.2.1)hept-2-en-2-yl trifluoroacetate The desired product was prepared by substituting camphor for 4-tert-butylcyclohexanone in Example 5A.

EXAMPLE 372B methyl 4-((1R,4R)-1,7,7-trimethylbicyclo(2.2.1)hept-2-en-2-yl)benzoate The desired product was prepared by substituting Example 372A for Example 5A in Example 5B. MS (DCI (+)) m/e 243 (M+H)⁺.

EXAMPLE 372C methyl 4-((1S,4R)-1,7,7-trimethylbicyclo(2.2.1)hept-2-yl)benzoate A mixture of Example 372B (100 mg) and 10% Pd/C (20 mg) in ethyl acetate (5 mL) and ethanol (5 mL) at room temperature was stirred under H₂ for 18 hours, filtered, and concentrated to provide the desired product. MS (DCI(+)) m/e 245 (M+H)⁺.

EXAMPLE 372D 3-nitro-4-((2-(phenylthio)ethyl)amino)-N-(4-((1S,4R)-1,7,7-trimethylbicyclo(2.2.1)hept-2-yl)benzoyl)benzenesulfonamide The desired product was prepared by substituting Example 372C for Example 230B in Example 230C. MS (ESI(−)) m/e 592 (M−H)⁻; ¹H NMR (300 MHz, DMSO-d₆) δ8.78 (br t, 1H), 8.60 (d, 1H), 7.92 (dd, 1H), 7.85 (d, 2H), 7.40–7.15 (m, 8H), 3.70 (m, 4H), 3.00(m, 1H), 2.30 (m, 1H), 1.95–1.10 (m, 6H), 1.00–0.70 (6s, 9H).

EXAMPLE 373 isopropyl 4-(4-((((3-nitro-4-((2-(phenylthio)ethyl) amino)phenyl)sulfonyl)amino)carbonyl)phenyl) piperazine-1-carboxylate The desired product was prepared by substituting isopropyl chloroformate for 2-methoxyethyl chloroformate in Example 325. MS (ESI(−)) m/e 626 (M−H)⁻; ¹H NMR (300 MHz, DMSO-d₆) δ8.74 (t, 1H), 8.58 (d, 1H), 7.90 (dd, 1H), 7.76 (d, 2H), 7.39–7.35 (m, 2H), 7.29–7.23 (m, 2H), 7.20–7.14 (m, 2H), 6.93 (d, 2H), 4.79 (hept, 2H), 4.06 (q, 2H), 3.66 (q, 2H), 3.50–3.44 (m, 4H), 3.32–3.23 (m, 6H), 1.20 (d, 6H).

EXAMPLE 374

N-(4-(2-cyanoquinolin-8-yl)benzoyl)-3-nitro-4-((2-(phenylthio)ethyl)amino)benzenesulfonamide

EXAMPLE 374A 2-cyanoquinolin-8-yl trifluoroacetate

The desired product was prepared by substituting 2-cyano-8-hydroxyquinoline for vanillin in Example 122H.

EXAMPLE 374B

N-(4-(2-cyanoquinolin-8-yl)benzoyl)-3-nitro-4-((2-(phenylthio)ethyl)amino)benzenesulfonamide The desired product was prepared by substituting Example 374A for Example 389A in Example 389B. MS (ESI(−)) m/e 626 (M−H)⁻; ¹H NMR (400 MHz, methanol-d₄) δ8.81 (d, 1H), 8.52 (d, 1H), 8.18 (d, 1H), 8.05 (m, 2H), 7.97–7.87 (m, 6H), 7.79 (m, 1H), 7.38 (m, 2H), 7.22 (tt, 2H), 7.17 (tt, 1H), 7.07 (d, 1H), 3.70 (q, 2H), 3.28 (t, 2H).

EXAMPLE 375

3-nitro-4-((2-(phenylthio)ethyl)amino)-N-(4-(1-(pyridin-4-ylmethyl)-1,2,3,6-tetrahydropyridin-4-yl) benzoyl)benzenesulfonamide The desired product was prepared by substituting 4-pyridinecarboxaldehyde for 3-pyridinecarboxaldehyde in Example 340B. MS (ESI(−)) m/e 628 (M−H)⁻; ¹H NMR (300 MHz, DMSO-d₆) δ8.78 (br t, 1H), 8.70 (d, 1H), 8.70 (dd, 1H), 8.60 (d, 1H), 8.05 (m, 1H), 7.95 (d, 2H), 7.62 (d, 2H), 7.60 (dd, 1H), 7.40–7.15 (m, 6H), 6.35 (m, 1H), 4.52 (d, 2H), 3.92 (m, 4H), 3.45 (t, 4H), 2.82 (m, 2H).

EXAMPLE 376

3-nitro-4-((2-(phenylthio)ethyl)amino)-N-(4-(1-(pyridin-2-ylmethyl)-1,2,3,6-tetrahydropyridin-4-yl) benzoyl)benzenesulfonamide The desired product was prepared by substituting 2-pyridinecarboxaldehyde for 3-pyridinecarboxaldehyde in Example 340B. MS (ESI(−)) m/e 628 (M−H)⁻; ¹H NMR (300 MHz, DMSO-d₆) δ8.78 (br t, 1H), 8.70 (d, 1H), 8.62 (d, 1H), 7.95 (dd, 1H), 7.92 (t, 1H), 7.90 (d, 2H), 7.62 (d, 2H), 7.58 (d, 1H), 7.50 (m, 1H), 7.40–7.15 (m, 6H), 6.35 (m, 1H), 4.52 (d, 2H), 3.92 (m, 2H), 3.65 (m, 2H), 3.55–3.35 (m 4H), 2.82 (m, 2H).

EXAMPLE 377 ethyl 4-(5-(4-((((3-nitro-4-((2-(phenylthio)ethyl) amino)phenyl)sulfonyl)amino)carbonyl)phenyl)-1,3-benzothiazol-2-yl)butanoate The desired product was prepared by substituting ethyl 3-bromopropionate for allyl bromide in Example 213. MS (ESI) m/e 703, 705 (M−H)⁻, (M+H)⁺; ¹H NMR (300 MHz, DMSO-d₆) δ1.19 (t, 3H), 2.08 (tt, 2H), 2.47 (t, 2H), 3.17 (t, 2H), 3.27 (t, 2H), 3.64 (dt, 2H), 4.07 (q, 2H), 7.09 (d, 1H), 7.18 (tt, 1H), 7.29 (td, 2H), 7.39 (d, 2H), 7.76 (d, 1H), 7.80 (d, 2H), 7.93 (dd, 1H), 7.98 (d, 2H), 8.18 (d, 1H), 8.27 (d, 1H), 8.57 (d, 1H), 8.64 (t, 1H).

EXAMPLE 378

N~2~-(tert-butoxycarbonyl)-N~1~-(1-(N-(tert-butoxycarbonyl)leucyl)-4-(4-((((3-nitro-4-((2-(phenylthio)ethyl)amino)phenyl)sulfonyl)amino) carbonyl)phenyl)-1,2,3,6-tetrahydropyridin-2-yl)-N~1~-(1-(N-(tert-butoxycarbonyl)leucyl)-4-(4-((((3-nitro-4-((2-(phenylthio)ethyl)amino)phenyl)sulfonyl) amino)carbonyl)phenyl)-1,2,5,6-tetrahydropyridin-2-yl)leucinamide A mixture of Example 340A (150 mg, 0.25 mmol), BOC-leucine (70 mg, 0.3 mmol), EDCI (77 mg, 0.40 mmol), HOBT (55 mg, 0.40 mmol), and diisopropylethylamine (0.2 mL) in THF (0.5 mL) at room temperature was stirred for 16 hours, diluted with ethyl acetate (50 mL), washed sequentially with 1N HCl (5 mL), water (30 mL) and brine (30 mL), dried (MgSO₄), filtered, and concentrated. The concentrate was purified by flash column chromatography on silica gel with 5% methanol/dichloromethane to provide the desired product. MS (ESI(−)) m/e 750 (M−H)⁻; ¹H NMR (300 MHz, DMSO-d₆) δ8.72 (br t, 1H), 8.60 (d, 1H), 7.92 (dd, 1H), 7.85 (d, 2H), 7.50 (br d, 1H), 7.55 (d, 2H), 7.40–7.15 (m, 6H), 6.35 (m, 1H), 4.50 (m, 1H), 4.18 (d, 2H), 3.65 (m, 4H), 3.40–3.25 (m, 4H), 1.65 (m, 1H), 1.35 (s, 9H), 0.95 (d, 6H).

EXAMPLE 379

3-methyl-5-(4-((((3-nitro-4-((2-(phenylthio)ethyl) amino)phenyl)sulfonyl)amino)carbonyl)phenyl)-1-benzothiophene-2-carboxamide A solution of Example 401D (100 mg, 0.16 mmol) in tert-butyl alcohol (5 mL) and water (0.5 mL) at room temperature was treated with KOH (500 mg, 8.90 mmol) and 18-crown-6 (400 mg, 1.51 mmol), heated to 100° C. for 90 minutes, treated with 1M HCl (20 mL), and extracted with 10% methanol/ethyl acetate (3×50 mL). The combined extracts were washed with brine (10 mL), dried (Na₂SO₄), filtered, and concentrated. The concentrate was purified by flash column chromatography on silica gel with 5–15% methanol/ethyl acetate to provide the desired product. MS (ESI) m/e 645, 647 (M−H)⁻, (M+H)⁺; ¹H NMR (300 MHz, DMSO-d₆) δ1.90 (s, 3H), 3.27 (t, 2H), 3.62 (dt, 2H), 6.98 (d, 1H), 7.20 (tt, 1H), 7.31 (td, 2H), 7.40 (dd, 1H), 7.68 (s, 2H), 7.74 (d, 2H), 7.80 (dd, 1H), 7.90 (dd, 1H), 7.99 (d, 2H), 8.04 (d, 1H), 8.14 (d, 1H), 8.50 (t, 1H), 8.52 (d, 1H).

EXAMPLE 380

N-(4-((((4'-fluoro-1,1'-biphenyl-4-yl)carbonyl) amino)sulfonyl)-2-nitrophenyl)adamantane-1-carboxamide

EXAMPLE 380A 4-amino-N-((4'-fluoro-1,1'-biphenyl-4-yl)carbonyl)-3-nitrobenzenesulfonamide A solution of Example 1D (1.0 g) in methanol (10 mL) and concentrated aqueous ammonia (3 mL) was heated in a sealed pressure tube to 60° C. for 16 hours, cooled to 0° C.,

EXAMPLE 380B

N-(4-((((4'-fluoro-1,1'-biphenyl-4-yl)carbonyl)
amino)sulfonyl)-2-nitrophenyl)adamantane-1-
carboxamide A solution of Example 380A (101 mg, 0.25 mmol) in THF (3 mL) was treated with 60% sodium hydride in oil (40 mg, 1.0 mmol), stirred for 30 minutes, treated with 1-adamantanecarbonyl chloride (60 mg, 0.30 mmol), stirred for 30 minutes, adjusted to pH<7 with 4M HCl in dioxane (0.5 mL), filtered, and concentrated. The concentrate was purified by flash column chromatography on silica gel with 30–100% ethyl acetate/hexanes to provide the desired product. MS (ESI(−)) m/e 576 (M−H)$^-$; $^1$H NMR (300 MHz, DMSO-d$_6$) δ10.23 (s, 1H), 8.52 (d, 1H), 8.23 (dd, 1H), 8.19 (d, 1H), 7.95 (d, 2 H, 7.75 (m, 4H), 7.31 (tt, 2H), 2.05 (3s, 3H), 1.90 (m, 6H), 1.70 (m, 6H).

EXAMPLE 381

N-(4-(2-hexyl-1,3-benzothiazol-5-yl)benzoyl)-3-
nitro-4-((2-(phenylthio)ethyl)amino)
benzenesulfonamide The desired product was prepared by substituting 1-iodopentane for allyl bromide in Example 213. MS (ESI) m/e 673, 675 (M−H)$^-$, (M+H)$^+$; $^1$H NMR (300 MHz, DMSO-d$_6$) δ0.87 (t, 3H), 1.17–1.44 (m, 6H), 1.82 (tt, 2H), 3.12 (t, 2H), 3.27 (t, 2H), 3.62 (dt, 2H), 7.02 (d, 1H), 7.19 (tt, 1H), 7.31 (t, 2H), 7.39 (d, 2H), 7.73 (d, 2H), 7.74 (d, 1H), 7.89 (dd, 1H), 7.98 (d, 2H), 8.12 (d, 1H), 8.22 (d, 1H), 8.53 (d, 1H), 8.55 (t, 1H).

EXAMPLE 382

N-((3,4'-difluoro-1,1'-biphenyl-4-yl)carbonyl)-3-
nitro-4-((2-(phenylthio)ethyl)amino)
benzenesulfonamide

EXAMPLE 382A methyl 4-chloro-2-fluorobenzoate

The desired product was prepared by substituting 3-chloro-2-fluorobenzoic acid for 4-bromo-3-fluorobenzoic acid in Example 311A.

EXAMPLE 382B methyl 3,4'-difluoro-1,1'-biphenyl-4-carboxylate

The desired product was prepared by substituting Example 382A and 4-fluorophenylboronic acid for 5-chloro-2-methyl-1,3-benzoxazole and 4-(methoxycarbonyl)phenylboronic acid in Example 54A.

EXAMPLE 382C

N-((3,4'-difluoro-1,1'-biphenyl-4-yl)carbonyl)-3-
nitro-4-((2-(phenylthio)ethyl)amino)
benzenesulfonamide The desired product was prepared by substituting Example 382B and Example 77B for Example 5C and Example 3A, respectively, in Example 5D. MS (ESI(−)) m/e 568 (M−H)$^-$; $^1$H NMR (300 MHz, DMSO-d$_6$) δ8.64 (t, 1H), 8.54 (d, 1H), 7.88 (dd, 1H), 7.78 (m, 2H), 7.70 (t, 1H), 7.49 (m, 2H), 7.39 (m, 2H), 7.30 (m, 4H)-7.20 (tt, 1H), 7.10 (d, 1H), 3.66 (q, 2H), 3.20 (t, 2H).

EXAMPLE 383

N-((2'-methoxy-4'-(2-morpholin-4-yl-2-oxoethyl)-1,
1'-biphenyl-4-yl)carbonyl)-3-nitro-4-((2-(phenylthio)
ethyl)amino)benzenesulfonamide

EXAMPLE 383A methyl 2'-methoxy-4'-(2-morpholin-4-yl-2-
oxoethyl)-1,1'-biphenyl-4-carboxylate The desired product was prepared by substituting morpholine for 1-methylpiperazine in Example 328B.

EXAMPLE 383B

N-((2'-methoxy-4'-(2-morpholin-4-yl-2-oxoethyl)-1,
1'-biphenyl-4-yl)carbonyl)-3-nitro-4-((2-(phenylthio)
ethyl)amino)benzenesulfonamide The desired product was prepared by substituting Example 383A and Example 77B for Example 5C and Example 3A, respectively, in Example 5D. MS (ESI(−)) m/e 689 (M−H)$^-$; $^1$H NMR (500 MHz, DMSO-d$_6$) δ8.77 (t, 1H), 8.62 (d, 1H), 7.93 (dd, 1H), 7.88 (d, 2H), 7.57 (d, 2H), 7.37 (m, 2H), 7.26 (m, 3H), 7.18 (m, 2H), 6.99 (d, 1H), 6.89 (dd, 1H), 3.76 (s, 2H), 3.75 (s, 3H), 3.67 (q, 2H), 3.56–3.52 (m, 6H), 3.47 (m, 2H), 3.26 (d, 2H).

EXAMPLE 384

4-((4-azido-1-((phenylthio)methyl)butyl)amino)-N-
((4'-fluoro-1,1'-biphenyl-4-yl)carbonyl)-3-
nitrobenzenesulfonamide

EXAMPLE 384A methyl (2E)-4-((tert-butoxycarbonyl)amino)-5-
(phenylthio)pent-2-enoate A solution of Example 175A (798 mg, 2.56 mmol) in toluene at −78° C. was treated with 1M DIBAL-H in toluene (3.1 mL), stirred for 2 hours, poured into a mixture of 1M HCl (5 mL) and ice (~15 g), and extracted with ethyl acetate (100 mL). The extract was washed with 0.1M HCl (20 mL) and brine (10 mL), dried (MgSO$_4$), filtered, and concentrated.

The concentrate was treated with methyl (triphenylphospharanylidene)acetate (1.35 g, 4.0 mmol).and THF (10 mL), stirred at room temperature for 16 hours, diluted with hexanes (20 mL), and filtered through silica gel (20 g). The silica gel pad was rinsed with 1:1 ethyl acetate/hexanes and the combined organic phases were concentrated. The concentrate was purified by flash column chromatography on silica gel with 10–20% ethyl acetate/hexanes to provide the desired product.

EXAMPLE 384B methyl 4-((tert-butoxycarbonyl)amino)-5-
(phenylthio)pentanoate A mixture of Example 384A (650 mg, 1.92 mmol) and 10% Pd/C (2.3 g, 2.2 mmol) in ethyl acetate (15 mL0 and methanol (5 mL) was stirred at room temperature under a hydrogen balloon for 6 hours and filtered through diatomaceous earth (Celite®). The pad was rinsed with hot ethyl acetate, and the combined organic phases were concentrated to provide the desired product.

EXAMPLE 384C tert-butyl 4-hydroxy-1-((phenylthio)methyl)butylcarbamate

A solution of Example 384B (538 mg, 1.6 mmol) in THF (4 mL) at −50° C. was treated with 1M lithium triethylborohydride in THF (4 mL), stirred for 1 hour, poured into ice (~15 g), and extracted with ethyl acetate (100 mL). The extract was washed with water (20 mL) and brine (10 mL), dried ($MgSO_4$), filtered, and concentrated to provide the desired product of sufficient purity for subsequent use.

EXAMPLE 384D tert-butyl 4-azido-1-((phenylthio)methyl)butylcarbamate

The desired product was prepared by substituting Example 384C for Example 434B in Example 434C.

EXAMPLE 384E 4-((4-azido-1-((phenylthio)methyl)butyl)amino)-N-((4'-fluoro-1,1'-biphenyl-4-yl)carbonyl)-3-nitrobenzenesulfonamide The desired product was prepared by substituting Example 384D for Example 175B in Example 175D. MS (ESI(−)) m/e 607 (M−H)−; $^1$H NMR (300 MHz, DMSO-$d_6$) δ8.57 (d, 1H), 8.33 (d, 1H), 7.98 (d, 1H), 7.87 (dd, 1H), 7.70 (m, 4H), 7.32 (m, 2H), 7.24 (m, 2H), 7.13 (m, 4H), 4.15 (m, 1H), 3.38 (m, 2H), 2.51 (m, 2H), 1.81 m, 2H), 1.60 (m, 2H).

EXAMPLE 385

N-butyl-3-(5-(4-((((3-nitro-4-((2-(phenylthio)ethyl)amino)phenyl)sulfonyl)amino)carbonyl)phenyl)-1,3-benzothiazol-2-yl)propanamide The desired product was prepared by substituting Example 330A and Example 77B for Example 1B and Example 1C, respectively, in Example 1D. MS (ESI) m/e 716, 718 (M−H)−, (M+H)+; $^1$H NMR (300 MHz, DMSO-$d_6$) δ0.83 (t, 3H), 1.24 (m, 2H), 1.35 (m, 2H), 2.66 (t, 2H), 3.05 (tt, 2H), 3.28 (t, 2H), 3.30 (t, 2H), 3.61 (dt, 2H), 7.01 (d, 1H), 7.20 (tt, 1H), 7.31 (td, 2H), 7.40 (dd, 2H), 7.72 (d, 2H), 7.74 (dd, 1H), 7.88 (dd, 1H), 7.92 (t, 1H), 7.98 (d, 2H), 8.11 (d, 1H), 8.12 (dd, 1H), 8.52 (d, 1H), 8.54 (t, 1H).

EXAMPLE 386

3-nitro-4-((2-(phenylthio)ethyl)amino)-N-(4-(4-(2-propylpentanoyl)piperazin-1-yl)benzoyl)benzenesulfonamide The desired product was prepared by substituting dipropylacetyl chloride for 2-methoxyethyl chloroformate in Example 325. MS (ESI(−)) m/e 666 (M−H)−; $^1$H NMR (300 MHz, DMSO-$d_6$) δ8.77 (t, 1H), 8.60 (d, 1H), 7.91 (dd, 1H), 7.76 (d, 2H), 7.39–7.35 (m, 2H), 7.29–7.14 (m, 4H), 6.95 (d, 2H), 4.79 (hept, 2H), 3.70–3.60 (m, 6H), 3.32–3.23 (m, 6H), 2.82–2.73 (m, 1H), 1.56–1.43 (m, 2H), 1.34–1.16 (m, 4H), 0.83 (t, 6H).

EXAMPLE 387

N-(4-(1-butyl-2-(2-methoxyethyl)-1H-benzimidazol-5-yl)benzoyl)-3-nitro-4-((2-(phenylthio)ethyl)amino)benzenesulfonamide

EXAMPLE 387A 5-bromo-1-butyl-2-(2-methoxyethyl)-1H-benzimidazole

The desired product was prepared by substituting Example 166B and 3-methoxypropionic acid for Example 343A and valeric acid, respectively, in Example 343B.

EXAMPLE 387B

N-(4-(1-butyl-2-(2-methoxyethyl)-1H-benzimidazol-5-yl)benzoyl)-3-nitro-4-((2-(phenylthio)ethyl)amino)benzenesulfonamide The desired product was prepared by substituting Example 387A and Example 214D for 6-bromoindole and 4-(dihydroxyboryl)benzoic acid, respectively, in Example 4A. MS (ESI) m/e 686, 688 (M−H)−, (M+H)+; $^1$H NMR (300 MHz, DMSO-$d_6$) δ0.92 (t, 3H), 1.35 (qt, 2H), 1.72 (tt, 2H), 2.12 (t, 2H), 3.26 (t, 2H), 3.28 (s, 3H), 3.61 (dt, 2H), 3.84 (t, 2H), 4.23 (t, 2H), 6.99 (d, 1H), 7.21 (tt, 1H), 7.32 (td, 2H), 7.40 (d, 2H), 7.46–7.68 (m, 4H), 7.89 (dd, 1H), 7.93–7.98 (m, 3H), 8.52 (d, 1H), 8.53 (t, 1H).

EXAMPLE 388

N-(4-((1S,4R)-bicyclo(2.2.1)hept-2-en-2-yl)benzoyl)-3-nitro-4-((2-(phenylthio)ethyl)amino)benzenesulfonamide

EXAMPLE 388A (1S,4R)-bicyclo(2.2.1)hept-2-en-2-yl trifluoroacetate

The desired product was prepared by substituting norcamphor for 4-tert-butylcyclohexanone in Example 5A.

EXAMPLE 388B methyl 4-((1S,4R)-bicyclo(2.2.1)hept-2-en-2-yl)benzoate

The desired product was prepared by substituting Example 388A for Example 5A in Example 5B. MS (DCI (+)) m/e 229 (M+H)+.

EXAMPLE 388C

N-(4-((1S,4R)-bicyclo(2.2.1.)hept-2-en-2-yl)benzoyl)-3-nitro-4-((2-(phenylthio)ethyl)amino)benzenesulfonamide The desired product was prepared by substituting Example 388B for Example 230B in Example 230C. MS (ESI(−)) m/e 548 (M−H)−; $^1$H NMR (300 MHz, DMSO-$d_6$) δ8.78 (br t, 1H), 8.60 (d, 1H), 7.92 (dd, 1H), 7.85 (d, 2H), 7.50 (d, 2H), 7.40–7.15 (m, 6H), 6.60 (d, 1H), 3.70 (m, 2H), 3.40 (m, 1H), 3.00 (m, 1H), 1.75 (m, 2H), 1.45 (m, 2H), 1.25 (m, 2H), 1.05 (m, 2H).

EXAMPLE 389

N-(4-(5-fluoroquinolin-8-yl)benzoyl)-3-nitro-4-((2-(phenylthio)ethyl)amino)benzenesulfonamide

EXAMPLE 389A 5-fluoroquinolin-8-yl trifluoroacetate

The desired product was prepared by substituting 5-fluoro-8-hydroxyquinoline for vanillin in Example 122H.

EXAMPLE 389B

N-(4-(5-fluoroquinolin-8-yl)benzoyl)-3-nitro-4-((2-(phenylthio)ethyl)amino)benzenesulfonamide A mixture of Example 108A (176 mg, 0.30 mmol), Example 389A (180 mg, 0.60 mmol), $Pd_2dba_3$ (27 mg, .0.03 mmol), triphenylarsine (37 mg, 0.12 mmol) and 1M Na$_2$CO$_3$ (3 mL) in 1,4-dioxane (6 mL) was heated to 90° C. for 16 hours, cooled to room temperature, diluted with ethyl acetate (200 mL), washed with water (100 mL) and brine (50 mL), dried (MgSO$_4$), filtered, and concentrated. The concentrate was purified by flash column chromatography on silica gel with 1:1 ethyl acetate/dichloromethane to provide the desired product. MS (ESI(−)) m/e 601 (M−H)$^-$; $^1$H NMR (300 MHz, DMSO-d$_6$) δ8.99 (dd, 1H), 8.74 (br t, 1H), 8.62 (d, 1H), 8.57 (dd, 1H), 7.95 (m, 4H), 7.82 (dd, 1H), 7.70 (m, 3H), 7.55 (dd, 1H), 7.48 (d, 2H), 7.28 (t, 2H), 7.19 (m, 2H), 3.67 (q, 2H), 3.28 (t, 2H).

EXAMPLE 390

N~2~-(4-((((4'-fluoro-1,1'-biphenyl-4-yl)carbonyl)amino)sulfonyl)-2-nitrophenyl)-S-phenylcysteinamide

EXAMPLE 390A

N$^2$-tert-butoxycarbonyl-S-phenylcysteinamide

The desired product was prepared by substituting 0.5M ammonia in dioxane for morpholine in Example 180A.

EXAMPLE 390B

N~2~-(4-((((4'-fluoro-1,1'-biphenyl-4-yl)carbonyl)amino)sulfonyl)-2-nitrophenyl)-S-phenylcysteinamide The desired product was prepared by substituting Example 390A for Example 175B in Example 175D. MS (ESI(−)) m/e 593 (M−H)$^-$; $^1$H NMR (300 MHz, DMSO-d$_6$) δ8.49 (d, 1H), 7.96 (d, 2H), 7.89 (dd, 1H), 7.75 (m, 3H), 7.60 (d, 2H), 7.45 (1H), 7.32–7.13 (m, 7H), 4.52 (m, 1H), 3.60 (m, 1H), 2.45 (m, 1H).

EXAMPLE 391

N-(4-(2-aminoquinolin-8-yl)benzoyl)-3-nitro-4-((2-(phenylthio)ethyl)amino)benzenesulfonamide The desired product was prepared by substituting Example 355A for Example 389A in Example 389B. MS (ESI(−)) m/e 598 (M−H)$^-$; $^1$H NMR (400 MHz, DMSO-d$_6$) δ8.67 (t, 1H), 8.58 (d, 1H), 7.95 (m, 5H), 7.80–7.45 (m, 6H), 7.39 (m, 2H), 7.30 (t, 2H), 7.20 (tt, 1H), 3.65 (q, 2H), 3.28 (t, 2H).

EXAMPLE 392

3-nitro-4-((2-(phenylthio)ethyl)amino)-N-(4-(1-(pyridin-3-ylcarbonyl)-1,2,3,6-tetrahydropyridin-4-yl)benzoyl)benzenesulfonamide The desired product was prepared by substituting nicotinoyl chloride for 4-morpholinecarbonyl chloride in Example 317. MS (ESI(−)) m/e 642 (M−H)$^-$; $^1$H NMR (300 MHz, DMSO-d$_6$) δ8.80 (br t, 1H), 8.70 (d, 2H), 8.62 (d, 1H), 7.92(m,2H), 7.89 (d, 2H), 7.58 (d, 2H), 7.55 (m, 1H), 7.40–7.15 (m, 6H), 6.45 and 6.25 (2m, 1H), 4.32 and 4.12 (2d, 2H), 3.92 (m, 2H), 3.65 (m, 2H), 3.25 (t,2H), 2.62 (m, 2H).

EXAMPLE 393

4-((3-tert-butoxy-2-(phenylthio)propyl)amino)-N-((4'-fluoro-1,1'-biphenyl-4-yl)carbonyl)-3-nitrobenzenesulfonamide and 4-((2-tert-butoxy-1-((phenylthio)methyl)ethyl)amino)-N-((4'-fluoro-1,1'-biphenyl-4-yl)carbonyl)-3-nitrobenzenesulfonamide

EXAMPLE 393A 3-tert-butoxy-2-(phenylthio)propan-1-ol and 1-tert-butoxy-3-(phenylthio)propan-2-ol The desired products were prepared by substituting tert-butyl glycidyl ether for cyclohexene oxide in Example 7A.

EXAMPLE 393B ((2-azido-1-(tert-butoxymethyl)ethyl)thio)benzene and ((2-azido-3-tert-butoxypropyl)thio)benzene The desired product was prepared by substituting Example 393A for Example 7A in Example 7B.

EXAMPLE 393C 4-((3-tert-butoxy-2-(phenylthio)propyl)amino)-3-nitrobenzenesulfonamide and 4-((2-tert-butoxy-1-((phenylthio)methyl)ethyl)amino)-3-nitrobenzenesulfonamide A mixture of Example 393B (877 mg, 3.03 mmol), triphenylphosphine (1.58 g, 6.0 mmol), and water (0.18 mL, 10 mmol) in THF (95 mL) at room temperature was stirred for 18 hours and concentrated. The concentrate was treated with Example 122C (801 mg, 3.64 mmol), N,N-diisopropylethylamine (1.0 mL), and 1,4-dioxane (5 mL), heated to 60° C. for 16 hours, diluted with ethyl acetate (100 mL), washed with water (45 mL) and brine (10 mL), dried (MgSO$_4$), filtered, and concentrated. The concentrate was purified by flash column chromatography on silica gel with 10–30% ethyl acetate/dichloromethane to provide the desired products as a 1.5:1 mixture. MS (ESI(+)) m/e 440 (M+H)$^+$.

EXAMPLE 393D 4-((3-tert-butoxy-2-(phenylthio)propyl)amino)-N-((4'-fluoro-1,1'-biphenyl-4-yl)carbonyl)-3-nitrobenzenesulfonamide and 4-((2-tert-butoxy-1-((phenylthio)methyl)ethyl)amino)-N-((4-fluoro-1,1'-biphenyl-4-yl)carbonyl)-3-nitrobenzenesulfonamide The desired product was prepared by substituting Example 393C for Example 1C in Example 1D. MS (ESI(−)) m/e 636 (M−H)$^-$; $^1$H NMR (300 MHz, DMSO-d$_6$), 2:1 mixture of isomers δ8.84 (br t, 2/3H), 8.68 (br d, 1/3H), 8.62, 8.61 (2d, 1H), 7.96 (2d, 2H), 7.92, 7.89 (2dd, 1H), 7.78 (m, 4H), 7.45–7.10 (m, 8H), 4.14 (m, 2/3H), 3.80–3.50 (m, 4H), 1.12, 1.11 (2s, 9H).

EXAMPLE 394

N-(4-(1-(cyclohexylmethyl)-1H-pyrazol-4-yl)benzoyl)-3-nitro-4-((2-(phenylthio)ethyl)amino)benzenesulfonamide

EXAMPLE 394A 1-(cyclohexylmethyl)-4-iodo-1H-pyrazole

The desired product was prepared by substituting (bromomethyl)cyclohexane for 1-bromooctane in Example 198A. MS (ESI(+)) m/e 291 (M+H)$^+$.

EXAMPLE 394B 4-(1-(cyclohexylmethyl)-1H-pyrazol-4-yl)benzoic acid

The desired product was prepared by substituting Example 394A for 6-bromoindole in Example 4. MS (ESI (−)) m/e 283 (M−H)$^-$.

EXAMPLE 394C

N-(4-(1-(cyclohexylmethyl)-1H-pyrazol-4-yl)benzoyl)-3-nitro-4-((2-(phenylthio)ethyl)amino)benzenesulfonamide The desired product was prepared by substituting Example 394B and Example 77B for Example 1B and Example 1C, respectively, in Example 1D. MS (ESI(−)) m/e 618 (M−H)⁻; ¹H NMR (300 MHz, DMSO-d₆) δ0.95 (m, 2H), 1.18 (m, 4H), 1.52 (m, 2H), 1.63 (m, 2H), 1.81 (m, 1H), 3.27 (t, 2H), 3.60 (dt, 2H), 3.92 (d, 2H), 6.99 (d, 1H), 7.19 (t, 1H), 7.30 (t, 2H), 7.40 (d, 2H), 7.51 (d, 2H), 7.87 (m, 4H), 8.18 (s, 1H), 8.51 (d, 1H), 8.54 (t, 1H).

EXAMPLE 395

N-(4-(6-methoxypyridin-3-yl)benzoyl)-3-nitro-4-((2-(phenylthio)ethyl)amino)benzenesulfonamide The desired product was prepared by substituting 5-bromo-2-methoxypyridine for 2,8-bistrifluoromethyl-3-chloroquinoline in Example 319. MS (ESI) m/e 565, 563 (M+H)⁺, (M−H)⁻; ¹H NMR (500 MHz, DMSO-d₆) δ8.78 (t,H), 8.63 (d, 1H), 8.57 (d, 1H), 8.09 (dd, 1H), 7.97–7.93 (m, 3H), 7.81 (d, 2H), 7.37 (dt, 2H), 7.27 (td, 2H), 7.22 (d, 1H), 7.17 (tt, 1H), 6.93 (d, 1H), 3.91 (s, 3H), 3.68 (q, 2H), 3.29 (t, 2H).

EXAMPLE 396

N-((2'-methoxy-4'-(2-morpholin-4-ylethyl-1,1'-biphenyl-4-yl)carbonyl)-3-nitro-4-((2-(phenylthio)ethyl)amino)benzenesulfonamide

EXAMPLE 396A methyl 2'-methoxy-4'-(2-morpholin-4-ylethyl)-1,1'-biphenyl-4-carboxylate The desired product was prepared by substituting Example 383A for Example 122F in Example 122G.

EXAMPLE 396B

N-((2'-methoxy-4'-(2-morpholin-4-ylethyl)-1,1'-biphenyl-4-yl)carbonyl)-3-nitro-4-((2-(phenylthio)ethyl)amino)benzenesulfonamide The desired product was prepared by substituting Example 396A and Example 77B for Example 5C and Example 3A, respectively, in Example 5D. MS (ESI(−)) m/e 675 (M−H)⁻; ¹H NMR (500 MHz, DMSO-d₆) δ10.3–10.1 (br s, 1H), 8.78 (t, 1H), 8.64 (d, 1 H), 7.94 (dd, 1H), 7.90 (d, 2H), 7.57 (d, 2H), 7.37 (m, 2H), 7.36–7.18 (m, 5H), 7.06 (d, 1H), 6.97 (dd, 1H), 4.00 (m, 2H), 3.78 (s, 3H), 3.67 (q, 2H), 3.42 (m, 2H), 3.29 (t, 2H), 3.15 (m, 2H), 3.05 (m, 2H), remaining 2 protons are buried under water peak (3.8–3.4 ppm).

EXAMPLE 397

N-((2'-methoxy-4'-(3-morpholin-4-yl-3-oxopropyl)-1,1'-biphenyl-4-yl)carbonyl)-3-nitro-4-((2-(phenylthio)ethyl)amino)benzenesulfonamide The desired product was prepared by substituting Example 122M and Example 77B for Example 5C and Example 3A, respectively, in Example 5D. MS (ESI(−)) m/e 703 (M−H)⁻; ¹H NMR (300 MHz, DMSO-d₆) δ8.79 (t, 1H), 8.63 (d, 1H), 7.94 (dd, 1H), 7.88 (d, 2H), 7.57 (d, 2H), 7.37 (m, 2H), 7.30–7.14 (m, 5H), 7.02 (d, 1H), 6.92 (dd, 1H), 3.76 (s, 3H), 3.67 (q, 2H), 3.53 (m, 4H), 3.44 (m, 4H), 3.28 (d, 2H), 2.85 (t, 2), 2.66 (t, 2H).

EXAMPLE 398

N-(2-hydroxyethyl)-3-methyl-5-(4-((((3-nitro-4-((2-(phenylthio)ethyl)amino)phenyl)sulfonyl)amino)carbonyl)phenyl)-1-benzothiophene-2-sulfonamide

EXAMPLE 398A 5-chloro-N-(2-hydroxyethyl)-3-methyl-1-benzothiophene-2-sulfonamide The desired product was prepared by substituting 2-chlorosulfonyl-5-chloro-3-methylbenzothiophene and ethanolamine for dimethylcarbamic chloride and Example 183D, respectively, in Example 200. MS (ESI(−)) m/e 304 (M−H)⁻.

EXAMPLE 398B methyl 4-(2-(((2-hydroxyethyl)amino)sulfonyl)-3-methyl-1-benzothien-5-yl)benzoate The desired product was prepared by substituting Example 398A for 5-chloro-2-methyl-1,3-benzoxazole in Example 54A. MS (ESI(−)) m/e 404 (M−H)⁻.

EXAMPLE 398C methyl 4-(2-(((2-((tert-butyl(dimethyl)silyl)oxy)ethyl)amino)sulfonyl)-3-methyl-1-benzothien-5-yl)benzoate A solution of Example 398B (200 mg, 0.5 mmol), tert-butyldimethylsilyl chloride (85 mg, 0.55 mmol) and imidazole (36 mg, 0.6 mmol) in DMF (5 mL) at room temperature was stirred for 24 hours, diluted with ether, filtered through a pad of silica gel, and concentrated to provide the desired product.

EXAMPLE 398D 4-(2-(((2-((tert-butyl(dimethyl)silyl)oxy)ethyl)amino)sulfonyl)-3-methyl-1-benzothien-5-yl)benzoic acid The desired product was prepared by substituting Example 398C for Example 1A in Example 1B. MS (ESI(−)) m/e 504 (M−H)⁻.

EXAMPLE 398E

N-(2-hydroxyethyl)-3-methyl-5-(4-((((3-nitro-4-((2-(phenylthio)ethyl)amino)phenyl)sulfonyl)amino)carbonyl)phenyl)-1-benzothiophene-2-sulfonamide The desired product was prepared by substituting Example 398D and Example 77B for Example 1B and Example 1C, respectively, in Example 1D. The product was treated with TFA (5 mL), stirred for 2 hours, concentrated, dissolved in toluene, and concentrated again to provide the desired product. MS (ESI(−)) m/e 725 (M−H)⁻; ¹H NMR (300 MHz, DMSO-d₆) δ2.70 (s, 3H), 2.95 (dt, 2H), 3.28 (t, 2H), 3.38 (dt, 2H), 3.66 (dt, 2H), 4.22 (m, 1H), 4.70 (m, 1H), 7.19 (d, 1H), 7.24–7.37 (m, 4H), 7.80 (m, 4H), 7.92 (dd, 1H), 7.96 (d, 2H), 8.61 (d, 1H), 8.78 (t, 1H).

EXAMPLE 399

N-(1,1'-biphenyl-4-ylcarbonyl)-3-nitro-4-((2-(phenylthio)ethyl)amino)benzenesulfonamide The desired product was prepared by substituting 4-biphenylcarboxylic acid and Example 77B for Example 1B and Example 1C, respectively, in Example 1D. MS (ESI(−)) m/e 532 (M−H)⁻; ¹H NMR (300 MHz, DMSO-d₆) δ8.78 (t, 1H), 8.62 (d, 1H), 7.97 (d, 2H), 7.94 (dd, 1H), 7.79 (m, 2H), 7.73 (d, 2H), 7.49 (t, 2H), 7.42 (t, 1H), 7.38 (m, 2H), 7.27 (m, 2H), 7.18 (m, 2H), 3.66 (q, 2H), 3.29 (t, 2H).

EXAMPLE 400

3-nitro-N-(4-(5-nitropyridin-2-yl)benzoyl)-4-((2-(phenylthio)ethyl)amino)benzenesulfonamide The desired product was prepared by substituting 2-chloro-5-nitropyridine for 2,8-bistrifluoromethyl-3- chloroquinoline in Example 319. MS (ESI) m/e 580 578 (M+H)$^+$, (M−H)$^−$; $^1$H NMR (500 MHz, DMSO-d$_6$) δ9.47 (d, 1H), 8.78 (t, 1H), 8.69 (dd, 1H), 8.64 (d, 1H), 8.36 (d, 1H), 8.31 (d, 2H), 8.05 (d, 2H), 7.95 (dd, 1H), 7.37 (dt, 2H), 7.27 (td, 2H), 7.22 (d, 1H), 7.17 (tt, 1H), 3.68 (q, 2H), 3.29 (t, 2H).

EXAMPLE 401

N-(4-(2-cyano-3-methyl-1-benzothien-5-yl) benzoyl)-3-nitro-4-((2-(phenylthio)ethyl)amino) benzenesulfonamide

EXAMPLE 401A 5-chloro-3-methyl-1-benzothiophene-2-carbonitrile

A mixture of 2-bromo-5-chloro-3-methylbenzo(b) thiophene (1.00 g, 3.82 mmol), zinc cyanide (247 mg, 2.10 mmol), and Pd(PPh$_3$)$_4$ (440 mg, 0.38 mmol) in DMF (15 mL) was heated to 80° C. for 16 hours, added to water (50 mL), and extracted with 30% ethyl acetate/hexanes (3×100 mL). The combined extracts were washed with brine (20 mL), dried (Na$_2$SO$_4$), filtered, and concentrated. The concentrate was purified by flash column chromatography on silica gel with 10% ethyl acetate/hexanes to provide the desired product.

EXAMPLE 401B methyl 4-(2-cyano-3-methyl-1-benzothien-5-yl) benzoate

A mixture of Example 401A (557 mg, 2.68 mmol), (4-methoxycarbonylphenyl)-boronic acid (675 mg, 3.75 mmol), Pd(OAc)$_2$ (36 mg, 0.16 mmol), 2-(di-tert-butylphosphino)biphenyl (63 mg, 0.21 mmol), and KF (467 mg, 8.04 mmol) in THF (10 mL) was heated to 60° C. for 16 hours and concentrated. The concentrate was purified by flash column chromatography on silica gel with 10% ethyl acetate/hexanes to provide the desired product.

EXAMPLE 401C 4-(2-cyano-3-methyl-1-benzothien-5-yl)benzoic acid

The desired product was prepared by substituting Example 401B for Example 1A in Example 1B.

EXAMPLE 401D

N-(4-(2-cyano-3-methyl-1-benzothien-5-yl) benzoyl)-3-nitro-4-((2-(phenylthio)ethyl)amino) benzenesulfonamide The desired product was prepared by substituting Example 401C and Example 77B for Example 1B and Example 1C, respectively, in Example 1D. MS (ESI) m/e 627, 629 (M−H)$^−$, (M+H)$^−$; $^1$H NMR (300 MHz, DMSO-d$_6$) δ2.70 (s, 3H), 3.27 (t, 2H), 3.62 (dt, 2H), 7.05 (d, 1H), 7.19 (tt, 1H), 7.29 (tt, 2H), 7.38 (dt, 2H), 7.82 (d, 2H), 7.91 (dd, 1H), 7.97 (dd, 1H), 8.01 (d, 2H), 8.20 (d, 1H), 8.30 (d, 1H), 8.55 (d, 1H), 8.58 (t, 1H).

EXAMPLE 402

N-((4'-fluoro-1,1'-biphenyl-4-yl)carbonyl)-4-((3-methoxy-2-(phenylthio)propyl)amino)-3-nitrobenzenesulfonamide and N-((4'-fluoro-1,1'-biphenyl-4-yl)carbonyl)-4-((2-methoxy-1-((phenylthio)methyl)ethyl)amino)-3-nitrobenzenesulfonamide

EXAMPLE 402A 3-methoxy-2-(phenylthio)propan-1-ol and 1-methoxy-3-(phenylthio)propan-2-ol The desired product was prepared by substituting glycidyl methyl ether for cyclohexene oxide in Example 7A.

EXAMPLE 402B ((2-azido-1-(methoxymethyl)ethyl)thio)benzene compound and ((2-azido-3-methoxypropyl)thio) benzene The desired product was prepared by substituting Example 402A for Example 7A in Example 7B.

EXAMPLE 402C 4-((3-methoxy-2-(phenylthio)propyl)amino)-3-nitrobenzenesulfonamide compound and 4-((2-methoxy-1-((phenylthio)methyl)ethyl)amino)-3-nitrobenzenesulfonamide The desired product was prepared by substituting Example 402B for Example 393B in Example 393C.

EXAMPLE 402D

N-((4'-fluoro-1,1'-biphenyl-4-yl)carbonyl)-4-((3-methoxy-2-(phenylthio)propyl)amino)-3-nitrobenzenesulfonamide and N-((4'-fluoro-1,1'-biphenyl-4-yl)carbonyl)-4-((2-methoxy-1-((phenylthio)methyl)ethyl)amino)-3-nitrobenzenesulfonamide The desired product was prepared by substituting Example 402C for Example 1C in Example 1D. MS (ESI (−)) m/e 594 (M−H)$^−$; $^1$H NMR (300 MHz, DMSO-d$_6$), mixture of two isomers, ratio (1.2:1) δ8.86 (br t, 1/2H), 8.61, 8.59 (2d, 1H), 8.53 (br d, 1/2H), 7.96 (2d, 2H), 7.89 (2dd, 1H), 7.78 (m, 4H), 7.45–7.10 (m, 8H), 4.25 (m, 1/2H), 3.80–3.50 (m, 4.5H), 3.29, 3.27 (2s, 3H).

EXAMPLE 403

N-(4-(2-hydroxyquinolin-8-yl)benzoyl)-3-nitro-4-((2-(phenylthio)ethyl)amino)benzenesulfonamide

EXAMPLE 403A 4-(2-hydroxyquinolin-8-yl)benzoic acid

The desired product was prepared by substituting Example 336B for Example 1A in Example 1B.

EXAMPLE 403B

N-(4-(2-hydroxyquinolin-8-yl)benzoyl)-3-nitro-4-((2-(phenylthio)ethyl)amino)benzenesulfonamide The desired product was prepared by substituting Example 403A and Example 77B for Example 1B and Example 1C, respectively, in Example 1D. MS (ESI(−)) m/e 599 (M−H)$^−$; $^1$H NMR (400 MHz, DMSO-d$_6$) δ8.77 (t, 1H), 8.53 (d, 1H), 8.02 (d, 2H), 8.00 (d, 1H), 7.95 (dd, 1H), 7.72 (dd, 1H), 7.60 (d, 2H), 7.40 (dd, 1H), 7.37 (m, 2H), 7.38 (t, 2H), 7.22 (d, 1H), 7.19 (tt, 1H), 6.53 (d, 1H), 3.67 (q, 2H), 3.28 (t, 2H).

EXAMPLE 404

N-((2'-methoxy-4'-(morpholin-4-ylmethyl)-1,1'-biphenyl-4-yl)carbonyl)-3-nitro-4-((2-(phenylthio) ethyl)amino)benzenesulfonamide

EXAMPLE 404A methyl 2'-methoxy-4'-(morpholin-4-ylmethyl)-1,1'-biphenyl-4-carboxylate A mixture of Example 122I (135 mg, 0.50 mmol), morpholine (100 mg), 1M sodium cyanoborohydride in THF (1 mL) in methanol (2 mL) and acetic acid (0.3 mL) was stirred for 18 hours, diluted with ethyl acetate (100 mL), washed sequentially with 2M sodium carbonate (10 mL), water (20 mL), and brine (10 mL), dried (MgSO$_4$), filtered, and concentrated. The concentrate was purified by flash column chromatography on silica gel with 30–100% ethyl acetate/hexanes to provide the desired product. MS (DCI(+)) m/e 342 (M+H)$^+$.

EXAMPLE 404B

N-((2'-methoxy-4'-(morpholin-4-ylmethyl)-1,1'-biphenyl-4-yl)carbonyl)-3-nitro-4-((2-(phenylthio)ethyl)amino)benzenesulfonamide The desired product was prepared by substituting Example 404A and Example 77B for Example 5C and Example 3A, respectively, in Example 5D. MS (ESI(–)) m/e 663 (M–H)$^-$; $^1$H NMR (300 MHz, DMSO-d$_6$) δ8.74 (t, 1H), 8.61 (d, 1H), 7.92 (m, 3H), 7.56 (d, 2H), 7.38 (m, 3H), 7.28 (m, 3H), 7.21–7.10 (m, 3H), 3.80 (s, 2H), 3.76 (s, 3H), 3.66 (q, 2H), 3.40–3.20 (m, 4 H, buried in water peak).

EXAMPLE 405 tert-butyl 4-(4-((((3-nitro-4-((2-(phenylthio)ethyl)amino)phenyl)sulfonyl)amino)carbonyl)phenyl)piperazine-1-carboxylate The desired product was prepared by substituting 4-(4-((neopentyloxy)carbonyl)piperazin-1-yl)benzoic acid and Example 77B for Example 1B and Example 1C, respecitvely, in Example 1D. MS (ESI(–)) m/e 640 (M–H)$^-$; $^1$H NMR (300 MHz, DMSO-d$_6$) δ8.77 (t, 1H), 8.60 (d, 1H), 7.91 (dd, 1H), 7.76 (d, 2H), 7.36 (d, 2H), 7.14–7.29 (m, 4H), 6.94 (d, 2H), 3.66 (q, 2H), 3.37–3.45 (m, 4H), 3.23–3.30 (m, 6H), 1.41 (s, 9H).

EXAMPLE 406

N~2~-(4-((((4'-fluoro-1,1'-biphenyl-4-yl)carbonyl)amino)sulfonyl)-2-nitrophenyl)-N~1~,N~1~-bis(4-(N-(4-((((4'-fluoro-1,1'-biphenyl-4-yl)carbonyl)amino)sulfonyl)-2-nitrophenyl)-S-phenylcysteinyl)morpholin-3-yl)-S-phenylcysteinamide The desired product was prepared by substituting Example 180B for Example 1C in Example 1D. MS (ESI(–)) m/e 663 (M–H)$^-$; $^1$H NMR (300 MHz, dmso-d$_6$) δ8.95 (d, 1H), 8.49 (d, 1H), 7.97 (d, 2H), 7.91 (dd, 1H), 7.72 (m, 4H), 7.60 (d, 2H), 7.27 (m, 4H), 7.15 (m, 4H), 5.27 (m, 1H), 3.57 (m, 4H), 3.50 (m, 4H), 3.37 (dd, 1H), 3.20 (m, 1H).

EXAMPLE 407

N-(4-(4,4-dimethylcyclohexyl)benzoyl)-4-((2-morpholin-4-yl-1-((phenylthio)methyl)ethyl)amino)-3-nitrobenzenesulfonamide The desired product was prepared by substituting Example 77A and Example 245A for Example 5C and Example 3A, respectively, in Example 5D. MS (ESI(–)) m/e 665 (M–H)$^-$; $^1$H NMR (400 MHz, methanol-d$_4$) δ8.66 (d, 1H), 7.90 (dd, 1H), 7.84 (d, 2H), 7.28 (m, 4H), 7.07 (m, 3H), 6.91 (d, 1H), 4.14 (m, 1H), 3.30 (t, 4H), 3.40 (dd, 1H), 3.21 (dd, 1H), 2.72 (m, 2H), 2.51 (m, 5H), 1.64 (m, 4H), 1.49 (m, 2H), 1.35 (m, 2H), 0.98 (s, 3H), 0.94 (s, 8H).

EXAMPLE 408

4-((2-amino-1-((phenylthio)methyl)ethyl)amino)-N-((4'-fluoro-1,1'-biphenyl-4-yl)carbonyl)-3-nitrobenzenesulfonamide The desired product was prepared by substituting Example 434D for Example 384E in Example 125. MS (ESI(–)) m/e 579 (M–H)$^-$; $^1$H NMR (300 MHz, dmso-d$_6$) δ8.59 (d, 1H), 8.33 (d, 1H), 8.05 (m, 3H), 7.97 (d, 2H), 7.87 (dd, 1H), 7.78 (m, 4H), 7.35–7.11 (m, 8H), 4.40 (m, 1H), 3.25 (m, 2H), (remaining 2 protons are buried under water peak, 3.50–3.30 ppm).

EXAMPLE 409 benzyl 4-(4-((((3-nitro-4-((2-(phenylthio)ethyl)amino)phenyl)sulfonyl)amino)carbonyl)phenyl)piperazine-1-carboxylate The desired product was prepared by substituting benzyloxyacetyl chloride for 2-methoxyethyl chloroformate in Example 325. MS (ESI(–)) m/e 674 (M–H)$^-$; $^1$H NMR (300 MHz, DMSO-d$_6$) δ8.74 (t, 1H), 8.58 (d, 1H), 7.90 (dd, 1H), 7.76 (d, 2H), 7.39–7.14 (m, 11H), 6.93 (d, 2H), 5.10 (s, 2H), 3.65 (q, 2H), 3.51–3.57 (m, 4H), 3.32–3.23 (m, 6H).

EXAMPLE 410

3-nitro-4-((2-(phenylthio)ethyl)amino)-N-(4-(1-(pyridin-2-ylcarbonyl)-1,2,3,6-tetrahydropyridin-4-yl)benzoyl)benzenesulfonamide The desired product was prepared by substituting picolinoyl chloride for 4-morpholinecarbonyl chloride in Example 317. MS (ESI(–)) m/e 642 (M–H)$^-$; $^1$H NMR (300 MHz, DMSO-d$_6$) δ8.80 (br t, 1H), 8.62 (d, 1H), 7.95 (m, 2H), 7.85 (d, 2H), 7.62–7.48 (m, 4H), 7.40–7.15 (m, 76H), 6.45 and 6.25 (2m, 1H), 4.32 and 4.12 (2d, 2H), 3.92 (t, 2H), 3.65 (m, 2H), 3.25 (t,2H), 2.62 (m, 2H).

EXAMPLE 411

N,N-diethyl-3-methyl-5-(4-((((3-nitro-4-((2-(phenylthio)ethyl)amino)phenyl)sulfonyl)amino)carbonyl)phenyl)-1-benzothiophene-2-sulfonamide

EXAMPLE 411A 5-chloro-N,N-diethyl-3-methyl-1-benzothiophene-2-sulfonamide

The desired product was prepared by substituting 2-chlorosulfonyl-5-chloro-3-methylbenzthiophene and dimethylamine for dimethylcarbamic chloride and Example 183D, respectively, in Example 200. MS (ESI(+)) m/e 318 (M+H)$^+$.

EXAMPLE 411B methyl 4-(2-((diethylamino)sulfonyl)-3-methyl-1-benzothien-5-yl)benzoate The desired product was prepared by substituting Example 411A for 5-chloro-2-methyl-1,3-benzoxazole in Example 54A.

EXAMPLE 411C 4-(2-((diethylamino)sulfonyl)-3-methyl-1-benzothien-5-yl)benzoic acid The desired product was prepared by substituting Example 411B for Example 1A in Example 1B. MS (ESI(–)) m/e 402 (M–H)$^-$.

EXAMPLE 411D

N,N-diethyl-3-methyl-5-(4-((((3-nitro-4-((2-(phenylthio)ethyl)amino)phenyl)sulfonyl)amino)carbonyl)phenyl)-1-benzothiophene-2-sulfonamide The desired product was prepared by substituting Example 411C and Example 77B for Example 1B and Example 1C, respectively, in Example 1D. MS (ESI(−)) m/e 737 (M−H)⁻; ¹H NMR (300 MHz, DMSO-d₆) δ1.10 (t, 6H), 2.72 (s, 3H), 3.28 (q, 4H), 3.36 (t, 2H), 3.62 (dt, 2H), 7.00 (d, 1H), 7.20 (t, 1H), 7.31 (t, 2H), 7.41 (d, 2H), 7.77 (d, 2H), 7.90 (d, 2H), 8.01 (d, 2H), 8.12 (d, 1H), 8.22 (s, 1H), 8.51 (t, 1H), 8.53 (t, 1H).

EXAMPLE 412

N-(4-(3-methyl-2-morpholin-4-yl-1-benzothien-5-yl)benzoyl)-3-nitro-4-((2-(phenylthio)ethyl)amino)benzenesulfonamide

EXAMPLE 412A 4-(5-chloro-3-methyl-1-benzothien-2-yl)morpholine

A mixture of 2-bromo-5-chloro-3-methylbenzthiophene (523 mg, 2 mmol), morpholine (210 uL, 2.4 mmol), Pd₂dba₃ (37 mg, 0.04 mmol), BINAP (62 mg, 0.1 mmol), and sodium tert-butoxide (270 mg, 2.8 mmol) in toluene (5 mL) was stirred at 80° C. for 18 hours. The reaction mixture was purified by flash column chromatography on silica gel with 20% ethyl acetate/hexanes to provide the desired product. MS (ESI(+)) m/e 268 (M+H)⁺.

EXAMPLE 412B methyl 4-(3-methyl-2-morpholin-4-yl-1-benzothien-5-yl)benzoate

The desired product was prepared by substituting Example 412A for 5-chloro-2-methyl-1,3-benzoxazole in Example 54A.

EXAMPLE 412C 4-(3-methyl-2-morpholin-4-yl-1-benzothien-5-yl)benzoic acid

The desired product was prepared by substituting Example 412B for Example 1A in Example 1B. MS (ESI(−)) m/e 352 (M−H)⁻.

EXAMPLE 412D

N-(4-(3-methyl-2-morpholin-4-yl-1-benzothien-5-yl)benzoyl)-3-nitro-4-((2-(phenylthio)ethyl)amino)benzenesulfonamide The desired product was preparede by substituting Example 412C and Example 77B for Example 1B and Example 1C, respectively, in Example 1D. MS (ESI(−)) m/e 687 (M−H)⁻; ¹H NMR (300 MHz, DMSO-d₆) δ2.31 (s, 3H), 2.95 (m, 4H), 3.28 (t, 2H), 3.67 (dt, 2H), 3.79 (m, 4H), 7.19 (m, 2H), 7.28 (t, 2H), 7.38 (d, 2H), 7.48 (t, 1H), 7.62 (d, 1H), 7.85–8.00 (m, 6H), 8.62 (d, 1H), 8.78 (t, 1H).

EXAMPLE 413

N-(4-(2-methyl-1,3-benzothiazol-5-yl)benzoyl)-3-nitro-4-((2-(phenylthio)ethyl)amino)benzenesulfonamide The desired product was prepared by substituting Example 17A and Example 77B for Example 1B and Example 1C, respectively, in Example 1D. MS (ESI) m/e 603, 605 (M−H)⁻, (M+H)⁺; ¹H NMR (300 MHz, DMSO-d₆) δ2.83 (s, 3H), 3.28 (t, 2H), 3.62 (dt, 2H), 7.02 (d, 1H), 7.19 (tt, 1H), 7.30 (td, 2H), 7.39 (dt, 2H), 7.73 (dd, 1H), 7.74 (d, 2H), 7.89 (dd, 1H), 7.98 (d, 2H), 8.10 (d, 1H), 8.19 (d, 1H), 8.53 (d, 1H), 8.55 (t, 1H).

EXAMPLE 414

N-(4-(3-methyl-1-pentyl-1H-pyrazol-4-yl)benzoyl)-3-nitro-4-((2-(phenylthio)ethyl)amino)benzenesulfonamide and N-(4-(5-methyl-1-pentyl-1H-pyrazol-4-yl)benzoyl)-3-nitro-4-((2-(phenylthio)ethyl)amino)benzenesulfonamide

EXAMPLE 414A 4-bromo-5-methyl-1-pentyl-1H-pyrazole and 4-bromo-3-methyl-1-pentyl-1H-pyrazole The desired product was prepared by substituting 1-iodopentane and 4-bromo-3-methylpyrazole for 1-bromooctane and 4-iodopyrazole, respectively, in Example 198A. MS (ESI(+)) m/e 231, 233 (M+H)⁺.

EXAMPLE 414B 4-(5-methyl-1-pentyl-1H-pyrazol-4-yl)benzoic acid and 4-(3-methyl-1-pentyl-1H-pyrazol-4-yl)benzoic acid The desired product was prepared by substituting Example 414A for 6-bromoindole in Example 4A. MS (ESI) m/e 271 (M−H)⁻.

EXAMPLE 414C

N-(4-(3-methyl-1-pentyl-1H-pyrazol-4-yl)benzoyl)-3-nitro-4-((2-(phenylthio)ethyl)amino)benzenesulfonamide and N-(4-(5-methyl-1-pentyl-1H-pyrazol-4-yl)benzoyl)-3-nitro-4-((2-(phenylthio)ethyl)amino)benzenesulfonamide The desired product was prepared by substituting Example 414B and Example 77B for Example 1B and Example 1C, respectively, in Example 1D. MS (ESI(−)) m/e 606 (M−H)⁻; ¹H NMR (300 MHz, DMSO-d₆) δ0.86 (t, 3H), 1.29 (m, 4H), 1.78 (m, 2H), 2.30 (s, 1.8H), 2.38 (s, 1.2H), 3.27 (t, 2H), 3.61 (dt, 2H), 4.01 (t, 2H), 7.01 (d, 1H), 7.20 (t, 1H), 7.31 (t, 2H), 7.40 (m, 4H), 7.90 (m, 3H), 7.99 (s, 1H), 8.51 (d, 1H), 8.54 (t, 1H).

EXAMPLE 415

4-((2-adamantylmethyl)amino)-N-(4-(5-fluoroquinolin-8-yl)benzoyl)-3-nitrobenzenesulfonamide The desired product was prepared by substituting Example 255A for Example 108A in Example 389B. MS (ESI(−)) m/e 613 (M−H)⁻; ¹H NMR (400 MHz, DMSO-d₆) δ8.99 (dd, 1H), 8.55 (m, 2H), 8.40 (t, 1H), 7.97 (d, 2H), 7.92 (dd, 1H), 7.78 (dd, 1H), 7.72 (d, 1H), 7.67 (dd, 1H), 7.60 (d, 2H), 7.54 (dd, 1H), 7.18 (d, 1H), 3.14 (d, 2H), 1.98 (m, 3H), 1.72–1.55 (m, 12H).

EXAMPLE 416 methyl 2-((4-((((4'-fluoro-1,1'-biphenyl-4-yl)carbonyl)amino)sulfonyl)-2-nitrophenyl)amino)-3-(phenylthio)propylcarbamate The desired product was prepared by substituting methyl chloroformate for acetyl chloride in Example 310. MS (ESI(−)) m/e 637 (M−H)⁻; ¹H NMR (300 MHz, DMSO-d₆) δ8.55 (d, 1H), 8.30 (d, 1H), 7.96 (d, 2H), 7.84 (dd, 1H), 7.75 (m, 4H), 7.45 (m, 1H), 7.35–7.10 (m, 8H), 4.06 (m, 1H), 4.02 (m, 2H), 2.49 (s, 3H), remaining two protons buried under solvent peaks.

EXAMPLE 417

N-((2'-methoxy-4'-(methoxymethyl)-1,1'-biphenyl-4-yl)carbonyl)-3-nitro-4-((2-(phenylthio)ethyl)amino)benzenesulfonamide

EXAMPLE 417A methyl 4'-(hydroxymethyl)-2'-methoxy-1,1'-biphenyl-4-carboxylate A solution of Example 122I (270 mg, 0.5 mmol), and sodium borohydride (80 mg) in methanol (5 mL) at room temperature was stirred for 30 minutes, diluted with ethyl acetate (70 mL), washed with water (20 mL) and brine (10 mL), dried (MgSO$_4$), filtered, and concentrated to provide the desired product.

EXAMPLE 417B methyl 2'-methoxy-4'-(methoxymethyl)-1,1'-biphenyl-4-carboxylate A solution of Example 417A (142 mg, 0.5 mmol) in THF (3 mL) at room temperature was treated with 60% sodium hydride in oil (40 mg, 1.0 mmol) and methyl iodide (0.30 mmol), stirred for 30 minutes, adjusted to pH<7 with 4M HCl in dioxane (0.5 mL), filtered, and concentrated. The concentrate was purified by flash column chromatography on silica gel with 10% ethyl acetate/hexanes to provide the desired product.

EXAMPLE 417C

N-((2'-methoxy-4'-(methoxymethyl)-1,1'-biphenyl-4-yl)carbonyl)-3-nitro-4-((2-(phenylthio)ethyl)amino)benzenesulfonamide The desired product was prepared by substituting Example 417B and Example 77B for Example 5C and Example 3A, respectively, in Example 5D. MS (ESI(−)) m/e 606 (M−H)$^-$; $^1$H NMR (300 MHz, DMSO-d$_6$) δ8.72 (t, 1H), 8.60 (d, 1H), 7.92 (dd, 1H), 7.89 (d, 2H), 7.54 (d, 2H), 7.37 (m, 2H), 7.28 (m, 3H), 7.18 (tt, 1H), 7.06 (s, 1H), 6.97 (d, 1H), 4.45 (s, 2H), 3.76 (s, 3H), 3.66 (q, 2H), 3.33 (s, 3H), 3.20 (t, 2H).

EXAMPLE 418 tert-butyl 7-(4-(4-((((3-nitro-4-((2-(phenylthio)ethyl)amino)phenyl)sulfonyl)amino)carbonyl)phenyl)-3,6-dihydropyridin-1(2H)-yl)-7-oxoheptylcarbamate The desired product was prepared by substituting BOC-7-aminoheptanoic acid for BOC-leucine in Example 378. MS (ESI(−)) m/e 764 (M−H)$^-$; $^1$H NMR (300 MHz, DMSO-d$_6$) δ8.72 (br t, 1H), 8.60 (d, 1H), 7.92 (dd, 1H), 7.85 (d, 2H), 7.55 (d, 2H), 7.40–7.15 (m, 6H), 6.75 (br t, 1H), 6.45 and 6.42 (2m, 1H), 4.18 and 4.12 (2d, 2H), 3.65 (m, 4H), 3.40–3.25 (m, 4H), 2.90 (m, 2H), 2.45 (m, 2H), 2.45 (m, 2H), 1.50 (m, 2H), 1.35 (s, 9H), 1.25 (m, 4H).

EXAMPLE 419

N-(4-(2-methyl-1-benzothien-5-yl)benzoyl)-3-nitro-4-((2-(phenylthio)ethyl)amino)benzenesulfonamide

EXAMPLE 419A methyl 4-(2-methyl-1-benzothien-5-yl)benzoate

The desired product was prepared by substituting 5-chloro-2-methylbenzothiophene for 5-chloro-2-methyl-1,3-benzoxazole in Example 54A.

EXAMPLE 419B 4-(2-methyl-1-benzothien-5-yl)benzoic acid

The desired product was prepared by substituting Example 419A for Example 1A in Example 1B. MS (ESI(−)) m/e 564 (M−H)$^-$.

EXAMPLE 419C

N-(4-(2-methyl-1-benzothien-5-yl)benzoyl)-3-nitro-4-((2-(phenylthio)ethyl)amino)benzenesulfonamide The desired product was prepared by substituting Example 419B and Example 77B for Example 1B and Example 1C, respectively, in Example 1D. MS (ESI(−)) m/e 602 (M−H)$^-$; $^1$H NMR (300 MHz, DMSO-d$_6$) δ2.59 (s, 3H), 3.28 (t, 2H), 3.61 (dt, 2H), 7.00 (d, 1H), 7.19 (s, 1H), 7.20 (d, 1H), 7.30 (t, 2H), 7.40 (d, 2H), 7.50 (dd, 1H), 7.68 (d, 2H), 7.90 (t, 2H), 7.96 (d, 2H), 8.02 (s, 1H), 8.51 (t, 1H), 8.52 (d, 1H).

EXAMPLE 420

N-(3-(4-hydroxy-4-methylcyclohex-1-en-1-yl)benzoyl)-3-nitro-4-((2-(phenylthio)ethyl)amino)benzenesulfonamide

EXAMPLE 420A 1,4-dioxaspiro(4.5)dec-7-en-8-yl trifluoroacetate

The desired product was prepared by substituting 1,4-dioxaspiro(4.5)decan-8-one for 4-tert-butylcyclohexanone in Example 5A.

EXAMPLE 420B methyl 4-(1,4-dioxaspiro(4.5)dec-7-en-8-yl)benzoate

The desired product was prepared by substituting Example 420A for Example 5A in Example 5B.

EXAMPLE 420C methyl 4-(4-oxocyclohex-1-en-1-yl)benzoate

A solution of Example 420B (2.2 g) and p-toluenesulfonic acid (100 mg) in acetone (10 mL) was heated to reflux for 10 hours, filtered through a pad of silica gel (20 g), and concentrated to provide the desired product.

EXAMPLE 420D methyl 4-(4-hydroxy-4-methylcyclohex-1-en-1-yl)benzoate

A suspension of anhydrous cerium(III) chloride (2.71 g, 11 mmol) in THF (10 mL) at −78° C. was slowly treated with 1.5M methyllithium complexed with lithium chloride in diethyl ether (6.7 mL), warmed to room temperature over 2 hours, and added to a solution of Example 420C (1.15 g, 5.0 mmol) in THF (10 mL) at −78° C. The reaction was gradually warmed to room temperature over 4 hours, diluted with ethyl acetate (100 mL), washed with water (45 mL) and brine (10 mL), dried (MgSO$_4$), filtered, and concentrated. The concentrate was purified by flash column chromatography on silica gel with 10–30% ethyl acetate/hexanes to provide the desired product.

EXAMPLE 420E 4-(4-hydroxy-4-methylcyclohex-1-en-1-yl)benzoic acid

The desired product was prepared by substituting Example 420D for Example 1A in Example 1B.

EXAMPLE 420F

N-(3-(4-hydroxy-4-methylcyclohex-1-en-1-yl)benzoyl)-3-nitro-4-((2-(phenylthio)ethyl)amino)benzenesulfonamide The desired product was prepared by substituting Example 420E and Example 77B for Example 1B and Example 1C, respectively, in Example 1D. MS (ESI(−)) m/e 566 (M−H)$^−$; $^1$H NMR (300 MHz, DMSO-d$_6$) δ8.78 (br t, 1H), 8.60 (d, 1H), 7.92 (dd, 1H), 7.85 (d, 2H), 7.50 (d, 2H), 7.40–7.15 (m, 6H), 6.20 (m, 1H), 3.70 (m, 2H), 2.40–0.90 (m, 8H), 1.25 (s, 3H).

EXAMPLE 421

N-((4'-fluoro-1,1'-biphenyl-4-yl)carbonyl)-4-((3-(2-furylmethoxy)-2-(phenylthio)propyl)amino)-3-nitrobenzenesulfonamide and N-((4'-fluoro-1,1'-biphenyl-4-yl)carbonyl)-4-((2-(2-furylmethoxy)-1-((phenylthio)methyl)ethyl)amino)-3-nitrobenzenesulfonamide

EXAMPLE 421A 3-(2-furylmethoxy)-2-(phenylthio)propan-1-ol and 1-(2-furylmethoxy)-3-(phenylthio)propan-2-ol The desired products were prepared by substituting furfuryl glycidyl ether for cyclohexene oxide in Example 7A.

EXAMPLE 421B 2-((3-azido-2-(phenylthio)propoxy)methyl)furan and 2-((2-azido-3-(phenylthio)propoxy)methyl)furan The desired product was prepared by substituting Example 421A for Example 7A in Example 7B.

EXAMPLE 421C

N-((4'-fluoro-1,1'-biphenyl-4-yl)carbonyl)-4-((3-(2-furylmethoxy)-2-(phenylthio)propyl)amino)-3-nitrobenzenesulfonamide and N-((4'-fluoro-1,1'-biphenyl-4-yl)carbonyl)-4-((2-(2-furylmethoxy)-1-((phenylthio)methyl)ethyl)amino)-3-nitrobenzenesulfonamide The desired compound was prepared by substituting Example 421B for Example 393B in Example 393C. MS (ESI(−)) m/e 660 (M−H)$^−$; $^1$H NMR (300 MHz, DMSO-d$_6$), mixture of two isomers, ratio (2:1) δ8.81 (br t, 2/3H), 8.61, 8.59 (2d, 1H), 8.51 (br d, 1/2H), 7.96 (2d, 2H), 7.92, 7.88 (2dd, 1H), 7.78 (m, 4H), 7.60, 7.58 (2m, 1H), 7.40–7.10 (m, 8H), 6.49 (m, 2H), 4.45 (s, 2H), 4.25 (m, 2/3H), 3.80–3.50 (m, 5H).

EXAMPLE 422 isobutyl 4-(4-((((3-nitro-4-((2-(phenylthio)ethyl)amino)phenyl)sulfonyl)amino)carbonyl)phenyl)piperazine-1-carboxylate The desired product was prepared by substituting isopropyl chloroformate for 2-methoxyethyl chloroformate in Example 325. MS (ESI(−)) m/e 640 (M−H)$^−$; $^1$H NMR (300 MHz, DMSO-d$_6$) δ8.75 (t, 1H), 8.59 (d, 1H), 7.91 (dd, 1H), 7.76 (d, 2H), 7.39–7.35 (m, 2H), 7.29–7.23 (m, 2H), 7.20–7.14 (m, 2H), 6.93 (d, 2H), 3.81 (d, 2H), 3.66 (q, 2H), 3.50–3.44 (m, 4H), 3.32–3.23 (m, 6H), 1.94–1.82 (m, 1H), 0.90 (d, 6H).

EXAMPLE 423

N-(4-(5-methylpyridin-2-yl)benzoyl)-3-nitro-4-((2-(phenylthio)ethyl)amino)benzenesulfonamide The desired product was prepared by substituting 2-chloro-5-methylpyridine for 2,8-bistrifluoromethyl-3-chloroquinoline in Example 319. MS (ESI) m/e 549 (M+H)$^+$, 547 (M−H)$^−$; $^1$H NMR (500 MHz, DMSO-d$_6$) δ7.78 (t, 1H), 8.63 (d, 1H), 8.53 (d, 1H), 8.17 (d, 2H), 7.98–7.93 (m, 4H), 7.74 (dd, 1H), 7.37 (dt, 2H), 7.27 (td, 2H), 7.21 (d, 1H), 7.17 (tt, 1H), 3.67 (q, 2H), 3.27 (t, 2H), 2.35 (s, 3H).

EXAMPLE 424

3-nitro-4-((2-(phenylthio)ethyl)amino)-N-(4-(1H-pyrrol-1-yl)benzoyl)benzenesulfonamide The desired product was prepared by substituting 4-(N-pyrrolyl)benzoic acid and Example 77B for Example 1B and Example 1C, respectively, in Example 1D. MS (ESI(−)) m/e 521 (M−H)$^−$; $^1$H NMR (300 MHz, DMSO-d$_6$) δ3.26 (t, 2H), 3.60 (dt, 2H), 6.27 (s, 2H), 7.00 (d, 1H), 7.20 (t, 1H), 7.31 (t, 2H), 7.40 (d, 2H), 7.42 (s, 2H), 7.52 (d, 2H), 7.89 (d, 1H), 7.93 (d, 2H), 8.51 (d, 1H), 8.52 (t, 1H).

EXAMPLE 425

N-(4-(3-methyl-1-benzothien-5-yl)benzoyl)-3-nitro-4-((2-(phenylthio)ethyl)amino)benzenesulfonamide

EXAMPLE 425A methyl 4-(3-methyl-1-benzothien-5-yl)benzoate

The desired product was prepared by substituting 5-chloro-3-methylbenzothiophene for 5-chloro-2-methyl-1,3-benzoxazole in Example 54A.

EXAMPLE 425B 4-(3-methyl-1-benzothien-5-yl)benzoic acid

The desired product was prepared by substituting Example 425A for Example 1A in Example 1B. MS (ESI(−)) m/e 267 (M−H)$^−$.

EXAMPLE 425C

N-(4-(3-methyl-1-benzothien-5-yl)benzoyl)-3-nitro-4-((2-(phenylthio)ethyl)amino)benzenesulfonamide The desired product was prepared by substituting Example 425B and Example 77B for Example 1B and Example 1C, respectively, in Example 1D. MS (ESI(−)) m/e 602 (M−H)$^−$; $^1$H NMR (300 MHz, DMSO-d$_6$) δ2.46 (s, 3H), 3.27 (t, 2H), 3.61 (dt, 2H), 7.00 (d, 1H), 7.20 (t, 1H), 7.31 (t, 2H), 7.41 (m, 3H), 7.70 (dd, 1H), 7.72 (d, 2H), 7.90 (dd, 1H), 7.99 (d, 2H), 8.02 (d, 2H), 8.51 (t, 1H), 8.52 (d, 1H).

EXAMPLE 426

N-((4'-fluoro-1,1'-biphenyl-4-yl)carbonyl)-4-(((1S)-3-hydroxy-1-((phenylthio)methyl)propyl)amino)-3-nitrobenzenesulfonamide

EXAMPLE 426A (3S)-3-((4-(aminosulfonyl)-2-nitrophenyl)amino)-4-(phenylthio)butanoic acid The desired product was prepared by substituting Fmoc-L-Asp(OtBu)-OH for Fmoc-D-Asp(OtBu)-OH in Examples 122A–122E.

EXAMPLE 426B

N-((4'-fluoro-1,1'-biphenyl-4-yl)carbonyl)-4-(((1S)-3-hydroxy-1-((phenylthio)methyl)propyl)amino)-3-nitrobenzenesulfonamide The desired product was prepared by substituting Example 426A for Example 122E in Example 280.

EXAMPLE 427

N-((4'-(3-(dimethylamino)propyl)-2'-methoxy-1,1'-biphenyl-4-yl)carbonyl)-3-nitro-4-((2-(phenylthio)ethyl)amino)benzenesulfonamide

EXAMPLE 427A methyl 4'-(3-(dimethylamino)-3-oxopropyl)-2'-methoxy-1,1'-biphenyl-4-carboxylate The desired product was prepared by substituting dimethylamine for morpholine in Example 122M.

EXAMPLE 427B methyl 4'-(3-(dimethylamino)propyl)-2'-methoxy-1'-biphenyl-4-carboxylate The desired product was prepared by substituting Example 427A for Example 122F in Example 122G.

EXAMPLE 427C

N-((4'-(3-(dimethylamino)propyl)-2'-methoxy-1,1'-biphenyl-4-yl)carbonyl)-3-nitro-4-((2-(phenylthio)ethyl)amino)benzenesulfonamide The desired product was prepared by substituting Example 427B and Example 77B for Example 5C and Example 3A, respectively, in Example 5D. MS (ESI(−)) m/e 647 (M−H)−; $^1$H NMR (500 MHz, methanol-$d_4$) δ8.80 (d, 1H), 8.02 (dd, 1H), 7.83 (d, 2H), 7.59 (d, 2H), 7.36 (m, 2H), 7.26 (d, 1H), 7.21 (tt, 2H), 7.16 (tt, 1H), 7.06 (d, 1H), 6.98 (d, 1H), 6.92 (dd, 1H), 4.06 (t, 2H), 3.80 (s, 3H), 3.69 (t, 2H), 3.28 (t, 2H), 3.15 (m, 2H), 2.08 (m, 2H), 2.01 (s, 3H), 1.99 (s, 3H).

EXAMPLE 428

4-((3-(dimethylamino)-1-((phenylthio)methyl)propyl)amino)-N-((4'-fluoro-1,1'-biphenyl-4-yl)carbonyl)-3-nitrobenzenesulfonamide

EXAMPLE 428A 4-((3-(dimethylamino)-1-((phenylthio)methyl)propyl)amino)-3-nitrobenzenesulfonamide The desired product was prepared by substituting Fmoc-DL-Asp(OtBu)-OH for Fmoc-D-Asp(OtBu)-OH in Examples 122A–122G.

EXAMPLE 428B 4-((3-(dimethylamino)-1-((phenylthio)methyl)propyl)amino)-N-((4'-fluoro-1,1'-biphenyl-4-yl)carbonyl)-3-nitrobenzenesulfonamide The desired product was prepared by substituting Example 428A for Example 3A in Example 5D. MS (ESI(−)) m/e 621 (M−H)−; $^1$H NMR (500 MHz, methanol-$d_4$) δ8.72 (d, 1H), 7.98 (m, 3H), 7.68 (m, 4H), 7.26 (m, 2H), 7.18 (tt, 2H), 7.11 (m, 3H), 7.02 (d, 1H), 4.17 (m, 1H), 3.40 (d, 1H), 3.25 (m, 3H), 2.88 (s, 6H), 2.30 (m, 1H), 2.20 (m, 1H).

EXAMPLE 429 tert-butyl 3-(2-methoxy-4'-((((3-nitro-4-((2-(phenylthio)ethyl)amino)phenyl)sulfonyl)amino)carbonyl)-1,1'-biphenyl-4-yl)propanoate The desired product was prepared by substituting Example 122K and Example 77B for Example 5C and Example 3A, respectively, in Example 5D. MS (ESI(−)) m/e 690 (M−H)−; $^1$H NMR (300 MHz, DMSO-$d_6$) δ8.79 (t, 1H), 8.62 (d, 1H), 7.94 (dd, 1H), 7.88 (d, 2H), 7.57 (d, 2H), 7.37 (m, 2H), 7.30–7.14 (m, 5H), 7.02 (d, 1H), 6.92 (dd, 1H), 3.76 (s, 3H), 3.67 (q, 2H), 3.28 (d, 2H), 2.85 (t, 2H), 2.57 (t, 2H), 1.39 (s, 9H).

EXAMPLE 430

N-(4-(1-(cyclohexylmethyl)-2-methyl-1H-benzimidazol-5-yl)benzoyl)-3-nitro-4-((2-(phenylthio)ethyl)amino)benzenesulfonamide

EXAMPLE 430A 4-bromo-N$^1$-(cyclohexylmethyl)benzene-1,2-diamine

The desired product was prepared by substituting cyclohexylmethylamine for butylamine in Examples 166A and 166B.

EXAMPLE 430B 5-bromo-1-(cyclohexylmethyl)-2-methyl-1H-benzimidazole

The desired product was prepared by substituting Example 430A and acetic acid for Example 343A and valeric acid, respectively, in Example 343B.

EXAMPLE 430C 4-(1-(cyclohexylmethyl)-2-methyl-1H-benzimidazol-5-yl)benzoic acid The desired product was prepared by substituting Example 430B for 6-bromoindole in Example 4A.

EXAMPLE 430D

N-(4-(1-(cyclohexylmethyl)-2-methyl-1H-benzimidazol-5-yl)benzoyl)-3-nitro-4-((2-(phenylthio)ethyl)amino)benzenesulfonamide The desired product was prepared by substituting Example 430C and Example 77B for Example 1B and Example 1C, respectively, in Example 1D. MS (ESI) m/e 682, 684 (M−H)−, (M+H)+; $^1$H NMR (300 MHz, DMSO-$d_6$) δ1.03–1.25 (m, 4H), 1.44–1.98 (m, 7H), 2.54 (s, 3H), 3.27 (t, 2H), 3.61 (dt, 2H), 4.04 (d, 2H), 6.99 (d, 1H), 7.20 (tt, 1H), 7.31 (td, 2H), 7.40 (dd, 2H), 7.50 (dd, 1H), 7.56 (d, 1H), 7.64 (d, 2H), 7.78 (s, 1H), 7.89 (dd, 1H), 7.95 (d, 2H), 8.53 (d, 1H), 8.53 (t, 1H).

EXAMPLE 431

N-((2'-methoxy-4'-(3-methoxypropyl)-1,1'-biphenyl-4-yl)carbonyl)-3-nitro-4-((2-(phenylthio)ethyl)amino)benzenesulfonamide

EXAMPLE 431A methyl 4'-(3-hydroxypropyl)-2'-methoxy-1,1'-biphenyl-4-carboxylate The desired product was prepared by substituting Example 122L for Example 122E in Example 280A.

EXAMPLE 431B methyl 2'-methoxy-4'-(3-methoxypropyl)-1,1'-biphenyl-4-carboxylate The desired product was prepared by substituting Example 431A for Example 417A in Example 417B.

EXAMPLE 431C

N-((2'-methoxy-4'-(3-methoxypropyl)-1,1'-biphenyl-4-yl)carbonyl)-3-nitro-4-((2-(phenylthio)ethyl)amino)benzenesulfonamide The desired product was prepared by substituting Example 431B and Example 77B for Example 5C and Example 3A, respectively, in Example 5D. MS (ESI(−)) m/e 634 (M−H)$^-$; $^1$H NMR (300 MHz, DMSO-d$_6$) δ8.65 (t, 1H), 8.57 (d, 1H), 7.90 (dd, 1H), 7.88 (d, 2H), 7.47 (d, 2H), 7.39 (m, 2H), 7.30 (tt, 2H), 7.20 (m, 2H), 7.09 (d, 1H), 6.95 (d, 1H), 6.86 (dd, 1H), 3.76 (s, 3H), 3.64 (q, 2H), 3.45 (t, 2H), 3.26 (t, 2H), 3.25 (s, 3H), 2.64 (t, 2H), 1.85 (m, 2H).

EXAMPLE 432

N-((4'-(4-(2,5-dimethoxyphenyl)-1,3-oxazol-2-yl)-1,1'-biphenyl-4-yl)carbonyl)-3-nitro-4-((2-(phenylthio)ethyl)amino)benzenesulfonamide

EXAMPLE 432A 2-(4-bromophenyl)-4-(2,5-dimethoxyphenyl)-1,3-oxazole

The desired product was prepared by substituting 2-bromo-2',5'-dimethoxyacetophenone for 2-bromo-4'-methylacetophenone in Example 186B. MS (DCI) m/e 360, 362 (M+H)$^+$; $^1$H NMR (300 MHz, DMSO-d$_6$) δ8.52 (s, 1H), 8.02–7.99 (m, 2H), 7.80–7.77 (m, 2H), 7.66 (d, 1H), 7.07 (d, 1H), 6.93 (dd, 1H), 3.91 (s, 3H), 3.79 (s, 3H).

EXAMPLE 432B ethyl 4'-(4-(2,5-dimethoxyphenyl)-1,3-oxazol-2-yl)-1,1'-biphenyl-4-carboxylate The desired product was prepared by substituting Example 432A for Example 186B in Example 186C. MS (DCI) m/e 430 (M+H)$^+$; $^1$H NMR (300 MHz, DMSO-d$_6$) δ8.54 (s, 1H), 8.21–8.18 (m, 2H), 8.10–8.07 (m, 2H), 7.98–7.95 (m, 2H), 7.94–7.92 (m, 2H), 7.70 (d, 1H), 7.09 (d, 1H), 6.94 (dd, 1H), 4.36 (q, 2H), 3.92 (s, 3H), 3.81 (s, 3H), 1.36 (t, 3H).

EXAMPLE 432C

4'-(4-(2,5-dimethoxyphenyl)-1,3-oxazol-2-yl)-1,1'-biphenyl-4-carboxylic acid

The desired product was prepared by substituting Example 432B for Example 186C in Example 186D. MS (DCI) m/e 402 (M+H)$^+$; $^1$H NMR (300 MHz, DMSO-d$_6$) δ8.53 (s, 1H), 8.19–8.18 (m, 2H), 8.07–8.06 (m, 2H), 7.96–7.95 (m, 2H), 7.91–7.89 (m, 2H), 7.70 (d, 1H), 7.09 (d, 1H), 6.94 (dd, 1H), 3.92 (s, 3H), 3.81 (s, 3H).

EXAMPLE 432D

N-((4'-(4-(2,5-dimethoxyphenyl)-1,3-oxazol-2-yl)-1,1'-biphenyl-4-yl)carbonyl)-3-nitro-4-((2-(phenylthio)ethyl)amino)benzenesulfonamide The desired product was prepared by substituting Example 432C and Example 77B for Example 1B and Example 1C, respectively, in Example 1D. MS (DCI) m/e 737 (M+H)$^+$; $^1$H NMR (300 MHz, DMSO-d$_6$) δ12.55 (br s, 1H), 8.81, (t, 1H), 8.65 (d, 1H), 8.54 (s, 1H), 8.19–8.16 (m, 2H), 8.03–8.00 (m, 2H), 7.97–7.89 (m, 5H), 7.68 (d, 1H), 7.39–7.36 (m, 2H), 7.30–7.18 (m, 4H), 7.08 (d, 1H), 6.93 (dd, 1H), 3.92 (s, 3H), 3.80 (s, 3H), 3.68 (q, 2H), 3.30 (q, 2H).

EXAMPLE 433

N-(4-(1-(cyclohexylmethyl)-1H-benzimidazol-5-yl)benzoyl)-3-nitro-4-((2-(phenylthio)ethyl)amino)benzenesulfonamide

EXAMPLE 433A 4-bromo-N$^1$-(cyclohexylmethyl)benzene-1,2-diamine

The desired product was prepared by substituting cyclohexylmethylamine for butylamine in Examples 166A and 166B.

EXAMPLE 433B 5-bromo-1-(cyclohexylmethyl)-1H-benzimidazole

The desired product was prepared by substituting Example 433A for Example 170A in Example 170B.

EXAMPLE 433C

N-(4-(1-(cyclohexylmethyl)-1H-benzimidazol-5-yl)benzoyl)-3-nitro-4-((2-(phenylthio)ethyl)amino)benzenesulfonamide The desired product was prepared by substituting Example 433B and Example 214E for 6-bromoindole and 4-(dihydroxyboryl)benzoic acid, respectively, in Example 4A. MS (ESI) m/e 668, 670 (M−H)$^-$, (M+H)$^+$; $^1$H NMR (300 MHz, DMSO-d$_6$) δ0.95–1.25 (m, 5H), 1.47–1.73 (m, 5H), 1.85 (m, 1H), 3.28 (t, 2H), 3.62 (dt, 2H), 4.12 (d, 2H), 6.99 (d, 1H), 7.19 (tt 1H), 7.30 (t, 2H), 7.39 (d, 2H), 7.45–7.62 (m, 2H), 7.66 (t, 2H), 7.85–7.94 (m, 4H), 8.22 (s, 1H), 8.52 (d, 1H), 8.54 (t, 1H).

EXAMPLE 434

4-((2-azido-1-((phenylthio)methyl)ethyl)amino)-N-((4'-fluoro-1,1'-biphenyl-4-yl)carbonyl)-3-nitrobenzenesulfonamide

EXAMPLE 434A methyl N-(4-(aminosulfonyl)-2-nitrophenyl)-S-phenylcysteinate

The desired product was prepared by substituting Example 175A and Example 122C for Example 175B and Example 175C, respectively, in Example 175D.

EXAMPLE 434B 4-((2-hydroxy-1-((phenylthio)methyl)ethyl)amino)-3-nitrobenzenesulfonamide A solution of Example 434A (1.42 g, 3.45 mmol) in THF (10 mL) and methanol (1 mL) at room temperature was slowly treated with lithium borohydride (100 mg), stirred for 3 hours, as diluted with ethyl acetate (100 mL), washed with water (45 mL) and brine (10 mL), dried (MgSO$_4$), filtered,

EXAMPLE 434C 4-((2-azido-1-((phenylthio)methyl)ethyl)amino)-3-nitrobenzenesulfonamide A solution of Example 434B (1.01 g, 2.6 mmol) and N,N-diisopropylethylamine (0.70 mL, 4.0 mmol) in dichloromethane (5 mL) and DMF (5 mL) at room temperature was treated with methanesulfonyl chloride (0.22 mL, 2.90 mmol), stirred for 1 hour, and concentrated to remove the dichloromethane. The resulting DMF solution was treated with sodium azide (1.95 g, 30 mmol) and tetrabutylammonium iodide (100 mg), heated to 50° C. for 16 hours, diluted with ethyl acetate (200 mL), washed with water (100 mL) and brine (50 mL), dried (MgSO$_4$), filtered, and concentrated to provide the desired product.

EXAMPLE 434D 4-((2-azido-1-((phenylthio)methyl)ethyl)amino)-N-((4'-fluoro-1,1'-biphenyl-4-yl)carbonyl)-3-nitrobenzenesulfonamide The desired product was prepared by substituting Example 434C for Example 1C in Example 1D. MS (ESI(−)) m/e 605 (M−H)$^-$; $^1$H NMR (300 MHz, DMSO-d$_6$) δ8.59 (d, 1H), 8.42 (d, 1H), 7.97 (d, 2H), 7.92 (dd, 1H), 7.78 (m, 4H), 7.35–7.1 (m, 7H), 4.34 (m, 1H), 3.82 (dd, 1H), 3.69 (dd, 1H), 3.37 (m, 2H).

EXAMPLE 435 tert-butyl (3R)-3-((4-((((4'-fluoro-1,1'-biphenyl-4-yl)carbonyl)amino)sulfonyl)-2-nitrophenyl)amino)-4-(phenylthio)butanoate The desired product was prepared by substituting Example 122D for Example 1C in Example 1D. MS (ESI(−)) m/e 664 (M−H)$^-$; $^1$H NMR (300 MHz, methanol-d$_4$) δ8.73 (d, 1H), 8.58 (d, 1H), 7.95 (dd, 1H), 7.93 (d, 2H), 7.70 (m, 4H), 7.28 (m, 2H), 7.23–7.12 (m, 5H), 6.98 (d, 1H), 4.40 (m, 1H), 2.78 (m, 2H), 1.36 (s, 9H), remaining two protons are buried under solvent peaks (3.35–3.28 ppm).

EXAMPLE 436

8-(4-((((3-nitro-4-((2-(phenylthio)ethyl)amino)phenyl)sulfonyl)amino)carbonyl)phenyl)quinoline-2-carboxylic acid

EXAMPLE 436A methyl 8-((trifluoroacetyl)oxy)quinoline-2-carboxylate

The desired product was prepared by substituting methyl 8-hydroxyquinoline-2-carboxylate for vanillin in Example 122H.

EXAMPLE 436B 8-(4-((((3-nitro-4-((2-(phenylthio)ethyl)amino)phenyl)sulfonyl)amino)carbonyl)phenyl)quinoline-2-carboxylic acid The desired product was prepared by substituting Example 436A for Example 389A in Example 389B. MS (ESI(−)) m/e 627 (M−H)$^-$; $^1$H NMR (400 MHz, DMSO-d$_6$) δ8.8.77 (t, 1H), 8.66 (d, 1H), 8.52 (d, 1H), 8.14 (d, 2H), 7.97 (d, 2H), 7.96 (dd, 1H), 7.93 (dd, 1H), 7.87 (d, 2H), 7.82 (dd, 1H), 7.38 (m, 2H), 7.28 (tt, 2H), 7.22 (d, 1H), 7.19 (tt, 1H), 3.67 9q, 2H), 3.28 (t, 2H).

EXAMPLE 437

3-(2-methoxy-4'-((((3-nitro-4-((2-(phenylthio)ethyl)amino)phenyl)sulfonyl)amino)carbonyl)-1,1'-biphenyl-4-yl)-N,N-dimethylpropanamide The desired product was prepared by substituting Example 427A and Example 77B for Example 5C and Example 3A, respectively, in Example 5D. MS (ESI(−)) m/e 661 (M−H)$^-$; $^1$H NMR (300 MHz, DMSO-d$_6$) δ8.79 (t, 1H), 8.62 (d, 1H), 7.94 (dd, 1H), 7.88 (d, 2H), 7.57 (d, 2H), 7.37 (m, 2H), 7.30–7.14 (m, 5H), 7.02 (d, 1H), 6.92 (dd, 1H), 3.76 (s, 3H), 3.67 (q, 2H), 3.28 (d, 2H), 2.95 (s, 3H), 2.85 (t, 2H), 2.83 (s, 3H), 2.64 (t, 2H).

EXAMPLE 438

N-((4'-(hydroxymethyl)-2'-methoxy-1,1'-biphenyl-4-yl)carbonyl)-3-nitro-4-((2-(phenylthio)ethyl)amino)benzenesulfonamide

EXAMPLE 438A methyl 4'-(((tert-butyl(dimethyl)silyl)oxy)methyl)-2'-methoxy-1,1'-biphenyl-4-carboxylate A solution of Example 417A (136 mg, 0.50 mmol), tert-butyldimethylsilyl chloride (91 mg, 0.60 mmol), and N,N-diisopropylethylamine (129 mg, 1.0 mmol) in dichloromethane (5 mL) at room temperature was stirred for 3 hours, and filtered through a pad of silica gel. The pad was rinsed with ether and the combined solutions were concentrated to provide the desired product.

EXAMPLE 438B

N-((4'-(hydroxymethyl)-2'-methoxy-1,1'-biphenyl-4-yl)carbonyl)-3-nitro-4-((2-(phenylthio)ethyl)amino)benzenesulfonamide A mixture of Example 438A (0.50 mmol) and 1M LiOH (0.60 mL) in THF (2 mL) was heated to 50° C., stirred for 3 hours, concentrated, dissolved in DMF (5 mL), and treated with a mixture of Example 77B (211 mg, 0.60 mmol), EDCI (193 mg, 1.0 mmol), and DMAP (50 mg). The mixture was stirred for 16 hours, treated with 1M HF (3 mL), stirred for 3 hours, diluted with ethyl acetate (100 mL), washed sequentially with 1M HCl (10 mL), water (20 mL), and brine (10 mL), dried (MgSO$_4$), filtered, and concentrated. The concentrate was purified by flash column chromatography on silica gel with 50–100% ethyl acetate/hexanes to provide the desired product. MS (ESI(−)) m/e 592 (M−H)$^-$; $^1$H NMR (300 MHz, DMSO-d$_6$) δ8.79 (t, 1H), 8.62 (d, 1H), 7.92 (dd, 1H), 7.89 (d, 2H), 7.54 (d, 2H), 7.37 (m, 2H), 7.28 (m, 3H), 7.18 (tt, 1H), 7.06 (s, 1H), 6.97 (d, 1H), 4.54 (s, 2H), 3.76 (s, 3H), 3.66 (q, 2H), 3.20 (t, 2H).

EXAMPLE 439

N-(4-(1-benzyl-1,2,3,6-tetrahydropyridin-4-yl)benzoyl)-3-nitro-4-((2-(phenylthio)ethyl)amino)benzenesulfonamide

EXAMPLE 439A 1-benzyl-1,2,3,6-tetrahydropyridin-4-yl trifluoroacetate

The desired product was prepared by substituting 1-benzyl-4-piperidone for 4-tert-butylcyclohexanone in Example 5A.

and concentrated to provide the desired product. MS (ESI (+)) m/e 384 (M+H).

EXAMPLE 439B methyl 4-(1-benzyl-1,2,3,6-tetrahydropyridin-4-yl)benzoate

The desired product was prepared by substituting Example 439A for Example 5A in Example 5B. MS (DCI (+)) m/e 308 (M+H)$^+$.

EXAMPLE 439C

N-(4-(1-benzyl-1,2,3,6-tetrahydropyridin-4-yl)benzoyl)-3-nitro-4-((2-(phenylthio)ethyl)amino)benzenesulfonamide The desired product was prepared by substituting Example 439B for Example 230B in Example 230C. MS (ESI(−)) m/e 627 (M−H)$^-$; $^1$H NMR (300 MHz, DMSO-d$_6$) δ8.55 (br t, 1H), 8.50 (d, 1H), 7.92 (dd, 1H), 7.85 (d, 2H), 7.55–7.15 (m, 12H), 7.00 (d, 1H), 6.35 (s, 1H), 4.21 (s, 2H), 3.65 (m, 2H), 3.52–2.50 (m, 10H).

EXAMPLE 440

N-(4-(1-butyl-1H-benzimidazol-5-yl)benzoyl)-3-nitro-4-((2-(phenylthio)ethyl)amino)benzenesulfonamide

EXAMPLE 440A 5-bromo-1-butyl-1H-benzimidazole

The desired product was prepared by substituting Example 166B and formic acid for Example 343A and valeric acid, respectively, in Example 343B.

EXAMPLE 440B

N-(4-(1-butyl-1H-benzimidazol-5-yl)benzoyl)-3-nitro-4-((2-(phenylthio)ethyl)amino)benzenesulfonamide The desired product was prepared by substituting Example 440A and Example 214E for 6-bromoindole and 4-(dihydroxyboryl)benzoic acid, respectively, in Example 4A. MS (ESI) m/e 628, 630 (M−H)$^-$, (M+H)$^+$; $^1$H NMR (300 MHz, DMSO-d$_6$) δ0.91 (t, 3H), 1.25 (qt, 2H), 1.79 (tt, 2H), 3.28 (t, 2H), 3.61 (dt, 2H), 4.27 (t, 2H), 6.99 (d, 1H), 7.19 (tt, 1H), 7.30 (td, 2H), 7.39 (dd, 2H), 7.47–7.62 (m, 3H), 7.66 (t, 2H), 7.88 (dd, 1H), 7.92–7.98 (m, 2H), 8.26 (s, 1H), 8.52 (d, 1H), 8.53 (t, 1H).

EXAMPLE 441

2-(2-methoxy-4'-((((3-nitro-4-((2-(phenylthio)ethyl)amino)phenyl)sulfonyl)amino)carbonyl)-1,1'-biphenyl-4-yl)-N,N-dimethylacetamide

EXAMPLE 441A methyl 4'-(2-(dimethylamino)-2-oxoethyl)-2'-methoxy-1,1'-biphenyl-4-carboxylate The desired product was prepared by substituting dimethylamine for 1-methylpiperazine in Example 328B.

EXAMPLE 441B 2-(2-methoxy-4'-((((3-nitro-4-((2-(phenylthio)ethyl)amino)phenyl)sulfonyl)amino)carbonyl)-1,1'-biphenyl-4-yl)-N,N-dimethylacetamide The desired product was prepared by substituting Example 441A and Example 77B for Example 5C and Example 3A, respectively, in Example 5D. MS (ESI(−)) m/e 647 (M−H)$^-$; $^1$H NMR (300 MHz, DMSO-d$_6$) δ8.79 (t, 1H), 8.62 (d, 1H), 7.93 (dd, 1H), 7.88 (d, 2H), 7.57 (d, 2H), 7.47 (m, 2H), 7.30–7.15 (m, 5H), 6.99 (d, 1H), 6.89 (dd, 1H), 3.74 (s, 3H), 3.73 (s, 2H), 3.67 (q, 2H), 3.26 (d, 2H), 3.03 (s, 3H), 2.84 (s, 3H).

EXAMPLE 442

8-(4-(((((4-((2-adamantylmethyl)amino)-3-nitrophenyl)sulfonyl)amino)carbonyl)phenyl)quinoline-2-carboxylic acid The desired product was prepared by substituting Example 436A and Example 255A for Example 389A and Example 108A, respectively, in Example 389B. MS (ESI (−)) m/e 639 (M−H)$^-$; $^1$H NMR (400 MHz, DMSO-d$_6$) δ8.69 (d, 1H), 8.62 (d, 1H), 8.57 (t, 1H), 8.14 (d, 2H), 7.97 (m, 3H), 7.93 (dd, 1H), 7.87 (d, 2H), 7.73 (dd, 1H), 7.36 (d, 1H), 3.19 (d, 2H), 1.98 (m, 3H), 1.72–1.55 (m, 12H).

EXAMPLE 443

4-((2-(benzyloxy)-1-((phenylthio)methyl)ethyl)amino)-N-((4'-fluoro-1,1'-biphenyl-4-yl)carbonyl)-3-nitrobenzenesulfonamide

EXAMPLE 443A methyl O-benzyl-N-(tert-butoxycarbonyl)serinate

A mixture of BOC-DL-Ser-OMe (434 mg, 2.0 mmol), benzyl bromide (513 mg, 3.0 mmol), and silver oxide (695 mg, 3.0 mmol) in dichloromethane (10 mL) at room temperature was stirred for 2 days, filtered, and concentrated. The concentrate was purified by flash column chromatography on silica gel with 20% ethyl acetate/hexanes to provide the desired product. MS (ESI(−)) m/e 308 (M−H)$^-$.

EXAMPLE 443B tert-butyl 2-(benzyloxy)-1-(hydroxymethyl)ethylcarbamate

The desired product was prepared by substituting Example 443A for Example 175A in Example 175B. MS (ESI(−)) m/e 280 (M−H)$^-$.

EXAMPLE 443C tert-butyl 2-(benzyloxy)-1-((phenylthio)methyl)ethylcarbamate

The desired product was prepared by substituting Example 443B for Example 122A in Example 122B. MS (ESI(−)) m/e 372 (M−H)$^-$.

EXAMPLE 443D 4-((2-(benzyloxy)-1-((phenylthio)methyl)ethyl)amino)-3-nitrobenzenesulfonamide The desired product was prepared by substituting Example 443C for Example 180A in Example 180B. MS (ESI(−)) m/e 472 (M−H)$^-$.

EXAMPLE 443E 4-((2-(benzyloxy)-1-((phenylthio)methyl)ethyl)amino)-N-((4'-fluoro-1,1'-biphenyl-4-yl)carbonyl)-3-nitrobenzenesulfonamide The desired product was prepared by substituting Example 443D for for Example 1C in Example 1D. MS (ESI(−)) m/e 670 (M−H)⁻; ¹H NMR (500 MHz, DMSO-d₆) δ8.61 (d, 1H), 8.60 (d, 1H), 7.97 (d, 2H), 7.79 (dd, 1H), 7.79 (m, 4H), 7.35–7.26 (m, 8H), 7.23 (m, 3H), 7.16 (m, 1H), 4.50 (s, 2H), 4.27 (m, 1H), 3.73 (dd, 1 H), 3,67 (dd, 1H), 3.38 (m, 2H).

EXAMPLE 445

N-((4'-(2-hydroxyethyl)-2'-methoxy-1,1'-biphenyl-4-yl)carbonyl)-3-nitro-4-((2-(phenylthio)ethyl)amino)benzenesulfonamide

EXAMPLE 445A methyl 2'-methoxy-4'-vinyl-1,1'-biphenyl-4-carboxylate

A suspension of methyltriphenylphosphonium bromide (785 mg, 2.2 mmoL) in THF (5 mL) was treated with 1M lithium bis(trimethylsilyl)amide in THF (2.2 mL), stirred for 30 minutes, treated with a solution of Example 122I (540 mg, 2.0 mmol) in THF (2 mL), stirred for 1 hour, and filtered through a pad of silica gel (20 g). The pad was rinsed with 1:1 ether/dichlormethane and concentrated. The concentrate was purified by flash column chromatography on silica gel with 20–50% dichloromethane/hexanes to provide the desired product.

EXAMPLE 445B methyl 4'-(2-hydroxyethyl)-2'-methoxy-1,1'-biphenyl-4-carboxylate A solution of Example 445A (228 mg) and 1M borane in THF (1.2 mL) in THF (2 mL) at room temperature was stirred for 5 hours, and treated sequentially with 2M sodium carbonate (1 mL) and 33% hydrogen peroxide (1 mL). The mixture was heated to 60° C. for 1 hour, diluted with ethyl acetate (100 mL), washed with water (45 mL) and brine (10 mL), dried (MgSO₄), filtered, and concentrated. The concentrate was purified by flash column chromatography on silica gel with 20–40% ethyl acetate/hexanes to provide the desired product.

EXAMPLE 445C methyl 4'-(2-((tert-butyl(dimethyl)silyl)oxy)ethyl)-2'-methoxy-1,1'-biphenyl-4-carboxylate The desired product was prepared by substituting Example 445B for Example 417A in Example 438A.

EXAMPLE 445D

N-((4'-(2-hydroxyethyl-2'-methoxy-1,1'-biphenyl-4-yl)carbonyl)-3-nitro-4-((2-(phenylthio)ethyl)amino)benzenesulfonamide The desired product was prepared by substituting Example 445C for Example 438A in Example 438B. MS (ESI(−)) m/e 606 (M−H)⁻; ¹H NMR (300 MHz, DMSO-d₆) δ8.64 (t, 1H), 8.56 (d, 1H), 7.90 (dd, 1H), 7.88 (d, 2H), 7.46 (d, 2H), 7.38 (m, 2H), 7.30 (m, 2H), 7.20 (m, 2H), 7.10 (d, 1H), 6.97 (d, 1H), 6.88 (dd, 1H), 4.65 (t, 1H), 3.76 (s, 3H), 3.64 (m, 4H), 3.20 (t, 2H), 2.75 (t, 2H).

EXAMPLE 446

N-((2'-methoxy-4'-(2-methoxyethyl)-1,1'-biphenyl-4yl)carbonyl)-3-nitro-4-((2-(phenylthio)ethyl)amino)benzenesulfonamide

EXAMPLE 446A methyl 2'-methoxy-4'-(2-methoxyethyl)-1,1'-biphenyl-4-carboxylate The desired product was prepared by substituting Example 445B for Example 417A in Example 417B.

EXAMPLE 446B

N-((2'-methoxy-4'-(2-methoxyethyl)-1,1'-biphenyl-4-yl)carbonyl)-3-nitro-4-((2-(phenylthio)ethyl)amino)benzenesulfonamide The desired product was prepared by substituting Example 446A and Example 77B for Example 5C and Example 3A, respectively, in Example 5D. MS (ESI(−)) m/e 620 (M−H)⁻; ¹H NMR (300 MHz, DMSO-d₆) δ8.64 (t, 1H), 8.56 (d, 1H), 7.90 (dd, 1H), 7.88 (d, 2H), 7.46 (d, 2H), 7.38 (m, 2H), 7.30 (m, 2H), 7.20 (m, 2H), 7.10 (d, 1H), 6.97 (d, 1H), 6.88 (dd, 1H), 3.78 (s, 3H), 3.64 (m, 4H), 3.44 (m, 2H), 3.28 (t, 23H), 3.13 (m, 2H), 3.08 (m, 2H), 2.69 (m, 2H), 2.03 (m, 2H), 1.53 (m, 2H).

EXAMPLE 447

N,N-diisopropyl-4-(4-(((((3-nitro-4-((2-(phenylthio)ethyl)amino)phenyl)sulfonyl)amino)carbonyl)phenyl)-3,6-dihydropyridine-1(2H)-carboxamide The desired product was prepared by substituting diisopropylcarbamyl chloride for 4-morpholinecarbonyl chloride in Example 317. MS (ESI(−)) m/e 664 (M−H)⁻; ¹H NMR (300 MHz, DMSO-d₆) δ8.78 (br t, 1H), 8.60 (d, 1H), 7.92 (dd, 1H), 7.85 (d, 2H), 7.40–7.15 (m, 8H), 6.20 (d, 1H), 3.70 (m, 2H), 2.40–1.20 (m, 10H), 0.85 (2s, 12H).

EXAMPLE 448

N-(4-(2-butyl-1-(cyclohexylmethyl)-1H-benzimidazol-5-yl)benzoyl)-3-nitro-4-((2-(phenylthio)ethyl)amino)benzenesulfonamide

EXAMPLE 448A 5-bromo-2-butyl-1-(cyclohexylmethyl)-1H-benzimidazole

The desired product was prepared by substituting Example 430A for Example 343A in Example 343B.

EXAMPLE 448B 4-(2-butyl-1-(cyclohexylmethyl)-1H-benzimidazol-5-yl)benzoic acid The desired product was prepared by substituting Example 448A for 6-bromoindole in Example 4A.

EXAMPLE 448C

N-(4-(2-butyl-1-(cyclohexylmethyl)-1H-benzimidazol-5-yl)benzoyl)-3-nitro-4-((2-(phenylthio)ethyl)amino)benzenesulfonamide The desired product was prepared by substituting Example 448B and Example 77B for Example 1B and Example 1C, respectively, in Example 1D. MS (ESI) m/e 724, 726 (M−H)⁻, (M+H)⁺; ¹H NMR (300 MHz, DMSO-d₆) δ0.96 (t, 3H), 1.03–1.55 (m, 5H), 1.45 (qt, 2H), 1.47–1.73 (m, 5H) 1.82 (m, 3H), 2.86 (t, 2H), 3.27 (t, 2H), 3.63 (dt, 2H), 4.06 (d, 2H), 7.08 (d, 1H), 7.19 (tt, 1H), 7.29 (td, 2H), 7.39 (dd, 2H), 7.53 (dd, 1H), 7.60 (d, 1H), 7.71 (d, 2H), 7.86 (s, 1H), 7.92 (dd, 1H), 7.96 (d, 2H), 8.56 (d, 1H), 8.53 (t, 1H).

EXAMPLE 449

N-(4-(5-chloropyridin-2-yl)benzoyl)-3-nitro-4-((2-(phenylthio)ethyl)amino)benzenesulfonamide The desired product was prepared by substituting 2,4-dichloropyridine for 2,8-bistrifluoromethyl-3- chloroquinoline in Example 319. MS (APCI(+)) m/e 569 (M+H)⁺; (APCI(−)) m/e 567(M−H)⁻; ¹H NMR (500 MHz, DMSO-d₆) δ8.78 (t, 1H), 8.74 (d, 1H), 8.63 (d, 1H), 8.19 (d, 2H), 8.15 (d, 1H), 8.05 (dd, 1H), 7.99 (d, 2H), 7.94 (dd, 1H), 7.36 (dt, 2H), 7.27 (td, 2H), 7.21 (d, 1H), 7.18 (tt, 1H), 3.68 (q, 2H), 3.25 (m, 2H).

EXAMPLE 450

N-((2'-methoxy-4'-(3-morpholin-4-ylpropyl)-1,1'-biphenyl-4-yl)carbonyl)-3-nitro-4-((2-(phenylthio)ethyl)amino)benzenesulfonamide The desired product was prepared by substituting Example 122O and Example 77B for Example 1B and Example 1C, respectively, in Example 1D. MS (ESI(−)) m/e 691 (M−H)⁻; ¹H NMR (500 MHz, DMSO-d₆) δ10.15 (br s, 1H), 8.79 (t, 1H), 8.63 (d, 1H), 7.93 (dd, 1H), 7.88 (d, 2H), 7.57 (d, 2H), 7.37 (m, 2H), 7.26 (m, 3H), 7.23 (d, 1H), 7.17 (tt, 1H), 7.02 (d, 1H), 6.92 (dd, 1H), 3.76 (s, 2H), 3.75 (s, 3H), 3.67 (q, 2H), 3.56–3.52 (m, 6H), 3.47 (m, 2H), 3.26 (d, 2H).

EXAMPLE 451

N-((4'-(3-hydroxypropyl)-2'-methoxy-1,1'-biphenyl-4-yl)carbonyl)-3-nitro-4-((2-(phenylthio)ethyl)amino)benzenesulfonamide

EXAMPLE 451A methyl 4'-(3-((tert-butyl(dimethyl)silyl)oxy)propyl)-2'-methoxy-1,1'-biphenyl-4-carboxylate The desired product was prepared by substituting Example 431A for Example 417A in Example 438A.

EXAMPLE 451B

4'-(3-((tert-butyl(dimethyl)silyl)oxy)propyl)-2'-methoxy-1,1'-biphenyl-4-carboxylic acid A mixture of Example 451A (828 mg, 2.0 mmol) and 1M LiOH (3 mL) in THF (10 mL) was heated to 50° C., stirred for 3 hours, diluted with ethyl acetate, washed with saturated sodium monobasic phosphate (10 mL), dried (MgSO₄), filtered, and concentrated to provide the desired product.

EXAMPLE 451C

N-((4'-(3-hydroxypropyl)-2'-methoxy-1,1'-biphenyl-4-yl)carbonyl)-3-nitro-4-((2-(phenylthio)ethyl)amino)benzenesulfonamide A mixture of Example 451B (200 mg, 0.5 mmol), Example 77B (211 mg, 0.60 mmol), EDCI (193 mg, 1.0 mmol), and DMAP (50 mg) at room temperature was stirred for 16 hours, treated with 1M HF (3 mL), stirred for 3 hours, diluted with ethyl acetate (100 mL), washed sequentially with 1M HCl (10 mL), water (20 mL), and brine (10 mL), dried (MgSO₄), filtered, and concentrated. The concentrate was purified by flash column chromatography on silica gel with 50–100% ethyl acetate/hexanes to provide the desired product. MS (ESI(−)) m/e 620 (M−H)⁻; ¹H NMR (300 MHz, DMSO-d₆) δ8.80 (t, 1H), 8.63 (d, 1H), 7.93 (dd, 1H), 7.88 (d, 2H), 7.57 (d, 2H), 7.47 (m, 2H), 7.30–7.15 (m, 5H), 6.97 (d, 1H), 6.88 (dd, 1H), 3.76 (s, 3H), 3.64 (m, 2H), 3.45 (t, 2H), 3.20 (t, 2H), 2.64 (t, 2H), 1.75 (m, 2H).

EXAMPLE 452

4-((5-amino-1-((phenylthio)methyl)pentyl)amino)-N-((4'-fluoro-1,1'-biphenyl-4-yl)carbonyl)-3-nitrobenzenesulfonamide A mixture of Example 345D (30 mg) and 4M HCl in 1,4-dioxane (3 mL) at room temperature was stirred for 5 hours and concentrated to provide the desired product as the HCl salt. MS (ESI(−)) m/e 621 (M−H)⁻; ¹H NMR (400 MHz, DMSO-d₆) δ8.57 (d, 1H), 8.31 (d, 1H), 7.98 (d, 2H), 7.89 (dd, 1H), 7.68 (m, 4H), 7.73 (m, 3H), 7.35–7.13 (m, 7H), 4.12 (m, 1H), 3.67 (m, 2H), 2.74 (m, 2H), 1.75(m, 2H), 1.53 (m, 2H), 1.40 (m, 2H).

EXAMPLE 453

(3R)-3-((4-((((4'-fluoro-1,1'-biphenyl-4-yl)carbonyl)amino)sulfonyl)-2-nitrophenyl)amino)-N,N-dimethyl-4-(phenylthio)butanamide The desired product was prepared by substituting Example 122F for Example 1C in Example 1D. MS (ESI(−)) m/e 635 (M−H)⁻; ¹H NMR (500 MHz, methanol-d₄) δ8.73 (d, 1H), 8.09 (d, 1H), 7.98 (d, 2H), 7.93 (dd, 1H), 7.67 (m, 4H), 7.32 (m, 2H), 7.18 (m, 4H), 7.01 (d, 1H), 4.44 (m, 1H), 3.35 (m, 2H), 2.95 (dd(1H), 2.87 (s, 3H), 2.86 (s, 3H), 2.82 (dd, 1H).

EXAMPLE 454

N-(4-(2-acetyl-3-methyl-1-benzothien-5-yl)benzoyl)-3-nitro-4-((2-(phenylthio)ethyl)amino)benzenesulfonamide

EXAMPLE 454A methyl 4-(2-acetyl-3-methyl-1-benzothien-5-yl)benzoate

The desired product was prepared by substituting 1-(5-chloro-3-methyl-1-benzothien-2-yl)ethanone for 5-chloro-2-methyl-1,3-in Example 54A.

EXAMPLE 454B 4-(2-acetyl-3-methyl-1-benzothien-5-yl)benzoic acid

The desired product was prepared by substituting Example 454A for Example 1A in Example 1B. MS (ESI(−)) m/e 309(M)⁻.

EXAMPLE 454C

N-(4-(2-acetyl-3-methyl-1-benzothien-5-yl)benzoyl)-3-nitro-4-((2-(phenylthio)ethyl)amino)benzenesulfonamide The desired product was prepared by substituting Example 454B and Example 77B for Example 1B and Example 1C, respectively, in Example 1D. MS (ESI(−)) m/e 521 (M−H)⁻; ¹H NMR (300 MHz, DMSO-d₆) δ3.26 (t, 2H), 3.60 (dt, 2H), 6.27 (s, 2H), 7.00 (d, 1H), 7.20 (t, 1H), 7.31 (t, 2H), 7.40 (d, 2H), 7.42 (s, 2H), 7.52 (d, 2H), 7.89 (d, 1H), 7.93 (d, 2H), 8.51 (d, 1H), 8.52 (t, 1H).

EXAMPLE 455 tert-butyl 4-(4-((((3-nitro-4-((2-(phenylthio)ethyl)amino)phenyl)sulfonyl)amino)carbonyl)phenyl)-3,6-dihydropyridine-1(2H)-carboxylate

EXAMPLE 455A tert-butyl 4-((trifluoroacetyl)oxy)-3,6-dihydropyridine-1(2H)-carboxylate The desired product was prepared by substituting tert-butyl-4-oxo-piperidinecarboxylate for 4-tert-butylcyclohexanone in Example 5A.

EXAMPLE 455B tert-butyl 4-(4-(methoxycarbonyl)phenyl)-3,6-dihydropyridine-1(2H)-carboxylate The desired product was prepared by substituting Example 455A for Example 5A in Example 5B. MS (DCI (+)) m/e 318 (M+H)⁺.

EXAMPLE 455C tert-butyl 4-(4-((((3-nitro-4-((2-(phenylthio)ethyl)amino)phenyl)sulfonyl)amino)carbonyl)phenyl)-3,6-dihydropyridine-1(2H)-carboxylate A mixture of Example 455B (1 g, 3.1 mmol) and LiOH (0.264 mg 6.2 mmol) in THF (15 mL), methanol (2.5 mL), and water (1.5 mL) was heated to 50° C. for 3 hours and concentrated. The concentrate was dissolved in DMF (10 mL) and treated with a mixture of Example 77B (1.059 g, 3 mmol), EDCI (1.146 g, 6 mmol), and DMAP (1.830, 15 mmol) in dichloroethane (10 mL), stirred for 16 hours, diluted with ethyl acetate (250 mL0, washed sequentially with 1N HCl (50 mL), water (100 mL) and brine (100 mL), dried (MgSO₄), filtered, and concentrated. The concentrate was purified by flash column chromatography on silica gel with 5% methanol/dichloromethane to provide the desired product. MS (ESI(−)) m/e 637 (M−H)⁻; ¹H NMR (300 MHz, DMSO-d₆) δ8.78 (br t, 1H), 8.60 (d, 1H), 7.92 (dd, 1H), 7.85 (d, 2H), 7.55 (d, 2H), 7.40–7.15 (m, 6H), 6.35 (m, 1H), 4.21 (d, 2H), 3.65 (m, 2H), 3.52 (t, 2H), 3.25 (m, 4H), 1.45 (s, 9H).

EXAMPLE 456

3-nitro-4-((2-(phenylthio)ethyl)amino)-N-(4-((1R,4R)-1,7,7-trimethylbicyclo(2.2.1)hept-2-en-2-yl)benzoyl)benzenesulfonamide The desired product was prepared by substituting Example 372B for Example 230B in Example 230C. MS (ESI(−)) m/e 590 (M−H)⁻; ¹H NMR (300 MHz, DMSO-d₆) δ8.78 (br t, 1H), 8.60 (d, 1H), 7.92 (dd, 1H), 7.85 (d, 2H), 7.40–7.15 (m, 8H), 6.20 (d, 1H), 3.70 (m, 2H), 2.40 (t, 1H), 1.95 (m, 2H), 1.65 (m, 2H), 1.25 (m, 4H), 1.05 (s, 3H), 0.85 (2s, 6H).

EXAMPLE 457

3-((4-((((4'-fluoro-1,1'-biphenyl-4-yl)carbonyl)amino)sulfonyl)-2-nitrophenyl)amino)-N,N-dimethyl-4-(phenylthio)butanamide

EXAMPLE 457A 3-((4-(aminosulfonyl)-2-nitrophenyl)amino)-N,N-dimethyl-4-(phenylthio)butanamide The desired product was prepared by substituting Fmoc-DL-Asp(OtBu)-OH for Fmoc-D-Asp(OtBu)-OH in Examples 122A–F.

EXAMPLE 457B 3-((4-((((4'-fluoro-1,1'-biphenyl-4-yl)carbonyl)amino)sulfonyl)-2-nitrophenyl)amino)-N, N-dimethyl-4-(phenylthio)butanamide The desired product was prepared by substituting Example 457A for Example 1C in Example 1D. MS (ESI (−)) m/e 635 (M−H)⁻; ¹H NMR (500 MHz, methanol-d₄) δ8.73 (d, 1H), 8.09 (d, 1H), 7.98 (d, 2H), 7.93 (dd, 1H), 7.67 (m, 4H), 7.32 (m, 2H), 7.18 (m, 4H), 7.01 (d, 1H), 4.44 (m, 1H), 3.35 (m, 2H), 2.95 (dd (1H), 2.87 (s, 3H), 2.86 (s, 3H), 2.82 (dd, 1H).

EXAMPLE 458 methyl N-(4-((((4'-fluoro-1,1'-biphenyl-4-yl)carbonyl)amino)sulfonyl)-2-nitrophenyl)-S-phenylcysteinate The desired product was prepared by substituting Example 434A for Example 1C in Example 1D. MS (ESI (−)) m/e 608 (M−H)⁻; ¹H NMR (300 MHz, DMSO-d₆) δ8.70 (d, 1H), 8.51 (d, 1H), 7.96 (d, 2H), 7.90 (dd, 1H), 7.75 (m, 3H), 7.66 (d, 2H), 7.32–7.25 (m, 4H), 7.20–7.00 (m, 4H), 5.04 (m, 1H), 3.70–3.57 (m, 2H), 3.59 (s, 3H).

EXAMPLE 459

N-(4-(4,4-dimethylpiperidin-1-yl)benzoyl)-3-nitro-4-((2-(phenylthio)ethyl)amino)benzenesulfonamide The desired product was prepared by substituting Example 119C and Example 77B for Example 1B and Example 1C, respectively, in Example 1D. MS(ESI(+)) m/e 569 (M+H)⁺; ¹H NMR (300 MHz, DMSO-d₆) δ11.96 (s, 1H), 8.77 (t, 1H), 8.60 (d, 1H), 7.91 (dd, 1H), 7.72 (d, 2H), 7.37 (m, 2H), 7.28–7.12 (m, 4H), 6.92 (d, 2H), 3.67 (m, 1H), 3.32 (m, 6H), 1.37 (t, 4H), 0.95 (s, 6H).

EXAMPLE 461

N-(4-(8-azaspiro(4.5)dec-8-yl)benzoyl)-3-nitro-4-((2-(phenylthio)ethyl)amino)benzenesulfonamide The desired product was prepared by substituting Example 257C and Example 77B for Example 1B and Example 1C, respectively, in Example 1D. MS(ESI(+)) m/e 569 (M+H)⁺; ¹H NMR (300 MHz, DMSO-d₆) δ11.96 (s, 1H), 8.77 (t, 1H), 8.51 (d, 1H), 7.88 (dd, 1H), 7.71 (d, 2H), 7.40 (m, 2H), 7.30 (m, 2H), 7.18 (m, 1H), 7.06 (d, 1H), 6.85 (d, 2H), 3.62 (m, 2H), 3.30 (m, 6H), 1.59 (m, 4H), 1.48 (m, 8H).

EXAMPLE 462

N-((4'-fluoro-1,1'-biphenyl-4-yl)carbonyl)-4-(((1R)-3-morpholin-4-yl-3-oxo-1-((phenylthio)methyl)propyl)amino)-3-nitrobenzenesulfonamide

EXAMPLE 462A 4-(((1R)-3-morpholin-4-yl-3-oxo-1-((phenylthio)methyl)propyl)amino)-3-nitrobenzenesulfonamide The desired product was prepared by substituting morpholine for dimethylamine in Example 122F.

EXAMPLE 462B

N-((4'-fluoro-1,1'-biphenyl-4-yl)carbonyl)-4-(((1R)-3-morpholin-4-yl-3-oxo-1-((phenylthio)methyl)propyl)amino)-3-nitrobenzenesulfonamide The desired product was prepared by substituting Example 462A for Example 1C in Example 1D. MS (ESI (−)) m/e 677 (M−H)⁻; ¹H NMR (300 MHz, methanol-d₄) δ8.79 (d, 1H), 8.75 (d, 1H), 7.94 (m, 3H), 7.70 (m, 4H), 7.30 (m, 2H), 7.24–7.13 (m, 5H), 7.01 (d, 1H), 4.50 (m, 1H), 3.62–3.52 (m, 4H), 3.52–3.46 (m, 4H), 3.37 (m, 2H), 3.00 (dd (1H), 2.85 (dd, 1H).

EXAMPLE 463

N-((2'-methoxy-4'-(3-morpholin-4-ylpropyl)-1,1'-biphenyl-4-yl)carbonyl)-4-(((1R)-3-morpholin-4-yl-1-((phenylthio)methyl)propyl)amino)-3-nitrobenzenesulfonamide

EXAMPLE 463A 4-(((1R)-3-morpholin-4-yl-1-((phenylthio)methyl)propyl)amino)-3-nitrobenzenesulfonamide The desired product was prepared by substituting Example 462A for Example 122F in Example 122G.

EXAMPLE 463B

N-((2'-methoxy-4'-(3-morpholin-4-ylpropyl)-1,1'-biphenyl-4-yl)carbonyl)-4-(((1R)-3-morpholin-4-yl-1-((phenylthio)methyl)propyl)amino)-3-nitrobenzenesulfonamide The desired product was prepared by substituting Example 122O and Example 463A for Example 1B and Example 1C, respectively, in Example 1D. MS (ESI(−)) m/e 802 (M−H)$^-$; $^1$H NMR (500 MHz, methanol-d$_4$) δ8.71 (d, 1H), 7.95 (dd, 1H), 7.90 (d, 2H), 7.52 (d, 2H), 7.29 (dd, 2H), 7.22 (d, 1H), 7.14 (m, 3H), 6.96 (d, 1H), 6.95 (s, 1H), 6.89 (d, 1H), 4.15 (m, 1H), 3.88 (m, 4H), 3.78 (s, 3H), 3.76 (m, 4H), 3.37 (dd, 1H), 3.24 (m, 4H), 3.11 (m, 2H), 2.94–2.80 (m, 4H), 2.76 (t, 2H), 2.21 (m, 1H), 2.08 (m, 3H).

EXAMPLE 464

N-(4-(1-(2-morpholin-4-ylethyl)-1H-benzimidazol-5-yl)benzoyl)-3-nitro-4-((2-(phenylthio)ethyl)amino)benzenesulfonamide

EXAMPLE 464A 4-bromo-N$^1$-(2-morpholin-4-ylethyl)benzene-1,2-diamine

The desired product was prepared by substituting 4-(2-aminoethyl)morpholine for butylamine in Examples 166A and 166B.

EXAMPLE 464B 5-bromo-1-(2-morpholin-4-ylethyl)-1H-benzimidazole

The desired product was prepared by substituting Example 464A for Example 349A in Example 349B.

EXAMPLE 464C

N-(4-(1-(2-morpholin-4-ylethyl)-1H-benzimidazol-5-yl)benzoyl)-3-nitro-4-((2-(phenylthio)ethyl)amino)benzenesulfonamide The desired product was prepared by substituting Example 464B and Example 214E for 6-bromoindole and 4-(dihydroxyboryl)benzoic acid, respectively, in Example 4. MS (ESI) m/e 685, 687 (M−H)$^-$, (M+H)$^+$, $^1$H NMR (300 MHz, DMSO-d$_6$) δ2.46 (t, 4H), 2.72 (t, 2H), 3.28 (t, 2H), 3.55 (t, 4H), 3.62 (dt, 2H), 4.39 (t, 2H), 7.02 (d, 1H), 7.02 (tt, 1H), 7.30 (t, 2H), 7.40 (d, 2H), 7.58 (dd, 1H), 7.66 (d, 2H), 7.70 (d, 1H), 7.91 (dd, 1H), 7.95 (d, 1H), 7.97 (d, 2H), 8.27 (s, 1H), 8.52 (t, 1H), 8.55 (d, 1H).

EXAMPLE 465

N-((2'-methoxy-4'-(3-morpholin-4-ylpropyl)-1,1'-biphenyl-4-yl)carbonyl)-4-(((1R)-3-(4-methylpiperazin-1-yl)-3-oxo-1-((phenylthio)methyl)propyl)amino)-3-nitrobenzenesulfonamide

EXAMPLE 465A 4-(((1R)-3-(4-methylpiperazin-1-yl)-3-oxo-1-((phenylthio)methyl)propyl)amino)-3-nitrobenzenesulfonamide The desired product was prepared by substituting 1-methylpiperidine for dimethylamine in Example 122F.

EXAMPLE 465B

N-((2'-methoxy-4'-(3-morpholin-4-ylpropyl)-1,1'-biphenyl-4-yl)carbonyl)-4-(((1R)-3-(4-methylpiperazin-1-yl)-3-oxo-1-((phenylthio)methyl)propyl)amino)-3-nitrobenzenesulfonamide The desired product was prepared by substituting Example 122O and Example 465A for Example 1B and Example 1C, respectively, in Example 1D. MS (ESI(−)) m/e 829 (M−H)$^-$; $^1$H NMR (500 MHz, methanol-d$_4$) δ8.71 (d, 1H), 7.95 (dd, 1H), 7.90 (d, 2H), 7.52 (d, 2H), 7.29 (dd, 2H), 7.22 (d, 1H), 7.14 (m, 3H), 6.96 (d, 1H), 6.95 (s, 1H), 6.89 (d, 1H), 4.40 (m, 1H), 3.78 (s, 3H), 3.76 (m, 4H), 3.52 (m, 4H), 3.37 (dd, 1H), 3.20 (s, 3H), 2.95 (dd, 1H), 2.68 (m, 4H), 2.58 (m, 4H), 2.50 (m, 4H), 2.18 (m, 2H), 1.90 (m, 2H).

EXAMPLE 466

N-(4-(4,4-dimethylpiperidin-1-yl)benzoyl)-4-(((1R)-3-(4-methylpiperazin-1-yl)-3-oxo-1-((phenylthio)methyl)propyl)amino)-3-nitrobenzenesulfonamide The desired product was prepared by substituting Example 119C and Example 465A for Example 1B and Example 1C, respectively, in Example 1D. MS(ESI(+)) m/e 709 (M+H)$^+$; $^1$H NMR (500 MHz, methanol-d$_4$) δ8.71 (d, 1H), 8.65 (d, 1H), 7.90 (dd, 1H), 7.77 (d, 2H), 7.31 (m, 2H), 7.17 (m, 3H), 6.88 (m, 3H), 3.82 (m, 1H), 3.53 (m, 4H) 3.33 (m, 4H), 3.05 (m, 1H), 2.95 (dd, 1H), 2.83 (m, 2H), 2.40 (m, 4H), 2.25 (s, 3H), 1.47 (m, 4H), 0.97 (s, 6H).

EXAMPLE 467

4-(((1R)-5-amino-1-(phenylsulfonyl)methyl)amino)-N-((2'-methoxy-4'-(3-morpholin-4-ylpropyl)-1,1'-biphenyl-4-yl)carbonyl)-3-nitrobenzenesulfonamide A mixture of Example 194 (100 mg) in acetonitrile (5 mL) and saturated aqueous sodium periodate (3 mL) at room temperature was stirred for 3 days and concentrated. The concentrate was purified by flash column chromatography on silica gel with 0–3% concentrated aqueous ammonia in 1:1 isopropanol/dichloromethane, and purified a second time by reverse phase column chromatography with 0–100% acetonitrile/water to provide the desired product. MS (ESI (−)) m/e 792 (M−H)$^-$; $^1$H NMR (500 MHz, DMSO-d$_6$) δ8.41 (1H), 7.92 (d, 2H), 7.84 (m, 2H), 7.65 (d, 2H), 7.56 (m, 3H), 7.41 (m, 3H), 7.20 (d, 1H), 6.96 (d, 1H), 6.95 (s, 1H), 6.87 (d, 1H), 4.24 (m, 1H), 4.05 (dd, 1H), 3.63 (m, 4H), 2.72 (m, 2H), 2.63 (t, 2H), 1.86 (m, 2H), 1.70 (m, 2H), 1.48 (2H), 1.33 (m, 2H).

EXAMPLE 468

N-(4-(5-(3-morpholin-4-ylpropyl)quinolin-8-yl)benzoyl)-3-nitro-4-((2-(phenylthio)ethyl)amino)benzenesulfonamide

EXAMPLE 468A methyl 4-(5-(3-morpholin-4-yl-3-oxopropyl)quinolin-8-yl)benzoate The desired product was prepared by substituting morpholine for 1-methylpiperazine in Example 201J.

EXAMPLE 468B methyl 4-(5-(3-morpholin-4-ylpropyl)quinolin-8-yl benzoate

The desired product was prepared by substituting Example 468A for Example 362A in Example 248A.

EXAMPLE 468C 4-(5-(3-morpholin-4-ylpropyl)quinolin-8-yl)benzoic acid

The desired product was prepared by substituting Example 468B for Example 1A in Example 1B.

EXAMPLE 468D

N-(4-(5-(3-morpholin-4-ylpropyl)quinolin-8-yl)benzoyl)-3-nitro-4-((2-(phenylthio)ethyl)amino)benzenesulfonamide The desired product was prepared by substituting Example 468C and Example 77B for Example 1B and Example 1C, respectively, in Example 1D. MS (ESI) m/e 710, 712 (M−H)$^-$, (M+H)$^+$; $^1$H NMR (300 MHz, DMSO-d$_6$) δ2.02 (m, 2H), 2.98 (m, 4H), 3.15 (t, 2H), 3.28 (t, 2H), 3.31 (t, 2H), 3.63 (dt, 2H), 3.72 (m, 4H), 7.06 (d, 1H), 7.20 (tt, 1H), 7.31 (tt, 2H), 7.40 (dt, 2H), 7.54–7.64 (m, 4H), 7.71 (d, 1H), 7.92 (dd, 1H), 7.96 (d, 2H), 8.56 (d, 1H), 8.61 (dd, 1H), 8.90 (dd, 1H).

EXAMPLE 469 tert-butyl 1'-(4-((((3-nitro-4-((2-(phenylthio)ethyl)amino)phenyl)sulfonyl)amino)carbonyl)phenyl)-4,4'-bipiperidine-1-carboxylate The desired product was prepared by substituting 4-(1'-(tert-butoxycarbonyl)-4,4'-bipiperidin-1-yl)benzoic acid and Example 77B for Example 1B and Example 1C, respectively, in Example 1D. MS (ESI(−)) m/e 722 (M−H)$^-$; $^1$H NMR (500 MHz, DMSO-d$_6$) δ8.72 (t, 1H), 8.58 (d, 1H), 7.90 (dd, 1H), 7.72 (d, 2H), 7.37 (d, 2H), 7.25 (t, 2H), 7.19–7.14 (m, 2H), 6.89 (d, 2H), 3.93 (br t, 4H), 3.66 (q, 2H), 3.28 (t, 2H), 2.74 (t, 2H), 2.66–2.54 (m, 2H), 1.68 (dd, 4H), 1.38 (s, 9H), 1.24–1.17 (m, 4H), 1.07–0.96 (m, 2H).

EXAMPLE 470

3-nitro-N-(4-(4-(phenylsulfonyl)piperazin-1-yl)benzoyl)-4-((2-(phenylthio)ethyl)amino)benzenesulfonamide The desired product was prepared by substituting benzenesulfonyl chloride for 2-methoxyethyl chloroformate in Example 325. MS (ESI(−)) m/e 680 (M−H)$^-$; $^1$H NMR (500 MHz, DMSO-d$_6$) δ12.01 (s, 1H), 8.75 (t, 1H), 8.59 (d, 1H), 7.90 (dd, 1H), 7.78–7.63 (m, 7H), 7.36 (d, 2H), 7.25 (t, 2H), 7.19–7.14 (m, 2H), 6.91 (d, 2H), 3.66 (q, 2H), 3.39–3.42 (m, 4H), 3.28 (t, 2H), 3.01–2.97 (m, 4H).

EXAMPLE 471

4-(((1R)-5-((aminocarbonyl)amino)-1-((phenylthio)methyl)pentyl)amino)-N-(4-(8-azaspiro(4.5)dec-8-yl)benzoyl)-3-nitrobenzenesulfonamide A solution of Example 287 (60 mg, 0.1 mmol) and potassium cyanate (20 mg, 0.25 mmol) in methanol (1 mL) was stirred at 55° C. for 1.5 hours, cooled to room temperature, treated with water, and extracted with dichloromethane. The combined extracts were washed with saturated sodium bicarbonate, dried (MgSO$_4$), filtered, and concentrated. The concentrate was purified by reverse phase HPLC with 0–100% acetonitrile/water containing 0.1% TFA to provide the desired product. MS (ESI(+)) m/e 709 (M+H)$^+$; $^1$H NMR (500 MHz, DMSO-d$_6$) δ11.97 (s, 1H), 8.53 (d, 1H), 8.32 (d, 1H), 7.85 (dd, 1H), 7.73 (d, 2H), 7.25–7.10 (m, 6H), 6.93 (d, 2H), 5.90 (s, 1H), 4.10 (m, 1H), 3.34 (m, 6H), 2.91 (t, 2H), 1.75 (m, 2H), 1.59 (m, 4H), 1.42 (m, 8H), 1.34 (m, 4H).

EXAMPLE 472 tert-butyl 4-((4-(((4-(8-azaspiro(4.5)dec-8-yl)benzoyl)amino)sulfonyl)-2-nitrophenyl)amino)-4-((phenylthio)methyl)piperidine-1-carboxylate

EXAMPLE 472A tert-butyl 4-(((9H-fluoren-9-ylmethoxy)carbonyl)amino)-4-(hydroxymethyl)piperidine-1-carboxylate The desired product was prepared by substituting 1-(tert-butoxycarbonyl)-4-(((9H-fluoren-9-ylmethoxy)carbonyl)amino)piperidine-4-carboxylic acid for Fmoc-D-Asp(OtBu)-OH in Example 122A. MS (ESI) m/e 451, 453 (M−H)$^-$, (M+H)$^+$.

EXAMPLE 472B tert-butyl 4-((4-(aminosulfonyl)-2-nitrophenyl)amino)-4-((hydroxymethyl)piperidine-1-carboxylate The desired product was prepared by substituting Example 472A for Example 122B in Example 122D. MS (ESI(−)) m/e 429 (M−H)$^-$.

EXAMPLE 472C tert-butyl 4-((4-(aminosulfonyl)-2-nitrophenyl)amino)-4-((hydroxymethyl)piperidine-1-carboxylate The desired product was prepared by substituting Example 472B for N-(tert-butoxycarbonyl)-L-serine methyl ester in Example 133A. MS (ESI(−)) m/e 521 (M−H)$^-$.

EXAMPLE 472D tert-butyl 4-((4-(((4-(8-azaspiro(4.5)dec-8-yl)benzoyl)amino)sulfonyl)-2-nitrophenyl)amino)-4-((phenylthio)methyl)piperidine-1-carboxylate The desired product was prepared by substituting Example 472C and Example 257C for Example 1C and Example 1B, respectively, in Example 1D. MS (ESI) m/e 762, 764 (M−H)$^-$, (M+H)$^+$; $^1$H NMR (300 MHz, DMSO-d$_6$) δ1.39 (s, 9H), 1.41 (m, 4H), 1.48 (m, 4H), 1.59 (m, 4H), 1.79 (dt, 2H), 2.22 (br d, 2H), 2.99 (m, 2H), 3.21 (m, 4H), 3.61 (s, 2H), 3.72 (br d, 2H), 6.81 (d, 2H), 6.95 (m, 1H), 7.02 (td, 2H), 7.21 (m, 3H), 7.74 (d, 2H), 7.80 (dd, 1H), 8.24 (br s, 1H), 8.41 (d, 1H).

EXAMPLE 473

N-(4-(5-(3-(4-methylpiperazin-1-yl)propyl)quinolin-8-yl)benzoyl)-3-nitro-4-((2-(phenylthio)ethyl)amino)benzenesulfonamide

EXAMPLE 473A methyl 4-(5-(3-(4-methylpiperazin-1-yl)propyl)quinolin-8-yl)benzoate The desired product was prepared by substituting Example 201J for Example 362A in Example 248A.

EXAMPLE 473B 4-(5-(3-(4-methylpiperazin-1-yl)propyl)quinolin-8-yl)benzoic acid The desired product was prepared by substituting Example 473A for Example 1A in Example 1B.

EXAMPLE 473C

N-(4-(5-(3-(4-methylpiperazin-1-yl)propyl)quinolin-8-yl)benzoyl)-3-nitro-4-((2-(phenylthio)ethyl)amino)benzenesulfonamide The desired product was prepared by substituting Example 473B and Example 77B for Example 1B and Example 1C, respectively, in Example 1D. MS (ESI) m/e 723, 725 (M−H)⁻, (M+H)⁺; ¹H NMR (300 MHz, DMSO-d₆) δ1.89 (m, 2H), 2.28 (s, 3H), 2.50 (m, 8H), 3.12 (t, 2H), 3.27 (t, 2H), 3.29 (t, 2H), 3.61 (dt, 2H), 6.98 (d, 1H), 7.20 (tt, 1H), 7.32 (tt, 2H), 7.41 (dd, 2H), 7.52–7.61 (m, 4H), 7.68 (d, 2H), 7.89 (dd, 1H), 7.96 (d, 2H), 8.52 (d, 1H), 8.58 (dd, 1H), 8.89 (dd, 1H).

EXAMPLE 474

N-((2'-methoxy-4'-(3-morpholin-4-ylpropyl)-1,1'-biphenyl-4-yl)carbonyl)-3-nitro-4-((4-((phenylthio)methyl)piperidin-4-yl)amino)benzenesulfonamide The desired product was prepared by substituting Example 472C and Example 122O for Example 1C and Example 1B, respectively, in Example 1D. The product was treated with TFA (5 mL), stirred for 90 minutes, concentrated, and concentrated again to provide the desired product. MS (ESI) m/e 758, 760 (M−H)⁻, (M+H)⁺; ¹H NMR (300 MHz, DMSO-d₆) δ1.89–2.08 (m, 4H), 2.65 (dt, 2H), 3.00 (m, 2H), 3.22 (br d, 2H), 3.65 (s, 2H), 3.74 (m, 4H), 3.76 (s, 3H), 6.88 (d, 1H), 6.96 (s, 1H), 7.05 (m, 2H), 7.23 (m, 4H), 7.41 (d, 2H), 7.85 (dd, 1H), 7.91 (d, 2H), 8.14 (s, 1H), 8.42 (d, 1H).

EXAMPLE 475

4-(((1R)-3-(dimethylamino)-1-((phenylthio)methyl)propyl)amino)-N-(4-(3,3-dimethylpyrrolidin-1-yl)benzoyl)-3-nitrobenzenesulfonamide The desired product was prepared by substituting Example 122G and Example 247C for Example 1C and Example 1B, respectively, in Example 1D. MS (ESI(+)) m/e 626 (M+H)⁺; ¹H NMR (500 MHz, DMSO-d₆) δ11.92 (s, 1H), 9.42 (s, 1H), 8.55 (d, 1H), 8.30 (d, 1H), 7.87 (dd, 1H), 7.73 (d, 2H), 7.25–7.10 (m, 6H), 6.50 (d, 2H), 4.18 (m, 1H), 3.40 (m, 4H), 3.15 (m, 2H), 3.07 (s, 2H), 2.74 (d, 6H), 2.14 (m, 2H), 1.77 (t, 2H), 1.08 (s, 6H).

EXAMPLE 476

4-(((1R)-3-(dimethylamino)-1-((phenylthio)methyl)propyl)amino)-N-(4-(4-ethyl-4-methylpiperidin-1-yl)benzoyl)-3-nitrobenzenesulfonamide The desired product was prepared by substituting Example 122G and Example 123C for Example 1C and Example 1B, respectively, in Example 1D. MS (ESI(+)) m/e 654 (M+H)⁺; ¹H NMR(500 MHz, DMSO-d₆) δ12.01 (s, 1H), 9.41 (s, 1H), 8.55 (d, 1H), 8.31 (d, 1H), 7.87 (dd, 1H), 7.73 (d, 2H), 7.25–7.10 (m, 6H), 6.93 (d, 2H), 4.17 (m, 1H), 3.45 (m, 2H), 3.40 (d, 2H), 3.26–3.10 (m, 6H), 2.74 (d, 6H), 2.14 (m, 2H), 1.38 (m, 4H), 1.28 (m, 2H), 0.90 (s, 3H), 0.80 (t, 3H).

EXAMPLE 477

N-(4-(8-azaspiro(4.5)dec-8-yl)benzoyl)-4-(((1R)-5-(dimethylamino)-1-((phenylsulfinyl)methyl)pentyl)amino)-3-nitrobenzenesulfonamide A solution of Example 124F (30 mg, 0.04 mmol) and sodium periodate (46 mg, 0.22 mmol) in acetonitrile (0.5 mL), dichloromethane (0.5 mL), and water (0.5 mL) was stirred at room temperature for 24 hours, treated with water, and extracted with dichloromethane. The combined extracts were dried (MgSO₄), filtered, and concentrated. The concentrate was purified by flash column chromatography on silica gel with 80% ethyl acetate/10% water/10% formic acid to provide the desired product. MS (ESI(+)) m/e 710 (M+H)⁺; ¹H NMR (500 MHz, DMSO-d₆) δ8.50 (d, 0.5H), 8.40 (d, 0.5H), 8.35 (d, 0.5H), 8.21 (s, 1H), 7.94 (d, 0.5H), 7.90 (dd, 0.5H), 7.82 (dd, 0.5H), 7.71 (d, 2H), 7.70 (d, 1H), 7.55 (m, 2H), 7.40 (m, 1H), 7.20 (m, 1H), 6.80 (d, 2H), 2.29 (m, 1H), 2.18 (d, 6H), 1.91 (s, 6H), 1.68 (m, 1H), 1.59 (m, 4H), 1.49 (m, 4H), 1.45–1.30 (m, 6H).

EXAMPLE 478

N~1~-((5R)-5-((4-(((4-(8-azaspiro(4.5)dec-8-yl)benzoyl)amino)sulfonyl)-2-nitrophenyl)amino)-6-(phenylthio)hexyl)-N~2~-,N~2~-dimethylglycinamide A mixture of Example 287 (33 mg, 0.05 mmol), N,N-dimethyglycine (10.3 mg, 0.10 mmol), EDCI (20 mg, 0.10 mmol) and HOBT (20 mg, 0.15 mmol) in DMA (0.6 mL) and dichloroethane (0.3 mL) at room temperature was stirred for 18 hours and concentrated. The concentrate was dissolved in 1:1 DMSO/methanol (1 mL) and loaded on a Nova-Pak HR C-18, 6 μM, 60A, 40×100 mm preparative HPLC column (eluted with 10–95% acetonitrile/water containing 0.1% TFA). The purified compound was dissolved in 1:1 dichloromethane/methanol (1 mL), treated with 2M HCl in diethyl ether (1 mL), and concentrated to provide the hydrochloride salt. MS (ESI) m/e 751.3, 749.4 (M+H)⁺, (M−H)⁻; ¹H NMR (500 MHz, DMSO-d₆) δ8.53 (d, 1H), 8.41 (m, 1H), 8.29 (d, 1H), 7.86 (dd, 1H), 7.73 (d, 2H), 7.25–7.09 (m, 5H), 6.92 (d, 2H), 4.12 (m, 1H), 3.80 (s, 2H), 3.34 (m, 4H), 3.10 (d, 2H), 2.75 (s, 6H), 1.78 (m, 2H), 1.60 (m, 4H), 1.52–1.34 (m, 12H).

EXAMPLE 479

N-((5R)-5-((4-(((4-(8-azaspiro(4.5)dec-8-yl)benzoyl)amino)sulfonyl)-2-nitrophenyl)amino)-6-(phenylthio)hexyl)cyclopropanecarboxamide The desired product was prepared by substituting cyclopropanecarboxylic acid for N,N-dimethyglycine in Example 478. MS (ESI) m/e 734.3, 732.4 (M+H)⁺, (M−H)⁻, ¹H NMR (500 MHz, DMSO-d₆) δ8.53 (d, 1H), 8.30 (d, 1H), 7.93 (m, 1H), 7.84 (dd, 1H), 7.73 (d, 2H), 7.25–7.09 (m, 5H), 6.92 (d, 2H), 4.12 (m, 1H), 3.34 (m, 4H), 3.01 (m, 2H), 1.78 (m, 2H), 1.60 (m, 4H), 1.52–1.34 (m, 12H), 0.61–0.56 (m, 5H).

EXAMPLE 480

(4R)-4-((4-((((2'-methoxy-4'-(3-morpholin-4-ylpropyl)-1,1'-biphenyl-4-yl)carbonyl)amino)sulfonyl)-2-nitrophenyl)amino)-N,N-dimethyl-5-(phenylthio)pentanamide

EXAMPLE 480A tert-butyl (2E,4R)-4-((tert-butoxycarbonyl)amino)-5-(phenylthio)pent-2-enoate Example 134A (5.74 g, 20.4 mmol) in THF (25 mL) at 0° C. was treated with a solution of (tert-butoxycarbonylmethylene)triphenylphosphorane (8.47 g, 22.5 mmol) in THF (25 mL), warmed to room temperature, stirred for 90 minutes, treated with hexanes (50 mL), filtered through a pad of silica gel, and concentrated. The concentrate was purified by flash column chromatography on silica gel with 15% ethyl acetate/hexanes to provide the desired product. MS (ESI(−)) m/e 378 (M−H)⁻.

EXAMPLE 480B (4R)-4-((tert-butoxycarbonyl)amino)-5-(phenylthio) pentanoic acid A mixture of Example 480A (5 g, 13.2 mmol) and Wilkinson's catalyst (1 g) in tolune (125 mL) was stirred under $H_2$ at 60° C. for 18 hours, cooled, filtered through silica gel, and concentrated. The concentrate was dissolved in 3:1:1 THF/water/MeOH (150 mL), treated with with a 10-fold excess of LiOH, and stirred for 24 hrs. The mixture was poured into saturated $NaH_2PO_4$ (200 mL) and extracted three times with ethyl acetate (200 mL). The combined extracts were washed with brine, dried ($Na_2SO_4$), filtered, and concentrated to provide the desired product. MS (ESI) m/e 324, 326 (M−H)⁻, (M+H)⁺.

EXAMPLE 480C tert-butyl(1R)-4-(dimethylamino)-4-oxo-1-((phenylthio)methyl)butylcarbamate The desired product was prepared by substituting Example 480B for Example 122E in Example 122F. MS (ESI) m/e 351, 353 (M−H)⁻, (M+H)⁺.

EXAMPLE 480D (4R)-4-((4-(aminosulfonyl)-2-nitrophenyl)amino)-N, N-dimethyl-5-(phenylthio)pentanamide The desired product was prepared by substituting Example 480C for Example 133A in Examples 133B and 133C. MS (ESI) m/e 451, 453 (M−H)⁻, (M+H)⁺.

EXAMPLE 480E (4R)-4-((4-((((2'-methoxy-4'-(3-morpholin-4-ylpropyl)-1,1'-biphenyl-4-yl)carbonyl)amino) sulfonyl)-2-nitrophenyl)amino)-N,N-dimethyl-5-(phenylthio)pentanamide The desired product was prepared by substituting Example 480D and Example 122O for Example 1C and Example 1B, respectively, in Example 1D. MS (ESI) m/e 788, 790 (M−H)⁻, (M+H)⁺; ¹H NMR (300 MHz, DMSO-d₆) δ1.78 (m, 2H), 1.95 (m, 2H), 2.35 (m, 2H), 2.40 (t, 4H), 2.62 (t, 2H), 2.82 (s, 3H), 2.96 (s, 3H), 3.30 (dd, 1H), 3.36 (dd, 1H), 3.58 (t, 4H), 3.76 (s, 3H), 4.07 (m, 1H), 6.85 (d, 1H), 6.95 (d, 2H), 7.18 (t, 2H), 7.23 (t, 2H), 7.31 (d, 2H), 7.40 (d, 2H), 7.82 (dd, 1H), 7.90 (d, 2H), 7.95 (d, 1H), 8.15 (d, 1H), 8.48 (d, 1H).

EXAMPLE 481

N-((2'-methoxy-4'-(3-morpholin-4-ylpropyl)-1,1'-biphenyl-4-yl)carbonyl)-4-(((1R)-3-(4-methylpiperazin-1-yl)-1-((phenylthio)methyl)propyl) amino)-3-nitrobenzenesulfonamide

EXAMPLE 481A 4-(((1R)-3-(4-methylpiperazin-1-yl)-1-((phenylthio) methyl)propyl)amino)-3-nitrobenzenesulfonamide The desired product was prepared by substituting Example 465A for Example 122F in Example 122G. MS (ESI(+)) m/e 480 (M+H)⁺.

EXAMPLE 481B

N-((2'-methoxy-4'-(3-morpholin-4-ylpropyl)-1,1'-biphenyl-4-yl)carbonyl)-4-(((1R)-3-(4-methylpiperazin-1-yl)-1-((phenylthio)methyl)propyl) amino)-3-nitrobenzenesulfonamide The desired product was prepared by substituting Example 481A and Example 122O for Example 1C and Example 1B, respectively, in Example 1D. MS (ESI) m/e 815, 817 (M−H)⁻, (M+H)⁺; ¹H NMR (300 MHz, DMSO-d₆) δ1.52 (m, 2H), 1.82 (m, 2H), 2.21 (m, 2H), 2.40 (t, 4H), 2.48 (t, 2H), 2.80 (m, 4H), 3.04 (m, 4H), 2.98 (dd, 1H), 3.05 (dd, 1H), 3.53 (s, 3H), 3.58 (t, 4H), 3.62 (s, 3H), 3.91 (m, 1H), 6.65 (d, 1H), 6.78 (m, 2H), 6.95 (t, 1H), 6.99 (m, 3H), 7.07 (d, 2H), 7.20 (d, 2H), 7.62 (dd, 1H), 7.67 (d, 2H), 8.05 (d, 1H), 8.26 (d, 1H).

EXAMPLE 482

3-(2-methoxy-4'-((((4-(((1R)-3-(4-methylpiperazin-1-yl)-1-((phenylthio)methyl)propyl)amino)-3-nitrophenyl)sulfonyl)amino)carbonyl)-1,1'-biphenyl-4-yl)-N,N-dimethylpropanamide

EXAMPLE 482A

4'-(3-(dimethylamino)-3-oxopropyl)-2'-methoxy-1, 1'-biphenyl-4-carboxylic acid

The desired product was prepared by substituting Example 427A for Example 1A in Example 1B.

EXAMPLE 482B 3-(2-methoxy-4'-((((4-(((1R)-3-(4-methylpiperazin-1-yl)-1-((phenylthio)methyl)propyl)amino)-3-nitrophenyl)sulfonyl)amino)carbonyl)-1,1'-biphenyl-4-yl)-N,N-dimethylpropanamide The desired product was prepared by substituting Example 482A and Example 481A for Example 1B and Example 1C, respectively, in Example 1D. MS (ESI) m/e 787, 789 (M−H)⁻, (M+H)⁺; ¹H NMR (300 MHz, DMSO-d₆) δ1.90 (m, 2H), 2.50 (m, 2H), 2.64 (m, 4H), 2.71 (t, 2H), 2.82 (s, 3H), 2.84 (m, 2H), 2.95 (s, 3H), 3.00 (dd, 2H), 3.34 (s, 3H), 3.36 (m, 4H), 3.76 (s, 3H), 4.18 (m, 1H), 5.21 (t, 1H), 6.90 (d, 1H), 7.01 (s, 1H), 7.14 (m, 2H), 7.21 (m 3H), 7.29 (d, 2H), 7.49 (d, 2H), 7.90 (d, 2H), 8.25 (d, 1H), 8.52 (d, 1H).

EXAMPLE 483

3-(2-methoxy-4'-((((4-(((1R)-3-(4-methylpiperazin-1-yl)-3-oxo-1-((phenylthio)methyl)propyl)amino)-3-nitrophenyl)sulfonyl)amino)carbonyl)-1,1'-biphenyl-4-yl)-N,N-dimethylpropanamide The desired product was prepared by substituting Example 482A and Example 465A for Example 1B and Example 1C, respectively, in Example 1D. MS (ESI) m/e 801, 803 (M−H)⁻, (M+H)⁺; ¹H NMR (300 MHz, DMSO-d₆) δ2.62 (m, 4H), 2.63 (t, 2H), 2.76 (dd, 1H), 2.81 (m, 2H), 2.82 (s, 3H), 2.95 (s, 3H), 3.00 (m, 2H), 3.31 (s, 3H), 3.36 (m, 4H), 3.40 (m, 1H), 3.76 (s, 3H), 4.34 (m, 1H), 6.83 (d, 1H), 6.99 (s, 1H), 7.19 (t, 2H), 7.25 (t, 2H), 7.32 (d, 1H), 7.39 (d, 2H), 7.59 (d, 1H), 7.80 (d, 1H), 7.88 (d, 2H), 7.95 (d, 1H), 8.46 (d, 1H), 8.55 (d, 1H).

EXAMPLE 484

4-(((1R)-4-(dimethylamino)-1-((phenylthio)methyl) butyl)amino)-N-((2'-methoxy-4'-(3-(4-methylpiperazin-1-yl)propyl)-1,1'-biphenyl-4-yl) carbonyl)-3-nitrobenzenesulfonamide

EXAMPLE 484A

2'-methoxy-4'-(3-(4-methylpiperazin-1-yl)propyl)-1, 1'-biphenyl-4-carboxylic acid The desired product was prepared by substituting Example 248A for Example 1A in Example 1B.

EXAMPLE 484B 4-(((1R)-4-(dimethylamino)-1-((phenylthio)methyl)butyl)amino)-N-((2'-methoxy-4'-(3-(4-methylpiperazin-1-yl)propyl)-1,1'-biphenyl-4-yl)carbonyl)-3-nitrobenzenesulfonamide The desired product was prepared by substituting Example 484A and Example 489A for Example 1B and Example 1C, respectively, in Example 1D. MS (ESI) m/e 787, 789 (M−H)⁻, (M+H)⁺; $^1$H NMR (300 MHz, DMSO-d$_6$) δ1.53 (m, 4H), 1.75 (m, 2H), 2.18 (s, 3H), 2.26 (s, 6H), 2.38 (m, 4H), 2.60 (t, 2H), 2.98 (m, 8H), 3.74 (s, 3H), 4.02 (m, 1H), 5.82 (m, 2H), 6.85 (d, 1H), 6.93 (s, 1H), 6.95 (d, 1H), 7.17 (dd, 2H), 7.25 (td, 2H), 7.33 (dt, 2H), 7.38 (d, 2H), 7.82 (dd, 1H), 7.88 (d, 2H), 8.15 (d, 1H), 8.46 (d, 1H).

EXAMPLE 485

N-(4-(4-ethyl-4-methoxypiperidin-1-yl)benzoyl)-3-nitro-4-((2-(phenylthio)ethyl)amino)benzenesulfonamide

EXAMPLE 485A tert-butyl 4-ethyl-4-methoxypiperidine-1-carboxylate

The desired product was prepared by substituting Example 495A for Example 494A in Example 494B.

EXAMPLE 485B 4-ethyl-4-methoxypiperidine

The desired product was prepared by substituting Example 485A for Example 494B in Example 494C.

EXAMPLE 485C tert-butyl 4-(4-ethyl-4-methoxypiperidin-1-yl)benzoate

The desired product was prepared by substituting Example 485B for Example 494C in Example 494D.

EXAMPLE 485D 4-(4-ethyl-4-methoxypiperidin-1-yl)benzoic acid

The desired product was prepared by substituting Example 485C for Example 493A in Example 493B.

EXAMPLE 485E

N-(4-(4-ethyl-4-methoxypiperidin-1-yl)benzoyl)-3-nitro-4-((2-(phenylthio)ethyl)amino)benzenesulfonamide The desired product was prepared by substituting Example 481D and Example 77B for Example 1B and Example 1C, respectively, in Example 1D. MS(ESI(+)) m/e 599 (M+H)⁺; $^1$H NMR (500 MHz, DMSO-d$_6$) δ11.98 (s, 1H), 8.78 (t, 1H), 8.60 (d, 1H), 7.91 (dd, 1H), 7.73 (d, 2H), 7.37 (d, 2H), 7.28 (m, 2H), 7.18 (m, 2H), 6.93 (d, 2H), 3.65 (m, 4H), 3.28 (t, 2H), 3.07 (m, 5H), 1.75 (m, 2H), 1.43 (m, 4H), 0.77 (t, 3H).

EXAMPLE 486

N-(4-(4-(benzylsulfonyl)piperazin-1-yl)benzoyl)-3-nitro-4-((2-(phenylthio)ethyl)amino)benzenesulfonamide The desired product was prepared by substituting benzylsulfonyl chloride for 2-methoxyethyl chloroformate in Example 325. MS (ESI(−)) m/e 694 (M−H)⁻; $^1$H NMR (500 MHz, DMSO-d$_6$) δ12.06 (s, 1H), 8.76 (t, 1H), 8.60 (d, 1H), 7.92 (dd, 1H), 7.76 (d, 2H), 7.44–7.35 (m, 7H), 7.30–7.16 (m, 4H), 6.96 (d, 2H), 4.46 (s, 2H), 3.66 (q, 2H), 3.36–3.28 (m, 6H), 3.23–3.19 (m, 4H).

EXAMPLE 487

N-(4-(4-(((4-methylphenyl)sulfonyl)piperazin-1-yl)benzoyl)-3-nitro-4-((2-(phenylthio)ethyl)amino)benzenesulfonamide The desired product was prepared by substituting p-toluenesulfonyl chloride for 2-methoxyethyl chloroformate in Example 325. MS (ESI(−)) m/e 694 (M−H)⁻; $^1$H NMR (500 MHz, DMSO-d$_6$) δ12.04 (s, 1H), 8.77 (t, 1H), 8.59 (d, 1H), 7.90 (dd, 1H), 7.72–7.63 (m, 2H), 7.64 (d, 2H), 7.45 (d, 2H), 7.36 (d, 2H), 7.26 (t, 2H), 7.18–7.14 (m, 2H), 6.91 (d, 2H), 3.66 (q, 2H), 3.42–3.39 (m, 4H), 3.28 (t, 2H), 2.97–2.94 (m, 4H), 2.39 (s, 3H).

EXAMPLE 488

N-(4-(4-benzylpiperidin-1-yl)benzoyl)-3-nitro-4-((2-(phenylthio)ethyl)amino)benzenesulfonamide

EXAMPLE 488A tert-butyl 4-(4-benzylpiperidin-1-yl)benzoate

The desired product was prepared by substituting 4-benzyl piperidine for 4-hydroxy-4-phenyl piperidine in Example 493A.

EXAMPLE 488B 4-(4-benzylpiperidin-1-yl)benzoic acid

The desired product was prepared by substituting Example 488A for Example 493A in Example 493B.

EXAMPLE 488C

N-(4-(4-benzylpiperidin-1-yl)benzoyl)-3-nitro-4-((2-(phenylthio)ethyl)amino)benzenesulfonamide The desired product was prepared by substituting Example 488B and Example 77B for Example 1B and Example 1C, respectively, in Example 1D. MS (ESI(+)) m/e 631 (M+H)⁺; $^1$H NMR (500 MHz, DMSO-d$_6$) δ11.98 (s, 1H), 8.78 (t, 1H), 8.60 (d, 1H), 7.91 (dd, 1H), 7.73 (d, 2H), 7.37 (d, 2H), 7.27 (m, 4H), 7.18 (m, 5H), 6.93 (d, 2H), 3.90 (2H, m) 3.66 (q, 2H), 3.28 (m, 2H), 2.78 (t, 2H), 2.53 (m, 2H), 1.77 (m, 1H), 1.63 (m, 2H), 1.19 (m, 2H).

EXAMPLE 489

4-(((1R)-4-(dimethylamino)-1-((phenylthio)m,ethyl)butyl)amino)-N-((2'-methoxy-4'-(2-(4-methylpiperazin-1-yl)ethyl)-1,1'-biphenyl-4-yl)carbonyl)-3-nitrobenzenesulfonamide

EXAMPLE 489A 4-(((1R)-4-(dimethylamino-1-((phenylthio)methyl)butyl)amino)-3-nitrobenzenesulfonamide The desired product was prepared by substituting Example 480D for Example 122F in Example 122G. MS (ESI) m/e 437, 439 (M−H)⁻, (M+H)⁺.

EXAMPLE 489B 4-(((1R)-4-(dimethylamino)-1-((phenylthio)methyl)butyl)amino)-N-((2'-methoxy-4'-(2-(4-methylpiperazin-1-yl)ethyl)-1,1'-biphenyl-4-yl)carbonyl)-3-nitrobenzenesulfonamide The desired product was prepared by substituting Example 242B and Example 489A for Example 1B and Example 1C, respectively, in Example 1D. MS (ESI) m/e 773, 775 (M–H)⁻, (M+H)⁺; ¹H NMR (300 MHz, DMSO-d₆) δ1.78 (m, 4H), 1.91 (m, 2H), 2.51 (m, 2H), 2.66 (s, 6H), 2.71 (m, 4H), 3.00 (m, 2H), 3.17 (s, 3H), 3.36 (m, 6H), 3.76 (s, 3H), 4.05 (m, 1H), 6.90 (d, 1H), 7.00 (m, 2H), 7.18 (m, 1H), 7.22 (m, 3H), 7.31 (d, 2H), 7.39 (m, 2H), 7.83 (dd, 1H), 7.90 (d, 2H), 8.15 (s, 1H), 8.48 (d, 1H).

EXAMPLE 490

3-(2-methoxy-4'-((((4-(((1R)-4-(4-methylpiperazin-1-yl)-1-((phenylthio)methyl)butyl)amino)-3-nitrophenyl)sulfonyl)amino)carbonyl)-1,1'-biphenyl-4-yl)-N,N-dimethylpropanamide

EXAMPLE 490A tert-butyl(1R)-4-(4-methylpiperazin-1-yl)-4-oxo-1-((phenylthio)methyl)butylcarbamate The desired product was prepared by substituting Example 480B and n-methylpiperazine for Example 122E and dimethylamine, respectively, in Example 122F. MS (ESI) m/e 406, 408 (M–H)⁻, (M+H)⁺.

EXAMPLE 490B 4-(((1R)-4-(4-methylpiperazin-1-yl)-1-((phenylthio)methyl)butyl)amino)-3-nitrobenzenesulfonamide The desired product was prepared by substituting Example 490A for Example 122F in Example 122G, then substituting the product obtained for Example 133A in Example 133B. MS (ESI) m/e 492, 494 (M–H)⁻, (M+H)⁺.

EXAMPLE 490C 3-(2-methoxy-4'-((((4-(((1R)-4-(4-methylpiperazin-1-yl)-1-(phenylthio)methyl)butyl)amino)-3-nitrophenyl)sulfonyl)amino)carbonyl)-1,1'-biphenyl-4-yl)-N,N-dimethylpropanamide The desired product was prepared by substituting Example 482A and Example 490B for Example 1B and Example 1C, respectively, in Example 1D. ¹H NMR (300 MHz, DMSO-d₆) δ1.78 (m, 4H), 2.52 (dd, 2H), 2.61 (m, 6H), 2.72 (s, 3H), 2.83 (s, 3H), 2.85 (m, 2H), 2.96 (s, 3H), 3.01 (m, 4H), 3.37 (m, 2H), 3.76 (s, 3H), 4.11 (m, 1H), 6.91 (d, 1H), 7.01 (s, 1H), 7.09 (d, 1H), 7.15 (d, 1H), 7.20 (m, 3H), 7.30 (d, 2H), 7.46 (d, 2H), 7.90 (dd, 1H), 7.93 (d, 2H), 8.21 (d, 1H), 8.52 (d, 1H).

EXAMPLE 491 tert-butyl 4-(2-(4'-((((4-(((1R)-3-(dimethylamino)-1-((phenylthio)methyl)propyl)amino)-3-nitrophenyl)sulfonyl)amino)carbonyl)-2-methoxy-1,1'-biphenyl-4-yl)ethyl)piperazine-1-carboxylate

EXAMPLE 491A 4-(2-hydroxyethyl)-2-methoxyphenol

The desired product was prepared by substituting homovanillyl alcohol for Example 201E in Example 201F.

EXAMPLE 491B methyl 4'-(2-hydroxyethyl)-2'-methoxy-1,1'-biphenyl-4-carboxylate The desired product was prepared by substituting Example 491A for Example 5A in Example 5B.

EXAMPLE 491C methyl 2'-methoxy-4'-(2-oxoethyl)-1,1'-biphenyl-4-carboxylate

A solution of Example 491B (2.47 g, 8.63 mmol) in dichloromethane (25 mL) at room temperature was treated with Dess-Martin periodinane (4.03 g, 9.49 mmol), stirred for 90 minutes, and concentrated. The concentrate was purified by flash column chromatography on silica gel with 1:1 ethyl acetate/hexanes to provide the desired product.

EXAMPLE 491D tert-butyl 4-(2-(2-methoxy-4'-(methoxycarbonyl)-1,1'-biphenyl-4-yl)ethyl)piperazine-1-carboxylate A solution of Example 491C (400 mg, 1.41 mmol) and tert-butyl 1-piperazinecarboxylate (289 mg, 1.55 mmol) in 1,2-dichloroethane (5 mL) at room temperature was treated with sodium triacetoxyborohydride (329 mg, 1.55 mmol), and stirred for 16 hours. The solution was purified by flash column chromatography on silica gel with 90:10:0.25 dichloromethane/methanol/concentrated ammonium hydroxide to provide the desired product.

EXAMPLE 491E

4'-(2-(4-(tert-butoxycarbonyl)piperazin-1-yl)ethyl)-2'-methoxy-1,1'-biphenyl-4-carboxylic acid The desired product was prepared by substituting Example 491D for Example 1A in Example 1B.

EXAMPLE 491F tert-butyl 4-(2-(4'-((((4-(((1R)-3-(dimethylamino)-1-((phenylthio)methyl)propyl)amino)-3-nitrophenyl)sulfonyl)amino)carbonyl)-2-methoxy-1,1'-biphenyl-4-yl)ethyl)piperazine-1-carboxylate The desired product was prepared by substituting Example 491E and Example 122G for Example 1B and Example 1C, respectively, in Example 1D. MS (ESI) m/e 845, 847 (M–H)⁻, (M+H)⁺; ¹H NMR (300 MHz, DMSO-d₆) δ1.39 (s, 9H), 2.08 (m, 2H), 2.52 (s, 6H), 2.42 (m, 4H), 2.58 (m, 2H), 2.76 (m, 6H), 3.06 (m, 2H), 3.33 (t, 2H), 3.73 (s, 3H), 4.09 (m, 1H), 6.88 (d, 1H), 6.90 (d, 1H), 6.98 (s, 1H), 7.18 (dd, 2H), 7.26 (tt, 2H), 7.32 (dt, 2H), 7.38 (d, 2H), 7.82 (dd, 1H), 7.88 (d, 2H), 8.23 (d, 1H), 8.48 (d, 1H).

EXAMPLE 492

4-(2-(4'-((((4-(((1R)-3-(dimethylamino)-1-((phenylthio)methyl)propyl)amino)-3-nitrophenyl)sulfonyl)amino)carbonyl)-2-methoxy-1,1'-biphenyl-4-yl)ethyl)piperazine-1-carboxamide A solution of Example 499 (40 mg, 0.05 mmol) in DMF (0.5 mL) at room temperature was treated with trimethylsilyl isocyanate (7 mg, 0.06 mmol), and stirred for 16 hours. The solution was purified by flash column chromatography on silica gel with 80:20:0.5 dichloromethane/methanol/concentrated ammonium hydroxide to provide the desired product. MS (ESI) m/e 788, 790 (M–H)⁻, (M+H)⁺; ¹H NMR (300 MHz, DMSO-d₆) δ2.11 (m, 2H), 2.69 (s, 6H), 2.71 (m, 2H), 2.86 (m, 4H), 3.05 (m, 2H), 3.08 (m, 4H), 3.16 (d, 2H), 3.34 (t, 2H), 3.75 (s, 3H), 4.09 (m, 1H), 6.13 (s, 2H), 6.88 (d, 1H), 6.95 (d, 1H), 7.00 (s, 1H), 7.15–7.33 (m, 6H), 7.40 (d, 2H), 7.83 (dd, 1H), 7.88 (d, 2H), 8.14 (d, 1H), 8.48 (d, 1H).

EXAMPLE 493

4-(((1R)-5-(dimethylamino)-1-((phenylthio)methyl)
pentyl)amino)-N-(4-(4-hydroxy-4-phenylpiperidin-
1-yl)benzoyl)-3-nitrobenzenesulfonamide

EXAMPLE 493A tert-butyl 4-(4-hydroxy-4-phenylpiperidin-1-yl)
benzoate

A solution of 4-hydroxy-4-phenyl piperidine (221 mg, 1.25 mmol) in DMSO (1 mL) was treated with tert-butyl-4-fluorobenzoate (196 mg, 1.00 mmol) and powdered potassium carbonate (173 mg, 1.25 mmol), stirred vigorously at 125° C. for 16 hours, cooled to room temperature, diluted with diethyl ether, washed with brine, dried (MgSO$_4$), filtered, and concentrated to provide the desired product. MS (DCI(+)) m/e 354 (M+H)$^+$.

EXAMPLE 493B 4-(4-hydroxy-4-phenylpiperidin-1-yl)benzoic acid

A solution of Example 493A (0.32 g, 0.91 mmol) in TFA (2 mL) at room temperature was stirred for 1 hour, and concentrated. The concentrate was azeotropically distilled with toluene three times and dried to provide the desired product. MS (ESI(+)) m/e 298 (M+H)$^+$.

EXAMPLE 493C 4-(((1R)-5-(dimethylamino)-1-((phenylthio)methyl)
pentyl)amino)-N-(4-(4-hydroxy-4-phenylpiperidin-
1-yl)benzoyl)-3-nitrobenzenesulfonamide The desired product was prepared by substituting Example 124E and Example 493B for Example 1C and Example 1B, respectively, in Example 1D. MS(ESI(+)) m/e 732 (M+H)$^+$; $^1$H NMR (500 MHz, DMSO-d$_6$) δ8.45 (d, 1H), 8.15 (d, 1H), 7.84 (dd, 1H), 7.75 (d, 2H), 7.45 (d, 2H), 7.30 (m, 4H), 7.20 (m, 4H), 6.95 (d, 1H), 6.87 (d, 2H), 5.00 (s, 1H), 4.02 (m, 1H), 3.65 (m, 2H), 3.18 (m, 2H), 2.90 (m, 2H), 2.67 (s, 6H), 2.00 (m, 2H) 1.85–1.50 (m, 6H), 1.35 (m, 2H).

EXAMPLE 494

4-(((1R)-5-(dimethylamino)-1-((phenylthio)methyl)
pentyl)amino)-N-(4-(4-methoxy-4-methylpiperidin-
1-yl)benzoyl)-3-nitrobenzenesulfonamide

EXAMPLE 494A tert-butyl 4-hydroxy-4-methylpiperidine-1-
carboxylate

A solution of 3M methyl magnesium bromide in diethyl ether (2.0 mL) in diethyl ether (3 mL) at 0° C. was treated with a solution of tert-butyl 4-oxo-1-piperidinecarboxylate (1.0 g, 5.00 mmol) in diethyl ether (5 mL), warmed to room temperature, stirred for 18 hours, treated with saturated NH$_4$Cl, and extracted with diethyl ether. The combined extracts were washed with brine, dried (MgSO$_4$), filtered, and concentrated. The concentratet was purified by flash chromatography on silica gel with 20%–50% ethyl acetate/heptane to provide the desired product. MS (DCI(+)) m/e 216 (M+H)$^+$.

EXAMPLE 494B tert-butyl 4-methoxy-4-methylpiperidine-1-
carboxylate

A suspension of 60% NaH in mineral oil (160 mg, 4 mmol) in THF (5 mL) at room temperature was treated with a solution of Example 494A (430 mg, 2.00 mmol) in THF (5 mL), heated to 55° C. for 2 hours, cooled to room temperature, treated with HMPA (2.5 mL) and methyl iodide (0.50 mL), heated to 55° C. for 16 hours, cooled to room temperature, quenched with 10% aqueous citric acid, and extracted twice with diethyl ether. The combined extracts were washed sequentially with water, saturated NaHCO$_3$, and brine, dried (MgSO$_4$), filtered, and concentrated. The concentrate was purified by flash column chromatography on silica gel with 10%–20% ethyl acetate/heptane to provide the desired product.

EXAMPLE 494C 4-methoxy-4-methylpiperidine

A solution of Example 494B (115 mg, 0.5 mmol) in TFA (1 mL) at room temperature was stirred for 1.5 hours and concentrated. The product was azeotropically distilled with toluene three times and concentrated to provide the desired product as the trifluoroacetate salt.

EXAMPLE 494D tert-butyl 4-(4-methoxy-4-methylpiperidin-1-yl)
benzoate

A solution of Example 494C (0.5 mmol) in DMSO (0.5 mL) at room temperature was treated with tert-butyl-4-fluorobenzoate (118 mg, 0.60 mmol) and powdered potassium carbonate (207 mg, 1.5 mmol), heated to 125° C. for 16 hours, and cooled to room temperature. The mixture was diluted with ethyl acetate, washed with brine, dried (MgSO$_4$), filtered, and concentrated. The concentrate was purified by flash column chromatography on silica gel with 10%–30% ethyl acetate/hexanes to provide the desired product. MS (DCI(+)) m/e 306 (M+H)$^+$.

EXAMPLE 494E 4-(4-methoxy-4-methylpiperidin-1-yl)benzoic acid

The desired product was prepared by substituting Example 494D for Example 493A in Example 493B.

EXAMPLE 494F 4-(((1R)-5-(dimethylamino)-1-((phenylthio)methyl)
pentyl)amino)-N-(4-(4-methoxy-4-methylpiperidin-
1-yl)benzoyl)-3-nitrobenzenesulfonamide The desired product was prepared by substituting Example 494E and Example 124E for Example 1B and Example 1C, respectively, in Example 1D. MS(ESI(+)) m/e 684 (M+H)$^+$; $^1$H NMR (500 MHz, DMSO-d$_6$) δ8.45 (d, 1H), 8.15 (d, 1H), 7.82 (dd, 1H), 7.73 (d, 2H), 7.30 (d, 2H), 7.25 (t, 2H), 7.15 (m, 1H), 6.95 (d, 1H), 6.80 (d, 2H), 4.02 (m, 1H), 3.35 (m, 2H), 3.10 (s, 3H), 3.05 (m, 2H), 2.90 (m, 2H), 2.68 (s, 6H), 1.75 (m, 4H), 1.55 (m, 4H), 1.30 (m, 4H), 1.10 (s, 3H).

EXAMPLE 495

4-(((1R)-5-(dimethylamino)-1-((phenylthio)methyl)
pentyl)amino)-N-(4-(4-ethyl-4-hydroxypiperidin-1-
yl)benzoyl)-3-nitrobenzenesulfonamide

EXAMPLE 495A tert-butyl 4-ethyl-4-hydroxypiperidine-1-carboxylate

The desired product was prepared by substituting ethyl magnesium bromide for methyl magnesium bromide in Example 494A.

EXAMPLE 495B 4-ethylpiperidin-4-ol

The desired product was prepared by substituting Example 495A for Example 492B in Example 492C.

EXAMPLE 495C tert-butyl 4-(4-ethyl-4-hydroxypiperidin-1-yl) benzoate

The desired product was prepared by substituting Example 495B for Example 494C in Example 494D.

EXAMPLE 495D 4-(4-ethyl-4-hydroxypiperidin-1-yl)benzoic acid

The desired product was prepared by substituting Example 495C for Example 493A in Example 493B.

EXAMPLE 495E 4-(((1R)-5-(dimethylamino)-1-((phenylthio)methyl) pentyl)amino)-N-(4-(4-ethyl-4-hydroxypiperidin-1-yl)benzoyl)-3-nitrobenzenesulfonamide The desired product was prepared by substituting Example 495D and Example 124E for Example 1B and Example 1C, respectively, in Example 1D. MS ESI(+)) m/e 684 (M+H)$^+$; $^1$H NMR (500 MHz, DMSO-d$_6$) δ11.95 (s, 1H), 9.25 (s, 1H), 8.55 (d, 1H), 8.31 (d, 1H), 7.88 (dd, 1H), 7.72 (d, 2H), 7.25–7.05 (m, 5H), 6.93 (d, 2H), 4.10 (m, 1H), 3.60 (m, 2H), 3.35 (m, 2H), 3.20 (m, 2H), 2.95 (m, 2H), 2.70 (d, 6H), 1.75 (m, 2H), 1.55 (m, 2H), 1.50–1.30 (m, 8H), 0.80 (t, 3H).

EXAMPLE 496

N-(4-(4-benzyl-4-hydroxypiperidin-1-yl)benzoyl)-4-(((1R)-5-(dimethylamino)-1-((phenylthio)methyl) pentyl)amino)-3-nitrobenzenesulfonamide

EXAMPLE 496A tert-butyl 4-(4-benzyl-4-hydroxypiperidin-1-yl) benzoate

The desired product was prepared by substituting 4-hydroxy-4-benzyl piperidine for 4-hydroxy-4-phenyl piperidine in Example 493A.

EXAMPLE 496B 4-(4-benzyl-4-hydroxypiperidin-1-yl)benzoic acid

The desired product was prepared by substituting Example 496A for Example 493A in Example 493B.

EXAMPLE 496C

N-(4-(4-benzyl-4-hydroxypiperidin-1-yl)benzoyl)-4-(((1R)-5-(dimethylamino)-1-((phenylthio)methyl) pentyl)amino)-3-nitrobenzenesulfonamide The desired product was prepared by substituting Example 124E and Example 496B for Example 1C and Example 1B, respectively, in Example 1D. MS (ESI(+)) m/e 746 (M+H)$^+$; $^1$H NMR (500 MHz, DMSO-d$_6$) δ8.45 (d, 1H), 8.15 (d, 1H), 7.80 (dd, 1H), 7.70 (d, 2H), 7.35–7.15 (m, 10H), 6.95 (d, 1H), 6.80 (d, 2H), 4.30 (s, 1H), 4.02 (s, 1H), 3.45 (m, 2H), 3.05 (m, 2H), 2.90 (m, 2H), 2.70 (s, 2H), 2.65 (s, 6H), 1.75 (m, 2H), 1.55 (m, 4H), 1.50–1.20 (m, 4H).

EXAMPLE 497

N~2~-((4'-((((4-(((1R)-4-(dimethylamino)-1-((phenylthio)methyl)butyl)amino)-3-nitrophenyl) sulfonyl)amino)carbonyl)-2-methoxy-1,1'-biphenyl-4-yl)methyl)-N~1~,N~1~,N~2~-trimethylglycinamide

EXAMPLE 497A methyl 4'-(((2-(dimethylamino)-2-oxoethyl)(methyl) amino)methyl)-2'-methoxy-1,1'-biphenyl-4-carboxylate The desired product was prepared by substituting Example 122I and sarcosine dimethylamide for Example 491C and tert-butyl 1-piperazinecarboxylate, respectively, in Example 491D.

EXAMPLE 497B

4'-(((2-(dimethylamino)-2-oxoethyl)(methyl)amino) methyl)-2'-methoxy-1,1'-biphenyl-4-carboxylic acid The desired product was prepared by substituting Example 497A for Example 1A in Example 1B.

EXAMPLE 497C

N~2~-((4'-((((4-(((1R)-4-(dimethylamino)-1-((phenylthio)methyl)butyl)amino)-3-nitrophenyl) sulfonyl)amino)carbonyl)-2-methoxy-1,1'-biphenyl-4-yl)methyl)-N~1~,N~1~,N~2~-trimethylglycinamide The desired product was prepared by substituting Example 497B and Example 489A for Example 1B and Example 1C, respectively, in Example 1D. MS (ESI) m/e 775, 777 (M–H)$^-$, (M+H)$^+$; $^1$H NMR (300 MHz, DMSO-d$_6$) δ1.55 (m, 4H), 1.75 (m, 2H), 2.20 (s, 3H), 2.32 (s, 6H), 2.45 (t, 2H), 2.81 (s, 3H), 3.02 (s, 3H), 3.23 (s, 2H), 3.58 (s, 2H), 3.74 (s, 3H), 4.02 (m, 1H), 6.95 (d, 2H), 7.04 (s, 1H), 7.18 (dt, 1H), 7.24 (m, 2H), 7.31 (m, 2H), 7.40 (d, 2H), 7.83 (dd, 1H), 7.89 (d, 2H), 8.11 (d, 2H), 8.47 (d, 1H).

EXAMPLE 498A methyl 4'-(((2-(dimethylamino)-2-oxoethyl)(methyl) amino)ethyl)-2'-methoxy-1,1'-biphenyl-4-carboxylate The desired product was prepared by substituting sarcosine dimethylamide for tert-butyl 1-piperazincarboxylate in Example 491D.

EXAMPLE 498B

4'-(((2-(dimethylamino)-2-oxoethyl)(methyl)amino) ethyl)-2'-methoxy-1,1'-biphenyl-4-carboxylic acid The desired product was prepared by substituting Example 498A for Example 1A in Example 1B.

EXAMPLE 498C

N~2~-(2-(4'-((((4-(((1R)-4-(dimethylamino)-1-((phenylthio)methyl)butyl)amino)-3-nitrophenyl) sulfonyl)amino)carbonyl)-2-methoxy-1,1'-biphenyl-4-yl)ethyl)-N~1~,N~1~,N~2~-trimethylglycinamide The desired product was prepared by substituting Example 498B and Example 489A for Example 1B and Example 1C, respectively, in Example 1D. MS (ESI) m/e 789, 791 (M−H)⁻, (M+H)⁺; ¹H NMR (300 MHz, DMSO-d$_6$) δ1.65 (m, 4H), 1.75 (m, 2H), 2.35 (s, 3H), 2.57 (s, 6H), 2.78 (s, 3H), 2.81 (m, 6H), 2.91 (s, 3H), 3.35 (s, 2H), 3.74 (s, 3H), 4.04 (m, 1H), 6.86 (d, 1H), 6.96 (m, 2H), 7.18 (m, 2H), 7.25 (t, 2H), 7.32 (m, 2H), 7.38 (d, 2H), 7.83 (dd, 1H), 7.88 (d, 2H), 8.14 (d, 1H), 8.47 (d, 1H).

EXAMPLE 499

4-(((1R)-3-(dimethylamino)-1-((phenylthio)methyl) propyl)amino)-N-((2'-methoxy-4'-(2-piperazin-1-ylethyl)-1,1'-biphenyl-4-yl)carbonyl)-3-nitrobenzenesulfonamide A solution of Example 491F (284 mg, 0.34 mmol) in 1,4-dioxane (1.5 mL) and 4M HCl (1.5 mL) at room temperature was stirred for 16 hours. The solution was purified by flash column chromatography on silica gel with 80:20:0.5 dichloromethane/methanol/concentrated ammonium hydroxide to provide the desired product. MS (ESI) m/e 745, 747 (M−H)⁻, (M+H)⁺; ¹H NMR (300 MHz, DMSO-d$_6$) δ2.11 (m, 2H), 2.62 (s, 6H), 2.67 (m, 4H), 2.77 (m, 2H), 3.00 (m, 2H), 3.06 (m, 4H), 3.16 (d, 2H), 3.33 (t, 2H), 3.75 (s, 3H), 4.09 (m, 1H), 6.88 (d, 1H), 6.95 (d, 1H), 6.98 (s, 1H), 7.15–7.22 (m, 2H), 7.24–7.33 (m, 4H), 7.38 (d, 2H), 7.82 (dd, 1H), 7.88 (d, 2H), 8.17 (d, 1H), 8.47 (d, 1H).

EXAMPLE 500 tert-butyl 4-((4'-((((4-(((1R)-3-(dimethylamino)-1-((phenylthio)methyl)propyl)amino)-3-nitrophenyl) sulfonyl)amino)carbonyl)-2-methoxy-1,1'-biphenyl-4-yl)methyl)-3-oxopiperazine-1-carboxylate

EXAMPLE 500A piperazin-2-one

A solution of ethylenediamine (66.40 g, 1106 mmol) in ethanol (300 mL) at room temperature was treated dropwise with a solution of ethyl chloroacetate (20.00 g, 184 mmol) in ethanol (100 mL) over 3 hours, stirred for 2 hours, treated with sodium ethoxide (13.13 g, 193 mmol), and filtered. The filtrate was concentrated, dissolved in DMF (200 mL), stirred for 16 hours, heated to 65° C. for 72 hours, cooled to room temperature, and concentrated. The concentrate was purified by flash column chromatography on silica gel with 80:20:0.5 dichloromethane/methanol/concentrated ammonium hydroxide to provide the desired product.

EXAMPLE 500B tert-butyl 3-oxopiperazine-1-carboxylate

A solution of Example 500A (500 mg, 4.99 mmol) in acetonitrile (25 mL) at room temperature was treated with BOC$_2$O (1198 mg, 5.49 mmol), stirred for 3 hours, and concentrated. The concentrate was purified by flash column chromatography on silica gel with 95:5 ethyl acetate/methanol to provide the desired product.

EXAMPLE 500C methyl 4'-(bromomethyl)-2'-methoxy-1,1'-biphenyl-4-carboxylate

A solution of Example 417A (1.50 g, 5.51 mmol) in DMF (18.0 mL) at 0° C. was treated with LiBr (526 mg, 6.06 mmol) and PBr$_3$ (1.64 g, 6.06 mmol), warmed to room temperature, and stirred for 30 minutes. The solution was purified by flash column chromatography on silica gel with 3:7 ethyl acetate/hexanes to provide the desired product.

EXAMPLE 500D tert-butyl 4-((2-methoxy-4'-(methoxycarbonyl)-1,1'-biphenyl-4-yl)methyl)-3-oxopiperazine-1-carboxylate A solution of Example 500B (328 mg, 1.64 mmol) in DMF (4 mL) at room temperature was treated with 15-crown-5 (361 mg, 1.64 mmol) and 60% sodium hydride in mineral oil (66 mg, 1.64 mmol). The mixture was treated with a solution of Example 500C (500 mg, 1.49 mmol) in DMF (2 mL), heated to 60° C. for 16 hours, cooled to room temperature, treated with water (20 mL), and extracted three times with ethyl acetate (50 mL). The combined extracts were washed with brine (10 mL), dried (Na$_2$SO$_4$), filtered, and concentrated. The concentrate was purified by flash column chromatography on silica gel with 1:1 ethyl acetate/hexanes to provide the desired product.

EXAMPLE 500E

4'-((4-(tert-butoxycarbonyl)-2-oxopiperazin-1-yl) methyl)-2'-methoxy-1,1'-biphenyl-4-carboxylic acid The desired product was prepared by substituting Example 500D for Example 1A in Example 1B.

EXAMPLE 500F tert-butyl 4-((4'-((((4-(((1R)-3-(dimethylamino)-1-((phenylthio)methyl)propyl)amino)-3-nitrophenyl) sulfonyl)amino)carbonyl)-2-methoxy-1,1'-biphenyl-4-yl)methyl)-3-oxopiperazine-1-carboxylate The desired product was prepared by substituting Example 500E and Example 122G for Example 1B and Example 1C, respectively, in Example 1D. MS (ESI) m/e 845, 847 (M−H)⁻, (M+H)⁺; ¹H NMR (300 MHz, DMSO-d$_6$) δ1.41 (s, 9H), 2.01 (m, 2H), 2.33 (s, 6H), 2.65 (m, 2H), 3.27 (d, 2H), 3.32 (t, 2H), 3.56 (t, 2H), 3.74 (s, 3H), 4.01 (s, 2H), 4.09 (m, 1H), 4.57 (s, 2H), 6.88 (m, 2H), 6.98 (s, 1H), 7.18 (dt, 1H), 7.26 (m, 3H), 7.32 (m, 2H), 7.39 (d, 2H), 7.81 (dd, 1H), 7.88 (d, 2H), 8.34 (d, 1H), 8.47 (d, 1H).

EXAMPLE 501

4-(((1R)-3-(dimethylamino)-1-((phenylthio)methyl) propyl)amino)-N-((2'-methoxy-4'-((2-oxopiperazin-1-yl)methyl)-1,1'-biphenyl-4-yl)carbonyl)-3-nitrobenzenesulfonamide A solution of Example 500F (73 mg, 0.09 mmol) in dioxane (1 mL) and 4M HCl (1 mL) at room temperature was stirred for 16 hours, and purified by flash column chromatography on silica gel with 80:20:0.5 dichloromethane/methanol/concentrated ammonium hydroxide to provide the desired product. MS (ESI) m/e 745, 747 (M−H)⁻, (M+H)⁺; ¹H NMR (300 MHz, DMSO-d$_6$) δ2.07 (m, 2H), 2.54 (d, 6H), 2.74 (m, 1H), 3.04 (m, 2H), 3.17 (d, 2H), 3.23 (t, 2H), 3.32 (t, 2H), 3.47 (s, 2H), 3.74 (s, 3H), 4.09 (m, 1H), 4.54 (s, 2H), 6.89–6.99 (m, 3H), 7.17 (tt, 2H), 7.22–7.34 (m, 4H), 7.39 (d, 2H), 7.81 (dd, 1H), 7.88 (dd, 2H), 8.21 (d, 1H), 8.47 (d, 1H).

EXAMPLE 502

N-(4-(4-(4-methoxybenzoyl)piperazin-1-yl) benzoyl)-3-nitro-4-((2-(phenylthio)ethyl)amino) benzenesulfonamide The desired product was prepared by substituting 4-methoxybenzoyl chloride for 2-methoxyethyl chloroformate in Example 325. MS (ESI(−)) m/e 674 (M−H)⁻; ¹H NMR (500 MHz, DMSO-d₆) δ12.02 (s, 1H), 8.76 (t, 1H), 8.61 (d, 1H), 7.92 (dd, 1H), 7.77 (d, 2H), 7.41 (d, 2H), 7.37 (d, 2H), 7.26 (t, 2H), 7.15–7.20 (m, 2H), 6.99 (d, 2H), 6.95 (d, 2H), 3.80 (s, 3H), 3.67 (q, 2H), 3.61 (br s, 4H), 3.39 (br s, 4H), 3.28 (t, 2H).

EXAMPLE 503

N-(4-(4-((3-fluorophenyl)sulfonyl)piperazin-1-yl) benzoyl)-3-nitro-4-((2-(phenylthio)ethyl)amino) benzenesulfonamide The desired product was prepared by substituting 3-fluorobenzenesulfonyl chloride for 2-methoxyethyl chloroformate in Example 325. MS (ESI(−)) m/e 698 (M−H)⁻; ¹H NMR (500 MHz, DMSO-d₆) δ12.04 (s, 1H), 8.77 (t, 1H), 8.59 (d, 1H), 7.89 (dd, 1H), 7.69–7.75 (m, 3H), 7.58–7.63 (m, 3H), 7.36 (d, 2H), 7.26 (t, 2H), 7.14–7.20 (m, 2H), 6.92 (d, 2H), 3.66 (q, 2H), 3.40–3.44 (m, 4H), 3.28 (t, 2H), 3.01–3.05 (m, 4H).

EXAMPLE 504

N-(4-(4-((4-fluorophenyl)sulfonyl)piperazin-1-yl) benzoyl)-3-nitro-4-((2-(phenylthio)ethyl)amino) benzenesulfonamide The desired product was prepared by substituting 4-fluorobenzenesulfonyl chloride for 2-methoxyethyl chloroformate in Example 325. MS (ESI(−)) m/e 698 (M−H)⁻; ¹H NMR (500 MHz, DMSO-d₆) δ12.04 (s, 1H), 8.77 (t, 1H), 8.59 (d, 1H), 7.90 (dd, 1H), 7.86–7.82 (m, 2H), 7.73 (d, 2H), 7.49 (t, 2H), 7.36 (d, 2H), 7.26 (t, 2H), 7.20–7.14 (m, 2H), 6.91 (d, 2H), 3.66 (q, 2H), 3.44–3.40 (m, 4H), 3.28 (t, 2H), 3.01–2.98 (m, 4H).

EXAMPLE 505

3-nitro-4-((2-(phenylthio)ethyl)amino)-N-(4-(4-((4-propylphenyl)sulfonyl)piperazin-1-yl)benzoyl) benzenesulfonamide The desired product was prepared by substituting 4-propylbenzenesulfonyl chloride for 2-methoxyethyl chloroformate in Example 325. MS (ESI(−)) m/e 722 (M−H)⁻; ¹H NMR (500 MHz, DMSO-d₆) δ12.01 (s, 1H), 8.75 (t, 1H), 8.58 (d, 1H), 7.89 (dd, 1H), 7.22 (d, 2H), 7.66 (d, 2H), 7.46 (d, 2H), 7.36 (d, 2H), 7.26 (t, 2H), 7.14–7.20 (m, 2H), 6.90 (d, 2H), 3.66 (q, 2H), 3.42–3.39 (m, 4H), 3.28 (t, 2H), 2.99–2.95 (m, 4H), 2.64 (t, 2H), 1.60 (hextet, 2H), 0.86 (t, 3H).

EXAMPLE 506

N-(4-(8-azaspiro(4.5)dec-8-yl)benzoyl)-3-nitro-4-((4-((phenylthio)methyl)piperidin-4-yl)amino) benzenesulfonamide The desired product was prepared by substituting Example 472C and Example 257C for Example 1C and Example 1B, respectively, in Example 1D. The crude product was purified by reverse-phase chromatography using a C-18 column and 50% CH₃CN/water containing 0.01M HCl to provide the desired product as the hydrochloride salt. MS (ESI) m/e 662, 664 (M−H)⁻, (M+H)⁺; ¹H NMR (300 MHz, DMSO-d₆) δ1,42 (m, 8H), 1.59 (m, 4H), 2.05 (m, 2H), 3.02 (m, 2H), 3.21 (m, 2H), 3.35 (m, 4H), 3.63 (m, 4H), 6.86 (m, 3H), 6.96 (d, 2H), 7.21 (d, 2H), 7.33 (d, 1H), 7.79 (m, 3H), 8.29 (d, 1H), 8.46 (d, 1H), 9.02 (br s, 2H).

EXAMPLE 507

(4R)-4-((4-(((4-(8-azaspiro(4.5)dec-8-yl)benzoyl) amino)sulfonyl)-2-nitrophenyl)amino)-N,N-dimethyl-5-(phenylthio)pentanamide The desired product was prepared by substituting Example 480D and Example 257C for Example 1C and Example 1B, respectively, in Example 1D. MS (ESI) m/e 692, 694 (M−H)⁻, (M+H)⁺; ¹H NMR (300 MHz, DMSO-d₆) δ1.41 (m, 4H), 1.48 (m, 4H), 1.59 (m, 4H), 1.93 (m, 2H), 2.38 (m, 2H), 2.75 (s, 3H), 2.83 (s, 3H), 3.19 (m, 4H), 3.32 (m, 3H), 4.04 (m, 1H), 6.80 (d, 2H), 6.91 (d, 1H), 7.15 (dd, 1H), 7.22 (dd, 2H), 7.31 (d, 2H), 7.72 (d, 2H), 7.79 (dd, 1H), 8.12 (d, 1H), 8.42 (d, 1H).

EXAMPLE 508

N-(4-(8-azaspiro(4.5)dec-8-yl)benzoyl)-4-(((1R)-4-(dimethylamino)-1-((phenylthio)methyl)butyl) amino)-3-nitrobenzenesulfonamide The desired product was prepared by substituting Example 489A and Example 257C for Example 1C and Example 1B, respectively, in Example 1D. MS (ESI) m/e 678 (M−H)⁻; ¹H NMR (300 MHz, DMSO-d₆) δ1.41 (m, 4H), 1.48 (m, 4H), 1.59 (m, 4H), 1.85 (m, 2H), 2.41 (s, 6H), 2.62 (m, 2H), 2.66 (m, 2H), 3.19 (M, 4H), 3.31 (ddd, 2H), 4.02 (m, 1H), 6.80 (d, 2H), 6.93 (d, 1H), 7.16 (dd, 1H), 7.22 (dd, 2H), 7.31 (d, 2H), 7.73 (d, 2H), 7.81 (dd, 1H), 8.12 (d, 1H), 8.46 (d, 1H).

EXAMPLE 509

4-(((1R)-4-(dimethylamino)-1-((phenylthio)methyl) butyl)amino)-N-((2'-methoxy-4'-(3-morpholin-4-ylpropyl)-1,1'-biphenyl-4-yl)carbonyl)-3-nitrobenzenesulfonamide The desired product was prepared by substituting Example 489A and Example 122O for Example 1C and Example 1B, respectively, in Example 1D. MS (ESI) m/e 774, 776 (M−H)⁻, (M+H)⁺; ¹H NMR (300 MHz, DMSO-d₆) δ1.77 (m, 4H), 2.05 (m, 2H), 2.68 (s, 6H), 2.96–3.05 (m, 9H), 3.37 (m, 4H), 3.77 (s, 3H), 3.84 (m, 4H), 4.08 (m, 1H), 6.90 (d, 1H), 6.99 (s, 1H), 7.03 (d, 1H), 7.16 (dd, 1H), 7.21 (s, 1H), 7.23 (dd, 2H), 7.30 (d, 2H), 7.42 (d, 2H), 7.85 (dd, 2H), 7.91 (d, 2H), 8.15 (d, 1H), 8.50 (d, 1H).

EXAMPLE 510

N-(4-(8-azaspiro(4.5)dec-8-yl)benzoyl)-4-(((1R)-3-(4-methylpiperazin-1-yl)-1-((phenylthio)methyl) propyl)amino)-3-nitrobenzenesulfonamide The desired product was prepared by substituting Example 481A and Example 257C for Example 1C and Example 1B, respectively, in Example 1D. MS (ESI) m/e 719, 721 (M−H)⁻, (M+H)⁺; ¹H NMR (300 MHz, DMSO-d₆) δ1.41 (m, 4H), 1.48 (m, 4H), 1.59 (m, 4H), 1.72 (m, 4H), 1.82 (m, 2H), 2.41 (s, 3H), 2.91 (m, 2H), 3.01 (m, 2H), 3.05 (m, 2H), 3.19 (m, 4H), 3.36 (m, 2H), 4.09 (m, 1H), 6.80 (d, 2H), 6.95 (d, 1H), 7.17 (dd, 1H), 7.22 (dd, 2H), 7.31 (d, 2H), 7.74 (d, 2H), 7.81 (dd, 1H), 8.23 (d, 1H), 8.46 (d, 1H).

EXAMPLE 511

N-((4'-(3-hydroxypropyl)-2'-methoxy-1,1'-biphenyl-4-yl)carbonyl)-4-(((1R)-3-(4-methylpiperazin-1-yl)-1-((phenylthio)methyl)propyl)amino)-3-nitrobenzenesulfonamide The desired product was prepared by substituting Example 481A and Example 451B for Example 1C and Example 1B, respectively, in Example 1D. The product was dissolved in TFA (5 mL) and stirred at room temperature for 90 minutes, concentrated, dissolved in toluene, and concentrated again to provide the desired product MS (ESI) m/e 746, 748 (M−H)⁻, (M+H)⁺; ¹H NMR (300 MHz, DMSO-d$_6$) δ1.77 (m, 4H), 2.63 (m, 2H), 2.66 (s, 6H), 3.00 (m, 6H), 3.04 (m, 4H), 3.37 (m, 2H), 3.42 (m, 2H), 3.84 (m, 4H), 4.15 (m, 2H), 6.85 (d, 1H), 6.93 (s, 1H), 7.03 (d, 1H), 7.16 (dd, 1H), 7.21 (s, 1H), 7.23 (dd, 2H), 7.30 (d, 2H), 7.44 (d, 2H), 7.88 (dd, 2H), 7.91 (d, 2H), 8.25 (d, 1H), 8.51 (d, 1H).

EXAMPLE 512

N-((2'-methoxy-4'-(3-morpholin-4-ylpropyl)-1,1'-biphenyl-4-yl)carbonyl)-4-(((1R)-4-(4-methylpiperazin-1-yl)-1-((phenylthio)methyl)butyl) amino)-3-nitrobenzenesulfonamide The desired product was prepared by substituting Example 490B and Example 122O for Example 1C and Example 1B, respectively, in Example 1D. MS (ESI) m/e 829, 831 (M−H)⁻, (M+H)⁺; ¹H NMR (300 MHz, DMSO-d$_6$) δ1.59 (m, 2H), 1.79 (m, 4H), 2.22 (dd, 2H), 2.29 (m, 4H), 2.34 (m, 2H), 2.52 (m, 2H), 2.62 (m, 2H), 3.01 (m, 6H), 3.02 (s, 3H), 3.14 (m, 1H), 3.32 (m, 2H), 3.59 (m, 4H), 3.76 (s, 3H), 4.00 (m, 1H), 6.85 (d, 1H), 6.93 (s, 1H), 6.96 (d, 1H), 7.18 (dd, 1H), 7.19 (s, 1H), 7.23 (dd, 2H), 7.31 (d, 2H), 7.40 (d, 2H), 7.85 (dd, 1H), 7.91 (d, 2H), 8.17 (d, 1H), 8.49 (d, 1H).

EXAMPLE 513

N-(4-(8-azaspiro(4.5)dec-8-yl)benzoyl)-4-(((1R)-4-(4-methylpiperazin-1-yl)-1-((phenylthio)methyl) butyl)amino)-3-nitrobenzenesulfonamide The desired product was prepared by substituting Example 490B and Example 257C for Example 1C and Example 1B, respectively, in Example 1D. MS (ESI) m/e 733, 735 (M−H)⁻, (M+H)⁺; ¹H NMR (300 MHz, DMSO-d$_6$) δ1.41 (m, 4H), 1.48 (m, 4H), 1.59 (m, 4H), 1.72 (m, 4H), 1.82 (m, 2H), 2.33 (s, 3H), 2.48 (m, 2H), 2.59 (s, 4H), 2.82 (m, 4H), 3.19 (m, 4H), 3.31 (m, 2H), 4.00 (m, 1H), 6.80 (d, 2H), 6.95 (d, 1H), 7.17 (dd, 1H), 7.22 (dd, 2H), 7.31 (d, 2H), 7.74 (d, 2H), 7.81 (dd, 1H), 8.15 (d, 1H), 8.43 (d, 1H).

EXAMPLE 514

N-((4'-(2-((2-(dimethylamino)ethyl)(methyl)amino) ethyl)-2'-methoxy-1,1'-biphenyl-4-yl)carbonyl)-4-(((1R)-3-(dimethylamino)-1-((phenylthio)methyl) propyl)amino)-3-nitrobenzenesulfonamide The desired product was prepared by substituting Example 122G and Example 191C for Example 1C and Example 1B, respectively, in Example 1D. MS (ESI) m/e 747, 749 (M−H)⁻, (M+H)⁺; ¹NMR (300 MHz, DMSO-d$_6$) δ1.75 (m, 4H), 2.20 (m, 2H), 2.66 (s, 6H), 2.70 (s, 6H), 2.96–3.04 (m, 8H), 3.36 (m, 2H), 3.78 (s, 3H), 4.18 (m, 1H), 6.97 (d, 1H), 7.01 (s, 1H), 7.04 (d, 1H), 7.18 (dd, 1H), 7.21 (s, 1H), 7.25 (dd, 2H), 7.31 (d, 2H), 7.43 (d, 2H), 7.84 (dd, 1H), 7.91 (d, 2H), 8.15 (d, 1H), 8.49 (d, 1H).

EXAMPLE 515

4-(((1R)-3-(dimethylamino)-1-((phenylthio)methyl) propyl)amino)-N-((2'-methoxy-4'-(2-(4-methylpiperazin-1-yl)ethyl)-1,1'-biphenyl-4-yl) carbonyl)-3-nitrobenzenesulfonamide The desired product was prepared by substituting Example 122G and Example 242B for Example 1C and Example 1B, respectively, in Example 1D. MS (ESI) m/e 759, 761 (M−H)⁻, (M+H)⁺; ¹H NMR (300 MHz, DMSO-d$_6$) δ2.20 (m, 2H), 2.48 (s, 3H), 2.68 (s, 6H), 2.72 (m, 2H), 2.97–3.05 (m, 4H), 3.14 (s, 2H), 3.17 (m, 2H), 3.36 (m, 6H), 3.76 (s, 3H), 4.18 (m, 1H), 6.91 (d, 1H), 7.01 (s, 1H), 7.04 (d, 1H), 7.18 (dd, 1H), 7.21 (s, 1H), 7.23 (dd, 2H), 7.31 (d, 2H), 7.41 (d, 2H), 7.83 (dd, 1H), 7.90 (d, 2H), 8.14 (d, 1H), 8.49 (d, 1H).

EXAMPLE 516

4-(((1R)-4-(dimethylamino)-1-((phenylthio)methyl) butyl)amino)-N-((2'-methoxy-4'-((4-methylpiperazin-1-yl)methyl)-1,1'-biphenyl-4-yl) carbonyl)-3-nitrobenzenesulfonamide

EXAMPLE 516A methyl 2'-methoxy-4'-((4-methylpiperazin-1-yl) methyl)-1,1'-biphenyl-4-carboxylate The desired product was prepared by substituting Example 122I and N-methylpiperazine for Example 134A and dimethylamine, respectively, in Example 134B.

EXAMPLE 516B

2'-methoxy-4'-((4-methylpiperazin-1-yl)methyl)-1,1'-biphenyl-4-carboxylic acid

The desired product was prepared by substituting Example 516A for Example 1A in Example 1B.

EXAMPLE 516C 4-(((1R)-4-(dimethylamino)-1-((phenylthio)methyl) butyl)amino)-N-((2'-methoxy-4'-((4-methylpiperazin-1-yl)methyl)-1,1'-biphenyl-4-yl) carbonyl)-3-nitrobenzenesulfonamide The desired product was prepared by substituting Example 489A and Example 516B for Example 1C and Example 1B, respectively, in Example 1D. MS (ESI) m/e 761 (M+H)⁺; ¹H NMR (300 MHz, DMSO-d$_6$) δ1.78 (m, 4H), 2.66 (s, 9H), 2.70 (m, 2H), 3.00 (m, 2H), 3.14 (s, 2H), 3.35 (m, 6H), 3.61 (m, 2H), 3.76 (s, 3H), 4.06 (m, 1H), 6.97 (d, 1H), 7.00 (s, 1H), 7.02 (d, 1H), 7.16 (dd, 1H), 7.22 (s, 1H), 7.24 (dd, 2H), 7.31 (d, 2H), 7.41 (d, 2H), 7.85 (dd, 1H), 7.90 (d, 2H), 8.14 (d, 1H), 8.49 (d, 1H).

EXAMPLE 517

N-((2'-methoxy-4'-(2-(4-methylpiperazin-1-yl) ethyl)-1,1'-biphenyl-4-yl)carbonyl)-4-(((1R)-4-(4-methylpiperazin-1-yl)-1-((phenylthio)methyl)butyl) amino)-3-nitrobenzenesulfonamide The desired product was prepared by substituting Example 490B and Example 242B for Example 1C and Example 1B, respectively, Example 1D. MS (ESI) m/e 828, 830 (M−H)⁻, (M+H)⁺; ¹H NMR (300 MHz, DMSO-d$_6$) δ1.57 (m, 2H), 1.77 (m, 2H), 2.46 (m, 2H), 2.50–2.63 (m, 10H), 2.82 (m, 4H), 2.91 (m, 4H), 3.02 (m, 6H), 3.27 (m, 2H), 3.37 (m, 2H), 3.76 (s, 3H), 4.18 (m, 1H), 6.90 (d, 1H), 6.96 (d, 1H), 7.01 (s, 1H), 7.18 (dd, 1H), 7.20 (s, 1H), 7.22 (dd, 2H), 7.31 (d, 2H), 7.40 (d, 2H), 7.84 (dd, 1H), 7.91 (d, 2H), 8.15 (d, 1H), 8.48 (d, 1H).

EXAMPLE 518

3-nitro-N-(4-(1-oxa-9-azaspiro(5.5)undec-3-en-9-yl) benzoyl)-4-((2-(phenylthio)ethyl)amino) benzenesulfonamide

EXAMPLE 518A tert-butyl 4-allyl-4-hydroxypiperidine-1-carboxylate

The desired product was prepared by substituting allyl magnesium bromide for methyl magnesium bromide in Example 494A. MS (DCI(+)) m/e 242 (M+H)⁺.

EXAMPLE 518B tert-butyl 4-allyl-4-(allyloxy)piperidine-1-carboxylate

The title compound was prepared by substituting Example 518A and allyl bromide for Example 494A and methyl iodide, respectively, in Example 494B. MS (DCI(+) m/e 282 (M+H)$^+$.

EXAMPLE 518C tert-butyl 1-oxa-9-azaspiro(5.5)undec-3-ene-9-carboxylate

A solution of Example 518B (0.79 g, 2.81 mmol) in degassed benzene (100 mL) at room temperature was treated with bis-tricyclohexylphosphine benzylidene ruthenium (IV) dichloride (150 mg), stirred for 18 hours, and concentrated. The concentrate was purified by flash column chromatography on silica gel with 10%–25% ethyl acetate/heptane to provide the desired product. MS (DCI(+)) m/e 254 (M+H)$^+$.

EXAMPLE 518D 1-oxa-9-azaspiro(5.5)undec-3-ene

The desired product was prepared by substituting Example 518C for Example 494B in Example 494C.

EXAMPLE 518E tert-butyl 4-(1-oxa-9-azaspiro(5.5)undec-3-en-9-yl)benzoate

The desired product was prepared by substituting Example 518D for Example 494C in Example 494D. MS (DCI(+)) m/e 330 (M+H)$^+$.

EXAMPLE 518F 4-(1-oxa-9-azaspiro(5.5)undec-3-en-9-yl)benzoic acid

The desired product was prepared by substituting Example 518F for Example 493A in Example 493B. MS (DCI(+)) m/e 274 (M+H)$^+$.

EXAMPLE 518G 3-nitro-N-(4-(1-oxa-9-azaspiro(5.5)undec-3-en-9-yl)benzoyl)-4-((2-(phenylthio)ethyl)amino)benzenesulfonamide The desired product was prepared by substituting Example 518F and Example 77B for Example 1B and Example 1C, respectively, in Example 1D. MS (ESI(+)) m/e 609 (M+H)$^+$; $^1$H NMR (500 MHz, DMSO-d$_6$) δ11.95 (s, 1H), 8.75 (t, 1H), 8.60 (d, 1H), 7.91 (dd, 1H), 7.73 (d, 2H), 7.37 (d, 2H), 7.27 (t, 2H), 7.18 (m, 2H), 6.93 (d, 2H), 5.73 (s, 2H), 4.05 (s, 2H), 3.65 (q, 2H), 3.59 (dt, 2H), 3.28 (m, 2H), 3.17 (m, 2H), 1.95 (m, 2H), 1.75 (d, 2H), 1.52 (m, 2H).

EXAMPLE 519

N-(4-(4-benzyl-4-hydroxypiperidin-1-yl)benzoyl)-3-nitro-4-((2-(phenylthio)ethyl)amino)benzenesulfonamide The desired product was prepared by substituting Example 496B and Example 77B for Example 1B and Example 1C, respectively, in Example 1D. MS (ESI(+)) m/e 647 (M+H)$^+$; $^1$H NMR (500 MHz, DMSO-d$_6$) δ11.93 (s, 1H), 8.75 (t, 1H), 8.60 (d, 1H), 7.91 (dd, 1H), 7.70 (d, 2H), 7.37 (d, 2H), 7.22 (m, 9H), 6.90 (d, 2H), 4.40 (s, 1H), 3.65 (m, 4H), 3.28 (m, 2H), 3.17 (m, 2H), 2.70 (s, 2H), 1.50 (m, 2H), 1.45 (m, 2H).

EXAMPLE 520

N-(4-(2-azaspiro(4.4)non-2-yl)benzoyl)-4-(((1R)-3-(dimethylamino)-1-((phenylthio)methyl)propyl)amino)-3-nitrobenzenesulfonamide The desired product was prepared by substituting Example 120C and Example 122G for Example 1B and Example 1C, respectively, in Example 1D. MS (ESI(+)) m/e 652 (M+H)$^+$; $^1$H NMR (300 MHz, DMSO-d$_6$) δ11.90 (s, 1H), 8.55 (d, 1H), 8.29 (d, 1H), 7.87 (dd, 1H), 7.73 (d, 2H), 7.24 (dd, 2H), 7.08–7.18 (m, 4H), 6.51 (d, 2H), 4.20 (m, 1H), 3.35 (m, 4H), 3.15 (m, 4H), 2.74 (s, 6H), 2.14 (m, 2H), 1.86 (t, 2H), 1.65 (m, 4H), 1.55 (m, 4H).

EXAMPLE 521 ethyl 4-methyl-1-(4-(((((3-nitro-4-((2-(phenylthio)ethyl)amino)phenyl)sulfonyl)amino)carbonyl)phenyl)piperidine-4-carboxylate The desired product was prepared by substituting Example 532F and Example 77B for Example 1B and Example 1C, respectively, in Example 1D. MS (ESI(+)) m/e 627 (M+H)$^+$; $^1$H NMR (300 MHz, DMSO-d$_6$) δ11.98 (s, 1H), 8.77 (t, 1H), 8.60 (d, 1H), 7.91 (dd, 1H), 7.73 (d, 2H), 7.35 (m, 2H), 7.26 (t, 2H), 7.18 (m, 2H), 6.93 (d, 2H), 4.13 (m, 2H), 3.66 (m, 4H), 3.30 (m, 4H), 3.03 (m, 2H), 2.00 (m, 2H), 1.46 (m, 2H), 1.18 (t, 3H), 1.17 (s, 3H).

EXAMPLE 522

N-((5R)-5-((4-(((4-(8-azaspiro(4.5)dec-8-yl)benzoyl)amino)sulfonyl)-2-nitrophenyl)amino)-6-(phenylthio)hexyl)acetamide The desired product was prepared by substituting acetic acid for N,N-dimethyglycine in Example 478. MS (ESI(+)) m/e 708, 706 (M+H)$^+$, (M–H)$^-$; $^1$H NMR (500 MHz, DMSO-d$_6$) δ8.53 (d, 1H), 8.29 (d, 1H), 7.85 (dd, 1H), 7.73 (d, 2H), 7.25–7.09 (m, 5H), 6.92 (d, 2H), 4.12 (m, 1H), 3.34 (m, 4H), 2.97 (m, 2H), 1.73 (s, 3H), 1.60 (m, 4H), 1.52–1.34 (m, 12H).

EXAMPLE 523

N-((5R)-5-((4-(((4-(8-azaspiro(4.5)dec-8-yl)benzoyl)amino)sulfonyl)-2-nitrophenyl)amino)-6-(phenylthio)hexyl)isonicotinamide The desired product was prepared by substituting isonicotinic acid for N,N-dimethylglycine in Example 478. MS (ESI) m/e 771.3, 769.4 (M+H)$^+$, (M–H)$^-$; $^1$H NMR (500 MHz, DMSO-d$_6$) δ8.69 (d, 2H), 8.52 (d, 1H), 8.30 (d, 1H), 7.84 (dd, 1H), 7.73 (d, 2H), 7.70 (d, 2H), 7.09–7.25 (m, 5H), 6.92 (d, 2H), 4.12 (m, 1H), 3.34 (m, 4H), 3.24 (m, 2H), 1.78 (m, 2H), 1.58 (m, 4H), 1.52–1.34 (m, 12H).

EXAMPLE 524

N$^1$-((5R)-5-((4-(((4-(8-azaspiro(4.5)dec-8-yl)benzoyl)amino)sulfonyl)-2-nitrophenyl)amino)-6-(phenylthio)hexyl)-N$^2$-(2-carboxymethyl)-N$^2$-methylglycinamide The desired product was prepared by substituting methyliminodiacetic acid for N,N-dimethylglycine in Example 478. MS (ESI) m/e 795.3, 793.4 (M+H)$^+$, (M−H)$^−$; $^1$H NMR (500 MHz, DMSO-d$_6$) δ8.53(d, 1H), 8.29(d, 1H), 8.12 (m, 1H), 7.85 (dd, 1H), 7.73 (d, 2H), 7.25–7.09 (m, 5H), 6.92 (d, 2H), 4.12 (m, 1H), 3.34 (m, 4H), 3.17 (s, 3H), 3.01 (m, 2H), 2.58 (m, 4H), 1.76 (m, 2H), 1.60 m, 4H), 1.52–1.34 (m, 12H).

EXAMPLE 525

N~1~-((5R)-5-((4-(((4-(8-azaspiro(4.5)dec-8-yl)benzoyl)amino)sulfonyl)-2-nitrophenyl)amino)-6-(phenylthio)hexyl)glycinamide The desired product was prepared by substituting N-(t-butoxycarbonyl)glycine for N,N-dimethylglycine in Example 478. MS (ESI) m/e 723.3, 721.4 (M+H)$^+$, (M−H)$^−$; $^1$H NMR (500 MHz, DMSO-d$_6$) δ8.53 (d, 1H), 8.30 (d, 1H), 7.99 (m, 2H), 7.86 (dd, 1H), 7.74 (d, 2H), 7.25–7.09 (m, 5H), 6.93 (d, 2H), 4.12 (m, 1H), 3.34 (m, 4H), 3.09 (m, 2H), 1.75 (m, 2H), 1.60 (m, 4H), 1.52–1.34 (m, 12H).

EXAMPLE 526

N-((5R)-5-((4-(((4-(8-azaspiro(4.5)dec-8-yl)benzoyl)amino)sulfonyl)-2-nitrophenyl)amino)-6-(phenylthio)hexyl)-1-methyl-L-prolinamide The desired product was prepared by substituting N-methylproline for N,N-dimethylglycine in Example 478. MS (ESI) m/e 777.3, 775.4 (M+H)$^+$, (M−H)$^−$; $^1$H NMR (500 MHz, DMSO-d$_6$) δ8.53 (d, 1H), 8.51 (m, 1H), 8.30 (d, 1H), 7.86 (dd, 1H), 7.73 (d, 2H), 7.58 (m, 1H), 7.25–7.09 (m, 5H), 6.92 (d, 2H), 4.12 (m, 1H), 3.89 (m, 1H), 3.51 (m, 1H), 3.34 (m, 4H), 3.10 (m, 2H), 3.01 (m, 2H), 2.74 (s, 3H), 1.78 (m, 2H), 1.60 (m, 4H), 1.52–1.34 (m, 14H).

EXAMPLE 527

N-((5R)-5-((4-(((4-(8-azaspiro(4.5)dec-8-yl)benzoyl)amino)sulfonyl)-2-nitrophenyl)amino)-6-(phenylthio)hexyl)-1-methylcyclopropanecarboxamide The desired product was prepared by substituting 1-methylcyclopropanecarboxylic acid for N,N-dimethylglycine in Example 478. MS (ESI) m/e 748.3, 746.4 (M+H)$^+$, (M−H)$^−$; $^1$H NMR (500 MHz, DMSO-d$_6$) δ8.53 (d, 1H), 8.30 (d, 1H), 7.84 (dd, 1H), 7.73 (d, 2H), 7.39 (t, 1H), 7.25–7.09 (m, 5H), 6.92 (d, 2H), 4.07 (m, 1H), 3.34 (m, 4H), 3.09 (m, 2H), 1.74 (m, 2H), 1.60 (m, 4H), 1.52–1.34 (m, 12H), 1.16 (s, 3H), 0.85 (q, 2H), 0.40 (q, 2H).

EXAMPLE 528

N-((5R)-5-((4-(((4-(8-azaspiro(4.5)dec-8-yl)benzoyl)amino)sulfonyl)-2-nitrophenyl)amino)-6-(phenylthio)hexyl)-2-hydroxyacetamide The desired product was prepared by substituting glycolic acid for N,N-dimethylglycine in Example 478. MS (ESI) m/e 724.3, 722.3 (M+H)$^+$, (M−H)$^−$; $^1$H NMR (500 MHz, DMSO-d$_6$) δ8.53 (d, 1H), 8.30 (d, 1H), 7.84 (dd, 1H), 7.73 (d, 2H), 7.65 (t, 1H), 7.25–7.09 (m, 5H), 6.92 (d, 2H), 4.09 (m, 1H), 3.75 (s, 2H), 3.34 (m, 4H), 3.06 (m, 2H), 1.78 (m, 2H), 1.60 (m, 4H), 1.52–1.34 (m, 12H).

EXAMPLE 529

N-((5R)-5-((4-(((4-(8-azaspiro(4.5)dec-8-yl)benzoyl)amino)sulfonyl)-2-nitrophenyl)amino)-6-(phenylthio)hexyl)-2,2,2-trifluoroacetamide The desired product was prepared by substituting trifluoroacetic acid for N,N-dimethylglycine in Example 478. MS (ESI) m/e 762.2, 760.3 (M+H)$^+$, (M−H)$^−$; $^1$H NMR (500 MHz, DMSO-d$_6$) δ9.33 (t, 1H), 8.53 (d, 1H), 8.30 (d, 1H), 7.84 (dd, 1H), 7.73 (d, 2H), 7.25–7.09 (m, 5H), 6.92 (d, 2H), 4.09 (m, 1H), 3.34 (m, 4H), 3.13 (m, 2H), 1.75 (m, 2H), 1.60 (m, 4H), 1.52–1.34 (m, 12H).

EXAMPLE 530

N-(4-(4-benzyl-4-methoxypiperidin-1-yl)benzoyl)-4-(((1R)-5-(dimethylamino)-1-((phenylthio)methyl)pentyl)amino)-3-nitrobenzenesulfonamide

EXAMPLE 530A tert-butyl 4-benzyl-4-hydroxypiperidine-1-carboxylate

A solution of 4-hydroxy-4-benzyl piperidine (0.66 g, 3.5 mmol) in 1M NaOH (7 mL, 7 mmol) and dioxane (5 mL) at 0° C. was treated with BOC$_2$O (0.76 g, 3.5 mmol), warmed to room temperature, stirred for 16 hours, adjusted to pH<7 with 10% citric acid, and extracted twice with ethyl acetate. The combined extracts were washed with water and brine, dried (Na$_2$SO$_4$), filtered, and concentrated to provide the desired product.

EXAMPLE 530B tert-butyl 4-benzyl-4-methoxypiperidine-1-carboxylate

The desired product was prepared by substituting Example 530A for Example 494A in Example 494B. MS (DCI(+)) m/e 306 (M+H)$^+$.

EXAMPLE 530C 4-benzyl-4-methoxypiperidine

The desired product was prepared by substituting Example 530B for Example 494B in Example 494C.

EXAMPLE 530D tert-butyl 4-(4-benzyl-4-methoxypiperidin-1-yl)benzoate

The desired product was prepared by substituting Example 530C for Example 494C in Example 494D.

EXAMPLE 530E 4-(4-benzyl-4-methoxypiperidin-1-yl)benzoic acid

The desired product was prepared by substituting Example 530D for Example 493A in Example 493B.

EXAMPLE 530F

N-(4-(4-benzyl-4-methoxypiperidin-1-yl)benzoyl)-4-(((1R)-5-(dimethylamino)-1-((phenylthio)methyl)pentyl)amino)-3-nitrobenzenesulfonamide The desired product was prepared by substituting Example 124E and Example 530E for Example 1C and Example 1B, respectively, in Example 1D. MS(ESI(+)) m/e 760 (M+H)$^+$; $^1$H NMR (500 MHz, DMSO-d$_6$) δ11.95 (s, 1H), 9.20 (s, 1H), 8.55 (d, 1H), 8.31 (d, 1H), 7.88 (dd, 1H), 7.70 (d, 2H), 7.30–7.05 (m, 11H), 6.90 (d, 2H), 4.10 (m, 1H), 3.65 (m, 2H), 3.35 (m, 2H), 3.28 (s, 3H), 3.00 (m, 4H), 2.80 (s, 2H), 2.72 (s, 6H), 1.78 (m, 2H), 1.68 (m, 2H), 1.60 (m, 2H), 1.50 (m, 2H), 1.30 (m, 2H).

227

EXAMPLE 531

N-((4-benzylpiperidin-1-yl)carbonyl)-4-(((1R)-5-(dimethylamino)-1-((phenylthio)methyl)pentyl)amino)-3-nitrobenzenesulfonamide The desired product was prepared by substituting Example 124E and Example 488B for Example 1C and Example 1B, respectively, in Example 1D. MS(ESI(+)) m/e 746 (M+H)+; $^1$H NMR (500 MHz, DMSO-$d_6$) δ11.95 (s, 1H), 9.20 (s, 1H), 8.55 (d, 1H), 8.31 (d, 1H), 7.88 (dd, 1H), 7.70 (d, 2H), 7.30–7.05 (m, 11H), 6.90 (d, 2H), 4.10 (m, 1H), 3.65 (m, 2H), 3.15 (m, 2H), 2.95 (m, 2H), 2.70 (m, 8H), 1.75 (m, 2H), 1.60–1.25 (m, 9H).

EXAMPLE 532

N-(4-(4-(hydroxymethyl)-4-methylpiperidin-1-yl)benzoyl)-3-nitro-4-((2-(phenylthio)ethyl)amino)benzenesulfonamide

EXAMPLE 532A 1-tert-butyl 4-ethyl piperidine-1,4-dicarboxylate

A solution of ethyl isonipecoate (2.5 g, 15.9 mmol) in dichloromethane (80 mL) at 0° C. was treated with (BOC)$_2$O (3.8 g, 17.3 mmol), warmed to room temperature, stirred for 2 hours, diluted with water, and extracted with dichloromethane. The combined extracts were washed sequentially with saturated sodium bicarbonate, 5% citric acid, and brine, dried (MgSO$_4$), filtered, and concentrated to provide the desired product. MS (ESI(+)) m/e 258 (M+H)+.

EXAMPLE 532B 1-tert-butyl 4-ethyl 4-methylpiperidine-1,4-dicarboxylate

A solution of Example 532A (2.1 g, 8.1 mmol) in THF (81 mL) at −78° C. was treated dropwise with 1.5M LDA in cyclohexane (6.0 mL, 8.9 mmol), stirred for 30 minutes, treated dropwise with methyl iodide (0.76 mmol), 12.1 mmol), stirred for 2.5 hours, quenched with saturated NH$_4$Cl, and extracted with diethyl ether. The combined extracts were washed with brine, dried (MgSO$_4$), filtered and concentrated to provide the desired product. MS (DCI) m/e 272 (M+H)+.

EXAMPLE 532C ethyl 4-methylpiperidine-4-carboxylate

A solution of Example 532B (2.1 g, 8.0 mmol) in 4HCl in dioxane (10 mL) at room temperature was stirred for 3 hours and concentrated to provide the desired product. MS (DCI) m/e 171 (M+H)+.

EXAMPLE 532D benzyl 4-fluorobenzoate

A mixture of 4-fluorobenzoic acid (4.9 g, 35.3 mmol), benzyl bromide (3.8 mL, 31.7 mmol), and cesium carbonate (17.2 g, 53 mmol) in DMF (50 mL) at room temperature was stirred for 24 hours, diluted with water, and extracted with diethyl ether. The combined extracts were washed with brine, dried (MgSO$_4$), filtered, and concentrated to provide the desired product. MS (DCI) m/e 248 (M+H)+.

EXAMPLE 532E ethyl 1-(4-((benzyloxy)carbonyl)phenyl)-4-methylpiperidine-4-carboxylate A mixture of Example 532C (2.2 g, 10.6 mmol), Example 532D (2.2 g, 9.9 mmol), and potassium carbonate (2.9 g, 21.2 mmol) in N-methylpyrrolidinone (8.8 mL) was stirred at 150° C. for 24 hours, cooled to room temperature, diluted with water, and extracted with dichloromethane. The combined extracts were washed with water and brine, dried (MgSO$_4$), filtered, and concentrated. The concentrate was purified by flash column chromatogaphy on silica gel with 10% ethyl acetate/hexanes to provide the desired product. MS (DCI) m/e 382 (M+H)+.

EXAMPLE 532F 4-(4-(ethoxycarbonyl)-4-methylpiperidin-1-yl)benzoic acid

A mixture of Example 532E (0.54 g, 1.4 mmol) in ethanol (6 mL) at room temperature was hydrogenated at 60 psi over 10% Pd/C (58 mg) for 1.5 hours, filtered, and concentrated to provide the desired product. MS (DCI) m/e 292 (M+H)+.

EXAMPLE 532G ethyl 4-methyl-1-(4-(((((3-nitro-4-((2-(phenylthio)ethyl)amino)phenyl)sulfonyl)amino)carbonyl)phenyl)piperidine-4-carboxylate The desired product was prepared by substituting Example 532F and Example 77B for Example 1B and Example 1C, respectively, in Example 1D. MS (ESI(+)) m/e 627 (M+H)+.

EXAMPLE 532H 4-methyl-1-(4-(((((3-nitro-4-((2-(phenylthio)ethyl)amino)phenyl)sulfonyl)amino)carbonyl)phenyl)piperidine-4-carboxylic acid The desired product was prepared by substituting Example 532G for Example 119B in Example 119C. MS (ESI(+)) m/e 599.

EXAMPLE 532I

N-(4-(4-(hydroxymethyl)-4-methylpiperidin-1-yl)benzoyl)-3-nitro-4-((2-(phenylthio)ethyl)amino)benzenesulfonamide A solution of Example 532H (35 mg, 0.06 mmol), 4-methylmorpholine (0.007 mL, 0.06 mmol), and DME (0.3 mL) at −15° C. was treated dropwise with isobutyl chloroformate (0.008 mL, 0.06 mmol), stirred for 15 minutes, and filtered. The filter cake was washed with DME and the filtrate and washings were combined. The solution was cooled to −15° C., treated sequentially with NaBH$_4$ (3.5 mg, 0.09 mmol) water (0.03 mL), and additional water (50 mL), and extracted with dichloromethane. The combined extracts were washed with brine, dried (MgSO$_4$), filtered, and concentrated. The concentrate was purifed by flash column chromatography on silica gel with 1–2% methanol/dichloromethane to provide the desired product. MS (ESI (−))) m/e 583 (M−H)−; $^1$H NMR (500 MHz, DMSO-$d_6$) δ11.92 (s, 1H), 8.75 (t, 1H), 8.58 (d, 1H), 7.90 (dd, 1H), 7.72 (d, 2H), 7.38 (d, 2H), 7.27 (t, 2H), 7.15 (m, 2H), 6.90 (d, 2H), 4.53 (t, 1H), 3.66 (m, 2H), 3.50 (m, 2H), 3.30 (m, 2H), 3.16 (m, 4H), 1.50 (m, 2H), 1.25 (m, 2H), 0.91 (s, 3H).

EXAMPLE 533

N-(4-(4-(2-naphthylsulfonyl)piperazin-1-yl)benzoyl)-3-nitro-4-((2-(phenylthio)ethyl)amino)benzenesulfonamide The desired product was prepared by substituting 2-napthalenesulfonyl chloride for 2-methoxyethyl chloroformate in Example 325. MS (ESI(−)) m/e 730 (M−H)⁻; ¹H NMR (500 MHz, DMSO-d₆) δ12.02 (s, 1H), 8.74 (t, 1H), 8.57 (d, 1H), 8.46 (d, 1H), 8.21 (d, 1H), 8.16 (d, 1H), 8.06 (d, 1H), 7.88 (dd, 1H), 7.77 (dd, 1H), 7.76–7.66 (m, 4H), 7.37–7.32 (m, 2H), 7.25 (t, 2H), 7.19–7.14 (m, 2H), 6.89 (d, 2H), 3.65 (q, 2H), 3.42 (t, 4H), 3.26 (t, 2H), 3.07 (t, 4H).

EXAMPLE 534

4-(((1R)-5-((amino(imino)methyl)amino)-1-((phenylthio)methyl)pentyl)amino)-N-(4-(8-azaspiro(4.5)dec-8-yl)benzoyl)-3-nitrobenzenesulfonamide A solution of Example 287 (30 mg, 0.05 mmol), aminoiminosulfonic acid (7 mg, 0.055 mmol), diisopropylethylamine (0.02 Ml), and DMF (0.3 mL) at room temperature was stirred for 24 hours and concentrated. The concentrate was purified by reverse phase chromatography with 0–90% methanol/0.1% aqueous TFA to provide the desired product. MS (ESI(+)) m/e 708 (M+H)⁺; ¹H NMR (500 MHz, DMSO-d₆) δ12.02 (s, 1H), 8.53 (d, 1H), 8.32 (d, 1H), 7.86 (dd, 1H), 7.73 (d, 2H), 7.39 (t, 1H), 7.25–7.10 (m, 6H), 6.93 (d, 2H), 4.12 (m, 1H), 3.35 (m, 6H), 3.05 (m, 2H), 1.75 (m, 2H), 1.59 (m, 4H), 1.42 (m, 8H).

It will be evident to one skilled in the art that the present invention is not limited to the forgoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims and therefore intended to be embraced therein.

What is claimed is:

1. A compound of formula (I):

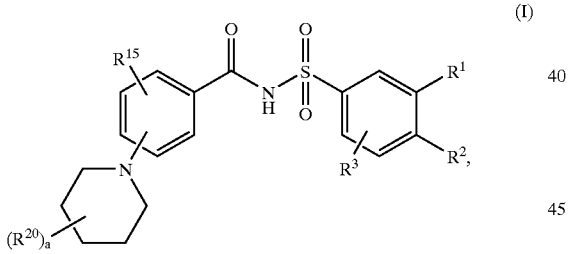

or a therapeutically acceptable salt thereof, wherein
$R^1$ is selected from the group consisting of alkyl, haloalkyl, nitro, and —$NR^5R^6$;
$R^2$, and $R^3$ are independently selected from the group consisting of hydrogen, alkenyl, alkoxy, alkyl, alkylsulfanyl, alkynyl, aryl, arylalkoxy, aryloxy, aryloxyalkoxy, arylsulfanyl, arylsulfanylalkoxy, carbonyloxy, cycloalkylalkoxy, cycloalkyloxy, halo, halolkoxy, haloalkyl, hydroxy, nitro, and —$NR^5R^6$; wherein the aryl and the aryl part of the arylalkoxy, the aryloxy, the aryloxyalkoxy, the arylsulfanyl, and arylsulfanylalkoxy can be optionally substituted with one, two, three, four, or five substituents independently selected from the group consisting of alkanoyl, alkenyl, alkoxy, alkoxyalkanoyl, alkoxyalkyl, alkoxycarbonyl, alkoxycarbonylalkyl, alkyl, alkynyl, carbonyloxy, cyano, halo, haloalkoxy, haloalkyl, hydroxy, hydroxyalkyl, nitro, —$NR^aR^b$, oxo, and —$C(NH)NH_2$; and wherein the cycloalkyl part of the cycloalkylalkoxy and the cycloalkyloxy can be optionally substituted with one, two, three, four, or five substituents independently selected from the group consisting of alkoxy, alkoxycarbonyl, alkyl, $NH_2CH_2$—, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy;
$R^5$ and $R^6$ are independently selected from the group consisting of hydrogen, alkenyl, alkoxyalkyl, alkoxycarbonylalkyl, alkyl, alkylsulfanylalkyl, alkylsulfonylalkyl, aryl, arylalkyl, arylalkylsulfanylalkyl, aryloxyalkyl, arylsulfanylalkyl, arylsulfinylalkyl, arylsulfonylalkyl, carboxyalkyl, cycloalkenyl, cycloalkenylalkyl, cycloalkyl, (cycloalkyl)alkyl, cycloalkylcarbonyl, (heterocycle)sulfanylalkyl, hydroxyalkyl, a nitrogen protecting group, and —$N=CR^7R^8$;
$R^7$ and $R^8$ are alkyl, or
$R^7$ and $R^8$, together with the carbon atom to which they are attached, form an aryl group which an be optionally substituted with one, two, three, four, or five substituents independently selected from the group consisting of alkanoyl, alkenyl, alkoxy, alkoxyalkanoyl, alkoxyalkyl, alkoxycarbonyl, alkoxycarbonylalkyl, alkyl, alkynyl, carbonyloxy, cyano, halo, haloalkoxy, haloalkyl, hydroxy, hydroxyalkyl, nitro, —$NR^aR^b$, oxo, and —$C(NH)NH_2$;
$R^{15}$ is selected from the group consisting of hydrogen, alkyl, and halo;
a is 0–5;
each $R^{20}$ is independently selected from the group consisting of alkanoyl, alkanoylalkyl, alkenyl, alkoxy, alkoxyalkoxycarbonyl, alkoxyalkyl, alkoxycarbonyl, alkoxycarbonylalkyl, alkyl, alkylsulfanylalkyl, alkynyl, aryl, arylalkoxyalkanoyl, arylalkoxycarbonyl, arylalkyl, arylalkylsulfonyl, arylcarbonyl, aryloxy, arylsulfanyl, arylsulfanylalkyl, arylsulfonyl, carbonyloxy, carboxy, cyano, cyanoalkyl, cycloalkyl, (cycloalkyl)alkyl, cycloalkylcarbonyl, formyl, formylalkyl, halo, haloalkoxy, haloalkyl, hydroxy, hydroxyalkyl, nitro, —$NR^aR^b$, oxo, spirocycle, and —$C(NH)NH_2$; wherein the aryl, the aryl part of the arylalkoxyalkanoyl, the arylalkoxycarbonyl, the arylalkyl, the arylalkylsulfonyl, the arylcarbonyl, the aryloxy, the arylsulfanyl, the arylsulfanylalkyl, and the arylsulfonyl can be optionally substituted with one, two, three, four, or five substituents independently selected from the group consisting of alkanoyl, alkenyl, alkoxy, alkoxyalkanoyl, alkoxyalkyl, alkoxycarbonyl, alkoxycarbonylalkyl, alkyl, alkynyl, carbonyloxy, cyano, halo, haloalkoxy, haloalkyl, hydroxy, hydroxyalkyl, nitro, —$NR^aR^b$, oxo, and —$C(NH)NH_2$; and wherein the cycloalkyl part of the cycloalkylalkoxy and the cycloalkyloxy can be optionally substituted with one, two, three, four, or five substituents independently selected from the group consisting of alkoxy, alkoxycarbonyl, alkyl, $NH_2CH_2$—, arylalkoxy, aryloxy, arylsulfanyl, halo, haloalkoxy, haloalkyl, and hydroxy, wherein the aryl part of the arylalkoxy, the aryloxy, and the arylsulfanyl can be further optionally substituted with one, two, or three substituents independently selected from the group consisting of alkoxy, alkyl, halo, haloalkoxy, haloalkyl, and hydroxy;

$R^a$ and $R^b$ are independently selected from the group consisting of hydrogen, alkanoyl, alkenyl, alkoxyalkyl, alkoxyalkoxyalkyl, alkoxycarbonyl, alkyl, unsubstituted aryl, unsubstituted arylalkyl, unsubstituted cycloalkyl, unsubstituted (cycloalkyl)alkyl, unsubstituted cycloalkylcarbonyl, haloalkanoyl, haloalkyl, hydroxyalkyl, and —CH(NH)NH$_2$.

2. The compound of claim 1 wherein $R^2$ is $NR^5R^6$.

3. The compound of claim 2 wherein one of $R^5$ and $R^6$ is hydrogen and the other is selected from the group consisting of arylsulfanylalkyl, arylsulfinylalkyl, and (cycloalkyl)alkyl.

4. The compound of claim 3 wherein $R^{20}$ is spirocycle.

5. The compound of claim 4 selected from the group consisting of

N-(4-(8-azaspiro(4.5)dec-8-yl)benzoyl)-4-(((1R)-5-(dimethylamino)-1-((phenylthio)methyl)pentyl)amino)-3-nitrobenzenesulfonamide;

N-(4-(8-azaspiro(4.5)dec-8-yl)benzoyl)-4-(((1R)-2-(dimethylamino)-1-((phenylthio)methyl)ethyl)amino)-3-nitrobenzenesulfonamide;

N-((5R)-5-((4-(((4-(8-azaspiro(4.5)dec-8-yl)benzoyl)amino)sulfonyl)-2-nitrophenyl)amino)-6-(phenylthio)hexyl)-1H-imidazole-1-carboxamide;

N-(4-(8-azaspiro(4.5)dec-8-yl)benzoyl)-4-(((1R)-2-morpholin-4-yl-1-((phenylthio)methyl)ethyl)amino)-3-nitrobenzenesulfonamide;

N-(4-(8-azaspiro(4.5)dec-8-yl)benzoyl)-4-(((1R)-2-(4-methylpiperazin-1-yl)-1-((phenylthio)methyl)ethyl)amino)-3-nitrobenzenesulfonamide;

4-(((1R)-5-amino-1-((phenylthio)methyl)pentyl)amino)-N-(4-(6-azaspiro(2.5)oct-6-yl)benzoyl)-3-nitrobenzenesulfonamide;

4-(((4-(aminomethyl)bicyclo(2.2.2)oct-1-yl)methyl)amino)-N-(4-(8-azaspiro(4.5)dec-8-yl)benzoyl)-3-nitrobenzenesulfonamide;

tert-butyl(5R)-5-((4-(((4-(6-azaspiro(2.5)oct-6-yl)benzoyl)amino)sulfonyl)-2-nitrophenyl)amino)-6-(phenylthio)hexylcarbamate;

N-(4-(8-azaspiro(4.5)dec-8-yl)benzoyl)-4-((2,2-difluoro-2-(phenylthio)ethyl)amino)-3-nitrobenzenesulfonamide;

N-(4-(8-azaspiro(4.5)dec-8-yl)benzoyl)-4-(((1R)-2-((2-(dimethylamino)ethyl)(methyl)amino)-1-((phenylthio)methyl)ethyl)amino)-3-nitrobenzenesulfonamide;

N-(4-(8-azaspiro(4.5)dec-8-yl)benzoyl)-4-((3-(dimethylamino)-2-(phenylthio)propyl)amino)-3-nitrobenzenesulfonamide;

tert-butyl(5R)-5-((4-(((4-(8-azaspiro(4.5)dec-8-yl)benzoyl)amino)sulfonyl)-2-nitrophenyl)amino)-6-(phenylthio)hexylcarbamate;

N-(4-(8-azaspiro(4.5)dec-8-yl)benzoyl)-4-((2-methyl-2-(phenylthio)propyl)amino)-3-nitrobenzenesulfonamide;

N-(4-(8-azaspiro(4.5)dec-8-yl)benzoyl)-4-((1,1-dimethyl-2-(phenylthio)ethyl)amino)-3-nitrobenzenesulfonamide;

N-(4-(8-azaspiro(4.5)dec-8-yl)benzoyl)-4-(((1R)-2-hydroxy-1-((phenylthio)methyl)ethyl)amino)-3-nitrobenzenesulfonamide;

4-(((1R)-5-amino-1-((phenylthio)methyl)pentyl)amino)-N-(4-(8-azaspiro(4.5)dec-8-yl)benzoyl)-3-nitrobenzenesulfonamide;

N-(4-(8-azaspiro(4.5)dec-8-yl)benzoyl)-3-nitro-4-((2-(phenylthio)ethyl)amino)benzenesulfonamide;

4-(((1R)-5-((aminocarbonyl)amino)-1-((phenylthio)methyl)pentyl)amino)-N-(4-(8-azaspiro(4.5)dec-8-yl)benzoyl)-3-nitrobenzenesulfonamide;

N-(4-(8-azaspiro(4.5)dec-8-yl)benzoyl)-4-(((1R)-5-(dimethylamino)-1-((phenylsulfinyl)methyl)pentyl)amino)-3-nitrobenzenesulfonamide;

N~1~-((5R)-5-((4-(((4-(8-azaspiro(4.5)dec-8-yl)benzoyl)amino)sulfonyl)-2-nitrophenyl)amino)-6-(phenylthio)hexyl)-N~2~,N~2~-dimethylglycinamide;

N-((5R)-5-((4-(((4-(8-azaspiro(4.5)dec-8-yl)benzoyl)amino)sulfonyl)-2-nitrophenyl)amino)-6-(phenylthio)hexyl)cyclopropanecarboxamide;

(4R)-4-((4-(((4-(8-azaspiro(4.5)dec-8-yl)benzoyl)amino)sulfonyl)-2-nitrophenyl)amino)-N,N-dimethyl-5-(phenylthio)pentanamide;

N-(4-(8-azaspiro(4.5)dec-8-yl)benzoyl)-4-(((1R)-4-(dimethylamino)-1-((phenylthio)methyl)butyl)amino)-3-nitrobenzenesulfonamide;

N-(4-(8-azaspiro(4.5)dec-8-yl)benzoyl)-4-(((1R)-3-(4-methylpiperazin-1-yl)-1-((phenylthio)methyl)propyl)amino)-3-nitrobenzenesulfonamide;

N-(4-(8-azaspiro(4.5)dec-8-yl)benzoyl)-4-(((1R)-4-(4-methylpiperazin-1-yl)-1-((phenylthio)methyl)butyl)amino)-3-nitrobenzenesulfonamide;

N-((5R)-5-((4-(((4-(8-azaspiro(4.5)dec-8-yl)benzoyl)amino)sulfonyl)-2-nitrophenyl)amino)-6-(phenylthio)hexyl)acetamide;

N-((5R)-5-((4-(((4-(8-azaspiro(4.5)dec-8-yl)benzoyl)amino)sulfonyl)-2-nitrophenyl)amino)-6-(phenylthio)hexyl)isonicotinamide;

$N^1$-((5R)-5-((4-(((4-(8-azaspiro(4.5)dec-8-yl)benzoyl)amino)sulfonyl)-2-nitrophenyl)amino)-6-(phenylthio)hexyl)-$N^2$-(2-carboxymethyl)-$N^2$-methylglycinamide;

N~1~-((5R)-5-((4-(((4-(8-azaspiro(4.5)dec-8-yl)benzoyl)amino)sulfonyl)-2-nitrophenyl)amino)-6-(phenylthio)hexyl)glycinamide;

N-((5R)-5-((4-(((4-(8-azaspiro(4.5)dec-8-yl)benzoyl)amino)sulfonyl)-2-nitrophenyl)amino)-6-(phenylthio)hexyl)-1-methyl-L-prolinamide;

N-((5R)-5-((4-(((4-(8-azaspiro(4.5)dec-8-yl)benzoyl)amino)sulfonyl)-2-nitrophenyl)amino)-6-(phenylthio)hexyl)-1-methylcyclopropanecarboxamide;

N-((5R)-5-((4-(((4-(8-azaspiro(4.5)dec-8-yl)benzoyl)amino)sulfonyl)-2-nitrophenyl)amino)-6-(phenylthio)hexyl)-2-hydroxyacetamide;

N-((5R)-5-((4-(((4-(8-azaspiro(4.5)dec-8-yl)benzoyl)amino)sulfonyl)-2-nitrophenyl)amino)-6-(phenylthio)hexyl)-2,2,2-trifluoroacetamide; and 4-(((1R)-5-((amino(imino)methyl)amino)-1-((phenylthio)methyl)pentyl)amino)-N-(4(8-azaspiro(4.5)dec-8-yl)benzoyl)-3-nitrobenzenesulfonamide.

6. The compound of claim 3 wherein $R^{20}$ is selected from the group consisting of alkoxy, alkoxycarbonyl, alkyl, aryl, arylalkyl, formylalkyl, hydroxy, and hydroxyalkyl.

7. The compound of claim 6 selected from the group consisting of

N-(4-(4,4-dimethylpiperidin-1-yl)benzoyl)-4-(((1R)-3-morpholin-4-yl-1-((phenylthio)methyl)propyl)amino)-3-nitrobenzenesulfonamide;

4-(((1R)-3-(dimethylamino)-1-((phenylthio)methyl)propyl)amino)-N-(4-(4,4-dimethylpiperidin-1-yl)benzoyl)-3-nitrobenzenesulfonamide;

4-(((1R)-5-amino-1-((phenylthio)methyl)pentyl)amino)-N-(4-(4-ethyl-4-methylpiperidin-1-yl)benzoyl)-3-nitrobenzenesulfonamide;

4-(((1R)-5-(dimethylamino)-1-((phenylthio)methyl)pentyl)amino)-N-(4-(4,4-dimethylpiperidin-1-yl)benzoyl)-3-nitrobenzenesulfonamide;

tert-butyl(5R)-5-((4-(((4-(4-ethyl-4-methylpiperidin-1-yl)benzoyl)amino)sulfonyl)-2-nitrophenyl)amino)-6-(phenylthio)hexylcarbamate;

3-nitro-N-(4-(4-(3-oxopropyl)piperidin-1-yl)benzoyl)-4-((2-(phenylthio)ethyl)amino)benzenesulfonamide;

N-(4-(4-(3-hydroxypropyl)piperidin-1-yl)benzoyl)-3-nitro-4-((2-(phenylthio)ethyl)amino)benzenesulfonamide;

N-(4-(3,3-dimethylpiperidin-1-yl)benzoyl)-3-nitro-4-((2-(phenylthio)ethyl)amino)benzenesulfonamide;

N-(4-(4-ethyl-4-methylpiperidin-1-yl)benzoyl)-3-nitro-4-((2-(phenylthio)ethyl)amino)benzenesulfonamide;

tert-butyl(5R)-5-((4-(((4-(4,4-dimethylpiperidin-1-yl)benzoyl)amino)sulfonyl)-2-nitrophenyl)amino)-6-(phenylthio)hexylcarbamate;

4-(((1R)-5-amino-1-((phenylthio)methyl)pentyl)amino)-N-(4-(4,4-dimethylpiperidin-1-yl)benzoyl)-3-nitrobenzenesulfonamide;

4-((1,1-dimethyl-2-(phenylthio)ethyl)amino)-N-(4-(4,4-dimethylpiperidin-1-yl)benzoyl)-3-nitrobenzenesulfonamide;

N-(4-(4,4-dimethylpiperidin-1-yl)benzoyl)-3-nitro-4-((2-(phenylthio)ethyl)amino)benzenesulfonamide;

4-(((1R)-3-(dimethylamino)-1-((phenylthio)methyl)propyl)amino)-N-(4-(4-ethyl-4-methylpiperidin-1-yl)benzoyl)-3-nitrobenzenesulfonamide;

N-(4-(4-ethyl-4-methoxypiperidin-1-yl)benzoyl)-3-nitro-4-((2-(phenylthio)ethyl)amino)benzenesulfonamide;

N-(4-(4-benzylpiperidin-1-yl)benzoyl)-3-nitro-4-((2-(phenylthio)ethyl)amino)benzenesulfonamide;

4-(((1R)-5-(dimethylamino)-1-((phenylthio)methyl)pentyl)amino)-N-(4-(4-hydroxy-4-phenylpiperidin-1-yl)benzoyl)-3-nitrobenzenesulfonamide;

4-(((1R)-5-(dimethylamino)-1-((phenylthio)methyl)pentyl)amino)-N-(4-(4-methoxy-4-methylpiperidin-1-yl)benzoyl)-3-nitrobenzenesulfonamide;

4-(((1R)-5-(dimethylamino)-1-((phenylthio)methyl)pentyl)amino)-N-(4-(4-ethyl-4-hydroxypiperidin-1-yl)benzoyl)-3-nitrobenzenesulfonamide;

N-(4-(4-benzyl-4-hydroxypiperidin-1-yl)benzoyl)-4-(((1R)-5-(dimethylamino)-1-((phenylthio)methyl)pentyl)amino)-3-nitrobenzenesulfonamide;

N-(4-(4-benzyl-4-hydroxypiperidin-1-yl)benzoyl)-3-nitro-4-((2-(phenylthio)ethyl)amino)benzenesulfonamide;

ethyl 4-methyl-1-(4-(((((3-nitro-4-((2-(phenylthio)ethyl)amino)phenyl)sulfonyl)amino)carbonyl)phenyl)piperidine-4-carboxylate;

N-(4-(4-benzyl-4-methoxypiperidin-1-yl)benzoyl)-4-(((1R)-5-(dimethylamino)-1-((phenylthio)methyl)pentyl)amino)-3-nitrobenzenesulfonamide;

N-((4-benzylpiperidin-1-yl)carbonyl)-4-(((1R)-5-(dimethylamino)-1-((phenylthio)methyl)pentyl)amino)-3-nitrobenzenesulfonamide; and N-(4-(4-(hydroxymethyl)-4-methylpiperidin-1-yl)benzoyl)-3-nitro-4-((2-(phenylthio)ethyl)amino)benzenesulfonamide.

8. The compound which is 4-(((1R)-3-(dimethylamino)-1-((phenylthio)methyl)propyl)amino)-N-(4-(4,4-dimethylpiperidin-1-yl)benzoyl)-3-nitrobenzenesulfonamide.

9. A pharmaceutical composition comprising a compound of claim 1 or a therapeutically acceptable salt thereof, in combination with a therapeutically acceptable carrier.

* * * * *